(12) United States Patent
Baeurle et al.

(10) Patent No.: US 12,239,630 B2
(45) Date of Patent: *Mar. 4, 2025

(54) CARBOXYLIC ACID AROMATIC AMIDES AS ANTAGONISTS OF BRADYKININ B1 RECEPTOR

(71) Applicant: Bayer Pharma Aktiengesellschaft, Berlin (DE)

(72) Inventors: Stefan Baeurle, Berlin (DE); Adam Davenport, Abingdon (GB); Christopher Stimson, Abingdon (GB); Jens Nagel, Daxweiler (DE); Nicole Schmidt, Wuppertal (DE); Andrea Rotgeri, Berlin (DE); Ina Groeticke, Berlin (DE); Alexandra Rausch, Berlin (DE); Juergen Klar, Wuppertal (DE); Thomas Dyrks, Berlin (DE)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 18/297,134

(22) Filed: Apr. 7, 2023

(65) Prior Publication Data

US 2023/0271931 A1  Aug. 31, 2023

Related U.S. Application Data

(63) Continuation of application No. 16/472,118, filed as application No. PCT/EP2017/083290 on Dec. 18, 2017, now Pat. No. 11,905,270.

(30) Foreign Application Priority Data

Dec. 23, 2016 (EP) ..................... 16206750

(51) Int. Cl.
| | |
|---|---|
| *A61K 31/381* | (2006.01) |
| *A61K 31/415* | (2006.01) |
| *A61K 31/4155* | (2006.01) |
| *A61K 31/416* | (2006.01) |
| *A61K 31/4164* | (2006.01) |
| *A61K 31/426* | (2006.01) |
| *A61K 31/4365* | (2006.01) |
| *A61K 31/4418* | (2006.01) |
| *A61K 31/4439* | (2006.01) |
| *A61K 31/4965* | (2006.01) |
| *A61P 3/04* | (2006.01) |
| *A61P 3/10* | (2006.01) |
| *A61P 13/10* | (2006.01) |
| *A61P 19/02* | (2006.01) |
| *A61P 25/02* | (2006.01) |
| *A61P 29/00* | (2006.01) |
| *A61P 35/00* | (2006.01) |
| *C07D 213/56* | (2006.01) |
| *C07D 231/12* | (2006.01) |
| *C07D 231/56* | (2006.01) |
| *C07D 233/64* | (2006.01) |
| *C07D 241/12* | (2006.01) |
| *C07D 277/56* | (2006.01) |
| *C07D 333/28* | (2006.01) |

(Continued)

(52) U.S. Cl.
CPC .......... *A61K 31/381* (2013.01); *A61K 31/415* (2013.01); *A61K 31/4155* (2013.01); *A61K 31/416* (2013.01); *A61K 31/4164* (2013.01); *A61K 31/426* (2013.01); *A61K 31/4365* (2013.01); *A61K 31/4418* (2013.01); *A61K 31/4439* (2013.01); *A61K 31/4965* (2013.01); *A61P 3/04* (2018.01); *A61P 3/10* (2018.01); *A61P 13/10* (2018.01); *A61P 19/02* (2018.01); *A61P 25/02* (2018.01); *A61P 29/00* (2018.01); *A61P 35/00* (2018.01); *C07D 213/56* (2013.01); *C07D 231/12* (2013.01); *C07D 231/56* (2013.01); *C07D 233/64* (2013.01); *C07D 241/12* (2013.01); *C07D 277/56* (2013.01); *C07D 333/28* (2013.01); *C07D 333/38* (2013.01); *C07D 333/58* (2013.01); *C07D 405/04* (2013.01); *C07D 495/04* (2013.01)

(58) Field of Classification Search
None
See application file for complete search history.

(56) References Cited

U.S. PATENT DOCUMENTS 11,905,270 B2 * 2/2024 Baeurle ..................... A61P 3/04

FOREIGN PATENT DOCUMENTS

| CL | 2018002759 A1 | 2/2019 |
|---|---|---|
| CL | 2019001740 A1 | 12/2019 |

(Continued)

OTHER PUBLICATIONS

Leeb-Lundberg, L.M., et al., "International Union of Pharmacology. XLV. Classification of the Kinin Receptor Family: from Molecular Mechanisms to Pathophysiological Consequences," Pharmacological Reviews, (2005), vol. 57: 27-77.

(Continued)

*Primary Examiner* — Brian J Davis
(74) *Attorney, Agent, or Firm* — James Dilmore

(57) ABSTRACT

The present invention relates to carboxylic acid aromatic amides compounds of general formula (I) as described and defined herein, to pharmaceutical compositions and combinations comprising said compounds and to the use of said compounds for manufacturing a pharmaceutical composition for the treatment or prophylaxis of a diseases a sole agent or in combination with other active ingredients.

3 Claims, 12 Drawing Sheets

Figure 1:
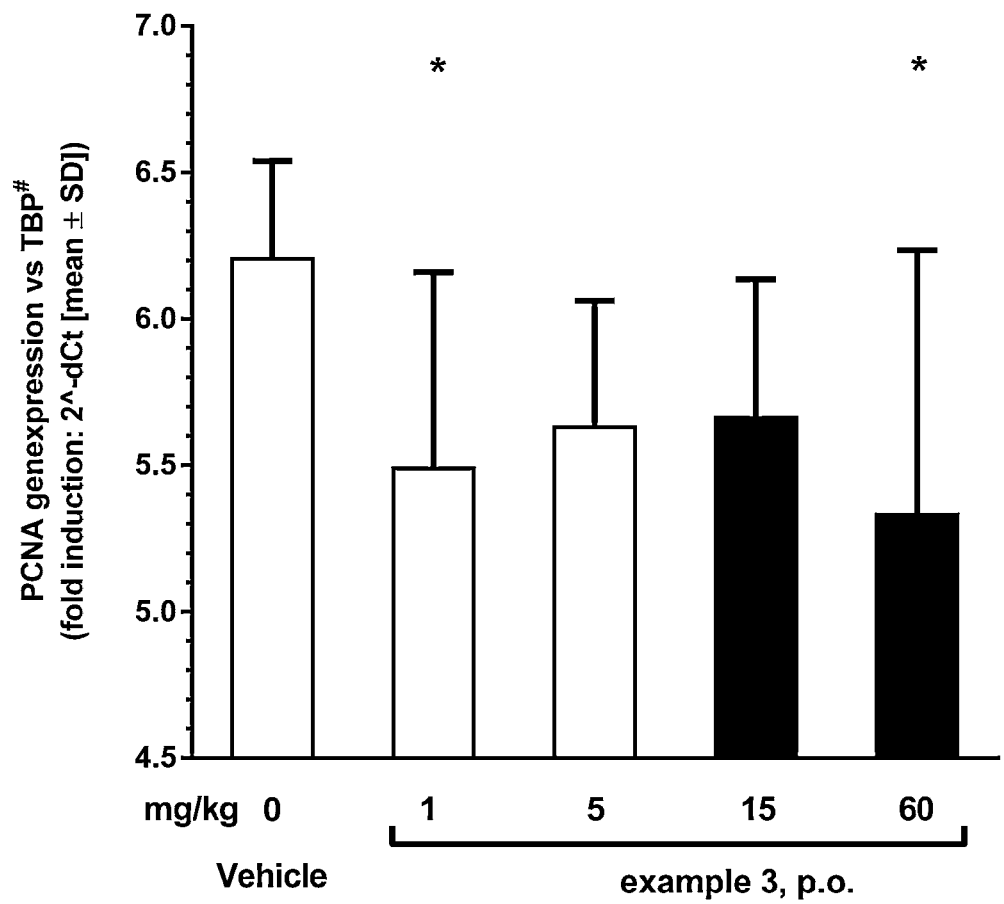

(51) Int. Cl.
  *C07D 333/38* (2006.01)
  *C07D 333/58* (2006.01)
  *C07D 405/04* (2006.01)
  *C07D 495/04* (2006.01)

(56) References Cited

FOREIGN PATENT DOCUMENTS

| DE | 19624155 A | 1/1998 |
|---|---|---|
| WO | 2003065789 A2 | 8/2003 |
| WO | 2007087006 A2 | 8/2007 |
| WO | 2009036996 A2 | 3/2009 |
| WO | 2012/059776 A1 | 5/2012 |
| WO | 2012/103583 A1 | 8/2012 |
| WO | 2012112363 A1 | 8/2012 |
| WO | 2012112567 A1 | 8/2012 |
| WO | 2017172596 A1 | 10/2017 |
| WO | 2018115466 A1 | 6/2018 |

OTHER PUBLICATIONS

GOUGAT Jean, et al., "SSR240612 [(2R)-2-[((3R)-3-(1,3-Benzodioxol-5-yl)-3-{[(6-methoxy-2-naphthyl)sulfonyl]amino} propanoyl)amino]-3-(4-{[2R.6S)-2,6-dimethylpiperidinyl]methyl}phenyl)-N-isopropyl-N-methylpropanamide Hydrochloride], a New Nonpeptide Antagonist of the Bradykinin B1 Receptor: Biochemical and Pharmacological Characterization," Journal of Pharmacology and Experimental Therapeutics, (2004), vol. 309, No. 2: 661-669.
Dias, JP, et al., "The kinin B1 receptor antagonist SSR240612 reverses tactile and cold allodynia in an experimental fat model of insulin resistance," British Journal of Pharmacology, (2007), vol. 152: 280-287.
Schuelert, N. et al., "The bradykinin B1 receptor antagonist BI113823 reverses inflammatory hyperalgesia by desensitization of peripheral and spinal neurons," European Journal of Pain, (2015), vol. 19: 132-142.
Phagoo, Stephen B., et al., "Autoregulation of Bradykinin Receptors: Agonists in the Presence of Interleukin-1β Shift the Repertoire of Receptor Subtypes from B2 to B1 in Human Lung Fibroblasts," Molecular Pharmacology, (1999), vol. 56: 325-333.
Westermann, Dirk, et al., "Gene Deletion of the Kinin Receptor B1 Attenuates Cardiac Inflammation and Fibrosis During the Development of Experimental Diabetic Cardiomyopathy," Diabetes, (2009), vol. 58: 1373-1381.
Walsh, David A., et al., "Tachykinis and the Cardiovascular System," Current Drug Targets, (2006), vol. 7: 1031-1042.
Farkas, Sandor, et al., "The therapeutic potential of bradykinin B1 inhibitors in chronic pain," Drugs of the Future, (2011), pp. 1-37.
Fincham, Christopher I., et al., "Bradykinin receptor antagonists—a review of the patent literature 2005-2008," Expert Opinion on Therapeutic Patents, (2009), vol. 19, No. 7: 919-941.
Menke, John G., et al., "Expression Cloning of a Human B1 Bradykinin Receptor," Journal of Biological Chemistry, (1994), vol. 269, No. 34: 21583-21586.
Marceau, Francois, "A possible common pharmacophore in the non-peptide antagonists of the bradykinin B1 receptor," Trends in Pharmacological Sciences, (2005), vol. 26, No. 3: 116-118.
Marceau, Francois, et al., "Bradykinin Receptor Ligands: Therapeutic Perspectives," Nature Reviews: Drug Discovery, (2004), vol. 3: 845-852.
Chen, Jian Jeffrey, et al., "Targeting the bradykinin B1 receptor to reduce pain," Expert Opinion on Therapeutic Targets, (2007), vol. 11, No. 1: 21-35.
Prado, Gregory N., et al., "Mechanisms Regulating the Expression, Self-Maintenance, and Signaling-Function of the Bradykinin B2 and B1 Receptors," Journal of Cellular Physiology, (2002), vol. 193: 275-286.

Eisenbarth, et al., "Sensitization to bradykinin B1 and B2 receptor activation in UV-B irradiated human skin," Pain, (2004), vol. 110: 197-204.
Campos, et al., "Non-peptide antagonists for kinin B1 receptors: new insights into their therapeutic potential for the management of inflammation and pain," TRENDS in Pharmacological Sciences, (2006), vol. 27, No. 12: 646-651.
Wang, et al., "Deletion of bradykinin B1 receptor reduces renal fibrosis," International Immunopharmacology, (2009), vol. 9: 653-657.
Passos, et al., "The Bradykinin B1 Receptor Regulates Aβ Deposition and Neuroinflammation in Tg-SwDI Mice," The American Journal of Pathology, (2013), vol. 182, No. 5: 1740-1749.
Gobeil Jr., et al., "Preclinical pharmacology, metabolic stability, pharmacokinetics and toxicology of the peptidic kinin B1 receptor antagonist R-954," Peptides, (2014), vol. 52: 82-89.
Huart, et al., "Kinin B1 receptor antagonism is equally efficient as angiotensin receptor 1 antagonism in reducing renal fibrosis in experimental obstructive nephropathy, but is not additive," Frontiers in Pharmacology, (2015), vol. 6, No. 8: 1-8.
Ferreira, et al., "Evidence for the participation of kinins in Freund's adjuvant-induced inflammatory and nociceptive responses in kinin B1 and B2 receptor knockout mice," Neuropharmacology, (2001), vol. 41: 1006-1012.
Ferreira, et al., "Reduced Nerve Injury-Induced Neuropathic Pain in Kinin B1 Receptor Knock-Out Mice," Journal of Neuroscience, (2005), vol. 25, No. 9: 2405-2412.
Fox, et al., "Antihyperalgesic activity of a novel nonpeptide bradykinin B1 receptor antagonist in transgenic mice expressing the human B1 receptor," British Journal of Pharmacology, (2005), vol. 144: 889-899.
Breivik, et al., "Survey of chronic pain in Europe: Prevalence, impact on daily life, and treatment," European Journal of Pain, (2006), vol. 10: 287-333.
Gao, et al., "Economic burden of endometriosis," Fertility and Sterility, (2006), vol. 86, No. 6: 1561-1572.
Simoens, et al., "The burden of endometriosis: costs and quality of life of women with endometriosis and treated in referral centres," Human Reproduction, (2012), vol. 27, No. 5: 1292-1299.
De Graaff, et al., "The significant effect of endometriosis on physical, mental and social wellbeing: results from an International cross-sectional survey," Human Reproduction, (2013), vol. 28, No. 10: 2677-2685.
Stratton, et al., "Chronic pelvic pain and endometriosis: translational evidence of the relationship and Implications," Human Reproduction Update, (2011), vol. 17, No. 3: 327-346.
Laux-Biehlmann, et al., "Menstruation pulls the trigger for inflammation and pain in endometriosis," Trends in Pharmacological Sciences, (2015), vol. 36, No. 5: 270-276.
Yoshino, et al., "The expression and the role of bradykinin (BK) receptor in endometriosis," Abstracts/Journal of Reproductive Immunology, (2015), vol. 112: 121-140.
Jingwei, et al., "Effect of Bushenwenyanghuayu decoction on nerve growth factor and bradykinin/bradykinin B1 receptor in a endometriosis dysmenorrhea mouse model," Journal of Traditional Chinese Medicine, (2015), vol. 35, No. 2: 184-191.
Kaufman, et al., "Nociceptive tolerance is improved by bradykinin receptor B1 antagonism and joint morphology is protected by both endothelin type A and bradykinin receptor B1 antagonism in a surgical model of osteoarthritis," Arthritis Research & Therapy, (2011), vol. 13, No. R76: 1-11.
Cassim, et al., "Kallikreins, kininogens and kinin receptors on circulating and synovial fluid neutrophils: role in kinin generation in rheumatoid arthritis," Rheumatology, (2009), vol. 48: 490-496.
Silva, et al., "The role of kinin B1 receptor and the effect of angiotensin I-converting enzyme inhibition on acute gout attacks in rodents," Ann Rheum Dis, (2016), vol. 75: 260-268.
Moyes, et al., "Bradykinin B1 receptor-mediated vasodilation is impaired in myometrial arteries from women with pre-eclampsia," Hypertension in Pregnancy, (2014), vol. 33, No. 2: 177-190.

(56) References Cited

OTHER PUBLICATIONS

Bascands, et al., "Molecular determinants of LPS-induced acute renal inflammation: Implication of the kinin B1 receptor," Biochemical and Biophysical Research Communications, (2009), vol. 386: 407-412.
Bertram, et al., "Expression of kinin receptors on eosinophils: comparison of asthmatic patients and healthy subjects," Journal of Leukocyte Biology, (2009), vol. 85: 544-552.
Dias, et al., "Suppression of Vascular Inflammation by Kinin B1 Receptor Antagonism in a Rat Model of Insulin Resistance," Journal of Cardiovascular Pharmacology, (2012), vol. 60, No. 1: 61-69.+.
Dias, et al., "Blockade of kinin B1 receptor reverses plasma fatty acids composition changes and body and tissue fat gain in a rat model of insulin resistance," Diabetes, Obesity and Metabolism, (2012), vol. 14: 244-253.
Parreiras-E-Silva, et al., "The kinin B1 receptor regulates muscle-specific E3 ligases expression and is involved in skeletal muscle mass control," Clinical Science, (2014), vol. 127: 185-194.
Luiz, et al., "Contribution and Interaction of Kinin Receptors and Dynorphin A in a Model of Trigeminal Neuropathic Pain in Mice," Neuroscience, (2015), vol. 300: 189-200.
Hosogi, et al., "Bradykinin is a potent pruritogen in atopic dermatitis: A switch from pain to itch," Pain, (2006), vol. 126: 16-23.
Da Costa, et al., "The role of kinin receptors in cancer and therapeutic opportunities," Cancer Letters, (2014), vol. 345: 27-38.
Lacoste, et al., "Cognitive and cerebrovascular improvements following kinin B1 receptor blockade in Alzheimer's disease mice," Journal of Neuroinflammation, (2013), vol. 10, No. 57: 1-18.
Forner, et al., "Effects of kinin B1 and B2 receptor antagonists on overactive urinary bladder syndrome induced by spinal cord injury in rats," British Journal of Pharmacology, (2012), vol. 167: 1737-1752.
Belichard, et al., "Pharmacological and molecular evidence for kinin B1 receptor expression in urinary bladder of cyclophosphamide-treated rats," British Journal of Pharmacology, (1999), vol. 128: 213-219.
Schremmer-Danninger, et al., "Visualisation of tissue kallikrein, kininogen and kinin receptors in human skin following trauma and in dermal diseases," Biol. Chem., (2004), vol. 385: 1069-1076.
Murugesan, et al., "Kinin B1 Receptor Inhibition With BI113823 Reduces Inflammatory Response, Mitigates Organ Injury, and Improves Survival Among Rats With Severe Sepsis," Journal of Infectious Diseases, (2016), vol. 213: 532-540.
Bozo, et al., "Bradykinin B1 receptor antagonists: a patent update 2009-2012," Expert Opinion on Therapeutic Patents, (2012), vol. 22, No. 12: 1443-1452.
Schaudt, et al., "Novel small molecule bradykinin B1 receptor antagonists. Part 1: Benzamides and semicarbazides," Bioorganic & Medicinal Chemistry Letters, (2010), vol. 20: 1225-1228.
"Isotopic Compositions of the Elements 1997," Pure & Appl. Chem., (1998), vol. 70, No. 1: 217-235.
Perrin, et al., "Secondary Deuterium Isotope Effects on the Acidity of Carboxylic Acids and Phenols," J. Am. Chem. Soc., (2007), vol. 129: 4490-4497.
Perrin, et al., "Stereochemistry of β-Deuterium Isotope Effects on Amine Basicity," J. Am. Chem. Soc., (2005), vol. 127: 9641-9647.
Tayar, et al., "The lipophilicity of deuterium atom. 1s. A comparison of shake-flask and HPLC methods," International Journal of Pharmaceutics, (1984), vol. 19: 271-281.
Mutlib, et al., "The Species-Dependent Metabolism of Efavirenz Produces a Nephrotoxic Glutathione Conjugate in Rats," Toxicology and Applied Pharmacology, (2000), vol. 169: 102-113.
Sharma, et al., "Nevirapine Bioactivation and Covalent Binding in the Skin," Chemical Research in Toxicology, (2013), vol. 26: 410-421.
Wenthur, et al., "Discovery of (R)-(2-Fluoro-4-((-4-methoxyphenyl)ethynyl)phenyl)(3-Hydroxypiperidin-1-yl)methanone (ML337), An mGlu3 Selective and CNS Penetrant Negative Allosteric Modulator (NAM)," Journal of Medicinal Chemistry, (2013), vol. 56: 5208-5212.
Schneider, et al., "Enhanced Plasma Concentration by Selective Deuteration of Rofecoxib in Rats," Arzneim.-Forsch./Drug Res., (2006), vol. 56, No. 4: 295-300.
Maltais, et al., "In Vitro and In Vivo Isotope Effects with Hepatitis C Protease Inhibitors: Enhanced Plasma Exposure of Deuterated Telaprevir versus Telaprevir in Rats," Journal of Medicinal Chemistry, (2009), vol. 52: 7993-8001.
"Rules for the Nomenclature of Organic Chemistry," Pure & Appl. Chem., (1976), vol. 45: 11-30.
Berge, et al., "Pharmaceutical Salts," Journal of Pharmaceutical Sciences, (1977), vol. 66, No. 1: 1-19.
Wu-Wong, et al., "Endothelin Receptor Antagonists: Effect of Serum Albumin on Potency and Comparison of Pharmacological Characteristics," Journal of Pharmacology and Experimental Therapeutics, (1997), vol. 281, No. 2: 791-798.
Yoshiyama, et al., "Role of spinal α1-adrenoceptor subtypes in the bladder reflex in anesthetized rats," Am. J. Physiol. Regulatory Integrative Comp. Physiol., (2001), vol. 280: R1414-R1419.
International Search Report for PCT/EP2017/083290, mailed on Feb. 22, 2018.

* cited by examiner

*p<0.05 ANOVA for example 3 followed by Dunnett's vs vehicle, 1 outlier removed (Grubb's test)
TBP: TATA-Binding Protein (reference signal)

*p<0.05, **p<0.01 ANOVA for example 3 & vehicle
followed by Dunnett's vs vehicle, 1 outlier removed (Grubb's test)

+p<0.05 t-test for 60 mg/kg example 3 & vehicle
4 outliers removed (Grubb's test) --> 0/1/5/60 mg/kg group

*p<0.05, **p<0,01 ANOVA followed by Dunnett's posthoc test.
5 outliers removed according Grubb's test ++p<0.01 ANOVA for 60 mg/kg example 3 vs vehicle in t-test,
3 outliers removed (GRUBB's test), ANOVA n.s.

*p<0.05, p<0.01, *p<0.005 ANOVA for example 3 vs vehicle followed by Dunnett's vs vehicle, 3 outliers removed (Grubb's test)

CARBOXYLIC ACID AROMATIC AMIDES AS ANTAGONISTS OF BRADYKININ B1 RECEPTOR

CROSS-REFERENCE TO RELATED APPLICATIONS

This application is a continuation of U.S. application Ser. No. 16/472,118, filed 20 Jun. 2019, which is a National Stage entry of International Application No. PCT/EP2017/083290, filed 18 Dec. 2017, which claims priority to European Patent Application No. 16206750.8, filed 23 Dec. 2016. The disclosures of the priority applications are incorporated in their entireties by reference herein.

The present invention relates to carboxylic acid aromatic amides of general formula (I) as described and defined herein, to pharmacological compositions and combinations comprising said compounds and to the use of said compounds for manufacturing a pharmaceutical composition for the treatment or prophylaxis of a disease or disorder and for the treatment of pains, which are associated with such diseases, in particular of Bradykinin B1 receptor associated disorders which are related to inflammation or at least partially driven by neurogenic events like diseases related to chronic pain or frequent pain conditions like but not restricted to osteoarthritis, rheumatoid arthritis, gout, inflammatory bowel disease, and endometriosis and diseases related to Bradykinin B1 receptor activation and/or up-regulation in affected tissue like but not restricted to asthma, fibrosis in various tissues or diabetes as a sole agent or in combination with other active ingredients.

BACKGROUND OF THE INVENTION

The present invention relates to chemical compounds that antagonize the effects of human Bradykinin B1 receptor (Gene Name BDKRB1, Gene ID 623).

The Bradykinin B1 receptor is a membrane-bound G-protein coupled receptor, which is linked to a second messenger system that triggers increase of intracellular calcium concentrations. The main signalling pathway is linked to Gq protein and phospholipase C (Leeb-Lundberg, L. M. et al. (2005), Pharmacol Rev 57(1): 27-77). Activation of Bradykinin B1 receptor has been shown to be pro-algesic, pro-fibrotic, and proinflammatory while Bradykinin B1 receptor antagonists had clear anti-inflammatory and analgesic effects in various animal models (Gougat, J. B. et al. (2004), J Pharmacol Exp Ther 309(2): 661-669; Dias, J. P. et al. (2007), Br J Pharmacol 152(2): 280-287; Schuelert, N. et al. (2015), Eur J Pain 19(1): 132-142). As consequence of Bradykinin B1 receptor activity increased gene expression and protein levels of proinflammatory cytokines like e.g. Il-6 and Il-8 that attract and activate inflammatory leucocytes, increase of PGE2 (Prostaglandin 2) levels and therefore activation of the inflammation related prostaglandin pathway, phosphorylation and upregulation of TRPV1 (Transient Receptor Potential Vanilloid 1) receptors which are important mediators of pain transduction and induction of neurogenic inflammation (neuropeptide release in inflamed tissue) were observed (Phagoo, S. B. et al. (1999). Mol Pharmacol 56(2): 325-333; Westermann, D. et al. (2009), Diabetes 58(6): 1373-1381; Walsh, D. A. et al. (2006), Curr Drug Targets 7(8): 1031-1042; Farkas S. et al. (2011), Drugs of the Future 36(4): 301-319). Bradykinin B1 receptor agonists are endogenously produced by the activated kallikrein-kinin system. This system consists of circulating kininogens, the ubiquitous expressed proteolytic enzymes kallikreins which are activated by tissue damage, and kinins which are formed by activated kallikreins out of kininogens (Review Fincham, C. I. et al. (2009), Expert Opin Ther Pat 19(7): 919-941). These kinins (e.g. bradykinin, kalidin, des-Arg9-bradykinin, des-Arg10-kalidin) are proinflammatory peptides that mediate vascular and pain responses to tissue injury, with functions in cardiovascular homeostasis, contraction or relaxation of smooth muscle, inflammation and nociception. They exert most of their effects by interacting with two classes of G-protein-coupled receptors called Bradykinin receptor 1 and 2. The classification of the kinin receptors was originally achieved by means of pharmacological studies originally carried out at the end of the 1970s. During the 1990s, the existence of Bradykinin B1 receptor and B2 receptors was further confirmed through cloning and genetic deletion studies (Menke, J. G. et al. (1994), J Biol Chem 269(34): 21583-21586). The past 30 years of research on the kinin system has indicated that both Bradykinin B1 receptor and B2 receptor are involved in pain and inflammation (Leeb-Lundberg, L. M. et al. (2005), Pharmacol Rev 57(1): 27-77; Marceau, F. (2005), Trends Pharmacol Sci 26(3): 116-118; Marceau, F. (2004), Nat Rev Drug Discov 3(10): 845-852; Chen, J. J. et al. (2007), Expert Opin Ther Targets 11(1): 21-35).

It has been demonstrated that the B2 receptor is widely expressed in a constitutive manner throughout most mammalian tissues. In contrast, the Bradykinin B1 receptor is not constitutively expressed to a great extent under normal conditions, but is up-regulated under various inflammatory conditions such as asthma, arthritis and osteoarthritis, sepsis and type-1 diabetes, as well as by some neuropathological diseases such as epilepsy, stroke and multiple sclerosis. Bradykinin B1 receptor up-regulation can be induced for example by Il-1beta (Phagoo, S. B. et al. (1999), Mol Pharmacol 56(2): 325-333) and Bradykinin B2 receptor activation (NF-kB activation leading to IL1b expression in fibroblasts) (Leeb-Lundberg, L. M. et al. (2005), Pharmacol Rev 57(1): 27-77).

Once upregulated, the Bradykinin B1 receptor is expressed on neurons, macrophages, neutrophils, fibroblasts, smooth muscle cells and the vascular endothelium (Fincham, C. I. et al. (2009), Expert Opin Ther Pat 19(7): 919-941). Recent findings suggest that the Bradykinin B1 receptor expressed in the peripheral and in the central nervous system is involved in processing of inflammatory pain (Schuelert, N. et al. (2015). Eur J Pain 19(1): 132-142).

In contrast to Bradykinin B2 receptor and many other GPCRs (G protein-coupled receptors), the Bradykinin B1 receptor does not show agonist induced internalization or relevant desensitization (Prado, G. N. et al. (2002), J Cell Physiol 193(3): 275-286; Eisenbarth, H. et al. (2004), Pain 110(1-2): 197-204). Activation of Bradykinin B1 receptor triggers auto-induction of the receptor. This might lead to an augmentation of the inflammatory or pain-inducing processes.

Therefore, Bradykinin B1 receptor has been suggested to have a pivotal role including but not limited to several chronic diseases involving diabetes, fibrosis, inflammation, neuroinflammation, neurodegeneration, inflammatory pain, and neuropathic pain (Campos, M. M. et al. (2006), Trends Pharmacol Sci 27(12): 646-651; Wang, P. H. et al. (2009), Int Immunopharmacol 9(6): 653-657; Passos, G. F. et al. (2013), Am J Pathol 182(5): 1740-1749; Gobeil, F. et al. (2014), Peptides 52: 82-89; Huart, A. (2015), Front Pharmacol 6: 8). The contribution of Bradykinin B1 receptor activation in inflammation and pain processes is supported by the demonstration that Bradykinin B1 receptor knockout mice have a largely decreased response to nociceptive and proinflammatory stimuli (Ferreira, J. et al. (2001), Neuropharmacology 41(8): 1006-1012; Ferreira, J. et al. (2005), J Neurosci 25(9): 2405-2412.). The therapeutic impact of Bradykinin B1 receptor blockage for inflammation related diseases is supported further by the pharmacological properties of Bradykinin B1 receptor antagonists shown in many inflammatory and neuropathic pain models (Gougat, J. B. et al. (2004), J Pharmacol Exp Ther 309(2): 661-669; Fox, A. et al. (2005), Br J Pharmacol 144(7): 889-899).

The fact that Bradykinin B1 receptor expression is induced under disease conditions clearly raises the possibility that therapeutic use of Bradykinin B1 receptor antagonists should be devoid of undesired adverse effects. This property supports the suitability of Bradykinin B1 receptor antagonists for treatment of benign diseases like endometriosis due the expected positive risk benefit ratio. The patient populations for nociceptive pain and neuropathic pain are large, and are driven by separate disease trends that necessitate pain relief. Chronic pain of moderate to severe intensity occurs in 19% of adult Europeans, seriously affecting the quality of their social and working lives (Breivik et al., Eur J Pain. 2006 May; 10(4):287-333.). Unfortunately, current treatments for pain are only partially effective, and many cause life-style altering, debilitating, and/or dangerous side effects. For example, non-steroidal anti-inflammatory drugs (NSAIDS) such as aspirin, ibuprofen, and indomethacin are moderately effective against inflammatory pain but they are also renally toxic, and high doses tend to cause gastrointestinal irritation, ulceration, bleeding, confusion and increased cardiovascular risk. Notably, Vioxx was withdrawn from the market in 2004 due to a risk of myocardial infarction and stroke. Patients treated with opioids frequently experience confusion and constipation, and long-term opioid use is associated with tolerance and addiction. Local anaesthetics such as lidocaine and mexiletine simultaneously inhibit pain and cause loss of normal sensation. In addition, when used systemically, local anaesthetics are associated with adverse cardiovascular effects. Thus, there is currently an unmet need in the treatment of chronic pain in general.

Especially in gynaecological therapy field, endometriosis is the diseases associated with chronic pelvic pain severely affecting quality of life of the patients. Globally, approximately 11% of women aged 15-49 years are affected by endometriosis and additional 6% of women suffer from symptoms suggestive for endometriosis. Main symptoms of endometriosis are chronic or frequent pelvic pain, dyspareunia, dyschezia, dysuria and sub- or infertility. These symptoms severely impair quality of life of patients. Diagnosis of the disease involves a complete medical history, a physical examination and a laparoscopy. As an ultimate confirmation of endometriosis can only be made invasively and symptoms are often unspecific, the mean time from initial symptoms to diagnosis of endometriosis is about 7-10 years. Therefore, endometriosis is under-diagnosed and the number of affected women might be much higher than anticipated. Recently published EndoCost study demonstrated that cost of productivity loss of €6,298 per woman were double the healthcare cost of €3,113 per women, driven mainly by surgery and monitoring visit (Gao, X. et al. (2006), Fertil Steril 86(6): 1561-1572; Simoens S, et al. Hum Reprod (2012), 27(5):1292-9; De Graaff A, et al. (2013), Hum Reprod; 28(10): 2677-85).

Endometriosis is characterized by growth of endometrial tissue outside of the uterine cavity forming benign tumours (lesions) in the affected part of the body. Depending on lesion location and innervation severity of pain symptoms is observed. Up-regulation of various inflammation markers observed in the affected tissue and in the peritoneal tissue underline the inflammatory character of the disease (Stratton, P. et al. (2011), Hum Reprod Update 17(3): 327-346; Gao, X. et al. (2006), Fertil Steril 86(6): 1561-1572; Laux-Biehlmann et al. (2015), Trends Pharmacol Sci 36(5): 270-276).

The Bradykinin B1 receptor was identified in endometriosis lesion by immune-histological-chemical (IHC) staining (Yoshino et al. Journal of Reproductive Immunology 112 (2015) 121-140; www.proteinatlas.org) and analysis of mRNA expression of Bradykinin B1 receptor in affected tissue shows a positive correlation to pain severity reported by endometriosis patients. Data describing a role of Bradykinin B1 receptors in affecting the outcome of an endometriosis mouse model (Jingwei, C. et al. (2015), J Tradit Chin Med 35(2): 184-191) further support the concept to treat endometriosis with Bradykinin B1 receptor antagonists.

Suspected endometriosis is initially treated with non-steroidal anti-inflammatory drugs (NSAID) or combined oral contraceptives (COC) which are used off label. This procedure delays endometriosis diagnosis. Laparoscopy is the gold standard for endometriosis diagnosis which is performed when the initial treatment options fail. During laparoscopy, endometriotic lesions are ablated. However, this procedure is accompanied by a high recurrence rate. Approximately, 70% of treated patients have persistent symptoms that are not managed. Currently, there is no long-term medication available in COC/P (Combined Oral Contraceptives/Progestin) non-responder endometriosis patients in which COCs and progestins failed. Treatment with Gonadotropin Releasing Hormone (GnRH) agonists, which are used as second line therapy (without proof of being superior versus first line) are only approved for short-term treatment (6 months). After GnRH agonist application, systemic estradiol levels are suppressed up to 90% leading to chemical castration with menopausal side effects like bone mass loss and hot flushes. Therefore, new and long-term treatment options with reduced side-effects and high efficacy for patients with COC/P non-responder endometriosis are urgently needed.

On this background the Bradykinin B1 receptor antagonists are of value for treatment of disorders which are related to inflammation or at least partially driven by neurogenic events like diseases related to chronic pain or frequent pain conditions like but not restricted to osteoarthritis (Kaufman, G. N. et al. (2011), Arthritis Res Ther 13(3): R76), rheumatoid arthritis (Cassim, B. et al. (2009), Rheumatology 48(5): 490-496), gout (Silva, C. R. et al. (2016), Ann Rheum Dis 75(1): 260-268), burn injuries and sunburn (Eisenbarth, H. et al. (2004), Pain 110(1-2): 197-204), inflammatory bowel disease, endometriosis (Yoshino et al. Journal of Reproductive Immunology 112 (2015) 121-140; Laux-Biehlmann et al. (2015), Trends Pharmacol Sci 36(5): 270-276; Jingwei, C. et al. (2015), J Tradit Chin Med 35(2): 184-191), pre-eclampsia (Moyes, A. J. et al. (2014), Hypertens Pregnancy 33(2): 177-190), diabetic neuropathy (Dias, J. P. et al. (2007), Br J Pharmacol 152(2): 280-287) including neuropathy related to diabetes type 1 and diabetes type 2, cardiac inflammation (Westermann, D. et al. (2009), Diabetes 58(6): 1373-1381), renal inflammation (Bascands, J. et al. (2009), Biochem Biophys Res Commun 386(2): 407-412), pancreatitis and diseases related to Bradykinin B1 receptor activation and/or up-regulation in affected tissue like but not restricted to asthma and cough (Bertram, C. M. et al. (2009), J Leukoc Biol 85(3): 544-552), atherosclerosis, diabetes (Dias, J. P. et al. (2012), J Cardiovasc Pharmacol 60(1): 61-69), adipositas including metabolic syndrome (Dias, J. P. et al. (2012), Diabetes Obes Metab 14(3): 244-253), diseases related to muscle atrophy including cachexia (Parreiras, E. S. L. T. et al. (2014), Clin Sci 127(3): 185-194) not limited to cancer cachexia, neuropathic pain (Luiz, A. P. et al. (2015), Neuroscience 300: 189-200), pruritus or itch (Hosogi, M. et al. (2006), Pain 126(1-3): 16-23), cancer (da Costa, P. L. et al. (2014), Cancer Lett 345(1): 27-38), neurodegenerative diseases such as amyotrophic lateral sclerosis (ALS) or Alzheimer's disease (Lacoste, et al. (2013) J Neuroinflammation 10: 57), fibrosis in cardiacs (Westermann, D. et al. (2009), Diabetes 58(6): 1373-1381), fibrosis in renal (Huart, A. et al. (2015), Front Pharmacol 6: 8) and fibrosis in lung tissues, overactive urinary bladder syndrome and cystitis (Forner, S. et al. (2012), Br J Pharmacol 167(8): 1737-1752 and Belichard, P. et at (1999), Br J Pharmacol 128(1):213-219), impaired or painful wound heating (Schremmer-Danninger, E. et al. (2004), Biol Chem 385 (11): 1069-1076) and sepsis (Murugesan, P et al. (2016), J Infect Dis 213(4): 532-540).

Several new Bradykinin B1 receptor antagonists are known from prior art (Expert Opinion on Therapeutic Patents (2012), 22:12, 1443-1452). Various approaches for finding new Bradykinin B1 receptor antagonists are described, in particular peptidic structures and small molecules. Especially, arylsulfonamides and so-called cyclopropyl-carboxamides as the two main types of small molecules were investigated during the last decade.

WO2003/065789 (Merck) disclose bradykinin B1 receptor antagonists or inverse agonists of the following general formula

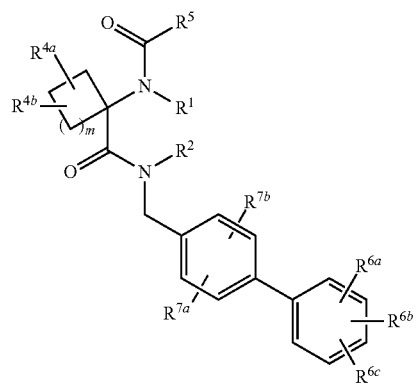

which are useful in the treatment or prevention of symptoms such as pain and inflammation associated with the bradykinin B1 pathway.

Merck was developing the bradykinin B1 receptor antagonist MK-0686 (structure shown below)

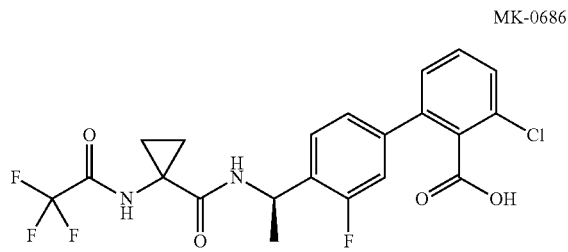 [SMILES: C[C@@H](NC(=O)C1(NC(=O)C(F)(F)F)CC1)c1ccc(-c2cccc(Cl)c2C(=O)O)cc1F]

MK-0686 for the potential treatment of pain and inflammation. Several phase II trials in subjects with osteoarthritis and with postherpetic neuralgia were initiated. Merck accounted that the compound has a suboptimal pharmacokinetic profile due to metabolic lability.

Jerini A G, now Shire Group, investigated active Bradykinin B1 receptor antagonists, for example (see WO2009/036996)

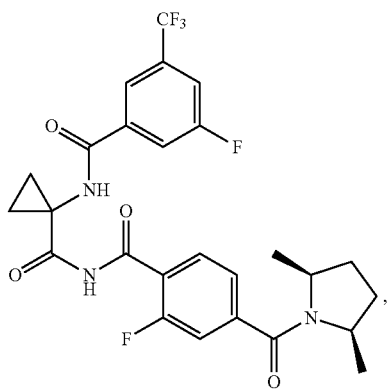 [SMILES: C[C@@H]1CC[C@H](C)N1C(=O)c1ccc(C(=O)NC(=O)C2(NC(=O)c3cc(F)cc(C(F)(F)F)c3)CC2)c(F)c1]

which was reported to have in addition to its activity and acceptable penetration profile reasonable aqueous solubility and pharmacokinetic profile in rat, whereas its human metabolic stability was still poor (Schaudt M, Locardi E, Zischinsky G, et al., Bioorg Med Chem Lett 2010; 20:1225-8). Jerini exchanged the cyclopropyl-carboxamide moiety to a semicarbazide or to a five-membered diamino-heterocyclic ring or even to hydroxyureas without any explanation.

Starting with arylsulfonamide compounds as Bradykinin B1 receptor antagonists, Boehringer Ingelheim reported about several cyclopropyl-carboxamides out of their further development compounds like of the following structure

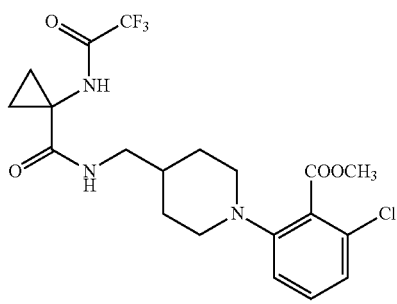 [SMILES: COC(=O)c1c(Cl)cccc1N1CCC(CNC(=O)C2(NC(=O)C(F)(F)F)CC2)CC1]

or related to that emerged with the highest binding affinity measured on human B1R-expressing CHO cells (Expert Opinion on Therapeutic Patents (2012), 22:12, 1443-1452).

In WO2012/059776 Gedeon Richter reported about cyclopropyl-carboxamides of the following formula

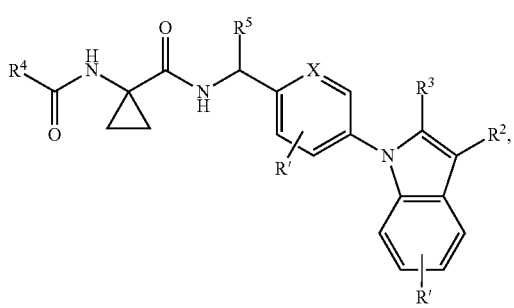

wherein R³ is selected from (1) —COOR; (2) —CN; (3) —CONR<sup>a</sup>R<sup>b</sup>;

(4) 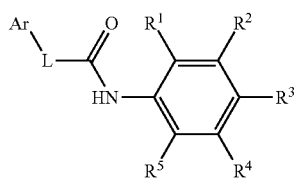

(5)

(6)

(7)

(8)

(9)

(10)

(11)

A majority of the compounds have a $K_i$ value below 20 nM on human recombinant Bradykinin receptors (expressed in CHO cells). Several indolyl compounds are disclosed and represented by the following compound:

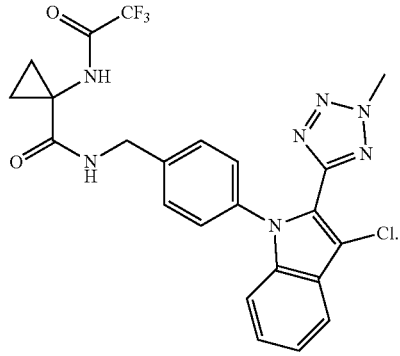 [SMILES: Cn1nnc(-c2c(Cl)c3ccccc3n2-c2ccc(CNC(=O)C3(NC(=O)C(F)(F)F)CC3)cc2)n1]

In WO2012/112567 (Georgetown University) small molecule inhibitors of ATP/GTP binding protein like 2 (AGBL2) of the formula

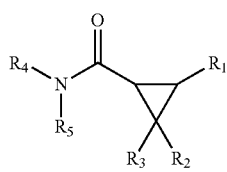

are disclosed wherein Ar is substituted or unsubstituted aryl or substituted or unsubstituted heteroaryl; L is absent or —(CHR⁶)—, wherein R⁶ is substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; and R¹, R², R³, R⁴, and R⁵ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl. The compounds can be used in methods for treating or preventing cancer and neurologic disorders were described Aromatic Amides with carboxylic acid groups and cyclopropyl moiety are not specifically disclosed.

WO2012/103583 (Bionomics) discloses 1,2-cyclopropyl-carboxamide compounds of formula (I)

wherein R⁴ is selected from optionally substituted heteroaryl, optionally substituted heterocyclyl, or optionally substituted aryl, and R⁵ is selected from hydrogen or optionally substituted alkyl. Such compounds are useful in the positive modulation of the alpha 7 nicotinic acetylcholine receptor (alpha7nAChR). The disclosure of WO2012103583 also relates to the use of these compounds in the treatment or prevention of a broad range of diseases in which the positive modulation of alpha7nAChR is advantageous, including neurodegenerative and neuropsychiatric diseases and inflammatory diseases. 1,1-cyclopropyl-carboxamide compounds are not disclosed.

WO2007/087066 (Vertex) discloses novel compounds and pharmaceutically acceptable compositions thereof, which are useful as modulators of ATP-Binding Cassette ("ABC") transporters or fragments thereof, including Cystic Fibrosis Transmembrane Conductance Regulator ("CFTR"), having a benzamide core structure (I)

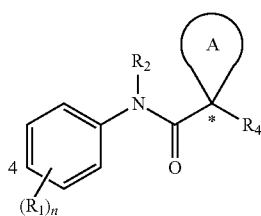

wherein ring A is an optionally substituted cycloaliphatic or an optionally substituted heterocycloaliphatic where the atoms of ring A adjacent to C* are carbon atoms. $R_4$ is an optionally substituted aryl or an optionally substituted heteroaryl. $R^1$ is independently an optionally substituted $C_1$-$C_6$ aliphatic, an optionally substituted aryl, an optionally substituted heteroaryl, an optionally substituted $C_3$-$C_{10}$ membered cycloaliphatic or an optionally substituted 4 to 10 membered heterocycloaliphatic, carboxy, amido, amino, halo, or hydroxy, provided that at least one $R^1$ is an optionally substituted aryl or an optionally substituted heteroaryl and said $R^1$ is attached to the 3- or 4-position of the phenyl ring. The compounds of the present invention are not disclosed.

So, the state of the art described above does not describe the compounds of general formula (I) of the present invention as defined herein or an isomer, enantiomer, diastereomer, racemate, hydrate, solvate, or a salt thereof, or a mixture of same, as described and defined herein, and as hereinafter referred to as "compounds of the present invention", or their pharmacological activity.

SUMMARY OF THE INVENTION

The present invention covers compounds of general formula (I):

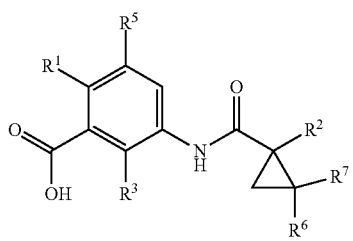

in which
$R^1$ represents
phenyl,
5- or 6-membered heteroaryl, wherein said 5-membered heteroaryl contains 1, 2 or 3 heteroatoms or heteroatom-containing groups independently selected from the group consisting of S, N, NH, and O, and wherein said 6-membered heteroaryl contains 1 or 2 nitrogen atoms, or
bicyclic 8- to 10-membered heteroaryl containing 1, 2 or 3 heteroatoms or heteroatom-containing groups independently selected from NH, N, O, S, SO and $SO_2$,
wherein said $R^1$ is optionally substituted at one or more carbon atoms with 1 to 3 substituents $R^{1a}$ which are the same or different, wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, $NHR^4$, $N(R^4)_2$, $NH(C_3$-$C_7$-cycloalkyl), halogen, CN, $NHSO_2R^4$, $SO_2R^4$, 5- to 7-membered lactam, or 4- to 7-membered heterocycloalkyl containing 1 or 2 heteroatoms or heteroatom-containing groups selected from NH, —$NR^4$, N, O, S, SO and $SO_2$, and
wherein independently, if $R^1$ represents 5-membered heteroaryl or bicyclic 8- to 10-membered heteroaryl, each ring nitrogen atom, if present, of said $R^1$ is optionally substituted with a substituent $R^{1b}$, wherein $R^{1b}$ represents $C_1$-$C_5$-alkyl, —($C_1$-$C_3$-alkyl)-($C_3$-$C_7$-cycloalkyl), $C_3$-$C_7$-cycloalkyl, $SO_2R^4$, or 4- to 7-membered heterocycloalkyl containing 1 or 2 heteroatoms or heteroatom-containing groups selected from NH, —$NR^4$, N, O, S, SO and $SO_2$, and
if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl,
said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl independently are optionally substituted with one or more substituents independently selected from the group consisting of methyl, ethyl, OH, $OR^4$ and F, and
if $R^{1a}$ and/or $R^{1b}$ represent 4- to 7-membered heterocycloalkyl, each carbon atom of said 4- to 7-membered heterocycloalkyl is optionally substituted with one or more substituents independently selected from the group consisting of OH, $OR^4$ and F;
$R^2$ represents
—$(CH_2)_p$—($C_5$-$C_7$-cycloalkyl),
—$(CH_2)_p$-phenyl,
5- or 6-membered heteroaryl wherein said 5-membered heteroaryl contains 1, 2 or 3 heteroatoms or heteroatom-containing groups independently selected from the group consisting of 5, N, NH, and O, and wherein said 6-membered heteroaryl contains 1 or 2 N, or
bicyclic 8- to 10-membered heteroaryl, containing 1, 2 or 3 heteroatoms or heteroatom-containing groups independently selected from NH, N, O, S, SO and $SO_2$,
wherein said $R^2$ is optionally substituted at one or more carbon atoms with 1 to 3 substituents $R^{2a}$ which are the same or different wherein $R^{2a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen, OH or CN, and
wherein independently, if $R^2$ represents 5-membered heteroaryl or bicyclic 8- to 10-membered heteroaryl, each ring nitrogen atom, if present, of said $R^2$ is optionally substituted with a substituent $R^{2b}$ wherein $R^{2b}$ represents of $C_1$-$C_5$-alkyl, $C_3$-$C_7$-cycloalkyl or —($C_1$-$C_3$-alkyl)-($C_3$-$C_7$-cycloalkyl), and if $R^{2a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{2b}$ represents $C_1$-$C_5$-alkyl, $C_3$-$C_7$-cycloalkyl or —($C_1$-$C_3$-alkyl)-($C_3$-$C_7$-cycloalkyl), said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$, and 1 to 5 fluorine atoms;

p 0 or 1;

$R^3$ represents H or F;

$R^4$ represents $C_1$-$C_5$-alkyl, optionally substituted with 1 to 5 fluorine atoms;

$R^5$ represents H, halogen, CN, $C_1$-$C_5$-alkyl, or —$OC_1$-$C_5$-alkyl wherein said $C_1$-$C_5$-alkyl and —$OC_1$-$C_5$-alkyl are optionally substituted with 1 to 5 fluorine atoms; and $R^6$ and $R^7$ represent H or $C_1$-$C_3$-alkyl, wherein said $C_1$-$C_3$-alkyl is optionally substituted with 1 to 5 fluorine atoms;

or an isomer, enantiomer, diastereomer, racemate, hydrate, solvate, or a salt thereof, or a mixture of the same.

The present invention further relates to pharmaceutical compositions and combinations comprising said compounds, to the use of said compounds for manufacturing a medicament for the treatment or prophylaxis of diseases or disorders and for the treatment of pains, which are associated with such diseases as well as for the treatment of inflammation, which are associated with such diseases; Furthermore, the present invention relates to pharmaceutical compositions and combinations comprising said compounds, to the use of said compounds for the treatment or prophylaxis of diseases or disorders and for the treatment of pains, which are associated with such diseases as well as for the treatment of inflammation, which are associated with such diseases.

It has now been found, and this constitutes the basis of the present invention, that said compounds of the present invention have surprising and advantageous properties.

In particular, said compounds of the present invention have surprisingly been found to effectively inhibit Bradykinin B1 receptor. Hence, the invention particularly relates to said compounds for use in the treatment or prophylaxis of following diseases or disorders:

Pain and inflammation, in particular any one of visceral pain e.g. related to pancreatitis, interstitial cystitis, bladder pain syndrome, renal colic, or prostatitis, chronic pelvic pain, or pain related to infiltrating endometriosis;

neuropathic pain such as post herpetic neuralgia, acute zoster pain, pain related to nerve injury, the dynias, including vulvodynia, phantom limb pain, pain related to root avulsions, pain related to radiculopathy, painful traumatic mononeuropathy, painful entrapment neuropathy, pain related to carpal tunnel syndrome, ulnar neuropathy, pain related to tarsal tunnel syndrome, painful diabetic neuropathy, painful polyneuropathy, trigeminal neuralgia, or pain related to familial amyloid polyneuropathy;

central pain syndromes potentially caused by virtually any lesion at any level of the nervous system including but not limited to pain related to stroke, multiple sclerosis, and spinal cord injury; and postsurgical pain syndromes (including postmastectomy pain syndrome, postthoracotomy pain syndrome, stump pain), bone and joint pain (osteoarthritis), spine pain (including acute and chronic low back pain, neck pain, pain related to spinal stenosis), shoulder pain, repetitive motion pain, dental pain, pain related to sore throat, cancer pain, burn pain including sun-burn, myofascial pain (pain related to muscular injury, fibromyalgia) postoperative and perioperative pain (including but not limited to general surgery, orthopaedic, and gynaecological surgery); and acute and chronic pain, chronic pelvic pain, endometriosis associated pain, dysmenorrhea associated pain (primary and secondary), pain associated with uterine fibroids, vulvodynia associated pain, as well as pain associated with angina, or inflammatory pain of varied origins (including but not limited to pain associated with osteoarthritis, rheumatoid arthritis, rheumatic disease, tenosynovitis, gout, ankylosing spondylitis, and bursitis);

and diseases selected from or related to any one of:

gynaecological disorders and/or diseases, or effects and/or symptoms which negatively influence women health including endometriosis, uterine fibroids, pre-eclampsia, hormonal deficiency, spasms of the uterus, or heavy menstrual bleeding;

the respiratory or excretion system including any of inflammatory hyperreactive airways, inflammatory events associated with airways disease like chronic obstructive pulmonary disease, asthma including allergic asthma (atopic or non-atopic) as well as exercise-induced bronchoconstriction, occupational asthma, viral or bacterial exacerbation of asthma, other non-allergic asthmas and wheezy-infant syndrome, chronic obstructive pulmonary disease including emphysema, adult respiratory distress syndrome, bronchitis, pneumonia, cough, lung injury, lung fibrosis, allergic rhinitis (seasonal and perennial), vasomotor rhinitis, angioedema (including hereditary angioedema and drug-induced angioedema including that caused by angiotensin converting enzyme (ACE) or ACE/neutral endopeptidase inhibitors like omepatrilat), pneumoconiosis, including aluminosis, anthracosis, asbestosis, chalicosis, ptilosis, siderosis, silicosis, tabacosis and byssinosis, bowel disease including Crohn's disease and ulcerative colitis, irritable bowel syndrome, pancreatitis, nephritis, cystitis (interstitial cystitis), bladder pain syndrome, kidney fibrosis, kidney failure, hyperactive bladder, and overactive bladder;

dermatology including pruritus, itch, inflammatory skin disorders including psoriasis, eczema, and atopic dermatitis;

affection of the joints or bones including rheumatoid arthritis, gout, osteoporosis, osteoarthritis, and ankylosing spondylitis;

affection of the central and peripheral nervous system including neurodegenerative diseases including Parkinson's and Alzheimer's disease, amyotrophic lateral sclerosis (ALS), epilepsy, dementia, headache including cluster headache, migraine including prophylactic and acute use, stroke, closed head trauma, and multiple sclerosis;

infection including HIV infection, and tuberculosis;

trauma associated with oedema including cerebral oedema, burns, sunburns, and sprains or fracture;

poisoning including aluminosis, anthracosis, asbestosis, chalicosis, ptilosis, siderosis, silicosis, tabacosis, and byssinosis uveitis;

diabetes cluster or metabolism like diabetes type 1, diabetes type 2, diabetic vasculopathy, diabetic neuropathy, diabetic retinopathy, post capillary resistance or diabetic symptoms associated with insulitis (e.g. hyperglycaemia, diuresis, proteinuria and increased nitrite and kallikrein urinary excretion), diabetic macular oedema, metabolic syndrome, insulin resistance, obesity, fat or muscle metabolism;

cachexia associated with or induced by any of cancer, AIDS, coeliac disease, chronic obstructive pulmonary disease, multiple sclerosis, rheumatoid arthritis, congestive heart failure, tuberculosis, familial amyloid polyneuropathy, mercury poisoning (acrodynia), and hormonal deficiency;

cardio-vascular system including congestive heart failure, atherosclerosis, congestive heart failure, myocardial infarct, and heart fibrosis; and other conditions including primary peritonitis, secondary peritonitis, septic shock, sepsis, muscle atrophy, spasms of the gastrointestinal tract, benign prostatic hyperplasia, and liver diseases such as non-alcoholic and alcoholic fatty liver disease, non-alcoholic and alcoholic steatohepatitis, liver fibrosis, or liver cirrhosis.

Additionally, compounds of the present invention reduce the release of inflammation related cytokines like IL-6 and IL-8. Hence, the present invention also relates to a method for reducing inflammation related cytokine production, the method comprising the step of administering an effective amount of a compound of the present invention to a patient in need thereof. The invention also relates to the compounds of the invention as defined herein for use in the treatment of a disease associated with increased release of inflammation related cytokines, preferably associated with increased release of IL-6 and/or IL-8.

FIGURE LEGENDS

Figure 2:
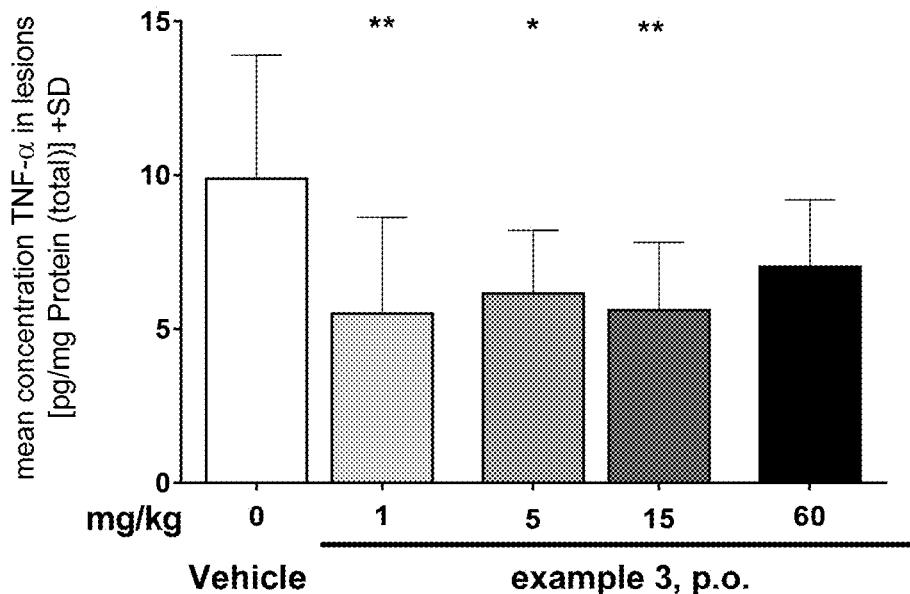
Figure 3:
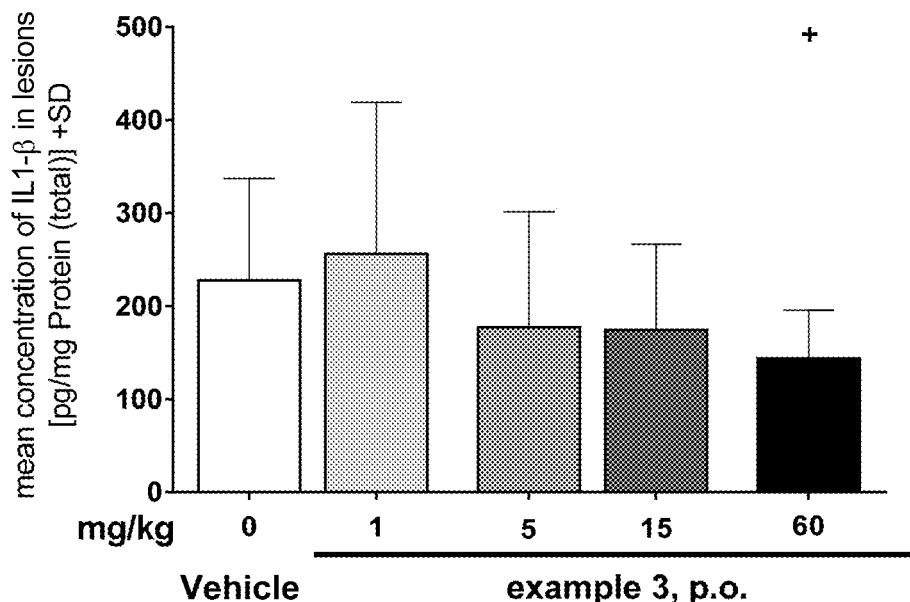
Figure 4:
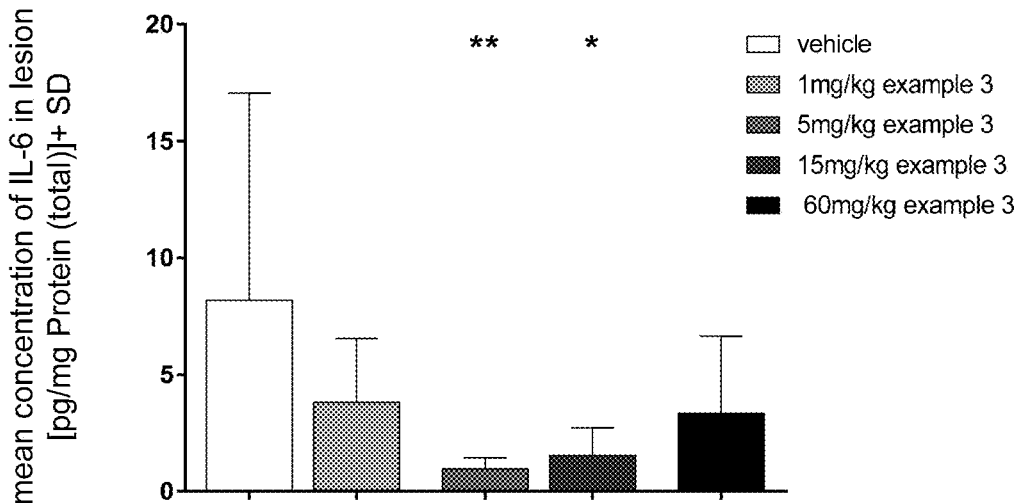

FIG. 1: Effect of Compound Example 3 on PCNA expression in lesions in rat 4 day endometriosis model FIG. 2: Effect of Compound Example 3 on tumor necrosis factor (TNF) alpha in lesions in rat 4 day endometriosis model FIG. 3: Effect of Compound Example 3 on interleukin 1 (IL-1) beta in lesions in rat 4 day endometriosis model FIG. 4: Effect of Compound Example 3 on interleukin 6 (IL-6) in lesions in rat 4 day endometriosis model FIG. 5: Effect of Compound Example 3 on interleukin 1 (IL-1) alpha in lesions in rat 15 day endometriosis model FIG. 6: Effect of Compound Example 3 on interleukin 1 (IL-1) beta in lesions in rat 15 day endometriosis model FIG. 7: Effect of Compound Example 3 on peroxidase signal reflecting neutrophil influx in mouse peritonitis model FIG. 8: Effect of Compound Example 3 on thermal stimulation in STZ model (warm plate)

Figure 9:
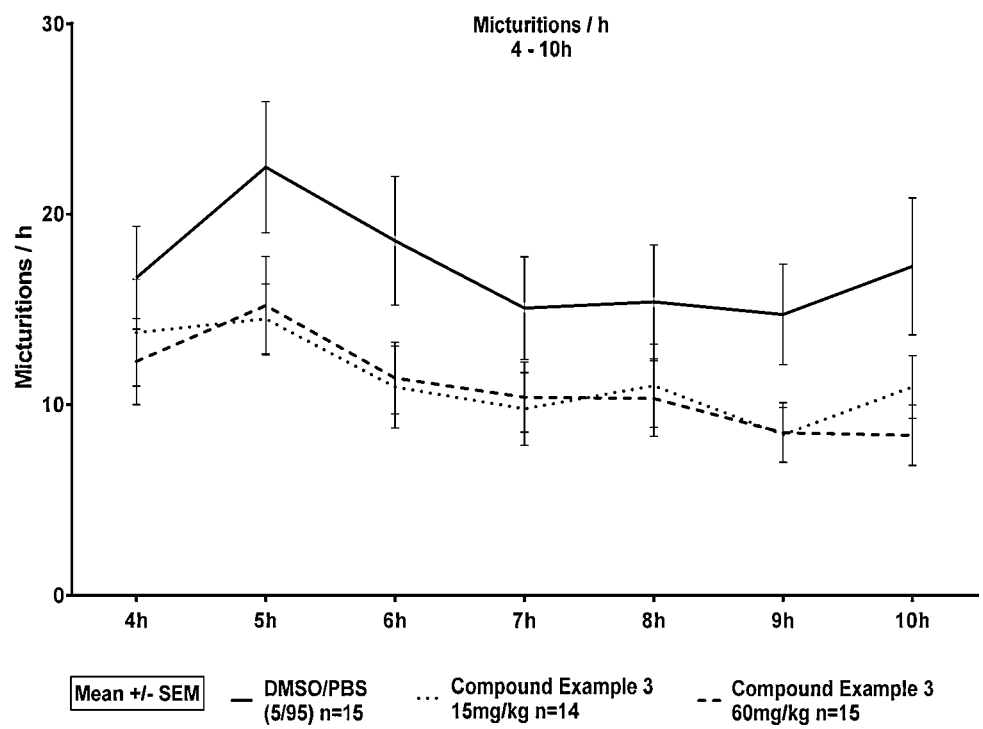
Figure 12:
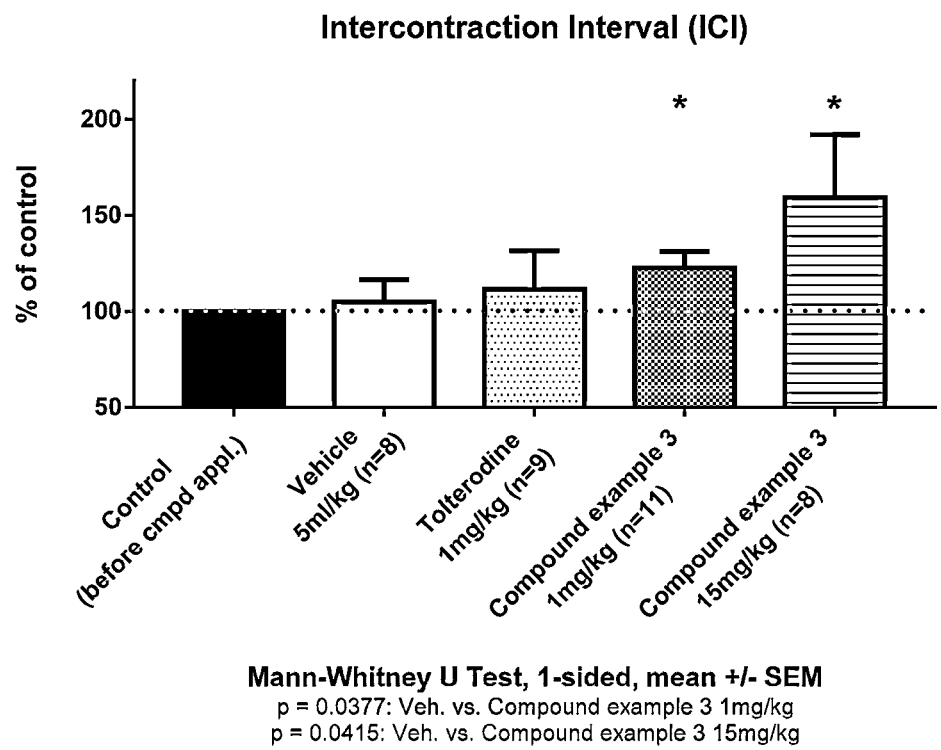
Figure 13:
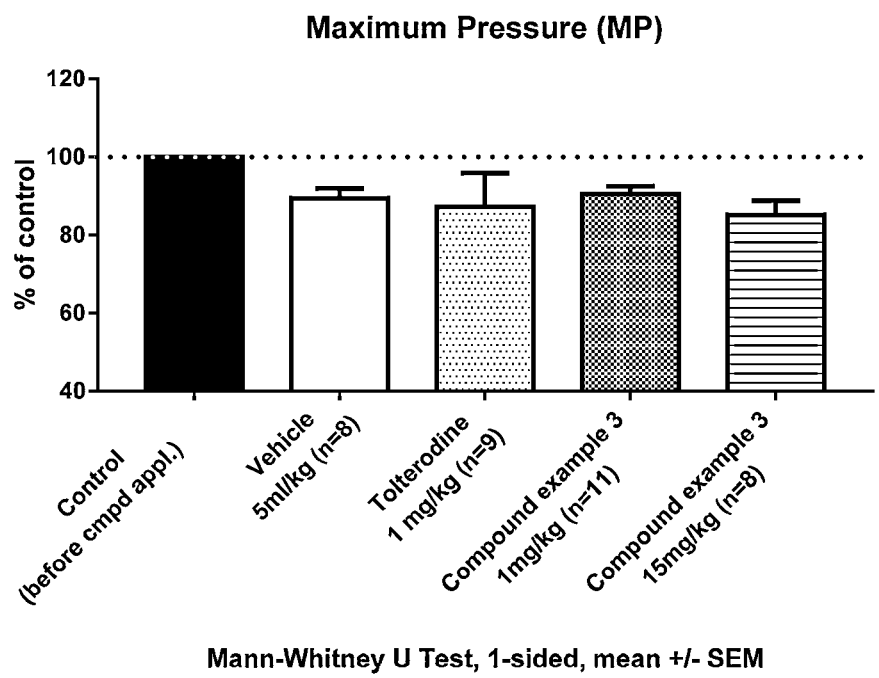

FIG. 9: Efficacy of Compound Example 3 on overactive bladder measured as number of micturitions/hour FIG. 10: AUC during plateau phase of micturition 4 to 10 hours after transfer to metabolic cages FIG. 11: Normalized bladder weight FIG. 12: Intercontraction Interval FIG. 13: Maximum Pressure of bladder contraction FIG. 14: Influence of treatment with Compound Example 3 on arthritis severity in rat AIA model. Disease activity score (A) and joint thickness (B) were evaluated on the day of CFA injection (day 0) and daily onwards (A) or three times per week (B) after showing first symptoms (>day 8). Treatment with Compound Example 3 (60, 15 or 3 mg/kg QD) started with the induction of arthritis. Healthy control group (control) and AIA group (AIA) were treated with vehicle only. Data are shown as mean±SD of n=8 rats per group. ANOVA with Dunett's Test, *$p<0.05$; $p<0.01$; *$p<0.005$; ****$p<0.001$ compared with AIA group.

Figure 15:
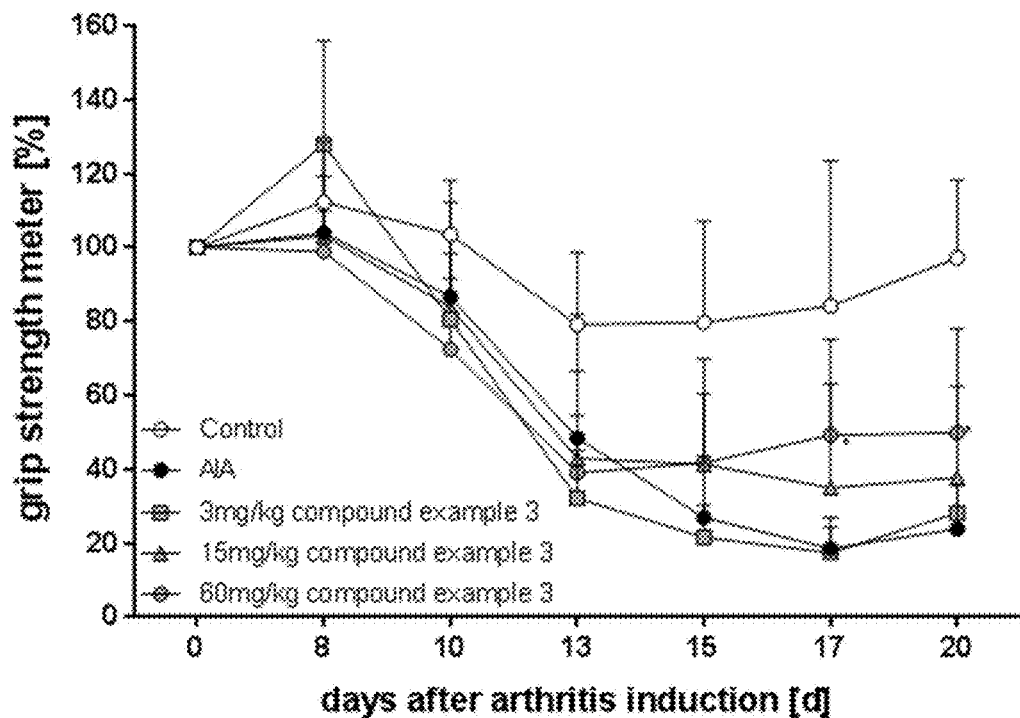

FIG. 15: Effect on hyperalgesia by Compound Example 3 treatment in rat AIA model. Grip strength was determined on the day of CFA injection (day 0) and 3 times weekly after showing first symptoms (>day 8). Treatment with Compound Example 3 (60, 15 or 3 mg/kg QD) started with the induction of arthritis. Healthy control group (control) and AIA group (AIA) were treated with vehicle only. Data are shown as mean±SD of n=8 rats per group. ANOVA with Dunett's Test, *$p<0.05$; $p<0.01$; *$p<0.005$; ****$p<0.001$ compared with AIA group.

Figure 16:
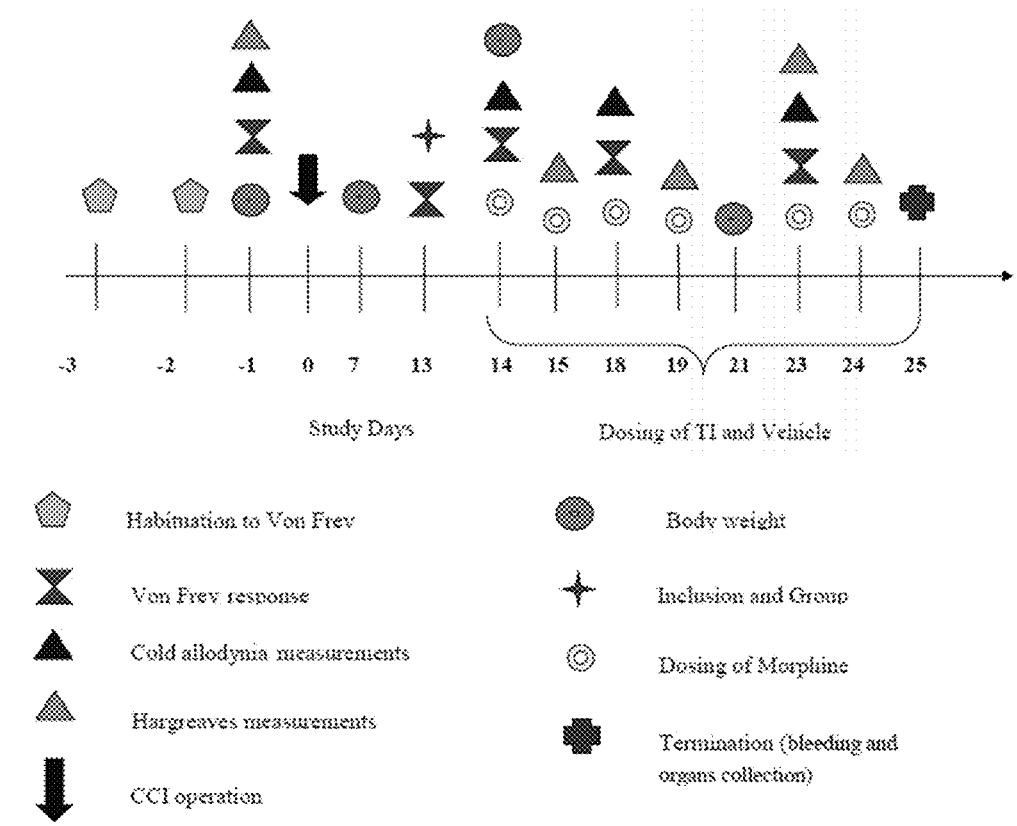

FIG. 16: Schematic description of operation and treatments for CCI model.

DETAILED DESCRIPTION OF THE INVENTION

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen or sulfur atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "one or a plurality up to the maximum possible amount", e.g. if the term refers to the carbon atoms of a $C_7$-cycloalkyl, it relates to "1, 2, 3, 4, 5, 6 or 7". In particular, "one or more" means "1, 2, 3, 4 or 5, particularly 1, 2, 3 or 4, more particularly 1, 2 or 3, even more particularly 1 or 2".

When groups in the compounds according to the invention are substituted, it is possible for said groups to be mono-substituted or poly-substituted with substituent(s), unless otherwise specified. Within the scope of the present invention, the meanings of all groups, which occur repeatedly, are independent from one another. It is possible that groups in the compounds according to the invention are substituted with one, two or three identical or different substituents, particularly with one substituent.

The term "comprising" when used in the specification includes but is not restricted to "consisting of".

The terms as mentioned in the present text have preferably the following meanings: The term "halogen atom", "halogen", "halo-" or "Hal-" is to be understood as meaning a fluorine, chlorine, bromine or iodine atom, preferably a fluorine or a chlorine atom.

The term "$C_1$-$C_5$-alkyl" means a linear or branched, saturated, monovalent hydrocarbon group having 1, 2, 3, 4 or 5 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl or 1,1-dimethylpropyl group, or an isomer thereof.

The term "$C_1$-$C_3$-alkyl" means a linear or branched, saturated, monovalent hydrocarbon group having 1, 2 or 3 carbon atoms ("$C_1$-$C_3$-alkyl"), e.g. a methyl, ethyl, n-propyl or isopropyl group.

The term "—O$C_1$-$C_5$-alkyl" means a linear or branched, saturated, monovalent group which is attached through an oxygen atom, and in which the term "$C_1$-$C_5$-alkyl" is as defined supra, e.g. a methoxy, ethoxy, n-propoxy, isopropoxy, n-butoxy, sec-butoxy, isobutoxy, tert-butoxy, pentyloxy or isopentyloxy, or an isomer thereof. The hyphen at the beginning of the group indicates the point of attachment of said O$C_1$-$C_5$-alkyl group to the rest of the molecule.

"$C_3$-$C_7$-cycloalkyl" is to be understood as meaning a saturated, monovalent, monocyclic or bicyclic hydrocarbon ring, which contains 3, 4, 5, 6 or 7 carbon atoms. Said $C_3$-$C_7$-cycloalkyl group is for example a monocyclic hydrocarbon ring, e.g. a cyclopropyl, cyclobutyl, cyclopentyl, cyclohexyl or cycloheptyl group, or a bicyclic hydrocarbon ring, e.g. a bicyclo[2.2.1]heptanyl or bicyclo[3.2.0]heptanyl group. Particularly, said ring contains 3, 4 or 5 carbon atoms ("$C_3$-$C_5$-cycloalkyl") or 5, 6 or 7 carbon atoms ("$C_5$-$C_7$-cycloalkyl").

The term "bicyclic cycloalkyl" includes by definition spirocycloalkyl, bridged, and fused bicycloalkyl groups.

The term "spirocycloalkyl" means a saturated, monovalent bicyclic hydrocarbon group in which the two rings share one common ring carbon atom, and wherein said bicyclic hydrocarbon group contains 5, 6, or 7 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl or spiro[2.4]heptyl.

The term "fused bicycloalkyl" means a bicyclic, saturated hydrocarbon ring with 6 or 7 ring atoms in total, in which the two rings share two adjacent ring atoms.

Said fused cycloalkyl group is, for example, a bicyclo[3.1.0]hexanyl or bicyclo[3.2.0]heptanyl group.

The term "bridged bicycloalkyl" means a bicyclic, saturated hydrocarbon ring with 6 or 7 ring atoms in total, in which the two rings share two common ring atoms which are not adjacent.

Said bridged cycloalkyl group is, for example, bicyclo[2.1.1]hexanyl or bicyclo[2.2.1]heptanyl group.

The term "—($C_1$-$C_3$-alkyl)-($C_3$-$C_7$-cycloalkyl)" is to be understood as a $C_3$-$C_7$-cycloalkyl group as defined above which is attached through any carbon atom of said $C_3$-$C_7$-cycloalkyl group to any atom of the $C_1$-$C_3$-alkyl group as defined above. The hyphen at the beginning of the group indicates the point of attachment of said ($C_1$-$C_3$-alkyl)-($C_3$-$C_7$-cycloalkyl) group to the rest of the molecule. Said ($C_1$-$C_3$-alkyl)-($C_3$-$C_7$-cycloalkyl) groups are, for example, cyclopropylmethyl, cyclobutylmethyl, cyclopentylmethyl, cyclohexylmethyl, 2-cyclopropylethyl, 1-cyclopropylethyl, 2-cyclobutylethyl, 1-cyclobutylethyl, 2-cyclopentylethyl, 1-cyclopentylethyl, 2-cyclobutylpropyl, or 1-cyclobutylpropyl.

The term "—O$C_3$-$C_7$-cycloalkyl" means a saturated, monovalent, monocyclic group, which contains 3, 4, 5, 6 or 7 carbon atoms, in which the term "$C_3$-$C_7$-cycloalkyl" is defined supra, e.g. a cyclopropyloxy, cyclobutyloxy, cyclopentyloxy, cyclohexyloxy, or cycloheptyloxy group.

The term "heterocycloalkyl" is to be understood as meaning a saturated, monovalent, monocyclic or bicyclic hydrocarbon ring with the number of ring atoms as specified in which one or two ring atoms of the hydrocarbon ring is/are replaced by one or two heteroatoms or heteroatom-containing groups independently selected from NH, —N$R^4$, N, O, S, SO and $SO_2$, wherein $R^4$ represents $C_1$-$C_5$-alkyl optionally substituted with 1 to 5 fluorine atoms.

4- to 7-membered heterocycloalkyl in the context of the invention means a monocyclic or bicyclic, saturated heterocycle with 4, 5, 6 or 7 ring atoms in total, which contains one or two identical or different ring heteroatoms or heteroatom-containing groups from the series NH, —N$R^4$, N, O, S, SO and $SO_2$, wherein $R^4$ represents $C_1$-$C_5$-alkyl optionally substituted with 1 to 5 fluorine atoms. Said 4- to 7-membered heterocycloalkyl can be bound via a ring carbon or nitrogen atom to the rest of the molecule.

Said heterocycloalkyl can be connected to the rest of the molecule through a carbon or a nitrogen atom, if said nitrogen atom is present.

Examples for monocyclic heterocycloalkyl groups are azetidinyl, oxetanyl, thietanyl, pyrrolidinyl, pyrazolidinyl, imidazolidinyl, tetrahydrofuranyl, thiolanyl, 1,1-dioxidothiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, 1,1-dioxidothiomorpholinyl, azepanyl, 1,4-diazepanyl, and 1,4-oxazepanyl.

Particularly, without being limited thereto, said heterocycloalkyl can be a 4-membered ring, such as an azetidinyl, oxetanyl or thietanyl, or a 5-membered ring, such as tetrahydrofuranyl, dioxolinyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, or a 6-membered ring such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, or a 7-membered ring, such as a azepanyl, 1,4-diazepanyl, or 1,4-oxazepanyl, for example.

The term "bicyclic heterocycloalkyl" includes by definition heterospirocycloalkyl, fused and bridged heterobicycloalkyl groups.

The term "heterospirocycloalkyl" means a bicyclic, saturated heterocycle with 6 or 7 ring atoms in total, in which the two rings share one common ring carbon atom, wherein the "heterospirocycloalkyl" contains one or two identical or different ring heteroatoms or heteroatom-containing groups from the series: NH, —N$R^4$, N, O, S, SO and $SO_2$, wherein $R^4$ represents $C_1$-$C_5$-alkyl optionally substituted with 1 to 5 fluorine atoms; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[2.4]-heptanyl, azaspiro[3.3]heptyl, oxazaspiro[3.3]heptyl, thiazaspiro[3.3]heptyl, oxaspiro[3.3]heptyl, diazaspiro[3.3]heptyl or thiazaspiro[3.3]heptyl, or one of the further homologous scaffolds such as spiro[2.3]-, spiro[2.4]-, spiro[3.3]-.

The term "fused heterocycloalkyl" means a bicyclic, saturated heterocycle with 6 or 7 ring atoms in total, in which the two rings share two adjacent ring atoms, which "fused heterocycloalkyl" contains one or two identical or different ring heteroatoms or heteroatom-containing groups from the series: NH, —N$R^4$, N, O, S, SO and $SO_2$, wherein $R^4$ represents $C_1$-$C_5$-alkyl optionally substituted with 1 to 5 fluorine atoms; it being possible for said fused heterocycloalkyl group to be attached to the rest of the molecule via any one of the carbon atoms or, if present, a nitrogen atom.

Said fused heterocycloalkyl group is, for example, 3-azabicyclo[3.1.0]hexanyl or 3-azabicyclo[3.2.0]heptanyl.

The term "bridged heterocycloalkyl" means a bicyclic, saturated heterocycle with 6 or 7 ring atoms in total, in which the two rings share two common ring atoms which are not adjacent, which "bridged heterocycloalkyl" contains one or two identical or different ring heteroatoms or heteroatom-containing groups from the series: NH, —NR$^4$, N, O, S, SO and SO$_2$, wherein R$^4$ represents C$_1$-C$_5$-alkyl optionally substituted with 1 to 5 fluorine atoms; it being possible for said bridged heterocycloalkyl group to be attached to the rest of the molecule via any one of the carbon atoms, except the bridgehead carbon atoms, or, if present, a nitrogen atom.

Said bridged heterocycloalkyl group is, for example, azabicyclo[2.2.1]heptyl, oxazabicyclo[2.2.1]heptyl, thiazabicyclo[2.2.1]heptyl, or diazabicyclo[2.2.1]heptyl.

The term "5- to 7-membered lactam" means cyclic amides of amino carboxylic acids, having a 1-azacycloalkan-2-one structure, or analogues having unsaturation or heteroatoms replacing one or more carbon atoms of the ring having a ring size of 5, 6 or 7 ring system atoms. In particular said "5- to 7-membered lactam" means a γ-lactam (gamma-lactam), a δ-lactam (delta-lactam), and an ε-lactam (epsilon-lactam).

The term "heteroaryl" is understood as meaning a monovalent, monocyclic or bicyclic hydrocarbon ring system with at least one aromatic ring, and wherein at least one ring atom of the monovalent, monocyclic or bicyclic hydrocarbon ring system can be replaced by at least one heteroatom or heteroatom-containing group, like NH, N, O, S, SO, and SO$_2$. The number of ring system atoms is as specified, e.g. a 5- or 6-membered heteroaryl.

"5- or 6-membered heteroaryl" is understood as meaning a monovalent, monocyclic heteroaryl having 5 or 6 ring atoms and wherein one, two or three ring atoms of a monovalent 5-membered hydrocarbon ring system is/are replaced by one, two or three heteroatoms or heteroatom-containing groups independently selected from S, N, NH and O; and wherein one or two ring atoms of a monovalent 6-membered hydrocarbon ring system is/are replaced by one or two nitrogen atoms.

The said 5-membered heteroaryl can be connected through a carbon or a nitrogen atom, if said nitrogen atom is present.

Said 5- or 6-membered heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl or thiadiazolyl; or a 6-membered heteroaryl group, such as, for example, pyridinyl, pyridazinyl, pyrimidinyl or pyrazinyl.

In general, and unless otherwise mentioned, the term "heteroaryl" includes all possible isomeric forms thereof, e.g. tautomers and positional isomers with respect to the point of linkage to the rest of the molecule. Thus, to give some illustrative non-restricting examples, the term pyridinyl includes pyridin-2-yl, pyridin-3-yl, and pyridin-4-yl; or the term pyrimidinyl includes pyrimidin-2-yl, pyrimidin-4-yl and pyrimidin-5-yl; or the term pyrazolyl includes 1H-pyrazolyl; or the term imidazolyl includes 1H-imidazolyl and 4H-imidazolyl; the term thiophenyl includes 2-thiophenyl and 3-thiophenyl; or the term thiazolyl includes 1,3-thiazol-5-yl, 1,3-thiazol-4-yl and 1,3-thiazol-2-yl.

"Bicyclic 8- to 10-membered heteroaryl" is understood as meaning a bicyclic, monovalent, fused heteroaryl having 8, 9 or 10 ring atoms with at least one aromatic ring and wherein one, two or three ring atoms of a monovalent, 8- to 10-membered bicyclic hydrocarbon ring system is/are replaced by one, two or three heteroatoms or heteroatom-containing groups independently selected from NH, N, O, S, SO and SO$_2$.

The said bicyclic 8- to 10-membered heteroaryl can be connected through a carbon or a nitrogen atom, if said nitrogen atom is present.

The term "bicyclic 8- to 10-membered heteroaryl" includes by definition fused and bridged heterobicycloalkyl groups.

Particularly, bicyclic heteroaryl is selected from for example, benzofuranyl, benzo-thienyl, benzothiazolyl, thienopyridinyl, thienopyrimidinyl, benzoxazolyl, benz-isoxazolyl, benzimidazolyl, benzotriazolyl, benzothiadiazolyl, indazolyl, indolyl, iso-indolyl, etc. or for example, quinolinyl, quinazolinyl, isoquinolinyl, etc.; indolizinyl, or cinnolinyl, phthalazinyl, quinazolinyl, quinoxalinyl, etc.

The term "C$_1$-C$_3$" as used throughout this text is to be understood as meaning a group having a finite number of carbon atoms of 1 to 3, i.e. 1, 2, or 3 carbon atoms, e.g. in the context of the definition of "C$_1$-C$_3$-alkyl", it is to be understood as meaning an alkyl group having a finite number of carbon atoms of 1 to 3, i.e. 1, 2, or 3 carbon atoms. It is to be understood further that said term "C$_1$-C$_3$" is to be interpreted as any sub-range comprised therein, e.g. C$_1$-C$_2$, or C$_2$-C$_3$.

The term "C$_1$-C$_5$" as used throughout this text is to be understood as meaning a group having a finite number of carbon atoms of 1 to 5, i.e. 1, 2, 3, 4, or 5 carbon atoms, e.g. in the context of the definition of "C$_1$-C$_5$-alkyl", it is to be understood as meaning an alkyl group having a finite number of carbon atoms of 1 to 5, i.e. 1, 2, 3, 4, or 5 carbon atoms. It is to be understood further that said term "C$_1$-C$_5$" is to be interpreted as any sub-range comprised therein, e.g. C$_1$-C$_5$, C$_1$-C$_5$, C$_3$-C$_4$, C$_2$-C$_3$, C$_2$-C$_4$, or C$_1$-C$_4$.

The term "C$_1$-C$_3$" as used in the context of the definition "—OC$_1$-C$_3$-alkyl" is to be understood as meaning an alkyl group, having a finite number of carbon atoms of 1 to 3, i.e. 1, 2 or 3 carbon atoms.

Similarly, the mentioned above applies to "C$_1$-C$_4$-alkyl", "C$_1$-C$_3$-alkyl", "C$_1$-C$_3$-alkoxy", "C$_1$-C$_2$-alkyl" or "C$_1$-C$_2$-alkoxy".

Further, as used herein, the term "C$_3$-C$_7$", as used throughout this text, is to be understood as meaning a group having a finite number of carbon atoms of 3 to 7, i.e. 3, 4, 5, 6 or 7 carbon atoms, e.g. in the context of the definition of "C$_3$-C$_7$-cycloalkyl", it is to be understood as meaning a cycloalkyl group having a finite number of carbon atoms of 3 to 7, i.e. 3, 4, 5, 6 or 7 carbon atoms. It is to be understood further that said term "C$_3$-C$_7$" is to be interpreted as any sub-range comprised therein, e.g. C$_3$-C$_6$, C$_4$-C$_5$, C$_3$-C$_5$, C$_3$-C$_4$, C$_4$-C$_6$, or C$_5$-C$_7$; particularly C$_3$-C$_6$.

Furthermore, as used herein, the term "C$_3$-C$_5$", as used in the present text, e.g. in the context of the definition of "C$_3$-C$_5$-cycloalkyl", means a cycloalkyl group having a finite number of carbon atoms of 3 to 5, i.e. 3, 4 or 5 carbon atoms.

When a range of values is given, said range encompasses each value and sub-range within said range.

For example:

"C$_1$-C$_6$" encompasses C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$;

"C$_1$-C$_6$" encompasses C$_2$, C$_3$, C$_4$, C$_5$, C$_6$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$;

"C$_3$-C$_{10}$" encompasses C$_3$, C$_4$, C$_5$, C$_6$, C$_7$, C$_8$, C$_9$, C$_{10}$, C$_3$-C$_{10}$, C$_3$-C$_9$, C$_3$-C$_8$, C$_3$-C$_7$, C$_3$-C$_6$, C$_3$-C$_5$, C$_3$-C$_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)-sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope, which is higher than its natural abundance. The natural abundances of isotopes to be applied in this context are described in "Isotopic Compositions of the Elements 1997", Pure Appl. Chem., 70(1), 217-235, 1998, which is incorporated herein by reference.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein the isotopic variant(s) of the compounds of general formula (I) preferably contain deuterium ("deuterium-containing compounds of formula (I)"). Isotopic variants of the compounds of general formula (I) in which one or more radioactive isotopes, such as 3H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271] and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases, deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102; both incorporated herein by reference). In other cases, the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208; incorporated herein by reference) and Odanacatib (K. Kassahun et al., WO2012/112363; incorporated herein by reference) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993; incorporated herein by reference). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976), thereby incorporated herein.

Further, the compounds of the present invention may exist as tautomers.

The present invention includes all possible tautomers of the compounds of the present invention as single tautomers, or as any mixture of said tautomers, in any ratio.

The present invention also relates to useful forms of the compounds as disclosed herein, such as hydrates, solvates, and salts, in particular pharmaceutically acceptable salts.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19, incorporated herein by reference. A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Unless otherwise indicated, the compounds of the present invention are also referred to isomers, enantiomers, diastereomers, racemates, hydrates, solvates, a salt thereof, or a mixture of same.

As used herein, the term "in vivo hydrolysable ester" is understood as meaning an in vivo hydrolysable ester of a compound of the present invention containing a carboxy or hydroxy group, for example, a pharmaceutically acceptable ester that is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_5$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention. An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters. Furthermore, the present invention includes all possible crystalline forms, or polymorphs, of the compounds of the present invention, either as single polymorphs, or as a mixture of more than one polymorph, in any ratio.

In accordance with a first aspect, the present invention covers compounds of general formula (I)
wherein
  $R^1$ represents
    phenyl,
    5- or 6-membered heteroaryl wherein said 5-membered heteroaryl contains 1, 2 or 3 heteroatoms or heteroatom-containing groups independently selected from the group consisting of S, N, NH, and O and wherein said 6-membered heteroaryl contains 1 or 2 nitrogen atoms, or
    bicyclic 9- to 10-membered heteroaryl containing 1, 2 or 3 heteroatoms or heteroatom-containing groups independently selected from NH, N, O, S, SO and $SO_2$,
      wherein $R^1$ is optionally substituted as defined in formula (I).

Also preferred are compounds of general formula (I), wherein
  $R^1$ represents
    phenyl,
    5- or 6-membered heteroaryl wherein said 5-membered heteroaryl contains 1, 2 or 3 heteroatoms or heteroatom-containing groups independently selected from the group consisting of S, N, NH, and O and wherein said 6-membered heteroaryl contains 1 or 2 nitrogen atoms, or
    bicyclic 9- to 10-membered heteroaryl containing 1, 2 or 3 heteroatoms or heteroatom-containing groups independently selected from NH, N, O, S, SO and $SO_2$,
      wherein said $R^1$ is optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and
      wherein independently, if $R^1$ represents 5-membered heteroaryl or bicyclic 9- or 10-membered heteroaryl, each ring nitrogen atom, if present, of said $R^1$ is optionally substituted with a substituent $R^{1b}$ wherein $R^{1b}$ represents $C_1$-$C_5$-alkyl, —($C_1$-$C_3$-alkyl)-($C_3$-$C_7$-cycloalkyl) or $C_3$-$C_7$-cycloalkyl, and
      if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl,
      said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl independently are optionally substituted with one or more substituents independently selected from the group consisting of methyl, OH, $OR^4$ and F; and
  $R^4$ has the same meaning as defined above in general formula (I).

Also preferred are compounds of general formula (I), wherein
  $R^1$ represents
    6-membered heteroaryl, in particular pyridinyl, pyrimidinyl or pyrazinyl, wherein said $R^1$ is optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and
    wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F; and wherein
  $R^4$ has the same meaning as defined above in general formula (I).

Also preferred are compounds of general formula (I), wherein
  $R^1$ represents pyridinyl, in particular pyridin-3-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and wherein the substituent or at least one of said substituents $R^{1a}$ is preferably positioned para to the carbon atom which links the pyridinyl, in particular pyridin-3-yl, to the rest of the molecule, and wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F; and wherein $R^4$ has the same meaning as defined above in general formula (I).

Also preferred are compounds of general formula (I), wherein $R^1$ represents pyridinyl, in particular pyridin-3-yl, substituted at one or more carbon atoms with 1 or 2 substituents $R^{1a}$ which are the same or different wherein $R^{1a}$ represents methyl, ethyl, cyclobutyl, methoxy, ethoxy, trifluoromethyl, difluoromethyl, 1,1-difluoroethyl, 1,1-difluoropropyl or 2,2,2-trifluoroethyl, and wherein the substituent or at least one of said substituents $R^{1a}$ is preferably positioned para to the carbon atom which links the pyridinyl, in particular pyridin-3-yl, to the rest of the molecule.

Also preferred are compounds of general formula (I), wherein $R^1$ represents pyridinyl, in particular pyridin-2-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and wherein the substituent or at least one of said substituents $R^{1a}$ is preferably positioned para to the carbon atom which links the pyridinyl, in particular pyridin-2-yl, to the rest of the molecule, and wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F; and wherein $R^4$ has the same meaning as defined above in general formula (I).

Also preferred are compounds of general formula (I), wherein $R^1$ represents pyridinyl, in particular pyridin-2-yl, substituted at one or more carbon atoms with 1 or 2 substituents $R^{1a}$ which are the same or different wherein $R^{1a}$ represents methyl, ethyl, cyclobutyl, methoxy, ethoxy, trifluoromethyl, difluoromethyl, 1,1-difluoroethyl, 1,1-difluoropropyl or 2,2,2-trifluoroethyl, and wherein the substituent or at least one of said substituents $R^{1a}$ is preferably positioned para to the carbon atom which links the pyridinyl, in particular pyridin-2-yl, to the rest of the molecule.

Also preferred are compounds of general formula (I), wherein $R^1$ represents
5-membered heteroaryl wherein said 5-membered heteroaryl contains 1, 2 or 3 heteroatoms or heteroatom-containing groups independently selected from the group consisting of S, N, NH, and O, in particular pyrazolyl, thiazolyl, imidazolyl, or thiophenyl, wherein said $R^1$ is optionally substituted at one or more carbon atoms with 1 or 2 substituents $R^{1a}$ which are the same or different, wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen, or CN, and wherein independently each ring nitrogen atom, if present, of said $R^1$ is optionally substituted with a substituent $R^{1b}$, wherein $R^{1b}$ represents $C_1$-$C_5$-alkyl, —($C_1$-$C_3$-alkyl)-($C_3$-$C_7$-cycloalkyl), or $C_3$-$C_7$-cycloalkyl, and if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, or —$OC_3$-$C_7$-cycloalkyl, and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, and —$OC_3$-$C_7$-cycloalkyl independently are optionally substituted with one or more substituents independently selected from the group consisting of methyl, ethyl, OH, $OR^4$ and F; and wherein $R^4$ has the same meaning as defined above in general formula (I).

Also preferred are compounds of general formula (I), wherein $R^1$ represents pyrazolyl, in particular pyrazol-4-yl, optionally substituted at one or more carbon atoms with 1 or 2 substituents $R^{1a}$ which are the same or different, wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen, or CN, and wherein independently each ring nitrogen atom of said $R^1$ is optionally substituted with a substituent $R^{1b}$, wherein $R^{1b}$ represents $C_1$-$C_5$-alkyl, —($C_1$-$C_3$-alkyl)-($C_3$-$C_7$-cycloalkyl), or $C_3$-$C_7$-cycloalkyl, and if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, or —$OC_3$-$C_7$-cycloalkyl, and/or if $R^{1b}$ represents $C_1$-$C_5$-alkyl, —($C_1$-$C_3$-alkyl)-($C_3$-$C_7$-cycloalkyl), or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_1$-$C_7$-cycloalkyl independently are optionally substituted with one or more substituents independently selected from the group consisting of methyl, ethyl, OH, $OR^4$ and F; and wherein $R^4$ has the same meaning as defined above in general formula (I).

Also preferred are compounds of general formula (I), wherein $R^1$ represents pyrazol-4-yl substituted at the nitrogen atom at position 1 with a substituent $R^{1b}$, wherein $R^{1b}$ represents $C_1$-$C_5$-alkyl, —($C_1$-$C_3$-alkyl)-($C_3$-$C_7$-cycloalkyl) or $C_3$-$C_7$-cycloalkyl, wherein said $C_1$-$C_5$-alkyl, $C_3$-$C_7$-cycloalkyl and —($C_1$-$C_3$-alkyl)-($C_3$-$C_7$-cycloalkyl) is optionally substituted with one or more substituents independently selected from the group consisting of methyl, ethyl, OH, $OR^4$ and F; and wherein $R^4$ has the same meaning as defined above in general formula (I).

Additionally preferred are compounds of general formula (I), wherein $R^1$ represents pyrazolyl, in particular pyrazol-4-yl, wherein said $R^1$ is optionally substituted with 1 or 2 $R^{1b}$ which are the same or different, wherein $R^{1a}$ represents $C_1$-$C_5$-alkyl, $C_3$-$C_7$-cycloalkyl and —($C_1$-$C_3$-alkyl)-($C_3$-$C_7$-cycloalkyl), and wherein one of said substituents $R^{1b}$ is attached to the pyrazolyl nitrogen atom at position 1, preferably attached to the pyrazol-4-yl nitrogen atom at position 1, and wherein said $C_1$-$C_5$-alkyl, $C_3$-$C_7$-cycloalkyl and —($C_1$-$C_3$-alkyl)-($C_3$-$C_7$-cycloalkyl) independently are optionally substituted with one or more substituents independently selected from the group consisting of methyl, ethyl, OH, $OR^4$, and F; and wherein $R^4$ has the same meaning as defined above in general formula (I).

Additionally preferred are compounds of general formula (I), wherein $R^1$ represents pyrazol-4-yl substituted at the nitrogen atom at position 1 with $C_3$-$C_7$-cycloalkyl, wherein said $C_3$-$C_7$-cycloalkyl is optionally substituted with one or more substituents independently selected from the group consisting of methyl, ethyl, OH, $OR^4$, and F; and wherein $R^4$ has the same meaning as defined above in general formula (I).

Additionally preferred are compounds of general formula (I), wherein $R^1$ represents pyrazol-4-yl substituted at the nitrogen atom at position 1 with $C_3$-$C_7$-cycloalkyl, wherein said $C_3$-$C_7$-cycloalkyl is optionally substituted with one or more substituents independently selected from the group consisting of methyl, OH, $OR^4$, and F; and wherein $R^4$ has the same meaning as defined above in general formula (I).

Also preferred are compounds of general formula (I), wherein $R^1$ represents pyrazol-4-yl substituted at the nitrogen atom at position 1 with a substituent selected from the group consisting of methyl, ethyl, propyl, propan-2-yl, 2-methylpropyl, tertbutyl, butan-2-yl, cyclobutyl, 2,2-dimethyl-propyl, 3-methylbutan-2-yl, cyclopentyl, cyclohexyl, 1-cyclopropylmethyl, 1-cyclopropylethyl, 1-cyclobutylmethyl, 1-(1-methylcyclopropyl)methyl and 2,2,2-trifluoroethyl, in particular ethyl, propan-2-yl, 2-methylpropyl, butan-2-yl, cyclobutyl, cyclopentyl, 2,2-dimethylpropyl, 1-cyclopropylmethyl, 1-cyclopropylethyl, 1-(1-methylcyclopropyl)methyl, and 1-cyclobutylmethyl.

Particularly preferred are compounds of general formula (I), wherein $R^1$ represents pyrazol-4-yl, substituted at the nitrogen atom at position 1 with cyclobutyl.

Also preferred are compounds of general formula (I), wherein $R^1$ represents thiazolyl, in particular thiazol-5-yl, optionally substituted at one or more carbon atoms with 1 or 2 substituents $R^{1a}$ which are the same or different, wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen, or CN, wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of methyl, ethyl, OH, $OR^4$, and F; and wherein $R^4$ has the same meaning as defined above in general formula (I).

Also preferred are compounds of general formula (I), wherein $R^1$ represents thiazolyl, in particular thiazol-5-yl, optionally substituted at one or more carbon atoms with 1 or 2 substituents $R^{1a}$ which are the same or different, wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen, or CN, wherein one of said substituents $R^{1a}$ is preferably positioned meta to the carbon atom which links the thiazolyl, in particular thiazol-5-yl, to the rest of the molecule, and wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of methyl, ethyl, OH, $OR^4$; and F; and wherein $R^4$ has the same meaning as defined above in general formula (I).

Also preferred are compounds of general formula (I), wherein $R^1$ represents thiazol-5-yl, optionally substituted at a carbon atom with a substituent $R^{1a}$, wherein $R^{1a}$ represents $C_1$-$C_5$-alkyl, —($C_1$-$C_3$-alkyl)-($C_3$-$C_7$-cycloalkyl), or $C_3$-$C_7$-cycloalkyl, wherein said $C_1$-$C_5$-alkyl, $C_3$-$C_7$-cycloalkyl, or —($C_1$-$C_3$-alkyl)-($C_3$-$C_7$-cycloalkyl) is optionally substituted with one or more substituents independently selected from the group consisting of methyl, ethyl, OH, $OR^4$, and F; and wherein $R^4$ has the same meaning as defined above in general formula (I).

Also preferred are compounds of general formula (I), wherein $R^1$ represents thiazol-5-yl, optionally substituted at a carbon atom with a substituent $R^{1a}$, wherein $R^{1a}$ represents $C_1$-$C_5$-alkyl, —($C_1$-$C_3$-alkyl)-($C_3$-$C_7$-cycloalkyl), or $C_3$-$C_7$-cycloalkyl, wherein the said substituent $R^{1a}$ is preferably linked to the carbon atom at position 2 of thiazol-5-yl, and wherein said $C_1$-$C_5$-alkyl, $C_3$-$C_7$-cycloalkyl, or —($C_1$-$C_3$-alkyl)-($C_3$-$C_7$-cycloalkyl) is optionally substituted with one or more substituents independently selected from the group consisting of methyl, ethyl, OH, $OR^4$, and F; and wherein $R^4$ has the same meaning as defined above in general formula (I).

Additionally preferred are compounds of general formula (I), wherein $R^1$ represents thiazol-5-yl substituted at the carbon atom at position 2 with $C_3$-$C_7$-cycloalkyl, wherein said $C_3$-$C_7$-cycloalkyl is optionally substituted with one or more substituents independently selected from the group consisting of methyl, ethyl, OH, $OR^4$, and F, and wherein $R^4$ has the same meaning as defined above in general formula (I).

Additionally preferred are compounds of general formula (I), wherein $R^1$ represents thiazol-5-yl substituted at the carbon atom at position 2 with $C_3$-$C_7$-cycloalkyl, wherein said $C_3$-$C_7$-cycloalkyl is optionally substituted with one or more substituents independently selected from the group consisting of methyl, OH, $OR^4$, and F, and wherein $R^4$ has the same meaning as defined above in general formula (I).

Also preferred are compounds of general formula (I), wherein $R^1$ represents thiazol-5-yl, substituted at the carbon atom at position 2 with a substituent selected from the group consisting of methyl, ethyl, propyl, propan-2-yl, 2-methylpropyl, tertbutyl, butan-2-yl, cyclopropyl, cyclobutyl, 2,2-dimethylpropyl, 3-methylbutan-2-yl, cyclopentyl, cyclohexyl, 1-cyclo-propylmethyl, 1-cyclopropylethyl, 1-cyclobutylmethyl, 1-(1-methyl-cyclopropyl)methyl and 2,2,2-trifluoroethyl, in particular ethyl, propan-2-yl, 2-methylpropyl, butan-2-yl, cyclobutyl, cyclopentyl, 2,2-dimethylpropyl, 1-cyclopropylmethyl, 1-cyclopropylethyl, 1-(1-methylcyclopropyl)methyl, and 1-cyclobutylmethyl.

Also preferred are compounds of general formula (I), wherein
$R^1$ represents thiazolyl, in particular thiazol-2-yl, optionally substituted at one or more carbon atoms with 1 or 2 substituents $R^{1a}$ which are the same or different, wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN,
wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, and —$OC_3$-$C_7$-cycloalkyl independently are optionally substituted with one or more substituents independently selected from the group consisting of methyl, ethyl, OH, $OR^4$, and F; and
$R^4$ has the same meaning as defined above in general formula (I).

Also preferred are compounds of general formula (I), wherein
$R^1$ represents thiazol-2-yl optionally substituted at one or more carbon atoms with 1 or 2 substituents $R^{1a}$ which are the same or different, wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen, or CN,
wherein one of said substituents $R^{1a}$ is preferably linked to the carbon atom in the position 5 of thiazol-2-yl, and
wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, and —$OC_3$-$C_7$-cycloalkyl independently are optionally substituted with one or more substituents independently selected from the group consisting of methyl, ethyl, OH, $OR^4$, and F; and wherein
$R^4$ has the same meaning as defined above in general formula (I).

Also preferred are compounds of general formula (I), wherein
$R^1$ represents thiazol-2-yl, optionally substituted at a carbon atom with a substituent $R^{1a}$, wherein $R^{1a}$ represents $C_1$-$C_5$-alkyl, —($C_1$-$C_3$-alkyl)-($C_3$-$C_7$-cycloalkyl) or $C_3$-$C_7$-cycloalkyl,
wherein said $C_1$-$C_5$-alkyl, $C_3$-$C_7$-cycloalkyl, or —($C_1$-$C_3$-alkyl)-($C_3$-$C_7$-cycloalkyl) is optionally substituted with one or more substituents independently selected from the group consisting of methyl, ethyl, OH, $OR^4$, and F; and wherein
$R^4$ has the same meaning as defined above in general formula (I).

Also preferred are compounds of general formula (I), wherein
$R^1$ represents thiazol-2-yl, optionally substituted at a carbon atom with a substituent $R^{1a}$, wherein $R^{1a}$ represents $C_1$-$C_5$-alkyl, —($C_1$-$C_3$-alkyl)-($C_3$-$C_7$-cycloalkyl), or $C_3$-$C_7$-cycloalkyl,
wherein the said substituent $R^{1a}$ is preferably linked to the carbon atom in the position 5 of thiazol-2-yl, and wherein said $C_1$-$C_5$-alkyl, $C_3$-$C_7$-cycloalkyl, or —($C_1$-$C_3$-alkyl)-($C_3$-$C_7$-cycloalkyl) is optionally substituted with one or more substituents independently selected from the group consisting of methyl, ethyl, OH, $OR^4$, and F; and
$R^4$ has the same meaning as defined above in general formula (I).

Additionally preferred are compounds of general formula (I), wherein
$R^1$ represents thiazol-2-yl, substituted at the carbon atom in position 5 with $C_3$-$C_7$-cycloalkyl, wherein said $C_3$-$C_7$-cycloalkyl is optionally substituted with one or more substituents independently selected from the group consisting of methyl, ethyl, OH, $OR^4$, and F; and wherein
$R^4$ has the same meaning as defined above in general formula (I).

Additionally preferred are compounds of general formula (I), wherein
$R^1$ represents thiazol-2-yl, substituted at the carbon atom in position 5 with $C_3$-$C_7$-cycloalkyl, wherein said $C_3$-$C_7$-cycloalkyl is optionally substituted with one or more substituents independently selected from the group consisting of methyl, OH, $OR^4$, and F; and wherein
$R^4$ has the same meaning as defined above in general formula (I).

Also preferred are compounds of general formula (I), wherein
$R^1$ represents thiazol-2-yl, substituted at the carbon atom in position 5 with a substituent selected from the group consisting of methyl, ethyl, propyl, propan-2-yl, 2-methylpropyl, tertbutyl, butan-2-yl, cyclopropyl, cyclobutyl, 2,2-dimethylpropyl, 3-methylbutan-2-yl, cyclopentyl, cyclohexyl, 1-cyclo-propylmethyl, 1-cyclopropylethyl, 1-cyclobutylmethyl, 1-(1-methyl-cyclopropyl)methyl and 2,2,2-trifluoroethyl, in particular ethyl, propan-2-yl, 2-methylpropyl, butan-2-yl, cyclobutyl, cyclopentyl, 2,2-dimethylpropyl, 1-cyclopropylmethyl, 1-cyclopropylethyl, 1-(1-methylcyclopropyl)methyl, and 1-cyclobutylmethyl.

Also preferred are compounds of general formula (I), wherein
$R^1$ represents
a bicyclic 9-membered heteroaryl containing 1, 2, or 3 heteroatoms or heteroatom-containing groups independently selected from NH, N, O, S, SO, and $SO_2$, in particular benzothiophenyl,
wherein said $R^1$ is optionally substituted at one or more carbon atoms with 1 or 2 substituents $R^{1a}$ which are the same or different, wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen, or CN, and
wherein independently each ring nitrogen atom of said $R^1$ is optionally substituted with 1 substituent $R^{1b}$, wherein $R^{1b}$ represents $C_1$-$C_5$-alkyl, —($C_1$-$C_3$-alkyl)-($C_3$-$C_7$-cycloalkyl), or $C_3$-$C_7$-cycloalkyl, and
if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl, and/or if $R^{1b}$ represents $C_1$-$C_5$-alkyl, —($C_1$-$C_3$-alkyl)-($C_3$-$C_7$-cycloalkyl), or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, and —$OC_3$-$C_7$-cycloalkyl independently are optionally substituted with one or more substituents independently selected from the group consisting of methyl, ethyl OH, OR$^4$, and F; and wherein R$^4$ has the same meaning as defined above in general formula (I).

Additionally preferred are compounds of general formula (I), wherein

R$^1$ represents phenyl, pyridinyl, pyrazolyl, thiazolyl, imidazolyl, thiophenyl, or benzothiophenyl, in particular pyridinyl, pyrazolyl, thiazolyl, or imidazolyl, wherein said R$^1$ is optionally substituted at one or more carbon atoms with 1 or 2 substituents R$^{1a}$ which are the same or different, wherein R$^{1a}$ represents C$_1$-C$_5$-alkyl, C$_3$-C$_7$-cycloalkyl, —(C$_1$-C$_3$-alkyl)-(C$_3$-C$_7$-cycloalkyl), —OC$_1$-C$_5$-alkyl, —OC$_3$-C$_7$-cycloalkyl, halogen or CN, and wherein independently, if R$^1$ represents pyrazolyl, thiazolyl, or imidazolyl, each ring nitrogen atom of said R$^1$, is optionally substituted with a substituent R$^{1b}$, wherein R$^{1b}$ represents C$_1$-C$_5$-alkyl, —(C$_1$-C$_3$-alkyl)-(C$_3$-C$_7$-cycloalkyl), or C$_3$-C$_7$-cycloalkyl, and if R$^{1a}$ represents C$_1$-C$_5$-alkyl, C$_3$-C$_7$-cycloalkyl, —(C$_1$-C$_3$-alkyl)-(C$_3$-C$_7$-cycloalkyl), —OC$_1$-C$_5$-alkyl or —OC$_3$-C$_7$-cycloalkyl, and/or if R$^{1b}$ represents C$_1$-C$_5$-alkyl, —(C$_1$-C$_3$-alkyl)-(C$_3$-C$_7$-cycloalkyl) or C$_3$-C$_7$-cycloalkyl, said C$_1$-C$_5$-alkyl, C$_3$-C$_7$-cycloalkyl, —(C$_1$-C$_3$-alkyl)-(C$_3$-C$_7$-cycloalkyl), —OC$_1$-C$_5$-alkyl and —OC$_3$-C$_7$-cycloalkyl independently are optionally substituted with one or more substituents independently selected from the group consisting of methyl, ethyl, OH, OR$^4$ and F; and wherein R$^4$ has the same meaning as defined above in general formula (I).

In accordance with a further aspect, the present invention covers compounds of general formula (I), wherein R$^4$ represents C$_1$-C$_5$-alkyl, in particular methyl, ethyl, propyl, or butyl optionally substituted with 1 to 3 fluorine atoms.

Also preferred are compounds of general formula (I), wherein

R$^4$ represents methyl, difluoromethyl, or trifluoromethyl.

In accordance with a further aspect, the present invention covers compounds of general formula (I), wherein R$^3$ represents H.

In accordance with a further aspect, the present invention covers compounds of general formula (I), wherein R$^5$ represents H, F, Cl, or methyl, in particular H or F.

Particularly preferred are compounds of general formula (I), wherein

R$^5$ represents H.

Also preferred are compounds of general formula (I), wherein

R$^5$ represents F.

Particularly preferred are compounds of general formula (I), wherein

R$^3$ represents H; and
R$^5$ represents H.

Particularly preferred are compounds of general formula (I), wherein

R$^3$ represents H; and
R$^5$ represents F.

In accordance with a further aspect, the present invention covers compounds of general formula (I), wherein R$^2$ represents
—(CH$_2$)$_p$—(C$_5$-C$_7$-cycloalkyl),
—(CH$_2$)$_p$-phenyl,
6-membered heteroaryl, containing 1 or 2 N, or
bicyclic 9- to 10-membered heteroaryl, containing 1, 2 or 3 heteroatoms or heteroatom-containing groups independently selected from NH, N, O, S, SO and SO$_2$, wherein said R$^2$ is optionally substituted at one or more carbon atoms with 1 or 2 substituents R$^{2a}$ which are the same or different, wherein R$^{2a}$ represents C$_1$-C$_5$-alkyl, C$_3$-C$_7$-cycloalkyl, —(C$_1$-C$_3$-alkyl)-(C$_3$-C$_7$-cycloalkyl), —OC$_1$-C$_5$-alkyl, —OC$_3$-C$_7$-cycloalkyl, halogen, OH or CN, and wherein independently each nitrogen atom of said R$^2$, if present, is optionally substituted with a substituent R$^{2b}$ wherein R$^{2b}$ represents C$_1$-C$_5$-alkyl, C$_3$-C$_7$-cycloalkyl or —(C$_1$-C$_3$-alkyl)-(C$_3$-C$_7$-cycloalkyl), and if R$^{2a}$ represents C$_1$-C$_5$-alkyl, C$_3$-C$_7$-cycloalkyl, —(C$_1$-C$_3$-alkyl)-(C$_3$-C$_7$-cycloalkyl), —OC$_1$-C$_5$-alkyl or —OC$_3$-C$_7$-cycloalkyl, and/or if R$^{2b}$ represents C$_1$-C$_5$-alkyl, —(C$_1$-C$_3$-alkyl)-(C$_3$-C$_7$-cycloalkyl) or C$_3$-C$_7$-cycloalkyl, said C$_1$-C$_5$-alkyl, C$_3$-C$_7$-cycloalkyl, —(C$_1$-C$_3$-alkyl)-(C$_3$-C$_7$-cycloalkyl), —OC$_1$-C$_5$-alkyl and —OC$_3$-C$_7$-cyclo-alkyl independently are optionally substituted with one or more substituents independently selected from the group consisting of OH, OR$^4$ and F; and wherein p and R$^4$ have the same meaning as defined in general formula (I).

A preferred embodiment of the present invention covers compounds of general formula (I), wherein R$^2$ represents
—(CH$_2$)$_p$—(C$_5$-C$_7$-cycloalkyl),
—(CH$_2$)$_p$-phenyl, or
6-membered heteroaryl containing 1 or 2 N, wherein said R$^2$ is optionally substituted at one or more carbon atoms with 1 or 2 substituents R$^{2a}$ which are the same or different, wherein R$^{2a}$ represents C$_1$-C$_5$-alkyl, C$_3$-C$_7$-cycloalkyl, OC$_1$-C$_5$-alkyl, halogen or CN, wherein said C$_1$-C$_5$-alkyl, —OC$_1$-C$_5$-alkyl and C$_3$-C$_7$-cycloalkyl independently are optionally substituted with OH, OR$^4$ or 1 to 5 fluorine atoms, and wherein p and R$^4$ have the same meaning as defined in general formula (I).

A preferred embodiment of the present invention covers compounds of general formula (I), wherein R$^2$ represents —(CH$_2$)$_p$—(C$_5$-C$_7$-cycloalkyl), optionally substituted at one or more carbon atoms with 1 or 2 substituents R$^{2a}$ which are the same or different, wherein R$^{2a}$ represents C$_1$-C$_5$-alkyl, C$_3$-C$_7$-cycloalkyl, OC$_1$-C$_5$-alkyl, halogen or CN, wherein said C$_1$-C$_5$-alkyl, —OC$_1$-C$_5$-alkyl and C$_3$-C$_7$-cycloalkyl independently are optionally substituted with OH, OR$^4$ or 1 to 5 fluorine atoms, and wherein p and R$^4$ have the same meaning as defined in general formula (I).

A preferred embodiment of the present invention covers compounds of general formula (I), wherein R$^2$ represents C$_5$-C$_7$-cycloalkyl, optionally substituted at one or more carbon atoms with 1 or 2 substituents R$^{2a}$ which are the same or different, wherein R$^{2a}$ represents C$_1$-C$_5$-alkyl, C$_3$-C$_7$-cycloalkyl, OC$_1$-C$_5$-alkyl, halogen or CN, wherein said C$_1$-C$_5$-alkyl, —OC$_1$-C$_5$-alkyl and C$_3$-C$_7$-cycloalkyl independently are optionally substituted with OH, OR$^4$ or 1 to 5 fluorine atoms, and wherein R$^4$ has the same meaning as defined in general formula (I).

A preferred embodiment of the present invention covers compounds of general formula (I), wherein $R^2$ represents —$(CH_2)_p$-phenyl, optionally substituted at one or more carbon atoms with 1 or 2 substituents $R^{2a}$ which are the same or different wherein $R^{2a}$ represents $C_1$-$C_5$-alkyl, $C_3$-$C_7$-cycloalkyl, $OC_1$-$C_5$-alkyl, halogen or CN, wherein said $C_1$-$C_5$-alkyl, —$OC_1$-$C_5$-alkyl and $C_3$-$C_7$-cycloalkyl independently are optionally substituted with OH, $OR^4$ or 1 to 5 fluorine atoms, and p and $R^4$ have the same meaning as defined in general formula (I).

Also preferred are compounds of general formula (I), wherein $R^2$ represents phenyl optionally substituted with 1 or 2 substituents $R^{2a}$ which are the same or different wherein $R^{2a}$ represents $C_1$-$C_5$-alkyl, $C_3$-$C_7$-cycloalkyl, $OC_1$-$C_5$-alkyl, halogen or CN, wherein said $C_1$-$C_5$-alkyl, —$OC_1$-$C_5$-alkyl and $C_3$-$C_7$-cycloalkyl independently are optionally substituted with OH, $OR^4$ or 1 to 5 fluorine atoms, and $R^4$ has the same meaning as defined in general formula (I).

Also preferred are compounds of general formula (I), wherein $R^2$ represents phenyl optionally substituted with 1 or 2 substituents $R^{2a}$ which are the same or different wherein $R^{2a}$ represents $C_1$-$C_5$-alkyl, $OC_1$-$C_5$-alkyl, F or Cl, wherein said $C_1$-$C_5$-alkyl and —$OC_1$-$C_5$-alkyl independently are optionally substituted with OH, $OR^4$ or 1 to 5 fluorine atoms, and $R^4$ has the same meaning as defined in general formula (I).

Also preferred are compounds of general formula (I), wherein $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, wherein if the substituent or at least one of said substituents is F, it is preferably positioned ortho to the carbon atom which links the phenyl to the rest of the molecule, and wherein said $C_1$-$C_5$-alkyl and —$OC_1$-$C_5$-alkyl independently are optionally substituted with 1 to 5 fluorine atoms.

Also preferred are compounds of general formula (I), wherein $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and wherein said $C_1$-$C_5$-alkyl and —$OC_1$-$C_5$-alkyl independently are optionally substituted with 1 to 5 fluorine atoms.

Also preferred are compounds of general formula (I), wherein $R^2$ represents phenyl substituted with 2 substituents $R^{2a}$ which are the same or different wherein $R^{2a}$ represents $C_1$-$C_5$-alkyl, $OC_1$-$C_5$-alkyl, F or Cl, wherein if the substituent or at least one of said substituents is F, it is preferably positioned ortho to the carbon atom which links the phenyl to the rest of the molecule, and wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule; and wherein said $C_1$-$C_5$-alkyl and —$OC_1$-$C_5$-alkyl independently are optionally substituted with 1 to 5 fluorine atoms.

Also preferred are compounds of general formula (I), wherein $R^2$ represents phenyl optionally substituted with 1 or 2 substituents $R^{2a}$ which are the same or different wherein $R^{2a}$ represents methyl, trifluoromethyl, trifluoromethoxy, F or Cl, wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule.

Also preferred are compounds of general formula (I), wherein $R^2$ represents 6-membered heteroaryl containing 1 or 2 N, in particular pyridinyl, wherein said $R^2$ is optionally substituted at one or more carbon atoms with 1 or 2 substituents $R^{2a}$ which are the same or different wherein $R^{2a}$ represents $C_1$-$C_5$-alkyl, $OC_1$-$C_5$-alkyl, $C_3$-$C_7$-cycloalkyl, halogen or CN, wherein said $C_1$-$C_5$-alkyl, —$OC_1$-$C_5$-alkyl and $C_3$-$C_7$-cycloalkyl independently are optionally substituted with OH, $OR^4$ or 1 to 5 fluorine atoms, and $R^4$ has the same meaning as defined in general formula (I).

Also preferred are compounds of general formula (I), wherein $R^2$ represents pyridinyl, in particular pyridin-2-yl, optionally substituted at one or more carbon atoms with 1 or 2 substituents $R^{2a}$ which are the same or different wherein $R^{2a}$ represents $C_1$-$C_5$-alkyl, $OC_1$-$C_5$-alkyl, F or Cl, wherein said $C_1$-$C_5$-alkyl and —$OC_1$-$C_5$-alkyl independently are optionally substituted with OH, $OR^4$ or 1 to 5 fluorine atoms, and $R^4$ has the same meaning as defined in general formula (I).

In accordance with a further aspect, the present invention covers compounds of general formula (I), wherein p represents 0.

In accordance with a further aspect, the present invention covers compounds of general formula (I), wherein $R^6$ and $R^7$ represent H.

In accordance with a further aspect, the present invention covers compounds of general formula (I), wherein $R^1$ represents phenyl, 5- or 6-membered heteroaryl wherein said 5-membered heteroaryl contains 1, 2 or 3 heteroatoms or heteroatom-containing groups independently selected from the group consisting of S, N, NH, and O and wherein said 6-membered heteroaryl contains 1 or 2 nitrogen atoms, or bicyclic 9- to 10-membered heteroaryl containing 1, 2 or 3 heteroatoms or heteroatom-containing groups independently selected from NH, N, O, S, SO and $SO_2$, wherein said $R^1$ is optionally substituted at one or more carbon atoms with 1 to 3 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, $NHR^4$, $N(R^4)_2$, $NH(C_3$-$C_7$-cycloalkyl), halogen, CN, $NHSO_2R^4$, $SO_2R^4$, 5- to 7-membered lactam or 4- to 7-membered heterocycloalkyl containing 1 or 2 heteroatoms or heteroatom-containing groups selected from NH, —$NR^4$, N, O, S, SO and $SO_2$, and wherein independently, if $R^1$ represents 5-membered heteroaryl or bicyclic 8- to 10-membered heteroaryl, each ring nitrogen atom, if present, of said $R^1$ is optionally substituted with a substituent $R^{1b}$ wherein $R^{1b}$ represents $C_1$-$C_5$-alkyl, —($C_1$-$C_3$-alkyl)-($C_3$-$C_7$-cycloalkyl), $C_3$-$C_7$-cycloalkyl, $SO_2R^4$ or 4- to 7-membered heterocycloalkyl containing 1 or 2 heteroatoms or heteroatom-containing groups selected from NH, —$NR^4$, N, O, S, SO and $SO_2$, and if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl independently are optionally substituted with one or more substituents independently selected from the group consisting of methyl, ethyl, OH, $OR^4$ and F, and if $R^{1a}$ and/or $R^{1b}$ represent 4- to 7-membered heterocycloalkyl, each carbon atom of said 4- to 7-membered heterocycloalkyl is optionally substituted with one or more substituents independently selected from the group consisting of OH, $OR^4$ and F, $R^3$ represents H or F, in particular H, $R^5$ represents H, F, Cl or methyl, in particular H or F, and $R^6$ and $R^7$ represent H.

In accordance with a further aspect, the present invention covers compounds of general formula (I), wherein $R^1$ represents
phenyl,
6-membered heteroaryl containing 1 or 2 N atoms,
wherein said $R^1$ is optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN,
wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

In accordance with another aspect, the present invention covers compounds of general formula (I), wherein $R^1$ represents
5-membered heteroaryl wherein said 5-membered heteroaryl contains 1, 2 or 3 heteroatoms or heteroatom-containing groups independently selected from the group consisting of S, N, NH, and O, in particular pyrazolyl, thiazolyl, imidazolyl or thiophenyl, wherein said $R^1$ is optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and wherein independently each ring nitrogen atom, if present, of said $R^1$ is optionally substituted with a substituent Rib which are the same or different wherein $R^{1b}$ represents $C_1$-$C_5$-alkyl, —($C_1$-$C_3$-alkyl)-($C_3$-$C_7$-cycloalkyl) and $C_3$-$C_7$-cycloalkyl, if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cyclo-alkyl independently are optionally substituted with one or more substituents independently selected from the group consisting of methyl, ethyl, OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

In accordance with another aspect, the present invention covers compounds of general formula (I), wherein $R^1$ represents pyridinyl, in particular pyridin-3-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and wherein one of said substituents is preferably positioned wherein one of said substituents $R^{1a}$ is preferably positioned para to the carbon atom which links the pyridinyl, in particular pyridin-3-yl, to the rest of the molecule, and wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of methyl, ethyl, OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

In accordance with another aspect, the present invention covers compounds of general formula (I), wherein $R^1$ represents pyridinyl, in particular pyridin-3-yl, substituted at one or more carbon atoms with 1 or 2 substituents $R^{1a}$ which are the same or different wherein $R^{1a}$ represents methyl, ethyl, methoxy, ethoxy, cyclobutyl, trifluoromethyl, difluoromethyl, 1,1-difluoroethyl, 1,1-difluoropropyl or 2,2,2-trifluoroethyl, and wherein the substituent or at least one of said substituents is preferably positioned para to the carbon atom which links the pyridinyl, in particular pyridin-3-yl, to the rest of the molecule, and $R^3$ represents H or F, in particular H, $R^5$ represents H, F, Cl or methyl, in particular H or F, and $R^6$ and $R^7$ represent H.

In accordance with another aspect, the present invention covers compounds of general formula (I), wherein
- $R^1$ represents pyridinyl, in particular pyridin-2-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and
  - wherein one of said substituents $R^{1a}$ is preferably positioned para to the carbon atom which links the pyridinyl, in particular pyridin-2-yl, to the rest of the molecule, and
  - wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of methyl, ethyl, OH, $OR^4$ and F,
- $R^3$ represents H or F, in particular H,
- $R^4$ represents $C_1$-$C_5$-alkyl, optionally substituted with 1 to 5 fluorine atoms,
- $R^5$ represents H, F, Cl or methyl, in particular H or F, and
- $R^6$ and $R^7$ represent H.

In accordance with another aspect, the present invention covers compounds of general formula (I), wherein
- $R^1$ represents pyridinyl, in particular pyridin-2-yl, substituted at one or more carbon atoms with 1 or 2 substituents $R^{1a}$ which are the same or different wherein $R^{1a}$ represents methyl, ethyl, methoxy, ethoxy, cyclobutyl, trifluoromethyl, difluoromethyl, 1,1-difluoroethyl, 1,1-difluoropropyl or 2,2,2-trifluoroethyl, and
  - wherein the substituent or at least one of said substituents is preferably positioned para to the carbon atom which links the pyridinyl, in particular pyridin-2-yl, to the rest of the molecule, and
- $R^3$ represents H or F, in particular H,
- $R^5$ represents H, F, Cl or methyl, in particular H or F, and
- $R^6$ and $R^7$ represent H.

In accordance with another aspect, the present invention covers compounds of general formula (I), wherein
- $R^1$ represents pyrazolyl, in particular pyrazol-4-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and
  - wherein independently each nitrogen atom of said $R^1$ is optionally substituted with a substituent $R^{1b}$ wherein $R^{1b}$ represents $C_1$-$C_5$-alkyl, —($C_1$-$C_3$-alkyl)-($C_3$-$C_7$-cycloalkyl) and $C_3$-$C_7$-cycloalkyl, and
  - if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cyclo-alkyl independently are optionally substituted with one or more substituents independently selected from the group consisting of methyl, OH, $OR^4$ and F,
- $R^3$ represents H or F, in particular H,
- $R^4$ represents $C_1$-$C_5$-alkyl, optionally substituted with 1 to 5 fluorine atoms,
- $R^5$ represents H, F, Cl or methyl, in particular H or F, and
- $R^6$ and $R^7$ represent H.

A preferred embodiment of the present invention covers compounds of general formula (I), wherein
- $R^1$ represents pyrazolyl, in particular pyrazol-4-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and
  - wherein independently each nitrogen atom of said $R^1$ is optionally substituted with a substituent $R^{1b}$ which are the same or different wherein $R^{1b}$ represents $C_1$-$C_5$-alkyl, —($C_1$-$C_3$-alkyl)-($C_3$-$C_7$-cycloalkyl) or $C_3$-$C_7$-cycloalkyl, and
  - if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cyclo-alkyl independently are optionally substituted with one or more substituents independently selected from the group consisting of methyl, OH, $OR^4$ and F,
- $R^3$ represents H or F, in particular H,
- $R^4$ represents $C_1$-$C_5$-alkyl, optionally substituted with 1 to 5 fluorine atoms,
- $R^5$ represents H, F, Cl or methyl, in particular H or F, and
- $R^6$ and $R^7$ represent H.

A preferred embodiment of the present invention covers compounds of general formula (I), wherein
- $R^1$ represents pyrazol-4-yl, optionally substituted at a nitrogen atom with 1 substituent $R^{1b}$ selected from the group consisting of $C_1$-$C_5$-alkyl, —($C_1$-$C_3$-alkyl)-($C_3$-$C_7$-cycloalkyl) and $C_3$-$C_7$-cycloalkyl, wherein independently said $C_1$-$C_5$-alkyl, $C_3$-$C_7$-cycloalkyl and —($C_1$-$C_3$-alkyl)-($C_3$-$C_7$-cycloalkyl) are optionally substituted with one or more substituents independently selected from the group consisting of methyl, OH, $OR^4$ and F,
- $R^3$ represents H or F, in particular H,
- $R^4$ represents $C_1$-$C_5$-alkyl, optionally substituted with 1 to 5 fluorine atoms,
- $R^5$ represents H, F, Cl or methyl, in particular H or F, and
- $R^6$ and $R^7$ represent H.

A preferred embodiment of the present invention covers compounds of general formula (I), wherein
- $R^1$ represents pyrazol-4-yl substituted at a nitrogen atom with a substituent $R^{1b}$ selected from the group consisting of methyl, ethyl, propyl, propan-2-yl, 2-methylpropyl, cyclopropyl, tertbutyl, butan-2-yl, cyclobutyl, 2,2-dimethyl-propyl, 3-methylbutan-2-yl, cyclopentyl, cyclohexyl, 1-cyclopropylmethyl, 1-cyclopropylethyl, 1-cyclobutylmethyl, 1-(1-methylcyclopropyl)methyl and 2,2,2-trifluoroethyl, in particular ethyl, propan-2-yl, 2-methylpropyl, butan-2-yl, cyclobutyl, cyclopentyl, 2,2-dimethylpropyl, 1-cyclopropylmethyl, 1-cyclopropylethyl, 1-(1-methylcyclopropyl)methyl and 1-cyclobutylmethyl,
- $R^3$ represents H or F, in particular H,
- $R^5$ represents H, F, Cl or methyl, in particular H or F, and
- $R^6$ and $R^7$ represent H.

In accordance with another aspect, the present invention covers compounds of general formula (I), wherein
- $R^1$ represents thiazolyl, in particular thiazol-5-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of methyl, OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazolyl, in particular thiazol-5-yl, substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, wherein one of said substituents $R^{1a}$ is preferably positioned meta to the carbon atom which links the thiazolyl, in particular thiazol-5-yl, to the rest of the molecule, and wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of methyl, OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-5-yl, optionally substituted at a carbon atom with a substituent $R^{1a}$ wherein $R^{1a}$ represents $C_1$-$C_5$-alkyl, —($C_1$-$C_3$-alkyl)-($C_3$-$C_7$-cycloalkyl) or $C_3$-$C_7$-cycloalkyl, wherein the said substituent $R^{1a}$ is preferably attached to the carbon atom at position 2 of thiazol-5-yl, and wherein said $C_1$-$C_5$-alkyl, $C_3$-$C_7$-cycloalkyl and —($C_1$-$C_3$-alkyl)-($C_3$-$C_7$-cycloalkyl) independently are optionally substituted with one or more substituents independently selected from the group consisting of methyl, OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-5-yl substituted at the carbon atom at position 2 with $C_3$-$C_7$-cycloalkyl, wherein said $C_3$-$C_7$-cycloalkyl is optionally substituted with one or more substituents independently selected from the group consisting of methyl, OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-5-yl, substituted at the carbon atom at position 2 with a substituent selected from the group consisting of methyl, ethyl, propyl, propan-2-yl, 2-methylpropyl, cyclopropyl, tertbutyl, butan-2-yl, cyclobutyl, 2,2-dimethylpropyl, 3-methylbutan-2-yl, cyclopentyl, cyclohexyl, 1-cyclo-propylmethyl, 1-cyclopropylethyl, 1-cyclobutylmethyl, 1-(1-methyl-cyclopropyl)methyl and 2,2,2-trifluoroethyl, in particular ethyl, propan-2-yl, cyclopropyl, 2-methylpropyl, butan-2-yl, cyclobutyl, cyclopentyl, 2,2-dimethylpropyl, 1-cyclopropylmethyl, 1-cyclopropylethyl, 1-(1-methyl-cyclopropyl)methyl and 1-cyclobutylmethyl, $R^3$ represents H or F, in particular H, $R^5$ represents H, F, Cl or methyl, in particular H or F, and $R^6$ and $R^7$ represent H.

In accordance with another aspect, the present invention covers compounds of general formula (I), wherein $R^1$ represents thiazol-2-yl, optionally substituted at a carbon atom with a substituent $R^{1a}$ wherein $R^{1a}$ represents $C_1$-$C_5$-alkyl, —($C_1$-$C_3$-alkyl)-($C_3$-$C_7$-cycloalkyl) or $C_3$-$C_7$-cycloalkyl, wherein said substituent $R^{1a}$ is preferably attached to the carbon atom in the position 5 of thiazol-2-yl, and wherein said $C_1$-$C_5$-alkyl, $C_3$-$C_7$-cycloalkyl and —($C_1$-$C_3$-alkyl)-($C_3$-$C_7$-cycloalkyl) independently are optionally substituted with one or more substituents independently selected from the group consisting of methyl, OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-2-yl substituted at the carbon atom in position 5 with $C_3$-$C_7$-cycloalkyl, and wherein said $C_3$-$C_7$-cycloalkyl is optionally substituted with one or more substituents independently selected from the group consisting of methyl, OH, $OR^4$ and F, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-2-yl substituted at the carbon atom in position 5 with a substituent selected from the group consisting of methyl, ethyl, propyl, propan-2-yl, cyclopropyl, 2-methylpropyl, tertbutyl, butan-2-yl, cyclobutyl, 2,2-dimethylpropyl, 3-methylbutan-2-yl, cyclopentyl, cyclohexyl, 1-cyclo-propylmethyl, 1-cyclopropylethyl, 1-cyclobutylmethyl, 1-(1-methyl-cyclopropyl)methyl and 2,2,2-trifluoroethyl, in particular ethyl, propan-2-yl, cyclopropyl, 2-methylpropyl, butan-2-yl, cyclobutyl, cyclopentyl, 2,2-dimethylpropyl, 1-cyclopropylmethyl, 1-cyclopropylethyl, 1-(1-methyl-cyclopropyl)methyl and 1-cyclobutylmethyl, $R^3$ represents H or F, in particular H, $R^5$ represents H, F, Cl or methyl, in particular H or F, and $R^6$ and $R^7$ represent H.

In accordance with a further aspect, the present invention covers compounds of general formula (I), wherein $R^2$ represents $C_5$-$C_7$-cycloalkyl, phenyl, or 6-membered heteroaryl containing 1 or 2 N, in particular pyridin-2-yl, wherein said $R^2$ is optionally substituted at one or more carbon atoms with 1 or 2 substituents $R^{2a}$ which are the same or different wherein $R^{2a}$ represents $C_1$-$C_5$-alkyl, $C_3$-$C_7$-cycloalkyl, $OC_1$-$C_5$-alkyl, halogen or CN,
  wherein said $C_1$-$C_5$-alkyl, —$OC_1$-$C_5$-alkyl and $C_3$-$C_7$-cycloalkyl independently are optionally substituted with OH, $OR^4$ or 1 to 5 fluorine atoms,
$R^3$ represents H or F, in particular H,
$R^4$ represents $C_1$-$C_5$-alkyl, optionally substituted with 1 to 5 fluorine atoms,
$R^5$ represents H, F, Cl or methyl, in particular H or F, and
$R^6$ and $R^7$ represent H.

A preferred embodiment of the invention relates to compounds of general formula (I), wherein
  $R^2$ represents phenyl optionally substituted at one or more carbon atoms with 1 or 2 substituents $R^{2a}$ which are the same or different wherein $R^{2a}$ represents $C_1$-$C_5$-alkyl, $C_3$-$C_7$-cycloalkyl, $OC_1$-$C_5$-alkyl, F and Cl, wherein said $C_1$-$C_5$-alkyl, —$OC_1$-$C_5$-alkyl or $C_3$-$C_7$-cycloalkyl are optionally substituted with 1 to 5 fluorine atoms,
  $R^3$ represents H or F, in particular H,
  $R^5$ represents H, F, Cl or methyl, in particular H or F, and
  $R^6$ and $R^7$ represent H.

A preferred embodiment of the invention relates to compounds of general formula (I), wherein
  $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, and
    wherein if the substituent or at least one of said substituents is F, it is preferably positioned ortho to the carbon atom which links the phenyl to the rest of the molecule, and
    wherein said $C_1$-$C_5$-alkyl and —$OC_1$-$C_5$-alkyl independently are optionally substituted with 1 to 5 fluorine atoms,
  $R^3$ represents H or F, in particular H,
  $R^5$ represents H, F, Cl or methyl, in particular H or F, and
  $R^6$ and $R^7$ represent H.

A preferred embodiment of the invention relates to compounds of general formula (I), wherein
  $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, and
    wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and
    wherein said $C_1$-$C_5$-alkyl and —$OC_1$-$C_5$-alkyl independently are optionally substituted with 1 to 5 fluorine atoms,
  $R^3$ represents H or F, in particular H,
  $R^5$ represents H, F, Cl or methyl, in particular H or F, and
  $R^6$ and $R^7$ represent H.

A preferred embodiment of the invention relates to compounds of general formula (I), wherein
  $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, and
    wherein if the substituent or at least one of said substituents is F, it is preferably positioned ortho to the carbon atom which links the phenyl to the rest of the molecule, and
    wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and
    wherein said $C_1$-$C_5$-alkyl and —$OC_1$-$C_5$-alkyl independently are optionally substituted with 1 to 5 fluorine atoms,
  $R^3$ represents H or F, in particular H,
  $R^5$ represents H, F, Cl or methyl, in particular H or F, and
  $R^6$ and $R^7$ represent H.

A preferred embodiment of the invention relates to compounds of general formula (I), wherein
  $R^2$ represents phenyl substituted with 1 or 2 substituents $R^{2a}$ which are the same or different wherein $R^{2a}$ represents methyl, trifluoromethyl, trifluoromethoxy, F or Cl, and
    wherein if the substituent or at least one of said substituents is F, it is preferably positioned ortho to the carbon atom which links the phenyl to the rest of the molecule, and
    wherein if the substituent or at least one of said substituents is methyl, trifluoromethyl, trifluoromethoxy or Cl, it is preferably positioned para to the carbon atom which links the phenyl to the rest of the molecule, and
  $R^3$ represents H or F, in particular H,
  $R^5$ represents H, F, Cl or methyl, in particular H or F, and
  $R^6$ and $R^7$ represent H.

In accordance with a further aspect, the present invention covers compounds of general formula (I), wherein
  $R^1$ represents pyridinyl, in particular pyridin-3-yl, optionally substituted as defined in general formula (I) and,
  $R^2$ represents phenyl or pyridin-2-yl, in particular phenyl, wherein $R^2$ is optionally substituted as defined in general formula (I),
  $R^3$ represents H or F, in particular H,
  $R^5$ represents H, F, Cl or methyl, in particular H or F, and
  $R^6$ and $R^7$ represent H.

A preferred embodiment of the present invention covers compounds of general formula (I), wherein
  $R^1$ represents pyridinyl, in particular pyridin-3-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN,
    wherein the substituent or at least one of said substituents is preferably positioned para to the carbon atom which links the pyridinyl, in particular pyridin-3-yl, to the rest of the molecule, and
    wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F,
  $R^2$ represents phenyl optionally substituted with 1 or 2 substituents $R^{2a}$ which are the same or different wherein $R^{2a}$ represents $C_1$-$C_5$-alkyl, $OC_1$-$C_5$-alkyl, F or Cl, and
    wherein said $C_1$-$C_5$-alkyl and —$OC_1$-$C_5$-alkyl independently are optionally substituted with 1 to 5 fluorine atoms,
  $R^3$ represents H or F, in particular H,
  $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein
$R^1$ represents pyridinyl, in particular pyridin-3-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN,
wherein the substituent or at least one of said substituents is preferably positioned para to the carbon atom which links the pyridinyl, in particular pyridin-3-yl, to the rest of the molecule, and
wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F,
$R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, and
wherein if the substituent or at least one of said substituents is F, it is preferably positioned ortho to the carbon atom which links the phenyl to the rest of the molecule, and
wherein said $C_1$-$C_5$-alkyl and —$OC_1$-$C_5$-alkyl independently are optionally substituted with 1 to 5 fluorine atoms,
$R^3$ represents H or F, in particular H,
$R^4$ represents $C_1$-$C_5$-alkyl, optionally substituted with 1 to 5 fluorine atoms,
$R^5$ represents H, F, Cl or methyl, in particular H or F, and
$R^6$ and $R^7$ represent H.

A preferred embodiment of the present invention covers compounds of general formula (I), wherein
$R^1$ represents pyridinyl, in particular pyridin-3-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN,
wherein the substituent or at least one of said substituents is preferably positioned para to the carbon atom which links the pyridinyl, in particular pyridin-3-yl, to the rest of the molecule; and
wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F,
$R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl,
wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and
wherein said $C_1$-$C_5$-alkyl and —$OC_1$-$C_5$-alkyl independently are optionally substituted with 1 to 5 fluorine atoms,
$R^3$ represents H or F, in particular H,
$R^4$ represents $C_1$-$C_5$-alkyl, optionally substituted with 1 to 5 fluorine atoms,
$R^5$ represents H, F, Cl or methyl, in particular H or F, and
$R^6$ and $R^7$ represent H.

A preferred embodiment of the present invention covers compounds of general formula (I), wherein
$R^1$ represents pyridinyl, in particular pyridin-3-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN,
wherein one of said substituents is preferably positioned para to the carbon atom which links the pyridinyl, in particular pyridin-3-yl, to the rest of the molecule, and
wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F,
$R^2$ represents phenyl substituted with 2 substituents $R^{2a}$ which are the same or different wherein $R^{2a}$ represents $C_1$-$C_5$-alkyl, $OC_1$-$C_5$-alkyl, F and Cl, and
wherein if the substituent or at least one of said substituents is F, it is preferably positioned ortho to the carbon atom which links the phenyl to the rest of the molecule, and
wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and
wherein said $C_1$-$C_5$-alkyl and —$OC_1$-$C_5$-alkyl independently are optionally substituted with 1 to 5 fluorine atoms,
$R^3$ represents H or F, in particular H,
$R^4$ represents $C_1$-$C_5$-alkyl, optionally substituted with 1 to 5 fluorine atoms,
$R^5$ represents H, F, Cl or methyl, in particular H or F, and
$R^6$ and $R^7$ represent H.

A preferred embodiment of the present invention covers compounds of general formula (I), wherein
$R^1$ represents pyridinyl, in particular pyridin-3-yl, substituted at one or more carbon atoms with 1 or 2 substituents $R^{1a}$ which are the same or different wherein $R^{1a}$ represents methyl, ethyl, methoxy, ethoxy, cyclobutyl, trifluoro-methyl, difluoromethyl, 1,1-difluoroethyl, 1,1-difluoropropyl or 2,2,2-trifluoroethyl, and
wherein the substituent or at least one of said substituents is preferably positioned para to the carbon atom which links the pyridinyl, in particular pyridin-3-yl, to the rest of the molecule, and
$R^2$ represents phenyl substituted with 1 or 2 substituents $R^{1a}$ which are the same or different wherein $R^{1a}$ represents methyl, trifluoromethyl, trifluoromethoxy, F or Cl, and
wherein if the substituent or at least one of said substituents is F, it is preferably positioned ortho to the carbon atom which links the phenyl to the rest of the molecule, and
wherein if the substituent or at least one of said substituents is methyl, trifluoromethyl, trifluoromethoxy or Cl, it is preferably positioned para to the carbon atom which links the phenyl to the rest of the molecule, and
$R^3$ represents H or F, in particular H, $R^5$ represents H, F, Cl or methyl, in particular H or F, and $R^6$ and $R^7$ represent H.

In accordance with a further aspect, the present invention covers compounds of general formula (I), wherein
- $R^1$ represents pyridinyl, in particular pyridin-2-yl, optionally substituted as defined in general formula (I),
- $R^2$ represents phenyl or pyridin-2-yl, in particular phenyl, optionally substituted as defined in general formula (I),
- $R^3$ represents H or F, in particular H,
- $R^5$ represents H, F, Cl or methyl, in particular H or F, and $R^6$ and $R^7$ represent H.

A preferred embodiment of the present invention covers compounds of general formula (I), wherein
- $R^1$ represents pyridinyl, in particular pyridin-2-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN,
  - wherein the substituent or at least one of said substituents is preferably positioned para to the carbon atom which links the pyridinyl, in particular pyridin-2-yl, to the rest of the molecule, and
  - wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F,
- $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl,
  - wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and
  - wherein said $C_1$-$C_5$-alkyl and —$OC_1$-$C_5$-alkyl independently are optionally substituted with 1 to 5 fluorine atoms,
- $R^3$ represents H or F, in particular H,
- $R^4$ represents $C_1$-$C_5$-alkyl, optionally substituted with 1 to 5 fluorine atoms,
- $R^5$ represents H, F, Cl or methyl, in particular H or F, and $R^6$ and $R^7$ represent H.

A preferred embodiment of the present invention covers compounds of general formula (I), wherein
- $R^1$ represents pyridinyl, in particular pyridin-2-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN,
  - wherein one of said substituents is preferably positioned para to the carbon atom which links the pyridinyl, in particular pyridin-2-yl, to the rest of the molecule, and
  - wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of OH, $OR^4$ and F,
- $R^2$ represents phenyl substituted with 2 substituents $R^{2a}$ which are the same or different wherein $R^{2a}$ represents $C_1$-$C_5$-alkyl, $OC_1$-$C_5$-alkyl, F and Cl, and
  - wherein if the substituent or at least one of said substituents is F, it is preferably positioned ortho to the carbon atom which links the phenyl to the rest of the molecule, and
  - wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and
  - wherein said $C_1$-$C_5$-alkyl and —$OC_1$-$C_5$-alkyl independently are optionally substituted with 1 to 5 fluorine atoms,
- $R^3$ represents H or F, in particular H,
- $R^4$ represents $C_1$-$C_5$-alkyl, optionally substituted with 1 to 5 fluorine atoms,
- $R^5$ represents H, F, Cl or methyl, in particular H or F, and $R^6$ and $R^7$ represent H.

A preferred embodiment of the present invention covers compounds of general formula (I), wherein
- $R^1$ represents pyridinyl, in particular pyridin-2-yl, substituted at one or more carbon atoms with 1 or 2 substituents $R^{1a}$ which are the same or different wherein $R^{1a}$ represents methyl, ethyl, methoxy, ethoxy, cyclobutyl, trifluoromethyl, difluoromethyl, 1,1-difluoroethyl, 1,1-difluoropropyl or 2,2,2-trifluoroethyl, and
  - wherein the substituent or at least one of said substituents is preferably positioned para to the carbon atom which links the pyridinyl, in particular pyridin-2-yl, to the rest of the molecule, and
- $R^2$ represents phenyl substituted with 1 or 2 substituents $R^{1a}$ which are the same or different wherein $R^{1a}$ represents methyl, trifluoromethyl, trifluoromethoxy, F or Cl, and
  - wherein if the substituent or at least one of said substituents is F, it is preferably positioned ortho to the carbon atom which links the phenyl to the rest of the molecule, and
  - wherein if the substituent or at least one of said substituents is methyl, trifluoromethyl, trifluoromethoxy or Cl, it is preferably positioned para to the carbon atom which links the phenyl to the rest of the molecule, and
- $R^3$ represents H or F, in particular H,
- $R^5$ represents H, F, Cl or methyl, in particular H or F, and $R^6$ and $R^7$ represent H.

A preferred embodiment of the present invention covers compounds of general formula (I), wherein
- $R^1$ represents 5-membered heteroaryl containing 1, 2 or 3 heteroatoms or heteroatom-containing groups independently selected from the group consisting of S, N, NH, and O, in particular pyrazolyl, thiazolyl, imidazolyl or thiophenyl,
  - wherein $R^1$ is optionally substituted as defined in general formula (I) and,
- $R^2$ represents phenyl optionally substituted with 1 or 2 substituents $R^{2a}$ which are the same or different wherein $R^{2a}$ represents $C_1$-$C_5$-alkyl, $OC_1$-$C_5$-alkyl, F or Cl, and
  - wherein said $C_1$-$C_5$-alkyl and —$OC_1$-$C_5$-alkyl are optionally substituted with 1 to 5 fluorine atoms,
- $R^3$ represents H or F, in particular H,
- $R^5$ represents H, F, Cl or methyl, in particular H or F, and $R^6$ and $R^7$ represent H.

A preferred embodiment of the present invention covers compounds of general formula (I), wherein
- $R^1$ represents 5-membered heteroaryl containing 1, 2 or 3 heteroatoms or heteroatom-containing groups independently selected from the group consisting of S, N, NH, and O, in particular pyrazolyl, thiazolyl, imidazolyl or thiophenyl,
  wherein $R^1$ is optionally substituted as defined in general formula (I) and,
$R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, and
  wherein if the substituent or at least one of said substituents is F, it is preferably positioned ortho to the carbon atom which links the phenyl to the rest of the molecule, and
  wherein said $C_1$-$C_5$-alkyl and —$OC_1$-$C_5$-alkyl independently are optionally substituted with 1 to 5 fluorine atoms,
$R^3$ represents H or F, in particular H,
$R^5$ represents H, F, Cl or methyl, in particular H or F, and
$R^6$ and $R^7$ represent H.

A preferred embodiment of the present invention covers compounds of general formula (I), wherein
$R^1$ represents 5-membered heteroaryl containing 1, 2 or 3 heteroatoms or heteroatom-containing groups independently selected from the group consisting of S, N, NH, and O, in particular pyrazolyl, thiazolyl, imidazolyl or thiophenyl,
  wherein $R^1$ is optionally substituted as defined in general formula (I) and,
$R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl,
  wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and
  wherein said $C_1$-$C_5$-alkyl and —$OC_1$-$C_5$-alkyl independently are optionally substituted with 1 to 5 fluorine atoms,
$R^3$ represents H or F, in particular H,
$R^5$ represents H, F, Cl or methyl, in particular H or F, and
$R^6$ and $R^7$ represent H.

A preferred embodiment of the present invention covers compounds of general formula (I), wherein
$R^1$ represents 5-membered heteroaryl containing 1, 2 or 3 heteroatoms or heteroatom-containing groups independently selected from the group consisting of S, N, NH, and O, in particular pyrazolyl, thiazolyl, imidazolyl or thiophenyl,
  wherein $R^1$ is optionally substituted as defined in general formula (I) and,
$R^2$ represents phenyl substituted with 2 substituents $R^{2a}$ which are the same or different wherein $R^{2a}$ represents $C_1$-$C_5$-alkyl, $OC_1$-$C_5$-alkyl, F or Cl, and
  wherein if the substituent or at least one of said substituents is F, it is preferably positioned ortho to the carbon atom which links the phenyl to the rest of the molecule, and
  wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and
  wherein said $C_1$-$C_5$-alkyl and —$OC_1$-$C_5$-alkyl independently are optionally substituted with 1 to 5 fluorine atoms,
$R^3$ represents H or F, in particular H,
$R^5$ represents H, F, Cl or methyl, in particular H or F, and
$R^6$ and $R^7$ represent H.

A preferred embodiment of the present invention covers compounds of general formula (I), wherein
$R^1$ represents 5-membered heteroaryl containing 1, 2 or 3 heteroatoms or heteroatom-containing groups independently selected from the group consisting of S, N, NH, and O, in particular pyrazolyl, thiazolyl, imidazolyl or thiophenyl,
  wherein $R^1$ is optionally substituted as defined in general formula (I) and,
$R^2$ represents phenyl substituted with 1 or 2 substituents $R^{2a}$ which are the same or different wherein $R^{2a}$ represents methyl, trifluoromethyl, trifluoromethoxy, F or Cl, and
  wherein if the substituent or at least one of said substituents is F, it is preferably positioned ortho to the carbon atom which links the phenyl to the rest of the molecule, and
  wherein if the substituent or at least one of said substituents is methyl, trifluoromethyl, trifluoromethoxy or Cl, it is preferably positioned para to the carbon atom which links the phenyl to the rest of the molecule, and
$R^3$ represents H or F, in particular H,
$R^5$ represents H, F, Cl or methyl, in particular H or F, and
$R^6$ and $R^7$ represent H.

A preferred embodiment of the present invention covers compounds of general formula (I), wherein
$R^1$ represents pyrazolyl, in particular pyrazol-4-yl, substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and
  wherein independently each nitrogen atom of said $R^1$ is optionally substituted with a substituent $R^{1b}$ which are the same or different wherein $R^{1b}$ represents $C_1$-$C_5$-alkyl, —($C_1$-$C_3$-alkyl)-($C_3$-$C_7$-cycloalkyl) or $C_3$-$C_7$-cycloalkyl, and
  if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cyclo-alkyl, —($C_1$-$C_3$-alkyl)-($C_3$-$C_7$-cycloalkyl), —$OC_1$-$C_5$-alkyl and $OC_3$-$C_7$-cycloalkyl independently are optionally substituted with one or more substituents independently selected from the group consisting of methyl, OH, $OR^4$ and F, and
$R^2$ represents phenyl optionally substituted with 1 or 2 substituents $R^{2a}$ which are the same or different wherein $R^{2a}$ represents $C_1$-$C_5$-alkyl, $OC_1$-$C_5$-alkyl, F or Cl, and
  wherein said $C_1$-$C_5$-alkyl and —$OC_1$-$C_5$-alkyl independently are optionally substituted with 1 to 5 fluorine atoms,
$R^3$ represents H or F, in particular H,
$R^4$ represents $C_1$-$C_5$-alkyl, optionally substituted with 1 to 5 fluorine atoms,
$R^5$ represents H, F, Cl or methyl, in particular H or F, and
$R^6$ and $R^7$ represent H.

A preferred embodiment of the present invention covers compounds of general formula (I), wherein
$R^1$ represents pyrazolyl, in particular pyrazol-4-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and wherein independently each nitrogen atom of said $R^1$ is optionally substituted with a substituent $R^{1b}$ which are the same or different wherein $R^{1b}$ represents $C_1$-$C_5$-alkyl, —($C_1$-$C_3$-alkyl)-($C_3$-$C_7$-cycloalkyl) or $C_3$-$C_7$-cycloalkyl, and if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and $OC_3$-$C_7$-cycloalkyl independently are optionally substituted with one or more substituents independently selected from the group consisting of methyl, OH, $OR^4$ and F, and $R^2$ represents phenyl substituted with 1 or 2 substituents $R^{2a}$ which are the same or different wherein $R^{2a}$ $C_1$-$C_5$-alkyl, $OC_1$-$C_5$-alkyl, F or Cl, and wherein if the substituent or at least one of said substituents is F, it is preferably positioned ortho to the carbon atom which links the phenyl to the rest of the molecule, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents pyrazolyl, in particular pyrazol-4-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and wherein independently each nitrogen atom of said $R^1$ is optionally substituted with a substituent $R^{1b}$ which are the same or different wherein $R^{1b}$ represents $C_1$-$C_5$-alkyl, —($C_1$-$C_3$-alkyl)-($C_3$-$C_7$-cycloalkyl) or $C_3$-$C_7$-cycloalkyl, if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and $OC_3$-$C_7$-cyclo-alkyl independently are optionally substituted with one or more substituents independently selected from the group consisting of methyl, OH, $OR^4$ and F, and $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, wherein if the substituent or at least one of said substituents is F, it is preferably positioned ortho to the carbon atom which links the phenyl to the rest of the molecule, and wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents pyrazolyl, in particular pyrazol-4-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and wherein independently each nitrogen atom of said $R^1$ is optionally substituted with a substituent $R^{1b}$ which are the same or different wherein $R^{1b}$ represents $C_1$-$C_5$-alkyl, —($C_1$-$C_3$-alkyl)-($C_3$-$C_7$-cycloalkyl) or $C_3$-$C_7$-cycloalkyl, $R^2$ represents phenyl substituted with 2 substituents $R^{2a}$ which are the same or different wherein $R^{2a}$ represents $C_1$-$C_5$-alkyl, $OC_1$-$C_5$-alkyl, F or Cl, and wherein if the substituent or at least one of said substituents is F, it is preferably positioned ortho to the carbon atom which links the phenyl to the rest of the molecule, and wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents pyrazolyl, in particular pyrazol-4-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, and wherein independently each nitrogen atom of said $R^1$ is optionally substituted with a substituent $R^{1b}$ which are the same or different wherein $R^{1b}$ represents $C_1$-$C_5$-alkyl, —($C_1$-$C_3$-alkyl)-($C_3$-$C_7$-cycloalkyl) or $C_3$-$C_7$-cycloalkyl, if $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl or —$OC_3$-$C_7$-cycloalkyl and/or if $R^{1b}$ represents $C_1$-$C_5$-alkyl, —($C_1$-$C_3$-alkyl)-($C_3$-$C_7$-cycloalkyl) or $C_3$-$C_7$-cycloalkyl, said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and $OC_3$-$C_7$-cycloalkyl independently are optionally substituted with one or more substituents independently selected from the group consisting of methyl, OH, OR$^4$ and F, and $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least if one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents pyrazol-4-yl optionally substituted at a nitrogen atom with a substituent $R^{1b}$ selected from the group consisting of $C_1$-$C_5$-alkyl, —($C_1$-$C_3$-alkyl)-($C_3$-$C_7$-cycloalkyl) and $C_3$-$C_7$-cycloalkyl, wherein said $C_1$-$C_5$-alkyl, $C_3$-$C_7$-cycloalkyl and —($C_1$-$C_3$-alkyl)-($C_3$-$C_7$-cycloalkyl) independently are optionally substituted with one or more substituents independently selected from the group consisting of methyl, OH, OR$^4$ and F, $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, and $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents pyrazol-4-yl substituted at a nitrogen atom with a substituent $R^{1b}$ selected from the group consisting of methyl, ethyl, propyl, propan-2-yl, cyclopropyl, 2-methylpropyl, tertbutyl, butan-2-yl, cyclobutyl, 2,2-dimethyl-propyl, 3-methylbutan-2-yl, cyclopentyl, cyclohexyl, 1-cyclopropylmethyl, 1-cyclopropylethyl, 1-cyclobutylmethyl, 1-(1-methylcyclopropyl)methyl and 2,2,2-trifluoroethyl, in particular ethyl, propan-2-yl, 2-methylpropyl, butan-2-yl, cyclobutyl, cyclopentyl, 2,2-dimethylpropyl, 1-cyclopropylmethyl, 1-cyclopropylethyl, 1-(1-methylcyclopropyl)methyl or 1-cyclobutylmethyl, $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, and $R^3$ represents H or F, in particular H, $R^5$ represents H, F, Cl or methyl, in particular H or F, and $R^6$ and $R^7$ represent H.

A preferred embodiment of the present invention covers compounds of general formula (I), wherein $R^1$ represents pyrazol-4-yl substituted at the nitrogen atom at position 1 with a substituent $R^{1b}$ selected from the group consisting of methyl, ethyl, propyl, propan-2-yl, cyclopropyl, 2-methylpropyl, tertbutyl, butan-2-yl, cyclobutyl, 2,2-dimethylpropyl, 3-methylbutan-2-yl, cyclopentyl, cyclohexyl, 1-cyclo-propylmethyl, 1-cyclopropylethyl, 1-cyclobutylmethyl, 1-(1-methylcyclopropyl)methyl and 2,2,2-trifluoroethyl, in particular ethyl, propan-2-yl, 2-methylpropyl, butan-2-yl, cyclobutyl, cyclopentyl, 2,2-dimethylpropyl, 1-cyclopropylmethyl, 1-cyclopropylethyl, 1-(1-methylcyclopropyl)methyl or 1-cyclobutylmethyl, $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, and $R^3$ represents H, $R^5$ represents H, and $R^6$ and $R^7$ represent H.

A preferred embodiment of the present invention covers compounds of general formula (I), wherein $R^1$ represents pyrazol-4-yl substituted at the nitrogen atom at position 1 with a substituent $R^{1b}$ selected from the group consisting of methyl, ethyl, propyl, propan-2-yl, cyclopropyl, 2-methylpropyl, tertbutyl, butan-2-yl, cyclobutyl, 2,2-dimethylpropyl, 3-methylbutan-2-yl, cyclopentyl, cyclohexyl, 1-cyclo-propylmethyl, 1-cyclopropylethyl, 1-cyclobutylmethyl, 1-(1-methylcyclopropyl)methyl and 2,2,2-trifluoroethyl, in particular ethyl, propan-2-yl, 2-methylpropyl, butan-2-yl, cyclobutyl, cyclopentyl, 2,2-dimethylpropyl, 1-cyclopropylmethyl, 1-cyclopropylethyl, 1-(1-methylcyclopropyl)methyl or 1-cyclobutylmethyl, $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, and $R^3$ represents H, $R^5$ represents F, and $R^6$ and $R^7$ represent H.

A preferred embodiment of the present invention covers compounds of general formula (I), wherein $R^1$ represents pyrazol-4-yl substituted at a nitrogen atom with a substituent $R^{1b}$ selected from the group consisting of $C_1$-$C_5$-alkyl, —($C_1$-$C_3$-alkyl)-($C_3$-$C_7$-cycloalkyl) and $C_3$-$C_7$-cycloalkyl, wherein said $C_1$-$C_5$-alkyl, $C_3$-$C_7$-cycloalkyl and —($C_1$-$C_3$-alkyl)-($C_3$-$C_7$-cycloalkyl) independently are optionally substituted with one or more substituents independently selected from the group consisting of OH, $OR^4$ and F, $R^2$ represents $C_5$-$C_7$-cycloalkyl optionally substituted with 1 or 2 substituents $R^{2a}$ which are the same or different wherein $R^{2a}$ represents $C_1$-$C_5$-alkyl, $OC_1$-$C_5$-alkyl, F or Cl, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

In accordance with another aspect, the present invention covers compounds of general formula (I), wherein $R^1$ represents thiazolyl, in particular thiazol-5-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of methyl, OH, $OR^4$ and F, $R^2$ represents phenyl optionally substituted with 1 or 2 substituents $R^{2a}$ which are the same or different wherein $R^{2a}$ represents $C_1$-$C_5$-alkyl, $OC_1$-$C_5$-alkyl, F or Cl, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazolyl, in particular thiazol-5-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl, —$OC_3$-$C_7$-cycloalkyl, halogen or CN, wherein the substituent or at least one of said substituents is preferably positioned meta to the carbon atom which links the thiazolyl, in particular thiazol-5-yl, to the rest of the molecule; and wherein said $C_1$-$C_5$-alkyl, $C_3$-$C_7$-cycloalkyl, —($C_1$-$C_3$-alkyl)-($C_3$-$C_7$-cycloalkyl), —$OC_1$-$C_5$-alkyl and —$OC_3$-$C_7$-cycloalkyl independently are optionally substituted with one or more substituents independently selected from the group consisting of methyl, OH, $OR^4$ and F, and $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, and wherein if the substituent or at least one of said substituents is F, it is preferably positioned ortho to the carbon atom which links the phenyl to the rest of the molecule, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-5-yl, wherein said $R^1$ is substituted at a carbon atom with a substituent $R^{1a}$ selected from the group consisting of $C_1$-$C_5$-alkyl, —($C_1$-$C_3$-alkyl)-($C_3$-$C_7$-cycloalkyl) and $C_3$-$C_7$-cycloalkyl, wherein said substituent $R^{1a}$ is preferably attached to the carbon atom at position 2 of thiazol-5-yl; and wherein said $C_1$-$C_5$-alkyl, $C_3$-$C_7$-cycloalkyl and —($C_1$-$C_3$-alkyl)-($C_3$-$C_7$-cycloalkyl) independently are optionally substituted with one or more substituents independently selected from the group consisting of methyl, OH, $OR^4$ and F, $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-5-yl substituted at the carbon atom at position 2 with $C_3$-$C_7$-cycloalkyl, wherein said $C_3$-$C_7$-cycloalkyl independently is optionally substituted with one or more substituents independently selected from the group consisting of methyl, OH, $OR^4$ and F, $R^2$ represents phenyl substituted with 1 or 2 substituents $R^{2a}$ which are the same or different wherein $R^{2a}$ represents methyl, trifluoromethyl, trifluoromethoxy, F or Cl, and
  wherein if the substituent or at least one of said substituents is F, it is preferably positioned ortho to the carbon atom which links the phenyl to the rest of the molecule, and
  wherein if the substituent or at least one of said substituents is methyl, trifluoromethyl, trifluoromethoxy or Cl, it is preferably positioned para to the carbon atom which links the phenyl to the rest of the molecule, and
$R^3$ represents H or F, in particular H,
$R^4$ represents $C_1$-$C_5$-alkyl, optionally substituted with 1 to 5 fluorine atoms,
$R^5$ represents H, F, Cl or methyl, in particular H or F, and
$R^6$ and $R^7$ represent H.

A preferred embodiment of the present invention covers compounds of general formula (I), wherein
  $R^1$ represents thiazol-5-yl, optionally substituted at the carbon atom at position 2 with a substituent $R^{1a}$ selected from the group consisting of methyl, ethyl, propyl, propan-2-yl, cyclopropyl, 2-methylpropyl, ter-tbutyl, butan-2-yl, cyclobutyl, 2,2-dimethylpropyl, 3-methylbutan-2-yl, cyclopentyl, cyclohexyl, 1-cyclopropylmethyl, 1-cyclopropylethyl, 1-cyclobutylmethyl, 1-(1-methyl-cyclopropyl)methyl and 2,2,2-trifluoroethyl, in particular ethyl, propan-2-yl, cyclopropyl, 2-methylpropyl, butan-2-yl, cyclobutyl, 2,2-dimethylpropyl, cyclopentyl, 1-cyclopropylmethyl, 1-cyclopropylethyl, 1-(1-methylcyclopropyl)methyl and 1-cyclobutylmethyl,
  $R^2$ represents phenyl substituted with 1 or 2 substituents $R^{2a}$ which are the same or different wherein $R^{2a}$ represents methyl, trifluoromethyl, trifluoromethoxy, F or Cl, and
    wherein if the substituent or at least one of said substituents is F, it is preferably positioned ortho to the carbon atom which links the phenyl to the rest of the molecule, and
    wherein if the substituent or at least one of said substituents is methyl, trifluoromethyl, trifluoromethoxy or Cl, it is preferably positioned para to the carbon atom which links the phenyl to the rest of the molecule,
  $R^3$ represents H or F, in particular H,
  $R^5$ represents H, F, Cl or methyl, in particular H or F, and
  $R^6$ and $R^7$ represent H.

A preferred embodiment of the present invention covers compounds of general formula (I), wherein
  $R^1$ represents thiazol-5-yl, optionally substituted at the carbon atom at position 2 with a substituent $R^{1a}$ selected from the group consisting of methyl, ethyl, propyl, propan-2-yl, cyclopropyl, 2-methylpropyl, ter-tbutyl, butan-2-yl, cyclobutyl, 2,2-dimethylpropyl, 3-methylbutan-2-yl, cyclopentyl, cyclohexyl, 1-cyclopropylmethyl, 1-cyclopropylethyl, 1-cyclobutylmethyl, 1-(1-methyl-cyclopropyl)methyl and 2,2,2-trifluoroethyl, in particular ethyl, propan-2-yl, cyclopropyl, 2-methylpropyl, butan-2-yl, cyclobutyl, 2,2-dimethylpropyl, cyclopentyl, 1-cyclopropylmethyl, 1-cyclopropylethyl, 1-(1-methylcyclopropyl)methyl and 1-cyclobutylmethyl, $R^2$ represents phenyl substituted with 1 or 2 substituents $R^{2a}$ which are the same or different wherein $R^{2a}$ represents methyl, trifluoromethyl, trifluoromethoxy, F or Cl, and
  wherein if the substituent or at least one of said substituents is F, it is preferably positioned ortho to the carbon atom which links the phenyl to the rest of the molecule, and
  wherein if the substituent or at least one of said substituents is methyl, trifluoromethyl, trifluoromethoxy or Cl, it is preferably positioned para to the carbon atom which links the phenyl to the rest of the molecule,
$R^3$ represents H,
$R^5$ represents H, and
$R^6$ and $R^7$ represent H.

A preferred embodiment of the present invention covers compounds of general formula (I), wherein
  $R^1$ represents thiazol-5-yl, optionally substituted at the carbon atom at position 2 with a substituent $R^{1a}$ selected from the group consisting of methyl, ethyl, propyl, propan-2-yl, cyclopropyl, 2-methylpropyl, ter-tbutyl, butan-2-yl, cyclobutyl, 2,2-dimethylpropyl, 3-methylbutan-2-yl, cyclopentyl, cyclohexyl, 1-cyclopropylmethyl, 1-cyclopropylethyl, 1-cyclobutylmethyl, 1-(1-methylcyclopropyl)methyl and 2,2,2-trifluoroethyl, in particular ethyl, propan-2-yl, cyclopropyl, 2-methylpropyl, butan-2-yl, cyclobutyl, 2,2-dimethylpropyl, cyclopentyl, 1-cyclopropylmethyl, 1-cyclopropylethyl, 1-(1-methylcyclopropyl)methyl and 1-cyclobutylmethyl,
  $R^2$ represents phenyl substituted with 1 or 2 substituents $R^{2a}$ which are the same or different wherein $R^{2a}$ represents methyl, trifluoromethyl, trifluoromethoxy, F or Cl, and
    wherein if the substituent or at least one of said substituents is F, it is preferably positioned ortho to the carbon atom which links the phenyl to the rest of the molecule, and
    wherein if the substituent or at least one of said substituents is methyl, trifluoromethyl, trifluoromethoxy or Cl, it is preferably positioned para to the carbon atom which links the phenyl to the rest of the molecule,
  $R^3$ represents H,
  $R^5$ represents F, and
  $R^6$ and $R^7$ represent H.

In accordance with another aspect, the present invention covers compounds of general formula (I), wherein
  $R^1$ represents thiazolyl, in particular thiazol-2-yl, optionally substituted at one or more carbon atoms with 1 or 2 substituents $R^{1a}$ which are the same or different wherein $R^{1a}$ represents $C_1$-$C_5$-alkyl, $C_3$-$C_7$-cycloalkyl, —($C_1$-$C_3$-alkyl)-($C_3$-$C_7$-cycloalkyl), —O$C_1$-$C_5$-alkyl, —O$C_3$-$C_7$-cycloalkyl, halogen or CN,
    wherein said $C_1$-$C_5$-alkyl, $C_3$-$C_7$-cycloalkyl, —($C_1$-$C_3$-alkyl)-($C_3$-$C_7$-cycloalkyl), —O$C_1$-$C_5$-alkyl and —O$C_3$-$C_7$-cycloalkyl independently are optionally substituted with one or more substituents independently selected from the group consisting of methyl, OH, OR$^4$ and F,
  $R^2$ represents phenyl optionally substituted with 1 or 2 substituents $R^{2a}$ which are the same or different wherein $R^{2a}$ represents $C_1$-$C_5$-alkyl, O$C_1$-$C_5$-alkyl, F or Cl, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-2-yl substituted at a carbon atom with a substituent $R^{1a}$ selected from the group consisting of $C_1$-$C_5$-alkyl, —($C_1$-$C_3$-alkyl)-($C_3$-$C_7$-cycloalkyl) and $C_3$-$C_7$-cycloalkyl, wherein said substituent $R^{1a}$ is preferably attached to the carbon atom in the position 5 of thiazol-2-yl; and wherein said $C_1$-$C_5$-alkyl, $C_3$-$C_7$-cycloalkyl and —($C_1$-$C_3$-alkyl)-($C_3$-$C_7$-cycloalkyl) independently are optionally substituted with one or more substituents independently selected from the group consisting of methyl, OH, $OR^4$ and F, $R^2$ represents phenyl substituted with 1 or 2 substituents $R^{2a}$ which are the same or different wherein $R^{2a}$ represents $C_1$-$C_5$-alkyl, $OC_1$-$C_5$-alkyl, F or Cl, wherein if the substituent or at least one of said substituents is $C_1$-$C_5$-alkyl, —$OC_1$-$C_5$-alkyl or Cl, it is preferably positioned para to the carbon atom which links the phenyl to the rest of the molecule, and wherein said $C_1$-$C_5$-alkyl and —$OC_1$-$C_5$-alkyl independently are optionally substituted with 1 to 5 fluorine atoms, $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-2-yl substituted at the carbon atom in position 5 with $C_3$-$C_7$-cycloalkyl, wherein said $C_3$-$C_7$-cycloalkyl independently is optionally substituted with one or more substituents independently selected from the group consisting of methyl, OH, $OR^4$ and F, $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, and $R^3$ represents H or F, in particular H, $R^4$ represents $C_1$-$C_5$-alkyl, optionally substituted with 1 to 5 fluorine atoms, $R^5$ represents H, F, Cl or methyl, in particular H or F, and $R^6$ and $R^7$ represent H.

A preferred embodiment of the present invention covers compounds of general formula (I), wherein $R^1$ represents thiazol-2-yl, optionally substituted at the carbon atom in position 5 with a substituent $R^{1a}$ selected from the group consisting of methyl, ethyl, propyl, propan-2-yl, cyclopropyl, 2-methylpropyl, tert-butyl, butan-2-yl, cyclobutyl, 2,2-dimethylpropyl, 3-methylbutan-2-yl, cyclopentyl, cyclohexyl, 1-cyclopropylmethyl, 1-cyclopropylethyl, 1-cyclobutylmethyl, 1-(1-methyl-cyclopropyl)methyl and 2,2,2-trifluoroethyl, in particular ethyl, propan-2-yl, cyclopropyl, 2-methylpropyl, butan-2-yl, cyclobutyl, 2,2-dimethylpropyl, cyclopentyl, 1-cyclopropylmethyl, 1-cyclopropylethyl, 1-(1-methylcyclopropyl)methyl and 1-cyclobutylmethyl, $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, $R^3$ represents H or F, in particular H, $R^5$ represents H, F, Cl or methyl, in particular H or F, and $R^6$ and $R^7$ represent H.

A preferred embodiment of the present invention covers compounds of general formula (I), wherein $R^1$ represents thiazol-2-yl, optionally substituted at the carbon atom in position 5 with a substituent $R^{1a}$ selected from the group consisting of methyl, ethyl, propyl, propan-2-yl, cyclopropyl, 2-methylpropyl, tert-butyl, butan-2-yl, cyclobutyl, 2,2-dimethylpropyl, 3-methylbutan-2-yl, cyclopentyl, cyclohexyl, 1-cyclopropylmethyl, 1-cyclopropylethyl, 1-cyclobutylmethyl, 1-(1-methyl-cyclopropyl)methyl and 2,2,2-trifluoroethyl, in particular ethyl, propan-2-yl, cyclopropyl, 2-methylpropyl, butan-2-yl, cyclobutyl, 2,2-dimethylpropyl, cyclopentyl, 1-cyclopropylmethyl, 1-cyclopropylethyl, 1-(1-methylcyclopropyl)methyl and 1-cyclobutylmethyl, $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, $R^3$ represents H, $R^5$ represents H, and $R^6$ and $R^7$ represent H.

A preferred embodiment of the present invention covers compounds of general formula (I), wherein $R^1$ represents thiazol-2-yl, optionally substituted at the carbon atom in position 5 with a substituent $R^{1a}$ selected from the group consisting of methyl, ethyl, propyl, propan-2-yl, cyclopropyl, 2-methylpropyl, tert-butyl, butan-2-yl, cyclobutyl, 2,2-dimethylpropyl, 3-methylbutan-2-yl, cyclopentyl, cyclohexyl, 1-cyclopropylmethyl, 1-cyclopropylethyl, 1-cyclobutylmethyl, 1-(1-methyl-cyclopropyl)methyl and 2,2,2-trifluoroethyl, in particular ethyl, propan-2-yl, cyclopropyl, 2-methylpropyl, butan-2-yl, cyclobutyl, 2,2-dimethylpropyl, cyclopentyl, 1-cyclopropylmethyl, 1-cyclopylethyl, 1-(1-methylcyclopropyl)methyl and 1-cyclobutylmethyl, $R^2$ represents phenyl substituted with 1 or 2 substituents $R^{2a}$ which are the same or different wherein $R^{2a}$ represents methyl, trifluoromethyl, trifluoromethoxy, F or Cl, and wherein if the substituent or at least one of said substituents is F, it is preferably positioned ortho to the carbon atom which links the phenyl to the rest of the molecule, and wherein if the substituent or at least one of said substituents is methyl, trifluoromethyl, trifluoromethoxy or Cl, it is preferably positioned para to the carbon atom which links the phenyl to the rest of the molecule, $R^3$ represents H,
$R^5$ represents F, and
$R^6$ and $R^7$ represent H.

Preferred compounds are, namely 2-(1-benzothiophen-2-yl)-5-[({1-[2-fluoro-4-(trifluoromethyl)phenyl]cyclopropyl}carbonyl)amino]benzoic acid 2-[6-(1,1-difluoropropyl)pyridin-3-yl]-5-[({1-[2-fluoro-4-(trifluoromethyl)phenyl]cyclopropyl}carbonyl)amino]benzoic acid 2-(1-cyclobutyl-1H-pyrazol-4-yl)-5-[({1-[2-fluoro-4-(trifluoromethyl)phenyl]cyclopropyl}carbonyl)amino]benzoic acid 2-(6-ethoxypyridin-3-yl)-5-[({1-[2-fluoro-4-(trifluoromethyl)phenyl]cyclopropyl}carbonyl)amino]benzoic acid 2-(6-ethoxypyridin-3-yl)-5-[({1-[2-fluoro-4-(trifluoromethoxy)phenyl]cyclopropyl}carbonyl)amino]benzoic acid 2-(1-cyclobutyl-1H-pyrazol-4-yl)-3-fluoro-5-({[1-(2-fluoro-4-methylphenyl)cyclopropyl]carbonyl}amino)benzoic acid 2-[6-(1,1-difluoropropyl)pyridin-3-yl]-5-[({1-[2-fluoro-4-(trifluoromethoxy)phenyl]cyclopropyl}carbonyl)amino]benzoic acid 3-fluoro-5-[({1-[2-fluoro-4-(trifluoromethyl)phenyl]cyclopropyl}carbonyl)amino]-2-[6-(trifluoromethyl)pyridin-3-yl]benzoic acid 5-[({1-[2-fluoro-4-(trifluoromethyl)phenyl]cyclopropyl}carbonyl)amino]-2-[1-(2,2,2-trifluoroethyl)-1H-pyrazol-4-yl]benzoic acid 5-({[1-(4-chlorophenyl)cyclopropyl]carbonyl}amino)-2-(1-cyclobutyl-1H-pyrazol-4-yl)-3-fluorobenzoic acid 2-(1-cyclobutyl-1H-pyrazol-4-yl)-3-fluoro-5-[({1-[4-(trifluoromethyl)phenyl]cyclopropyl}carbonyl)amino]benzoic acid 2-(1-cyclobutyl-1H-pyrazol-4-yl)-3-fluoro-5-[({1-[4-(trifluoromethoxy)phenyl]cyclopropyl}carbonyl)amino]benzoic acid 2-(1-cyclobutyl-1H-pyrazol-4-yl)-5-({[1-(3,4-difluorophenyl)cyclopropyl]carbonyl}amino)-3-fluorobenzoic acid 2-(1-cyclobutyl-1H-pyrazol-4-yl)-3-fluoro-5-[({1-[3-fluoro-4-(trifluoromethyl)phenyl]cyclopropyl}carbonyl)amino]benzoic acid 2-(1-cyclobutyl-1H-pyrazol-4-yl)-5-({[1-(2,4-difluorophenyl)cyclopropyl]carbonyl}amino)-3-fluorobenzoic acid 5-({[1-(4-chloro-2-fluorophenyl)cyclopropyl]carbonyl}amino)-2-(1-cyclobutyl-1H-pyrazol-4-yl)-3-fluorobenzoic acid 2-(1-cyclobutyl-1H-pyrazol-4-yl)-3-fluoro-5-[({1-[2-fluoro-4-(trifluoromethyl)phenyl]cyclopropyl}carbonyl)amino]benzoic acid 2-(1-cyclobutyl-1H-pyrazol-4-yl)-3-fluoro-5-[({1-[2-fluoro-4-(trifluoromethoxy)phenyl]cyclopropyl}carbonyl)amino]benzoic acid 2-(1-cyclobutyl-1H-pyrazol-4-yl)-3-fluoro-5-({[[1-(5-fluoropyridin-2-yl)cyclopropyl]carbonyl}amino)benzoic acid 2-(1-cyclobutyl-3-fluoro-1H-pyrazol-4-yl)-5-[({1-[2-fluoro-4-(trifluoromethyl)phenyl]cyclopropyl}carbonyl)amino]benzoic acid 5-({[1-(4-chloro-3-fluorophenyl)cyclopropyl]carbonyl}amino)-2-(1-cyclobutyl-1H-pyrazol-4-yl)benzoic acid 2-(1-cyclobutyl-1H-pyrazol-4-yl)-5-[({1-[2-fluoro-4-(trifluoromethoxy)phenyl]cyclopropyl}carbonyl)amino]benzoic acid 5-({[1-(4-chloro-2-fluorophenyl)cyclopropyl]carbonyl}amino)-2-(1-cyclobutyl-1H-pyrazol-4-yl)benzoic acid 5-({[1-(5-chloro-2-fluorophenyl)cyclopropyl]carbonyl}amino)-2-(1-cyclobutyl-1H-pyrazol-4-yl)benzoic acid 2-(1-ethyl-1H-pyrazol-4-yl)-5-[({1-[2-fluoro-4-(trifluoromethyl)phenyl]cyclopropyl}carbonyl)amino]benzoic acid 2-(1-ethyl-1H-pyrazol-4-yl)-5-[({1-[2-fluoro-4-(trifluoromethoxy)phenyl]cyclopropyl}carbonyl)amino]benzoic acid 5-[({1-[2-fluoro-4-(trifluoromethyl)phenyl]cyclopropyl}carbonyl)amino]-2-[1-(propan-2-yl)-1H-pyrazol-4-yl]benzoic acid 5-[({1-[2-fluoro-4-(trifluoromethoxy)phenyl]cyclopropyl}carbonyl)amino]-2-[1-(propan-2-yl)-1H-pyrazol-4-yl]benzoic acid 2-(1-tert-butyl-1H-pyrazol-4-yl)-5-[({1-[2-fluoro-4-(trifluoromethyl)phenyl]cyclopropyl}carbonyl)amino]benzoic acid 2-(1-tert-butyl-1H-pyrazol-4-yl)-5-[({1-[2-fluoro-4-(trifluoromethoxy)phenyl]cyclopropyl}carbonyl)amino]benzoic acid 5-[({1-[2-fluoro-4-(trifluoromethyl)phenyl]cyclopropyl}carbonyl)amino]-2-[1-(2-methylpropyl)-1H-pyrazol-4-yl]benzoic acid 5-[({1-[2-fluoro-4-(trifluoromethoxy)phenyl]cyclopropyl}carbonyl)amino]-2-[1-(2-methylpropyl)-1H-pyrazol-4-yl]benzoic acid 2-[1-(2,2-dimethylpropyl)-1H-pyrazol-4-yl]-5-[({1-[2-fluoro-4-(trifluoromethyl)phenyl]cyclopropyl}carbonyl)amino]benzoic acid 2-[1-(2,2-dimethylpropyl)-1H-pyrazol-4-yl]-5-[({1-[2-fluoro-4-(trifluoromethoxy)phenyl]cyclopropyl}carbonyl)amino]benzoic acid 3-fluoro-5-({[1-(2-fluoro-4-methylphenyl)cyclopropyl]carbonyl}amino)-2-[1-(propan-2-yl)-1H-pyrazol-4-yl]benzoic acid 3-fluoro-5-[({1-[2-fluoro-4-(trifluoromethyl)phenyl]cyclopropyl}carbonyl)amino]-2-[1-(propan-2-yl)-1H-pyrazol-4-yl]benzoic acid 3-fluoro-5-[({1-[2-fluoro-4-(trifluoromethoxy)phenyl]cyclopropyl}carbonyl)amino]-2-[1-(propan-2-yl)-1H-pyrazol-4-yl]benzoic acid 2-(4-tert-butyl-1H-imidazol-1-yl)-3-fluoro-5-[({1-[2-fluoro-4-(trifluoromethyl)phenyl]cyclopropyl}carbonyl)amino]benzoic acid 2-(4-tert-butyl-1H-imidazol-1-yl)-3-fluoro-5-[({1-[2-fluoro-4-(trifluoromethoxy)phenyl]cyclopropyl}carbonyl)amino]benzoic acid 3-fluoro-5-[({1-[2-fluoro-4-(trifluoromethyl)phenyl]
    cyclopropyl}carbonyl)amino]-2-[1-(2-methylpropyl)-
    1H-pyrazol-4-yl]benzoic acid
2-[6-(difluoromethyl)pyridin-3-yl]-3-fluoro-5-[({1-[2-
    fluoro-4-(trifluoromethyl)phenyl]cyclopropyl}carbonyl)
    amino]benzoic acid
2-[6-(difluoromethyl)pyridin-3-yl]-3-fluoro-5-[({1-[2-
    fluoro-4-(trifluoromethoxy)phenyl]
    cyclopropyl}carbonyl)amino]benzoic acid
2-[6-(1,1-difluoropropyl)pyridin-3-yl]-3-fluoro-5-[({1-[2-
    fluoro-4-(trifluoromethyl)phenyl]cyclopropyl}carbonyl)
    amino]benzoic acid
2-[6-(1,1-difluoropropyl)pyridin-3-yl]-3-fluoro-5-[({1-[2-
    fluoro-4-(trifluoromethoxy)phenyl]
    cyclopropyl}carbonyl)amino]benzoic acid
3-chloro-2-(1-cyclobutyl-1H-pyrazol-4-yl)-5-[({1-[2-
    fluoro-4-(trifluoromethyl)phenyl]cyclopropyl}carbonyl)
    amino]benzoic acid
3-chloro-2-(1-cyclobutyl-1H-pyrazol-4-yl)-5-[({1-[2-
    fluoro-4-(trifluoromethoxy)phenyl]
    cyclopropyl}carbonyl)amino]benzoic acid
3-chloro-2-[6-(1,1-difluoropropyl)pyridin-3-yl]-5-[({1-[2-
    fluoro-4-(trifluoromethyl)phenyl]cyclopropyl}carbonyl)
    amino]benzoic acid
3-chloro-2-[6-(1,1-difluoropropyl)pyridin-3-yl]-5-[({1-[2-
    fluoro-4-(trifluoromethoxy)phenyl]
    cyclopropyl}carbonyl)amino]benzoic acid
2-(1-cyclobutyl-1H-pyrazol-4-yl)-5-[({1-[2-fluoro-4-(trif-
    luoromethyl)phenyl]cyclopropyl}carbonyl)amino]-3-
    methylbenzoic acid
2-(1-cyclobutyl-1H-pyrazol-4-yl)-5-[({1-[2-fluoro-4-(trif-
    luoromethoxy)phenyl]cyclopropyl}carbonyl)amino]-3-
    methylbenzoic acid
2-[1-(cyclobutylmethyl)-1H-pyrazol-4-yl]-5-[({1-[2-fluoro-
    4-(trifluoromethyl)phenyl]cyclopropyl}carbonyl)amino]
    benzoic acid
2-[1-(cyclobutylmethyl)-1H-pyrazol-4-yl]-5-[({1-[2-fluoro-
    4-(trifluoromethoxy)phenyl]cyclopropyl}carbonyl)
    amino]benzoic acid
2-(1-cyclopentyl-1H-pyrazol-4-yl)-5-[({1-[2-fluoro-4-(trif-
    luoromethyl)phenyl]cyclopropyl}carbonyl)amino]ben-
    zoic acid
2-(1-cyclohexyl-1H-pyrazol-4-yl)-5-[({1-[2-fluoro-4-(trif-
    luoromethyl)phenyl]cyclopropyl}carbonyl)amino]ben-
    zoic acid
2-(1-cyclohexyl-1H-pyrazol-4-yl)-5-[({1-[2-fluoro-4-(trif-
    luoromethoxy)phenyl]cyclopropyl}carbonyl)amino]ben-
    zoic acid
2-[1-(cyclopropylmethyl)-1H-pyrazol-4-yl]-3-fluoro-5-
    [({1-[2-fluoro-4-(trifluoromethyl)phenyl]
    cyclopropyl}carbonyl)amino]benzoic acid
2-[1-(cyclopropylmethyl)-1H-pyrazol-4-yl]-3-fluoro-5-
    [({1-[2-fluoro-4-(trifluoromethoxy)phenyl]
    cyclopropyl}carbonyl)amino]benzoic acid
3-fluoro-5-[({1-[2-fluoro-4-(trifluoromethyl)phenyl]
    cyclopropyl}carbonyl)amino]-2-(6-methylpyridin-3-yl)
    benzoic acid
2-{1-[(2S)-butan-2-yl]-1H-pyrazol-4-yl}-5-[({1-[2-fluoro-
    4-(trifluoromethyl)phenyl]cyclopropyl}carbonyl)amino]
    benzoic acid
2-{1-[(2R)-butan-2-yl]-1H-pyrazol-4-yl}-5-[({1-[2-fluoro-
    4-(trifluoromethoxy)phenyl]cyclopropyl}carbonyl)
    amino]benzoic acid
2-{1-[(2S)-butan-2-yl]-1H-pyrazol-4-yl}-3-fluoro-5-[({1-
    [2-fluoro-4-(trifluoromethyl)phenyl]
    cyclopropyl}carbonyl)amino]benzoic acid
2-{1-[(2R)-butan-2-yl]-1H-pyrazol-4-yl}-3-fluoro-5-[({1-
    [2-fluoro-4-(trifluoromethyl)phenyl]
    cyclopropyl}carbonyl)amino]benzoic acid
2-(1-ethyl-1H-pyrazol-4-yl)-3-fluoro-5-[({1-[2-fluoro-4-
    (trifluoromethyl)phenyl]cyclopropyl}carbonyl)amino]
    benzoic acid
2-(1-ethyl-1H-pyrazol-4-yl)-3-fluoro-5-[({1-[2-fluoro-4-
    (trifluoromethoxy)phenyl]cyclopropyl}carbonyl)amino]
    benzoic acid
5-({[1-(4-chloro-2-fluorophenyl)cyclopropyl]
    carbonyl}amino)-3-fluoro-2-[1-(propan-2-yl)-1H-pyra-
    zol-4-yl]benzoic acid
5-({[1-(4-chloro-2-fluorophenyl)cyclopropyl]
    carbonyl}amino)-2-(2-cyclobutyl-1,3-thiazol-5-yl)ben-
    zoic acid
2-(2-cyclobutyl-1,3-thiazol-5-yl)-5-({[1-(2-fluoro-4-meth-
    ylphenyl)cyclopropyl]carbonyl}amino)benzoic acid
2-(2-cyclobutyl-1,3-thiazol-5-yl)-5-[({1-[2-fluoro-4-(trif-
    luoromethyl)phenyl]cyclopropyl}carbonyl)amino]ben-
    zoic acid
2-(2-cyclobutyl-1,3-thiazol-5-yl)-5-[({1-[2-fluoro-4-(trif-
    luoromethoxy)phenyl]cyclopropyl}carbonyl)amino]ben-
    zoic acid
5-[({1-[2-fluoro-4-(trifluoromethyl)phenyl]
    cyclopropyl}carbonyl)amino]-2-{1-[(1-methylcyclopro-
    pyl)methyl]-1H-pyrazol-4-yl}benzoic acid
5-[({1-[2-fluoro-4-(trifluoromethoxy)phenyl]
    cyclopropyl}carbonyl)amino]-2-{1-[(1-methylcyclopro-
    pyl)methyl]-1H-pyrazol-4-yl}benzoic acid
2-{1-[(1S)-1-cyclopropylethyl]-1H-pyrazol-4-yl}-5-[({1-
    [2-fluoro-4-(trifluoromethyl)phenyl]
    cyclopropyl}carbonyl)amino]benzoic acid
2-(6-ethylpyridin-3-yl)-5-[({1-[2-fluoro-4-(trifluoromethyl)
    phenyl]cyclopropyl}carbonyl)amino]benzoic acid
2-(6-ethylpyridin-3-yl)-5-[({1-[2-fluoro-4-(trifluo-
    romethoxy)phenyl]cyclopropyl}carbonyl)amino]benzoic
    acid
2-(6-ethylpyridin-3-yl)-3-fluoro-5-[({1-[2-fluoro-4-(trifluo-
    romethyl)phenyl]cyclopropyl}carbonyl)amino]benzoic
    acid
3-fluoro-5-[({1-[2-fluoro-4-(trifluoromethoxy)phenyl]
    cyclopropyl}carbonyl)amino]-2-(1-methyl-1H-indazol-
    6-yl)benzoic acid
2-(2-cyclopentyl-1,3-thiazol-5-yl)-5-[({1-[2-fluoro-4-(trif-
    luoromethyl)phenyl]cyclopropyl}carbonyl)amino]ben-
    zoic acid
2-(2-cyclobutyl-1,3-thiazol-5-yl)-3-fluoro-5-[({1-[2-fluoro-
    4-(trifluoromethyl)phenyl]cyclopropyl}carbonyl)amino]
    benzoic acid
3-fluoro-5-[({1-[2-fluoro-4-(trifluoromethyl)phenyl]
    cyclopropyl}carbonyl)amino]-2-[1-(2,2,2-trifluoroethyl)-
    1H-pyrazol-4-yl]benzoic acid or an isomer, enantiomer, diastereomer, tautomer, racemate, hydrate, solvate, or a salt thereof, or a mixture of same.

It is to be understood that the present invention relates also to any combination of the preferred embodiments described above.

As mentioned above, compounds of the present invention effectively inhibit Bradykinin B1 receptor and may therefore be used for the treatment or prophylaxis of diseases that are related to pain and to inflammation.

Additionally, compounds of the present invention reduce the release of inflammation related cytokines like IL-6 and IL-8.

Pharmaceutical Compositions of the Compounds of the Invention

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixture agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations.

For example, the compounds of this invention can be combined with known hormonal therapeutical agents.

In particular, the compounds of the present invention can be administered in combination or as comedication with hormonal contraceptives. Hormonal contraceptives are for example Combined Oral Contraceptives (COCs) or Progestin-Only-Pills (POPs) or hormone-containing devices.

COCs include but are not limited to birth control pills or a birth control method that includes a combination of an estrogen (estradiol) and a progestogen (progestin). The estrogenic part is in most of the COCs ethinyl estradiol. Some COCs contain estradiol or estradiol valerate.

Said COCs contain the progestins norethynodrel, norethindrone, norethindrone acetate, ethynodiol acetate, norgestrel, levonorgestrel, norgestimate, desogestrel, gestodene, drospirenone, dienogest, or nomegestrol acetate.

Birth control pills include for example but are not limited to Yasmin, Yaz, both containing ethinyl estradiol and drospirenone; Microgynon or Miranova containing levonorgestrel and ethinyl estradiol; Marvelon containing ethinyl estradiol and desogestrel; Valette containing ethinyl estradiol and dienogest; Belara and Enriqa containing ethinyl estradiol and chlormadinonacetate; Qlaira containing estradiol valerate and dienogest as active ingredients; and Zoely containing estradiol and normegestrol.

POPs are contraceptive pills that contain only synthetic progestogens (progestins) and do not contain estrogen. They are colloquially known as mini pills.

POPs include but are not limited to Cerazette containing desogestrel; and Micronor containing norethindrone.

Other Progeston-Only forms are intrauterine devices (IUDs), for example Mirena containing levonorgestrel or injectables, for example Depo-Provera containing medroxyprogesterone acetate, or implants, for example Implanon containing etonogestrel.

Other hormone-containing devices with contraceptive effect which are suitable for a combination with the compounds of the present invention are vaginal rings like Nuvaring containing ethinyl estradiol and etonogestrel, or transdermal systems like contraceptive patches, for example Ortho-Evra containing ethinyl estradiol and norelgestromin or Apleek (Lisvy) containing ethinyl estradiol and gestodene.

A preferred embodiment of the present invention is the administration of a compound of general formula (I) in combination with a COC or a POP or other Progestin-Only forms, as well as in combination with vaginal rings or contraceptive patches as mentioned above.

Furthermore, the compounds of the present invention can be combined with therapeutic agents or active ingredients, that are already approved or that are still under development for the treatment and/or prophylaxis of diseases which are related to or mediated by the Bradykinin B1 receptor.

For the treatment and/or prophylaxis of urinary tract diseases, the compounds of the present invention can be administered in combination or as co-medication with any substance that can be applied as therapeutic agent in the following indications: Urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular interstitial cystitis; bladder pain syndrome; idiopathic bladder hypersensitivity.

For the treatment and/or prophylaxis of overactive bladder and symptoms related to overactive bladder, the compounds of the present invention can be administered in combination or as co-medication in addition to behavioural therapy like diet, lifestyle or bladder training with anticholinergics like oxybutynin, tolterodine, propiverine, solifenacin, darifenacin, trospium, fesoterdine; β-3 agonists like mirabegron; neurotoxins like onabutolinumtoxin A; or antidepressants like imipramine, duloxetine.

For the treatment and/or prophylaxis of interstitial cystitis and/or bladder pain syndrome, the compounds of the present invention can be administered in combination or as co-medication in addition to behavioural therapy like diet, lifestyle or bladder training with pentosans like elmiron; antidepressants like amitriptyline, imipramine; or antihistamines like loratadine.

For the treatment and/or prophylaxis of gynaecological diseases, the compounds of the present invention can be administered in combination or as co-medication with any substance that can be applied as therapeutic agent in the following indications: dysmenorrhea, including primary and secondary; dyspareunia; endometriosis; endometriosis-associated pain; endometriosis-associated symptoms, such as and in particular dysmenorrhea, dyspareunia, dysuria, or dyschezia.

For the treatment and/or prophylaxis of dysmenorrhea, including primary and secondary; dyspareunia; endometriosis and endometriosis-associated pain, the compounds of the present invention can be administered in in combination with ovulation inhibiting treatment, in particular COCs as mentioned above or contraceptive patches like Ortho-Evra or Apleek (Lisvy); or with progestogenes like dienogest (Visanne); or with GnRH analogous, in particular GnRH agonists and antagonists, for example leuprorelin, nafarelin, goserelin, cetrorelix, abarelix, ganirelix, degarelix; or with androgens: danazol.

For the treatment and/or prophylaxis of diseases, which are associated with pain, or pain syndromes, the compounds of the present invention can be administered in combination or as co-medication with any substance that can be applied as therapeutic agent in the following indications:

pain-associated diseases or disorders like hyperalgesia, allodynia, functional bowel disorders (such as irritable bowel syndrome) and arthritis (such as osteoarthritis, rheumatoid arthritis and ankylosing spondylitis), burning mouth syndrome, burns, migraine or cluster headache, nerve injury, traumatic nerve injury, post-traumatic injuries (including fractures and sport injuries), neuritis, neuralgia, poisoning, ischemic injury, interstitial cystitis, bladder pain syndrome, viral, trigeminal neuralgia, small fiber neuropathy, diabetic neuropathy, chronic arthritis and related neuralgias, HIV and HIV treatment-induced neuropathy.

The compounds of the present invention can be combined with other pharmacological agents and compounds that are intended to treat inflammatory diseases, inflammatory pain or general pain conditions.

In addition to well-known medicaments which are already approved and on the market, the compounds of the present invention can be administered in combination with inhibitors of the P2X purinoceptor family (P2X3, P2X4), with inhibitors of IRAK4 and with antagonists of the prostanoid EP4 receptor.

In particular, the compounds of the present invention can be administered in combination with pharmacological endometriosis agents, intended to treat inflammatory diseases, inflammatory pain or general pain conditions and/or interfering with endometriotic proliferation and endometriosis associated symptoms, namely with inhibitors of Aldo-keto-reductase1C3 (AKR1C3) and with functional blocking antibodies of the prolactin receptor.

The compounds of the present invention can be combined with other pharmacological agents and compounds that are intended for the treatment, prevention or management of cancer.

In particular, the compounds of the present invention can be administered in combination with 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, or zorubicin.

Furthermore, the compounds of the present invention can be combined with active ingredients, which are well known for the treatment of cancer-related pain and chronic pain. Such combinations include, but are not limited to step II opioids like codeine phosphate, dextropropoxyphene, dihydro-codeine, Tramadol), step III opioids like morphine, fentanyl, buprenorphine, oxymorphone, oxycodone and hydromorphone; and other medications used for the treatment of cancer pain like steroids as Dexamethasone and methylprednisolone; bisphosphonates like Etidronate, Clodronate, Alendronate, Risedronate, and Zoledronate; tricyclic antidepressants like Amitriptyline, Clomipramine, Desipramine, Imipramine and Doxepin; class I antiarrhythmics like mexiletine and lidocaine; anticonvulsants like carbamazepine, Gabapentin, oxcarbazepine, phenytoin, pregabalin, topiramate, alprazolam, diazepam, flurazepam, pentobarbital and phenobarbital.

In addition to those mentioned above, the inventive Bradykinin B1 inhibitors can also be combined with any of the following active ingredients:

active ingredients for Alzheimer's therapy, for example acetylcholinesterase inhibitors (e.g. donepezil, rivastigmine, galantamine, tacrine), NMDA (N-methyl-D-aspartate) receptor antagonists (e.g. memantine); L-DOPA/carbidopa (L-3,4-dihydroxyphenylalanine), COMT (catechol-O-methyltransferase) inhibitors (e.g. entacapone), dopamine agonists (e.g. ropinrole, pramipexole, bromocriptine), MAO-B (monoaminooxidase-B) inhibitors (e.g. selegiline), anticholinergics (e.g. trihexyphenidyl) and NMDA antagonists (e.g. amantadine) for treatment of Parkinson's; beta-interferon (IFN-beta) (e.g. IFN beta-1b, IFN beta-1a Avonex® and Betaferon®), glatiramer acetate, immunoglobulins, natalizumab, fingolimod and immunosuppressants such as mitoxantrone, azathioprine and cyclophosphamide for treatment of multiple sclerosis; substances for treatment of pulmonary disorders, for example beta-2-sympathomimetics (e.g. salbutamol), anticholinergics (e.g. glycopyrronium), methylxanthines (e.g. theophylline), leukotriene receptor antagonists (e.g. montelukast), PDE-4 (phosphodiesterase type 4) inhibitors (e.g. roflumilast), methotrexate, IgE antibodies, azathioprine and cyclophosphamide, cortisol-containing preparations; substances for treatment of osteoarthritis such as non-steroidal anti-inflammatory substances (NSAIDs). In addition to the two therapies mentioned, methotrexate and biologics for B-cell and T-cell therapy (e.g. rituximab, abatacept) should be mentioned for rheumatoid disorders such as rheumatoid arthritis and juvenile idiopathic arthritis. Neurotrophic substances such as acetylcholinesterase inhibitors (e.g. donepezil), MAO (monoaminooxidase) inhibitors (e.g. selegiline), interferons und anticonvulsives (e.g. gabapentin); active ingredients for treatment of cardiovascular disorders such as beta-blockers (e.g. metoprolol), ACE inhibitors (e.g. benazepril), diuretics (e.g. hydrochlorothiazide), calcium channel blockers (e.g. nifedipine), statins (e.g. simvastatin); anti-diabetic drugs, for example metformin and glibenclamide, sulphonylureas (e.g. tolbutamide) and insulin therapy for treatment of diabetes and metabolic syndrome. Active ingredients such as mesalazine, sulfasalazine, azathioprine, 6-mercaptopurine or methotrexate, probiotic bacteria (Mutaflor, VSL #3@, *Lactobacillus* GG, *Lactobacillus plantarum, L. acidophilus, L. casei, Bifidobacterium infantis* 35624, *Enterococcus fecium* SF68, *Bifidobacterium longum, Escherichia coli* Nissle 1917), antibiotics, for example ciprofloxacin and metronidazole, antidiarrhoea drugs, for example loperamide, or laxatives (bisacodyl) for treatment of chronic-inflammatory bowel disorders. Immunosuppressants such as glucocorticoids and non-steroidale anti-inflammatory substances (NSAIDs), cortisone, chloroquine, cyclosporine, azathioprine, belimumab, rituximab, cyclophosphamide for treatment of lupus erythematosus. By way of example but not exclusively, calcineurin inhibitors (e.g. tacrolimus and ciclosporin), cell division inhibitors (e.g. azathioprine, mycophenolate mofetil, mycophenolic acid, everolimus or sirolimus), rapamycin, basiliximab, daclizumab, anti-CD3 antibodies, anti-T-lymphocyte globulin/anti-lymphocyte globulin for organ transplants, Vitamin D3 analogues, for example calcipotriol, tacalcitol or calcitriol, salicylic acid, urea, ciclosporine, methotrexate, or efalizumab for dermatological disorders.

Methods of Treating

The present invention relates to a method for using the compounds of the present invention and compositions thereof, to inhibit the Bradykinin B1 receptor.

The present invention relates to a method for using the compounds of the present invention and compositions thereof, to treat mammalian disorders and diseases which include but are not limited to:

Diseases related to pain and inflammation, in particular selected from the group consisting of
visceral pain e.g. related to pancreatitis, interstitial cystitis, bladder pain syndrome, renal colic, or prostatitis, chronic pelvic pain, or pain related to infiltrating endometriosis;
neuropathic pain such as post herpetic neuralgia, acute zoster pain, pain related to nerve injury, the dynias, including vulvodynia, phantom limb pain, pain related to root avulsions, pain related to radiculopathy, painful traumatic mononeuropathy, painful entrapment neuropathy, pain related to carpal tunnel syndrome, ulnar neuropathy, pain related to tarsal tunnel syndrome, painful diabetic neuropathy, painful polyneuropathy, trigeminal neuralgia, or pain related to familial amyloid polyneuropathy;
central pain syndromes potentially caused by virtually any lesion at any level of the nervous system including but not limited to pain related to stroke, multiple sclerosis, and spinal cord injury;
postsurgical pain syndromes (including postmastectomy pain syndrome, postthoracotomy pain syndrome, stump pain), bone and joint pain (osteoarthritis), spine pain (including acute and chronic low back pain, neck pain, pain related to spinal stenosis), shoulder pain, repetitive motion pain, dental pain, pain related to sore throat, cancer pain, burn pain including sun-burn, myofascial pain (pain related to muscular injury, fibromyalgia) postoperative, and perioperative pain (including but not limited to general surgery, orthopaedic, and gynaecological surgery); and
acute and chronic pain, chronic pelvic pain, endometriosis associated pain, dysmenorrhea associated pain (primary and secondary), pain associated with uterine fibroids, vulvodynia associated pain, as well as pain associated with angina, or inflammatory pain of varied origins (including but not limited to pain associated with osteoarthritis, rheumatoid arthritis, rheumatic disease, tenosynovitis, gout, ankylosing spondylitis, and bursitis);
and diseases like or related to a disease selected from related to the group consisting of:
gynaecological disorders and/or diseases, or effects and/or symptoms which negatively influence women health including endometriosis, uterine fibroids, preeclampsia, hormonal deficiency, spasms of the uterus, or heavy menstrual bleeding;

the respiratory or excretion system including any of inflammatory hyperreactive airways, inflammatory events associated with airways disease like chronic obstructive pulmonary disease, asthma including allergic asthma (atopic or non-atopic) as well as exercise-induced bronchoconstriction, occupational asthma, viral or bacterial exacerbation of asthma, other non-allergic asthmas and wheezy-infant syndrome, chronic obstructive pulmonary disease including emphysema, adult respiratory distress syndrome, bronchitis, pneumonia, cough, lung injury, lung fibrosis, allergic rhinitis (seasonal and perennial), vasomotor rhinitis, angioedema (including hereditary angioedema and drug-induced angioedema including that caused by angiotensin converting enzyme (ACE) or ACE/neutral endopeptidase inhibitors like omepatrilat), pneumoconiosis, including aluminosis, anthracosis, asbestosis, chalicosis, ptilosis, siderosis, silicosis, tabacosis and byssinosis, bowel disease including Crohn's disease and ulcerative colitis, irritable bowel syndrome, pancreatitis, nephritis, cystitis (interstitial cystitis), bladder pain syndrome, kidney fibrosis, kidney failure, hyperactive bladder, and overactive bladder;

dermatology including pruritus, itch, inflammatory skin disorders including psoriasis, eczema, and atopic dermatitis;

affection of the joints or bones including rheumatoid arthritis, gout, osteoporosis, osteoarthritis, and ankylosing spondylitis;

affection of the central and peripheral nervous system including neurodegenerative diseases including Parkinson's and Alzheimer's disease, amyotrophic lateral sclerosis (ALS), epilepsy, dementia, headache including cluster headache, migraine including prophylactic and acute use, stroke, closed head trauma, and multiple sclerosis;

infection including HIV infection, and tuberculosis;

trauma associated with oedema including cerebral oedema, burns, sunburns, and sprains or fracture;

poisoning including aluminosis, anthracosis, asbestosis, chalicosis, ptilosis, siderosis, silicosis, tabacosis, and byssinosis uveitis;

diabetes cluster or metabolism like diabetes type 1, diabetes type 2, diabetic vasculopathy, diabetic neuropathy, diabetic retinopathy, post capillary resistance or diabetic symptoms associated with insulitis (e.g. hyperglycaemia, diuresis, proteinuria and increased nitrite and kallikrein urinary excretion), diabetic macular oedema, metabolic syndrome, insulin resistance, obesity, or fat or muscle metabolism;

cachexia associated with or induced by any of cancer, AIDS, coeliac disease, chronic obstructive pulmonary disease, multiple sclerosis, rheumatoid arthritis, congestive heart failure, tuberculosis, familial amyloid polyneuropathy, mercury poisoning (acrodynia), and hormonal deficiency;

cardio-vascular system including congestive heart failure, atherosclerosis, congestive heart failure, myocardial infarct, and heart fibrosis; and other conditions including primary peritonitis, secondary peritonitis, septic shock, sepsis, muscle atrophy, spasms of the gastrointestinal tract, benign prostatic hyperplasia, and liver diseases such as non-alcoholic and alcoholic fatty liver disease, non-alcoholic and alcoholic steatohepatitis, liver fibrosis, or liver cirrhosis.

A preferred embodiment of the present invention relates to a method for using the compounds of the present invention and compositions thereof, to treat a gynaecological disease, preferably dysmenorrhea, dyspareunia or endometriosis, endometriosis-associated pain, or other endometriosis-associated symptoms, wherein said symptoms include dysmenorrhea, dyspareunia, dysuria, or dyschezia. Additionally the present invention relates to a method for using the compounds of the present invention and compositions thereof, to treat osteoarthritis, rheumatoid arthritis, gout, neuropathic pain, asthma, cough, lung injury, lung fibrosis, pneumonia, kidney fibrosis, kidney failure pruritus, irritable bowel disease, overactive urinary bladder, diabetes type 1, diabetes type 2, diabetic neuropathy, diabetic retinopathy, diabetic macular oedema, metabolic syndrome, obesity, heart fibrosis, cachexia, muscle atrophy, Alzheimer's disease, bladder pain syndrome and interstitial cystitis.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a gynaecological disease.

Dose and Administration

Based upon standard laboratory techniques known to evaluate compounds useful for the treatment of disorders and/or diseases which are mediated by Bradykinin B1 receptor, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed the mode of administration, the period of treatment, the age and sex of the patient treated, and the nature and extent of the condition treated.

The total amount of the active ingredient to be administered will generally range from about 0.001 mg/kg to about 200 mg/kg body weight per day, preferably from about 0.01 mg/kg to about 20 mg/kg body weight per day. A preferred administration of the compound of the present invention includes but is not limited to 0.1 mg/kg to about 10 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. A preferred oral unit dosage for administration of the compounds of the present invention includes but is not limited to 0.1 mg/kg to about 10 mg/kg body weight one to three times a day to once a week. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg of total body weight. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases treated with said method are gynaecological disorders, more preferably dysmenorrhea, dyspareunia or endometriosis, endometriosis-associated pain, or other endometriosis-associated symptoms, wherein said symptoms include dysmenorrhea, dyspareunia, dysuria, or dyschezia. Further diseases which can be treated with said method are osteoarthritis, rheumatoid arthritis, gout, neuropathic pain, asthma, cough, lung injury, lung fibrosis, pneumonia, kidney fibrosis, kidney failure pruritus, irritable bowel disease, overactive urinary bladder, diabetes type 1, diabetes type 2, diabetic neuropathy, diabetic retinopathy, diabetic macular oedema, metabolic syndrome, obesity, heart fibrosis, cachexia, muscle atrophy, Alzheimer's disease, bladder pain syndrome and interstitial cystitis.

Preferably, the method of treating the diseases mentioned above is not limited to the treatment of said disease but also includes the treatment of pain related to or associated with said diseases.

The compounds of the present invention can be used in particular in therapy and prevention, i.e. prophylaxis, of genitourinary, gastrointestinal, respiratory or pain-related disease, condition or disorder.

Methods of testing for a particular pharmacological or pharmaceutical property are well known to persons skilled in the art.

The example testing experiments described herein serve to illustrate the present invention and the invention is not limited to the examples given.

Synthesis of Compounds of General Formula (I) of the Present Invention

Compounds of general formula (I) with the meaning of $R^1$, $R^2$, $R^3$, $R^5$, $R^6$ and $R^7$ as defined in general formula (I), can be synthesised according to various general procedures.

Scheme 1 depicts the synthesis starting from synthons of the formula (II), wherein Hal stands for Cl, Br or I, Br being preferred; and wherein ALK stands for $C_1$-$C_5$-alkyl, methyl, ethyl and propyl being preferred). The aryl halides of the general formula (II) can be cross-coupled with boronic acids of the general formula (III) or alternatively with their respective pinacol esters to yield compounds of general formula (IV) by Pd-mediated reactions (Suzuki coupling) known to those skilled in the art. A suitable solvent (for example N,N-dimethylformamide, tetrahydrofuran, 1,4-dioxane, 1,2-dimethoxyethane and optionally water) is used and a base (such as triethylamine, potassium carbonate, caesium carbonate) and a catalyst-ligand mixture, for example of palladium(II) acetate/triphenylphosphine, tetrakis(triphenylphosphine)palladium(0), bis(triphenylphosphine)palladium(II) dichloride, bis(diphenylphosphino)ferrocenedichloropalladium (II) is utilised at temperatures between 20° C. and 120° C., preferred at 100° C.

Aromatic amines of general formula (IV) may react with carboxylic acids of general formula (V) by methods known to those skilled in the art to give the amide compounds of general formula (VI). The reaction is mediated by activating a carboxylic acid of general formula (V) with reagents such as dicyclohexylcarbodiimide (DCC), 1-(3-dimethylaminopropyl)-3-ethylcarbodiimide (EDCI), N-hydroxybenzotriazole (HOBT), N-[(dimethylamino)-(3H-[1,2,3]triazolo[4,5-b]pyridin-3-yloxy)methyliden]-N-methylmethanaminium hexafluorophosphate (HATU) or propylphosphonic anhydride (T3P). For example, the reaction with HATU takes place in an inert solvent, such as N,N-dimethylformamide, dichloromethane or dimethyl sulfoxide in the presence of the appropriate aniline of general formula (IV) and a tertiary amine (such as triethylamine or diisopropylethylamine) at temperatures between −30° C. and +60° C.

It is also possible to convert a carboxylic acid of the general formula (V) into the corresponding carboxylic acid chloride with an inorganic acid chloride (such as phosphorus pentachloride, phosphorus trichloride or thionyl chloride) and then into the amide compounds of general formula (VI), in pyridine or a solvent (such as dichloromethane, or N,N-dimethylformamide), in the presence of the appropriate amine formula (IV) and a tertiary amine (for example triethylamine) at temperatures between −30° C. and +60° C. The ester moiety of compounds of general formula (VI) are then converted to the final target compounds of general formula (I) by ester group saponification in a solvent (such as tetrahydrofuran, methanol or N,N-dimethylformamide) using an appropriate base (for example aqueous lithium hydroxide or aqueous sodium hydroxide) at temperatures between 0° C. and +80° C. Alternatively, the ester compounds of general formula (VI) can be converted to the final target compounds of general formula (I) by ester group saponification using an appropriate inorganic acid (for example hydrochloric acid or sulfuric acid) at temperatures between 0° C. and +80° C., usually at circa +60° C.

Aryl halides of the general formula (II) are either commercially available or can be synthesised by those skilled in the art from the corresponding carboxylic acid compound. For example, by reacting the corresponding carboxylic acid with an alcohol (such as methanol, ethanol or propanol) in inorganic acid (for example hydrochloric acid or sulfuric acid) at temperatures between 0° C. and 100° C.

The starting materials of the general formula (II) are either commercially available or can be synthesized via methods known to those skilled in the art from appropriate precursors. For example, the amino group may be obtained by reduction of the corresponding nitro group with hydrogen in the presence of a palladium catalyst in solvents like ethanol, ethyl acetate or mixtures thereof. Alternatively, the nitro group may be reduced using iron powder in solvents like methanol or ethanol in the presence of acid (such as hydrochloric or acetic acid). The nitro group may be introduced by classical methods like treatment with nitric acid/sulphuric acid or potassium nitrate/sulphuric acid (with appropriate concentration and volume ratio) at temperatures between 0° C. and 25° C. The sequence of reaction steps (nitro reduction, Suzuki reaction, amide formation, nitrile hydrolysis) may be changed as appropriate.

The carboxylic acids of the general formula (V) are either commercially available or can be synthesised via methods known to those skilled in the art from appropriate precursors. For example, arylcyclopropanecarboxylic acids may be prepared from the corresponding arylacetonitrile by cyclopropanation with 1-bromo-2-chloroethane (1.5 eq) in aqueous base (such as sodium hydroxide solution) in the presence of benzyltriethylammonium chloride (0.02 eq.) and subsequent acidic or basic hydrolysis of the nitrile with e.g. lithium hydroxide in water or concentrated hydrochloric acid at temperatures between 20° C. and 100° C.

ride, bis(diphenylphosphino)ferrocenedichloropalladium (II) is utilised at temperatures between 20° C. and 120° C., preferred at 100° C. The nitro group of a compound of general formula (VIII) is then reduced to the corresponding aniline of general formula (IX) by reaction under a hydrogen atmosphere in the presence of a palladium catalyst (for example 5-10% palladium on carbon) in an appropriate solvent (for example ethanol or ethyl acetate) at temperatures between 0° C. and 100° C. In analogy to the procedures described for Scheme 1, amide coupling gives compounds of the general formula (X). The nitrile moiety of formula (X) is hydrolysed to carboxylic acid of general formula (I) by reaction with either an inorganic base (for example aqueous lithium hydroxide or aqueous sodium hydroxide) or an inorganic acid (for example hydrochloric acid or sulfuric acid) optionally in an inert solvent (such as tetrahydrofuran, 1,4-dioxane or N,N-dimethylformamide) at temperatures between 10° C. and 100° C.

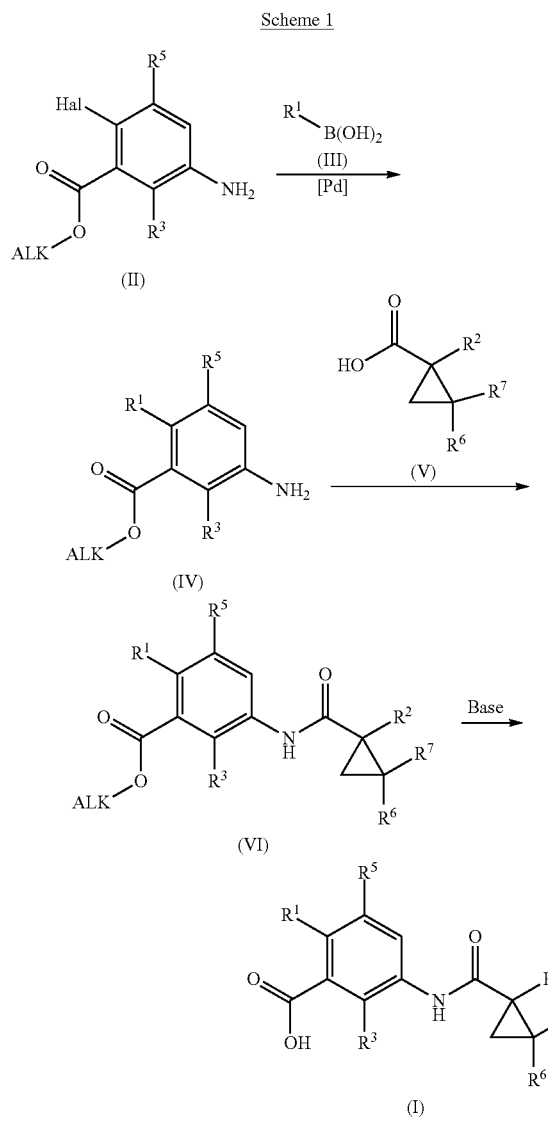

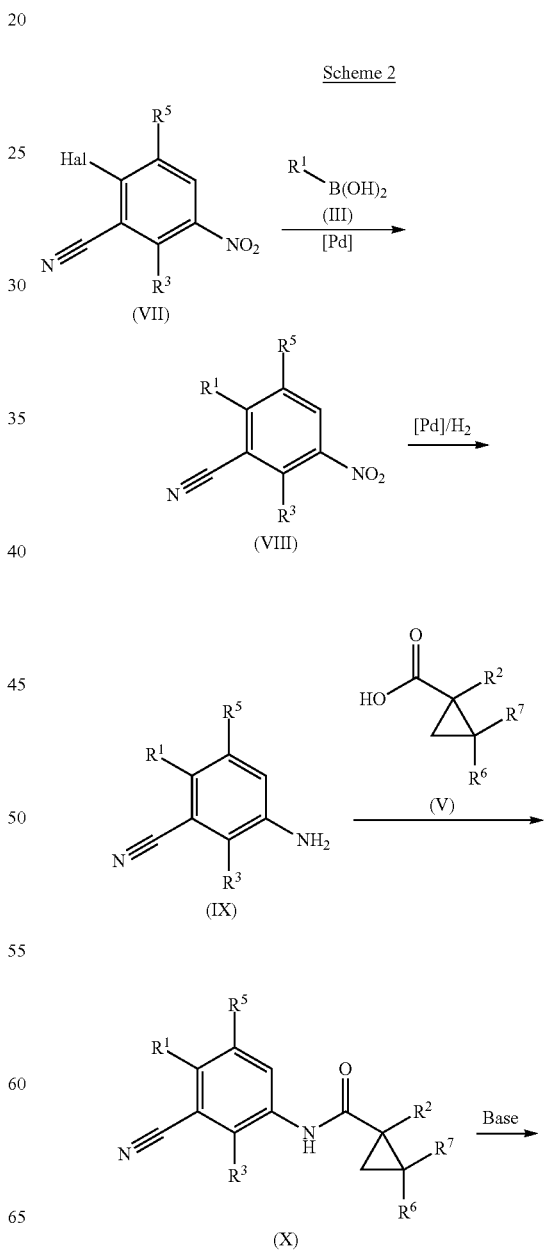

Scheme 2 depicts the synthesis starting from synthons of the formula (VII), wherein Hal stands for Cl, Br or I, Br being preferred. The aryl halides of the general formula (VII) can be cross-coupled with boronic acids of the general formula (III) or alternatively with their respective pinacol esters to yield compounds of general formula (VIII) by Pd-mediated reactions (Suzuki coupling) known to those skilled in the art. A suitable solvent (for example N,N-dimethylformamide, tetrahydrofuran, 1,4-dioxane, 1,2-dimethoxyethane and optionally water) is used and a base (such as potassium carbonate or caesium carbonate) and a catalyst-ligand mixture, for example of palladium(II) acetate/triphenylphosphine, tetrakis(triphenylphosphine) palladium(0), bis(triphenylphosphine)-palladium(II) dichlo-

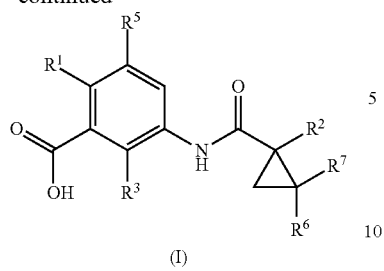

(I)

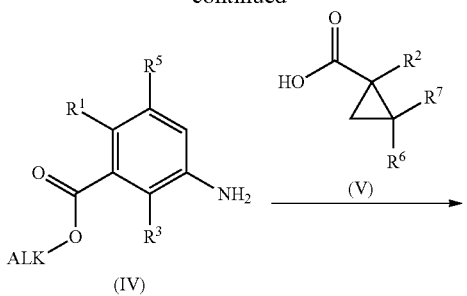

(IV)

Scheme 3 shows an alternative approach in which the sequence of reaction steps is changed and the nitrite moiety of general formula (IX) is transformed into an ester group in two steps (wherein ALK stands for methyl, ethyl or propyl) and later revealed as the carboxylic acid group. Starting from synthons of general formula (IX), first the nitrile is converted into the carboxylic acid of general formula (XI) and then reacted with a suitable alcohol (such as methanol, ethanol or propanol) in inorganic acid (for example hydrochloric acid or sulfuric acid) at temperatures between 0° C. and 100° C. to form ester compounds of general formula (IV). In analogy to the procedures described for Scheme 1, amide coupling gives compounds of the general formula (VI), followed by ester group saponification to yield the target compounds of general formula (I).

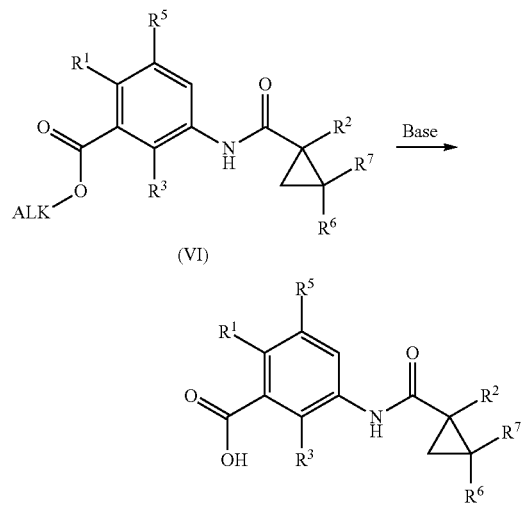

Scheme 3

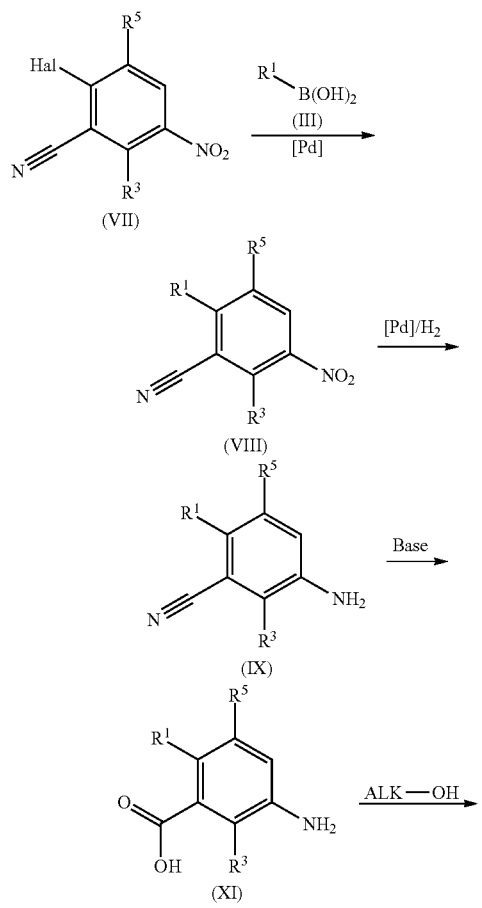

Scheme 4 shows an alternative approach to synthesis of compounds of general formula (I) where $R^1$ is an N-linked optionally substituted 5-membered heteroaryl group, for example pyrazolyl or imidazolyl, or alternatively $R^1$ is an N-linked optionally substituted bicyclic 8- to 10-membered heteroaryl group, for example indole. Starting from synthons of the general formula (VII) (wherein Hal stands for F, Cl or Br) the aryl halide can first be substituted by a nucleophile of general formula (XIV) to yield a compound of general formula (VIII). The substitution takes place in a dipolar aprotic solvent such as acetonitrile, dimethylsulfoxide or N,N-dimethylformamide and in the presence of an appropriate base (for example potassium carbonate or sodium hydride) at temperatures between 20° C. and 100° C., preferably at 60° C. In analogy to the procedures described for Scheme 2, nitro group reduction followed by amide formation gives compounds of general formula (X) that are subsequently converted to the final targets of general formula (I) by nitrile group hydrolysis.

Scheme 4

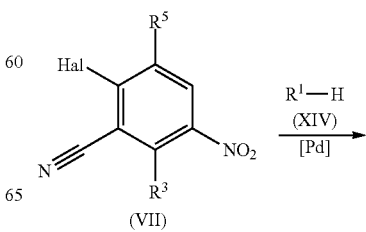

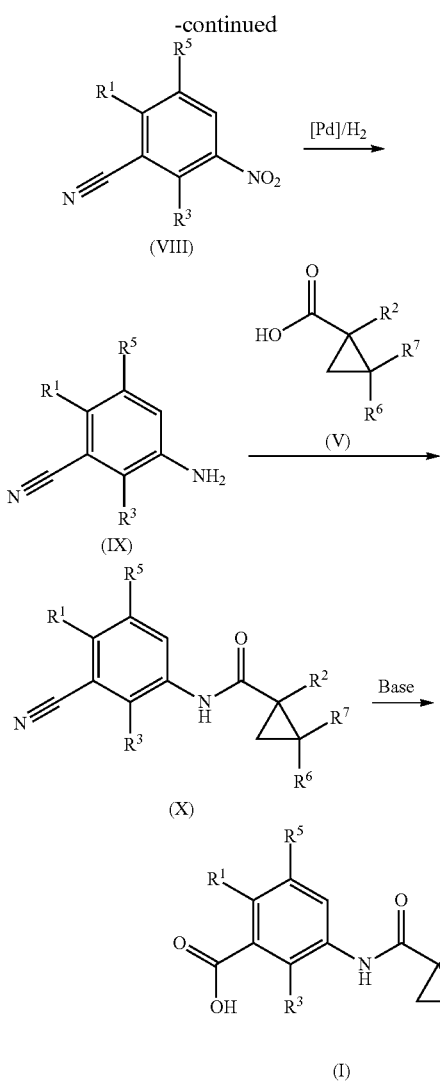

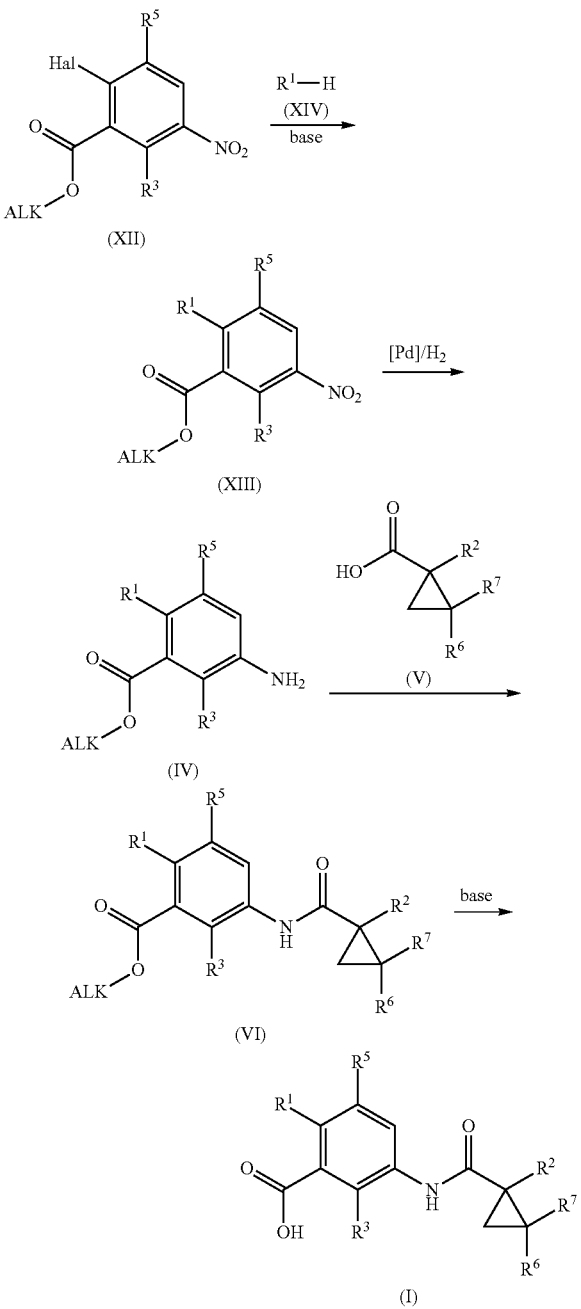

In Scheme 4 general formula (XIV) represents $R^1$—H wherein $R^1$ is an optionally substituted 5-membered heteroaryl group linked through a ring nitrogen atom to the hydrogen atom, or $R^1$ is an optionally substituted bicyclic 8- to 10-membered heteroaryl linked through a ring nitrogen atom to the hydrogen atom.

Scheme 5 shows an alternative approach to synthesis compounds of general formula (I) where $R^1$ is an N-linked optionally substituted 5-membered heteroaryl group, for example pyrazolyl or imidazolyl, or alternatively $R^1$ is an N-linked optionally substituted bicyclic 8- to 10-membered heteroaryl group, for example indole. Starting from synthons of the general formula (XII) (wherein Hal stands for F, Cl or Br; and wherein ALK stands for methyl, ethyl or propyl), the aryl halide can first be substituted by a nucleophile of general formula (XIV) to yield a compound of general formula (XIII). The substitution takes place in a dipolar aprotic solvent such as acetonitrile, dimethylsulfoxide or N,N-dimethylformamide and in the presence of an appropriate base (for example potassium carbonate or sodium hydride) at temperatures between 20° C. and 100° C., preferably at 60° C. In analogy to the procedures described for Scheme 2, nitro reduction gives compounds of general formula (IV), followed by amide coupling gives compounds of the general formula (VI), followed by ester group saponification to yield the target compounds of general formula (I).

In Scheme 5 general formula (XIV) represents $R^1$—H wherein $R^1$ is an optionally substituted 5-membered heteroaryl group linked through a ring nitrogen atom to the hydrogen atom, or $R^1$ is an optionally substituted bicyclic 8- to 10-membered heteroaryl linked through a ring nitrogen atom to the hydrogen atom.

Scheme 6 depicts the synthesis starting from synthons of the formula (XV), wherein Hal stands for Br or I, Br being preferred. The aryl halides of the general formula (XV) can be cross-coupled with boronic acids of the general formula (III) or alternatively with their respective pinacol esters to yield compounds of general formula (XVI) by Pd-mediated reactions (Suzuki coupling) known to those skilled in the art. A suitable solvent (for example N,N-dimethylformamide, tetrahydrofuran, 1,4-dioxane, 1,2-dimethoxyethane and optionally water) is used and a base (such as triethylamine, potassium carbonate, caesium carbonate) and a catalyst-ligand mixture, for example of palladium(II) acetate/triphenylphosphine, tetrakis(triphenylphosphine)palladium(0), bis(triphenylphosphine)-palladium(II) dichloride, bis(diphenylphosphino)ferrocenedichloropalladium (II) is utilised at temperatures between 20° C. and 120° C., preferred at 100° C. The chloro group of a compound of general formula (XVI) is converted to a nitrile group to yield compounds of general formula (IX), by Pd-mediated cyanation reactions with potassium ferrocyanide known to those skilled in the art. A suitable solvent mixture (for example 1,4-dioxane or tetrahydrofuran and optionally water) is used and a base (such as potassium acetate) and a catalyst-ligand mixture (for example tris[dibenzylideneacetone]dipalladium/dicyclohexyl[2',4',6'-tri(propan-2-yl)biphenyl-2-yl]phosphane) is utilised at temperatures between 20° C. and 120° C., usually 100° C. In analogy to the procedures described for Scheme 3, the nitrile moiety of general formula (IX) is converted into the carboxylic acid of general formula (XI) and then reacted with a suitable alcohol (such as methanol, ethanol or propanol; wherein ALK stands for methyl, ethyl or propyl) in inorganic acid (for example hydrochloric acid or sulfuric acid) at temperatures between 0° C. and 100° C. to form ester compounds of general formula (IV). In analogy to the procedures described for Scheme 1, amide coupling gives compounds of the general formula (VI), followed by ester group saponification to yield the target compounds of general formula (I). The sequence of reaction steps (nitrile hydrolysis, amide formation) may be changed as appropriate. In analogy with Scheme 2, final compounds of general formula (I) can be accessed directly via nitrile group hydrolysis carried out as a final transformation.

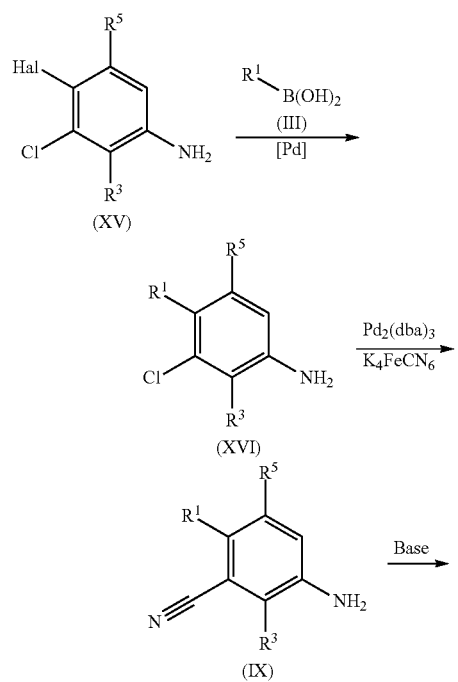

Scheme 6

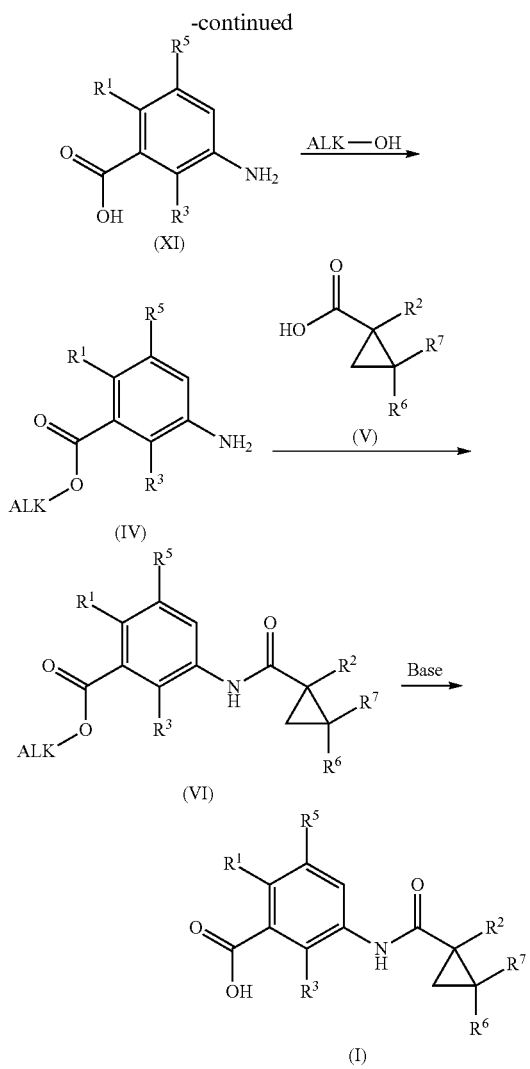

Scheme 7 shows an alternative approach to synthesis of compounds of general formula (I) with the meaning of $R^1$, $R^2$, X and $R^3$ as defined in general formula (I). The aryl group of general formula (XVII) can be nitrated by reaction with a mixture of nitric acid and sulfuric acid at temperatures between −20° C. and +20° C., preferred below +10° C. The carboxylic acid group of a compound of general formula (XVIII) is reacted with a suitable alcohol (such as methanol, ethanol or propanol; wherein ALK stands for methyl, ethyl or propyl) in inorganic acid (for example hydrochloric acid or sulfuric acid) at temperatures between 0° C. and 100° C. to form ester compounds of general formula (XIX). The hydroxy group of a compound of general formula (XIX) is converted to a triflate group to yield compounds of general formula (XX), by reaction with trifluoromethanesulfonic anhydride in base (for example triethylamine) and an inert solvent (such as dichloromethane) at temperatures between −20° C. and +40° C., usually at 0° C. The aryl triflates of the general formula (XX) can be cross-coupled with boronic acids of general formula (III) or alternatively with their respective pinacol esters to yield compounds of general formula (XIII), by Pd-mediated reactions (Suzuki coupling) known to those skilled in the art. A suitable solvent (for example N,N-dimethylformamide, tetrahydrofuran, 1,4-dioxane, 1,2-dimethoxyethane and optionally water) is used and a base (such as triethylamine, potassium carbonate, caesium carbonate) and a catalyst-ligand mixture, for example of palladium(II) acetate/triphenylphosphine, tetrakis(triphenylphosphine)palladium(0), bis(triphenylphosphine)-palladium(II) dichloride, bis(diphenylphosphino)ferrocenedichloropalladium (II) is utilised at temperatures between 20° C. and 120° C., preferred at 100° C. In analogy to the procedures described for Scheme 2, nitro group reduction followed by amide formation gives compounds of general formula (VI) that are subsequently converted to the final targets of general formula (I) by ester group hydrolysis as detailed in Scheme 1.

Scheme 7

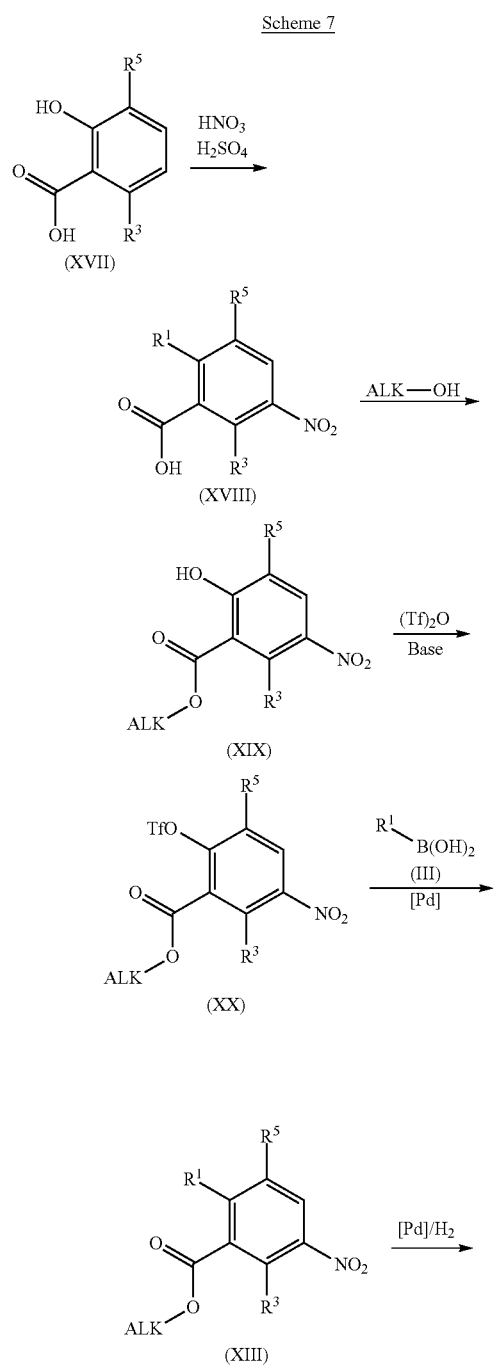

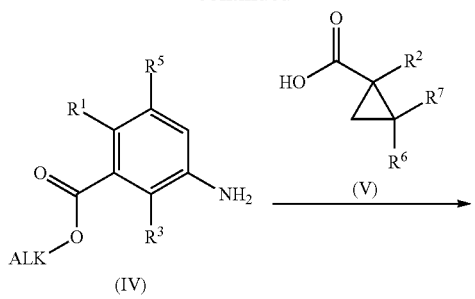

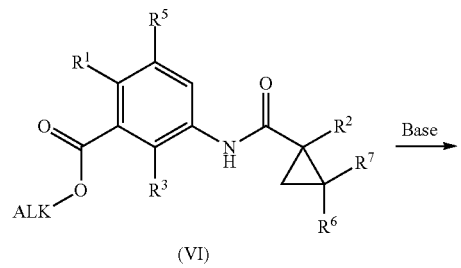

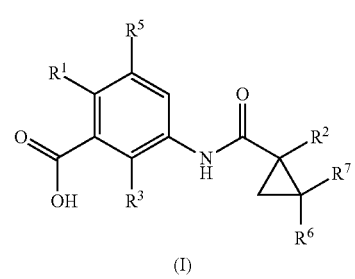

Scheme 8 shows an alternative approach to synthesis of compounds of general formula (I). Starting from synthons of general formula (XXI), the aniline can first be protected using a combination of two equivalents of a strong base (such as nBuLi) and 1,2-bis(chlorodimethylsilyl)ethane. The intermediate obtained can then be lithiated in situ using nBuLi and then quenched with an alkylchloroformate (such as ethylchloroformate). Subsequent treatment with an inorganic aqueous acid (such as hydrochloric acid) gives compounds of general formula (XXII) wherein ALK stands for methyl, ethyl or propyl. In analogy to the procedures described for Scheme 1, Suzuki coupling followed by amide coupling gives compounds of the general formula (VI). Subsequent ester group saponification yields the target compounds of general formula (I).

Scheme 8

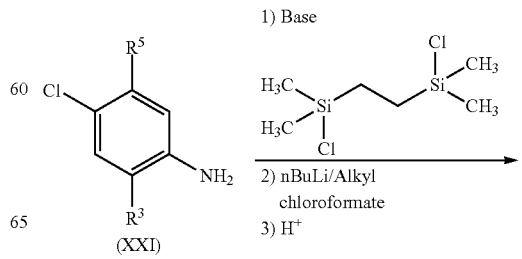

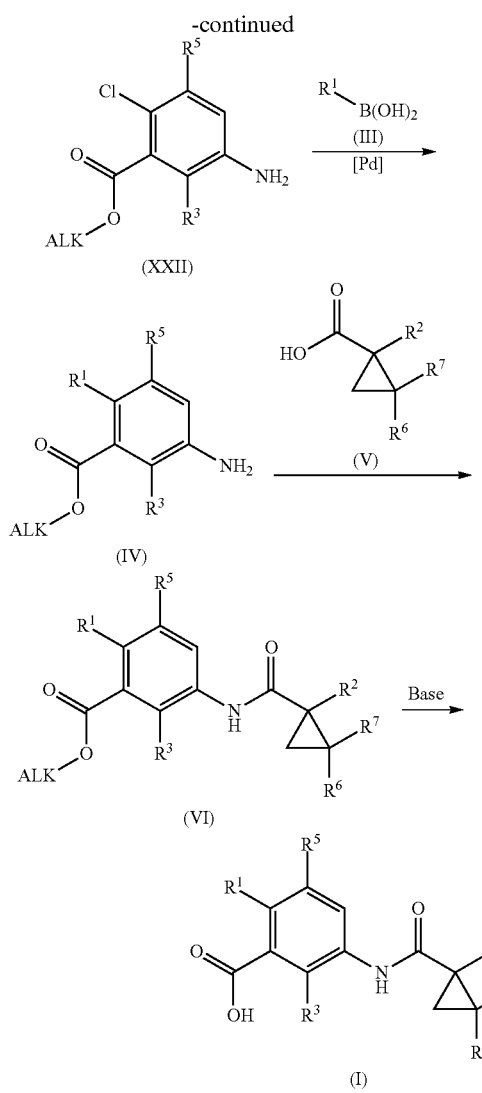

(XXII)

(IV)

(VI)

(I)

Scheme 9 shows an alternative approach to synthesis of compounds of general formula (I) in which the sequence of reaction steps is changed in comparison to Scheme 1, wherein Hal stands for Cl, Br or I, Br being preferred; and wherein ALK stands for methyl, ethyl or propyl. Starting from synthons of the general formula (II), the aromatic amine may react with carboxylic acids of general formula (V) by methods known to those skilled in the art to give the amide compounds of general formula (XXIII). The reaction is mediated by activating a carboxylic acid of general formula (V) with reagents such as dicyclohexylcarbodiimide (DCC), 1-(3-dimethyl-aminopropyl)-3-ethylcarbodiimide (EDCI), N-hydroxybenzotriazole (HOBT), N-[(di-methyl-amino)-(3H-[1,2,3]triazolo[4,5-b]pyridin-3-yloxy)methyl-iden]-N-methyl-methanaminium hexafluorophosphate (HATU) or propylphosphonic anhydride (T3P). For example, the reaction with T3P takes place in an inert solvent, such as N,N-dimethylformamide or dichloromethane in the presence of the appropriate aniline general formula (II) and a tertiary amine (such as triethylamine or diisopropyl-ethylamine) at temperatures between −30° C. and +60° C.

The aryl halides of the general formula (XXIII) can be cross-coupled with boronic acids of the general formula (III) or alternatively with their respective pinacol esters to yield compounds of general formula (VI) by Pd-mediated reactions (Suzuki coupling) known to those skilled in the art. A suitable solvent (for example N,N-dimethyl-formamide, tetrahydrofuran, 1,4-dioxane, 1,2-dimethoxyethane and optionally water) is used and a base (such as potassium carbonate or caesium carbonate) and a catalyst-ligand mixture, for example of palladium(II) acetate/triphenylphosphine, tetrakis(triphenylphosphine)palladium(0), bis(triphenylphosphine)palladium(II) dichloride, bis(diphenylphosphino)ferrocenedichloropalladium (II) is utilised at temperatures between 20° C. and 120° C., preferred at 100° C. In analogy to the procedures described for Scheme 1, ester group saponification of an intermediate compound of general formula (VI) yields the target compounds of general formula (I).

Scheme 9

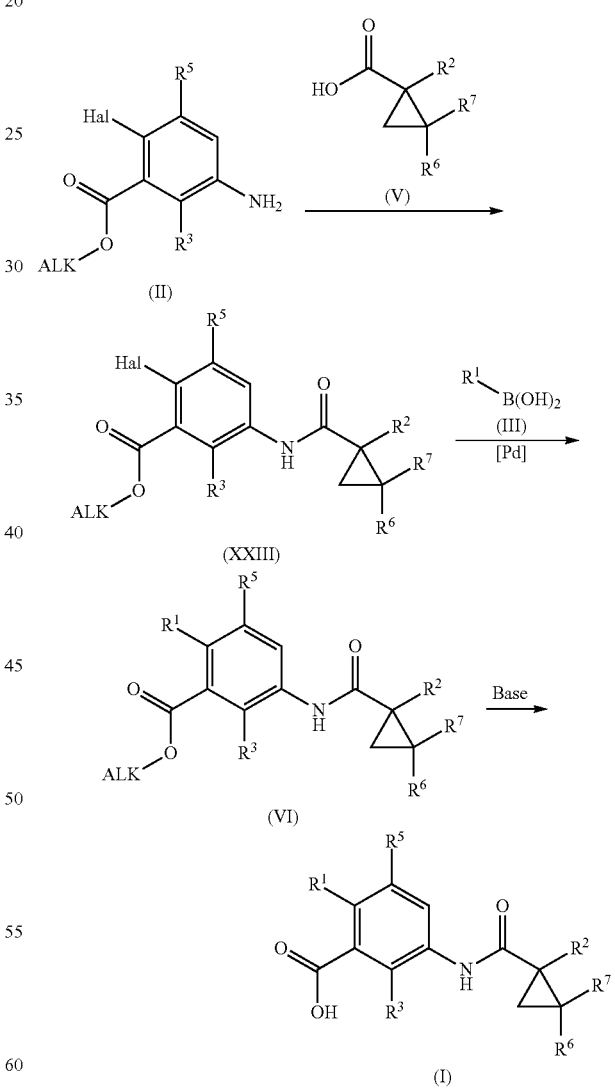

(II)

(XXIII)

(VI)

(I)

Scheme 10 shows an alternative approach to synthesis of compounds of general formula (I). Alkylation of 2-acetyl-butyrolactones of general formula (XXIV) can be achieved with an alkylating agent of general formula (XXV) wherein X stands for Cl, Br or I, Br being preferred in the presence of a base (such as potassium carbonate or sodium carbonate) in an apolar solvent (such as acetonitrile or tetrahydrofuran) at a temperature between 20° C. and 60° C. Subsequent rearrangement of compounds of general formula (XXVI) to give cyclopropanes of general formula (XXVII) can be achieved via reaction with lithium iodide in a polar solvent (such as dimethylformamide or 1-methyl-2-pyrrolidinone) at temperatures between 100° C. and 200° C. Carboxylic acids of general formula (V) can then be formed via reaction of compounds of general formula (XXVII) with bromine or iodine in the presence of a sodium hydroxide in a solvent (such as tetrahydrofuran or 1,4-dioxane) at temperatures between 0° C. to 20° C. In analogy to the procedures described for Scheme 1, amide coupling gives compounds of the general formula (VI). Subsequent ester group saponification yields the target compounds of general formula (I).

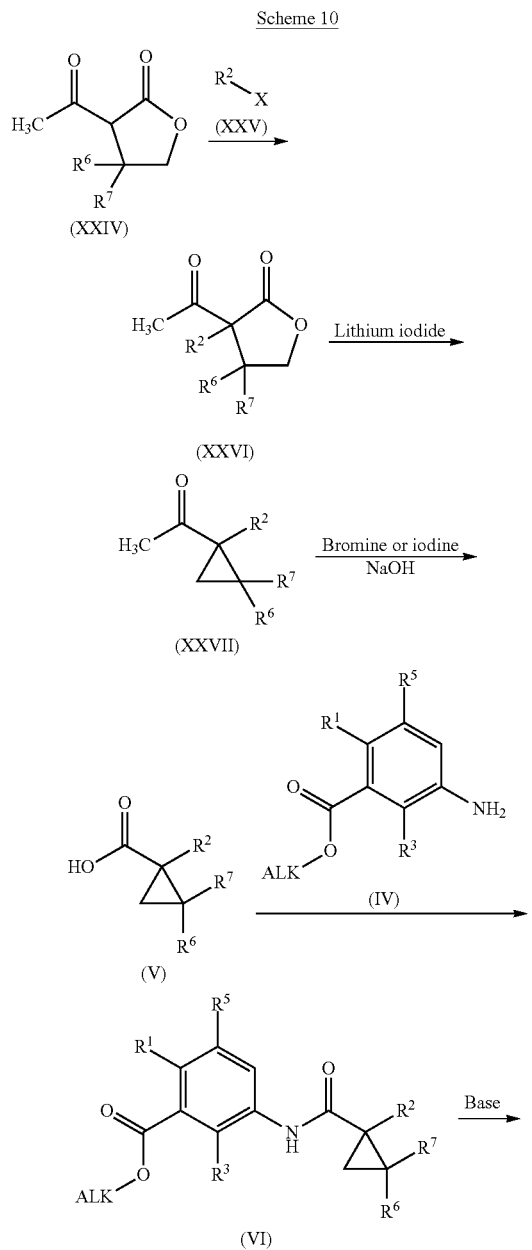

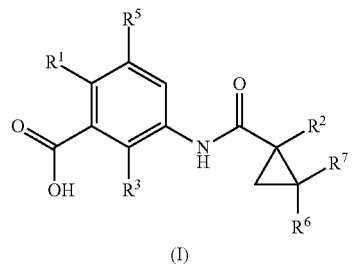

Scheme 11 shows an alternative approach to synthesis of compounds of general formula (I). Starting from synthons of the general formula (XII) (wherein Hal stands for Cl, Br or I; and wherein ALK stands for methyl, ethyl or propyl) the aryl halide can first be converted to a stannane of general formula (XXVIII) via reaction with hexabutyldistannane in the presence of a palladium catalyst (such as tetrakis-(triphenylphosphine)palladium(0), bis(triphenylphosphine)-palladium(II) dichloride) in a suitable solvent (for example N,N-dimethylformamide, tetrahydrofuran, 1,4-dioxane or 1,2-dimethoxyethane) at temperatures between 20° C. and 120° C., preferred at 100° C. The aryl stannane of the general formula (XXVIII) can then be cross-coupled with aryl halides of the general formula (XXIX), with the meaning of $R^1$ as defined in general formula (I), by Pd-mediated reactions (Stille coupling) known to those skilled in the art. A suitable solvent (for example N,N-dimethylformamide, tetrahydrofuran, 1,4-dioxane or 1,2-dimethoxyethane) is used with a catalyst-ligand mixture, for example of palladium(II) acetate/triphenylphosphine, tetrakis(triphenylphosphine)palladium(0), bis(triphenylphosphine)-palladium(II) dichloride, bis(diphenylphosphino)ferrocenedichloropalladium (II) is utilised at temperatures between 20° C. and 120° C., preferred at 100° C. In analogy to the procedures described for Scheme 1, nitro reduction gives compounds of general formula (IV), followed by amide coupling gives compounds of the general formula (VI), followed by ester group saponification to yield the target compounds of general formula (I).

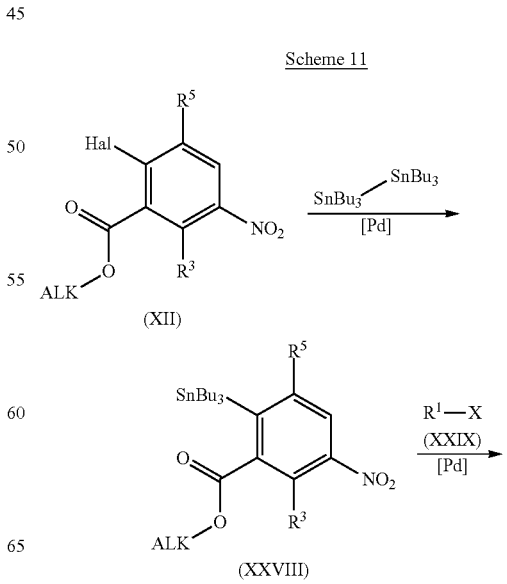

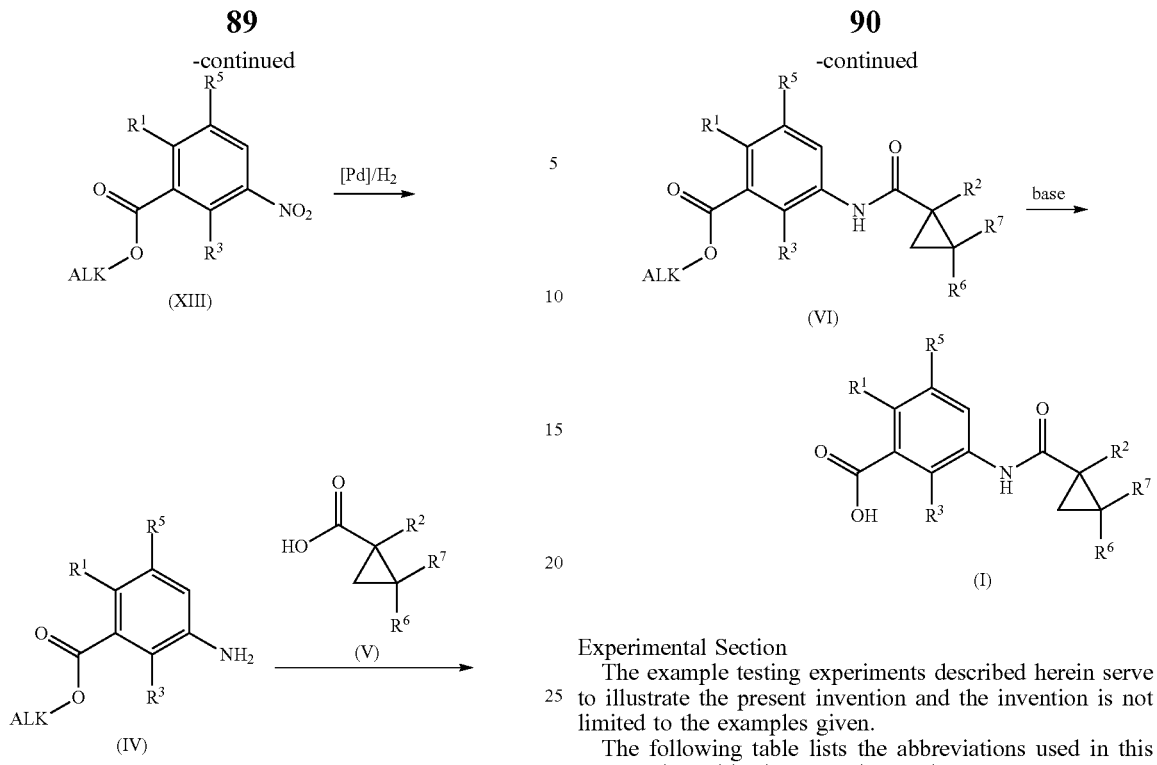

Experimental Section

The example testing experiments described herein serve to illustrate the present invention and the invention is not limited to the examples given.

The following table lists the abbreviations used in this paragraph, and in the examples section.

| Abbreviation | Meaning |
|---|---|
| $Cs_2CO_3$ | Cesium carbonate |
| Cu(I)Cl | Copper(I) chloride |
| ca. | circa |
| DCE | 1,2-Dichloroethane |
| DCM | Dichloromethane |
| DIAD | Diisopropyl azodicarboxylate |
| DIPEA | N-Ethyl-N-isopropylpropan-2-amine |
| DMAP | N,N-Dimethylpyridin-4-amine |
| DME | 1,2-Dimethoxyethane |
| DMF | N,N-Dimethylformamide |
| DMSO | Dimethyl sulfoxide |
| DP | Desired product |
| EE | Ethyl acetate |
| h | Hour |
| HATU | N-[(Dimethylamino)(3H-[1,2,3]triazolo[4,5-b]pyridin-3-yloxy)methylene]-N-methylmethanaminium hexafluorophosphate |
| HBr | Hydrogen bromide |
| HCl | Hydrochloric acid |
| hex | n-Hexane |
| HPLC | High performance liquid chromatography |
| $HNO_3$ | Nitric acid |
| $H_2SO_4$ | Sulfuric acid |
| Int | Intermediate |
| IPC | In process check |
| $K_2CO_3$ | Potassium carbonate |
| LC-MS | liquid chromatography - mass spectrometry |
| LCMS | liquid chromatography - mass spectrometry |
| LiOH | Lithium hydroxide |
| M | Molar |
| μW | Microwave |
| MeCN | Acetonitrile |
| MeOH | Methanol |
| $MgSO_4$ | Magnesium sulfate |
| min | Minute(s) |
| N | Normal |
| $Na_2CO_3$ | Sodium carbonate |
| NaH | Sodium hydride |
| $NaHCO_3$ | Sodium bicarbonate |
| NaI | Sodium iodide |
| NaOH | Sodium hydroxide |
| $Na_2SO_4$ | Sodium sulfate |
| $NH_4Cl$ | Ammonium chloride |
| NMR | nuclear magnetic resonance spectroscopy |

| Abbreviation | Meaning |
|---|---|
| PdCl$_2$(PPh$_3$)$_2$ | Bis(triphenylphosphine)palladium(II) dichloride |
| Pd(dppf)Cl$_2$ | [1,1'-Bis(diphenylphosphino)ferrocene]dichloropalladium(II) |
| Pd(dppf)Cl$_2$·CH$_2$Cl$_2$ | 1,1'-Bis(diphenylphosphino)ferrocene-palladium(II)dichloride dichloromethane complex |
| PPh$_3$ | Triphenylphosphine |
| ppm | parts per million |
| Py | Pyridine |
| RT | Room temperature |
| rt | Retention time |
| Rt | Retention time |
| sat. | Saturated |
| SEM | 2-(trimethylsilyl)ethoxymethyl |
| SM | Starting material |
| STAB | Sodium triacetoxyborohydride |
| HSnBu$_3$ | Tributyltin hydride |
| TMS-azide | Azidotrimethylsilane |
| TMS-N$_3$ | Azidotrimethylsilane |
| T3P | Propylphosphonic anhydride |
| TBAB | Tetra-N-butylammonium bromide |
| TBAI | Tetra-N-butylammonium iodide |
| TBME | tert-Butyl methyl ether |
| TEA | Triethylamine |
| TFA | Trifluoroacetic acid |
| (Tf)$_2$O | Trifluoromethanesulfonic anhydride |
| TfO— | Trifluoromethanesulfonate |
| THF | Tetrahydrofuran |

Analysis Methods

Analytical LCMS Methods

Method 1: Instrument: Waters Acquity Platform ZQ4000; column: Waters BEHC 18, 50 mm×2.1 mm, 1.7μ; eluent A: water/0.05% formic acid, eluent B: acetonitrile/0.05% formic acid; gradient: 0.0 min 98% A→0.2 min: 98% A→1.7 min: 10% A→1.9 min: 10% A→2 min: 98% A→2.5 min: 98% A; flow: 1.3 ml/min; column temperature: 60° C.; UV-detection: 200-400 nm.

Method 2: Instrument: Waters Acquity LCT; column: Phenomenex Kinetex C18, 50 mm×2.1 mm, 2.6μ; eluent A: water/0.05% formic acid, eluent B: acetonitrile/0.05% formic acid; gradient: 0.0 min 98% A→0.2 min: 98% A→1.7 min: 10% A→1.9 min: 10% A→2 min: 98% A→2.5 min: 98% A; flow: 1.3 ml/min; column temperature: 60° C.; UV-detection: 200-400 nm.

Method 3: Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 4: Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

LC-MS, Analytical Method A: Routine High Throughput Analysis

Column: Kinetex Core-Shell C18, 2.1×50 mm, 5 μm; Eluent A: Water+0.1% Formic acid, Eluent B: Acetonitrile+0.1% Formic acid; Gradient 0.00 mins 95% A→1.20 mins 100% B→1.30 mins 100% B→1.31 mins 95% A; column temperature: 40° C.; flow rate 1.2 ml/min; injection volume: 3 μl; UV-detection range: 210-420 nm.

LC-MS, Analytical Method B: Routine High Throughput Analysis

Column: Waters Atlantis dC18, 2.1×50 mm, 3 μm; Eluent A: Water+0.1% Formic acid, Eluent B: Acetonitrile+0.1% Formic acid; Gradient 0.00 mins 95% A→2.5 mins 100% B→2.7 mins 100% B→2.71 mins 5% A→3.5 mins 5% A; column temperature: 40° C.; flow rate 1.0 ml/min; injection volume: 3 μl; UV-detection range: 210-420 nm.

LC-MS, Analytical Method C: Routine High Throughput Analysis at High pH

Column: Phenomenex Gemini-NX C18, 2.0×50 mm, 3 μm; Eluent A: 2 mM ammonium bicarbonate, buffered to pH10, Eluent B: Acetonitrile; Gradient 0.00 mins 99% A→1.80 mins 100% B→2.10 mins 100% B→2.30 mins 99% A→3.50 mins 99% A; column temperature: 40° C.; flow rate 1.0 ml/min; injection volume: 3 μl; UV-detection range: 210-420 nm.

LC-MS, Analytical Method D:

Column: Waters Atlantis dC18, 2.1×100 mm, 3 μm; Eluent A: Water+0.1% Formic acid, Eluent B: Acetonitrile+0.1% Formic acid; Gradient 0.00 mins 95% A→5.00 mins 100% B→5.40 mins 100% B→5.42 mins 95% A→7.00 mins 95% A; column temperature: 40° C.; flow rate 0.6 ml/min; injection volume: 3 μl; UV-detection range: 210-420 nm.

LC-MS, Analytical Method E: High pH

Column: Phenomenex Gemini-NX C18, 2.0×100 mm, 3 μm; Eluent A: 2 mM ammonium bicarbonate, buffered to pH10, Eluent B: Acetonitrile; Gradient 0.00 mins 95% A→5.50 mins 100% B→5.90 mins 100% B→5.92 mins 95% A→7.00 mins 95% A; column temperature: 40° C.; flow rate 0.5 ml/min; injection volume: 3 μl; UV-detection range: 210-420 nm.

LC-MS, Analytical Method F:

Column: Phenomenex Kinetix-XB C18, 2.1×100 mm, 1.7 μm; Eluent A: Water+0.1% Formic acid, Eluent B: Acetonitrile+0.1% Formic acid; Gradient 0.00 mins 95% A→5.30 mins 100% B→5.80 mins 100% B→5.82 mins 95% A→7.00 mins 95% A; column temperature: 40° C.; flow rate 0.6 ml/min; injection volume: 1 μl; UV-detection range: 200-400 nm.

Purification Methods:

Biotage Isolera™ chromatography system using pre-packed silica and pre-packed modified silica cartridges.

Preparative HPLC, Method A: High pH

Column: Waters Xbridge C18, 30×100 mm, 10 μm; Solvent A: Water+0.2% Ammonium hydroxide, Solvent B: Acetonitrile+0.2% Ammonium hydroxide; Gradient 0.00 mins 90% A→0.55 mins 90% A→14.44 mins 95% B→16.55 mins 95% B→16.75 90% A; column temperature: room temperature; flow rate 40 ml/min; injection volume: 1500 μl; Detection: UV 215 nm.

Preparative HPLC, Method B: Low pH

Column: Waters Sunfire C18, 30×100 mm, 10 μm; Solvent A: Water+0.1% Formic acid, Solvent B: Acetonitrile+0.1% Formic acid; Gradient 0.00 mins 90% A→0.55 mins 90% A→14.44 mins 95% B→16.55 mins 95% B→16.75 90% A; column temperature: room temperature; flow rate 40 ml/min; injection volume: 1500 μl; Detection: UV 215 nm.

Preparative HPLC Methods

Preparative HPLC, Method 1:

System: Waters autopurification system: Pump 2545, Sample Manager 2767, CFO, DAD 2996, ELSD 2424, SQD; Column: XBrigde C18 5 μm 100×30 mm; Solvent: A=H2O+0.1% Vol. formic acid (99%), B=acetonitrile; Gradient: 0-8 min 10-100% B, 8-10 min 100% B; Flow: 50 mL/min; temperature: room temp.; Solution: Max. 250 mg/max. 2.5 mL DMSO o. DMF; Injection: 1×2.5 mL; Detection: DAD scan range 210-400 nm; MS ESI+, ESI−, scan range 160-1000 m/z.

Preparative HPLC, Method 2:

System: Waters autopurification system: Pump 2545, Sample Manager 2767, CFO, DAD 2996, ELSD 2424, SQD; Column: XBrigde C18 5 μm 100×30 mm; Solvent: A=H2O+0.1% Vol. ammonia (99%), B=acetonitrile; Gradient: 0-8 min 10-100% B, 8-10 min 100% B; Flow: 50 mL/min; temperature: room temp.; Solution: Max. 250 mg/max. 2.5 mL DMSO o. DMF; Injection: 1×2.5 mL; Detection: DAD scan range 210-400 nm; MS ESI+, ESI−, scan range 160-1000 m/z.

EXAMPLES

Chemical naming of the Examples (also referred to as Compound Examples) and Intermediates was performed using ACD software by ACD/LABS or Marvin software by ChemAxon.

Reaction times are either specified explicitly in the protocols of the experimental section, or reactions were run until completion. Chemical reactions were monitored and their completion was judged using methods well known to the person skilled in the art, such as thin layer chromatography, e.g. on plates coated with silica gel, or by LCMS methods.

Intermediate 1A: Methyl 5-amino-2-bromobenzoate

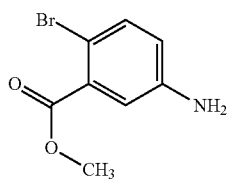

To a 0° C. solution of 5-amino-2-bromobenzoic acid (9.85 g, 45.6 mmol) in methanol (100 mL) was added thionyl chloride (1.1 eq., 3.7 mL, 50 mmol) dropwise at 0° C. The resulting mixture was stirred at 70° C. for 16 h. The mixture was evaporated to dryness. The resulting grey solid was used without further purification.

$^1$H NMR (400 MHz, DMSO-d6) δ [ppm] 3.83 (s, 3H), 6.92 (dd, 1H), 7.22 (d, 1H), 7.49 (d, 1H).

LCMS (method 3): Rt=0.87 min, MS (ESIpos) m/z=230/232 (M+H)$^+$, Br isotope pattern.

Intermediate 2A:
1-(5-Bromopyridin-2-yl)propan-1-one

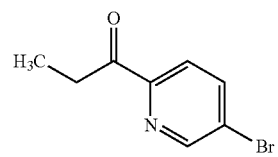

A solution of 5-bromopyridine-2-carbonitrile (5.0 g, 27.3 mmol) was dissolved in dry tetrahydrofuran (100 mL) and cooled to −20° C. Ethylmagnesium bromide (11.4 mL of a 3M solution in diethyl ether, 34.1 mmol) was added dropwise at this temperature, with the reaction mixture allowed to warm to RT over 2 hours. The reaction mixture was cooled to −20° C. and 1M aqueous HCl solution slowly added and the mixture allowed to re-warm to room temperature. The reaction mixture was diluted with ethyl acetate, the organic layer collected and washed with brine, dried (MgSO$_4$), filtered and concentrated at reduced pressure. The golden coloured oil crystallised to give the title compound (5.25 g, 85% yield).

$^1$H NMR (250 MHz, Chloroform-d) δ [ppm] 8.74 (dd, J=2.0, 0.9 Hz, 1H), 8.04-7.89 (m, 2H), 3.22 (q, J=7.3 Hz, 2H), 1.23 (t, J=7.3 Hz, 3H).

Intermediate 3A:
5-Bromo-2-(1,1-difluoropropyl)pyridine

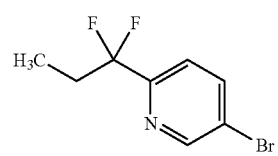

To a solution of 1-(5-bromopyridin-2-yl)propan-1-one (Int 2A, 5.25 g, 24.5 mmol) dissolved in 1,2-dichloroethane (61.5 mL) under nitrogen was added diethylaminosulfur trifluoride (12.96 mL, 98.1 mmol) dropwise giving an orange solution. The reaction was warmed to 60° C. and stirred for 16 hours. The cooled reaction mixture was diluted with aqueous NaOH (2M) dropwise (CAUTION: vigorous reaction). The organic layer was removed, washed with brine, dried (MgSO$_4$), filtered and concentrated at reduced pressure and purified by Biotage Isolera™ chromatography (silica gel, eluting with TBME/Heptane; 0-20%) to give the title compound (3.25 g, 50% yield) as a pale yellow oil.

$^1$H NMR (250 MHz, Chloroform-d) δ [ppm] 8.74 (d, J=2.1 Hz, 1H), 7.95 (dd, J=8.4, 2.3 Hz, 1H), 7.55 (d, J=8.4 Hz, 1H), 2.34 (m, 2H), 1.02 (t, J=7.5 Hz, 3H).

Intermediate 4A: 2-(1,1-Difluoropropyl)-5-(4,4,5,5-tetramethyl-1,3,2-dioxaborolan-2-yl)pyridine

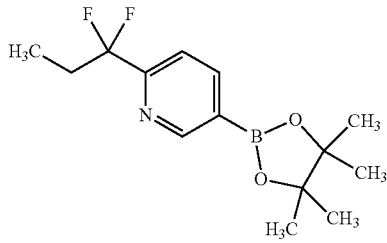 [SMILES: CCC(F)(F)c1ccc(B2OC(C)(C)C(C)(C)O2)cn1]

A solution of 5-bromo-2-(1,1-difluoropropyl)pyridine (Int 3A, 3.25 g, 12.39 mmol), bis(pinacolato)diboron (3.46 g, 13.63 mmol), potassium acetate (3.65 g, 37.17 mmol) and 1,1'-bis(diphenylphosphino)ferrocenepalladium(II) chloride (453 mg, 0.62 mmol) in 1,4-dioxane (70 mL) was degassed via nitrogen gas balloon for 5 minutes. The reaction mixture was heated at 100° C. for 16 hours, cooled to RT and diluted with EtOAc, filtered through a plug of Celite and concentrated in vacuo. The filtrate was collected and concentrated at reduced pressure and purified by Biotage Isolera™ chromatography (silica cartridge, eluting with a gradient of eluents; 0-30% EtOAc in Heptane) to give the title compound (3.25 g, 83% yield) as a golden oil that crystallised upon standing.

$^1$H NMR (250 MHz, Chloroform-d) δ [ppm] 9.00 (s, 1H), 8.19 (dd, J=7.8, 1.5 Hz, 1H), 7.62 (dd, J=7.8, 0.8 Hz, 1H), 2.35 (m, 2H), 1.38 (s, 12H), 1.00 (t, J=7.5 Hz, 3H).

LCMS (Analytical Method A): Rt=0.89 mins; MS (ESI-pos) m/z=201.95 (mass of boronic acid+H)$^+$.

Intermediate 5A: 2-(Difluoromethyl)-5-(4,4,5,5-tetramethyl-1,3,2-dioxaborolan-2-yl)pyridine

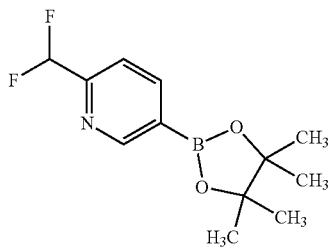 [SMILES: CC1(C)OB(c2ccc(C(F)F)nc2)OC1(C)C]

To a solution of 5-bromo-2-(difluoromethyl)pyridine (1.0 g, 4.8 mmol) and bis(pinacolato)diboron (1.34 g, 5.3 mmol) in dioxane (5 mL) at RT was added potassium acetate (1.4 g, 14.4 mmol). Nitrogen gas was bubbled through the mixture for 5 mins and 1,1'-bis(diphenylphosphino)ferrocenepalladium(II) chloride (264 mg, 0.36 mmol) was added and the mixture heated at 100° C. for 1 hour. The reaction mixture was then diluted with EtOAc (50 mL), filtered over Celite and washed with EtOAc (50 mL). The filtrate was concentrated at reduced pressure and the residue purified by Biotage Isolera™ chromatography (Biotage SNAP Cartridge KP-Sil 50 g; eluting with 0-100% EtOAc in heptane) to give the title compound (1.15 g, 89% yield) as a pale yellow crystalline solid.

$^1$H NMR (500 MHz, Chloroform-d) δ [ppm] 8.97 (s, 1H), 8.21 (dd, J=7.7, 1.4 Hz, 1H), 7.62 (d, J=7.7 Hz, 1H), 6.64 (t, J=55.4 Hz, 1H), 1.36 (s, 12H).

LCMS (Analytical Method A): Rt=0.78 mins, MS (ESI-Pos) m/z=173.9 (mass of boronic acid+H)$^+$.

Intermediate 6A: 2-(1,1-Difluoroethyl)-5-(4,4,5,5-tetramethyl-1,3,2-dioxaborolan-2-yl)pyridine

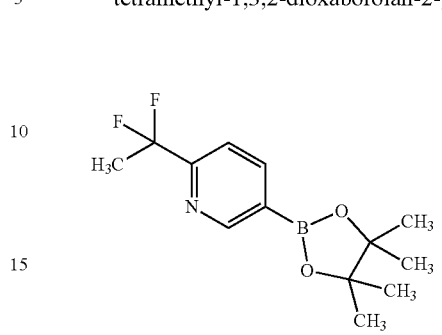

To a solution of 5-bromo-2-(1,1-difluoroethyl)pyridine (1.69 g, 6.70 mmol) in dioxane (30 mL) was added bis(pinacolato)diboron (1.87 g, 7.37 mmol), potassium acetate (1.97 g, 20.09 mmol). The resulting mixture was degassed for five minutes with nitrogen prior to the addition of [1,1'-Bis(diphenylphosphino)ferrocene]dichloropalladium (II) complex with dichloromethane (328 mg, 0.40 mmol). The mixture was heated to 100° C. and was stirred at that temperature for 2.5 hours. After this time no starting material remained according to LCMS analysis. The heat was removed and the reaction allowed to cool to room temperature, at which point it was filtered over a Celite pad, washing with MeOH (3×10 mL). The filtrate was concentrated under reduced pressure and purified by Biotage Isolera™ chromatography (eluting with 0-100% EtOAc in Heptane). The title compound was obtained as an off white powder solid (1.39 g, 66% yield).

$^1$H NMR (250 MHz, DMSO-d6) δ [ppm] 1.32 (s, 12H), 1.99 (t, J=19.1 Hz, 3H), 7.71 (dd, J=7.8, 0.9 Hz, 1H), 8.18 (dd, J=7.8, 1.7 Hz, 1H), 8.79-8.87 (m, 1H).

LCMS (Analytical Method A): Rt=0.87 mins; mass ion not observed.

Intermediate 7A: 1-[5-(4,4,5,5-tetramethyl-1,3,2-dioxaborolan-2-yl)pyridin-2-yl]ethanone

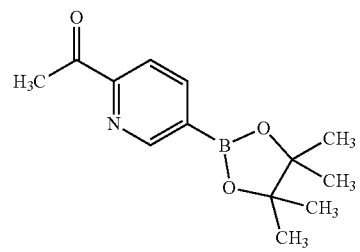 [SMILES: CC(=O)c1ccc(B2OC(C)(C)C(C)(C)O2)cn1]

To a solution of 1-(5-bromopyridin-2-yl)ethanone (2.0 g, 9.98 mmol) in dioxane (50 mL) was added bis(pinacolato) diboron (2.8 g, 11.0 mmol), potassium acetate (2.94 g, 30.0 mmol) and [1,1'-Bis(diphenylphosphino)ferrocene]dichloropalladium(II) complex with dichloromethane (244 mg, 0.30 mmol) under a nitrogen atmosphere. The mixture was heated at reflux for 4 hours. The mixture was then cooled to room temperature then filtered over Celite (washing with EtOAc) and concentrated at reduced pressure. The residue was purified directly via Biotage Isolera™ chromatography (eluting with a gradient of eluents; 0-50% EtOAc in heptane) giving the desired product (2.22 g, 90% yield) as a pale yellow solid. 1H NMR (500 MHz, DMSO-d6) δ [ppm] 8.89 (s, 1H), 8.20 (dd, J=7.7, 1.6 Hz, 1H), 7.95 (d, J=7.7 Hz, 1H), 2.65 (s, 3H), 1.33 (s, 12H).

LCMS (Analytical Method A): Rt=0.74 mins, mass ion not observed.

Intermediate 8A:
5,5,5-Trifluoro-1-(trimethylsilyl)pent-1-yn-3-one

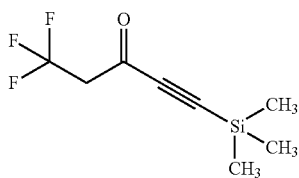

To a stirred solution of ethyne-1,2-diylbis(trimethylsilane) (1.0 g, 5.868 mmol) and 3,3,3-trifluoropropanoyl chloride (0.946 g, 6.455 mmol) in dichloromethane (15 mL) was added aluminium trichloride (0.939 g, 7.042 mmol) at 0° C. The reaction mixture was stirred at 0° C. for 1 hour and then poured into a mixture of 2M HCl (20 mL) and crushed ice (~20 g). Dichloromethane (20 mL) was added and the mixture was left standing for approximately 2 hours. The organic layer was separated and the aqueous layer was extracted with dichloromethane (20 mL). The combined organic layers were washed with brine (20 mL), dried (MgSO₄), filtered and concentrated at reduced pressure to give the title compound (1.18 g, 75% yield) as pale yellow oil.

¹H NMR (500 MHz, Chloroform-d) δ [ppm] 3.38 (q, J=10.0 Hz, 2H), 0.26 (s, 9H).

Intermediate 9A:
3-(2,2,2-Trifluoroethyl)-1H-pyrazole

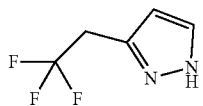

To a solution 5,5,5-trifluoro-1-(trimethylsilyl)pent-1-yn-3-one (Int 8A, 1.18 g, 4.82 mmol) in ethanol (10 mL) was added hydrazine hydrate (0.469 mL, 9.63 mmol) at room temperature (an exothermic reaction was observed). The mixture was stirred for 1 hour and then concentrated at reduced pressure (~50 mbar). The residue was dissolved in dichloromethane (50 mL), washed with 2M K₂CO₃ (20 mL), brine (20 mL), dried (Na₂SO₄), filtered and concentrated at reduced pressure to give the title compound (630 mg, 73% yield) as yellow oil.

¹H NMR (500 MHz, Chloroform-d) δ [ppm] 7.57 (d, J=2.2 Hz, 1H), 6.35 (d, J=1.8 Hz, 1H), 3.51 (q, J=10.7 Hz, 2H).

LCMS (Analytical Method A): Rt=0.81 mins; MS (ESIPos) m/z=150.9 (M+H)⁺.

Intermediate 10A:
1-Cyclobutyl-3-fluoro-1H-pyrazole

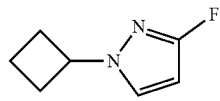

3-Fluoro-1H-pyrazole (150 mg, 2.91 mmol) were dissolved in DMF (10 mL) at RT. Sodium hydride (152 mg, 3.49 mmol, 1.2 eq) was added and the mixture stirred for 10 min. Then cyclobutylbromide (0.82 mL, 8.71 mmol, 3 eq.) was added and the mixture stirred for 2 h at 50° C. After cooling to RT, the mixture was poured into water and extracted 4× with ethyl acetate. The combined organic layers were washed with brine, dried with sodium sulfate and the solvents removed in vacuo. The crude product afforded no further purification: 400 mg (98% of theory) pale yellow oil.

¹H NMR (400 MHz, DMSO-d6) δ [ppm] 1.68-1.79 (m, 2H), 2.28-2.43 (m, 4H), 4.88 (quint, 1H), 5.91 (dd, 1H), 7.71 (t, 1H).

LCMS (method 1): Rt=0.84 min; MS (ESIPos) m/z=141 (M+H)⁺.

Intermediate 11A:
4-Bromo-1-cyclobutyl-3-fluoro-1H-pyrazole

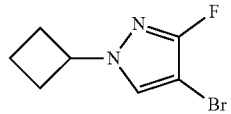 [SMILES: Fc1nn(C2CCC2)cc1Br]

1-Cyclobutyl-3-fluoro-1H-pyrazole (Int 10A, 400 mg, 2.85 mmol) were dissolved in 17 mL chloroform and cooled to 0° C. for 10 min. Then bromine (480 mg, 3.00 mmol, 1.05 eq), dissolved in 5 mL chloroform, were added drop wise at 0° C. The mixture was stirred for 1 h, then diluted with dichloromethane. The mixture was washed with saturated sodium thiosulfate solution, then with brine, then dried with sodium sulfate and the solvents evaporated. The crude product (400 mg, 63% of theory, colourless oil) was used without further purification.

¹H NMR (400 MHz, DMSO-d6) δ [ppm] 1.68-1.79 (m, 2H), 2.27-2.42 (m, 4H), 4.69 (quint, 1H), 8.07 (d, 1H).

LCMS (method 1): Rt=1.13 min; MS (ESIPos) m/z=219/212 (M+H)+, Br isotope pattern.

Intermediate 12A: 1-Cyclobutyl-3-fluoro-4-(4,4,5,5-tetramethyl-1,3,2-dioxaborolan-2-yl)-1H-pyrazole

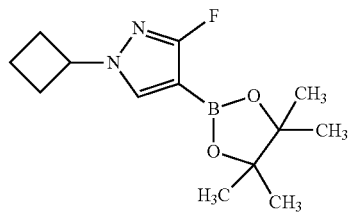 [SMILES: CC1(C)OB(c2cn(C3CCC3)nc2F)OC1(C)C]

4-Bromo-1-cyclobutyl-3-fluoro-1H-pyrazole (Int 11A, 400 mg, 1.83 mmol) and 4,4,4',4',5,5,5',5'-octamethyl-2,2'-bi-1,3,2-dioxaborolane (510 mg, 2.01 mmol, 1.1 eq) were dissolved in 1,4-dioxane and degassed in an Argon flow. Then (1,1'-bis(diphenylphosphino)ferrocene)-dichloropalladium(II) (100 mg, 0.14 mmol, 0.075 eq) and potassium acetate (538 mg, 5.48 mmol, 3 eq) were added and the mixture stirred for 1 h at 100° C. and for additional 2 hours at RT. The mixture was diluted with ethyl acetate, filtered through Celite and the filtrate concentrated in vacuo. The residue was filtered through silica gel (hex/EE 0-40%) to yield the title compound (420 mg) as a pale yellow oil, which crystallised on standing.

LCMS (method 3): Rt=0.98 min; MS (ESIPos) m/z=367 (M+H)⁺.

Intermediate 13A: 1-Tert-butyl-4-(4,4,5,5-tetramethyl-1,3,2-dioxaborolan-2-yl)-1H-pyrazole

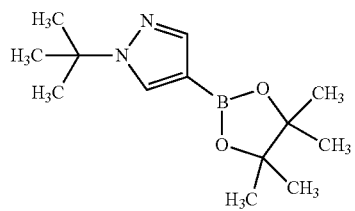 [SMILES: CC(C)(C)n1cc(B2OC(C)(C)C(C)(C)O2)cn1]

To a solution of 4-bromo-1-tert-butyl-1H-pyrazole (2.40 g, 9.836 mmol) and bis(pinacolato)diboron (1.64 g, 7.995 mmol) in dioxane (30 mL) was added potassium acetate (2.54 g, 29.5 mmol) at room temperature. Nitrogen gas was bubbled through the mixture for 5 mins and 1,1'-bis(diphenylphosphino)ferrocenepalladium(II) chloride (125 mg, 0.153 mmol) was then added. The mixture was heated at 100° C. for 8 hours. The reaction mixture was diluted with EtOAc (50 mL), filtered over Celite and washed with EtOAc (50 mL). The filtrate was concentrated at reduced pressure and the residue was purified by Biotage Isolera™ chromatography [SNAP Cartridge KP-Sil 100 g; eluting with a gradient of eluents; 0-100% EtOAc in heptane] giving the title product (0.65 g, 29% yield) as white solid.

¹H NMR (500 MHz, Chloroform-d) δ [ppm] 7.78 (d, J=0.6 Hz, 1H), 7.76 (s, 1H), 1.53 (s, 9H), 1.26 (s, 12H).

LCMS (Analytical Method A): Rt=1.18 mins; MS (ESI-Pos) m/z=251.05 (M+H)⁺.

Intermediate 14A: 1-(2,2-Dimethylpropyl)-4-(4,4,5,5-tetramethyl-1,3,2-dioxaborolan-2-yl)-1H-pyrazole

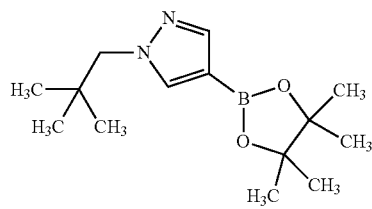 [SMILES: CC(C)(C)Cn1cc(B2OC(C)(C)C(C)(C)O2)cn1]

A mixture of 4-(tetramethyl-1,3,2-dioxaborolan-2-yl)-1H-pyrazole (2.0 g, 10.2 mmol), 1-iodo-2,2-dimethylpropane (3.03 g, 15.3 mmol) and potassium carbonate (4.23 g, 30.6 mmol) in N,N-dimethylformamide (20 mL) was heated at 100° C. for 20 hours. The reaction mixture was then diluted with TBME (100 mL) and water (50 mL). The organic layer was separated, washed with water (2×50 mL) and brine (30 mL), dried (Na₂SO₄) and concentrated under reduced pressure. Heptane (50 mL) was added to the residue and the mixture was briefly heated at reflux. After cooling to room temperature, the solid starting material was removed via filtration. The filtrate was concentrated under reduced pressure and purified by Biotage Isolera™ chromatography [Biotage SNAP Cartridge KP-Sil 25 g; eluting with a gradient of eluents; 0-30% EtOAc in heptane]. The product containing fractions were combined and concentrated in vacuo to afford the title product (0.27 g, 9% yield) as a white solid.

¹H NMR (500 MHz, Chloroform-d) δ [ppm] 7.75 (s, 1H), 7.63 (s, 1H), 3.90 (s, 2H), 1.31 (s, 12H), 0.94 (s, 9H).

LCMS (Analytical Method A): Rt=1.32 mins; MS (ESI-Pos) m/z=264.8 (M+H)⁺.

Intermediate 15A: 1-(cyclobutylmethyl)-4-(4,4,5,5-tetramethyl-1,3,2-dioxaborolan-2-yl)-1H-pyrazole

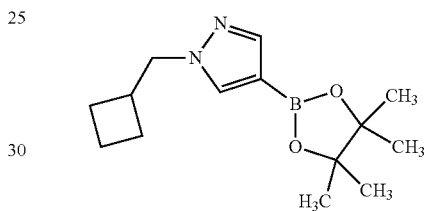

A mixture of 4-(tetramethyl-1,3,2-dioxaborolan-2-yl)-1H-pyrazole (0.58 g, 2.96 mmol), (bromomethyl)cyclobutane (0.50 mL, 4.44 mmol) and potassium carbonate (1.23 g, 8.88 mmol) in N,N-dimethylformamide (6 mL) was heated at 100° C. for 20 hours. The reaction mixture was cooled to RT, diluted with EtOAc (50 mL) and water (50 mL). The organic layer was separated, washed with water (50 mL) and brine (30 mL), dried (MgSO₄), concentrated under reduced pressure and purified by Biotage Isolera™ chromatography (25 g Silica column, using a gradient of eluents; 0-30% EtOAc in heptane) to afford the title compound (330 mg, 41% yield) as a colourless oil.

¹H NMR (250 MHz, Chloroform-d) δ [ppm] 7.76 (s, 1H), 7.64 (s, 1H), 4.13 (d, J=7.3 Hz, 2H), 2.95-2.70 (m, 1H), 2.20-1.64 (m, 6H), 1.31 (s, 12H).

LCMS (Analytical Method A): Rt=1.13 min, MS (ESI-pos): m/z=262.9 (M+H)⁺.

Intermediate 306A: 4-(4,4,5,5-tetramethyl-1,3,2-dioxaborolan-2-yl)-1-{[2-(trimethylsilyl)ethoxy]methyl}-1H-pyrazole

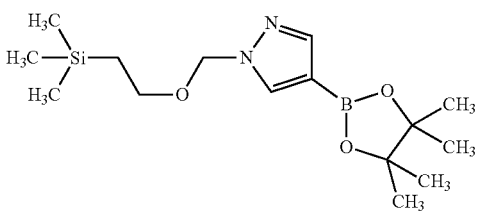

To a solution of methyl 4-(tetramethyl-1,3,2-dioxaborolan-2-yl)-1H-pyrazole (1.238 g, 6.316 mmol) in DMF (20 mL) was added potassium carbonate (2.62 g, 18.95 mmol) and [2-(chloromethoxy)ethyl](trimethyl)silane (1.68 mL, 9.48 mmol) at room temperature. The mixture was stirred for 3 hours and then partitioned between TBME (100 mL) and water (50 mL). The organic layer was separated, washed with water (2×30 mL) and brine (30 mL), dried (Na$_2$SO$_4$) and concentrated at reduced pressure. The residue was purified by Biotage Isolera™ chromatography [Biotage SNAP Cartridge KP-Sil 50 g; using a gradient of eluents, 0-50% EtOAc in heptane]. The product containing fractions were combined, concentrated in vacuo to give the title compound (1.20 g, 56% yield) as colourless oil.

$^1$H NMR (500 MHz, Chloroform-d) δ [ppm] 7.88 (s, 1H), 7.84 (s, 1H), 5.46 (s, 2H), 3.61-3.55 (m, 2H), 1.35 (s, 12H), 0.96-0.90 (m, 2H), 0.00 (s, 9H).

LCMS (Analytical Method A): Rt=1.34 mins; MS (ESI-Pos) m/z=324.95 (M+H)$^+$.

Intermediate 307A: 1-(2-Methoxyethyl)-4-(4,4,5,5-tetramethyl-1,3,2-dioxaborolan-2-yl)-1H-pyrazole

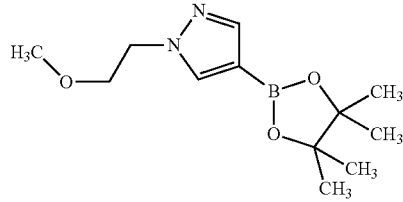

To a solution of 4-(tetramethyl-1,3,2-dioxaborolan-2-yl)-1H-pyrazole (1.00 g, 5.1 mmol) in DMF (5 mL) was added sodium hydride (245 mg of a 60% dispersion in mineral oil, 6.1 mmol) at room temperature. The mixture was then stirred at room temperature for 60 minutes. The mixture was cooled to 0° C. and 2-bromoethyl methyl ether (0.72 mL, 7.7 mmol) was added drop wise via syringe. After complete addition, the mixture was allowed to warm to room temperature and stirred for an hour prior to addition of ethyl acetate (70 mL) and water (30 mL). The organic layer was separated, washed with water (2×30 mL) and brine (30 mL), dried (Na$_2$SO$_4$), filtered and concentrated at reduced pressure. The residue was purified by Biotage Isolera™ chromatography [Biotage SNAP Cartridge KP-Sil 50 g; using a gradient of eluents, 0-50% EtOAc in heptane] to give the title compound (333 mg, 26% yield) as a colourless oil.

$^1$H NMR (250 MHz, DMSO-d6) δ [ppm] 7.88 (s, 1H), 7.57 (s, 1H), 4.32-4.20 (m, 2H), 3.73-3.60 (m, 2H), 3.21 (s, 3H), 1.25 (s, 12H).

LCMS (Analytical Method A): Rt=1.01 mins, MS (ESI-Pos): m/z=253 (M+H)$^+$.

Intermediate 308A: 1-(1-cyclopropylethyl)-4-(4,4,5,5-tetramethyl-1,3,2-dioxaborolan-2-yl)-1H-pyrazole as a 1:1 mixture of enantiomers

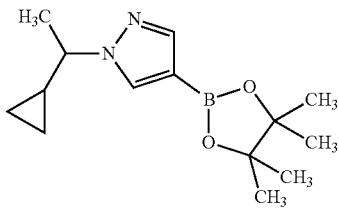 [SMILES: CC(C1CC1)n1cc(B2OC(C)(C)C(C)(C)O2)cn1]

To an ice-cooled solution of 4-(tetramethyl-1,3,2-dioxaborolan-2-yl)-1H-pyrazole (600 mg, 3.09 mmol), racemic 1-cyclopropylethanol (346 mg, 4.02 mmol) and triphenylphosphine (1054 mg, 4.02 mmol) in anhydrous THF (40 mL) was dropwise added diisopropyl azodicarboxylate (0.79 mL, 4.02 mmol) and the reaction was allowed to warm up to room temperature and was stirred overnight. The following day further 1-cyclopropylethanol (133 mg, 1.55 mmol), triphenylphosphine (406 mg, 1.55 mmol) and diisopropyl azodicarboxylate (0.30 mL, 1.55 mmol) were added and the reaction was continued to be stirred for further 6 hours. The reaction mixture was then concentrated under reduced pressure and diethyl ether was added. The resulting mixture was cooled 0° C. giving a white precipitate. The precipitate was filtered and removed and the resulting filtrate was concentrated at reduced pressure and then purified by Biotage Isolera™ chromatography (50 g SiO$_2$ column; eluting with a gradient of eluents, 0-35% EtOAc in heptane) to afford the title compound (260 mg, 32% yield) as a pale yellow oil.

$^1$H NMR (250 MHz, Chloroform-d) δ [ppm] 7.83 (s, 1H), 7.80 (s, 1H), 3.70-3.51 (m, 1H), 1.58 (d, J=6.1 Hz, 3H), 1.32 (s, 12H), 1.28-1.15 (m, 1H), 0.73-0.62 (m, 1H), 0.61-0.48 (m, 1H), 0.43-0.24 (m, 2H).

LCMS (Analytical Method A): Rt=1.36 min, MS (ESI-pos): m/z=263.1 (M+H)$^+$.

Intermediate 309A: 2-ethyl-5-(4,4,5,5-tetramethyl-1,3,2-dioxaborolan-2-yl)pyridine

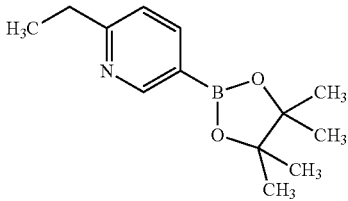 [SMILES: CCc1ccc(B2OC(C)(C)C(C)(C)O2)cn1]

To a solution of 5-bromo-2-ethylpyridine (0.55 g, 2.956 mmol) and bis(pinacolato)diboron (0.826 g, 9.8 mmol) in 1,4-dioxane (8 mL) was added potassium acetate (0.87 g, 8.87 mmol) at room temperature. Nitrogen gas was bubbled through the mixture for 5 mins and 1,1'-bis(diphenylphosphino)ferrocenepalladium(II) chloride (65 mg, 0.089 mmol) was then added. The mixture was heated at 100° C. in a sealed tube for 5 hours. The reaction mixture was cooled to room temperature and diluted with EtOAc (20 mL), filtered over Celite and washed with EtOAc (30 mL). The filtrate was concentrated at reduced pressure and the residue was purified by Biotage Isolera™ chromatography [Biotage SNAP Cartridge KP-Sil 25 g; eluting with a gradient of eluents, 0-100% EtOAc in heptane] to give the title compound (213 mg, 29% yield) as an orange oil.

$^1$H NMR (500 MHz, Chloroform-d) δ [ppm] 8.89-8.82 (m, 1H), 7.97 (dd, J=7.7, 1.8 Hz, 1H), 7.15 (d, J=7.7 Hz, 1H), 2.83 (q, J=7.6 Hz, 2H), 1.34 (s, 12H), 1.30 (t, J=7.6 Hz, 3H).

Intermediate 16A: Thieno[2,3-b]pyridin-2-yl boronic acid

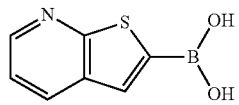 [SMILES: OB(O)c1cc2cccnc2s1]

Thieno[2,3-b]pyridin (950 mg, 7.09 mmol) was dissolved in THF and the solution cooled to −45° C. n-Butyl lithium (1.1 eq., 7.73 mmol, 4.83 mL, 1.6 M in hexane) was added dropwise and the mixture stirred for further 1 h at −45° C. Triisopropyl borate (1.2 eq., 1.59 g, 8.43 mmol, 1.95 mL) was added dropwise and the mixture stirred for further 2 hours at RT. Ortho phosphoric acid (85%, 0.57 mL, 140 mmol) was added dropwise and the mixture stirred for a further 15 min. The resulting yellow suspension was diluted with diethyl ether (40 mL) and water (40 mL). The precipitate collected by filtration, washed with diethyl ether and dried under vacuum to give the title compound (810 mg, 64% yield) as a yellow solid. Upon standing the filtrate at RT, a second precipitate formed which was isolated in the same manner to give an additional title compound (410 mg, 33% yield).

$^1$H NMR (400 MHz, DMSO-d6) δ [ppm] 7.41 (dd, 1H), 7.94 (s, 1H), 8.30 (dd, 1H), 8.58 (dd, 1H), 8.62 (s, br, 2H).

LCMS (method 2): Rt=0.50 min; MS (ESIPos) m/z=180 (M+H)$^+$.

Intermediate 17A: 4-iodo-1-{[2-(trimethylsilyl)ethoxy]methyl}-1H-pyrazole

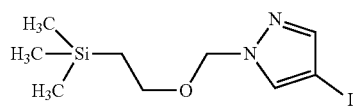

To a solution of 4-iodo-1H-pyrazole (2.0 g, 10.31 mmol) in tetrahydrofuran (20 mL) was added sodium hydride (619 mg, 15.47 mmol) at 0° C. The resulting white suspension was stirred at 0° C. for 2 hours. 2-(Chloromethoxyethyl)trimethyl silane (SEM-Cl, 90% purity, 2.101 g, 2.230 mL, 11.34 mmol) was added dropwise at 0° C. The suspension was then allowed to warm up to room temperature and stirred for 16 hours. The reaction was quenched with water (0.5 mL), and concentrated to −5 mL at reduced pressure. The mixture was then partitioned between EtOAc (50 mL) and saturated NaHCO$_3$ solution (30 mL). The organic layer was separated, washed with brine (20 mL), dried (Na$_2$SO$_4$) and concentrated at reduced pressure. The residue was purified by Biotage Isolera™ chromatography [SNAP Cartridge KP-Sil 50 g; eluting with a gradient of eluents; 0-20% EtOAc in heptane] to give the title compound (3.27 g, 91% yield) as a colourless oil.

$^1$H NMR (500 MHz, Chloroform-d) δ [ppm] 7.62 (s, 1H), 7.54 (s, 1H), 5.40 (s, 2H), 3.59-3.51 (m, 2H), 0.94-0.85 (m, 2H), −0.02 (s, 9H).

LCMS (Analytical Method A): Rt=1.36 mins; MS (ESI-Pos) m/z=324.9 (M+H)$^+$.

Intermediate 18A: 4-cyclobutyl-1-{[2-(trimethylsilyl)ethoxy]methyl}-1H-pyrazole

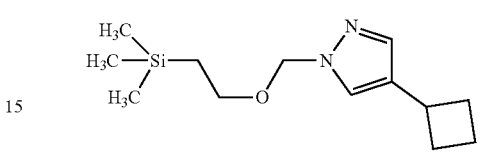

To a de-gassed mixture of 4-iodo-1-{[2-(trimethylsilyl)ethoxy]methyl}-1H-pyrazole (Int 17A, 1.50 g, 4.626 mmol) in THF (20 mL) was added 1,1'-bis(diphenylphosphino)ferrocenedichloropalladium(II) (50 mg, 0.068 mmol). The mixture was stirred for 5 minutes at room temperature, then a 0.5M solution of bromo(cyclobutyl)zinc in THF (11.5 mL, 5.75 mmol) was added. The mixture was heated at 65° C. for two hours then cooled to room temperature and the reaction was quenched by addition of water (1 mL). The mixture was partitioned between EtOAc (100 mL) and water (30 mL), the organic layer was separated, washed with brine (30 mL), dried (Na$_2$SO$_4$) and concentrated under reduced pressure. The residue was purified by Biotage Isolera™ chromatography [SNAP Cartridge KP-Sil 50 g; eluting with a gradient of eluents; 0-20% EtOAc in heptane], to give the title compound (540 mg, 46% yield) as a colourless oil.

$^1$H NMR (500 MHz, Chloroform-d) δ [ppm] 7.40 (s, 1H), 7.34 (s, 1H), 5.36 (s, 2H), 3.58-3.51 (m, 2H), 3.44-3.35 (m, 1H), 2.37-2.26 (m, 2H), 2.08-1.84 (m, 4H), 0.94-0.85 (m, 2H), −0.03 (s, 9H).

LCMS (Analytical Method A): Rt=1.52 mins; MS (ESI) m/z=253.05 (M+H)$^+$.

Intermediate 19A: (3S)-Tetrahydrofuran-3-yl methanesulfonate

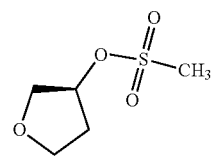

To a solution of (3S)-tetrahydrofuran-3-ol (1.00 g, 11.4 mmol) and N,N-diisopropylethylamine (2.4 mL, 13.6 mmol) at 0° C. in dichloromethane (20 mL) was added dropwise methanesulfonyl chloride (1.05 mL, 13.6 mmol) and the reaction mixture was allowed to warm up to room temperature and was stirred for 2 h. The reaction mixture was diluted with dichloromethane (20 mL) and washed with saturated sodium bicarbonate (30 mL), the organic layer dried over anhydrous sodium sulfate, filtered and concentrated in vacuo to give the title compound (1.58 g) as an orange oil. This was used in the next step without purification.

$^1$H NMR (250 MHz, Chloroform-d) δ [ppm] 5.40-5.24 (m, 1H), 4.09-3.82 (m, 4H), 3.04 (s, 3H), 2.30-2.17 (m, 2H).

In analogy to the procedure described for Intermediate 19A, the following intermediate was prepared using methanesulfonyl chloride and the appropriate alcohol.

| Int. | Structure | Name | Analytical Data |
|---|---|---|---|
| 20A | 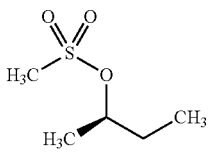 | (3R)-tetrahydrofuran-3-yl methanesulfonate | $^1$H NMR (250 MHz, Chloroform-d) δ 5.37-5.25 (m, 1H), 4.10-3.79 (m, 4H), 3.04 (s, 3H), 2.34-2.16 (m, 2H). |

Intermediate 21A: (2R)-butan-2-yl methanesulfonate

To a solution of (2R)-butan-2-ol (0.90 g, 12.2 mmol) and N,N-diisopropylethylamine (1.88 mL, 15.6 mmol) at 0° C. in dichloromethane (21 mL) was added dropwise methanesulfonyl chloride (1.67 mL, 14.6 mmol). The reaction mixture was allowed to warm to RT and stirred for 16 hours. The reaction mixture was washed with saturated aqueous sodium chloride solution, dried (MgSO$_4$), filtered and concentrated at reduced pressure to give the title compound (1.60 g) as a pale yellow oil. This was used in the next step without further purification.

$^1$H NMR (250 MHz, Chloroform-d) δ [ppm] 4.77 (m, 1H), 3.02 (s, 3H), 1.79-1.66 (m, 2H), 1.44 (d, J=6.3 Hz, 3H), 1.01 (t, J=7.4 Hz, 3H).

In analogy to the procedure described for Intermediate 21A, the following intermediate was prepared using methanesulfonyl chloride and the appropriate alcohol.

Intermediate 23A: 1-[(3R)-Tetrahydrofuran-3-yl]-4-(4,4,5,5-tetramethyl-1,3,2-dioxaborolan-2-yl)-1H-pyrazole

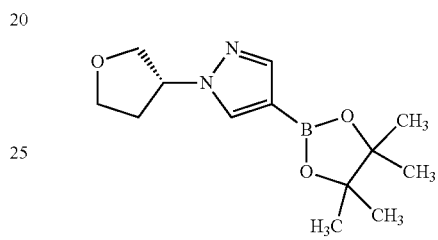

To a solution of 4-(tetramethyl-1,3,2-dioxaborolan-2-yl)-1H-pyrazole (674 mg, 3.47 mmol) in anhydrous DMF (14 mL) was added NaH (60% dispersion in mineral oil, 180 mg, 4.51 mmol) and the reaction mixture was stirred at 0° C. for 15 mins. (3S)-Tetrahydrofuran-3-yl methanesulfonate (750 mg, 4.51 mmol) was then added and the reaction was heated to 100° C. for 2 hours. The reaction was cooled to room temperature, concentrated under reduced pressure and partitioned between EtOAc and water. The aqueous layer was extracted once with EtOAc and the combined organic extracts were dried over MgSO$_4$, filtered, concentrated under reduced pressure and purified by Biotage Isolera™ chromatography (50 g silica cartridge, eluting with a gradient of eluents; 0-60% EtOAc in heptane) to afford the title compound (380 mg, 40% yield) as a colourless oil that solidified on standing.

$^1$H NMR (250 MHz, Chloroform-d) δ [ppm] 7.78 (s, 2H), 5.05-4.91 (m, 1H), 4.19-4.02 (m, 3H), 4.00-3.86 (m, 1H), 2.55-2.21 (m, 2H), 1.31 (s, 12H).

LCMS (Analytical Method A): Rt=1.10 min, MS (ESI-pos): m/z=264.8 (M+H)$^+$.

In analogy to the procedure described for Intermediate 23A, the following intermediates were prepared using 4-(tetramethyl-1,3,2-dioxaborolan-2-yl)-1H-pyrazole and the appropriate mesylate.

| Int. | Structure | Name | Analytical Data |
|---|---|---|---|
| 22A | 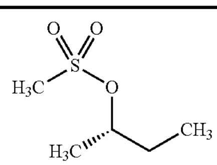 | (2S)-butan-2-yl methanesulfonate | $^1$H NMR (250 MHz, Chloroform-d) δ [ppm] 4.81-4.72 (m, 1H), 3.02 (s, 3H), 1.79-1.66 (m, 2H), 1.44 (d, J = 6.3 Hz, 3H), 1.01 (t, J = 7.4 Hz, 3H). |

| Int. | Structure | Name | Analytical Data |
|---|---|---|---|
| 24A | 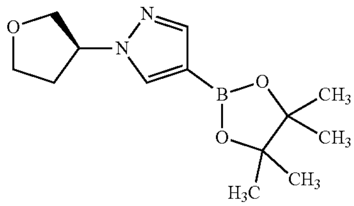 [SMILES: CC1(C)OB(c2cnn([C@H]3CCOC3)c2)OC1(C)C] | 1-[(3S)-tetrahydrofuran-3-yl]-4-(4,4,5,5-tetramethyl-1,3,2-dioxaborolan-2-yl)-1H-pyrazole | $^1$H NMR (250 MHz, Chloroform-d) δ [ppm] 7.78 (s, 2H), 5.07-4.85 (m, 1H), 4.19-4.02 (m, 3H), 3.99-3.88 (m, 1H), 2.55-2.16 (m, 2H), 1.31 (s, 12H). LCMS (Analytical Method A): Rt = 1.12 min, MS (ESIpos): m/z = 264.9 (M + H)$^+$. |
| 25A | 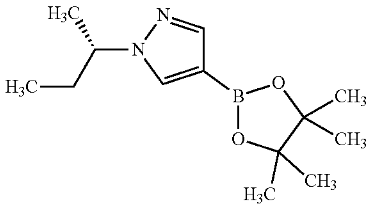 [SMILES: CC[C@H](C)n1cc(B2OC(C)(C)C(C)(C)O2)cn1] | 1-[(2S)-butan-2-yl]-4-(4,4,5,5-tetramethyl-1,3,2-dioxaborolan-2-yl)-1H-pyrazole | $^1$H NMR (250 MHz, Chloroform-d) δ [ppm] 7.82 (s, 1H), 7.73 (s, 1H), 4.35-4.19 (m, 1H), 2.03-1.72 (m, 2H), 1.51 (d, J = 6.8 Hz, 3H), 1.35 (s, 12H), 0.83 (t, J = 7.4 Hz, 3H). LCMS (Analytical Method A): Rt = 1.20 min, MS (ESIPos): m/z = 250.85 (M + H)$^+$. |
| 26A | 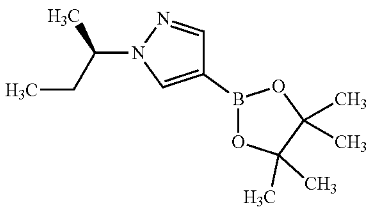 [SMILES: CC[C@@H](C)n1cc(B2OC(C)(C)C(C)(C)O2)cn1] | 1-[(2R)-butan-2-yl]-4-(4,4,5,5-tetramethyl-1,3,2-dioxaborolan-2-yl)-1H-pyrazole | $^1$H NMR (250 MHz, Chloroform-d) δ [ppm] 7.82 (s, 1H), 7.73 (s, 1H), 4.35-4.17 (m, 1H), 2.02-1.72 (m, 2H), 1.61 (s, 3H), 1.51 (d, J = 6.8 Hz, 3H), 0.82 (t, J = 7.4 Hz, 3H). LCMS (Analytical Method A): Rt = 1.34 min, MS (ESIPos): m/z = 251 (M + H)$^+$. |
| 27A | 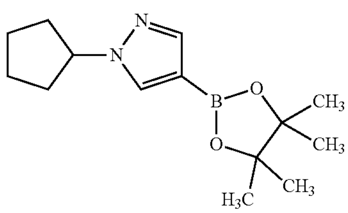 [SMILES: CC1(C)OB(c2cnn(C3CCCC3)c2)OC1(C)C] | 1-cyclopentyl-4-(4,4,5,5-tetramethyl-1,3,2-dioxaborolan-2-yl)-1H-pyrazole | $^1$H NMR (250 MHz, Chloroform-d) δ [ppm] 7.78 (s, 1H), 7.73 (s, 1H), 4.66 (m, 1H), 2.28-1.50 (m, 8H), 1.32 (s, 12H). LCMS (Analytical Method A): Rt = 1.34 min, MS (ESIpos): m/z = 262.9 (M + H)$^+$. |

Intermediate 297A:
5-bromo-2-cyclobutyl-1,3-thiazole

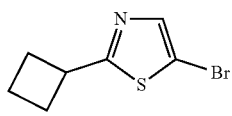

Bromo(cyclobutyl)zinc (9.1 mL of a 0.5 M solution in THF, 4.5 mmol) was added to 2,5-dibromo-1,3-thiazole (1.0 g, 4.1 mmol) and dry THF (10 mL) under a nitrogen atmosphere. To this was added 1,1'-Bis(diphenylphosphino)ferrocenedichloropalladium(II) (60 mg, 82 □mol) and the resulting mixture was heated at 70° C. for 2 hours in a sealed tube. The mixture was then cooled to room temperature. The reaction was quenched by addition of water (20 mL) and the mixture was then extracted with ethyl acetate (50 mL). The organics were then washed with brine (20 mL), dried (Na$_2$SO$_4$), filtered and concentrated at reduced pressure. The residue was purified by Biotage Isolera™ chromatography (eluting with a gradient of eluents; 0-40% ethyl acetate in heptane) giving the title compound (800 mg, 89% yield) as a pale yellow oil.

$^1$H NMR (500 MHz, Chloroform-d) δ [ppm] 7.54 (s, 1H), 3.85-3.74 (m, 1H), 2.49-2.40 (m, 2H), 2.38-2.28 (m, 2H), 2.13-2.00 (m, 1H), 2.00-1.91 (m, 1H).

LCMS (Analytical Method A): Rt=1.24 mins, MS (ESI-Pos): m/z=218 E& 220 (M+H)$^+$.

Intermediate 310A:
5-bromo-2-cyclopentyl-1,3-thiazole

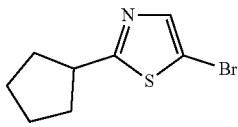 [SMILES: Brc1cnc(C2CCCC2)s1]

Cyclopentylzinc bromide (9.1 mL of a 0.5 M solution in THF, 4.5 mmol) was added to 2,5-dibromo-1,3-thiazole (1.0 g, 4.1 mmol) and dry THF (10 mL) under a nitrogen atmosphere. To this was added 1,1'-Bis(diphenylphosphino)ferrocenedichloropalladium(II) (60 mg, 82 □mol) and the resulting mixture was heated at 70° C. for 2 hours in a sealed tube. The mixture was then cooled to room temperature. The reaction was quenched by addition of water (20 mL) and the mixture was then extracted with ethyl acetate (50 mL). The organics were then washed with brine (20 mL), dried (Na$_2$SO$_4$), filtered and concentrated at reduced pressure. The residue was purified by Biotage Isolera™ chromatography (eluting with a gradient of eluents, 0-40% ethyl acetate in heptane) giving the title compound (780 mg, 78% yield) as a pale yellow oil.

¹H NMR (500 MHz, Chloroform-d) δ [ppm] 7.52 (s, 1H), 3.43-3.32 (m, 1H), 2.23-2.09 (m, 2H), 1.87-1.63 (m, 6H).

LCMS (Analytical Method A): Rt=1.30 mins, MS (ESI-Pos): m/z=233 (M+H)$^+$.

Intermediate 311A:
1-cyclobutyl-4-iodo-1H-imidazole

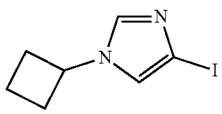

To a solution of 4-iodo-1H-imidazole (4.0 g, 20.62 mmol) in N,N-dimethylformamide (30 mL) was added sodium hydride (60% in mineral oil, 907 mg, 22.68 mmol) at room temperature. The mixture was stirred for 15 minutes until the production of gas ceased. Bromocyclobutane (3.88 mL, 41.24 mmol) was added and the mixture was stirred at 80° C. for 16 hours. After cooling to room temperature, the reaction mixture was diluted with TBME (50 mL) and the solids were removed by filtration. The filtrate was concentrated at reduced pressure and the residue obtained was purified by Biotage Isolera™ chromatography [Biotage SNAP Cartridge KP-Sil 50 g; using a gradient of eluents, 0-100% EtOAc in heptane] and the residue obtained was recrystallized from TBME/heptane to afford the title compound (2.06 g, 40% yield) as colourless crystalline solid.

¹H NMR (500 MHz, Chloroform-d) δ [ppm] 7.40 (s, 1H), 7.07 (d, J=1.4 Hz, 1H), 4.66-4.49 (m, 1H), 2.54-2.44 (m, 2H), 2.38-2.26 (m, 2H), 1.96-1.80 (m, 2H).

LCMS (Analytical Method A): Rt=0.67 mins; MS (ESI-Pos) m/z=248.85 (M+H)$^+$.

Intermediate 312A:
2-Cyclobutyl-5-(tributylstannyl)-1,3-thiazole

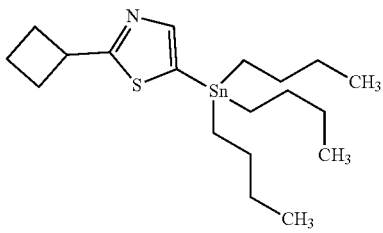 [SMILES: CCC[CH2][Sn]([CH2]CCC)([CH2]CCC)[c]1cnc(C2CCC2)s1]

5-bromo-2-cyclobutyl-1,3-thiazole (410 mg, 1.88 mmol) was dissolved in THF (5 mL) and cooled to −78° C. n-Butyllithium (1.41 mL of a 1.6M solution in hexane, 2.26 mmol) was added dropwise over 5 minutes giving a brown solution. After 15 minutes at −78° C., tri-n-butyltin chloride (0.61 mL, 2.26 mmol) was added dropwise over 5 minutes and the mixture was then allowed to warm to room temperature. The reaction was diluted with water (20 mL) and then extracted with ethyl acetate (50 mL). The organics were then washed with brine (20 mL), dried (Na$_2$SO$_4$), filtered and concentrated at reduced pressure. The residue was purified by Biotage Isolera™ chromatography (Biotage SNAP Cartridge KP-Sil 50 g; eluting with a gradient of eluents, 0-30% EtOAc in heptane) giving the title compound (540 mg, 54% yield) as a colourless oil.

¹H NMR (500 MHz, Chloroform-d) δ [ppm] 7.59 (s, 1H), 4.00-3.85 (m, 1H), 2.54-2.31 (m, 4H), 2.15-2.00 (m, 1H), 2.00-1.91 (m, 1H), 1.58-1.50 (m, 6H), 1.37-1.26 (m, 6H), 1.15-1.04 (m, 6H), 0.89 (t, J=7.3 Hz, 9H).

LCMS (Analytical Method A): Rt=1.22 mins, the product did not ionise.

Intermediate 28A: Methyl 5-amino-2-(6-ethoxypyridin-3-yl)benzoate

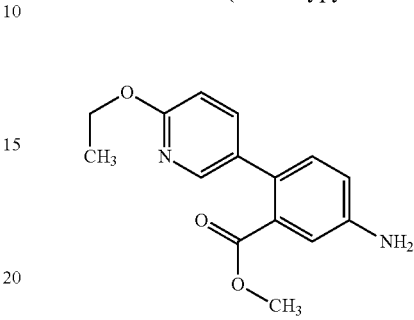

Under an atmosphere of nitrogen, methyl 5-amino-2-bromobenzoate (Int 1A, 1.0 g, 4.35 mmol), (6-ethoxypyridin-3-yl)boronic acid (1.09 mg, 6.52 mmol) and potassium carbonate (1.98 g, 14.3 mmol) were dissolved in 1,2-dimethoxyethane (15.8 mL) and water (7.8 mL). Pd(PPh$_3$)$_2$Cl$_2$ (36.7 mg, 0.052 mmol) was added and the reaction mixture heated at 90° C. until completion. The reaction mixture was cooled to RT, diluted with water (30 mL) and extracted with ethyl acetate (20 mL). The organic layer was washed with water (15 mL), brine (15 mL), dried (Na$_2$SO$_4$), filtered and concentrated at reduced pressure to give the title compound (1.37 g, 115% yield, approximately 87% purity) as a yellow solid. The material was used in the next step without further purification.

LCMS (method 4): Rt=1.03 min, MS (ESIpos) m/z=273 (M+H)$^+$.

Intermediate 29A: Methyl 5-amino-2-(1-cyclobutyl-1H-pyrazol-4-yl)benzoate

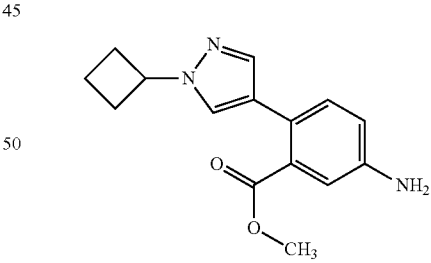

Methyl 5-amino-2-bromobenzoate (Int 1A, 4.21 g, 18.3 mmol), 1-cyclobutyl-4-(4,4,5,5-tetramethyl-1,3,2-dioxaborolan-2-yl)-1H-pyrazole (5.00 g, 20.2 mmol) and potassium carbonate (8.36 g, 60.5 mmol) were dissolved in 1,2-dimethoxyethane (67 mL) and water (33 mL) under an atmosphere of nitrogen. Pd(PPh$_3$)$_2$Cl$_2$ (155 mg, 0.22 mmol) was added and the reaction mixture heated at 90° C. until completion. The reaction was cooled to RT, diluted with water (100 mL) and extracted with ethyl acetate (75 mL). The organic layer was washed with water (50 mL), brine (50 mL), dried (Na$_2$SO$_4$), filtered and concentrated at reduced pressure. The crude product was purified by Biotage Isolera™ chromatography to give the title compound (4.34 g, 87% yield) as a yellow oil.

¹H NMR (500 MHz, DMSO-d6) δ [ppm] 7.73 (d, J=0.7 Hz, 1H), 7.37 (d, J=0.6 Hz, 1H), 7.11 (d, J=8.3 Hz, 1H), 6.80 (d, J=2.5 Hz, 1H), 6.70 (dd, J=8.3, 2.5 Hz, 1H), 5.31 (s, 2H), 4.86-4.73 (m, 1H), 3.69 (s, 3H), 2.48-2.31 (m, 4H), 1.83-1.71 (m, 2H).

LCMS (method 4): Rt=0.94 min, MS (ESIpos) m/z=272 (M+H)⁺.

1-cyclobutyl-4-(4,4,5,5-tetramethyl-1,3,2-dioxaborolan-2-yl)-1H-pyrazole (CAS 1002309-48-9) is commercially available. Alternatively, it was synthesized as follows:

4-(4,4,5,5-Tetramethyl-1,3,2-dioxaborolan-2-yl)-1H-pyrazole (CAS 269410-08-4, 1.20 g, 6.18 mmol) was dissolved in DMF (23 mL) and sodium hydride (0.81 g, 18.6 mmol) was added at room temperature (rt). After 10 min, cyclobutyl bromide (2.51 g, 18.6 mmol) was added and the mixture stirred for 2 g at 50° C. and further 16 h at rt. The mixture was partitioned between water and ethyl acetate, extracted with ethyl acetate, and the combined organic layers washed with water, dried (Na₂SO₄) and concentrated. The crude product (1.14 g, 87% purity, 64% yield) was used without further purification.

As an alternative, instead of sodium hydride, caesium carbonate was used as base. 4-(4,4,5,5-Tetramethyl-1,3,2-dioxaborolan-2-yl)-1H-pyrazole was stirred with 1.5 equivalents cyclobutyl bromide and 1.5 equivalents caesium carbonate in DMF at 65° C. until the conversion was complete. If needed, additional 0.5 equivalents cyclobutyl bromide and 0.5 equivalents caesium carbonate were added.

¹H NMR (400 MHz, DMSO-d6) δ [ppm] 1.24 (s, 12H), 1.71-1.80 (m, 2H), 2.31-2.48 (m, 4H), 4.83 (quint, 1H), 7.60 (s, 1H), 8.00 (s, 1H).

In analogy to the procedure described for Intermediate 29A, the following intermediates were prepared using methyl 5-amino-2-bromobenzoate (Int 1A) and the appropriate boronic acids or, respectively, the corresponding pinacol boronic esters as starting materials.

| Int. | Structure | Name | Analytical Data |
|---|---|---|---|
| 30A | 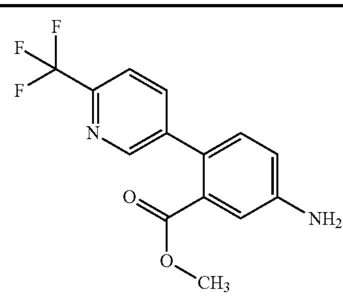 | Methyl 5-amino-2-[6-(trifluoromethyl)pyridin-3-yl]benzoate | LCMS (method 4): R_t = 1.12 min, MS (ESIpos) m/z = 297 (M + H)⁺. |
| 31A | 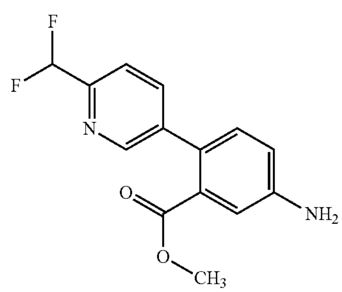 [SMILES: COC(=O)c1cc(N)ccc1-c1ccc(C(F)F)nc1] | Methyl 5-amino-2-[6-(difluoromethyl)pyridin-3-yl]benzoate | LCMS (method 3): R_t = 0.92 min, MS (ESIpos) m/z = 279 (M + H)⁺. |
| 32A | 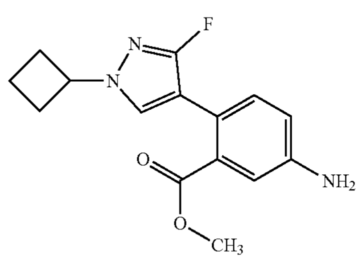 [SMILES: COC(=O)c1cc(N)ccc1-c1cn(C2CCC2)nc1F] | Methyl 5-amino-2-(1-cyclobutyl-3-fluoro-1H-pyrazol-4-yl)benzoate | ¹H NMR (400 MHz, DMSO-d6) δ [ppm] 1.71-1.78 (m, 2H), 2.30-2.45 (m, 4H), 3.68 (s, 3H), 4.68 (quint, 1H), 5.45 (s, 2H), 6.74 (dd, 1H), 6.96 (d, 1H), 7.05 (d, 1H), 7.75 (d, 1H). LCMS (method 1): Rt = 0.94 min; MS (ESIPos) m/z = 290 (M + H)⁺. |
| 33A | 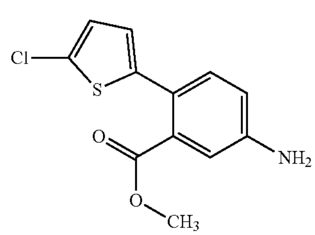 [SMILES: COC(=O)c1cc(N)ccc1-c1ccc(Cl)s1] | Methyl 5-amino-2-(5-chloro-2-thienyl)benzoate | LCMS (method 3): R_t = 1.21 min, MS (ESIpos) m/z = 268 (M + H)⁺. |

| Int. | Structure | Name | Analytical Data |
|---|---|---|---|
| 34A | 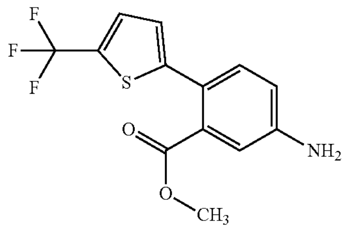 [SMILES: COC(=O)c1cc(N)ccc1-c1ccc(C(F)(F)F)s1] | Methyl 5-amino-2-[5-(trifluoromethyl)-2-thienyl]benzoate | LCMS (method 3): $R_t$ = 1.27 min, MS (ESIpos) m/z = 302 (M + H)$^+$. |
| 35A | 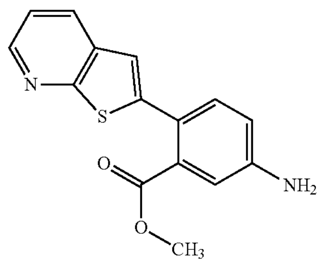 [SMILES: COC(=O)c1cc(N)ccc1-c1cc2cccnc2s1] | Methyl 5-amino-2-(thieno[2,3-b]pyridin-2-yl)benzoate | $^1$H NMR (400 MHz, DMSO-d6) δ [ppm] 3.67 (s, 3H), 5.78 (s, 2H), 6.78 (dd, 1H), 6.90 (d, 1H), 7.16 (s, 1H), 7.30 (d, 1H), 7.41 (dd, 1H), 8.18 (dd, 1H), 8.49 (dd, 1H). LCMS (method 1): $R_t$ = 0.87 min, MS (ESIpos) m/z = 285 (M + H)$^+$. |

Intermediate 36A: Methyl 2-(1-benzothiophen-2-yl)-5-nitrobenzoate

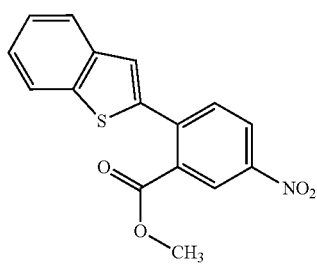

To a solution of 2-bromo-5-nitrobenzoate (591 mg, 2.273 mmol), (1-benzothiophen-2-yl)boronic acid (425 mg, 2.387 mmol) and Pd(PPh$_3$)$_2$Cl$_2$ (16 mg, 0.023 mmol) in 1,2-dimethoxyethane (10 mL) was added 2M aq. potassium carbonate (3.8 mL, 7.6 mmol) and the mixture degassed with a stream of nitrogen gas for 5 mins. The reaction mixture was heated at 100° C. for 16 hours. The reaction was cooled to RT, diluted with saturated Na$_2$CO$_3$ (20 mL) and the aqueous layer extracted with EE (2×20 mL). The combined organics were dried (MgSO$_4$), filtered, concentrated at reduced pressure and purified by Biotage Isolera™ chromatography (silica gel) to give the title compound (497 mg, 70% yield) as a yellow solid.

$^1$H NMR (250 MHz, DMSO-d6) δ [ppm] 8.53 (d, J=2.5 Hz, 1H), 8.47 (d, J=2.5 Hz, 1H), 8.09-8.02 (m, 1H), 7.96 (d, J=8.6 Hz, 2H), 7.63 (s, 1H), 7.51-7.40 (m, 2H), 3.79 (s, 3H).

LCMS (Analytical Method D) Rt=4.83; MS (ESIpos) m/z=282 (M-OMe)$^+$.

Intermediate 37A: Methyl 2-(1-cyclobutyl-1H-pyrazol-4-yl)-5-nitrobenzoate

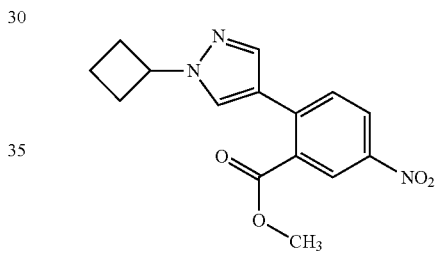

1-Cyclobutyl-4-(4,4,5,5-tetramethyl-1,3,2-dioxaborolan-2-yl)-1H-pyrazole (1.5 g, 6.0 mmol) and methyl 2-bromo-5-nitrobenzoate (1.66 g, 6.0 mmol) in DME (30 mL) and water (15 mL) was degassed with nitrogen for 5 minutes. Bis(triphenylphosphine)-palladium(II) dichloride (127 mg, 0.18 mmol) and potassium carbonate (2.5 g, 18.1 mmol) were added and the reaction heated with stirring at 100° C. for 2 hours. The reaction mixture was cooled to room temperature, diluted with water (30 mL) and extracted with EtOAc (50 mL). The organic layer was washed with brine (2×30 mL), dried (Na$_2$SO$_4$), filtered and concentrated at reduced pressure. The residue was purified by Biotage Isolera™ chromatography (silica gel; using a gradient of eluents; 0-50% EtOAc in heptane) to give the title compound (1.72 g, 72% yield) as a yellow oil.

$^1$H NMR (500 MHz, DMSO-d6) δ [ppm] 8.43 (d, J=2.5 Hz, 1H), 8.33 (dd, J=8.7, 2.6 Hz, 1H), 8.20 (s, 1H), 7.83 (d, J=8.7 Hz, 1H), 7.72 (s, 1H), 4.97-4.81 (m, 1H), 3.85 (s, 3H), 2.45-2.33 (m, 2H), 1.87-1.76 (m, 2H).

LCMS (Analytical Method A): Rt=1.19 mins, MS (ESI-Pos): m/z=302 (M+H)$^+$.

In analogy to the procedure described for Intermediate 37A, the following intermediates were prepared using methyl 2-bromo-5-nitrobenzoate and the appropriate boronic acids or, respectively, the corresponding pinacol boronic esters as starting materials.

| Int. | Structure | Name | Analytical Data |
|---|---|---|---|
| 38A | 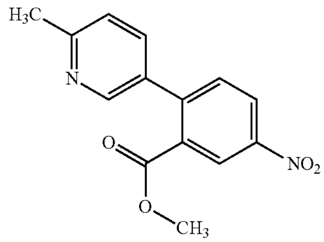 [SMILES: COC(=O)c1cc([N+](=O)[O-])ccc1-c1ccc(C)nc1] | Methyl 2-(6-methylpyridin-3-yl)-5-nitrobenzoate | ¹H NMR (500 MHz, DMSO-d6) δ [ppm] 8.60 (d, J = 2.5 Hz, 1H), 8.46 (dd, J = 8.5, 2.5 Hz, 1H), 8.43 (d, J = 2.3 Hz, 1H), 7.77 (d, J = 8.5 Hz, 1H), 7.71 (dd, J = 8.0, 2.4 Hz, 1H), 7.36 (d, J = 8.0 Hz, 1H), 3.72 (s, 3H), 2.54 (s, 3H). LCMS (Analytical Method A): Rt = 0.96 mins; m/z (ESIPos) = 273.0 (M + H)⁺. |
| 39A | 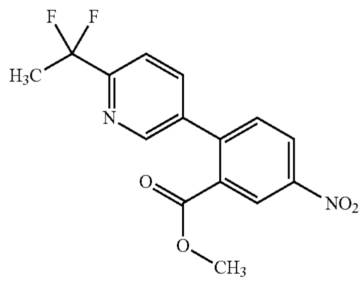 [SMILES: COC(=O)c1cc([N+](=O)[O-])ccc1-c1ccc(C(C)(F)F)nc1] | Methyl 2-[6-(1,1-difluoroethyl)pyridin-3-yl]-5-nitrobenzoate | ¹H NMR (500 MHz, DMSO-d6) δ [ppm] 8.69-8.66 (m, 2H), 8.51 (dd, J = 8.5, 2.5 Hz, 1H), 8.01 (dd, J = 8.1, 2.3 Hz, 1H), 7.83-7.79 (m, 2H), 3.74 (s, 3H), 2.06 (t, J = 19.1 Hz, 3H). LCMS (Analytical Method A): Rt = 1.19 mins; m/z (ESIPos) = 323 (M + H)⁺. |
| 40A | 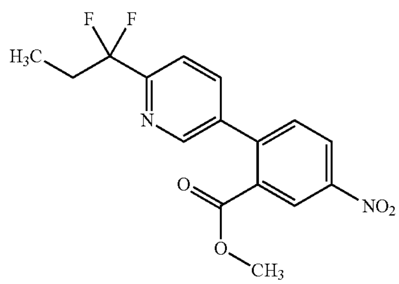 [SMILES: CCC(F)(F)c1ccc(-c2ccc([N+](=O)[O-])cc2C(=O)OC)cn1] | Methyl 2-[6-(1,1-difluoropropyl)pyridin-3-yl]-5-nitrobenzoate | ¹H NMR (250 MHz, DMSO-d6) δ [ppm] 8.68-8.69 (m, 2H), 8.52 (dd, J = 8.5, 2.5 Hz, 1H), 8.02 (dd, J = 8.1, 2.2 Hz, 1H), 7.84 (d, J = 8.5 Hz, 1H), 7.79 (d, J = 8.1 Hz, 1H), 3.73 (s, 3H), 2.47-2.30 (m, 2H), 0.97 (t, J = 7.5 Hz, 3H). LCMS (Analytical Method A): R$_t$ = 1.24 min; MS (ESIPos), m/z = 337 (M + H)⁺. |
| 41A | 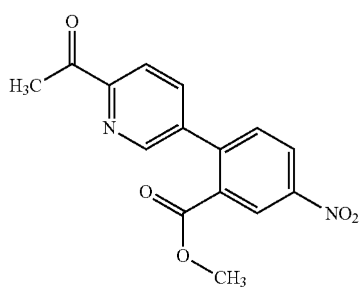 [SMILES: COC(=O)c1cc([N+](=O)[O-])ccc1-c1ccc(C(C)=O)nc1] | Methyl 2-(6-acetylpyridin-3-yl)-5-nitrobenzoate | ¹H NMR (500 MHz, DMSO-d6) δ [ppm] 8.73 (dd, J = 1.9, 0.9 Hz, 1H), 8.68 (d, J = 2.5 Hz, 1H), 8.52 (dd, J = 8.5, 2.5 Hz, 1H), 8.03 (dd, J = 3.7, 1.5 Hz, 2H), 7.82 (d, J = 8.5 Hz, 1H), 3.73 (s, 3H), 2.69 (s, 3H). LCMS (Analytical Method A): Rt = 1.17 mins, MS (ESIPos): m/z = 301 (M + H)⁺. |
| 42A | 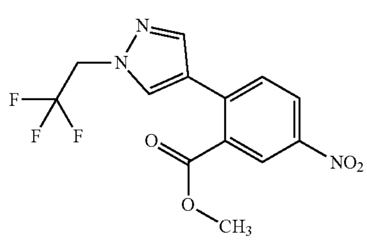 [SMILES: COC(=O)c1cc([N+](=O)[O-])ccc1-c1cnn(CC(F)(F)F)c1] | Methyl 5-nitro-2-[1-(2,2,2-trifluoroethyl)-1H-pyrazol-4-yl]benzoate | ¹H NMR (250 MHz, DMSO-d6) δ [ppm] 8.47 (d, J = 2.4 Hz, 1H), 8.37 (dd, J = 8.6, 2.6 Hz, 1H), 8.19 (s, 1H), 7.94-7.88 (m, 1H), 7.85 (d, J = 8.6 Hz, 1H), 5.23 (q, J = 9.1 Hz, 2H), 3.83 (s, 3H). LCMS (Analytical Method A): Rt = 1.19 mins; MS (ESIPos), m/z = 330 (M + H)⁺. |
| 43A | 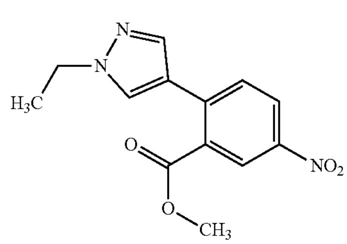 [SMILES: CCn1cc(-c2ccc([N+](=O)[O-])cc2C(=O)OC)cn1] | Methyl 2-(1-ethyl-1H-pyrazol-4-yl)-5-nitrobenzoate | ¹H NMR (500 MHz, Chloroform-d) δ [ppm] 8.58 (d, J = 2.5 Hz, 1H), 8.30 (dd, J = 8.6, 2.5 Hz, 1H), 7.72 (s, 1H), 7.67-7.64 (m, 1H), 7.59 (d, J = 8.6 Hz, 1H), 4.23 (q, J = 7.3 Hz, 2H), 3.89 (s, 3H), 1.55 (t, J = 7.3 Hz, 3H). LCMS (Analytical Method A): Rt = 1.09 mins; MS (ESIPos), m/z = 275.95 (M + H)⁺. |

| Int. | Structure | Name | Analytical Data |
|---|---|---|---|
| 44A | 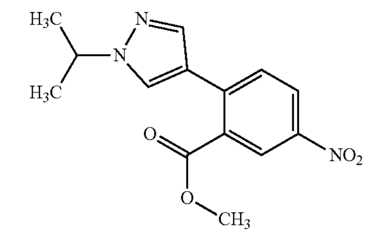 [SMILES: COC(=O)c1cc([N+](=O)[O-])ccc1-c1cnn(C(C)C)c1] | Methyl 2-(1-isopropyl-1H-pyrazol-4-yl)-5-nitrobenzoate | $^1$H NMR (500 MHz, Chloroform-d) δ [ppm] 8.56 (d, J = 2.4 Hz, 1H), 8.29 (dd, J = 8.6, 2.5 Hz, 1H), 7.73 (s, 1H), 7.66 (s, 1H), 7.60 (d, J = 8.6 Hz, 1H), 4.55 (hept, J = 6.7 Hz, 1H), 3.88 (s, 3H), 1.56 (d, J = 6.7 Hz, 6H). LCMS (Analytical Method A): Rt = 1.15 mins; MS (ESI) m/z = 290 (M + H)$^+$. |
| 45A | 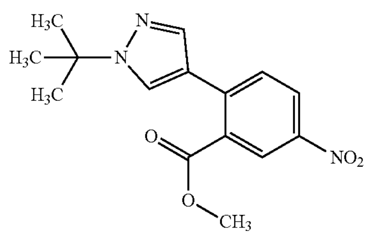 [SMILES: COC(=O)c1cc([N+](=O)[O-])ccc1-c1cnn(C(C)(C)C)c1] | Methyl 2-(1-tert-butyl-1H-pyrazol-4-yl)-5-nitrobenzoate | $^1$H NMR (500 MHz, Chloroform-d) δ [ppm] 8.57 (d, J = 2.5 Hz, 1H), 8.31 (dd, J = 8.6, 2.5 Hz, 1H), 7.83 (d, J = 0.7 Hz, 1H), 7.73-7.69 (m, 1H), 7.62 (d, J = 8.6 Hz, 1H), 3.90 (s, 3H), 1.66 (s, 9H). LCMS (Analytical Method A): Rt = 1.31 mins; MS (ESIPos), m/z = 304.05 (M + H)$^+$. |
| 46A | 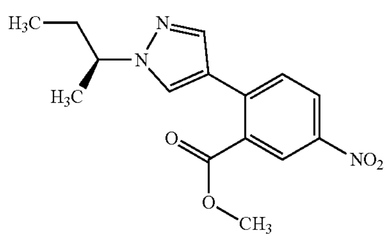 [SMILES: CC[C@H](C)n1cc(-c2ccc([N+](=O)[O-])cc2C(=O)OC)cn1] | Methyl 2-{1-[(2S)-butan-2-yl]-1H-pyrazol-4-yl}-5-nitrobenzoate | $^1$H NMR (500 MHz, Chloroform-d) δ [ppm] 8.58 (d, J = 2.5 Hz, 1H), 8.31 (dd, J = 8.6, 2.5 Hz, 1H), 7.72-7.70 (m, 1H), 7.69 (s, 1H), 7.62 (d, J = 8.6 Hz, 1H), 4.33-4.24 (m, 1H), 3.89 (s, 3H), 2.02-1.92 (m, 1H), 1.90-1.80 (m, 1H), 1.57 (d, J = 6.8 Hz, 3H), 0.88 (t, J = 7.4 Hz, 3H). LCMS (Analytical Method A): Rt = 1.25 mins, MS (ESIPos): m/z = 304.00 (M + H)$^+$. |
| 47A | 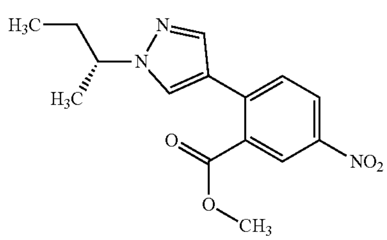 [SMILES: CC[C@@H](C)n1cc(-c2ccc([N+](=O)[O-])cc2C(=O)OC)cn1] | Methyl 2-{1-[(2R)-butan-2-yl]-1H-pyrazol-4-yl}-5-nitrobenzoate | $^1$H NMR (250 MHz, Chloroform-d) δ [ppm] 8.59 (d, J = 2.4 Hz, 1H), 8.32 (dd, J = 8.6, 2.5 Hz, 1H), 7.70 (d, J = 3.7 Hz, 2H), 7.63 (d, J = 8.6 Hz, 1H), 4.37-4.21 (m, 1H), 3.90 (s, 3H), 2.08-1.78 (m, 2H), 1.57 (d, J = 6.7 Hz, 3H), 0.89 (t, J = 7.4 Hz, 3H). LCMS (Analytical Method A): Rt = 1.38 mins, MS (ESIPos): m/z = 304.00 (M + H)$^+$. |
| 48A | 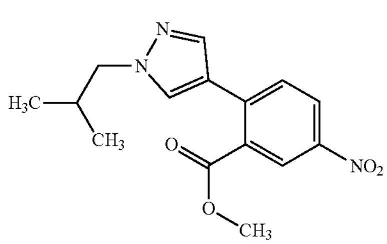 [SMILES: COC(=O)c1cc([N+](=O)[O-])ccc1-c1cnn(CC(C)C)c1] | Methyl 2-(1-isobutyl-1H-pyrazol-4-yl)-5-nitrobenzoate | $^1$H NMR (500 MHz, Chloroform-d) δ [ppm] 8.57 (d, J = 2.5 Hz, 1H), 8.30 (dd, J = 8.6, 2.5 Hz, 1H), 7.66 (s, 1H), 7.66 (s, 1H), 7.59 (d, J = 8.6 Hz, 1H), 3.96 (d, J = 7.3 Hz, 2H), 3.88 (s, 3H), 2.25 (m, 1H), 0.95 (d, J = 6.7 Hz, 6H). LCMS (Analytical Method A): Rt = 1.20 mins; MS (ESIPos), m/z = 304.05 (M + H)$^+$. |
| 49A | 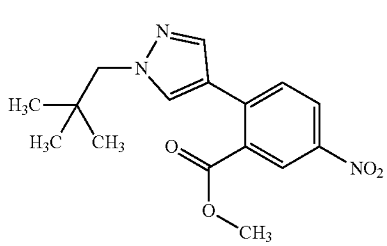 [SMILES: COC(=O)c1cc([N+](=O)[O-])ccc1-c1cnn(CC(C)(C)C)c1] | Methyl 2-[1-(2,2-dimethylpropyl)-1H-pyrazol-4-yl]-5-nitrobenzoate | $^1$H NMR (500 MHz, Chloroform-d) δ [ppm] 8.59 (d, J = 2.5 Hz, 1H), 8.35-8.29 (m, 1H), 7.67 (s, 1H), 7.66 (s, 1H), 7.62 (d, J = 8.6 Hz, 1H), 3.97 (s, 2H), 3.90 (s, 3H), 1.03 (s, 9H). LCMS (Analytical Method A): Rt = 1.33 mins; MS (ESIPos), m/z = 318.0 (M + H)$^+$. |

| Int. | Structure | Name | Analytical Data |
|---|---|---|---|
| 50A | 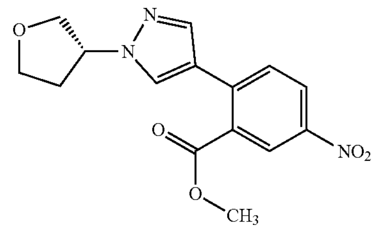 [SMILES: COC(=O)c1cc([N+](=O)[O-])ccc1-c1cnn([C@@H]2CCOC2)c1] | Methyl 5-nitro-2-{1-[(3R)-tetrahydrofuran-3-yl]-1H-pyrazol-4-yl}benzoate | $^1$H NMR (500 MHz, Chloroform-d) δ [ppm] 8.59 (d, J = 2.5 Hz, 1H), 8.30 (dd, J = 8.6, 2.5 Hz, 1H), 7.79 (s, 1H), 7.67 (s, 1H), 7.59 (d, J = 8.6 Hz, 1H), 5.08-4.97 (m, 1H), 4.20-4.12 (m, 2H), 4.08 (m, 1H), 3.97 (m, 1H), 3.89 (s, 3H), 2.56-2.45 (m, 1H), 2.42-2.32 (m, 1H). LCMS (Analytical Method A) Rt = 1.14 min, MS (ESIpos): m/z = 318.0 (M + H)$^+$ |
| 51A | 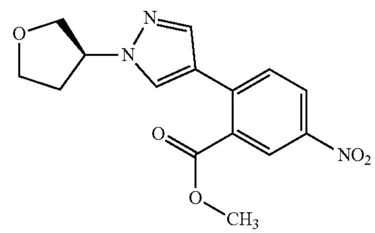 [SMILES: COC(=O)c1cc([N+](=O)[O-])ccc1-c1cnn([C@H]2CCOC2)c1] | Methyl 5-nitro-2-{1-[(3S)-tetrahydrofuran-3-yl]-1H-pyrazol-4-yl}benzoate | $^1$H NMR (500 MHz, Chloroform-d) δ [ppm] 8.59 (d, J = 2.5 Hz, 1H), 8.30 (dd, J = 8.6, 2.5 Hz, 1H), 7.79 (s, 1H), 7.67 (s, 1H), 7.59 (d, J = 8.6 Hz, 1H), 5.03 (m, 1H), 4.20-4.12 (m, 2H), 4.08 (m, 1H), 3.97 (m, 1H), 3.89 (s, 3H), 2.58-2.45 (m, 1H), 2.38 (m, 1H). LCMS (Analytical Method A) Rt = 1.17 min, MS (ESIPos): m/z = 318.0 (M + H)$^+$. |
| 52A | 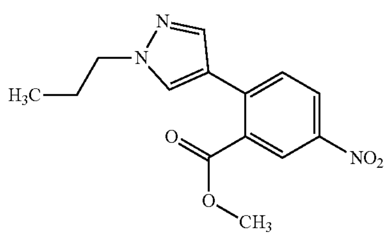 [SMILES: CCCn1cc(-c2ccc([N+](=O)[O-])cc2C(=O)OC)cn1] | Methyl 5-nitro-2-(1-propyl-1H-pyrazol-4-yl)benzoate | $^1$H NMR (500 MHz, DMSO-d6) δ [ppm] 8.42 (d, J = 2.5 Hz, 1H), 8.33 (dd, J = 8.7, 2.5 Hz, 1H), 8.09 (s, 1H), 7.82 (d, J = 8.7 Hz, 1H), 7.72 (s, 1H), 4.12 (t, J = 6.9 Hz, 2H), 3.84 (s, 3H), 1.86-1.75 (m, 2H), 0.84 (t, J = 7.4 Hz, 3H). LCMS (Analytical Method A) Rt = 1.20 min, MS (ESIpos): m/z = 290.0 (M + H)$^+$. |
| 53A | 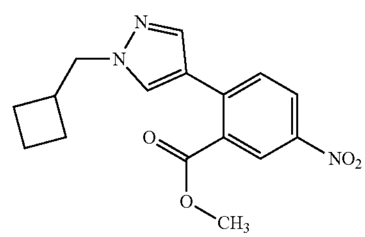 [SMILES: COC(=O)c1cc([N+](=O)[O-])ccc1-c1cnn(CC2CCC2)c1] | Methyl 2-[1-(cyclobutylmethyl)-1H-pyrazol-4-yl]-5-nitrobenzoate | $^1$H NMR (500 MHz, DMSO-d6) δ [ppm] 8.42 (d, J = 2.5 Hz, 1H), 8.33 (dd, J = 8.7, 2.5 Hz, 1H), 8.06 (s, 1H), 7.82 (d, J = 8.7 Hz, 1H), 7.72 (s, 1H), 4.18 (d, J = 7.3 Hz, 2H), 3.84 (s, 3H), 2.83-2.70 (m, 1H), 2.03-1.95 (m, 2H), 1.91-1.73 (m, 4H). LCMS (Analytical Method A) Rt = 1.26 min, MS (ESIpos): m/z = 316.0 (M + H)$^+$. |
| 54A | 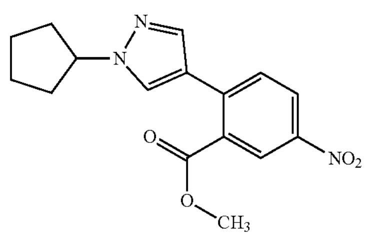 [SMILES: COC(=O)c1cc([N+](=O)[O-])ccc1-c1cnn(C2CCCC2)c1] | Methyl 2-(1-cyclopentyl-1H-pyrazol-4-yl)-5-nitrobenzoate | $^1$H NMR (250 MHz, Chloroform-d) δ [ppm] 8.56 (d, J = 2.4 Hz, 1H), 8.29 (dd, J = 8.6, 2.5 Hz, 1H), 7.73 (s, 1H), 7.66 (s, 1H), 7.59 (d, J = 8.6 Hz, 1H), 4.70 (m, 1H), 3.89 (s, 3H), 2.32-2.11 (m, 2H), 2.16-1.97 (m, 2H), 1.95-1.82 (m, 2H), 1.80-1.65 (m, 2H). LCMS (Analytical Method A) Rt = 1.38 min, MS (ESIpos): m/z = 316.0 (M + H)$^+$. |
| 55A | 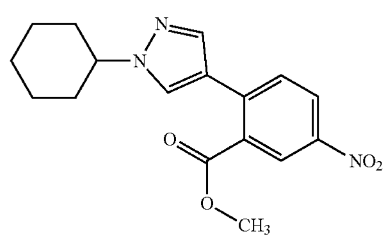 [SMILES: COC(=O)c1cc([N+](=O)[O-])ccc1-c1cnn(C2CCCCC2)c1] | Methyl 2-(1-cyclohexyl-1H-pyrazol-4-yl)-5-nitrobenzoate | $^1$H NMR (500 MHz, DMSO-d6) δ [ppm] 8.42 (d, J = 2.5 Hz, 1H), 8.33 (dd, J = 8.7, 2.6 Hz, 1H), 8.14 (s, 1H), 7.83 (d, J = 8.7 Hz, 1H), 7.70 (s, 1H), 4.25-4.12 (m, 1H), 3.85 (s, 3H), 2.12-1.98 (m, 2H), 1.90-1.60 (m, 5H), 1.50-1.34 (m, 2H), 1.30-1.16 (m, 1H). LCMS (Analytical Method A): Rt = 1.33 mins, MS (ESIPos): m/z = 330 (M + H)$^+$. |

| Int. | Structure | Name | Analytical Data |
|---|---|---|---|
| 313A | 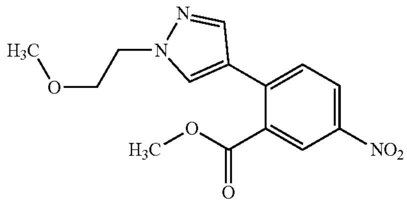 [SMILES: COCCn1cc(-c2ccc([N+](=O)[O-])cc2C(=O)OC)cn1] | Methyl 2-[1-(2-methoxyethyl)-1H-pyrazol-4-yl]-5-nitrobenzoate | $^1$H NMR (500 MHz, DMSO-d6) δ [ppm] 8.42 (d, J = 2.5 Hz, 1H), 8.33 (dd, J = 8.7, 2.5 Hz, 1H), 8.06 (s, 1H), 7.83 (d, J = 8.7 Hz, 1H), 7.75 (s, 1H), 4.32 (t, J = 5.3 Hz, 2H), 3.85 (s, 3H), 3.71 (t, J = 5.3 Hz, 2H), 3.25 (s, 3H). LCMS (Analytical Method A): Rt = 1.07 mins, MS (ESIPos): m/z = 306 (M + H)$^+$. |
| 314A | 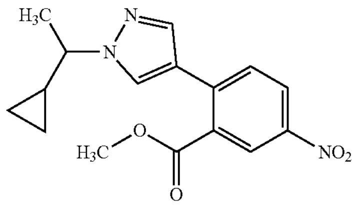 [SMILES: COC(=O)c1cc([N+](=O)[O-])ccc1-c1cnn(C(C)C2CC2)c1] | Methyl 2-[1-(1-cyclopropylethyl)-1H-pyrazol-4-yl]-5-nitrobenzoate as a 1:1 mixture of enantiomers | $^1$H NMR (500 MHz, Chloroform-d) δ [ppm] 8.49 (d, J = 2.5 Hz, 1H), 8.22 (dd, J = 8.6, 2.5 Hz, 1H), 7.75 (s, 1H), 7.61 (s, 1H), 7.54 (d, J = 8.6 Hz, 1H), 3.81 (s, 3H), 3.62-3.52 (m, 1H), 1.57 (d, J = 6.8 Hz, 3H), 1.24-1.16 (m, 1H), 0.70-0.62 (m, 1H), 0.59-0.52 (m, 1H), 0.39-0.27 (m, 2H). LCMS (Analytical Method A): Rt = 1.20 mins, MS (ESIPos): m/z = 316.00 (M + H)$^+$. |
| 315A | 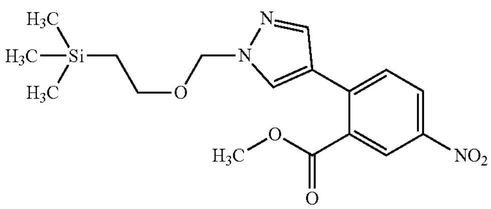 [SMILES: COC(=O)c1cc([N+](=O)[O-])ccc1-c1cnn(COCC[Si](C)(C)C)c1] | Methyl 5-nitro-2-(1-{[2-(trimethylsilyl)ethoxy]methyl}-1H-pyrazol-4-yl)benzoate | $^1$H NMR (500 MHz, Chloroform-d) δ 8.61 (d, J = 2.5 Hz, 1H), 8.32 (dd, J = 8.6, 2.5 Hz, 1H), 7.87 (s, 1H), 7.69 (s, 1H), 7.60 (d, J = 8.6 Hz, 1H), 5.47 (s, 2H), 3.88 (s, 3H), 3.66-3.61 (m, 2H), 0.99-0.90 (m, 2H), 0.00 (s, 9H). LCMS (Analytical Method A): Rt = 1.34 min; MS(ESIPos): m/z = 378 (M + H)$^+$. |
| 316A | 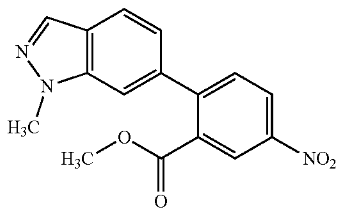 [SMILES: COC(=O)c1cc([N+](=O)[O-])ccc1-c1ccc2cnn(C)c2c1] | Methyl 2-(1-methyl-1H-indazol-6-yl)-5-nitrobenzoate | $^1$H NMR (250 MHz, Chloroform-d) δ [ppm] 8.75 (d, J = 2.4 Hz, 1H), 8.42 (dd, J = 8.5, 2.4 Hz, 1H), 8.11-7.98 (m, 1H), 7.80 (d, J = 8.3 Hz, 1H), 7.67 (d, J = 8.5 Hz, 1H), 7.42-7.35 (m, 1H), 7.09 (dd, J = 8.3, 1.3 Hz, 1H), 4.13 (s, 3H), 3.72 (s, 3H). LCMS (Analytical Method A) Rt = 1.16 min, MS (ESIpos): m/z = 312.0 (M + H)$^+$. |

Intermediate 56A: Methyl 2-(5-methylpyridin-2-yl)-5-nitrobenzoate

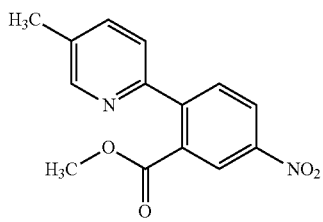 [SMILES: COC(=O)c1cc([N+](=O)[O-])ccc1-c1ccc(C)cn1]

A mixture of methyl 2-bromo-5-nitrobenzoate (0.20 g, 0.77 mmol), 2-(5-methylpyridin-2-yl)-5-phenyl-1,3,5,2-dioxazaborinane (489 mg, 1.92 mmol), Pd(PPh3)$_2$Cl$_2$ (67.5 mg, 0.10 mmol), CuI (73.2 mg, 0.39 mmol) and potassium carbonate (266 mg, 1.92 mmol) in tetrahydrofuran (3.8 mL) was degassed with nitrogen gas and the Ace® pressure tube sealed. The reaction mixture was heated at 80° C. for 16 h then cooled to room temperature, diluted with EtOAc and saturated aqueous sodium hydrogen carbonate solution, and filtered through a pad of Celite®. The organic layer was isolated, washed with saturated aqueous sodium chloride solution, dried (MgSO$_4$), filtered and concentrated in vacuo. The residual material was purified by Biotage Isolera™ flash column chromatography (25 g silica cartridge; eluting with a gradient of eluents; 0-50% EtOAc in heptane) to give the title compound (180 mg, 75% yield) as an orange oil.

$^1$H NMR (250 MHz, DMSO-d6) δ [ppm] 8.51 (m, 1H), 8.48-8.38 (m, 2H), 8.01 (d, J=8.7 Hz, 1H), 7.83-7.71 (m, 2H), 3.68 (s, 3H), 2.38 (s, 3H).

LCMS (Analytical Method A) Rt=1.08 min, MS (ESIpos) m/z=273.15 (M+H)$^+$.

Intermediate 298A: Methyl 5-nitro-2-(tributylstannyl)benzoate

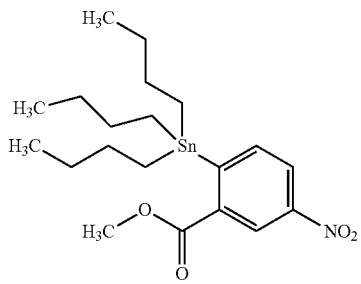 [SMILES: CCC[CH2][Sn]([CH2]CCC)([CH2]CCC)[c]1ccc([N+](=O)[O-])cc1C(=O)OC]

To a solution of hexabutyldistannane (10.0 mL, 19.8 mmol) and methyl 2-bromo-5-nitrobenzoate (5.1 g, 19.8 mmol) in degassed toluene (100 mL) was added Pd(PPh$_3$)$_4$ (457 mg, 0.40 mmol). The resulting mixture was heated at 120° C. for 20 hours and then allowed to cool to room temperature. Aqueous potassium fluoride (5.7 g in 75 mL) was then added to the mixture and after stirring for 30 minutes the resulting solids were removed via filtration through Celite. The aqueous layer of the filtrate was separated and the organic phase was washed with brine (50 mL), dried (MgSO$_4$), filtered and concentrated under reduced pressure. The residue was purified by Biotage Isolera™ chromatography (eluting with a gradient of eluents; 0-15% EtOAc in heptane) to afford the title compound (6.1 g, 46% yield) as a pale yellow oil.

$^1$H NMR (500 MHz, Chloroform-d) δ [ppm] 8.87 (d, J=2.3 Hz, 1H), 8.28 (dd, J=8.0, 2.3 Hz, 1H), 7.84 (d, J=8.0 Hz, 1H), 3.98 (s, 3H), 1.52-1.43 (m, 6H), 1.32-1.26 (m, 6H), 1.13-1.08 (m, 6H), 0.87 (t, J=7.3 Hz, 9H).

LCMS (Analytical Method A): Rt=1.34 mins, the product did not ionise.

Intermediate 299A: Methyl 2-(2-cyclobutyl-1,3-thiazol-5-yl)-5-nitrobenzoate

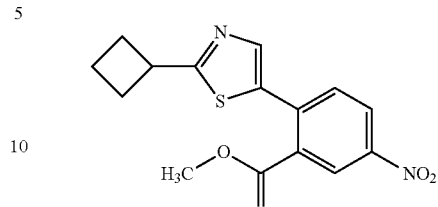

A solution of 5-bromo-2-cyclobutyl-1,3-thiazole (300 mg, 1.38 mmol) and methyl 5-nitro-2-(tributylstannyl)benzoate (1.02 g, 1.51 mmol) in anhydrous 1,4-dioxane (8 mL) was degassed by bubbling nitrogen through the mixture for 5 minutes. Pd(PPh$_3$)$_4$ (50 mg, 0.043 mmol) and CuI (9 mg, 0.047 mmol) were then added and the reaction was heated at 100° C. for 2 hours in a sealed tube. The reaction was then cooled to room temperature. The solids were removed by filtration over Celite and washed with EtOAc (50 mL). The filtrate was concentrated at reduced pressure and the residue was purified by Biotage Isolera™ chromatography (eluting with a gradient of eluents; 0-50% EtOAc in DCM) giving the title compound (390 mg, 87% yield) as a yellow oil.

$^1$H NMR (500 MHz, Chloroform-d) δ [ppm] 8.63 (d, J=2.4 Hz, 1H), 8.33 (dd, J=8.5, 2.5 Hz, 1H), 7.68 (s, 1H), 7.63 (d, J=8.5 Hz, 1H), 3.94-3.87 (m, 1H), 3.86 (s, 3H), 2.57-2.46 (m, 2H), 2.46-2.34 (m, 2H), 2.17-2.05 (m, 1H), 2.04-1.94 (m, 1H).

LCMS (Analytical Method A): Rt=1.28 min; MS (ESI-Pos): m/z=319 (M+H)$^+$.

In analogy to the procedure described for Intermediate 299A, the following intermediates were prepared using methyl 5-nitro-2-(tributylstannyl)benzoate (Intermediate 298A) and the appropriate heteroaromatic input as starting materials.

| Int. | Structure | Name | Analytical Data |
|---|---|---|---|
| 323A | (cyclopentyl-thiazole-nitrobenzoate structure) | Methyl 2-(2-cyclopentyl-1,3-thiazol-5-yl)-5-nitrobenzoate | $^1$H NMR (500 MHz, Chloroform-d) δ [ppm] 8.63 (d, J = 2.4 Hz, 1H), 8.33 (dd, J = 8.5, 2.5 Hz, 1H), 7.67 (s, 1H), 7.63 (d, J = 8.5 Hz, 1H), 3.86 (s, 3H), 3.52-3.42 (m, 1H), 2.29-2.15 (m, 2H), 1.94-1.81 (m, 4H), 1.80-1.69 (m, 2H). LCMS (Analytical Method A): Rt = 1.32 mins, MS (ESIPos): m/z = 333 (M + H)$^+$. |
| 324A | (methylpyrazine-nitrobenzoate structure) | Methyl 2-(5-methylpyrazin-2-yl)-5-nitrobenzoate | $^1$H NMR (500 MHz, Chloroform-d) δ [ppm] 8.74 (d, J = 2.3 Hz, 1H), 8.67 (d, J = 1.2 Hz, 1H), 8.53-8.51 (m, 1H), 8.44 (dd, J = 8.5, 2.4 Hz, 1H), 7.78 (d, J = 8.5 Hz, 1H), 3.81 (s, 3H), 2.66 (s, 3H). LCMS (Analytical Method A) Rt = 1.05 min, MS (ESIPos): m/z = 274.0 (M + H)$^+$. |

-continued

| Int. | Structure | Name | Analytical Data |
|---|---|---|---|
| 325A | 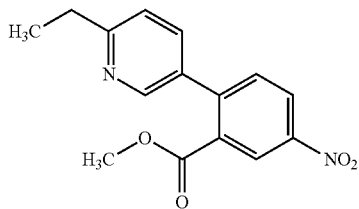 | Methyl 2-(1-cyclobutyl-1H-imidazol-4-yl)-5-nitrobenzoate | $^1$H NMR (500 MHz, Chloroform-d) δ [ppm] 8.44 (d, J = 2.4 Hz, 1H), 8.28 (dd, J = 8.7, 2.4 Hz, 1H), 7.97 (d, J = 8.7 Hz, 1H), 7.58 (d, J = 1.2 Hz, 1H), 7.46 (d, J = 1.2 Hz, 1H), 4.71-4.56 (m, 1H), 3.92 (s, 3H), 2.61-2.51 (m, 2H), 2.46-2.34 (m, 2H), 2.02-1.85 (m, 2H). LCMS (Analytical Method A): Rt = 1.04 min; MS (ESIPos): m/z = 302 (M + H)$^+$. |

Intermediate 321A—Methyl 2-(6-ethylpyridin-3-yl)-5-nitrobenzoate

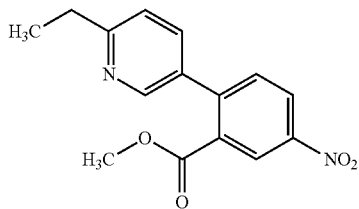 [SMILES: CCc1ccc(-c2ccc([N+](=O)[O-])cc2C(=O)OC)cn1]

A solution of 5-bromo-2-ethylpyridine (300 mg, 1.612 mmol) and methyl 5-nitro-2-(tributylstannyl)benzoate (70% purity, 1.19 g, 1.77 mmol) in anhydrous 1,4-dioxane (8 mL) was degassed by bubbling nitrogen through the mixture for 5 minutes. Tetrakis(triphenylphosphine)palladium(0) (50 mg, 0.043 mmol) and CuI (9 mg, 0.047 mmol) were then added and the reaction was heated at 100° C. for 18 hours in a sealed tube. After this time further tetrakis(triphenylphosphine)palladium(0) (50 mg, 0.043 mmol) and CuI (307 mg, 1.61 mmol, 1 eq.) were added and the reaction was heated at 100° C. for a further 2 hours. The mixture was then cooled to room temperature and the solids were removed by filtration over Celite and washed with EtOAc (50 mL). The filtrate was concentrated in vacuo and the residue was purified by Biotage Isolera™ chromatography (Biotage SNAP Cartridge KP-Sil 50 g; eluting with a gradient of eluents, 0-100% EtOAc in heptane) then again using Biotage Isolera™ chromatography (Biotage SNAP Cartridge KP-Sil 25 g; eluting with a gradient of eluents, 0-100% EtOAc in DCM) giving the desired product (173 mg, 36% yield) as a yellow solid.

$^1$H NMR (500 MHz, Chloroform-d) δ [ppm] 8.78 (d, J=2.4 Hz, 1H), 8.49-8.47 (m, 1H), 8.40 (dd, J=8.4, 2.4 Hz, 1H), 7.59 (dd, J=8.0, 2.4 Hz, 1H), 7.55 (d, J=8.5 Hz, 1H), 7.26 (d, J=8.0 Hz, 1H), 3.78 (s, 3H), 2.91 (q, J=7.6 Hz, 2H), 1.36 (t, J=7.6 Hz, 3H).

LCMS (Analytical Method A): Rt=1.00 min; MS (ESI-Pos): m/z=287 (M+H)$^+$.

Intermediate 57A: 2-(1-cyclopropyl-1H-pyrazol-4-yl)-5-nitrobenzoic acid

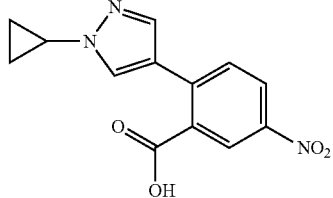 [SMILES: O=C(O)c1cc([N+](=O)[O-])ccc1-c1cnn(C2CC2)c1]

A mixture of 1-cyclopropyl-4-(4,4,5,5-tetramethyl-1,3,2-dioxaborolan-2-yl)-1H-pyrazole (1.00 g, 4.27 mmol), methyl 2-bromo-5-nitrobenzoate (1.01 g, 3.88 mmol), dichlorobis(triphenylphosphine)palladium(II) (51 mg, 0.07 mmol) and potassium carbonate (1.77 g, 12.82 mmol) were dissolved in dimethoxyethane (13 mL) and water (6.5 mL) then degassed via bubbling nitrogen gas through the solution for 10 minutes. The mixture was then heated at 100° C. for 16 hours. The reaction mixture was then cooled to room temperature, diluted with EtOAc (50 mL) and washed with 2M aq. lithium hydroxide solution (20 mL), 2M aqueous hydrogen chloride solution (30 mL), saturated aqueous sodium chloride solution (20 mL), dried (MgSO$_4$), filtered and concentrated at reduced pressure giving the title compound (0.9 g, 77% yield) as a yellow solid.

$^1$H NMR (250 MHz, DMSO-d6) δ [ppm] 13.67 (s, 1H), 8.38 (d, J=2.5 Hz, 1H), 8.30 (dd, J=8.6, 2.6 Hz, 1H), 8.20 (s, 1H), 7.80 (d, J=8.6 Hz, 1H), 7.72 (d, J=0.6 Hz, 1H), 3.89-3.72 (m, 1H), 1.13-0.96 (m, 4H).

LCMS (Analytical Method A): Rt=1.03 mins; MS (ESI-Pos) m/z=273.95 (M+H)$^+$.

Intermediate 58A: Methyl 2-(1-cyclopropyl-1H-pyrazol-4-yl)-5-nitrobenzoate

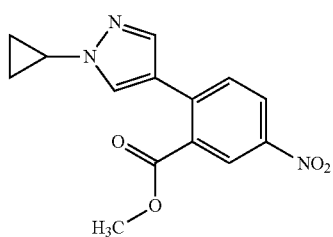 [SMILES: COC(=O)c1cc([N+](=O)[O-])ccc1-c1cnn(C2CC2)c1]

To a mixture of 2-(1-cyclopropyl-1H-pyrazol-4-yl)-5-nitrobenzoic acid (Int 57A, 0.97 g, 3.55 mmol) in methanol (35 mL) was added concentrated aqueous sulfuric acid (0.02 mL, 0.36 mmol) and the resulting solution was heated at 90° C. for 3 days. After cooling to room temperature, the reaction mixture was concentrated at reduced pressure then partitioned between EtOAc and 1M aqueous sodium hydroxide solution. The organic layer was separated, washed with saturated aqueous sodium chloride solution, dried (MgSO$_4$) and concentrated at reduced pressure. The residue was purified by Biotage Isolera™ chromatography [Biotage SNAP Cartridge KP-Sil 50 g; using a gradient of eluents 0-30% EtOAc in heptane] giving the title compound (0.85 g, 83%) as yellow oil that solidified upon standing. 1H NMR (250 MHz, Chloroform-d) δ [ppm] 8.60 (d, J=2.5 Hz, 1H), 8.32 (dd, J=8.6, 2.5 Hz, 1H), 7.79 (s, 1H), 7.64 (s, 1H), 7.59 (d, J=8.6 Hz, 1H), 3.92 (s, 3H), 3.73-3.64 (m, 1H), 1.23-1.04 (m, 4H).

LCMS (Analytical Method A): Rt=1.18 mins; MS (ESI-Pos) m/z=287.95 (M+H)$^+$.

Intermediate 326A: Methyl 5-nitro-2-(1H-pyrazol-4-yl)benzoate

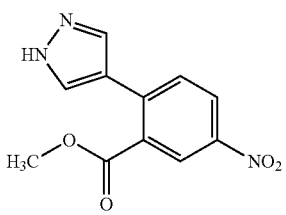 [SMILES: COC(=O)c1cc([N+](=O)[O-])ccc1-c1cn[nH]c1]

To a solution of 4M hydrochloric acid in 1,4-dioxane (6.95 mL, 27.8 mmol) was added methyl 5-nitro-2-(1-{[2-(trimethylsilyl)ethoxy]methyl}-1H-pyrazol-4-yl)benzoate (1.05 g, 2.78 mmol) at room temperature and the resulting mixture was stirred for 18 hours. The reaction mixture was then diluted with water (20 mL) and EtOAc (50 mL) and stirred for 20 minutes. After this time 2M aq. K$_2$CO$_3$ solution (20 mL, 40 mmol) was added and the organic layer was separated, washed with brine (20 mL), dried (Na$_2$SO$_4$) and concentrated at reduced pressure. The residue was purified by Biotage Isolera™ chromatography [Biotage SNAP Cartridge KP-Sil 50 g; eluting with a gradient of eluents, 0-100% EtOAc in DCM]. The product containing fractions were combined and concentrated in vacuo to afford the title compound (383 mg, 50% yield) as yellow solid.

$^1$H NMR (500 MHz, DMSO-d6) δ [ppm] 13.23 (s, 1H), 8.43 (d, J=2.5 Hz, 1H), 8.33 (dd, J=8.7, 2.6 Hz, 1H), 8.16-7.69 (m, 3H), 3.84 (s, 3H).

LCMS (Analytical Method A): Rt=1.01 mins; MS (ESI-Pos): m/z=248 (M+H)$^+$.

Intermediate 327A: Ethyl 3-fluoro-5-nitro-2-(1H-pyrazol-4-yl)benzoate

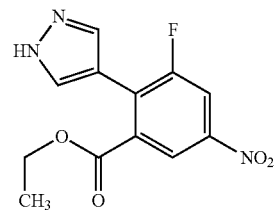 [SMILES: CCOC(=O)c1cc([N+](=O)[O-])cc(F)c1-c1cn[nH]c1]

To a solution of ethyl 3-fluoro-5-nitro-2-(1-{[2-(trimethylsilyl)ethoxy]methyl}-1H-pyrazol-4-yl)benzoate (520 mg, 1.27 mmol) in ethanol (10 mL) was added 2M aq. HCl (1.0 mL, 2.0 mmol). The mixture was heated at reflux for 16 hours then cooled to room temperature. The reaction mixture was concentrated under reduced pressure and the residue was partitioned between ethyl acetate (30 mL) and concentrated aq. NaHCO$_3$ solution (10 mL). The organic layer was separated, washed with brine (10 mL), dried (Na$_2$SO$_4$) and concentrated under reduced pressure. The residue was purified by Biotage Isolera™ chromatography [Biotage SNAP Cartridge KP-Sil 25 g; eluting with a gradient of eluents, 0-100% EtOAc in heptane]. The product containing fractions were combined and concentrated in vacuo to afford the title compound (0.27 g, 75% yield) as yellow solid.

$^1$H NMR (500 MHz, Chloroform-d) δ [ppm] 11.14 (s, 1H), 8.38 (dd, J=2.2, 1.1 Hz, 1H), 8.11 (dd, J=9.4, 2.3 Hz, 1H), 7.88-7.81 (m, 2H), 4.33 (q, J=7.1 Hz, 2H), 1.29 (t, J=7.2 Hz, 3H).

LCMS (Analytical Method A): Rt=1.05 mins; MS(ESI-Pos): m/z=280 (M+H)$^+$.

Intermediate 328A: Methyl 2-{1-[(1-methylcyclopropyl)methyl]-1H-pyrazol-4-yl}-5-nitrobenzoate

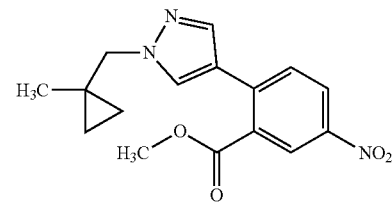 [SMILES: COC(=O)c1cc([N+](=O)[O-])ccc1-c1cnn(CC2(C)CC2)c1]

To a solution of diisopropyl azodicarboxylate (0.572 ml, 2.73 mmol) in dry THF (5 mL) was added a solution of triphenylphosphine (716 mg, 2.73 mmol) in THF (5 mL) at 0° C. The reaction mixture was stirred for 20 minutes and a solution of methyl 5-nitro-2-(1H-pyrazol-4-yl)benzoate (90% purity, 375 mg, 1.365 mmol) and (1-methylcyclopropyl)methanol (0.20 mL, 2.05 mmol) in THF (5 mL) was added dropwise at 0° C. The reaction mixture was allowed to warm to RT and was stirred for 1 hour at this temperature. The reaction mixture was concentrated under reduced pressure and the residue was purified by Biotage Isolera™ chromatography [Biotage SNAP Cartridge KP-Sil 50 g; using a gradient of eluents, 0-50% EtOAc in heptane] followed by preparative HPLC (Method B) giving the title compound (275 mg, 61% yield) as pale yellow oil that solidified upon standing.

$^1$H NMR (500 MHz, Chloroform-d) δ [ppm] 8.57 (d, J=2.5 Hz, 1H), 8.30 (dd, J=8.6, 2.5 Hz, 1H), 7.77-7.75 (m, 1H), 7.66 (d, J=0.6 Hz, 1H), 7.61 (d, J=8.6 Hz, 1H), 4.01 (s, 2H), 3.88 (s, 3H), 1.07 (s, 3H), 0.71-0.61 (m, 2H), 0.55-0.44 (m, 2H).

LCMS (Analytical Method A): Rt=1.21 min; MS (ESI-Pos): m/z=316 (M+H)$^+$.

In analogy to Intermediate 328A, the following intermediate was prepared using the corresponding pyrazole and appropriate alcohol coupling partner.

| Int. | Structure | Name | Analytical Data |
|---|---|---|---|
| 329A | (structure) | Ethyl 3-fluoro-2-{1-[(1-methylcyclopropyl)methyl]-1H-pyrazol-4-yl}-5-nitrobenzoate | $^1$H NMR (500 MHz, Chloroform-d) δ [ppm] 8.31 (dd, J = 2.3, 1.0 Hz, 1H), 8.07 (dd, J = 9.6, 2.3 Hz, 1H), 7.77 (d, J = 2.1 Hz, 1H), 7.65-7.60 (m, 1H), 4.32 (q, J = 7.2 Hz, 2H), 4.02 (s, 2H), 1.28 (t, J = 7.1 Hz, 3H), 1.06 (s, 3H), 0.68-0.61 (m, 2H), 0.52-0.44 (m, 2H). LCMS (Analytical Method A): Rt = 1.28 min; MS (ESIPos): m/z = 348 (M +H)$^+$. |

Intermediate 59A: Methyl 2-(3-tert-butyl-1H-pyrazol-1-yl)-5-nitrobenzoate

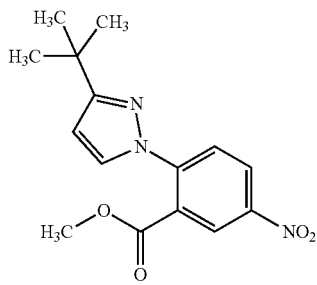 [SMILES: COC(=O)c1cc([N+](=O)[O-])ccc1-n1ccc(C(C)(C)C)n1]

To a pressure tube were added 3-tert-butyl-1H-pyrazole (500 mg, 4.026 mmol), methyl 2-fluoro-5-nitrobenzoate (882 mg, 4.429 mmol), acetonitrile (20 mL) and K$_2$CO$_3$ (1.67 g, 12.08 mmol) at RT. The tube was sealed and the mixture heated at 90° C. for 29 h. The reaction mixture was diluted with EtOAc, filtered and the filtrate concentrated under reduced pressure. The residual material was purified by Biotage Isolera™ chromatography to give the title compound (1.219 g, 86% yield) as a yellow oil.

$^1$H NMR (500 MHz, Chloroform-d) δ [ppm] 8.52 (d, J=2.6 Hz, 1H), 8.37 (dd, J=8.9, 2.6 Hz, 1H), 7.74 (d, J=2.6 Hz, 1H), 7.62 (d, J=8.9 Hz, 1H), 6.40 (d, J=2.6 Hz, 1H), 3.86 (s, 3H), 1.34 (s, 9H).

LCMS (Analytical Method D): Rt=4.61 min, MS (ESI-pos) m/z=304.05 (M+H)$^+$.

In analogy to the procedure described for Intermediate 59A, the following intermediates were prepared using methyl 2-fluoro-5-nitrobenzoate and the appropriate heteroaromatic input as starting materials.

| Int. | Structure | Name | Analytical Data |
|---|---|---|---|
| 60A | (structure) | Methyl 2-(4-tert-butyl-1H-pyrazol-1-yl)-5-nitrobenzoate | $^1$H NMR (500 MHz, Chloroform-d) δ [ppm] 8.55 (d, J = 2.6 Hz, 1H), 8.38 (dd, J = 8.9, 2.6 Hz, 1H), 7.70-7.64 (m, 2H), 7.57 (d, J = 0.6 Hz, 1H), 3.84 (s, 3H), 1.32 (s, 9H). LCMS (Analytical Method D): Rt = 4.55 min, MS (ESIpos) m/z = 304.05 (M + H)$^+$. |
| 61A | (structure) | Methyl 5-nitro-2-[3-(2,2,2-trifluoroethyl)-1H-pyrazol-1-yl]benzoate | $^1$H NMR (500 MHz, Chloroform-d) δ [ppm] 8.63 (d, J = 2.6 Hz, 1H), 8.42 (dd, J = 8.8, 2.6 Hz, 1H), 7.80 (d, J = 2.5 Hz, 1H), 7.68 (d, J = 8.8 Hz, 1H), 6.54 (d, J = 2.4 Hz, 1H), 3.81 (s, 3H), 3.54 (q, J = 10.6 Hz, 2H). LCMS (Analytical Method D): Rt = 4.20 min, MS (ESIpos) m/z = 330 (M + H)$^+$. |

| Int. | Structure | Name | Analytical Data |
|---|---|---|---|
| 62A | 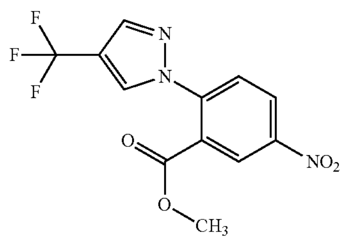 [SMILES: COC(=O)c1cc([N+](=O)[O-])ccc1-n1cc(C(F)(F)F)cn1] | Methyl 5-nitro-2-[4-(trifluoromethyl)-1H-pyraozl-1-yl]benzoate | ¹H NMR (500 MHz, DMSO-d6) δ [ppm] 9.16 (s, 1H), 8.59-8.55 (m, 2H), 8.29 (s, 1H), 8.09-8.05 (m, 1H), 3.74 (s, 3H). LCMS (Analytical Method A): Rt = 1.20 min, MS (ESIpos): m/z = 316.0 (M + H)⁺. |
| 63A | 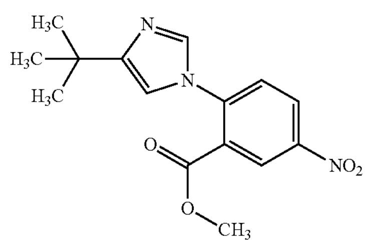 [SMILES: COC(=O)c1cc([N+](=O)[O-])ccc1-n1cnc(C(C)(C)C)c1] | Methyl 2-(4-tert-butyl-1H-imidazol-1-yl)-5-nitrobenzoate | ¹H NMR (400 MHz, DMSO-d6) δ [ppm] 1.25 (s, 9H), 3.75 (s, 3H), 7.12 (d, 1H), 8.83-8.85 (m, 2H), 8.51 (dd, 1H), 8.62 (d, 1H). LCMS (method 1): Rt = 0.70 mins, MS (ESIpos): m/z = 304 (M + H)⁺. |

Intermediate 64A: Methyl 2-(4-cyclobutyl-1H-pyrazol-1-yl)-5-nitrobenzoate

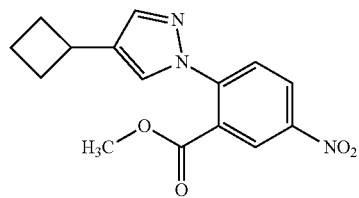 [SMILES: COC(=O)c1cc([N+](=O)[O-])ccc1-n1cc(C2CCC2)cn1]

To 4-cyclobutyl-1-{[2-(trimethylsilyl)ethoxy]methyl}-1H-pyrazole (0.50 g, 1.98 mmol) was added 4M hydrochloric acid in 1,4-dioxane (4.95 mL) at room temperature. The mixture was stirred at room temperature for 18 hours. The volatiles were then removed at reduced pressure and acetonitrile (10 mL) and potassium carbonate (1.37 g, 9.90 mmol) were added and the mixture was stirred at reflux for 6 hours. After cooling to room temperature, the solids were removed by filtration and washed with acetonitrile (30 mL). The filtrate was concentrated under reduced pressure and the residue purified by Biotage Isolera™ chromatography [SNAP Cartridge KP-Sil 25 g; eluting with a gradient of eluents; 0-100% EtOAc in heptane] to give the title compound (401 mg, 62% yield) as an orange oil.

¹H NMR (500 MHz, Chloroform-d) δ [ppm] 8.52 (d, J=2.6 Hz, 1H), 8.36 (dd, J=8.9, 2.6 Hz, 1H), 7.63 (d, J=8.9 Hz, 1H), 7.62 (s, 1H), 7.60 (s, 1H), 3.83 (s, 3H), 3.50-3.41 (m, 1H), 2.42-2.31 (m, 2H), 2.12-1.86 (m, 4H).

LCMS (Analytical Method A): Rt=1.42 mins; MS (ESI-Pos) m/z=302.0 (M+H)⁺.

Intermediate 65A: Methyl 5-amino-2-(1-benzothiophen-2-yl)benzoate

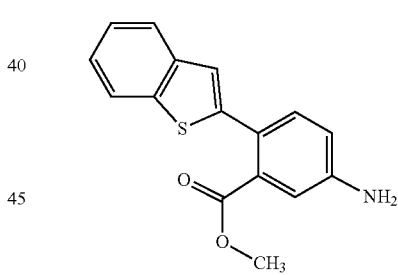

To a de-gassed solution of methyl 2-(1-benzothiophen-2-yl)-5-nitrobenzoate (Int 36A, 450 mg, 1.44 mmol) in methanol (10 mL) was added Pd/C (10%, 76 mg, 0. 0.072 mmol). The mixture was stirred at room temperature under an atmosphere of hydrogen for 18 hours. The catalyst was removed by filtration through Celite and washed with MeOH. The filtrate was concentrated at reduced pressure to give the title compound (287 mg, 71% yield).

¹H NMR (250 MHz, DMSO-d6) δ [ppm] 7.90 (d, J=7.1 Hz, 1H), 7.84-7.75 (m, 1H), 7.41-7.24 (m, 3H), 7.16 (s, 1H), 6.87 (d, J=2.4 Hz, 1H), 6.76 (dd, J=8.4, 2.4 Hz, 1H), 5.69 (s, 2H), 3.66 (s, 3H).

LCMS (Analytical Method D) Rt=4.27 mins; MS (ESIpos) m/z=284 (M+H)⁺.

Alternatively, Intermediate 29A was synthesised by the procedure described below.

Intermediate 29A: Methyl 5-amino-2-(1-cyclobutyl-1H-pyrazol-4-yl)benzoate

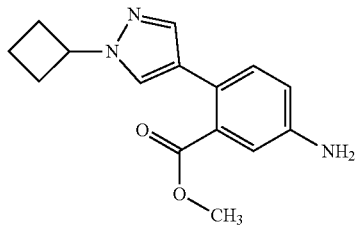 [SMILES: COC(=O)c1cc(N)ccc1-c1cnn(C2CCC2)c1]

Methyl 2-(1-cyclobutyl-1H-pyrazol-4-yl)-5-nitrobenzoate (1.32 g, 4.4 mmol) was dissolved in methanol (30 mL) and 10% Palladium on Carbon (45 mg) was added. The resulting mixture was stirred under a hydrogen atmosphere overnight at room temperature, filtered through Celite®, washed with methanol (50 mL) and concentrated at reduced pressure. The residue was purified by Biotage Isolera™ chromatography (silica gel; using a gradient of eluents; 95:5 to 20:80 heptane/EtOAc) to give the title compound (920 mg, 77% yield) as a yellow oil.

$^1$H NMR (500 MHz, DMSO-d6) δ [ppm] 7.73 (d, J=0.71 Hz, 1H), 7.37 (d, J=0.6 Hz, 1H), 7.11 (d, J=8.3 Hz, 1H), 6.80 (d, J=2.5 Hz, 1H), 6.70 (dd, J=8.3, 2.5 Hz, 1H), 5.31 (s, 2H), 4.86-4.73 (m, 1H), 3.69 (s, 3H), 2.48-2.31 (m, 4H), 1.83-1.71 (i, 2H).

LCMS (Analytical Method A): Rt=1.00 mins; MS (ESIPos) m/z=272 (M+H)$^+$.

In analogy to the procedure described for Intermediate 65A, the following intermediates were prepared using Pd/C hydrogenation from the corresponding nitrobenzene as starting material.

| Int. | Structure | Name | Analytical Data |
| --- | --- | --- | --- |
| 66A | 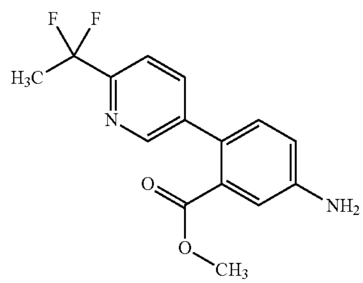 | Methyl 5-amino-2-[6-(1,1-difluoroethyl)pyridin-3-yl]benzoate | $^1$H NMR (500 MHz, Chloroform-d) δ [ppm] 8.58-8.47 (m, 1H), 7.68 (dd, J = 8.1, 2.2 Hz, 1H), 7.63 (d, J = 8.1 Hz, 1H), 7.25 (d, J = 2.5 Hz, 1H), 7.12 (d, J = 8.2 Hz, 1H), 6.87 (dd, J = 8.2, 2.6 Hz, 1H), 3.91 (s, 2H), 3.67 (s, 3H), 2.06 (t, J = 18.6 Hz, 3H). LCMS (Analytical Method A): Rt = 1.06 mins; MS (ESIPos) m/z = 293 (M + H)$^+$. |
| 67A | 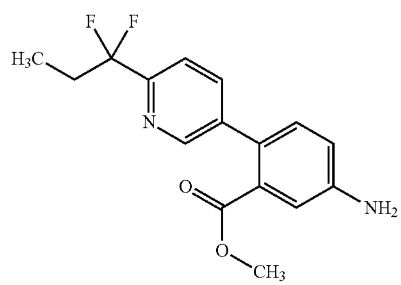 | Methyl 5-amino-2-[6-(1,1-difluoropropyl)pyridin-3-yl]benzoate | $^1$H NMR (250 MHz, DMSO-d6) δ [ppm] 8.48 (m, 1H), 7.76 (dd, J = 8.1, 2.2 Hz, 1H), 7.64 (d, J = 8.1 Hz, 1H), 7.15 (d, J = 8.3 Hz, 1H), 7.09 (d, J = 2.4 Hz, 1H), 6.83 (dd, J = 8.3, 2.4 Hz, 1H), 5.65 (s, 2H), 3.61 (s, 3H), 2.44-2.27 (m, 2H), 0.95 (t, J = 7.5 Hz, 3H). LCMS (Analytical Method A): Rt = 1.11 min, MS (ESIpos) m/z = 307.5 (M + H)$^+$. |
| 68A | 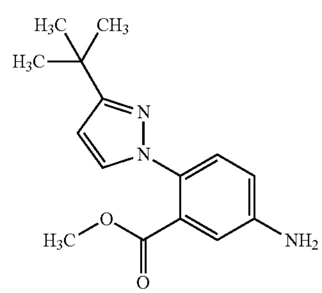 [SMILES: COC(=O)c1cc(N)ccc1-n1ccc(C(C)(C)C)n1] | Methyl 5-amino-2-(3-tert-butyl-1H-pyrazol-1-yl)benzoate | $^1$H NMR (250 MHz, DMSO-d6) δ [ppm] 7.76 (d, J = 2.4 Hz, 1H), 7.17 (d, J = 8.5 Hz, 1H), 6.82 (d, J = 2.5 Hz, 1H), 6.73 (dd, J = 8.5, 2.6 Hz, 1H), 6.24 (d, J = 2.4 Hz, 1H), 5.51 (s, 2H), 3.54 (s, 3H), 1.23 (s, 9H). LCMS (Analytical Method D): Rt = 3.85 min, MS (ESIpos) m/z = 274.1 (M + H)$^+$. |
| 69A | 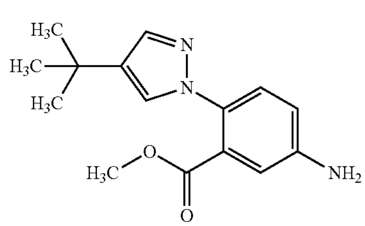 [SMILES: COC(=O)c1cc(N)ccc1-n1cc(C(C)(C)C)cn1] | Methyl 5-amino-2-(4-tert-butyl-1H-pyrazol-1-yl)benzoate | $^1$H NMR (250 MHz, DMSO-d6) δ [ppm] 7.65 (d, J = 0.8 Hz, 1H), 7.46 (d, J = 0.7 Hz, 1H), 7.18 (d, J = 8.5 Hz, 1H), 6.84 (d, J = 2.6 Hz, 1H), 6.74 (dd, J = 8.5, 2.6 Hz, 1H), 5.54 (s, 2H), 3.53 (s, 3H), 1.25 (s, 9H). LCMS (Analytical Method D) Rt = 3.87 min, MS (ESIpos) m/z = 274.0 (M + H)$^+$. |

| Int. | Structure | Name | Analytical Data |
|------|-----------|------|-----------------|
| 70A | 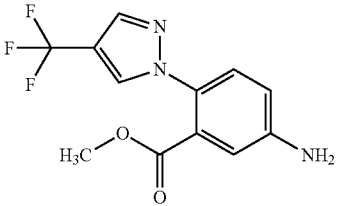 [SMILES: COC(=O)c1cc(N)ccc1-n1cc(C(F)(F)F)cn1] | Methyl 5-amino-2-[4-(trifluoromethyl)-1H-pyrazol-1-yl]benzoate | $^1$H NMR (250 MHz, DMSO-d6) δ [ppm] 8.61 (s, 1H), 8.00 (s, 1H), 7.24 (d, J = 8.5 Hz, 1H), 7.01 (d, J = 2.6 Hz, 1H), 6.80 (dd, J = 8.5, 2.6 Hz, 1H), 5.77 (s, 2H), 3.57 (s, 3H). LCMS (Analytical Method A) Rt = 1.08 min, MS (ESIpos): m/z = 285.90 (M + H)$^+$. |
| 71A | 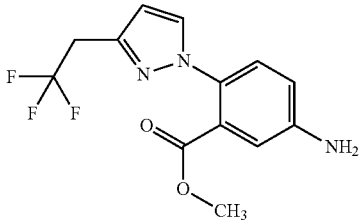 | Methyl 5-amino-2-[3-(2,2,2-trifluoroethyl)-1H-pyrazol-1-yl]benzoate | $^1$H NMR (250 MHz, Chloroform-d) δ [ppm] 7.62 (d, J = 2.3 Hz, 1H), 7.26 (d, J = 8.5 Hz, 1H), 7.16 (d, J = 2.7 Hz, 1H), 6.84 (dd, J = 8.5, 2.7 Hz, 1H), 6.45 (d, J = 2.0 Hz, 1H), 4.03 (s, 2H), 3.70 (s, 3H), 3.58 (q, J = 10.8 Hz, 2H). LCMS (Analytical Method A) Rt = 1.05 min, MS (ESIpos) m/z = 300 (M + H)$^+$. |
| 72A | 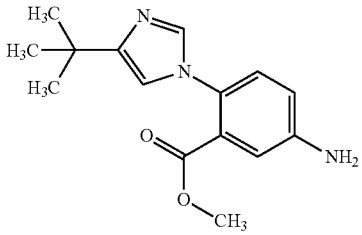 | Methyl 5-amino-2-(4-tert-butyl-1H-imidazol-1-yl)benzoate | $^1$H NMR (400 MHz, DMSO-d6) δ [ppm] 1.22 (s, 9H), 3.56 (s, 3H), 5.66 (s, 2H), 6.76-6.79 (m, 2H), 7.00 (d, 1H), 7.10 (d, 1H), 7.47 (s, 1H). LCMS (method 1): Rt = 0.56 mins, MS (ESIpos): m/z = 274 (M + H)$^+$. |
| 73A | 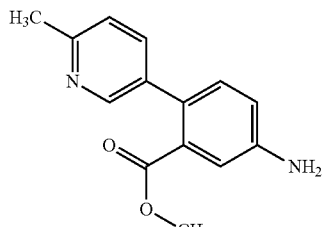 | Methyl 2-(6-methylpyridin-3-yl)-5-nitrobenzoate | $^1$H NMR (500 MHz, Chloroform-d) δ [ppm] 8.37 (d, J = 2.3 Hz, 1H), 7.45 (dd, J = 7.9, 2.4 Hz, 1H), 7.17 (d, J = 2.5 Hz, 1H), 7.12 (d, J = 7.9 Hz, 1H), 7.08 (d, J = 8.2 Hz, 1H), 6.81 (dd, J = 8.2, 2.6 Hz, 1H), 3.90 (s, 2H), 3.64 (s, 3H), 2.56 (s, 3H). LCMS (Analytical Method A) Rt = 0.72 min, MS (ESIpos) m/z = 243 (M + H)$^+$. |
| 74A | 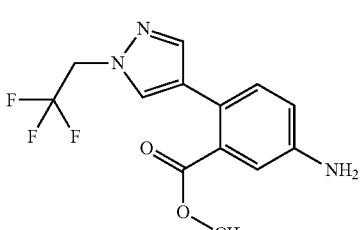 | Methyl 5-amino-2-[1-(2,2,2-trifluoroethyl)-1H-pyrazol-4-yl]benzoate | $^1$H NMR (500 MHz, DMSO-d6) δ [ppm] 7.75 (s, 1H), 7.54 (s, 1H), 7.12 (d, J = 8.3 Hz, 1H), 6.83 (d, J = 2.4 Hz, 1H), 6.72 (dd, J = 8.3, 2.4 Hz, 1H), 5.38 (s, 2H), 5.10 (q, J = 9.2 Hz, 2H), 3.68 (s, 3H). LCMS (Analytical Method A): Rt = 0.93 mins, MS (ESIPos): m/z = 300 (M + H)$^+$. |
| 75A | 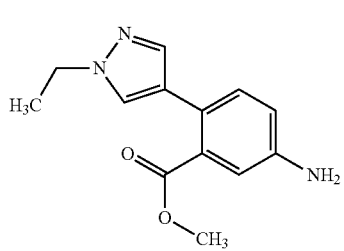 | Methyl 5-amino-2-(1-ethyl-1H-pyrazol-4-yl)benzoate | $^1$H NMR (500 MHz, Chloroform-d) δ [ppm] 7.50-7.47 (m, 1H), 7.45 (s, 1H), 7.16 (d, J = 8.3 Hz, 1H), 7.00 (d, J = 2.6 Hz, 1H), 6.76 (dd, J = 8.3, 2.6 Hz, 1H), 4.17 (q, J = 7.3 Hz, 2H), 3.91-3.60 (m, 5H), 1.50 (t, J = 7.3 Hz, 3H). LCMS (Analytical Method A): Rt = 0.82 mins; MS (ESIpos) m/z = 246 (M + H)$^+$. |

-continued

| Int. | Structure | Name | Analytical Data |
|---|---|---|---|
| 76A | 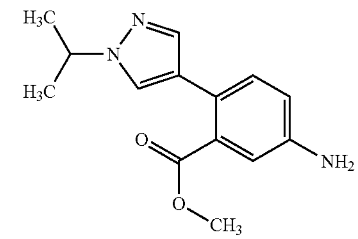 [SMILES: COC(=O)c1cc(N)ccc1-c1cnn(C(C)C)c1] | Methyl 5-amino-2-(1-isopropyl-1H-pyrazol-4-yl)benzoate | ¹H NMR (500 MHz, Chloroform-d) δ [ppm] 7.51-7.45 (m, 2H), 7.18 (d, J = 8.3 Hz, 1H), 7.01 (d, J = 2.6 Hz, 1H), 6.78 (dd, J = 8.3, 2.6 Hz, 1H), 4.50 (hept, J = 6.7 Hz, 1H), 3.85-3.63 (m, 5H), 1.53 (d, J = 6.7 Hz, 6H). LCMS (Analytical Method A): Rt = 0.89 mins; MS (ESIPos) m/z = 260.05 (M + H)⁺. |
| 77A | 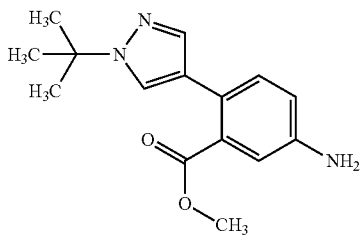 [SMILES: COC(=O)c1cc(N)ccc1-c1cnn(C(C)(C)C)c1] | Methyl 5-amino-2-(1-tert-butyl-1H-pyrazol-4-yl)benzoate | ¹H NMR (500 MHz, DMSO-d6) δ [ppm] 7.73 (d, J = 0.7 Hz, 1H), 7.36 (d, J = 0.6 Hz, 1H), 7.14 (d, J = 8.3 Hz, 1H), 6.78 (d, J = 2.5 Hz, 1H), 6.70 (dd, J = 8.3, 2.5 Hz, 1H), 5.31 (s, 2H), 3.69 (s, 3H), 1.52 (s, 9H). LCMS (Analytical Method A): Rt = 1.07 mins; MS (ESIPos) m/z = 274.05 (M + H)⁺. |
| 78A | 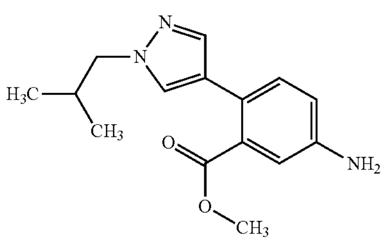 [SMILES: COC(=O)c1cc(N)ccc1-c1cnn(CC(C)C)c1] | Methyl 5-amino-2-(1-isobutyl-1H-pyrazol-4-yl)benzoate | ¹H NMR (500 MHz, Chloroform-d) δ [ppm] 7.50-7.46 (m, 1H), 7.42-7.37 (m, 1H), 7.17 (d, J = 8.3 Hz, 1H), 7.00 (d, J = 2.6 Hz, 1H), 6.77 (dd, J = 8.3, 2.6 Hz, 1H), 3.90 (d, J = 7.3 Hz, 2H), 3.83-3.67 (m, 5H), 2.30-2.14 (m, 1H), 0.92 (d, J = 6.7 Hz, 6H). LCMS (Analytical Method A): Rt = 1.02 mins; MS (ESIPos) m/z = 274.35 (M + H)⁺. |
| 79A | 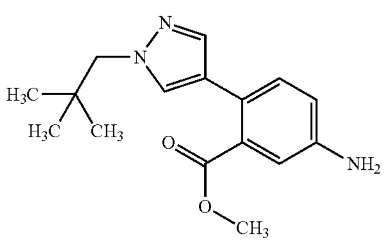 [SMILES: COC(=O)c1cc(N)ccc1-c1cnn(CC(C)(C)C)c1] | Methyl 5-amino-2-[1-(2,2-dimethylpropyl)-1H-pyrazol-4-yl]benzoate | ¹H NMR (500 MHz, Chloroform-d) δ [ppm] 7.47 (s, 1H), 7.39 (s, 1H), 7.18 (d, J = 8.3 Hz, 1H), 7.01 (d, J = 2.6 Hz, 1H), 6.78 (dd, J = 8.3, 2.6 Hz, 1H), 3.90 (s, 2H), 3.81-3.68 (m, 5H), 0.98 (s, 9H). LCMS (Analytical Method A): Rt = 1.16 mins; MS (ESI) m/z = 288.05 (M + H)⁺. |
| 80A | 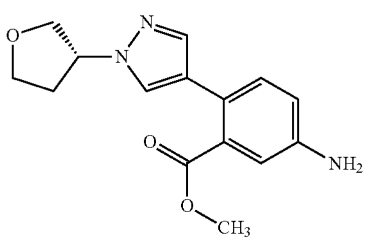 [SMILES: COC(=O)c1cc(N)ccc1-c1cnn([C@@H]2CCOC2)c1] | Methyl 5-amino-2-{1-[(3R)-tetrahydrofuran-3-yl]-1H-pyrazol-4-yl}benzoate | ¹H NMR (500 MHz, Chloroform-d) δ [ppm] 7.57-7.52 (m, 1H), 7.52-7.48 (m, 1H), 7.17 (d, J = 8.3 Hz, 1H), 7.03 (d, J = 2.6 Hz, 1H), 6.79 (dd, J = 8.3, 2.6 Hz, 1H), 5.02-4.93 (m, 1H), 4.19-4.04 (m, 3H), 3.95 (m, 1H), 3.77 (s, 3H), 3.76 (m, 2H), 2.53-2.41 (m, 1H), 2.40-2.33 (m, 1H). LCMS (Analytical Method A) Rt = 0.93 min, MS (ESIPos) m/z = 288.0 (M + H)⁺. |
| 81A | 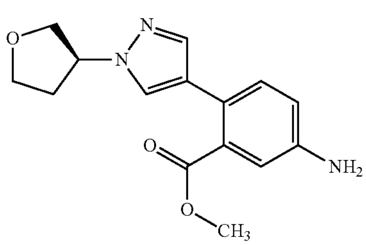 [SMILES: COC(=O)c1cc(N)ccc1-c1cnn([C@H]2CCOC2)c1] | Methyl 5-amino-2-{1-[(3S)-tetrahydrofuran-3-yl]-1H-pyrazol-4-yl}benzoate | ¹H NMR (250 MHz, DMSO-d6) δ [ppm] 7.70 (s, 1H), 7.39 (s, 1H), 7.12 (d, J = 8.3 Hz, 1H), 6.80 (d, J = 2.4 Hz, 1H), 6.70 (dd, J = 8.3, 2.5 Hz, 1H), 5.32 (s, 2H), 5.06-4.92 (m, 1H), 4.04-3.76 (m, 4H), 3.69 (s, 3H), 2.42-2.17 (m, 2H). LCMS (Analytical Method A) Rt = 0.95 min, MS (ESIpos): m/z = 288.0 (M + H)⁺. |

| Int. | Structure | Name | Analytical Data |
|---|---|---|---|
| 82A | 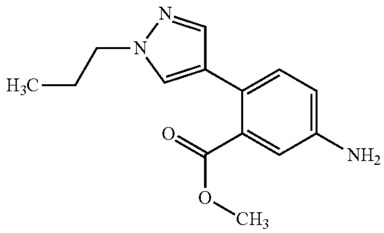 [SMILES: CCCn1cc(-c2ccc(N)cc2C(=O)OC)cn1] | Methyl 5-amino-2-(1-propyl-1H-pyrazol-4-yl)benzoate | ¹H NMR (250 MHz, DMSO-d6) δ [ppm] 7.63 (s, 1H), 7.35 (s, 1H), 7.10 (d, J = 8.3 Hz, 1H), 6.78 (d, J = 2.4 Hz, 1H), 6.70 (dd, J = 8.3, 2.5 Hz, 1H), 5.31 (s, 2H), 4.03 (t, J = 6.9 Hz, 2H), 3.68 (s, 3H), 1.90-1.65 (m, 2H), 0.83 (t, J = 7.4 Hz, 3H). LCMS (Analytical Method A) Rt = 0.96 min, MS (ESIpos): m/z = 260.0 (M + H)⁺. |
| 83A | 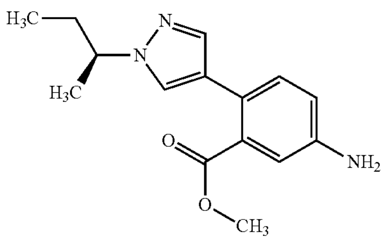 [SMILES: CC[C@H](C)n1cc(-c2ccc(N)cc2C(=O)OC)cn1] | Methyl 5-amio-2-{1-[(2S)-butan-2-yl]-1H-pyrazol-4-yl}benzoate | ¹H NMR (500 MHz, DMSO-d6) δ [ppm] 7.65 (s, 1H), 7.36 (s, 1H), 7.12 (d, J = 8.3 Hz, 1H), 6.79 (d, J = 2.5 Hz, 1H), 6.71 (dd, J = 8.3, 2.5 Hz, 1H), 5.31 (s, 2H), 4.23 (m, 1H), 3.68 (s, 3H), 1.85-1.66 (m, 2H), 1.41 (d, J = 6.7 Hz, 3H), 0.73 (t, J = 7.4 Hz, 3H). LCMS (Analytical Method A) Rt = 1.05 min, MS (ESIpos): m/z = 274.05 (M + H)⁺. |
| 84A | 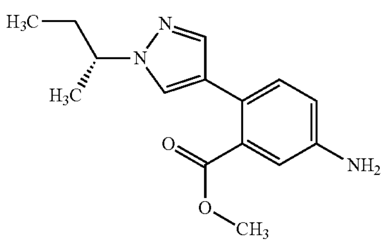 [SMILES: CC[C@@H](C)n1cc(-c2ccc(N)cc2C(=O)OC)cn1] | Methyl 5-amino-2-{1-[(2R)-butan-2-yl]-1H-pyrazol-4-yl}benzoate | ¹H NMR (250 MHz, Methanol-d4) δ [ppm] 7.66-7.58 (m, 1H), 7.45 (s, 1H), 7.17 (d, J = 8.3 Hz, 1H), 7.01 (d, J = 2.5 Hz, 1H), 6.86 (dd, J = 8.3, 2.5 Hz, 1H), 4.34-4.17 (m, 1H), 3.75 (s, 3H), 1.99-1.75 (m, 2H), 1.51 (d, J = 6.8 Hz, 3H), 0.83 (t, J = 7.4 Hz, 3H). LCMS (Analytical Method A) Rt = 0.96 min, MS (ESIpos): m/z = 274.05 (M + H)⁺. |
| 85A | 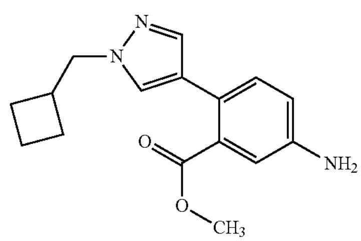 [SMILES: COC(=O)c1cc(N)ccc1-c1cnn(CC2CCC2)c1] | Methyl 5-amino-2-[1-(cyclobutylmethyl)-1H-pyrazol-4-yl]benzoate | ¹H NMR (250 MHz, DMSO-d6) δ [ppm] 7.60 (s, 1H), 7.35 (s, 1H), 7.10 (d, J = 8.3 Hz, 1H), 6.78 (d, J = 2.4 Hz, 1H), 6.69 (dd, J = 8.3, 2.5 Hz, 1H), 5.30 (s, 2H), 4.09 (d, J = 7.2 Hz, 2H), 3.68 (s, 3H), 2.83-2.63 (m, 1H), 2.07-1.62 (m, 6H). LCMS (Analytical Method A) Rt = 1.07 min, MS (ESIpos): m/z = 286.1 (M + H)⁺. |
| 86A | 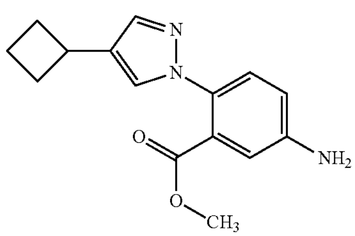 [SMILES: COC(=O)c1cc(N)ccc1-n1cc(C2CCC2)cn1] | Methyl 5-amino-2-(4-cyclobutyl-1H-pyrazol-1-yl)benzoate | ¹H NMR (500 MHz, Chloroform-d) δ [ppm] 7.49 (s, 1H), 7.36 (s, 1H), 7.17 (d, J = 8.5 Hz, 1H), 7.01 (d, J = 2.7 Hz, 1H), 6.74 (dd, J = 8.5, 2.7 Hz, 1H), 3.89 (s, 2H), 3.65 (s, 3H), 3.49-3.37 (m, 1H), 2.41-2.25 (m, 2H), 2.14-1.80 (m, 4H). LCMS (Analytical Method A): Rt = 1.12 mins; MS (ESIPos): m/z = 272.0 (M + H)⁺. |
| 87A | 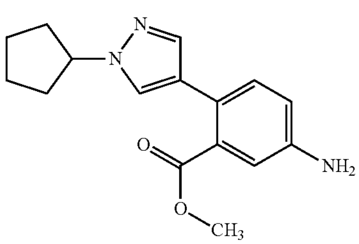 [SMILES: COC(=O)c1cc(N)ccc1-c1cnn(C2CCCC2)c1] | Methyl 5-amino-2-(1-cyclopentyl-1H-pyrazol-4-yl)benzoate | ¹H NMR (500 MHz, DMSO-d6) δ [ppm] 7.67 (s, 1H), 7.34 (s, 1H), 7.12 (d, J = 8.3 Hz, 1H), 6.78 (d, J = 2.5 Hz, 1H), 6.69 (dd, J = 8.3, 2.5 Hz, 1H), 5.30 (s, 2H), 4.66 (m, 1H), 3.69 (s, 3H), 2.10-2.01 (m, 2H), 1.96-1.86 (m, 2H), 1.83-1.73 (m, 2H), 1.69-1.58 (m, 2H). LCMS (Analytical Method A) Rt = 1.03 min, MS ESIpos): m/z = 286.0 (M + H)⁺. |

-continued

| Int. | Structure | Name | Analytical Data |
|---|---|---|---|
| 88A | 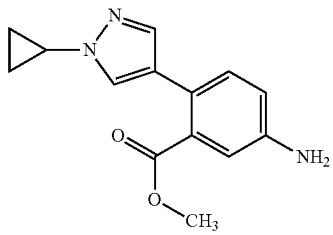 [SMILES: COC(=O)c1cc(N)ccc1-c1cnn(C2CC2)c1] | Methyl 5-amino-2-(1-cyclopropyl-1H-pyrazol-4-yl)benzoate | $^1$H NMR (250 MHz, DMSO-d6) δ [ppm] 7.71 (s, 1H), 7.32 (d, J = 0.7 Hz, 1H), 7.11 (d, J = 8.3 Hz, 1H), 6.81 (d, J = 2.4 Hz, 1H), 6.70 (dd, J = 8.3, 2.5 Hz, 1H), 5.32 (s, 2H), 3.77-3.62 (m, 4H), 1.11-0.87 (m, 4H). LCMS (Analytical Method A) Rt = 1.00 min, MS (ESIpos): m/z = 257.95 (M + H)$^+$. |
| 89A | 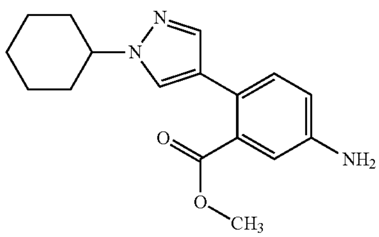 [SMILES: COC(=O)c1cc(N)ccc1-c1cnn(C2CCCCC2)c1] | Methyl 5-amino-2-(1-cyclohexyl-1H-pyrazol-4-yl)benzoate | $^1$H NMR (250 MHz, DMSO-d6) δ [ppm] 7.67 (d, J = 0.6 Hz, 1H), 7.35 (d, J = 0.7 Hz, 1H), 7.13 (d, J = 8.3 Hz, 1H), 6.79 (d, J = 2.4 Hz, 1H), 6.71 (dd, J = 8.3, 2.5 Hz, 1H), 5.31 (s, 2H), 4.18-4.03 (m, 1H), 3.70 (s, 3H), 2.09-1.92 (m, 2H), 1.88-1.76 (m, 2H), 1.75-1.60 (m, 3H), 1.51-1.31 (m, 2H), 1.31-1.16 (m, 1H). LCMS (Analytical Method A) Rt = 1.20 min, MS (ESIpos): m/z = 300.05 (M + H)$^+$. |
| 300A | 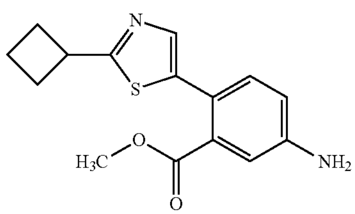 | Methyl 5-amino-2-(2-cyclobutyl-1,3-thiazol-5-yl)benzoate | $^1$H NMR (500 MHz, Chloroform-d) δ [ppm] 7.45 (s, 1H), 7.20 (d, J = 8.3 Hz, 1H), 7.07 (d, J = 2.6 Hz, 1H), 6.78 (dd, J = 8.3, 2.6 Hz, 1H), 3.98-3.78 (m, 3H), 3.74 (s, 3H), 2.52-2.43 (m, 2H), 2.43-2.34 (m, 2H), 2.13-2.01 (m, 1H), 2.01-1.92 (m, 1H). LCMS (Analytical Method A): Rt = 1.14 min; MS (ESIPos): m/z = 289 (M + H)$^+$. |
| 330A | 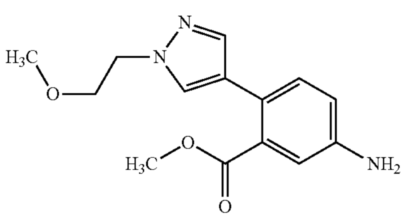 [SMILES: COCCn1cc(-c2ccc(N)cc2C(=O)OC)cn1] | Methyl 5-amino-2-[1-(2-methoxyethyl)-1H-pyrazol-4-yl]benzoate | $^1$H NMR (250 MHz, Chloroform-d) δ [ppm] 7.52 (m, 2H), 7.18 (d, J = 8.3 Hz, 1H), 7.01 (d, J = 2.5 Hz, 1H), 6.77 (dd, J = 8.3, 2.6 Hz, 1H), 4.29 (t, J = 5.3 Hz, 2H), 3.86-3.73 (m, 7H), 3.34 (s, 3H). LCMS (Analytical Method A): Rt = 0.78 mins, MS (ESIPos): m/z = 276 (M + H)$^+$. |
| 331A | 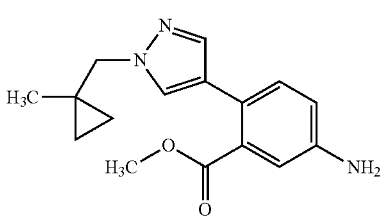 [SMILES: COC(=O)c1cc(N)ccc1-c1cnn(CC2(C)CC2)c1] | Methyl 5-amino-2-{1-[(1-methylcyclopropyl)methyl]-1H-pyrazol-4-yl}benzoate | $^1$H NMR (500 MHz, Chloroform-d) δ [ppm] 7.50 (s, 1H), 7.49 (s, 1H), 7.18 (d, J = 8.2 Hz, 1H), 7.01 (s, 1H), 6.78 (d, J = 8.2 Hz, 1H), 3.96 (s, 2H), 3.77 (s, 3H), 3.75 (s, 3H), 1.05 (s, 3H), 0.68-0.56 (m, 2H), 0.51-0.39 (m, 2H). LCMS (Analytical Method A): Rt = 1.02 min; MS (ESIPos): m/z = 286 (M + H)$^+$. |
| 332A | 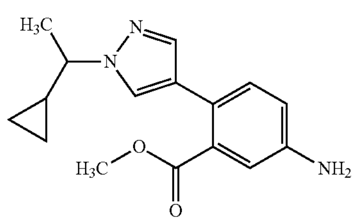 [SMILES: COC(=O)c1cc(N)ccc1-c1cnn(C(C)C2CC2)c1] | Methyl 5-amino-2-[1-(1-cyclopropylethyl)-1H-pyrazol-4-yl]benzoate as a 1:1 mixture of enantiomers | $^1$H NMR (250 MHz, Chloroform-d) δ [ppm] 7.58 (s, 1H), 7.53 (s, 1H), 7.22 (d, J = 8.3 Hz, 1H), 7.03 (d, J = 2.5 Hz, 1H), 6.81 (dd, J = 8.3, 2.6 Hz, 1H), 3.78 (s, 3H), 3.71-3.57 (m, 1H), 1.63 (d, J = 6.8 Hz, 3H), 1.36-1.20 (m, 1H), 0.76-0.53 (m, 2H), 0.48-0.30 (m, 2H). LCMS (Analytical Method A) Rt = 0.99 min, MS (ESIpos): m/z = 286.05 (M + H)$^+$. |

| Int. | Structure | Name | Analytical Data |
|---|---|---|---|
| 335A | 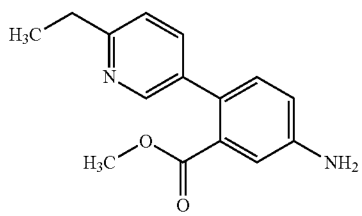 | Methyl 5-amino-2-(6-ethylpyridin-3-yl)benzoate | $^1$H NMR (500 MHz, Chloroform-d) δ [ppm] 8.38-8.32 (m, 1H), 7.43 (dd, J = 8.0, 2.4 Hz, 1H), 7.12 (d, J = 2.5 Hz, 1H), 7.08 (d, J = 8.0 Hz, 1H), 7.05 (d, J = 8.2 Hz, 1H), 6.78 (dd, J = 8.2, 2.6 Hz, 1H), 3.79 (s, 2H), 3.59 (s, 3H), 2.79 (q, J = 7.6 Hz, 2H), 1.27 (t, J = 7.6 Hz, 3H). LCMS (Analytical Method A): Rt = 0.78 min; MS (ESIPos): m/z = 257 (M + H)$^+$. |
| 337A | 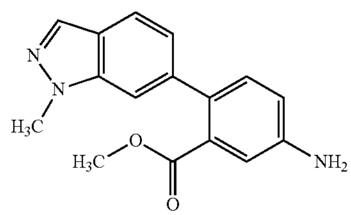 [SMILES: COC(=O)c1cc(N)ccc1-c1ccc2cnn(C)c2c1] | Methyl 5-amino-2-(1-methyl-1H-indazol-6-yl)benzoate | $^1$H NMR (250 MHz, DMSO-d6) δ [ppm] 8.03-7.99 (m, 1H), 7.68 (d, J = 8.4 Hz, 1H), 7.46-7.36 (m, 1H), 7.20 (d, J = 8.3 Hz, 1H), 6.95 (d, J = 2.4 Hz, 1H), 6.92 (dd, J = 8.4, 1.2 Hz, 1H), 6.80 (dd, J = 8.3, 2.4 Hz, 1H), 5.49 (s, 2H), 4.04 (s, 3H), 3.53 (s, 3H). LCMS (Analytical Method A) Rt = 1.00 min, MS (ESIPos): m/z = 282.0 (M + H)$^+$. |
| 339A | 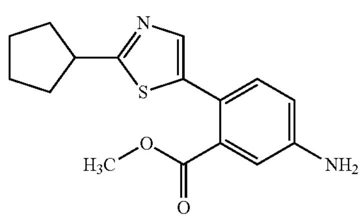 | Methyl 5-amino-2-(2-cyclopentyl-1,3-thiazol-5-yl)benzoate | $^1$H NMR (500 MHz, Chloroform-d) δ [ppm] 7.43 (s, 1H), 7.20 (d, J = 8.3 Hz, 1H), 7.07 (d, J = 2.5 Hz, 1H), 6.78 (dd, J = 8.3, 2.6 Hz, 1H), 3.73 (s, 3H), 3.47-3.39 (m, 1H), 2.25-2.15 (m, 2H), 1.92-1.76 (m, 4H), 1.76-1.65 (m, 2H). LCMS (Analytical Method A): Rt = 1.21 mins, MS (ESIPos): m/z = 303 (M + H)$^+$. |
| 340A | 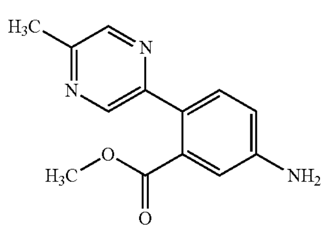 [SMILES: COC(=O)c1cc(N)ccc1-c1cnc(C)cn1] | Methyl 2-(5-methylpyrazin-2-yl)-5-nitrobenzoate | $^1$H NMR (500 MHz, Chloroform-d) δ 8.56 (d, J = 1.3 Hz, 1H), 8.43-8.40 (m, 1H), 7.38 (d, J = 8.3 Hz, 1H), 7.12 (d, J = 2.5 Hz, 1H), 6.85 (dd, J = 8.3, 2.5 Hz, 1H), 3.94 (s, 2H), 3.70 (s, 3H), 2.58 (s, 3H). LCMS (Analytical Method A) Rt = 0.84 min, MS (ESIpos): m/z = 244.0 (M + H)$^+$. |
| 341A | 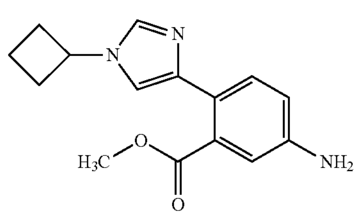 | Methyl 5-amino-2-(1-cyclobutyl-1H-imidazol-4-yl)benzoate | $^1$H NMR (500 MHz, Chloroform-d) δ [ppm] 7.50-7.46 (m, 2H), 7.09 (d, J = 1.3 Hz, 1H), 6.90 (d, J = 2.5 Hz, 1H), 6.77 (dd, J = 8.3, 2.5 Hz, 1H), 4.62-4.50 (m, 1H), 3.80 (s, 3H), 3.75 (s, 2H), 2.54-2.45 (m, 2H), 2.43-2.32 (m, 2H), 1.95-1.79 (m, 2H). LCMS (Analytical Method A): Rt = 0.98 min; MS (ESIPos): m/z = 272 (M + H)$^+$. |

Intermediate 90A: Methyl 5-amino-2-(5-methylpyridin-2-yl)benzoate

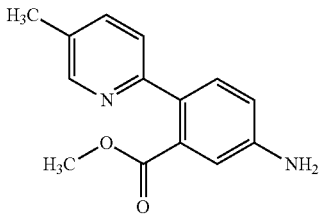

Methyl 2-(5-methylpyridin-2-yl)-5-nitrobenzoate (Int 56A, 180 mg, 0.66 mmol) was dissolved in MeOH (3.5 mL). Iron powder (185 mg, 3.31 mmol) was added followed by concentrated aqueous hydrogen chloride solution (0.2 mL, 0.20 mmol) and the reaction mixture stirred at 80° C. for 3 h. After this time further equivalents of iron powder (185 mg, 3.31 mmol) were added and heating was continued for 16 hours. After this time the reaction mixture was allowed to cool to room temperature, filtered through a pad of Celite® and concentrated in vacuo. The residual material was purified by Biotage Isolera™ chromatography (25 g silica cartridge; eluting with DCM/MeOH/AcOH/H2O [90:18:3:2 mL v/v]/DCM using a gradient of eluents) to give the title compound (25 mg, 8% yield) as a pale yellow oil.

$^1$H NMR (250 MHz, Chloroform-d) δ [ppm] 8.36-8.33 (m, 1H), 7.48-7.38 (m, 1H), 7.34-7.27 (m, 1H), 7.27-7.24 (m, 1H), 6.97-6.95 (m, 1H), 6.75-6.69 (m, 1H), 3.61 (s, 3H), 2.27 (s, 3H).

LCMS (Analytical Method A) Rt=0.84 min, MS (ESIpos) m/z=242.95 (M+H)$^+$.

Intermediate 91A: Methyl 5-amino-2-[6-(1-hydroxyethyl)pyridin-3-yl]benzoate

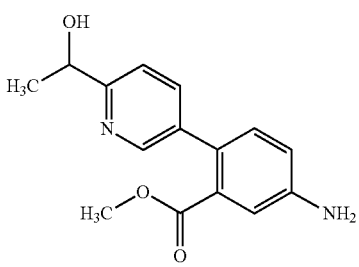 [SMILES: COC(=O)c1cc(N)ccc1-c1ccc(C(C)O)nc1]

Methyl 2-(6-acetylpyridin-3-yl)-5-nitrobenzoate (Int 41A, 706 mg, 2.35 mmol) was dissolved in methanol (5 mL) and ethyl acetate (50 ml) and 10% Palladium on carbon (125 mg) was added and the resulting solution was stirred under a hydrogen atmosphere overnight. The following day the mixture was filtered through a pad of Celite, washed with EtOAc (50 ml) and concentrated at reduced pressure. The mixture was dissolved in methanol (5 mL) and ethyl acetate (50 ml) and 10% Palladium on carbon (125 mg) was added and the resulting solution was stirred under a hydrogen atmosphere overnight for a further 2 days. The mixture was then filtered over Celite (washing with EtOAc) and concentrated at reduced pressure. The residue was purified via Biotage Isolera™ chromatography (using a gradient of eluents; 10-100% EtOAc in heptane) giving the desired product (268 mg, 42% yield) as a pale yellow solid. The product was isolated as a mixture of enantiomers.

$^1$H NMR (500 MHz, DMSO-d6) δ 9.10 (d, J=2.2 Hz, 1H), 8.40 (dd, J=8.1, 2.3 Hz, 1H), 8.29 (d, J=8.1 Hz, 1H), 7.92 (d, J=8.3 Hz, 1H), 7.85 (d, J=2.4 Hz, 1H), 7.62 (dd, J=8.3, 2.5 Hz, 1H), 6.36 (s, 2H), 6.16 (d, J=4.7 Hz, 1H), 5.63-5.52 (m, 1H), 4.43 (s, 3H), 2.21 (d, J=6.5 Hz, 3H).

LCMS (Analytical Method A): Rt=0.77 mins, MS (ESI-Pos): m/z=273 (M+H)$^+$.

Intermediate 92A: 2-Bromo-3-fluoro-5-nitrobenzoic acid

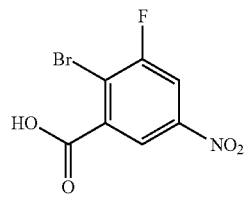 [SMILES: O=C(O)c1cc([N+](=O)[O-])cc(F)c1Br]

To a cooled solution of 2-bromo-3-fluoro-benzoic acid (5.00 g, 22.83 mmol) in sulfuric acid (45.5 mL) at 0° C. was added potassium nitrate portion wise (2.31 g, 22.83 mmol) over 5 minutes. The resulting solution turned yellow and was stirred at ambient temperature for 3 hours. The reaction mixture was poured onto ice and the resultant off-white precipitate was filtered, washed with water and dried in vacuo overnight to afford the title compound (1.50 g, 24% yield) as an off-white solid.

$^1$H NMR (250 MHz, DMSO-d6) δ [ppm] 8.43 (dd, J=8.2 E& 2.1 Hz, 1H), 8.38-8.36 (m, 1H).

Intermediate 93A: Ethyl 2-bromo-3-fluoro-5-nitrobenzoate

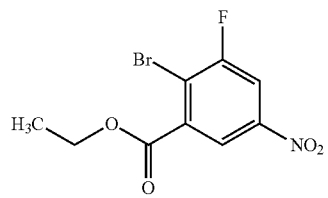 [SMILES: CCOC(=O)c1cc([N+](=O)[O-])cc(F)c1Br]

A solution of 2-bromo-3-fluoro-5-nitrobenzoic acid (Int 92A, 1.5 g, 5.68 mmol) and sulfuric acid (0.3 mL) in EtOH (12.4 mL) was heated at 100° C. for 16 h. After this time the reaction mixture cooled to room temperature and then diluted with EtOAc and 2M aqueous sodium hydroxide solution. The organic phase isolated and the aqueous layer back-extracted with further EtOAc. The organic layers were combined, washed with saturated aqueous sodium chloride solution, dried (MgSO$_4$), filtered and concentrated in vacuo to afford the title compound (1.45 g, 80% yield) as an orange solid.

$^1$H NMR (250 MHz, DMSO-d6) δ [ppm] 8.49 (dd, J=8.3, 2.6 Hz, 1H), 8.40 (dd, J=2.6, 1.4 Hz, 1H), 4.41 (q, J=7.1 Hz, 2H), 1.36 (t, J=7.1 Hz, 3H).

Intermediate 94A: Ethyl 5-amino-2-bromo-3-fluorobenzoate

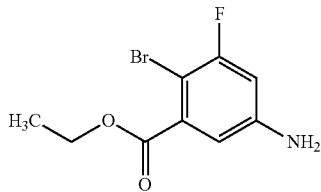

A mixture of ethyl 2-bromo-3-fluoro-5-nitrobenzoate (Int 93A, 0.80 g, 2.74 mmol) and 10% Palladium on carbon (146 mg) in EtOAc/EtOH (27 mL; 8:2 v:v) were stirred under a hydrogen atmosphere for 16 hours. The reaction mixture was filtered through Celite® and concentrated at reduced pressure. The residue was purified by Biotage Isolera™ chromatography (eluting with a gradient of eluents; 100% heptane to 6:4 heptane/EtOAc) giving the title compound (330 mg, 43% yield) as an orange oil.

$^1$H NMR (250 MHz, DMSO-d6) δ [ppm] 6.79 (dd, J=2.6, 1.0 Hz, 1H), 6.62 (dd, J=11.4, 2.6 Hz, 1H), 5.87 (s, 2H), 4.30 (q, J=7.1 Hz, 2H), 1.31 (t, J=7.1 Hz, 3H).

LCMS (Analytical Method A) Rt=1.11 min, MS (ESIpos) m/z=263.75 (M+H)$^+$.

Intermediate 95A: Ethyl 5-amino-3-fluoro-2-[6-(trifluoromethyl)pyridin-3-yl]benzoate

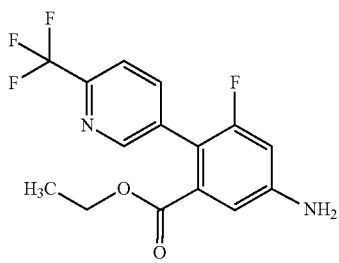

To a pressure tube was added [6-(trifluoromethyl)pyridin-3-yl]boronic acid (361 mg, 1.89 mmol), ethyl 5-amino-2-bromo-3-fluorobenzoate (Int 94A, 330 mg, 1.26 mmol), palladium(II) acetate (14 mg, 0.06 mmol), 2-dicyclohexylphosphino-2',6'-dimethoxybiphenyl (52 mg, 0.13 mmol) and potassium phosphate (802 mg, 3.78 mmol) in tetrahydrofuran (6.3 mL). The tube was degassed with nitrogen, sealed and the reaction mixture heated at 60° C. for 16 h. The reaction mixture was cooled to room temperature and then partitioned between EtOAc and saturated aqueous sodium hydrogen carbonate solution. The aqueous layer was removed and the organic layer was washed with saturated aqueous sodium chloride solution, dried (MgSO$_4$), filtered and concentrated at reduced pressure. The residual material was purified by Biotage Isolera™ chromatography (eluting with a gradient of eluents; 100% heptane to 1:1 heptane/EtOAc) giving the title compound (475 mg, 77% yield) as a pale yellow solid.

$^1$H NMR (250 MHz, DMSO-d6) δ [ppm] 8.57 (s, 1H), 7.92-7.91 (m, 2H), 7.02 (d, J=2.1 Hz, 1H), 6.66 (dd, J=12.4, 2.3 Hz, 1H), 6.02 (s, 2H), 4.01 (q, J=7.1 Hz, 2H), 0.92 (t, J=7.1 Hz, 3H).

LCMS (Analytical Method A) Rt=1.19 min, MS (ESIpos) m/z=328.95 (M+H)$^+$.

Intermediate 96A: Ethyl 2-[6-(difluoromethyl)pyridin-3-yl]-3-fluoro-5-nitrobenzoate

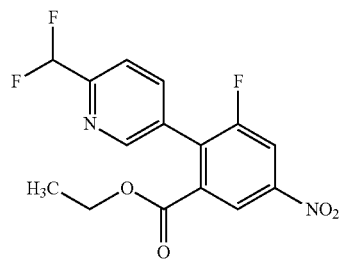 [SMILES: CCOC(=O)c1cc([N+](=O)[O-])cc(F)c1-c1ccc(C(F)F)nc1]

A mixture of ethyl 2-bromo-3-fluoro-5-nitrobenzoate (Int 93A, 0.58 g, 2.00 mmol), 2-(difluoromethyl)-5-(4,4,5,5-tetramethyl-1,3,2-dioxaborolan-2-yl)pyridine (Int 5A, 0.765 g, 3.00 mmol), potassium carbonate (0.829 g, 6.00 mmol) and dichlorobis(triphenylphosphine)-palladium(II) (28 mg, 0.040 mmol) in dimethoxyethane/water (10 mL; 2:1 v/v) was degassed by bubbling nitrogen through the mixture for 5 minutes. The mixture was then heated at 100° C. for 16 h and after this time the reaction mixture was allowed to cool to room temperature and was filtered through a plug of Celite, washing with EtOAc. The organic layer was isolated, washed with saturated aqueous sodium chloride solution, dried (MgSO$_4$), filtered and concentrated in vacuo. The residual material was purified by Biotage Isolera™ chromatography (eluting with a gradient of 0-20% EtOAc in heptane) giving the title compound (0.18 g, 26% yield) as a colourless crystalline solid.

$^1$H NMR (250 MHz, Chloroform-d) δ [ppm] 8.71 (dd, J=2.3, 1.3 Hz, 1H), 8.58 (m, 1H), 8.24 (dd, J=8.4, 2.3 Hz, 1H), 7.88-7.75 (m, 2H), 6.74 (t, J=55.3 Hz, 1H), 4.21 (q, J=7.1 Hz, 2H), 1.13 (t, J=7.1 Hz, 3H).

LCMS (Analytical Method A) Rt=1.26 min, MS (ESI-pos): m/z=340.95 (M+H)$^+$.

In analogy to Intermediate 96A, the following intermediate was prepared using the corresponding aryl halide and appropriate boronic acids or, respectively, the corresponding pinacol boronic esters as starting materials.

| Int. | Structure | Name | Analytical Data |
|---|---|---|---|
| 97A | 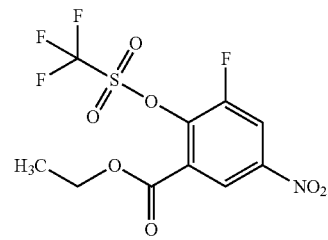 | Ethyl 2-[6-(1,1-difluoropropyl)pyridin-3-yl]-3-fluoro-5-nitrobenzoate | $^1$H NMR (250 MHz, Chloroform-d) δ [ppm] 8.69 (dd, J = 2.3, 1.3 Hz, 1H), 8.58 (s, 1H), 8.23 (dd, J = 8.4, 2.3 Hz, 1H), 7.80-7.76 (m, 2H), 4.20 (q, J = 7.1 Hz, 2H), 2.57-2.26 (m, 2H), 1.13-1.03 (m, 6H). LCMS (Analytical Method A) Rt = 1.32 min, MS (ESIpos): m/z = 368.95 (M + H)$^+$. |

Intermediate 98A:
3-fluoro-2-hydroxy-5-nitrobenzoic acid

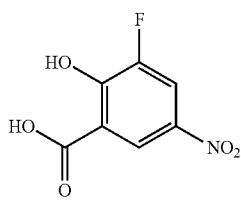 [SMILES: O=C(O)c1cc([N+](=O)[O-])cc(F)c1O]

3-Fluoro-2-hydroxybenzoic acid (24 g, 153 mmol) was dissolved in concentrated sulfuric acid (240 mL) and cooled to 0° C. Concentrated nitric acid (11.5 mL, 181 mmol, 69% solution) was then added dropwise over 30 minutes and the internal temperature was maintained below 10° C. After stirring at 0° C. for a further 60 minutes the mixture was poured onto ice water and the desired product precipitated as an off white solid. This was filtered, washed with water (500 mL) and dried in the vacuum oven giving the desired product (26.0 g, 84% yield) as a tan solid.

$^1$H NMR (250 MHz, DMSO-d6) δ [ppm] 8.39 (dd, J=2.8, 1.3 Hz, 1H), 8.23 (dd, J=10.8, 2.9 Hz, 1H).

LCMS (Analytical Method A): Rt=0.93 mins, MS (ESINeg): m/z=200 (M−H)$^−$.

Intermediate 99A: Ethyl 3-fluoro-2-hydroxy-5-nitrobenzoate

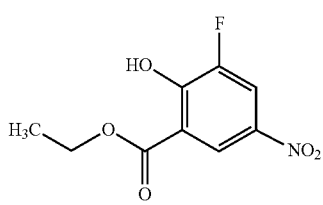 [SMILES: CCOC(=O)c1cc([N+](=O)[O-])cc(F)c1O]

3-Fluoro-2-hydroxy-5-nitrobenzoic acid (Int 98A, 26.0 g, 129 mmol) was dissolved in ethanol (520 mL) and concentrated sulfuric acid (7.0 mL, 129 mmol) was added and the resulting solution was heated at reflux for 4 days. The mixture was then allowed to cool to room temperature and product precipitated as a white solid. This was filtered and washed with heptane (150 mL) giving the desired product (9.0 g, 30% yield) as white needles. The filtrate was concentrated at reduced pressure and the residue obtained was dissolved in TBME (300 mL) and washed with water (100 mL) and brine (2×100 mL), dried (Na$_2$SO$_4$), filtered and concentrated at reduced pressure. The solids obtained were purified by Biotage Isolera™ chromatography (using a gradient of eluents; 95:5 to 7:3 heptane/TBME) giving further product (12.0 g, 41% yield) as an off white solid. The fractions were combined to give the desired product (21.0 g, 71% yield) as an off white solid.

$^1$H NMR (500 MHz, DMSO-d6) δ [ppm] 8.42-8.32 (m, 2H), 4.40 (q, J=7.1 Hz, 2H), 1.36 (t, J=7.1 Hz, 3H).

LCMS (Analytical Method A): Rt=1.25 mins, MS (ESINeg): m/z=228 (M−H)$^−$.

Intermediate 100A: Ethyl 3-fluoro-5-nitro-2-{[(trifluoromethyl)sulfonyl]oxy}-benzoate Ethyl 3-fluoro-2-hydroxy-5-nitrobenzoate (Int 99A, 15.0 g, 65.4 mmol) was stirred in dichloromethane (300 mL) and cooled to 0° C. and triethylamine (11.0 mL, 78.5 mmol) was added giving a bright yellow solution. Trifluoromethanesulfonic anhydride (12.2 mL, 72.0 mmol) was then added dropwise and the internal temperature was maintained below 10° C. and upon complete addition a colourless solution was observed. Further triethylamine (2.7 mL, 19.6 mmol) followed by trifluoromethanesulfonic anhydride (2.2 mL, 13.0 mmol) were added at 0° C. and the resulting mixture was stirred for 10 minutes giving complete conversion to the desired product. The mixture was allowed to warm to room temperature then washed with 1M aq. HCl (2×150 mL) and brine (100 mL), dried (Na$_2$SO$_4$), filtered and concentrated at reduced pressure. The residue was purified by Biotage Isolera™ chromatography (using a gradient of eluents; 98:2 to 8:2 heptane/TBME) giving the desired product (21.6 g, 91% yield) as a pale yellow oil.

$^1$H NMR (500 MHz, DMSO-d6) δ [ppm] 8.88 (dd, J=9.6, 2.8 Hz, 1H), 8.56 (dd, J=2.7, 1.9 Hz, 1H), 4.44 (q, J=7.1 Hz, 2H), 1.36 (t, J=7.1 Hz, 3H).

LCMS (Analytical Method A): Rt=1.33 mins, the product did not ionise.

Intermediate 101A: Ethyl 2-(1-cyclobutyl-1H-pyrazol-4-yl)-3-fluoro-5-nitrobenzoate

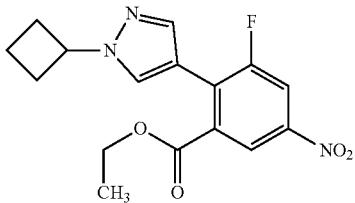 [SMILES: CCOC(=O)c1cc([N+](=O)[O-])cc(F)c1-c1cnn(C2CCC2)c1]

A mixture of 1-cyclobutyl-4-(4,4,5,5-tetramethyl-1,3,2-dioxaborolan-2-yl)-1H-pyrazole (7.56 g, 30.45 mmol), Pd(PPh$_3$)$_2$Cl$_2$ (388 mg, 0.55 mmol), K$_2$CO$_3$ (7.65 g, 55.37 mmol) and ethyl 3-fluoro-5-nitro-2-{[(trifluoromethyl)sulfonyl]oxy}benzoate (Int 100A, 10.00 g, 27.68 mmol) was split equally between 8 pressure tubes and dissolved in DME/water (10:1, 8×17.3 mL) and the resulting solutions were degassed with nitrogen for 5 minutes. The reaction vessels were sealed and heated to 100° C. for 1 hour. The reaction mixtures were then cooled to room temperature, combined and diluted with ethyl acetate and washed with 1M aqueous sodium hydroxide solution, then saturated aqueous sodium chloride solution, dried (MgSO$_4$), filtered and concentrated at reduced pressure. The residue was purified by Biotage Isolera™ chromatography (eluting with a gradient of eluents; 100% heptane to 85:15 heptane/EtOAc) giving the desired product (8.65 g, 94% yield) as a pale yellow oil.

$^1$H NMR (250 MHz, Chloroform-d) δ [ppm] 8.34 (dd, J=2.3, 1.2 Hz, 1H), 8.10 (dd, J=9.6, 2.4 Hz, 1H), 7.77 (d, J=2.2 Hz, 1H), 7.68 (s, 1H), 4.84 (m, 1H), 4.35 (q, J=7.1 Hz, 2H), 2.71-2.47 (m, 4H), 2.04-1.84 (m, 2H), 1.30 (t, J=7.1 Hz, 3H).

LCMS (Analytical Method A): Rt=1.30 mins; MS (ESIPos): m/z=334.0 (M+H)$^+$.

In analogy to Intermediate 101A, the following intermediates were prepared using the corresponding aryl triflate and appropriate boronic acids or, respectively, the corresponding pinacol boronic esters as starting materials.

| Int. | Structure | Name | Analytical Data |
|---|---|---|---|
| 102A | 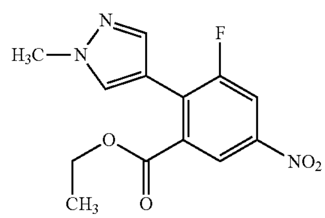 [SMILES: CCOC(=O)c1cc([N+](=O)[O-])cc(F)c1-c1cnn(C)c1] | Ethyl 3-fluoro-2-(1-methyl-1H-pyrazol-4-yl)-5-nitrobenzoate | $^1$H NMR (250 MHz, Chloroform-d) δ [ppm] 8.35 (dd, J = 2.3, 1.1 Hz, 1H), 8.10 (dd, J = 9.6, 2,3 Hz, 1H), 7.71 (d, J = 2.2 Hz, 1H), 7.68-7.58 (m, 1H), 4.36 (q, J = 7.1 Hz, 2H), 4.00 (s, 3H), 1.32 (t, J = 7.1 Hz, 3H). LCMS (Analytical Method A): Rt = 1.21 min; MS (ESIPos): m/z = 294.0 (M + H)$^+$. |
| 103A | 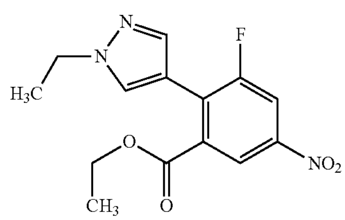 [SMILES: CCOC(=O)c1cc([N+](=O)[O-])cc(F)c1-c1cnn(CC)c1] | Ethyl 2-(1-ethyl-1H-pyrazol-4-yl)-3-fluoro-5-nitrobenzoate | $^1$H NMR (250 MHz, Chloroform-d) δ [ppm] 8.33 (dd, J = 2.2, 1.0 Hz, 1H), 8.09 (dd, J = 9.6, 2,3 Hz, 1H), 7.74 (d, J = 2.2 Hz, 1H), 7.66-7.62 (m, 1H), 4.42-4.18 (m, 4H), 1.56 (t, J = 7.3 Hz, 3H), 1.30 (t, J = 7.2 Hz, 3H). LCMS (Analytical Method A): Rt = 1.26 min; MS (ESIPos): m/z = 308.0 (M + H)$^+$. |
| 104A | 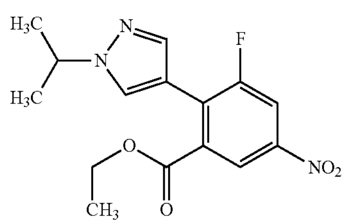 | Ethyl 3-fluoro-2-(1-isopropyl-1H-pyrazol-4-yl)-5-nitrobenzoate | $^1$H NMR (250 MHz, Chloroform-d) δ [ppm] 8.33 (dd, J = 2.3, 1.1 Hz, 1H), 8.10 (dd, J = 9.6, 2.4 Hz, 1H), 7.76 (d, J = 2.4 Hz, 1H), 7.66 (s, 1H), 4.65-4.52 (m, 1H), 4.34 (q, J = 7.1 Hz, 2H), 1.59 (d, J = 6.7 Hz, 6H), 1.30 (t, J = 7.1 Hz, 3H). LCMS (Analytical Method A): Rt = 1.31 mins, MS (ESIPos): m/z = 322.0 (M + H)$^+$. |
| 105A | 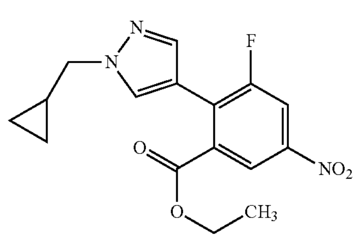 [SMILES: CCOC(=O)c1cc([N+](=O)[O-])cc(F)c1-c1cnn(CC2CC2)c1] | Ethyl 2-[1-(cyclopropylmethyl)-1H-pyrazol-4-yl]-3-fluoro-5-nitrobenzoate | $^1$H NMR (250 MHz, Chloroform-d) δ [ppm] 8.29-8.19 (m, 1H), 8.01 (dd, J = 9.6, 2.3 Hz, 1H), 7.75 (d, J = 2.3 Hz, 1H), 7.58 (d, J = 0.8 Hz, 1H), 4.26 (q, J = 7.1 Hz, 2H), 3.99 (d, J = 7.1 Hz, 2H), 1.31-1.17 (m, 4H), 0.70-0.58 (m, 2H), 0.39-0.30 (m, 2H). LCMS (Analytical Method A): Rt = 1.36 mins, MS (ESIpos): m/z = 334.0 (M + H)$^+$. |

| Int. | Structure | Name | Analytical Data |
|---|---|---|---|
| 106A | 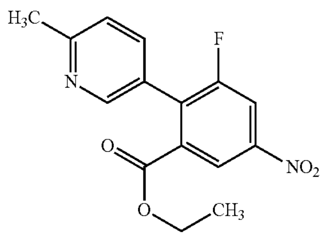 [SMILES: CCOC(=O)c1cc([N+](=O)[O-])cc(F)c1-c1ccc(C)nc1] | Ethyl 3-fluoro-2-(6-methylpyridin-3-yl)-5-nitrobenzoate | $^1$H NMR (500 MHz, DMSO-d6) δ [ppm] 8.52-8.45 (m, 2H), 8.38 (d, J = 2.1 Hz, 1H), 7.71 (dd, J = 8.0, 2.2 Hz, 1H), 7.39 (d, J = 8.0 Hz, 1H), 4.11 (q, J = 7.1 Hz, 2H), 2.55 (s, 3H), 1.02 (t, J = 7.1 Hz, 3H). LCMS (Analytical Method A): Rt = 1.07 mins, MS (ESIpos): m/z = 305 (M + H)$^+$. |
| 107A | 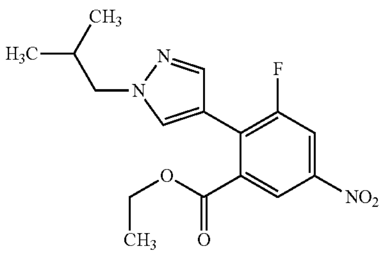 [SMILES: CCOC(=O)c1cc([N+](=O)[O-])cc(F)c1-c1cnn(CC(C)C)c1] | Ethyl 3-fluoro-2-(1-isobutyl-1H-pyrazol-4-yl)-5-nitrobenzoate | $^1$H NMR (400 MHz, DMSO-d6) δ [ppm] 0.85 (d, 6H), 1.19 (t, 3H), 2.08-2.18 (m, 1H), 4.00 (d, 2H), 4.26 (q, 2H), 7.61 (d, 1H), 8.05 (d, 1H), 8.30 (dd, 1H), 8.36 (dd, 1H). LCMS (method 1): Rt = 1.29 min; MS (ESIPos) m/z = 336 (M + H)$^+$. |
| 108A | 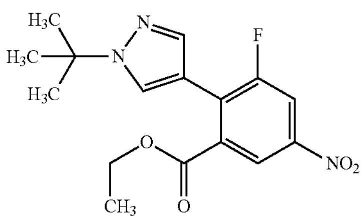 [SMILES: CCOC(=O)c1cc([N+](=O)[O-])cc(F)c1-c1cnn(C(C)(C)C)c1] | Ethyl 2-(1-tert-butyl-1H-pyrazol-4-yl)-3-fluoro-5-nitrobenzoate | $^1$H NMR (400 MHz, DMSO-d6) δ [ppm] 1.17 (t, 3H), 1.56 (s, 9H), 4.25 (q, 2H), 7.63 (d, 1H), 8.08 (d, 1H), 8.31 (dd, 1H), 8.37 (dd, 1H). LCMS (method 1): Rt = 1.29 min; MS (ESIPos) m/z = 336 (M + H)$^+$. |
| 109A | 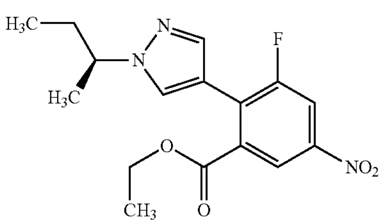 [SMILES: CCOC(=O)c1cc([N+](=O)[O-])cc(F)c1-c1cnn([C@@H](C)CC)c1] | Ethyl 2-{1-[(2S)-butan-2-yl]-1H-pyrazol-4-yl}-3-fluoro-5-nitrobenzoate | $^1$H NMR (250 MHz, Chloroform-d) δ [ppm] 8.33 (dd, J = 2.3, 1.1 Hz, 1H), 8.10 (dd, J = 9.6, 2.4 Hz, 1H), 7.73 (d, J = 2.3 Hz, 1H), 7.67 (s, 1H), 4.42-4.26 (m, 3H), 2.11-1.80 (m, 2H), 1.57 (m, 2H), 1.30 (m, 3H), 0.88 (t, J = 7.4 Hz, 3H). LCMS (Analytical Method A): Rt = 1.45 mins, MS (ESIPos): m/z = 336 (M + H)$^+$. |
| 110A | 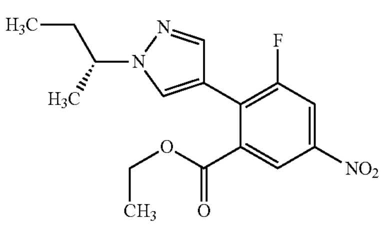 [SMILES: CCOC(=O)c1cc([N+](=O)[O-])cc(F)c1-c1cnn([C@H](C)CC)c1] | Ethyl 2-{1-[(2R)-butan-2-yl]-1H-pyrazol-4-yl}-3-fluoro-5-nitrobenzoate | $^1$H NMR (250 MHz, Chloroform-d) δ [ppm] 8.33 (dd, J = 2.3, 1.1 Hz, 1H), 8.10 (dd, J = 9.6, 2.3 Hz, 1H), 7.73 (d, J = 2.1 Hz, 1H), 7.68 (s, 1H), 4.42-4.24 (m, 3H), 2.08-1.78 (m, 2H), 1.57 (m, 2H), 1.30 (m, 3H), 0.88 (t, J = 7.4 Hz, 3H). LCMS (Analytical Method A): Rt = 1.43 mins, MS (ESIPos): m/z = 336 (M + H)$^+$. |
| 317A | 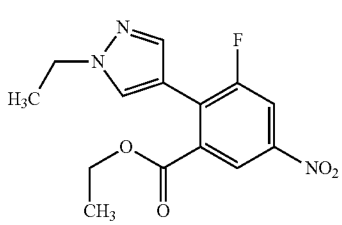 [SMILES: CCOC(=O)c1cc([N+](=O)[O-])cc(F)c1-c1cnn(CC)c1] | Ethyl 2-(1-ethyl-1H-pyrazol-4-yl)-3-fluoro-5-nitrobenzoate | $^1$H NMR (250 MHz, Chloroform-d) δ [ppm] 8.33 (dd, J = 2.2, 1.0 Hz, 1H), 8.09 (dd, J = 9.6, 2.3 Hz, 1H), 7.74 (d, J = 2.2 Hz, 1H), 7.66-7.62 (m, 1H), 4.42-4.18 (m, 4H), 1.56 (t, J = 7.3 Hz, 3H), 1.30 (t, J = 7.2 Hz, 3H). LCMS (Analytical Method A) Rt = 1.26 min, MS (ESIPos): m/z = 308.0 (M + H)$^+$. |

| Int. | Structure | Name | Analytical Data |
|---|---|---|---|
| 318A | 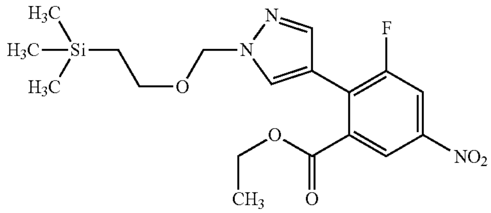 [SMILES: CCOC(=O)c1cc([N+](=O)[O-])cc(F)c1-c1cnn(COCC[Si](C)(C)C)c1] | Ethyl 3-fluoro-5-nitro-2-(1-{[2-(trimethylsilyl)eth-oxy]methyl}-1H-pyrazol-4-yl)benzoate | $^1$H NMR (500 MHz, Chloroform-d) δ [ppm] 8.35 (dd, J = 2.3, 1.1 Hz, 1H), 8.09 (dd, J = 9.4 ,2.3 Hz, 1H), 7.87 (d, J = 2.0 Hz, 1H), 7.71-7.63 (m, 1H), 5.48 (s, 2H), 4.32 (q, J = 7.1 Hz, 2H), 3.66-3.58 (m, 2H), 1.28 (t, J = 7.2 Hz, 3H), 0.97-0.89 (m, 2H), −0.01 (s, 9H). LCMS (Analytical Method A): Rt = 1.39 mins; m/z (ESIPos) = 410.1 (M + H)$^+$. |
| 319A | 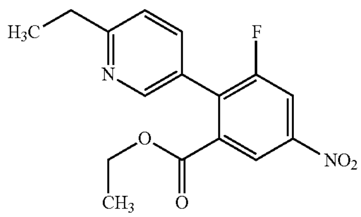 [SMILES: CCOC(=O)c1cc([N+](=O)[O-])cc(F)c1-c1ccc(CC)nc1] | Ethyl 2-(6-ethylpyridin-3-yl)-3-fluoro-5-nitrobenzoate | $^1$H NMR (500 MHz, Chloroform-d) δ [ppm] 8.60-8.58 (m, 1H), 8.42 (d, J = 2.3 Hz, 1H), 8.17 (dd, J = 8.5, 2.3 Hz, 1H) ,7.61-7.55 (m, 1H), 7.29 (d, J = 8.0 Hz, 1H), 4.17 (q, J = 7.1 Hz, 2H), 2.91 (q, J = 7.6 Hz, 2H), 1.36 (t, J = 7.6 Hz, 3H), 1.08 (t, J = 7.1 Hz, 3H). LCMS (Analytical Method A): Rt = 1.13 min; MS (ESIPos): m/z = 319 (M + H)$^+$. |
| 320A | 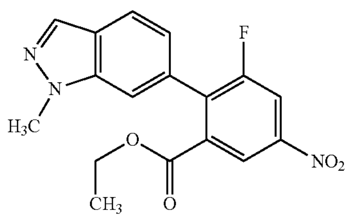 [SMILES: CCOC(=O)c1cc([N+](=O)[O-])cc(F)c1-c1ccc2cnn(C)c2c1] | Ethyl 3-fluoro-2-(1-methyl-1H-indazol-6-yl)-5-nitrobenzoate | $^1$H NMR (250 MHz, Chlorofm-d) δ [ppm] 8.55 (dd, J = 2.2, 1.2 Hz, 1H), 8.17 (dd, J = 8.5, 2.3 Hz, 1H), 8.04 (d, J = 0.9 Hz, 1H), 7.86-7.74 (m, 1H), 7.40-7.30 (m, 1H), 7.10-6.97 (m, 1H), 4.10 (s, 3H), 4.09 (q, J = 7.2 Hz, 2H), 0.94 (t, J = 7.1 Hz, 3H). LCMS (Analytical Method A) Rt = 1.27 min, MS (ESIPos): m/z = 344.0 (M + H)$^+$. |
| 363A | 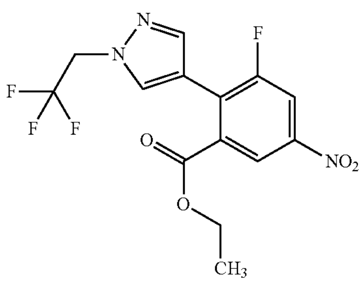 [SMILES: CCOC(=O)c1cc([N+](=O)[O-])cc(F)c1-c1cnn(CC(F)(F)F)c1] | Ethyl 3-fluoro-5-nitro-2-[1-(2,2,2-trifluoroethyl)-1H-pyrazol-4-yl]benzoate | $^1$H NMR (400 MHz, DMSO-d6) δ [ppm] 1.16 (t, 3H), 4.24 (q, 2H), 5.26 (q, 2H), 7.77 (d, 1H), 8.19 (d, 1H), 8.34 (dd, 1H), 8.40 (dd, 1H). LCMS (method 1): Rt = 11.7 min; MS (ESIPos) m/z = 362 (M + H)$^+$. |

Intermediate 322A—Ethyl 2-(2-cyclobutyl-1,3-thi-azol-5-yl)-3-fluoro-5-nitrobenzoate

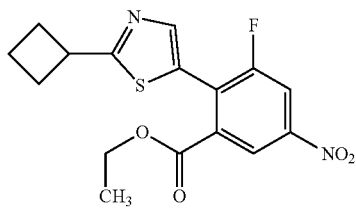 [SMILES: CCOC(=O)c1cc([N+](=O)[O-])cc(F)c1-c1cnc(C2CCC2)s1]

A solution of 2-cyclobutyl-5-(tributylstannyl)-1,3-thiaz-ole (540 mg, 80% purity, 1.01 mmol) and ethyl 3-fluoro-5-nitro-2-{[(trifluoromethyl)sulfonyl]oxy}benzoate (364 mg, 1.01 mmol) in anhydrous 1,4-dioxane (10 mL) were degassed by bubbling nitrogen through the mixture for 5 minutes. Tetrakis(triphenylphosphine) palladium(0) (23 mg, 0.02 mmol) and CuI (19 mg, 0.10 mmol) were then added and the reaction was heated at 110° C. for 8 hours in a sealed tube. The reaction was then cooled to room temperature. The solids were removed by filtration over Celite and washed with EtOAc (50 mL). The organics were then washed with brine (2×20 mL), dried (Na$_2$SO$_4$), filtered and concentrated at reduced pressure. The residue was purified by Biotage Isolera™ chromatography [Biotage SNAP Cartridge KP-Sil 50 g; using a gradient of eluents, 0-50% EtOAc in DCM] giving the desired compound (220 mg, 56% yield) as a yellow oil.

$^1$H NMR (500 MHz, Chloroform-d) δ [ppm] 8.46 (dd, J=2.3, 1.2 Hz, 1H), 8.13 (dd, J=8.7, 2.3 Hz, 1H), 7.64 (s, 1H), 4.26 (q, J=7.1 Hz, 2H), 3.96-3.86 (m, 1H), 2.60-2.48 (m, 2H), 2.48-2.33 (m, 2H), 2.17-1.96 (m, 2H), 1.19 (t, J=7.1 Hz, 3H).

LCMS (Analytical Method A): Rt=1.32 mins, MS (ESI-Pos): m/z=351 (M+H)$^+$.

Intermediate 111A: Ethyl 2-(4-tert-butyl-1H-imidazol-1-yl)-3-fluoro-5-nitrobenzoate

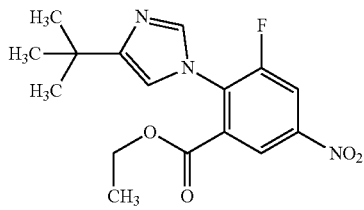 [SMILES: CCOC(=O)c1cc([N+](=O)[O-])cc(F)c1-n1cnc(C(C)(C)C)c1]

To a solution of ethyl 2,3-difluoro-5-nitrobenzoate (1.14 g, 2.81 mmol, 57% purity) and 4-tert-butyl-1H-imidazole (0.553 g, 4.453 mmol) in acetonitrile (15 mL) was added potassium carbonate (1.166 g, 8.433 mmol) at room temperature. The mixture was stirred at reflux for 3 hours. After cooling to room temperature, the solids were removed by filtration and washed with acetonitrile (30 mL). The filtrate was concentrated in vacuo and the residue was purified by Biotage Isolera™ chromatography (using a gradient of eluents; 0-50% EtOAc in heptane) giving the title compound (1.01 g, 91% yield) as yellow solid. Analysis showed 15 mol % of the undesired by-product (ethyl 3-(4-tert-butyl-1H-imidazol-1-yl)-2-fluoro-6-nitrobenzoate) was present.

$^1$H NMR (500 MHz, Chloroform-d) δ [ppm] 8.58 (dd, J=2.4, 1.6 Hz, 1H), 8.28 (dd, J=8.7, 2.5 Hz, 1H), 7.54 (s, 1H), 6.78 (m, 1H), 4.24 (q, J=7.2 Hz, 2H), 1.36 (s, 9H), 1.17 (t, J=7.2 Hz, 3H).

LCMS (Analytical Method A): Rt=1.06 mins; MS (ESI-Pos) m/z=336.1 (M+H)$^+$.

Intermediate 112A: Ethyl 5-amino-2-(4-tert-butyl-1H-imidazol-1-yl)-3-fluorobenzoate

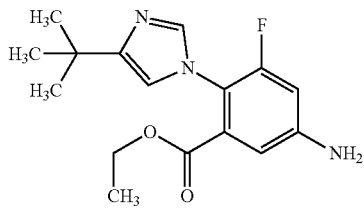 [SMILES: CCOC(=O)c1cc(N)cc(F)c1-n1cnc(C(C)(C)C)c1]

To a de-gassed solution of ethyl 2-(4-tert-butyl-1H-imidazol-1-yl)-3-fluoro-5-nitrobenzoate (Int 111A, 1.01 g, 2.56 mmol, 85% purity) in EtOH (25 mL) was added 10% palladium on carbon (100 mg, 0.094 mmol). The mixture was stirred at room temperature under an atmosphere of hydrogen for 18 hours. The catalyst was then removed by filtration (Celite) and washed with EtOH (50 mL). The filtrate was concentrated in vacuo and the residue was purified by silica flash column chromatography (using a gradient of eluents; 0-100% EtOAc in heptane) giving the title product (0.85 g) as yellow oil. The material was further purified via preparative HPLC (Method B) giving the title compound (647 mg, 81% yield) as white solid.

$^1$H NMR (500 MHz, DMSO-d6) δ [ppm] 7.48-7.39 (m, 1H), 6.88-6.84 (m, 1H), 6.76 (d, J=1.1 Hz, 1H), 6.65 (dd, J=12.3, 2.5 Hz, 1H), 6.00 (s, 2H), 3.98 (q, J=7.1 Hz, 2H), 1.22 (s, 9H), 0.97 (t, J=7.1 Hz, 3H).

LCMS (Analytical Method A): Rt=1.0 mins; MS (ESI-Pos) m/z=306.0 (M+H)$^+$.

Intermediate 113A: Ethyl 5-amino-2-(1-cyclobutyl-1H-pyrazol-4-yl)-3-fluorobenzoate

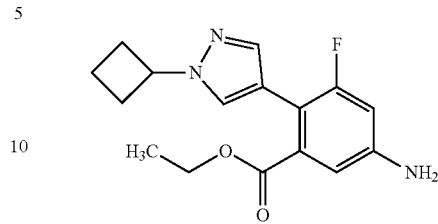

A mixture of 1-cyclobutyl-4-(4,4,5,5-tetramethyl-1,3,2-dioxaborolan-2-yl)-1H-pyrazole (440 mg, 1.77 mmol), ethyl 5-amino-2-bromo-3-fluorobenzoate (310 mg, 1.18 mmol), palladium(II) acetate (13 mg, 0.06 mmol), 2-dicyclohexylphosphino-2',6'-dimethoxybiphenyl (48 mg, 0.12 mmol) and potassium phosphate (752 mg, 3.55 mmol) in tetrahydrofuran/water (7:1 v/v/; 5.9 mL) in a pressure tube was degassed with nitrogen for 5 minutes. After this time the tube was sealed and the reaction mixture warmed to 60° C. for 16 h. The reaction mixture was allowed to cool to room temperature and was partitioned between EtOAc and saturated aqueous sodium hydrogen carbonate solution. The aqueous layer was removed and the organic layer was washed with saturated aqueous sodium chloride solution, dried (MgSO$_4$), filtered and concentrated at reduced pressure. The residue was purified by Biotage Isolera™ chromatography (eluting with a gradient of eluents; 100% heptane to 6:4 heptane/EtOAc) giving the title compound (470 mg, 86% yield) as a pale yellow solid.

$^1$H NMR (250 MHz, DMSO-d6) δ [ppm] 7.70 (s, 1H), 7.33 (s, 1H), 6.66 (d, J=2.3 Hz, 1H), 6.53 (dd, J=12.6, 2.3 Hz, 1H), 5.67 (s, 2H), 4.83 (m, 1H), 4.11 (q, J=7.1 Hz, 2H), 2.45-2.28 (m, 4H), 1.87-1.69 (m, 2H), 1.07 (t, J=7.1 Hz, 3H).

LCMS (Analytical Method A) Rt=1.11 min, MS (ESI-Pos): m/z=304.05 (M+H)$^+$.

Alternatively, Intermediate 113A was synthesized by the procedure described below.

Intermediate 113A: Ethyl 5-amino-2-(1-cyclobutyl-1H-pyrazol-4-yl)-3-fluorobenzoate

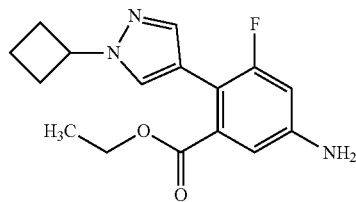 [SMILES: CCOC(=O)c1cc(N)cc(F)c1-c1cnn(C2CCC2)c1]

A mixture of ethyl 2-(1-cyclobutyl-1H-pyrazol-4-yl)-3-fluoro-5-nitrobenzoate (Int 101A, 8.65 g, 25.95 mmol) and 10% palladium on carbon (1.38 g) in EtOAc/EtOH (230 mL; 8:2 v:v) were stirred under a hydrogen atmosphere for 16 hours. The reaction mixture was then filtered through Celite® (washing with ethyl acetate) and concentrated at reduced pressure. The residual pale yellow oil was allowed to crystallise and the solid material triturated with diethyl ether and isolated by filtration to afford the title compound (5.85 g, 73% yield) as an off-white solid. The filtrate obtained was concentrated at reduced pressure and the residue was purified by Biotage Isolera™ chromatography (eluting with a gradient of eluents; 100% heptane to 6:4 heptane/EtOAc) and the pale yellow crystalline solid obtained was triturated with diethyl ether to remove the coloration to afford more of the title compound (1.35 g, 17% yield) as an off-white solid.

In analogy to Intermediate 112A, the following intermediates were prepared by reduction of the nitro group to give the corresponding aniline:

| Int. | Structure | Name | Analytical Data |
| --- | --- | --- | --- |
| 114A | 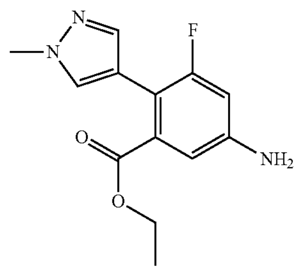 [SMILES: CCOC(=O)c1cc(N)cc(F)c1-c1cnn(C)c1] | Ethyl 5-amino-3-fluoro-2-(1-methyl-1H-pyrazol-4-yl)benzoate | $^1$H NMR (250 MHz, Chloroform-d) δ [ppm] 7.53-7.39 (m, 2H), 6.80 (d, J = 1.8 Hz, 1H), 6.56 (dd, J = 11.4, 2.4 Hz, 1H), 4.23 (q, J = 7.1 Hz, 2H), 3.94 (s, 3H), 3.90 (s, 2H), 1.22 (t, J = 7.1 Hz, 3H). LCMS (Analytical Method A): Rt = 1.06 min; MS (ESIPos): m/z = 264.0 (M + H)$^+$. |
| 115A | 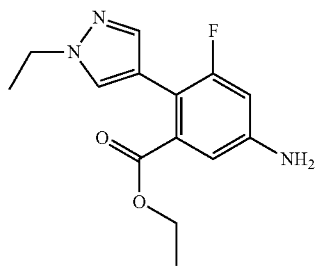 [SMILES: CCOC(=O)c1cc(N)cc(F)c1-c1cnn(CC)c1] | Ethyl 5-amino-2-(1-ethyl-1H-pyrazol-4-yl)-3-fluorobenzoate | $^1$H NMR (250 MHz, Chloroform-d) δ [ppm] 7.49 (d, J = 1.2 Hz, 2H), 6.79 (d, J = 1.8 Hz, 1H), 6.56 (dd, J = 11.4, 2.4 Hz, 1H), 4.29-4.15 (m, 4H), 3.89 (s, 2H), 1.53 (t, J = 7.3 Hz, 3H), 1.20 (t, J = 7.1 Hz, 3H). LCMS (Analytical Method A): Rt = 1.10 min; MS (ESIPos): m/z = 278.0 (M + H)$^+$. |
| 116A | 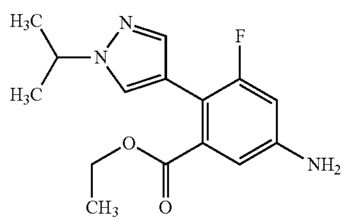 | Ethyl 5-amino-3-fluoro-2-(1-isopropyl-1H-pyrazol-4-yl)benzoate | $^1$H NMR (250 MHz, DMSO-d6) δ [ppm] 7.65 (s, 1H), 7.30 (s, 1H), 6.64 (d, J = 2.2 Hz, 1H), 6.52 (dd, J = 12.6, 2.3 Hz, 1H), 5.66 (s, 2H), 4.59-4.41 (m, 1H), 4.10 (q, J = 7.1 Hz, 2H), 1.42 (d, J = 6.7 Hz, 6H), 1.08 (t, J = 7.1 Hz, 3H). LCMS (Analytical Method A): Rt = 1.17 mins; MS (ESIPos) m/z = 291.95 (M + H)$^+$. |
| 117A | 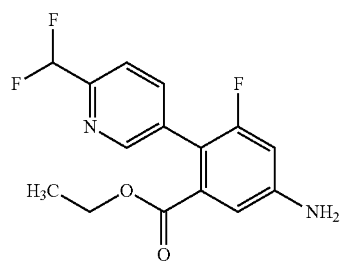 | Ethyl 5-amino-2-[6-(difluoromethyl)pyridin-3-yl]-3-fluorobenzoate | $^1$H NMR (250 MHz, DMSO-d6) δ [ppm] 8.47 (s, 1H), 7.83 (d, J = 7.9 Hz, 1H), 7.70 (d, J = 8.0 Hz, 1H), 7.24-6.75 (m, 2H), 6.64 (m, 1H), 5.97 (s, 2H), 4.00 (q, J = 7.1 Hz, 2H), 0.92 (t, J = 7.1 Hz, 3H). LCMS (Analytical Method A): Rt = 1.23 mins; MS (ESIPos) m/z = 310.95 (M + H)$^+$. |
| 118A | 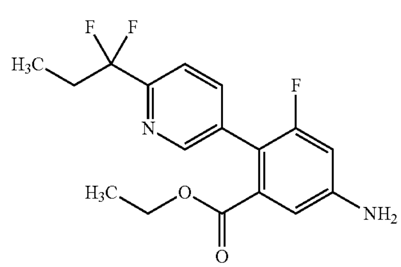 | Ethyl 5-amino-2-[6-(1,1-difluoropropyl)pyridin-3-yl]-3-fluorobenzoate | $^1$H NMR (250 MHz, DMSO-d6) δ [ppm] 8.46 (s, 1H), 7.79 (dd, J = 8.0, 1.6 Hz, 1H), 7.69 (dd, J = 8.1, 0.6 Hz, 1H), 6.98 (d, J = 2.0 Hz, 1H), 6.64 (dd, J = 12.4, 2.2 Hz, 1H), 5.96 (s, 2H), 3.99 (q, J = 7.1 Hz, 2H), 2.45-2.24 (m, 2H), 1.01-0.86 (m, 6H). LCMS (Analytical Method A) Rt = 1.21 min, MS (ESIpos): m/z = 339.05 (M + H)$^+$. |

| Int. | Name | Analytical Data |
|---|---|---|
| 119A | Ethyl 5-amino-2-[1-(cyclopropylmethyl)-1H-pyrazol-4-yl]-3-fluorobenzoate | ¹H NMR (250 MHz, DMSO-d6) δ [ppm] 7.67 (s, 1H), 7.35-7.25 (m, 1H), 6.68-6.61 (m, 1H), 6.53 (dd, J = 12.6, 2.3 Hz, 1H), 5.66 (s, 2H), 4.12 (q, J = 7.1 Hz, 2H), 3.97 (d, J = 7.0 Hz, 2H), 1.32-1.17 (m, 1H), 1.10 (t, J = 7.1 Hz, 3H), 0.58-0.48 (m, 2H), 0.40-0.34 (m, 2H). LCMS (Analytical Method A) Rt = 1.24 min, (MS ESIpos): m/z = 304.0 (M + H)⁺. |
| 120A | Ethyl 5-amino-3-fluoro-2-(6-methylpyridin-3-yl)benzoate | ¹H NMR (250 MHz, DMSO-d6) δ [ppm] 8.24-8.10 (m, 1H), 7.52-7.38 (m, 1H), 7.24 (d, J = 8.0 Hz, 1H), 6.88 (d, J = 2.0 Hz, 1H), 6.59 (dd, J = 12.4, 2.2 Hz, 1H), 5.84 (s, 2H), 3.99 (q, J = 7.1 Hz, 2H), 3.32 (s, 3H), 0.94 (t, J = 7.1 Hz, 3H). LCMS (Analytical Method A): Rt = 0.89 mins, MS (ESIpos): m/z = 275 (M + H)⁺. |
| 121A | Ethyl 5-amino-3-fluoro-2-(1-isobutyl-1H-pyrazol-4-yl)benzoate | ¹H NMR (400 MHz, DMSO-d6) δ [ppm] 0.83 (d, 6H), 1.10 (t, 3H), 2.03-2.14 (m, 1H), 3.90 (d, 2H), 4.10 (q, 2H), 5.68 (s, br, 2H), 6.52 (dd, 1H), 6.63 (d, 1H), 7.29 (s, 1H), 7.61 (s, 1H). LCMS (method A): Rt = 1.02 min; MS (ESIPos) m/z = 306 (M + H)⁺. |
| 122A | Ethyl 5-amino-2-(1-tert-butyl-1H-pyrazol-4-yl)-3-fluorobenzoate | ¹H NMR (400 Mzjz, DMSO-d6) δ [ppm] 1.06 (t, 3H), 1.51 (s, 9H), 4.08 (q, 2H), 5.66 (s, br, 2H), 6.52 (dd, 1H), 7.63 (d, 1H), 7.31 (s, 1H), 7.67 (s, 1H). LCMS (method 1): Rt = 1.01 min; MS (ESIPos) m/z = 306 (M + H)⁺. |
| 123A | Ethyl 5-amino-2-{1-[(2S)-butan-2-yl]-1H-pyrazol-4-yl}-3-fluorobenzoate | ¹H NMR (250 MHz, Chloroform-d) δ [ppm] 7.52-7.46 (m, 2H), 6.77 (dd, J = 2.4, 0.8 Hz, 1H), 6.56 (dd, J = 11.5, 2.4 Hz, 1H), 4.33-4.15 (m, 3H), 3.86 (s, 2H), 2.03-1.74 (m, 2H), 1.54 (d, J = 6.8 Hz, 3H), 1.19 (t, J = 7.1 Hz, 3H), 0.86 (t, J = 7.4 Hz, 3H). LCMS (Analytical Method A) Rt = 1.31 min, MS (ESIpos): m/z = 306.05 (M + H)⁺. |
| 124A | Ethyl 5-amino-2-{1-[(2R)-butan-2-yl]-1H-pyrazol-4-yl}-3-fluorobenzoate | ¹H NMR (250 MHz, Chloroform-d) δ [ppm] 7.46-7.35 (m, 2H), 6.72-6.62 (m, 1H), 6.46 (dd, J = 11.5, 2.4 Hz, 1H), 4.11 (m, 3H), 3.79 (s, 2H), 1.93-1.64 (m, 2H), 1.44 (d, J = 6.8 Hz, 3H), 1.10 (t, J = 7.1 Hz, 3H), 0.77 (t, J = 7.4 Hz, 3H). LCMS (Analytical Method A) Rt = 1.30 min, MS (ESIpos): m/z = 306.05 (M + H)⁺. |

| Int. | Structure | Name | Analytical Data |
|---|---|---|---|
| 333A | 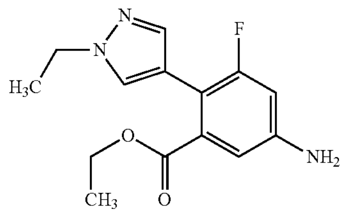 | Ethyl 5-amino-2-(1-ethyl-1H-pyrazol-4-yl)-3-fluorobenzoate | $^1$H NMR (250 MHz, Chloroform-d) δ [ppm] 7.49 (m, 2H), 6.79 (d, J = 1.8 Hz, 1H), 6.56 (dd, J = 11.4, 2.4 Hz, 1H), 4.29-4.15 (m, 4H), 3.89 (s, 2H), 1.53 (t, J = 7.3 Hz, 3H), 1.20 (t, J = 7.1 Hz, 3H). LCMS (Analytical Method A) Rt = 1.10 min, MS (ESIPos): m/z = 278.0 (M + H)$^+$. |
| 334A | 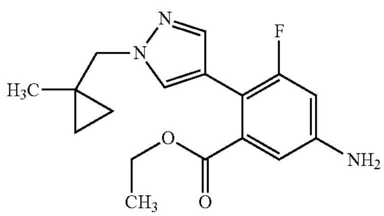 | Ethyl 5-amino-3-fluoro-2-{1-[(1-methylcyclopropyl)methyl]-1H-pyrazol-4-yl}benzoate | $^1$H NMR (500 MHz, Chloroform-d) δ [ppm] 7.55-7.49 (m, 1H), 7.45 (s, 1H), 6.74 (d, J = 2.4 Hz, 1H), 6.51 (dd, J = 11.5, 2.4 Hz, 1H), 4.18 (q, J = 7.1 Hz, 2H), 3.96 (s, 2H), 3.92 (s, 2H), 1.17 (t, J = 7.1 Hz, 3H), 1.03 (s, 3H), 0.64-0.57 (m, 2H), 0.46-0.39 (m, 2H). LCMS (Analytical Method F): Rt = 2.96 min; MS (ESIPos): m/z = 318.2 (M + H)$^+$. |
| 336A | 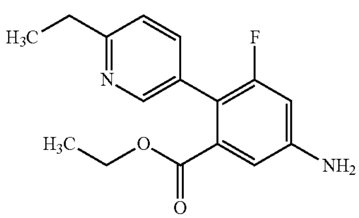 [SMILES: CCOC(=O)c1cc(N)cc(F)c1-c1ccc(CC)nc1] | Ethyl 5-amino-2-(6-ethylpyridin-3-yl)-3-fluorobenzoate | $^1$H NMR (500 MHz, Chloroform-d) δ [ppm] 8.36 (d, J = 2.2 Hz, 1H), 7.53-7.49 (m, 1H), 7.18 (d, J = 8.0 Hz, 1H), 7.00 (dd, J = 2.4, 0.8 Hz, 1H), 6.58 (dd, J = 11.0, 2.4 Hz, 1H), 4.06 (q, J = 7.1 Hz, 2H), 3.98 (s, 2H), 2.86 (q, J = 7.6 Hz, 2H), 1.33 (t, J = 7.6 Hz, 3H), 0.97 (t, J = 7.1 Hz, 3H). LCMS (Analytical Method A): Rt = 0.85 min; MS (ESIPos): m/z = 289 (M + H)$^+$. |
| 338A | 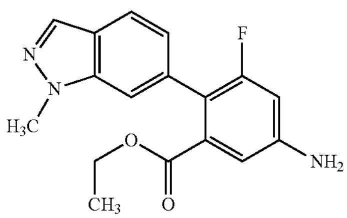 [SMILES: CCOC(=O)c1cc(N)cc(F)c1-c1ccc2cnn(C)c2c1] | Ethyl 5-amino-3-fluoro-2-(1-methyl-1H-indaozl-6-yl)benzoate | $^1$H NMR (500 MHz, DMSO-d6) δ [ppm] 8.03 (d, J = 0.9 Hz, 1H), 7.70 (dd, J = 8.3, 0.7 Hz, 1H), 7.42-7.38 (m, 1H), 6.93-6.89 (m, 1H), 6.83 (d, J = 2.2 Hz, 1H), 6.59 (dd, J = 12.3, 2.3 Hz, 1H), 5.79 (s, 2H), 4.01 (s, 3H), 3.91 (q, J = 7.1 Hz, 2H), 0.76 (t, J = 7.1 Hz, 3H). LCMS (Analytical Method A) Rt = 1.12 min, MS (ESIpos): m/z = 314.2 (M + H)$^+$. |
| 364A | 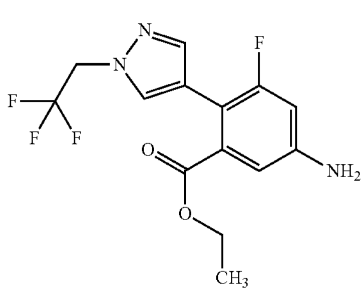 [SMILES: CCOC(=O)c1cc(N)cc(F)c1-c1cnn(CC(F)(F)F)c1] | Ethyl 5-amino-3-fluoro-2-[1-(2,2,2-trifluoroethyl)-1H-pyrazol-4-yl]benzoate | $^1$H NMR (400 MHz, DMSO-d6) δ [ppm] 1.07 (t, 3H), 4.09 (q, 2H), 5.14 (q, 2H), 6.54 (dd, 1H), 6.68 (d, 1H), 7.45 (s, 1H), 7.77 (s, 1H). LCMS (method 1): Rt = 0.92 min; MS (ESIPos) m/z = 332 (M + H)$^+$. |

Intermediate 125A: Ethyl 3-amino-6-chloro-2-fluorobenzoate

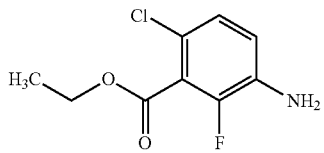

To a solution of 4-chloro-2-fluoroaniline (1.00 g, 6.87 mmol) in tetrahydrofuran (10 mL) at −78° C. was added n-BuLi (2.94 mL of a 2.5M solution in hexanes, 7.35 mmol) and the resulting solution was stirred at this temperature for 20 minutes. After this time a solution of 1,2-bis(chlorodimethylsilyl)ethane (1.55 g, 7.21 mmol) in tetrahydrofuran (5 mL) was added dropwise via cannula. After 1 hour at −78° C., further n-BuLi (3.02 mL of a 2.5M solution in hexanes, 7.56 mmol) was added and the resulting mixture was stirred for 20 minutes and then allowed to warm room temperature and stirred for a further 1 hour. The mixture was then cooled to −78° C. and further n-BuLi (3.02 mL of a 2.5M solution in hexanes, 7.56 mmol) was added and the resulting mixture was stirred for 1 hour at this temperature. Ethylchloroformate (0.90 mL, 8.28 mmol) was then added and the reaction was then allowed to warm to room temperature and stirred for 16 hours. After this time the reaction mixture was diluted with EtOAc and 2M aqueous hydrogen chloride solution. The organic layer was removed, the aqueous layer basified by addition of saturated aqueous sodium hydrogen carbonate, extracted with EtOAc and the organic layer isolated, washed with saturated aqueous sodium chloride solution, dried (MgSO$_4$), filtered and concentrated at reduced pressure. The combined organics were purified by Biotage Isolera™ chromatography (eluting with a gradient of eluents; 100 heptane to 8:2 heptane/EtOAc) giving the title product (1.30 g, 68% yield) as a brown oil.

$^1$H NMR (250 MHz, DMSO-d6) δ [ppm] 7.06 (dd, J=8.7, 1.1 Hz, 1H), 6.92-6.79 (m, 1H), 5.58 (s, 2H), 4.37 (q, J=7.1 Hz, 2H), 1.32 (t, J=7.1 Hz, 3H).

LCMS (Analytical Method A) Rt=1.15 min, MS (ESI-pos): m/z=217.85 (M+H)$^+$.

Intermediate 126A: Ethyl 3-amino-6-(1-cyclobutyl-1H-pyrazol-4-yl)-2-fluorobenzoate

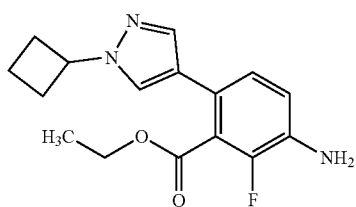 [SMILES: CCOC(=O)c1c(-c2cnn(C3CCC3)c2)ccc(N)c1F]

A mixture of 1-cyclobutyl-4-(4,4,5,5-tetramethyl-1,3,2-dioxaborolan-2-yl)-1H-pyrazole (934 mg, 3.76 mmol), ethyl 3-amino-6-chloro-2-fluorobenzoate (Int 125A, 700 mg, 2.51 mmol), palladium(II) acetate (28 mg, 0.13 mmol), 2-dicyclohexylphosphino-2',6'-dimethoxybiphenyl (103 mg, 0.25 mmol) and potassium phosphate (1.60 g, 3.55 mmol) in tetrahydrofuran/water (7:1 v/v; 12.5 mL) in a pressure tube was degassed with nitrogen for 5 minutes. After this time the reaction mixture heated at 80° C. for 16 h. The reaction mixture was allowed to cool to room temperature and was then partitioned between EtOAc and saturated aqueous sodium hydrogen carbonate solution. The aqueous layer was removed and the organic layer was washed with saturated aqueous sodium chloride solution, dried (MgSO$_4$), filtered and concentrated at reduced pressure. The residue was purified by Biotage Isolera™ chromatography (eluting with a gradient of eluents; 100% heptane to 6:4 heptane/EtOAc) giving the title compound (733 mg, 94% yield) as a dark yellow oil.

$^1$H NMR (250 MHz, DMSO-d6) δ [ppm] 7.65 (d, J=0.6 Hz, 1H), 7.34-7.28 (m, 1H), 6.91 (dd, J=8.3, 0.7 Hz, 1H), 6.73 (dd, J=9.3, 8.4 Hz, 1H), 5.24 (s, 2H), 4.71 (m, 1H), 4.15 (q, J=7.1 Hz, 2H), 2.36-2.19 (m, 4H), 1.75-1.59 (m, 2H), 1.08 (t, J=7.1 Hz, 3H).

LCMS (Analytical Method A) Rt=1.11 min, MS (ESI-pos): m/z=304.55 (M+H)$^+$.

Intermediate 127A: 2-Bromo-3-chloro-5-nitrobenzoic acid

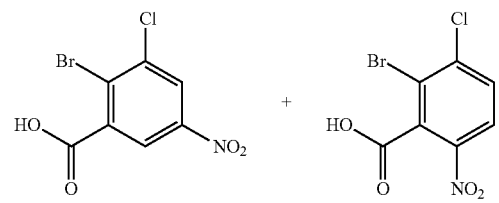 [SMILES: O=C(O)c1cc([N+](=O)[O-])cc(Cl)c1Br ; O=C(O)c1c([N+](=O)[O-])ccc(Cl)c1Br]

To a cooled solution of acid 2-bromo-3-chlorobenzoic acid (4.00 g, 17.0 mmol) in concentrated sulfuric acid (34 mL) at 0° C. was added potassium nitrate portion wise (1.72 g, 17.0 mmol) over 5 minutes with the resulting solution turned yellow and was stirred at ambient temperature for 4 hours over which time an off-white precipitate formed. The reaction mixture was then poured onto ice and the resultant off-white precipitate was filtered, washed with water and dried in the vacuum oven for 5 hours to afford the title compound as a 1:1 mixture with 2-bromo-3-chloro-6-nitrobenzoic acid (4.71 g) as an off-white solid.

$^1$H NMR (250 MHz, DMSO-d6) δ [ppm] 8.55 (d, J=2.6 Hz, 1H), 8.37 (d, J=2.6 Hz, 1H), 8.26 (d, J=8.9 Hz, 1H), 7.99 (d, J=8.9 Hz, 1H).

Intermediate 128A: Ethyl 2-bromo-3-chloro-5-nitrobenzoate

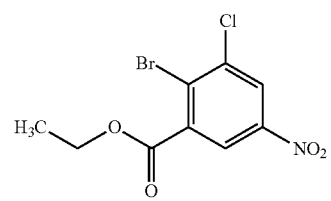 [SMILES: CCOC(=O)c1cc([N+](=O)[O-])cc(Cl)c1Br]

A 1:1 mixture of 2-bromo-3-chloro-5-nitrobenzoic acid and 2-bromo-3-chloro-6-nitrobenzoic acid (Int 127A, 4.7 g) and sulfuric acid (0.46 mL) in EtOH (19 mL) was heated at 100° C. for 16 h. After this time the reaction mixture was cooled to 0° C., diluted with EtOAc and 1M aqueous sodium hydroxide solution was added to basify. The organic layer was isolated and washed with saturated aqueous sodium chloride solution, dried (MgSO₄), filtered, concentrated under reduced pressure. The residue obtained was purified by Biotage Isolera™ chromatography (using a gradient of eluents, 0-20% EtOAc in heptane) to afford the title compound (2.32 g, 43% yield) as an off-white solid.

$^1$H NMR (500 MHz, DMSO-d6) δ [ppm] 8.60 (d, J=2.6 Hz, 1H), 8.43 (d, J=2.6 Hz, 1H), 4.40 (q, J=7.1 Hz, 2H), 1.36 (t, J=7.1 Hz, 3H).

LCMS (Analytical Method A) Rt=1.27 min, the product did not ionise.

Intermediate 129A: Ethyl 3-chloro-2-(1-cyclobutyl-1H-pyrazol-4-yl)-5-nitrobenzoate

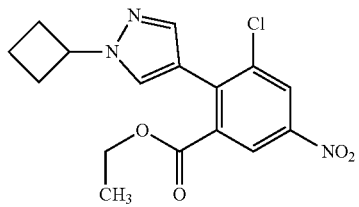 [SMILES: CCOC(=O)c1cc([N+](=O)[O-])cc(Cl)c1-c1cnn(C2CCC2)c1]

In a sealed tube, 1-cyclobutyl-4-(4,4,5,5-tetramethyl-1,3,2-dioxaborolan-2-yl)-1H-pyrazole (500 mg, 2.02 mmol) and ethyl 2-bromo-3-chloro-5-nitrobenzoate (Int 128A, 478 mg, 1.55 mmol) in DME (8 mL) and water (1.5 mL) was degassed with nitrogen for 5 minutes. Pd(PPh₃)₂Cl₂ (22 mg, 0.03 mmol) and potassium carbonate (643 mg, 4.65 mmol) were then added and the reaction was heated to 100° C. for 2.5 hours. The reaction was then cooled to room temperature and diluted with water and EtOAc. The layers were separated and the aqueous was extracted twice with EtOAc. Combined organic extracts were dried over MgSO₄, filtered, concentrated under reduced pressure and the residue obtained was purified by Biotage Isolera™ chromatography (eluting with a gradient of eluents, 0-25% EtOAc in heptane) to afford the title compound (385 mg, 52% yield) as a viscous pale yellow oil.

$^1$H NMR (250 MHz, Chloroform-d) δ [ppm] 8.44 (d, J=2.4 Hz, 1H), 8.40 (d, J=2.4 Hz, 1H), 7.65 (m, 1H), 7.60 (m, 1H), 4.84 (m, 1H), 4.24 (q, J=7.1 Hz, 2H), 2.69-2.48 (m, 4H), 2.06-1.81 (m, 2H), 1.18 (t, J=7.1 Hz, 3H).

LCMS (Analytical Method A) Rt=1.29 min, MS (ESIpos): m/z=350.0 (M+H)⁺.

In analogy to Intermediate 129A, the following intermediates were prepared using the corresponding aryl halide and appropriate boronic acids or, respectively, the corresponding pinacol boronic esters as starting materials:

| Int. | Structure | Name | Analytical Data |
|---|---|---|---|
| 130A | 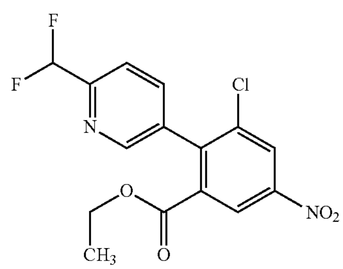 [SMILES: CCOC(=O)c1cc([N+](=O)[O-])cc(Cl)c1-c1ccc(C(F)F)nc1] | Ethyl 3-chloro-2-[6-(difluoromethyl)pyridin-3-yl]-5-nitrobenzoate | $^1$H NMR (500 MHz, DMSO-d6) δ [ppm] 8.71 (d, J = 2.3 Hz, 1H), 8.63 (d, J = 2.3 Hz, 1H), 8.60 (d, J = 1.8 Hz, 1H), 7.98 (dd, J = 8.0, 2.1 Hz, 1H), 7.84 (d, J = 8.0 Hz, 1H), 7.06 (t, J = 54.8 Hz, 1H), 4.10-4.01 (m, 2H), 0.94 (t, J = 7.1 Hz, 3H). LCMS (Analytical Method A) Rt = 1.35 min, MS (ESIpos): m/z = 356.9/358.7 (M + H)⁺. |
| 131A | 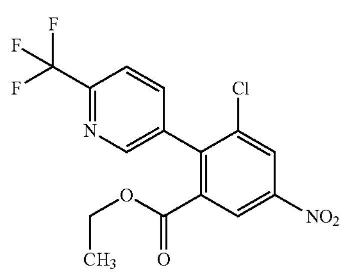 [SMILES: CCOC(=O)c1cc([N+](=O)[O-])cc(Cl)c1-c1ccc(C(F)(F)F)nc1] | Ethyl 3-chloro-5-nitro-2-[6-(trifluoromethyl)pyridin-3-yl]benzoate | $^1$H NMR (250 MHz, Chloroform-d) δ [ppm] 8.79 (d, J = 2.3 Hz, 1H), 8.60-8.58 (m, 1H), 8.57 (d, J = 2.3 Hz, 1H), 7.84 (d, J = 7.9 Hz, 1H), 7.79 (dd, J = 8.2, 1.8 Hz, 1H), 4.17 (q, J = 7.1 Hz, 2H), 1.10 (t, J = 7.1 Hz, 3H). LCMS (Analytical Method A) Rt = 1.30 min, MS (ESIpos): m/z = 375.0 (M + H)⁺. |
| 132A | 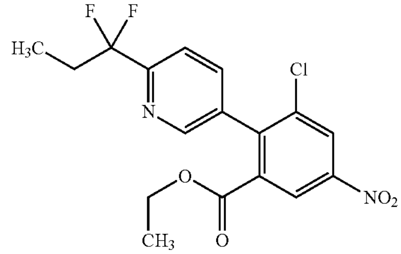 | Ethyl 3-chloro-2-[6-(1,1-difluoropropyl)pyridin-3-yl]-5-nitrobenzoate | $^1$H NMR (500 MHz, DMSO-d6) δ [ppm] 8.70 (d, J = 2.3 Hz, 1H), 8.62 (d, J = 2.3 Hz, 1H), 8.58 (d, J = 1.8 Hz, 1H), 7.95 (dd, J = 8.1, 2.2 Hz, 1H), 7.85-7.79 (m, 1H), 4.09-4.00 (m, 2H), 2.44-2.31 (m, 2H), 0.97 (t, J = 7.5 Hz, 3H), 0.92 (t, J = 7.1 Hz, 3H). LCMS (Analytical Method A) Rt = 1.43 min, MS (ESIpos): m/z = 385.0/386.7 (M + H)⁺. |

Intermediate 133A: Ethyl 5-amino-3-chloro-2-(1-cyclobutyl-1H-pyrazol-4-yl)benzoate

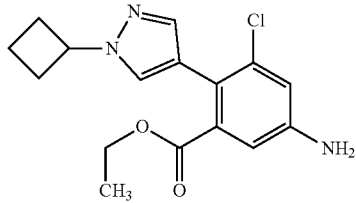 [SMILES: CCOC(=O)c1cc(N)cc(Cl)c1-c1cnn(C2CCC2)c1]

Ethyl 3-chloro-2-(1-cyclobutyl-1H-pyrazol-4-yl)-5-nitrobenzoate (Int 129A, 380 mg, 1.09 mmol) was dissolved in ethanol (10 mL) at room temperature. 10 mol % Pd/C (23 mg) was added and the reaction mixture was then stirred under an atmosphere of hydrogen at room temperature for 8 hours. The reaction mixture was then filtered through a Celite pad (washing with EtOAc) and the filtrate was then concentrated under reduced pressure and this was dissolved in ethanol (10 mL). 10 mol % Pd/C (23 mg) was added and the mixture was stirred under a hydrogen atmosphere for a further 6 hours then filtered through a Celite pad (washing with EtOAc) and concentrated under reduced pressure to yield crude material that was purified by Biotage Isolera™ chromatography (eluting with a gradient of eluents, 0-35% EtOAc in heptane) to afford the title compound (260 mg, 74% yield) as a pale yellow solid.

$^1$H NMR (250 MHz, DMSO-d6) δ [ppm] 7.66 (s, 1H), 7.29 (s, 1H), 6.82 (d, J=2.3 Hz, 1H), 6.73 (d, J=2.3 Hz, 1H), 5.65 (s, 2H), 4.82 (m, 1H), 4.00 (q, J=7.1 Hz, 2H), 2.46-2.26 (m, 4H), 1.88-1.66 (m, 2H), 0.96 (t, J=7.1 Hz, 3H).

LCMS (Analytical Method A) Rt=1.15 min, MS (ESIpos): m/z=320.0 (M+H)$^+$.

In analogy to Intermediate 133A, the following intermediates were prepared from reduction of the nitro group to give the corresponding aniline:

| Int. | Structure | Name | Analytical Data |
| --- | --- | --- | --- |
| 134A | 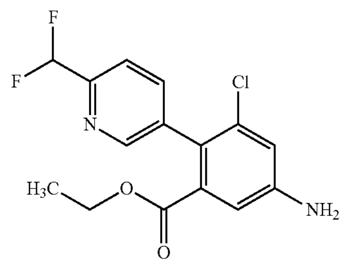 | Ethyl 5-amino-3-chloro-2-[6-(difluoromethyl)pyridin-3-yl]benzoate | $^1$H NMR (500 MHz, DMSO-d6) δ [ppm] 8.41 (d, J = 1.8 Hz, 1H), 7.77 (dd, J = 8.0, 2.1 Hz, 1H), 7.70 (d, J = 8.0 Hz, 1H), 7.08 (d, J = 2.3 Hz, 1H), 6.99 (t, J = 55.0 Hz, 1H), 6.93 (d, J = 2.3 Hz, 1H), 5.91 (s, 2H), 3.93 (q, J = 7.1 Hz, 2H), 0.86 (t, J = 7.1 Hz, 3H). LCMS (Analytical Method A) Rt = 1.24 min, MS (ESIPos): m/z = 327.0/329.0 (M + H)$^+$. |
| 135A | 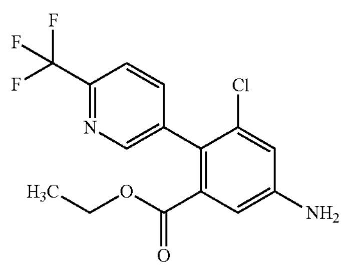 [SMILES: CCOC(=O)c1cc(N)cc(Cl)c1-c1ccc(C(F)(F)F)nc1] | Ethyl 5-amino-3-chloro-2-[6-(trifluoromethyl)pyridin-3-yl]benzoate | $^1$H NMR (250 MHz, Chloroform-d) δ [ppm] 8.55 (s, 1H), 7.80-7.67 (m, 2H), 7.22 (d, J = 2.5 Hz, 1H), 6.98 (d, J = 2.5 Hz, 1H), 4.12-3.97 (m, 4H), 0.97 (t, J = 7.1 Hz, 3H). LCMS (Analytical Method A) Rt = 1.21 min, MS (ESIPos): m/z = 344.9 (M + H)$^+$. |
| 136A | 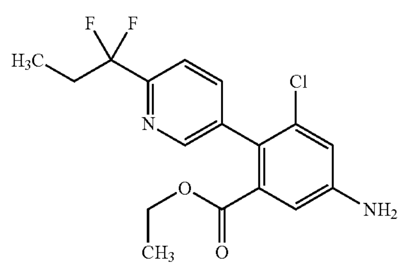 [SMILES: CCOC(=O)c1cc(N)cc(Cl)c1-c1ccc(C(F)(F)CC)nc1] | Ethyl 5-amino-3-chloro-2-[6-(1,1-difluoropropyl)pyridin-3-yl]benzoate | $^1$H NMR (500 MHz, DMSO-d6) δ [ppm] 8.40 (d, J = 1.6 Hz, 1H), 7.74 (dd, J = 8.0, 2.1 Hz, 1H), 7.70-7.63 (m, 1H), 7.07 (d, J = 2.3 Hz, 1H), 6.93 (d, J = 2.3 Hz, 1H), 5.90 (s, 2H), 3.92 (q, J = 7.1 Hz, 2H), 2.35 (m, 2H), 0.95 (t, J = 7.5 Hz, 3H), 0.84 (t, J = 7.1 Hz, 3H). LCMS (Analytical Method A) Rt = 1.33 min, MS (ESIPos): m/z = 355.0/356.8 (M + H)$^+$. |

Intermediate 137A:
2-bromo-3-methyl-5-nitrobenzoic acid

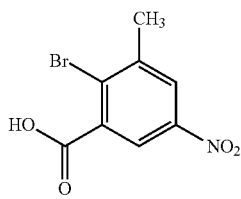

To a cooled solution of 2-bromo-3-methyl-benzoic acid (5.00 g, 23.25 mmol) in sulfuric acid (46.3 mL) at 0° C. was added potassium nitrate portion wise (2.35 g, 23.25 mmol) over 5 minutes with the resulting solution turned yellow and was stirred at ambient temperature for 3 h. After this time, the reaction mixture was poured onto ice and the resultant off-white precipitate was filtered, washed with water and dried in vacuo to afford the title compound (5.95 g, 89% yield) as an off-white solid. The 2-bromo-3-methyl-5-nitrobenzoic acid contained 10 mol % of 2-bromo-3-methyl-6-nitrobenzoic acid by-product.

$^1$H NMR (250 MHz, DMSO-d6) δ [ppm] 8.36 (d, J=2.3 Hz, 1H), 8.24 (d, J=2.8 Hz, 1H), 2.54 (s, 3H).

Intermediate 138A: Ethyl 2-bromo-3-methyl-5-nitrobenzoate

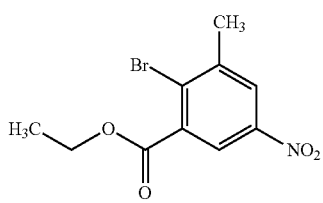 [SMILES: CCOC(=O)c1cc([N+](=O)[O-])cc(C)c1Br]

A solution of 2-bromo-3-methyl-5-nitrobenzoic acid (Int 137A, 5.95 g, 20.59 mmol, containing 10 mol % of 2-bromo-3-methyl-6-nitrobenzoic acid) and sulfuric acid (1.1 mL) in EtOH (45 mL) was heated at 100° C. for 8 h. After this time the reaction mixture was concentrated in vacuo and partitioned between EtOAc and 2M aqueous sodium hydroxide solution. The organic phase isolated and the aqueous layer back-extracted with further EtOAc. The organic layers were combined, washed with saturated aqueous sodium chloride solution, dried (MgSO$_4$), filtered and concentrated in vacuo to afford the title product (4.75 g, 80% yield) as a pale orange oil that crystallised upon standing.

$^1$H NMR (250 MHz, Chloroform-d) δ [ppm] 8.35-8.26 (m, 1H), 8.23-8.14 (m, 1H), 4.45 (q, J=7.1 Hz, 2H), 2.58 (s, 3H), 1.43 (t, J=7.1 Hz, 3H).

LCMS (Analytical Method A): Rt=1.25 min, MS (ESI-pos): no desired mass ion observed.

Intermediate 139A: Ethyl 2-(1-cyclobutyl-1H-pyrazol-4-yl)-3-methyl-5-nitrobenzoate

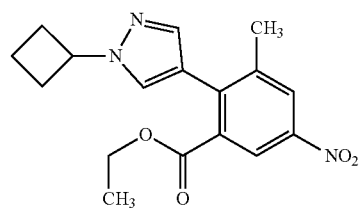 [SMILES: CCOC(=O)c1cc([N+](=O)[O-])cc(C)c1-c1cnn(C2CCC2)c1]

A mixture of ethyl 2-bromo-3-methyl-5-nitrobenzoate (Int 138A, 0.576 g, 2.00 mmol), 1-cyclobutyl-4-(4,4,5,5-tetramethyl-1,3,2-dioxaborolan-2-yl)-1H-pyrazole (0.744 g, 3.00 mmol), potassium carbonate (0.829 g, 6.00 mmol) and dichlorobis(triphenylphosphine)palladium(II) (28 mg, 0.04 mmol) in dimethoxyethane/water (10 mL; 2:1 v/v) was degassed by bubbling nitrogen through the mixture for 5 minutes and then heated at 100° C. for 16 hours. The mixture was then allowed to cool to room temperature and filtered through Celite (washing with EtOAc). The organic layer was washed with saturated aqueous sodium chloride solution, dried (MgSO$_4$), filtered and concentrated at reduced pressure. The residue purified by Biotage Isolera™ chromatography (eluting with a gradient of eluents; 100% heptane to 8:2 heptane/EtOAc) giving the title compound (0.56 g, 84% yield) as a pate yellow oil.

$^1$H NMR (250 MHz, Chloroform-d) δ [ppm] 8.35 (d, J=2.2 Hz, 1H), 8.22 (d, J=1.9 Hz, 1H), 7.49 (i, 1H), 7.46 (i, 1H), 4.83 (i, 1H), 4.18 (q, J=7.1 Hz, 2H), 2.66-2.50 (m, 4H), 2.39 (s, 3H), 2.02-1.86 (i, 2H), 1.14 (t, J=7.1 Hz, 3H).

LCMS (Analytical Method A): Rt=1.35 mJ, MS (ESI-Pos): m/z=330.05 (M+H)$^+$.

In analogy to Intermediate 139A, the following intermediates were prepared using the corresponding aryl halide and appropriate boronic acids or, respectively, the corresponding pinacol boronic esters as starting materials:

| Int. | Structure | Name | Analytical Data |
|---|---|---|---|
| 140A | ![structure] | Ethyl 2-[6-(difluoromethyl)pyridin-3-yl]-3-methyl-5-nitrobenzoate | $^1$H NMR (250 MHz, Chloroform-d) δ [ppm] 8.70 (d, J = 2.0 Hz, 1H), 8.51-8.45 (m, 1H), 8.34 (d, J = 1.8 Hz, 1H), 7.78 (d, J = 8.0 Hz, 1H), 7.69 (dd, J = 8.0, 2.1 Hz, 1H), 6.74 (t, J = 55.4 Hz, 1H), 4.13 (q, J = 7.1 Hz, 2H), 2.23 (s, 3H), 1.09 (t, J = 7.1 Hz, 3H). LCMS (Analytical Method A): Rt = 1.28 min, MS (ESIPos): m/z = 337.0 (M + H)$^+$. |

| Int. | Structure | Name | Analytical Data |
|---|---|---|---|
| 141A | 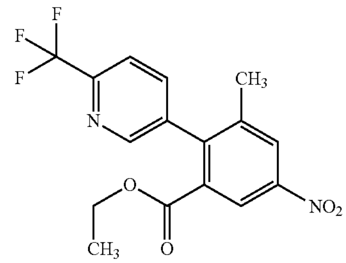 [SMILES: CCOC(=O)c1cc([N+](=O)[O-])cc(C)c1-c1ccc(C(F)(F)F)nc1] | Ethyl 3-methyl-5-nitro-2-[6-(trifluoromethyl)pyridin-3-yl]benzoate | $^1$H NMR (250 MHz, Chloroform-d) δ [ppm] 8.73 (d, J = 2.4 Hz, 1H), 8.55 (s, 1H), 8.36 (d, J = 1.9 Hz, 1H), 7.83 (d, J = 7.6 Hz, 1H), 7.76-7.68 (m, 1H), 4.14 (q, J = 7.1 Hz, 2H), 1.58 (s, 3H), 1.10 (t, J = 7.1 Hz, 3H). LCMS (Analytical Method A): Rt = 1.28 min, MS (ESIPos): m/z = 354.95 (M + H)$^+$. |
| 142A | 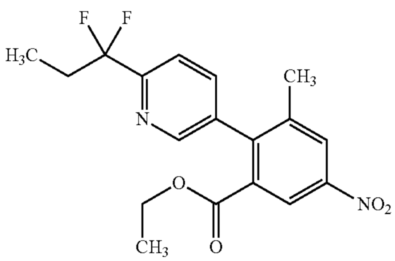 [SMILES: CCOC(=O)c1cc([N+](=O)[O-])cc(C)c1-c1ccc(C(F)(F)CC)nc1] | Ethyl 2-[6-(1,1-difluoropropyl)pyridin-3-yl]-3-methyl-5-nitrobenzoate | $^1$H NMR (250 MHz, Chloroform-d) δ [ppm] 8.68 (d, J = 2.0 Hz, 1H), 8.47 (d, J = 1.3 Hz, 1H), 8.37-8.29 (m, 1H), 7.77 (dd, J = 8.1, 0.8 Hz, 1H), 7.65 (dd, J = 8.0, 2.2 Hz, 1H), 4.18-4.05 (m, 2H), 2.56-2.31 (m, 2H), 2.23 (s, 3H), 1.14-1.02 (m, 6H). LCMS (Analytical Method A): Rt = 1.34 min, MS (ESIPos): m/z = 365.35 (M + H)$^+$. |

Intermediate 143A: Ethyl 5-amino-2-(1-cyclobutyl-1H-pyrazol-4-yl)-3-methylbenzoate

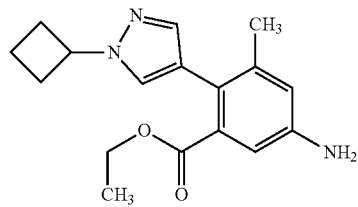 [SMILES: CCOC(=O)c1cc(N)cc(C)c1-c1cnn(C2CCC2)c1]

A mixture of ethyl 2-(1-cyclobutyl-1H-pyrazol-4-yl)-3-methyl-5-nitrobenzoate (Int 139A, 0.56 g, 1.68 mmol) and 10% Palladium on carbon (90 mg) in EtOAc/EtOH (10.7 mL; 8:2 v/v) was stirred under a hydrogen atmosphere for 16 hours. After this time the reaction mixture filtered through Celite and concentrated at reduced pressure. The residue was purified by Biotage Isolera™ chromatography (using a gradient of eluents; 100% heptane to 1:1 heptane/EtOAc) giving the title compound (470 mg, 92% yield) as an off-white solid.

$^1$H NMR (250 MHz, DMSO-d6) δ [ppm] 7.60 (s, 1H), 7.24 (s, 1H), 6.65-6.55 (m, 2H), 5.23 (s, 2H), 4.81 (m, 1H), 3.96 (q, J=7.1 Hz, 2H), 2.48-2.31 (m, 4H), 2.04 (s, 3H), 1.87-1.69 (m, 2H), 0.95 (t, J=7.1 Hz, 3H).

LCMS (Analytical Method A): Rt=1.16 mins; MS (ESI) m/z=300.05 (M+H)$^+$.

In analogy to Intermediate 143A, the following intermediates were prepared from reduction of the nitro group to give the corresponding aniline:

| Int. | Structure | Name | Analytical Data |
|---|---|---|---|
| 144A | 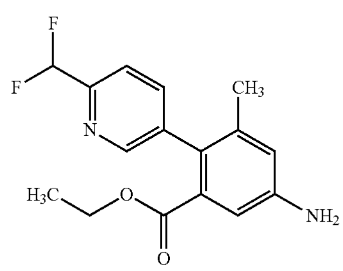 [SMILES: CCOC(=O)c1cc(N)cc(C)c1-c1ccc(C(F)F)nc1] | Ethyl 5-amino-2-[6-(difluoromethyl)pyridin-3-yl]-3-methylbenzoate | $^1$H NMR (250 MHz, DMSO-d6) δ [ppm] 8.37 (s, 1H), 7.76-7.65 (m, 2H), 7.25-6.75 (m, 2H), 6.71 (d, J = 2.3 Hz, 1H), 5.48 (s, 2H), 3.91 (q, J = 7.1 Hz, 2H), 1.92 (s, 3H), 0.86 (t, J = 7.1 Hz, 3H). LCMS (Analytical Method A): Rt = 1.20 mins; MS (ESI) m/z = 306.95 (M + H)$^+$. |

| Int. | Structure | Name | Analytical Data |
|---|---|---|---|
| 145A | 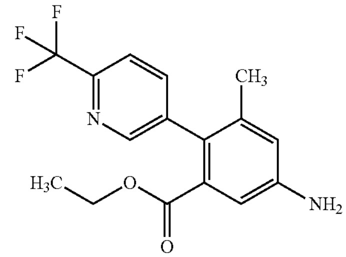 [SMILES: CCOC(=O)c1cc(N)cc(C)c1-c1ccc(C(F)(F)F)nc1] | Ethyl 5-amino-3-methyl-2-[6-(trifluoromethyl)pyridin-3-yl]benzoate | $^1$H NMR (250 MHz, DMSO-d6) δ [ppm] 8.48 (s, 1H), 7.89 (d, J = 7.4 Hz, 1H), 7.85-7.77 (m, 1H), 6.99 (d, J = 2.3 Hz, 1H), 6.72 (d, J = 1.9 Hz, 1H), 5.52 (s, 2H), 3.92 (q, J = 7.1 Hz, 2H), 1.93 (s, 3H), 0.86 (t, J = 7.1 Hz, 3H). LCMS (Analytical Method A) Rt = 1.16 min, MS (ESIPos) m/z = 324.65 (M + H)$^+$. |
| 146A | 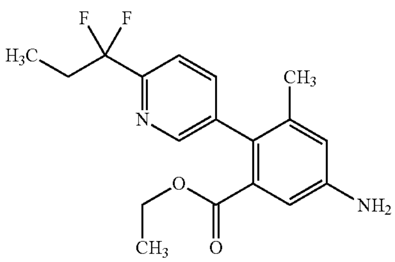 [SMILES: CCOC(=O)c1cc(N)cc(C)c1-c1ccc(C(F)(F)CC)nc1] | Ethyl 5-amino-2-[6-(1,1-difluoropropyl)pyridin-3-yl]-3-methylbenzoate | $^1$H NMR (250 MHz, DMSO-d6) δ [ppm] 8.36 (s, 1H), 7.75-7.60 (m, 2H), 6.94 (d, J = 2.3 Hz, 1H), 6.71 (d, J = 2.0 Hz, 1H), 5.47 (s, 2H), 3.89 (q, J = 7.1 Hz, 2H), 2.46-2.25 (m, 2H), 1.92 (s, 3H), 0.96 (t, J = 7.5 Hz, 3H), 0.84 (t, J = 7.1 Hz, 3H). LCMS (Analytical Method A): Rt = 1.19 mins; MS (ESIPos) m/z = 335.10 (M + H)$^+$. |

Intermediate 147A: 1-[2-Fluoro-4-(trifluoromethyl)phenyl]cyclopropanecarbonitrile

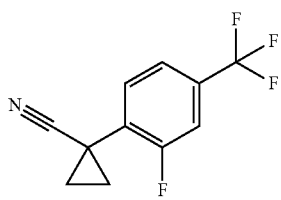 [SMILES: N#CC1(c2ccc(C(F)(F)F)cc2F)CC1]

Potassium hydroxide (22.1 g, 0.39 mol) was dissolved in water (32 mL) and added slowly to a mixture of tetra-n-butylammonium bromide (317 mg, 0.98 mmol), [2-fluoro-4-(trifluoromethyl)phenyl]acetonitrile (10.0 g, 49.2 mmol) and 1-bromo-2-chloroethane (21.2 g, 148 mmol) over 30 mins. An exotherm was observed on addition and the internal temperature was maintained below 80° C. using an ice bath. A dark red solution and white precipitate formed on complete addition and the mixture was allowed to cool to room temperature. The reaction was stirred for 2 hours then the mixture was diluted with water (100 mL) and EtOAc (300 mL) and the organic layer was decanted off then washed with brine (2×75 mL), then dried (Na$_2$SO$_4$), filtered and concentrated at reduced pressure. The residue was purified by Biotage Isolera™ chromatography (using a gradient of eluents; 98:2 to 85:15 heptane/EtOAc) giving the title compound (11.1 g, quantitative yield) as a yellow oil.

$^1$H NMR (500 MHz, DMSO-d6) δ [ppm] 7.85-7.76 (m, 1H), 7.76-7.66 (m, 1H), 7.66-7.55 (m, 1H), 1.80-1.71 (m, 2H), 1.58-1.51 (m, 2H).

LCMS (Analytical method A): Rt=0.62 mins, MS (ESI-Pos) m/z=210 (M+H)$^+$.

In analogy to Intermediate 147A, the following intermediate was prepared using 1-bromo-2-chloroethane and the corresponding substituted phenylacetonitrile starting material:

| Int. | Structure | Name | Analytical Data |
|---|---|---|---|
| 148A | 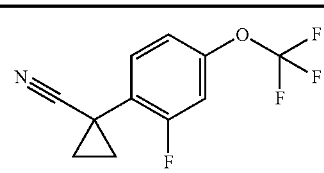 | 1-[2-Fluoro-4-(trifluoromethoxy)phenyl]cyclopropanecarbonitrile | $^1$H NMR (250 MHz, DMSO-d6) δ [ppm] 7.70-7.56 (m, 1H), 7.51 (dd, J = 10.6, 1.7 Hz, 1H), 7.33-7.21 (m, 1H), 1.79-1.66 (m, 2H), 1.55-1.40 (m, 2H). |

Intermediate 149A: 1-[2-Fluoro-4-(trifluoromethyl) phenyl]cyclopropanecarboxylic acid

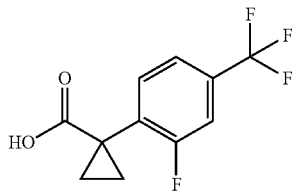 [SMILES: O=C(O)C1(c2ccc(C(F)(F)F)cc2F)CC1]

1-[2-Fluoro-4-(trifluoromethyl)phenyl]cyclopropanecarbonitrile (Int 147A, 11.1 g, 48 mmol) was dissolved in concentrated HCl (50 mL) and heated at 90° C. overnight. The mixture was diluted with water (150 mL) and extracted with EtOAc (150 mL). The organics were then separated and washed with brine (2×50 mL), dried (Na$_2$SO$_4$), filtered and concentrated at reduced pressure. The residue was crystallised in heptane giving the title product (8.4 g, 70% yield) as a white solid.

$^1$H NMR (250 MHz, DMSO-d6) δ [ppm] 12.61 (s, 1H), 7.72-7.40 (m, 3H), 1.64-1.46 (m, 2H), 1.31-1.15 (m, 2H).

LCMS (Analytical method A); Rt=1.13 mins, MS (ESI-Pos) m/z=289 (M+MeCN)$^+$.

Alternatively, Intermediate 149A was obtained via one of the following methods:

a) 1-[2-Fluoro-4-(trifluoromethyl)phenyl]cyclopropanecarbonitrile (Int 147A, 28.6 g, 125 mmol) was suspended in water (450 mL) and 29.9 g (1.25 mol) lithium hydroxide was added. The mixture was stirred vigorously at 120° C. overnight. After cooling, the mixture was acidified with 6M hydrochloric acid and extracted with ethyl acetate. The organic layers were washed with brine, dried (Na$_2$SO$_4$) and concentrated to give the pure title product (30.1 g, 97% yield).

b) 1-[2-Fluoro-4-(trifluoromethyl)phenyl]cyclopropanecarbonitrile (Int 147A, 1.17 g, 5.0 mmol) was dissolved in ethanol (22 mL) and lithium hydroxide hydrate (3.15 g, 75.0 mmol) and hydogenperoxide solution (21.9 ml, 35% in water) were added. The mixture was stirred at 100° C. for 6 h. Under cooling, the mixture was acidified with 6M hydrochloric acid and extracted with ethyl acetate. The organic layers were washed with aq. Sodium hydrogensulfate, dried (Na$_2$SO$_4$) and concentrated to give the title product.

In analogy to Intermediate 149A, the following intermediate was prepared using the corresponding substituted phenylcyclopropane-1-carbonitrile starting materials:

| Int. | Structure | Name | Analytical Data |
|---|---|---|---|
| 150A | ![structure] | 1-[2-Fluoro-4-(trifluoromethoxy) phenyl]cyclopropanecarboxylic acid | $^1$H NMR (250 MHz, DMSO-d6) δ [ppm] 12.51 (s, 1H), 7.54-7.41 (m, 1H), 7.33 (dd, J = 10.4, 1.7 Hz, 1H), 7.20-7.12 (m, 1H), 1.56-1.44 (m, 2H), 1.25-1.13 (m, 2H). |

Intermediate 151A: 1-[2-Fluoro-4-(trifluoromethyl) phenyl]cyclopropanecarbonyl chloride

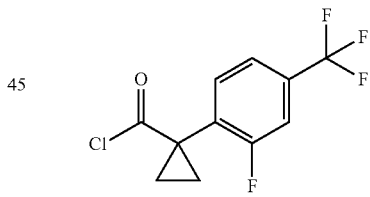

1-[2-Fluoro-4-(trifluoromethyl)phenyl]cyclopropanecarboxylic acid (Int 149A, 8.4 g, 33.8 mmol) was stirred in thionyl chloride (20 mL) and DMF (4 drops) was added. The mixture was stirred at room temperature for 1 hour then heated to 90° C. for 1 hour. The mixture was then concentrated at reduced pressure. The residue was diluted with heptane (5 mL) and concentrated twice to remove excess thionyl chloride giving the desired product (8.40 g, 93% yield) as an orange oil.

This was used in the next step without further purification.

$^1$H NMR (250 MHz, Chloroform-d) δ [ppm] 7.51-7.30 (m, 3H), 2.11-1.99 (m, 2H), 1.53-1.43 (m, 2H).

In analogy to Intermediate 151A, the following intermediates were prepared using thionyl chloride and the corresponding carboxylic acid as starting materials:

| Int. | Structure | Name | Analytical Data |
|---|---|---|---|
| 152A | 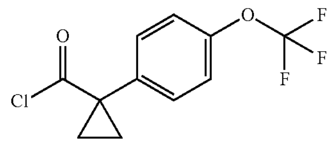 [SMILES: O=C(Cl)C1(c2ccc(OC(F)(F)F)cc2)CC1] | 1-[4-(Trifluoromethoxy)phenyl]cyclopropanecarbonyl chloride | ¹H NMR (250 MHz, Chloroform-d) δ [ppm] 7.46-7.37 (m, 2H), 7.25-7.18 (m, 2H), 2.06-1.95 (m, 2H), 1.55-1.46 (m, 2H). |
| 153A | 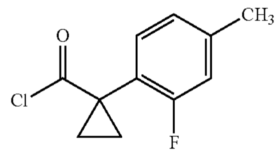 | 1-(2-Fluoro-4-methylphenyl)cyclopropanecarbonyl chloride | ¹H NMR (250 MHz, Chloroform-d) δ [ppm] 1.31-1.43 (m, 2H), 1.89 (m, 2H), 2.27 (s, 3H), 6.83 (m, 2H), 6.97-7.22 (m, 1H). |
| 154A | 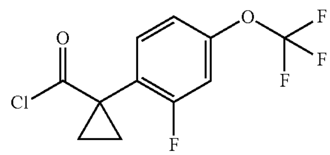 [SMILES: O=C(Cl)C1(c2ccc(OC(F)(F)F)cc2F)CC1] | 1-[2-Fluoro-4-(trifluoromethoxy)phenyl]cyclopropanecarbonyl chloride | ¹H NMR (250 MHz, Chloroform-d) δ [ppm] 7.41-7.19 (m, 1H), 7.07-6.89 (m, 2H), 2.09-1.96 (m, 2H), 1.54-1.39 (m, 2H). |

Intermediate 155A: Methyl 5-({[1-(3-chlorophenyl)cyclopropyl]carbonyl}amino)-2-(1-cyclobutyl-1H-pyrazol-4-yl)benzoate Intermediate 156A: Methyl 2-(1-cyclobutyl-1H-pyrazol-4-yl)-5-[({1-[2-fluoro-4-(trifluoromethyl)phenyl]cyclopropyl}carbonyl)amino]benzoate

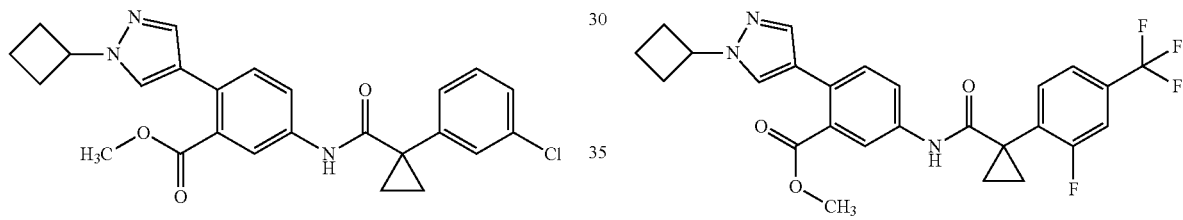

Methyl 5-amino-2-(1-cyclobutyl-1H-pyrazol-4-yl)benzoate (Intermediate 29A, 300 mg, 1.11 mmol) and 1-(3-chlorophenyl)cyclopropane-1-carboxylic acid (260 mg, 1.33 mmol) were dissolved in DMF (9 mL) and N,N-diisopropylethylamine (0.39 mL, 2.21 mmol) and HATU (505 mg, 1.33 mmol) were added giving a light brown solution. This was stirred at 80° C. for 3 h. The mixture was partitioned between EtOAc and water. The aqueous layer was extracted with EtOAc (3×15 mL). The combined organic layers were washed with 2M aq. HCl (10 mL) and brine (10 mL), dried (Na₂SO₄), filtered and concentrated. The residue was purified by Biotage Isolera™ chromatography to give title compound (372 mg, 75% yield) as a white solid.

¹H NMR (400 MHz, DMSO-d6) δ [ppm] 1.15-1.18 (m, 2H), 1.46-1.49 (m, 2H), 1.75-1.81 (m, 2H), 2.34-2.42 (m, 2H), 2.43-248 (m, 2H), 3.74 (s, 3H), 4.83 (quint, 1H), 7.34-7.43 (m, 5H), 7.49 (d, 1H), 7.72 (dd, 1H), 7.85 (d, 1H), 7.92 (d, 1H), 9.39 (s, 1H).

LCMS (method 1): Rt=1.37 min; MS (ESIPos) m/z=450 (M+H)⁺.

Methyl 5-amino-2-(1-cyclobutyl-1H-pyrazol-4-yl)benzoate (Intermediate 29A, 300 mg, 1.11 mmol) and 1-[2-fluoro-4-(trifluoromethyl)phenyl]cyclopropanecarboxylic acid (Int 149A, 330 mg, 1.33 mmol) were dissolved in DMF (8.5 mL) and N,N-diisopropylethylamine (0.39 mL, 2.21 mmol) and HATU (505 mg, 1.33 mmol) was added giving a light brown solution. The mixture was stirred at 80° C. for 3 h. The cooled reaction mixture was partitioned between EtOAc (15 mL) and water (10 mL) and the separated aqueous layer re-extracted with EtOAc (3×15 mL). The combined organic layers were washed with 2M aq. HCl (10 mL), brine (10 mL), dried (Na₂SO₄), filtered and concentrated at reduced pressure. The residue was purified by Biotage Isolera™ chromatography to give the title compound (365 mg, 66% yield) as a solid.

¹H NMR (400 MHz, DMSO-d6) δ [ppm] 1.21-1.24 (m, 2H), 1.61-1.64 (m, 2H), 1.73-1.81 (m, 2H), 2.32-2.50 (m, 4H), 3.73 (s, 3H), 4.83 (quint, 1H), 7.40 (d, 1H), 7.49 (d, 1H), 7.60 (dd, 1H), 7.66-7.72 (m, 3H), 7.77 (d, 1H), 7.93 (d, 1H), 9.14 (s, 1H).

LCMS (method 1): Rt=1.39 min; MS (ESIPos) m/z=502 (M+H)⁺.

Alternatively, Intermediate 156A was obtained in analogy to Intermediate 193A by reaction of intermediate 29A with the carboxylic acid chloride 151A.

In analogy to Intermediate 156A, the following intermediates were prepared via HATU coupling using the corresponding amine and carboxylic acid as starting materials:

| Int. | Name | Analytical Data |
|---|---|---|
| 157A | Methyl 2-[6-(difluoromethyl)pyridin-3-yl]-5-[({1-[2-fluoro-4-(trifluoromethyl)phenyl]cyclopropyl}carbonyl)amino]benzoate | $^1$H NMR (400 MHz, DMSO-d6) δ [ppm] 1.25-1.28 (m, 2H), 1.65-1.67 (m, 2H), 3.64 (s, 3H), 7.01 (t, J = 55 Hz, 1H), 7.41 (d, 1H), 7.62 (dd, 1H), 7.68-7.73 (m, 3H), 7.87-7.92 (m, 2H), 8.12 (d, 1H), 8.56 (d, 1H), 9.34 (s, 1H). LCMS (method 1): Rt = 1.39 min; MS (ESIPos) m/z = 509 (M + H)$^+$. |
| 158A | Methyl 2-[6-(difluoromethyl)pyridin-3-yl]-5-[({1-[2-fluoro-4-(trifluoromethoxy)phenyl]cyclopropyl}carbonyl)amino]benzoate | $^1$H NMR (400 MHz, DMSO-d6) δ [ppm] 1.21-1.24 (m, 2H), 1.62-1.64 (m, 2H), 3.64 (s, 3H), 7.01 (t, J = 55 Hz, 1H), 7.26 (d, br, 1H), 7.39-7.42 (m, 2H), 7.61 (t, 1H), 7.71 (d, 1H), 7.87-7.92 (m, 2H), 8.13 (d, 1H), 8.56 (d, 1H), 9.31 (s, 1H). LCMS (method 1): Rt = 1.41 min; MS (ESIPos) m/z = 525 (M + H)$^+$. |
| 159A | Methyl 5-[({1-[2-fluoro-4-(trifluoromethyl)phenyl]cyclopropyl}carbonyl)amino]-2-[6-(trifluoromethyl)pyridin-3-yl]benzoate | $^1$H NMR (400 MHz, DMSO-d6) δ [ppm] 1.25-1.28 (m, 2H), 1.65-1.68 (m, 2H), 3.65 (s, 3H), 7.43 (d, 1H), 7.62 (dd, 1H), 7.69-7.74 (m, 2H), 7.91-7.99 (m, 3H), 8.16 (d, 1H), 8.66 (d, 1H), 9.36 (s, 1H). LCMS (method 1): Rt = 1.47 min; MS (ESIPos) m/z = 527 (M + H)$^+$. |
| 160A | Methyl 5-[({1-[2-fluoro-4-(trifluoromethoxy)phenyl]cyclopropyl}carbonyl)amino]-2-[6-(trifluoromethyl)pyridin-3-yl]benzoate | $^1$H NMR (400 MHz, DMSO-d6) δ [ppm] 1.21-1.24 (m, 2H), 1.62-1.65 (m, 2H), 3.65 (s, 3H), 7.24-7.27 (m, 1H), 7.40 (dd, br, 1H), 7.43 (d, 1H), 7.61 (t, 1H), 7.91-7.95 (m, 2H), 7.98 (dd, 1H), 8.17 (d, 1H), 8.66 (d, 1H), 9.33 (s, 1H). LCMS (method 1): Rt = 1.48 min; MS (ESIPos) m/z = 543 (M + H)$^+$. |
| 161A | Methyl 5-({[1-(2,4-difluorophenyl)cyclopropyl]carbonyl}amino)-2-[6-(1,1-difluoropropyl)pyridin-3-yl]benzoate | $^1$H NMR (250 MHz, Methanol-d4) δ [ppm] 8.50 (s, 1H), 8.09 (d, J = 2.2 Hz, 1H), 7.86 (dd, J = 8.1, 2.2 Hz, 1H), 7.79 (dd, J = 8.4, 2.3 Hz, 1H), 7.72 (d, J = 8.1 Hz, 1H), 7.61-7.50 (m, 1H), 7.37 (d, J = 8.4 Hz, 1H), 7.10-7.00 (m, 2H), 3.69 (s, 3H), 2.45-2.27 (m, 2H), 1.76-1.68 (m, 2H), 1.26-1.20 (m, 2H), 1.02 (t, J = 7.5 Hz, 3H). LCMS (Analytical Method A): Rt = 1.37 mins; MS (ESIPos) m/z = 487.05 (M + H)$^+$. |

-continued

| Int. | Structure | Name | Analytical Data |
|---|---|---|---|
| 162A | 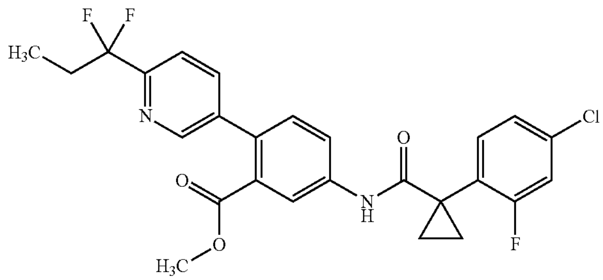 [SMILES: CCC(F)(F)c1ccc(-c2ccc(NC(=O)C3(c4ccc(Cl)cc4F)CC3)cc2C(=O)OC)cn1] | Methyl 5-({[1-(4-chloro-2-fluorophenyl)cyclopropyl]carbonyl}amino)-2-[6-(1,1-difluoropropyl)pyridin-3-yl]benzoate | $^1$H NMR (250 MHz, Methanol-d4) δ [ppm] 8.50 (d, J = 1.5 Hz, 1H), 8.09 (d, J = 2.2 Hz, 1H), 7.86 (dd, J = 8.1, 2.2 Hz, 1H), 7.79 (dd, J = 8.4, 2.3 Hz, 1H), 7.72 (dd, J = 8.1, 0.7 Hz, 1H), 7.51 (m, 1H), 7.37 (d, J = 8.4 Hz, 1H), 7.33-7.26 (m, 2H), 3.69 (s, 3H), 2.46-2.26 (m, 2H), 1.76-1.67 (m, 2H), 1.27-1.20 (m, 2H), 1.02 (t, J = 7.5 Hz, 3H). LCMS (Analytical Method A): Rt = 1.42 mins; MS (ESIPos) m/z = 503.0 (M + H)$^+$. |
| 163A | 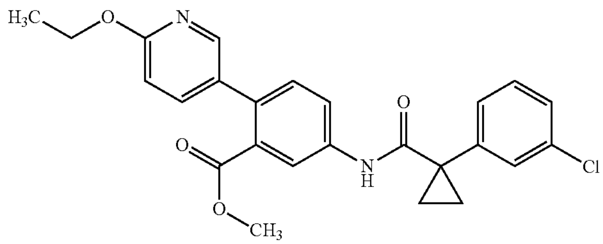 [SMILES: CCOc1ccc(-c2ccc(NC(=O)C3(c4cccc(Cl)c4)CC3)cc2C(=O)OC)cn1] | Methyl 5-({[1-(3-chlorophenyl)cyclopropyl]carbonyl}amino)-2-(6-ethoxypyridin-3-yl)benzoate | $^1$H NMR (400 MHz, DMSO-d6) δ [ppm] 1.17-1.20 (m, 2H), 1.33 (t, 3H), 1.47-1.50 (m, 2H), 3.63 (s, 3H), 4.32 (q, 2H), 6.80 (d, 1H), 7.33-7.40 (m, 4H), 7.43-7.44 (m, 1H), 7.57 (dd, 1H), 7.85 (dd, 1H), 8.02 (d, 1H), 8.06 (d, 1H), 9.53 (s, 1H). LCMS (method 4): Rt = 1.42 min; MS (ESIPos) m/z = 451 (M + H)$^+$. |
| 164A | 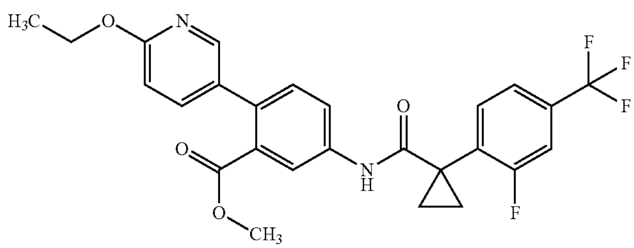 [SMILES: CCOc1ccc(-c2ccc(NC(=O)C3(c4ccc(C(F)(F)F)cc4F)CC3)cc2C(=O)OC)cn1] | Methyl 2-(6-ethoxypyridin-3-yl)-5-[({1-[2-fluoro-4-(trifluoromethyl)phenyl]cyclopropyl}carbonyl)amino]benzoate | $^1$H NMR (400 MHz, DMSO-d6) δ [ppm] 1.23-1.26 (m, 2H), 1.33 (t, 3H), 1.63-1.66 (m, 2H), 3.63 (s, 3H), 4.32 (q, 2H), 6.80 (dd, 1H), 7.34 (d, 1H), 7.57 (dd, 1H), 7.60-7.62 (m, 1H), 7.67-7.73 (m, 2H), 7.83 (dd, 1H), 7.99 (d, 1H), 8.01 (dd, 1H), 9.26 (s, 1H). LCMS (method 4): Rt = 1.44 min; MS (ESIPos) m/z = 503 (M + H)$^+$. |
| 165A | 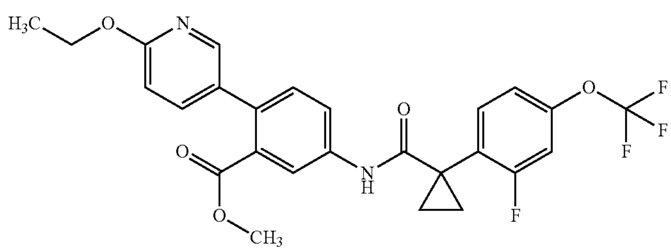 [SMILES: CCOc1ccc(-c2ccc(NC(=O)C3(c4ccc(OC(F)(F)F)cc4F)CC3)cc2C(=O)OC)cn1] | Methyl 2-(6-ethoxypyridin-3-yl)-5-[({1-[2-fluoro-4-(trifluoromethoxy)phenyl]cyclopropyl}carbonyl)amino]benzoate | $^1$H NMR (400 MHz, DMSO-d6) δ [ppm] 1.19-1.22 (m, 2H), 1.33 (t, 3H), 1.60-1.63 (m, 2H), 3.63 (s, 3H), 4.32 (q, 2H), 6.80 (dd, 1H), 7.23-7.27 (m, 1H), 7.33 (d, 1H), 7.40 (dd, br, 1H), 7.57 (dd, 1H), 7.60 (t, 1H), 7.83 (dd, 1H), 8.00 (d, 1H), 8.02 (dd, 1H), 9.22 (s, 1H). LCMS (method 1): Rt = 1.49 min; MS (ESIPos) m/z = 519 (M + H)$^+$. |
| 166A | 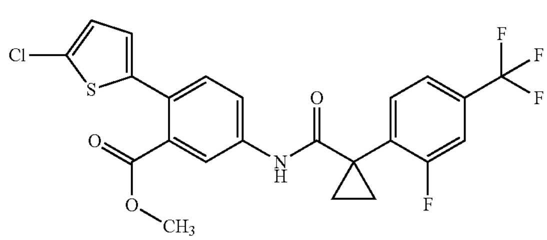 [SMILES: COC(=O)c1cc(NC(=O)C2(c3ccc(C(F)(F)F)cc3F)CC2)ccc1-c1ccc(Cl)s1] | Methyl 2-(5-chloro-2-thienyl)-5-[({1-[2-fluoro-4-(trifluoromethyl)phenyl]cyclopropyl}carbonyl)amino]benzoate | LCMS (method 3): Rt = 1.59 min; MS (ESIPos) m/z = 498 (M + H)$^+$ |
| 167A | 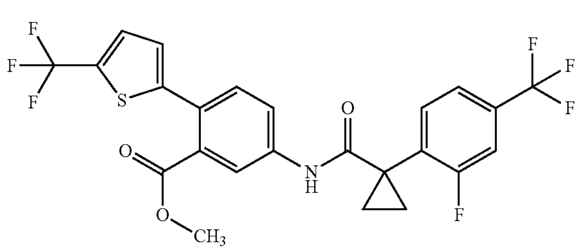 | Methyl 5-[({1-[2-fluoro-4-(trifluoromethyl)phenyl]cyclopropyl}carbonyl)amino]-2-[5-(trifluoromethyl)-2-thienyl]benzoate | LCMS (method 3): Rt = 1.40 min; MS (ESIPos) m/z = 495 (M + H)$^+$ |

| Int. | Structure | Name | Analytical Data |
|---|---|---|---|
| 168A | 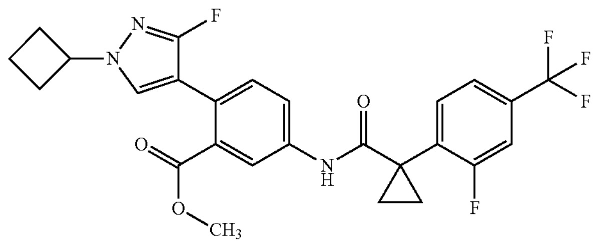 [SMILES: COC(=O)c1cc(NC(=O)C2(c3ccc(C(F)(F)F)cc3F)CC2)ccc1-c1cn(C2CCC2)nc1F] | Methyl 2-(1-cyclobutyl-3-fluoro-1H-pyrazol-4-yl)-5-[({1-[2-fluoro-4-(trifluoromethyl)phenyl]cyclopropyl}carbonyl)amino]benzoate | $^1$H NMR (500 MHz, DMSO-d6) δ [ppm] 1.22-1.24 (m, 2H), 1.63-1.65 (m, 2H), 1.74-1.79 (m, 2H), 2.32-2.40 (m, 2H), 2.41-2.47 (m, 2H), 3.72 (s, 3H), 4.71 (quint, 1H), 7.34 (d, 1H), 7.59-7.61 (m, 1H), 7.66-7.71 (m, 2H), 7.79 (dd, 1H), 7.93-7.94 (m, 2H), 9.20 (s, 1H). LCMS (method 1): Rt = 1.46 min; MS (ESIPos) m/z = 520 (M + H)$^+$. |
| 169A | 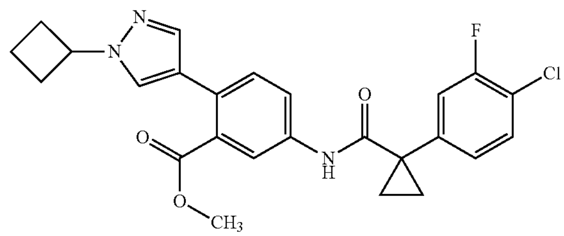 [SMILES: COC(=O)c1cc(NC(=O)C2(c3ccc(Cl)c(F)c3)CC2)ccc1-c1cnn(C2CCC2)c1] | Methyl 5-({[1-(4-chloro-3-fluorophenyl)cyclopropyl]carbonyl}amino)-2-(1-cyclobutyl-1H-pyrazol-4-yl)benzoate | $^1$H NMR (400 MHz, DMSO-d6) δ [ppm] 1.16-1.19 (m, 2H), 1.48-1.50 (m, 2H), 1.73-1.81 (m, 2H), 2.32-2.49 (m, 4H), 3.74 (s, 3H), 4.83 (quint, 1H), 7.27 (dd, 1H), 7.41 (d, 1H), 7.45 (dd, 1H), 7.49 (s, 1H), 7.56 (t, 1H), 7.72 (dd, 1H), 7.82 (d, 1H), 7.92 (s, 1H), 9.25 (s, 1H). LCMS (method 1): Rt = 1.37 min; MS (ESIPos) m/z = 468 (M + H)$^+$. |
| 170A | 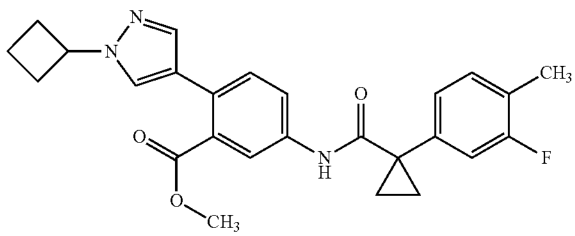 [SMILES: COC(=O)c1cc(NC(=O)C2(c3ccc(C)c(F)c3)CC2)ccc1-c1cnn(C2CCC2)c1] | Methyl 2-(1-cyclobutyl-1H-pyrazol-4-yl)-5-({[1-(3-fluoro-4-methylphenyl)cyclopropyl]carbonyl}amino)benzoate | $^1$H NMR (400 MHz, DMSO-d6) δ [ppm] 1.10-1.13 (m, 2H), 1.43-1.46 (m, 2H), 1.72-1.82 (m, 2H), 2.22 (s, 3H), 2.33-2.50 (m, 4H), 3.74 (s, 3H), 4.83 (quint, 1H), 7.12-7.17 (m, 2H), 7.26 (t, 1H), 7.40 (d, 1H), 7.49 (s, 1H), 7.72 (dd, 1H), 7.85 (d, 1H), 7.92 (s, 1H), 9.25 (s, 1H). LCMS (method 1): Rt = 1.36 min; MS (ESIPos) m/z = 448 (M + H)$^+$. |
| 171A | 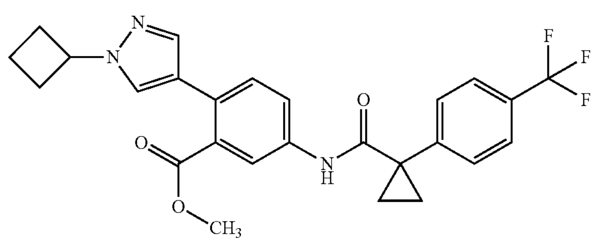 [SMILES: COC(=O)c1cc(NC(=O)C2(c3ccc(C(F)(F)F)cc3)CC2)ccc1-c1cnn(C2CCC2)c1] | Methyl 2-(1-cyclobutyl-1H-pyrazol-4-yl)-5-[({1-[4-(trifluoromethyl)phenyl]cyclopropyl}carbonyl)amino]benzoate | $^1$H NMR (400 MHz, DMSO-d6) δ [ppm] 1.19-1.22 (m, 2H), 1.52-1.55 (m, 2H), 1.73-1.82 (m, 2H), 2.32-2.49 (m, 4H), 3.74 (s, 3H), 4.83 (quint, 1H), 7.41 (d, 1H), 7.49 (s, 1H), 7.59 (d, 2H), 7.90-7.74 (m, 3H), 7.85 (d, 1H), 7.92 (s, 1H), 9.48 (s, 1H). LCMS (method 1): Rt = 1.38 min; MS (ESIPos) m/z = 484 (M + H)$^+$. |
| 172A | 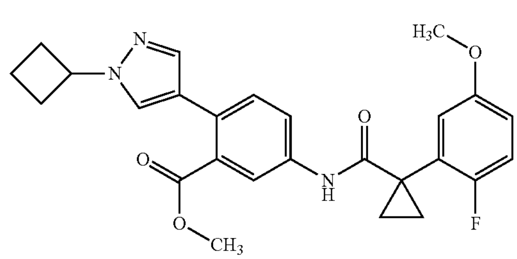 [SMILES: COC(=O)c1cc(NC(=O)C2(c3cc(OC)ccc3F)CC2)ccc1-c1cnn(C2CCC2)c1] | Methyl 2-(1-cyclobutyl-1H-pyrazol-4-yl)-5-({[1-(2-fluoro-5-methoxyphenyl)cyclopropyl]carbonyl}amino)benzoate | $^1$H NMR (400 MHz, DMSO-d6) δ [ppm] 1.14-1.16 (m, 2H), 1.52-1.55 (m, 2H), 1.73-1.81 (m, 2H), 2.35-2.49 (m, 4H), 3.73 (s, 3H), 3.77 (s, 3H), 4.83 (quint, 1H), 6.89-6.93 (m, 1H), 6.98 (dd, 1H), 7.12 (t, 1H), 7.39 (d, 1H), 7.49 (s, 1H), 7.71 (dd, 1H), 7.80 (d, 1H), 7.92 (s, 1H), 9.01 (s, 1H). LCMS (method 1): Rt = 1.27 min; MS (ESIPos) m/z = 464 (M + H)$^+$. |

| Int. | Structure | Name | Analytical Data |
|---|---|---|---|
| 173A | 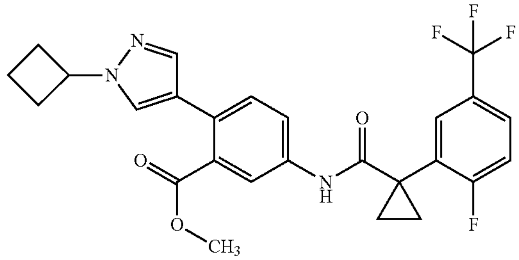 [SMILES: COC(=O)c1cc(NC(=O)C2(c3cc(C(F)(F)F)ccc3F)CC2)ccc1-c1cnn(C2CCC2)c1] | Methyl 2-(1-cyclobutyl-1H-pyrazol-4-yl)-5-[({1-[2-fluoro-5-(trifluoromethyl)phenyl]cyclopropyl}carbonyl)amino]benzoate | $^1$H NMR (400 MHz, DMSO-d6) δ [ppm] 1.24-1.26 (m, 2H), 1.60-1.63 (m, 2H), 1.73-1.81 (m, 2H), 2.32-2.47 (m, 4H), 3.73 (s, 3H), 4.83 (quint, 1H), 7.40 (d, 1H), 7.45 (t, 1H), 7.49 (s, 1H), 7.69 (dd, 1H), 7.77-7.82 (m, 3H), 7.92 (s, 1H), 9.16 (s, 1H). LCMS (method 1): Rt = 1.37 min; MS (ESIPos) m/z = 502 (M + H)$^+$. |
| 174A | 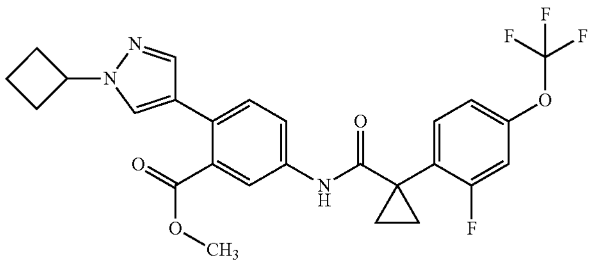 [SMILES: COC(=O)c1cc(NC(=O)C2(c3ccc(OC(F)(F)F)cc3F)CC2)ccc1-c1cnn(C2CCC2)c1] | Methyl 2-(1-cyclobutyl-1H-pyrazol-4-yl)-5-[({1-[2-fluoro-4-(trifluoromethoxy)phenyl]cyclopropyl}carbonyl)amino]benzoate | $^1$H NMR (400 MHz, DMSO-d6) δ [ppm] 1.17-1.20 (m, 2H), 1.58-1.61 (m, 2H), 1.73-1.81 (m, 2H), 2.33-2.48 (m, 4H), 3.73 (s, 3H), 4.83 (quint, 1H), 7.23-7.26 (m, 1H), 7.37-7.41 (m, 1H), 7.40 (d, 1H), 7.49 (s, 1H), 7.59 (t, 1H), 7.70 (dd, 1H), 7.78 (d, 1H), 7.93 (s, 1H), 9.11 (s, 1H). LCMS (method 1): Rt = 1.40 min; MS (ESIPos) m/z = 518 (M + H)$^+$. |
| 175A | 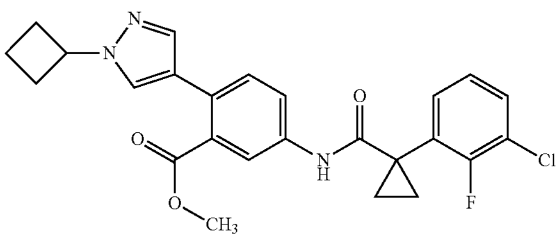 | Methyl 5-({[1-(3-chloro-2-fluorophenyl)cyclopropyl]carbonyl}amino)-2-(1-cyclobutyl-1H-pyrazol-4-yl)benzoate | $^1$H NMR (400 MHz, DMSO-d6) δ [ppm] 1.17-1.20 (m, 2H), 1.59-1.62 (m, 2H), 1.73-1.81 (m, 2H), 2.33-2.49 (m, 4H), 3.74 (s, 3H), 4.83 (quint, 1H), 7.23 (t, 1H), 7.40 (d, 1H), 7.44 (dt, 1H), 7.49 (s, 1H), 7.56 (dt, 1H), 7.70 (dd, 1H), 7.78 (d, 1H), 7.93 (s, 1H), 9.10 (s, 1H). LCMS (method 1): Rt = 1.32 min; MS (ESIPos) m/z = 468 (M + H)$^+$. |
| 176A | 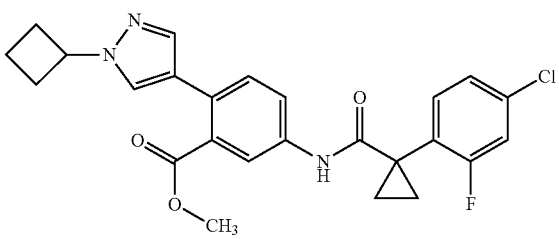 [SMILES: COC(=O)c1cc(NC(=O)C2(c3ccc(Cl)cc3F)CC2)ccc1-c1cnn(C2CCC2)c1] | Methyl 5-({[1-(4-chloro-2-fluorophenyl)cyclopropyl]carbonyl}amino)-2-(1-cyclobutyl-1H-pyrazol-4-yl)benzoate | $^1$H NMR (400 MHz, DMSO-d6) δ [ppm] 1.13-1.16 (m, 2H), 1.56-1.59 (m, 2H), 1.72-1.81 (m, 2H), 2.33-2.49 (m, 4H), 3.73 (s, 3H), 4.83 (quint, 1H), 7.30 (dd, 1H), 7.39 (d, 1H), 7.44 (dd, 1H), 7.47-7.51 (m, 1H), 7.49 (s, 1H), 7.71 (dd, 1H), 7.78 (d, 1H), 7.92 (s, 1H), 9.06 (s, 1H). LCMS (method 1): Rt = 1.35 min; MS (ESIPos) m/z = 468 (M + H)$^+$. |
| 177A | 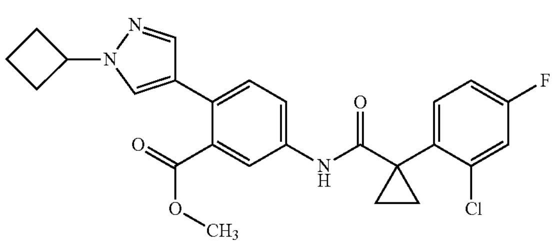 | Methyl 5-({[1-(2-chloro-4-fluorophenyl)cyclopropyl]carbonyl}amino)-2-(1-cyclobutyl-1H-pyrazol-4-yl)benzoate | $^1$H NMR (400 MHz, DMSO-d6) δ [ppm] 1.12-1.15 (m, 2H), 1.61-1.64 (m, 2H), 1.72-1.83 (m, 2H), 2.33-2.48 (m, 4H), 3.73 (s, 3H), 4.83 (quint, 1H), 7.25 (dt, 1H), 7.39 (d, 1H), 7.48 (s, 1H), 7.49 (dd, 1H), 7.58 (dd, 1H), 7.69 (d, 1H), 7.76 (d, 1H), 7.92 (s, 1H), 8.86 (s, 1H). LCMS (method 1): Rt = 1.34 min; MS (ESIPos) m/z = 468 (M + H)$^+$. |

| Int. | Structure | Name | Analytical Data |
|---|---|---|---|
| 178A | 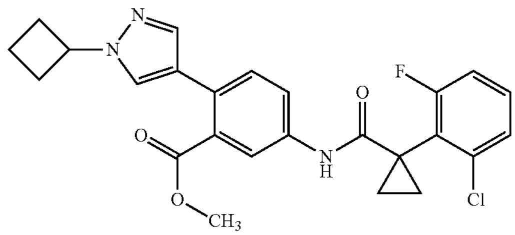 [SMILES: COC(=O)c1cc(NC(=O)C2(c3c(F)cccc3Cl)CC2)ccc1-c1cnn(C2CCC2)c1] | Methyl 5-({[1-(2-chloro-6-fluorophenyl)cyclopropyl]carbonyl}amino)-2-(1-cyclobutyl-1H-pyrazol-4-yl)benzoate | ¹H NMR (400 MHz, DMSO-d6) δ [ppm] 1.15-1.21 (m, 2H), 1.72-1.83 (m, 4H), 2.32-2.47 (m, 4H), 3.73 (s, 3H), 4.83 (quint, 1H), 7.24-7.29 (m, 1H), 7.36-7.47 (m, 3H), 7.49 (s, 1H), 7.71 (dd, 1H), 7.77 (d, 1H), 7.93 (s, 1H), 9.03 (s, 1H). LCMS (method 1): Rt = 1.32 min; MS (ESIPos) m/z = 468 (M + H)⁺. |
| 179A | 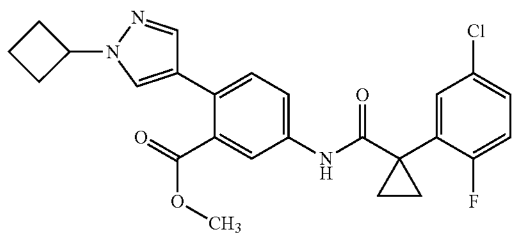 [SMILES: COC(=O)c1cc(NC(=O)C2(c3cc(Cl)ccc3F)CC2)ccc1-c1cnn(C2CCC2)c1] | Methyl 5-({[1-(5-chloro-2-fluorophenyl)cyclopropyl]carbonyl}amino)-2-(1-cyclobutyl-1H-pyrazol-4-yl)benzoate | ¹H NMR (400 MHz, DMSO-d6) δ [ppm] 1.18-1.21 (m, 2H), 1.55-1.57 (m, 2H), 1.73-1.81 (m, 2H), 2.33-2.47 (m, 4H), 3.73 (s, 3H), 4.83 (quint, 1H), 7.26 (dd, 1H), 7.40 (d, 1H), 7.43-7.47 (m, 1H), 7.49 (s, 1H), 7.53 (dd, 1H), 7.71 (dd, 1H), 7.79 (d, 1H), 7.92 (s, 1H), 9.14 (s, 1H). LCMS (method 1): Rt = 1.34 min; MS (ESIPos) m/z = 468 (M + H)⁺. |
| 180A | 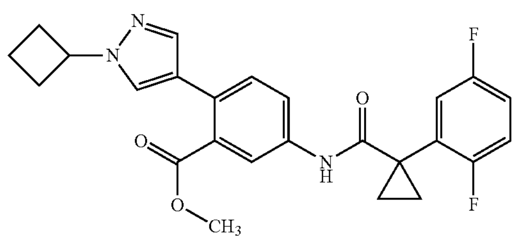 | Methyl 2-(1-cyclobutyl-1H-pyrazol-4-yl)-5-({[1-(2,5-difluorophenyl)cyclopropyl]carbonyl}amino)benzoate | ¹H NMR (400 MHz, DMSO-d6) δ [ppm] 1.17-1.20 (m, 2H), 1.55-1.57 (m, 2H), 1.72-1.81 (m, 2H), 2.33-2.47 (m, 4H), 3.73 (s, 3H), 4.83 (quint, 1H), 7.19-7.28 (m, 2H), 7.31-7.36 (m, 1H), 7.40 (d, 1H), 7.49 (s, 1H), 7.71 (dd, 1H), 7.79 (d, 1H), 7.92 (s, 1H), 9.10 (s, 1H). LCMS (method 1): Rt = 1.26 min; MS (ESIPos) m/z = 452 (M + H)⁺. |
| 181A | 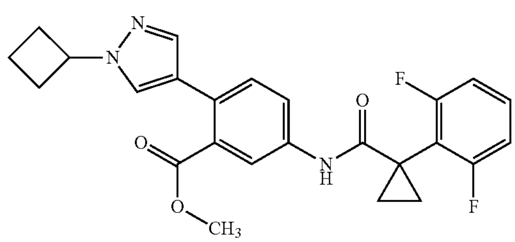 [SMILES: COC(=O)c1cc(NC(=O)C2(c3c(F)cccc3F)CC2)ccc1-c1cnn(C2CCC2)c1] | Methyl 2-(1-cyclobutyl-1H-pyrazol-4-yl)-5-({[1-(2,6-difluorophenyl)cyclopropyl]carbonyl}amino)benzoate | ¹H NMR (400 MHz, DMSO-d6) δ [ppm] 1.16-1.19 (m, 2H), 1.69-1.72 (m, 2H), 1.75-1.81 (m, 2H), 2.33-2.47 (m, 4H), 3.73 (s, 3H), 4.83 (quint, 1H), 7.09-7.15 (m, 2H), 7.40 (d, 1H), 7.43-7.48 (m, 1H), 7.49 (s, 1H), 7.72 (dd, 1H), 7.78 (d, 1H), 7.93 (s, 1H), 9.11 (s, 1H). LCMS (method 1): Rt = 1.27 min; MS (ESIPos) m/z = 452 (M + H)⁺. |
| 182A | 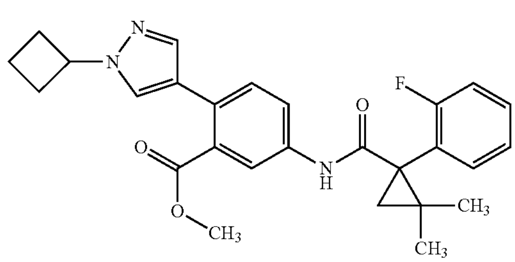 [SMILES: COC(=O)c1cc(NC(=O)C2(c3ccccc3F)CC2(C)C)ccc1-c1cnn(C2CCC2)c1] | Methyl 2-(1-cyclobutyl-1H-pyrazol-4-yl)-5-({[1-(2-fluorophenyl)-2,2-dimethylcyclopropyl]carbonyl}amino)benzoate | ¹H NMR (400 MHz, DMSO-d6) δ [ppm] 0.96 (s, 3H), 1.00 (d, 1H), 1.25 (s, 3H), 1.66 (d, 1H), 1.73-1.81 (m, 2H), 2.32-2.49 (m, 4H), 3.74 (s, 3H), 4.82 (quint, 1H), 7.15-7.22 (m, 2H), 7.31-7.36 (m, 1H), 7.40 (d, 1H), 7.48 (s, 1H), 7.66 (dt, 1H), 7.74 (dd, 1H), 7.89 (d, 1H), 7.91 (s, 1H), 9.51 (s, 1H). LCMS (method 1): Rt = 1.38 min; MS (ESIPos) m/z = 462 (M + H)⁺. |

| Int. | Structure | Name | Analytical Data |
|---|---|---|---|
| 183A | 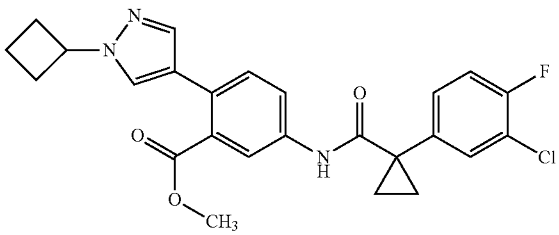 [SMILES: COC(=O)c1cc(NC(=O)C2(c3ccc(F)c(Cl)c3)CC2)ccc1-c1cnn(C2CCC2)c1] | Methyl 5-({[1-(3-chloro-4-fluorophenyl)cyclopropyl]carbonyl}amino)-2-(1-cyclobutyl-1H-pyrazol-4-yl)benzoate | ¹H NMR (400 MHz, DMSO-d6) δ [ppm] 1.14-1.17 (m, 2H), 1.47-1.49 (m, 2H), 1.73-1.81 (m, 2H), 2.33-2.49 (m, 4H), 3.74 (s, 3H), 4.83 (quint, 1H), 7.37-7.45 (m, 3H), 7.49 (d, 1H), 7.62 (dd, 1H), 7.72 (dd, 1H), 7.82 (d, 1H), 7.92 (d, 1H), 9.19 (s, 1H). LCMS (method 1): Rt = 1.36 min; MS (ESIPos) m/z = 468 (M + H)⁺ |
| 184A | 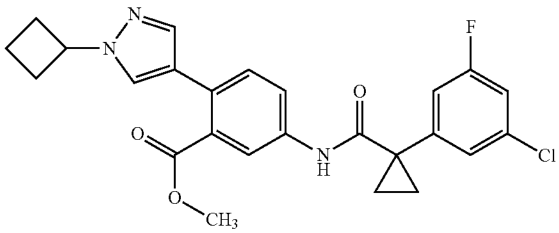 [SMILES: COC(=O)c1cc(NC(=O)C2(c3cc(F)cc(Cl)c3)CC2)ccc1-c1cnn(C2CCC2)c1] | Methyl 5-({[1-(3-chloro-5-fluorophenyl)cyclopropyl]carbonyl}amino)-2-(1-cyclobutyl-1H-pyrazol-4-yl)benzoate | ¹H NMR (400 MHz, DMSO-d6) δ [ppm] 1.20-1.22 (m, 2H), 1.48-1.50 (m, 2H), 1.73-1.81 (m, 2H), 2.34-2.42 (m, 2H), 2.43-2.49 (m, 2H), 3.74 (s, 3H), 4.83 (quint, 1H), 7.26 (ddd, 1H), 7.32 (t, 1H), 7.37 (dt, 1H), 7.41 (d, 1H), 7.49 (s, 1H), 7.73 (dd, 1H), 7.84 (d, 1H), 7.93 (s, 1H), 9.35 (s, 1H). LCMS (method 1): Rt = 1.37 min; MS (ESIPos) m/z = 468 (M + H)⁺. |
| 185A | 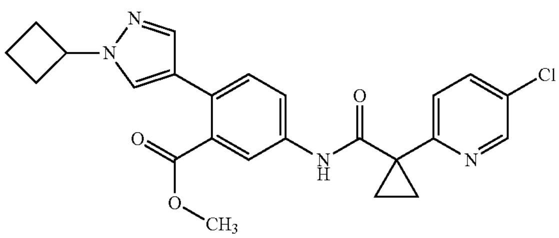 [SMILES: COC(=O)c1cc(NC(=O)C2(c3ccc(Cl)cn3)CC2)ccc1-c1cnn(C2CCC2)c1] | Methyl 5-({[1-(5-chloropyridin-2-yl)cyclopropyl]carbonyl}amino)-2-(1-cyclobutyl-1H-pyrazol-4-yl)benzoate | ¹H NMR (400 MHz, DMSO-d6) δ [ppm] 1.35-1.38 (m, 2H), 1.51-1.53 (m, 2H), 1.73-1.82 (m, 2H), 2.34-2.49 (m, 4H), 3.75 (s, 3H), 4.84 (quint, 1H), 7.40 (dd, 1H), 7.44 (d, 1H), 7.51 (s, 1H), 7.76 (dd, 1H), 7.88 (dd, 1H), 7.93 (s, 1H), 7.94 (d, 1H), 8.58 (s, 1H), 10.11 (s, 1H). LCMS (method 1): Rt = 1.24 min; MS (ESIPos) m/z = 451 (M + H)⁺. |
| 186A | 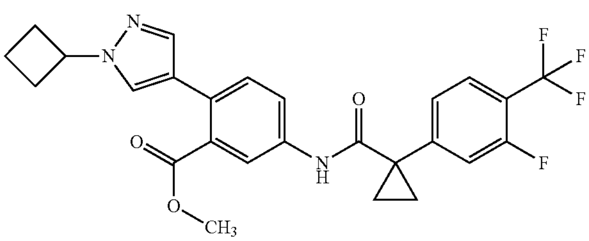 [SMILES: COC(=O)c1cc(NC(=O)C2(c3ccc(C(F)(F)F)c(F)c3)CC2)ccc1-c1cnn(C2CCC2)c1] | Methyl 2-(1-cyclobutyl-1H-pyrazol-4-yl)-5-[({1-[3-fluoro-4-(trifluoromethyl)phenyl]cyclopropyl}carbonyl)amino]benzoate | ¹H NMR (250 MHz, Methanol-d4) δ [ppm] 7.90-7.79 (m, 2H), 7.78-7.61 (m, 2H), 7.56-7.53 (m, 1H), 7.50-7.35 (m, 3H), 3.79 (s, 3H), 2.68-2.43 (m, 4H), 2.02-1.80 (m, 2H), 1.72-1.63 (m, 2H), 1.36-1.26 (m, 2H). LCMS (Analytical Method A) Rt = 1.50 min, MS (ESIPos): m/z = 502.1 (M + H)⁺. |
| 187A | 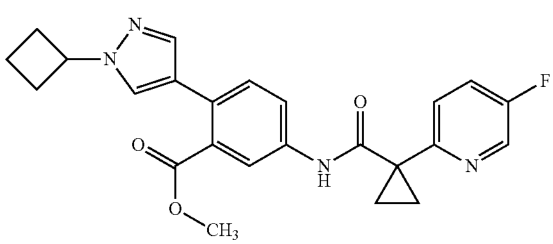 [SMILES: COC(=O)c1cc(NC(=O)C2(c3ccc(F)cn3)CC2)ccc1-c1cnn(C2CCC2)c1] | Methyl 2-(1-cyclobutyl-1H-pyrazol-4-yl)-5-({[1-(5-fluoropyridin-2-yl)cyclopropyl]carbonyl}amino)benzoate | ¹H NMR (250 MHz, Chloroform-d) δ [ppm] 10.57 (s, 1H), 8.52 (d, J = 2.9 Hz, 1H), 7.82 (d, J = 2.3 Hz, 1H), 7.77-7.69 (m, 1H), 7.60-7.51 (m, 2H), 7.51-7.39 (m, 1H), 7.39-7.30 (m, 1H), 7.25-7.16 (m, 1H), 4.93-4.65 (m, 1H), 3.80 (s, 3H), 2.69-2.36 (m, 4H), 2.01-1.69 (m, 4H), 1.35-1.16 (m, 2H). LCMS (Analytical Method A): Rt = 1.24 mins, MS (ESIPos): m/z = 435 (M + H)⁺. |

-continued

| Int. | Structure | Name | Analytical Data |
|---|---|---|---|
| 188A | 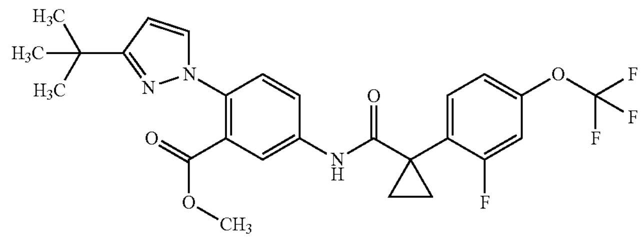 [SMILES: COC(=O)c1cc(NC(=O)C2(c3ccc(OC(F)(F)F)cc3F)CC2)ccc1-n1ccc(C(C)(C)C)n1] | Methyl 2-(3-tert-butyl-1H-pyrazol-1-yl)-5-[({1-[2-fluoro-4-(trifluoromethoxy)phenyl]cyclopropyl}carbonyl)amino]benzoate | $^1$H NMR (400 MHz, DMSO-d6) δ [ppm] 1.19-1.21 (m, 2H), 1.24 (s, 9H), 1.60-1.63 (m, 2H), 3.61 (s, 3H), 6.36 (d, 1H), 7.24-7.26 (m, 1H), 7.38-7.41 (m, 1H), 7.51 (d, 1H), 7.60 (t, 1H), 7.79-7.82 (m, 2H), 8.01 (d, 1H), 9.20 (s, 1H). LCMS (method 2) Rt = 1.51 min; MS (ESIpos) m/z = 519 (M + H)$^+$. |
| 189A | 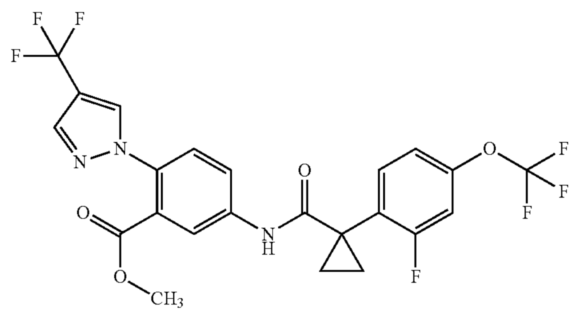 [SMILES: COC(=O)c1cc(NC(=O)C2(c3ccc(OC(F)(F)F)cc3F)CC2)ccc1-n1cc(C(F)(F)F)cn1] | Methyl 5-[({1-[2-fluoro-4-(trifluoromethoxy)phenyl]cyclopropyl}carbonyl)amino]-2-[4-(trifluoromethyl)-1H-pyrazol-1-yl]benzoate | $^1$H NMR (400 MHz, DMSO-d6) δ [ppm] 1.21-1.24 (m, 2H), 1.62-1.65 (m, 2H), 3.62 (s, 3H), 7.25-7.27 (m, 1H), 7.39-7.42 (m, 1H), 7.58-7.63 (m, 2H), 7.93 (dd, 1H), 8.02 (d, 1H), 8.10 (s, 1H), 8.84 (s, 1H), 9.34 (s, 1H). LCMS (method 1) Rt = 1.45 min; MS (ESIpos) m/z = 532 (M + H)$^+$. |
| 190A | 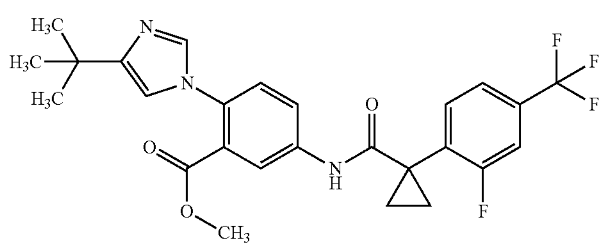 [SMILES: COC(=O)c1cc(NC(=O)C2(c3ccc(C(F)(F)F)cc3F)CC2)ccc1-n1cnc(C(C)(C)C)c1] | Methyl 2-(4-tert-butyl-1H-imidazol-1-yl)-5-[({1-[2-fluoro-4-(trifluoromethyl)phenyl]cyclopropyl}carbonyl)amino]benzoate | $^1$H NMR (400 MHz, DMSO-d6) δ [ppm] 1.28-1.31 (m, 2H), 1.33 (s, 9H), 1.66-1.69 (m, 2H), 3.69 (s, 3H), 7.51-7.74 (m, 6H), 8.06 (dd, 1H), 8.30 (d, 1H), 9.51 (s, 1H). LCMS (method 1) Rt = 1.05 min; MS (ESIpos) m/z = 504 (M + H)$^+$. |
| 191A | 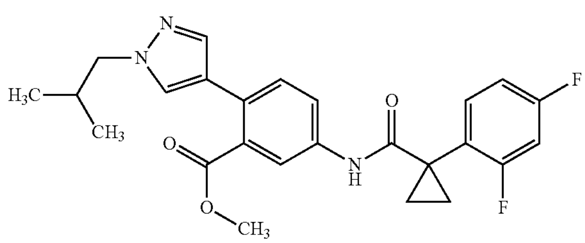 [SMILES: COC(=O)c1cc(NC(=O)C2(c3ccc(F)cc3F)CC2)ccc1-c1cnn(CC(C)C)c1] | Methyl 5-({[1-(2,4-difluorophenyl)cyclopropyl]carbonyl}amino)-2-(1-isobutyl-1H-pyrazol-4-yl)benzoate | $^1$H NMR (500 MHz, Chloroform-d) δ [ppm] 7.62 (dd, J = 8.5, 2.4 Hz, 1H), 7.57 (d, J = 2.4 Hz, 1H), 7.51 (s, 1H), 7.47-7.42 (m, 2H), 7.30 (d, J = 8.4 Hz, 1H), 7.06 (s, 1H), 7.01-6.90 (m, 2H), 3.91 (d, J = 7.3 Hz, 2H), 3.75 (s, 3H), 2.22 (m, 1H), 1.78 (m, 2H), 1.15 (m, 2H), 0.92 (d, J = 6.7 Hz, 6H). LCMS (Analytical Method A): Rt = 1.37 mins; MS (ESI) m/z = 454.1 (M + H)$^+$. |
| 192A | 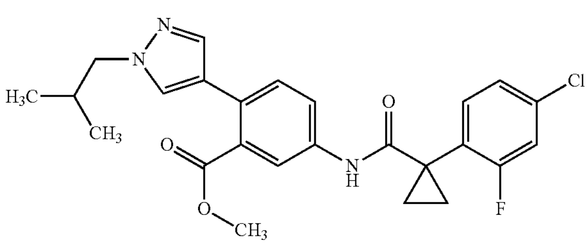 [SMILES: COC(=O)c1cc(NC(=O)C2(c3ccc(Cl)cc3F)CC2)ccc1-c1cnn(CC(C)C)c1] | Methyl 5-({[1-(4-chloro-2-fluorophenyl)cyclopropyl]carbonyl}amino)-2-(1-isobutyl-1H-pyrazol-4-yl)benzoate | $^1$H NMR (500 MHz, Chloroform-d) δ [ppm] 7.63 (dd, J = 8.5, 2.4 Hz, 1H), 7.57 (d, J = 2.4 Hz, 1H), 7.51 (s, 1H), 7.46 (s, 1H), 7.43-7.38 (m, 1H), 7.31 (d, J = 8.4 Hz, 1H), 7.26-7.20 (m, 2H), 7.03 (s, 1H), 3.91 (d, J = 7.3 Hz, 2H), 3.75 (s, 3H), 2.28-2.16 (m, 1H), 1.83-1.74 (m, 2H), 1.20-1.09 (m, 2H), 0.92 (d, J = 6.7 Hz, 6H). LCMS (Analytical Method A): Rt = 1.41 mins; MS (ESIpos) m/z = 470.1 (M + H)$^+$. |

Intermediate 193A: Methyl 2-(1-Benzothiophen-2-yl)-5-[({1-[2-fluoro-4-(trifluoromethyl)phenyl]cyclopropyl}carbonyl)amino]benzoate

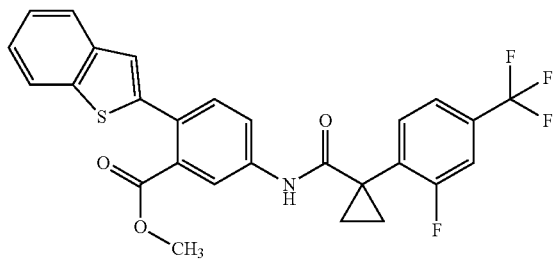

To methyl 5-amino-2-(1-benzothiophen-2-yl)benzoate (Int 65A, 152 mg, 0.536 mmol) in pyridine (2 mL) was added 1-[2-fluoro-4-(trifluoromethyl)phenyl]cyclopropane-1-carbonyl chloride (172 mg, 0.644 mmol) in DCM (1.0 mL) at room temperature and the resulting mixture stirred for 1 hour. The reaction mixture was then concentrated in vacuo to give the crude product. The product was purified by Biotage Isolera™ chromatography to give the title compound as a yellow solid (289 mg, quantitative yield).

$^1$H NMR (250 MHz, Chloroform-d) δ [ppm] 7.85-7.69 (N, 3H), 7.67-7.58 (m, 2H), 7.50 (m, 3H), 7.40-7.27 (m, 2H), 7.19 (m, 1H), 7.04 (m, 1H), 3.69 (s, 3H), 1.86 (m, 2H), 1.21 (in, 2H).

LCMS (Analytical Method D): Rt=5.38 mins; MS (ESI-Pos) m/z=536 (M+Na)$^+$.

In analogy to Intermediate 193A, the following intermediates were prepared using the corresponding amine and carboxylic acid chlorides as starting materials:

| Int. | Structure | Name | Analytical Data |
| --- | --- | --- | --- |
| 194A | 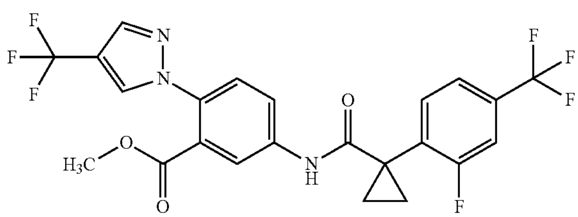 [SMILES: COC(=O)c1cc(NC(=O)C2(c3ccc(C(F)(F)F)cc3F)CC2)ccc1-n1cc(C(F)(F)F)cn1] | Methyl 5-[({1-[2-fluoro-4-(trifluoromethyl)phenyl]cyclopropyl}carbonyl)amino]-2-[4-(trifluoromethyl)-1H-pyrazol-1-yl]benzoate | $^1$H NMR (250 MHz, Chloroform-d) δ [ppm] 7.94-7.83 (m, 2H), 7.73-7.36 (m, 5H), 7.08 (s, 1H), 3.72 (s, 3H), 1.86 (m, 2H), 1.24 (m, 2H). LCMS (Analytical Method A) Rt = 1.40 min, MS (ESIpos): m/z = 516.0 (M + H)$^+$. |
| 195A | 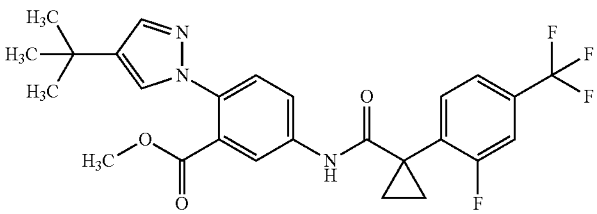 [SMILES: COC(=O)c1cc(NC(=O)C2(c3ccc(C(F)(F)F)cc3F)CC2)ccc1-n1cc(C(C)(C)C)cn1] | Methyl 2-(3-tert-butyl-1H-pyrazol-1-yl)-5-{1-[2-fluoro-4-(trifluoromethyl)phenyl]cyclopropaneamido}benzoate | $^1$H NMR (250 MHz, Chloroform-d) δ [ppm] 7.80 (dd, J = 8.7, 2.5 Hz, 1H), 7.62 (d, J = 7.2 Hz, 1H), 7.56 (m, 3H), 7.50 (d, J = 5.2 Hz, 1H), 7.43 (d, J = 9.5 Hz, 2H), 7.13 (s, 1H), 3.68 (s, 3H), 1.85 (m, 2H), 1.31 (s, 9H), 1.24-1.19 (m, 2H). LCMS (Analytical Method A) Rt = 1.43 min; MS (ESIpos) m/z = 504.3 (M + H)$^+$. |
| 196A | 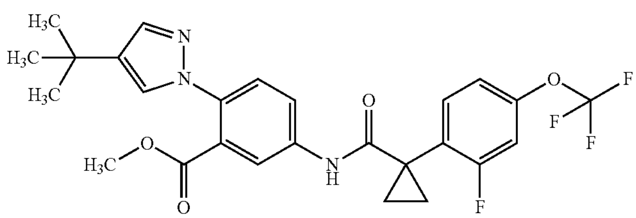 [SMILES: COC(=O)c1cc(NC(=O)C2(c3ccc(OC(F)(F)F)cc3F)CC2)ccc1-n1cc(C(C)(C)C)cn1] | Methyl 2-(4-tert-butyl-1H-pyrazol-1-yl)-5-[({1-[2-fluoro-4-(trifluoromethoxy)phenyl]cyclopropyl}carbonyl)amino]benzoate | $^1$H NMR (500 MHz, DMSO-d6) δ [ppm] 9.21 (s, 1H), 7.97 (s, 1H), 7.85-7.80 (m, 2H), 7.64-7.57 (m, 2H), 7.54 (d, J = 8.5 Hz, 1H), 7.43-7.37 (m, 1H), 7.29-7.22 (m, 1H), 3.61 (s, 3H), 1.65-1.60 (m, 2H), 1.26 (s, 9H), 1.23-1.20 (m, 2H). LCMS (Analytical Method A) Rt = 1.44 min, MS (ESIpos): m/z = 520.5 (M + H)$^+$. |
| 197A | 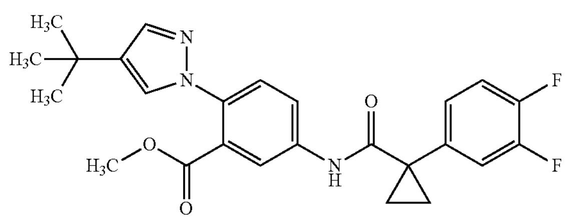 [SMILES: COC(=O)c1cc(NC(=O)C2(c3ccc(F)c(F)c3)CC2)ccc1-n1cc(C(C)(C)C)cn1] | Methyl 2-(4-tert-butyl-1H-pyrazol-1-yl)-5-({[1-(3,4-difluorophenyl)cyclopropyl]carbonyl}amino)benzoate | $^1$H NMR (500 MHz, DMSO-d6) δ [ppm] 9.26 (s, 1H), 7.92 (s, 1H), 7.87 (d, J = 2.4 Hz, 1H), 7.83 (dd, J = 8.8, 2.4 Hz, 1H), 7.58 (s, 1H), 7.56-7.48 (m, 2H), 7.46-7.38 (m, 1H), 7.32-7.25 (m, 1H), 3.61 (s, 3H), 1.53-1.48 (m, 2H), 1.26 (s, 9H), 1.21-1.16 (m, 2H). LCMS (Analytical Method A) Rt = 1.38 min, MS (ESIpos): m/z = 454.5 (M + H)$^+$. |

| Int. | Structure | Name | Analytical Data |
|---|---|---|---|
| 198A | 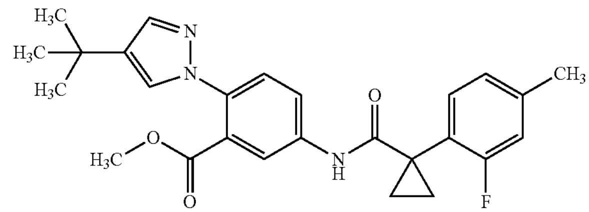 [SMILES: COC(=O)c1cc(NC(=O)C2(c3ccc(C)cc3F)CC2)ccc1-n1cc(C(C)(C)C)cn1] | Methyl 2-(4-tert-butyl-1H-pyrazol-1-yl)-5-({[1-(2-fluoro-4-methylphenyl)cyclopropyl]carbonyl}amino)benzoate | $^1$H NMR (500 MHz, DMSO-d6) δ [ppm] 9.10 (s, 1H), 7.92 (s, 1H), 7.87-7.80 (m, 2H), 7.57 (s, 1H), 7.52 (d, J = 8.7 Hz, 1H), 7.37-7.30 (m, 1H), 7.07-7.01 (m, 2H), 3.60 (s, 3H), 2.34 (s, 3H), 1.61-1.53 (m, 2H), 1.26 (s, 9H), 1.14-1.06 (m, 2H). LCMS (Analytical Method A) Rt = 1.40 min, MS (ESIpos): m/z = 450.5 (M + H)$^+$. |
| 199A | 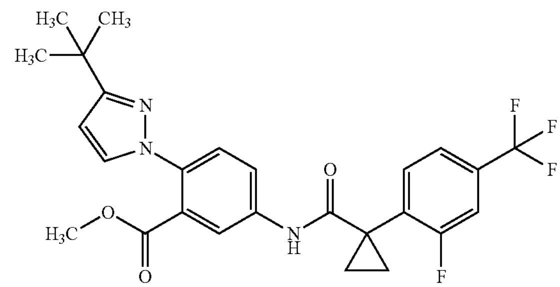 [SMILES: COC(=O)c1cc(NC(=O)C2(c3ccc(C(F)(F)F)cc3F)CC2)ccc1-n1ccc(C(C)(C)C)n1] | Methyl 2-(3-tert-butyl-1H-pyrazol-1-yl)-5-{1-[2-fluoro-4-(trifluoromethyl)phenyl]cyclopropaneamido}benzoate | $^1$H NMR (250 MHz, Chloroform-d) δ [ppm] 7.78 (dd, J = 8.7, 2.5 Hz, 1H), 7.60 (d, J = 7.2 Hz, 1H), 7.54 (d, J = 2.4 Hz, 1H), 7.53-7.48 (m, 2H), 7.39-7.32 (m, 1H), 7.04 (s, 1H), 6.26 (d, J = 2.4 Hz, 1H), 3.68 (s, 3H), 1.83 (m, 2H), 1.31 (s, 9H), 1.20 (m, 2H). LCMS (Analytical Method A) Rt = 1.43 min; MS (ESIpos) m/z = 504.3 (M + H)$^+$. |
| 200A | 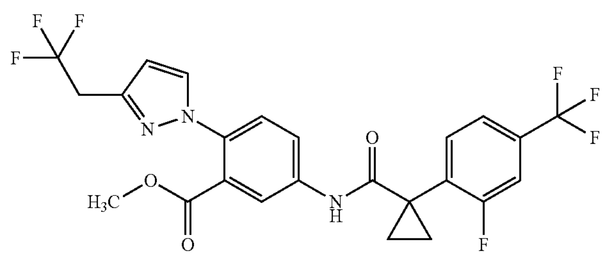 [SMILES: COC(=O)c1cc(NC(=O)C2(c3ccc(C(F)(F)F)cc3F)CC2)ccc1-n1ccc(CC(F)(F)F)n1] | Methyl 5-[({1-[2-fluoro-4-(trifluoromethyl)phenyl]cyclopropyl}carbonyl)amino]-2-[3-(2,2,2-trifluoroethyl)-1H-pyrazol-1-yl]benzoate | $^1$H NMR (500 MHz, Chloroform-d) δ [ppm] 7.86 (dd, J = 8.7, 2.5 Hz, 1H), 7.66-7.59 (m, 2H), 7.58 (d, J = 2.5 Hz, 1H), 7.56-7.51 (m, 1H), 7.49-7.45 (m, 1H), 7.37 (d, J = 8.7 Hz, 1H), 7.06 (s, 1H), 6.41 (d, J = 2.3 Hz, 1H), 3.65 (s, 3H), 3.50 (q, J = 10.8 Hz, 2H), 1.84 (m, 2H), 1.24-1.19 (m, 2H). LCMS (Analytical Method D): Rt = 1.34 min; MS (ESI) m/z = 530.0 (M + H)$^+$. |
| 201A | 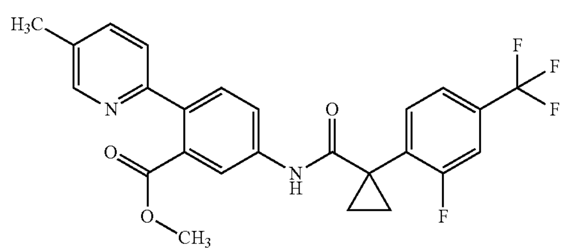 [SMILES: COC(=O)c1cc(NC(=O)C2(c3ccc(C(F)(F)F)cc3F)CC2)ccc1-c1ccc(C)cn1] | Methyl 5-[({1-[2-fluoro-4-(trifluoromethyl)phenyl]cyclopropyl}carbonyl)amino]-2-(5-methylpyridin-2-yl)benzoate | $^1$H NMR (250 MHz, Chloroform-d) δ 8.46 (s, 1H), 7.82 (dd, J = 8.4, 2.2 Hz, 1H), 7.66 (d, J = 7.5 Hz, 1H), 7.60-7.46 (m, 4H), 7.43-7.30 (m, 2H), 7.04 (s, 1H), 3.69 (s, 3H), 2.38 (s, 3H), 1.88 (m, 2H), 1.23 (m, 2H). LCMS (Analytical Method A) Rt = 1.19 min, MS (ESIPos) m/z = 473.2 (M + H)$^+$. |
| 202A | 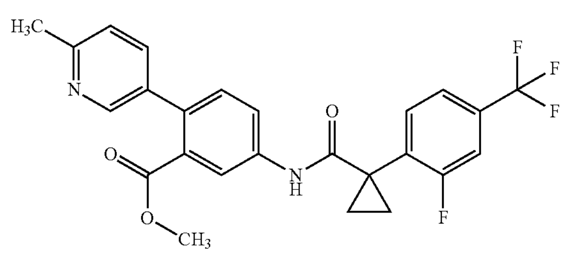 | Methyl 5-[({1-[2-fluoro-4-(trifluoromethyl)phenyl]cyclopropyl}carbonyl)amino]-2-(6-methylpyridin-3-yl)benzoate | $^1$H NMR (500 MHz, Chloroform-d) δ [ppm] 8.35 (d, J = 2.0 Hz, 1H), 7.77-7.70 (m, 2H), 7.65-7.58 (m, 1H), 7.52 (d, J = 8.1 Hz, 1H), 7.49-7.43 (m, 2H), 7.24 (d, J = 8.2 Hz, 1H), 7.15 (d, J = 8.0 Hz, 1H), 7.11 (s, 1H), 3.65 (s, 3H), 2.57 (s, 3H), 1.84 (m, 2H), 1.24-1.17 (m, 2H). LCMS (Analytical Method A): Rt = 1.18 mins; MS (ESIPos) m/z = 473.45 (M + H)$^+$. |
| 203A | 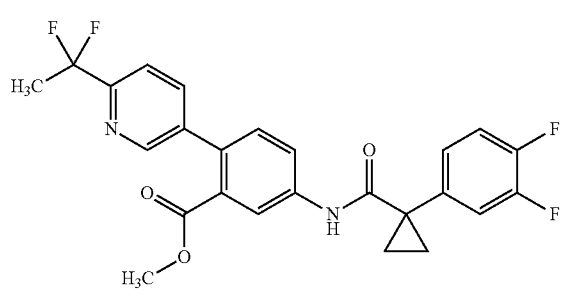 [SMILES: COC(=O)c1cc(NC(=O)C2(c3ccc(F)c(F)c3)CC2)ccc1-c1ccc(C(C)(F)F)nc1] | Methyl 2-[6-(1,1-difluoroethyl)pyridin-3-yl]-5-({[1-(3,4-difluorophenyl)cyclopropyl]carbonyl}amino)benzoate | $^1$H NMR (500 MHz, Chloroform-d) δ [ppm] 8.53-8.45 (m, 1H), 7.81-7.72 (m, 2H), 7.72-7.63 (m, 2H), 7.41-7.30 (m, 1H), 7.30-7.19 (m, 3H), 7.14-7.05 (m, 1H), 3.68 (s, 3H), 2.05 (t, J = 18.6 Hz, 3H), 1.81-1.70 (m, 2H), 1.24-1.15 (m, 2H). LCMS (Analytical Method A): Rt = 1.32 mins; MS (ESIPos) m/z = 473 (M + H)$^+$. |

-continued

| Int. | Structure | Name | Analytical Data |
|---|---|---|---|
| 204A | 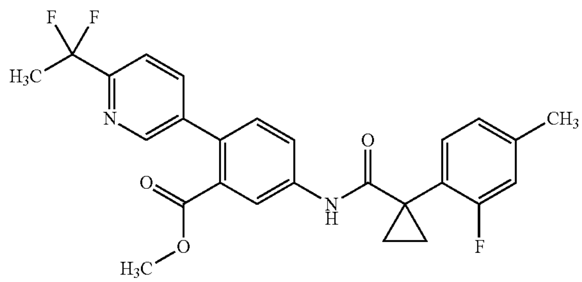 [SMILES: COC(=O)c1cc(NC(=O)C2(c3ccc(C)cc3F)CC2)ccc1-c1ccc(C(C)(F)F)nc1] | Methyl 2-[6-(1,1-difluoroethyl)pyridin-3-yl]-5-({[1-(2-fluoro-4-methylphenyl)cyclopropyl]carbonyl}amino)benzoate | ¹H NMR (500 MHz, Chloroform-d) δ [ppm] 8.50 (s, 1H), 7.84-7.74 (m, 2H), 7.70-7.60 (m, 2H), 7.33 (m, 1H), 7.28-7.17 (m, 2H), 7.08-6.93 (m, 2H), 3.66 (s, 3H), 2.42 (s, 3H), 2.11-1.98 (m, 3H), 1.82-1.73 (m, 2H), 1.21-1.13 (m, 2H). LCMS (Analytical Method A): Rt = 1.34 mins; MS (ESIPos) m/z = 469 (M + H)⁺. |
| 205A | 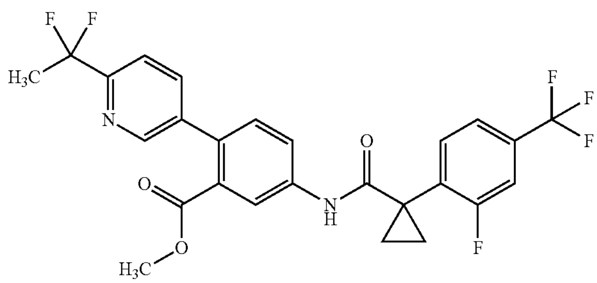 [SMILES: COC(=O)c1cc(NC(=O)C2(c3ccc(C(F)(F)F)cc3F)CC2)ccc1-c1ccc(C(C)(F)F)nc1] | Methyl 2-[6-(1,1-difluoroethyl)pyridin-3-yl]-5-[({1-[2-fluoro-4-(trifluoromethyl)phenyl]cyclopropyl}carbonyl)amino]benzoate | ¹H NMR (500 MHz, DMSO-d6) δ [ppm] 9.32 (s, 1H), 8.58-8.50 (m, 1H), 8.11 (d, J = 2.3 Hz, 1H), 7.91 (dd, J = 8.5, 2.3 Hz, 1H), 7.86 (dd, J = 8.1, 2.3 Hz, 1H), 7.73-7.67 (m, 3H), 7.64-7.58 (m, 1H), 7.40 (d, J = 8.4 Hz, 1H), 3.64 (s, 3H), 2.08-1.97 (m, 3H), 1.69-1.63 (m, 2H), 1.29-1.23 (m, 2H). LCMS (Analytical Method A): Rt = 1.38 mins; MS (ESI) m/z = 523.4 (M + H)⁺. |
| 206A | 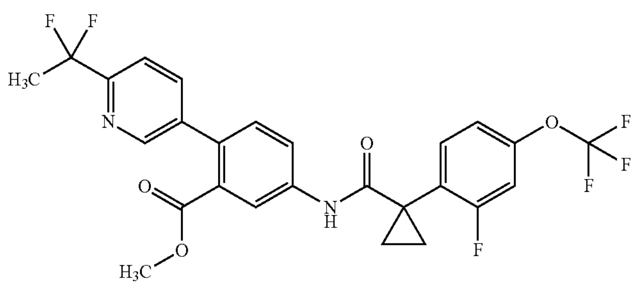 [SMILES: COC(=O)c1cc(NC(=O)C2(c3ccc(OC(F)(F)F)cc3F)CC2)ccc1-c1ccc(C(C)(F)F)nc1] | Methyl 2-[6-(1,1-difluoroethyl)pyridin-3-yl]-5-[({1-[2-fluoro-4-(trifluoromethoxy)phenyl]cyclopropyl}carbonyl)amino]benzoate | ¹H NMR (500 MHz, DMSO-d6) δ [ppm] 9.29 (s, 1H), 8.54 (d, J = 1.7 Hz, 1H), 8.12 (d, J = 2.3 Hz, 1H), 7.90 (dd, J = 8.5, 2.3 Hz, 1H), 7.86 (dd, J = 8.1, 2.3 Hz, 1H), 7.74 - 7.68 (m, 1H), 7.64-7.58 (m, 1H), 7.42-7.36 (m, 2H), 7.28-7.23 (m, 1H), 3.64 (s, 3H), 2.04 (t, J = 19.1 Hz, 3H), 1.68-1.60 (m, 2H), 1.25-1.21 (m, 2H). LCMS (Analytical Method A): Rt = 1.39 mins; MS (ESI) m/z = 539.4 (M + H)⁺. |
| 207A | 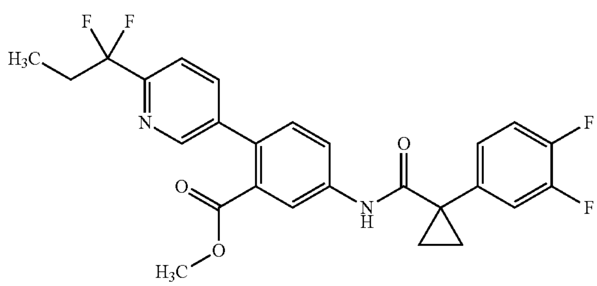 [SMILES: CCC(F)(F)c1ccc(-c2ccc(NC(=O)C3(c4ccc(F)c(F)c4)CC3)cc2C(=O)OC)cn1] | Methyl 5-({[1-(3,4-difluorophenyl)cyclopropyl]carbonyl}amino)-2-[6-(1,1-difluoropropyl)pyridin-3-yl]benzoate | ¹H NMR (500 MHz, DMSO-d6) δ [ppm] 9.38 (s, 1H), 8.55 (d, J = 1.7 Hz, 1H), 8.16 (d, J = 2.2 Hz, 1H), 7.93 (dd, J = 8.4, 2.3 Hz, 1H), 7.86 (dd, J = 8.1, 2.2 Hz, 1H), 7.70 (d, J = 8.1 Hz, 1H), 7.51 (m, 1H), 7.46-7.38 (m, 2H), 7.32-7.24 (m, 1H), 3.64 (s, 3H), 2.45-2.30 (m, 2H), 1.54-1.50 (m, 2H), 1.22-1.17 (m, 2H), 0.95 (t, J = 7.5 Hz, 3H). LCMS (Analytical Method A) Rt = 1.45 min, MS (ESIpos): m/z = 487.5 (M + H)⁺. |
| 208A | 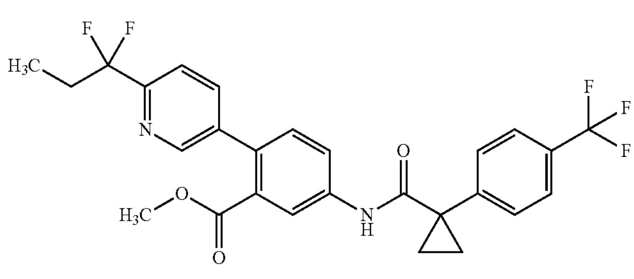 [SMILES: CCC(F)(F)c1ccc(-c2ccc(NC(=O)C3(c4ccc(C(F)(F)F)cc4)CC3)cc2C(=O)OC)cn1] | Methyl 2-[6-(1,1-difluoropropyl)pyridin-3-yl]-5-[({1-[4-(trifluoromethyl)phenyl]cyclopropyl}carbonyl)amino]benzoate | ¹H NMR (250 MHz, Chloroform-d) δ [ppm] 8.53 (s, 1H), 7.82-7.74 (m, 4H), 7.74-7.61 (m, 4H), 7.31-7.25 (m, 1H), 7.06 (s, 1H), 3.67 (s, 3H), 2.39 (td, J = 16.7, 7.5 Hz, 2H), 1.87-1.80 (m, 2H), 1.27-1.22 (m, 2H), 1.05 (t, J = 7.5 Hz, 3H). LCMS (Analytical Method A): Rt = 1.37 mins; MS (ESIpos) m/z = 519.50 (M + H)⁺. |

| Int. | Structure | Name | Analytical Data |
|---|---|---|---|
| 209A | 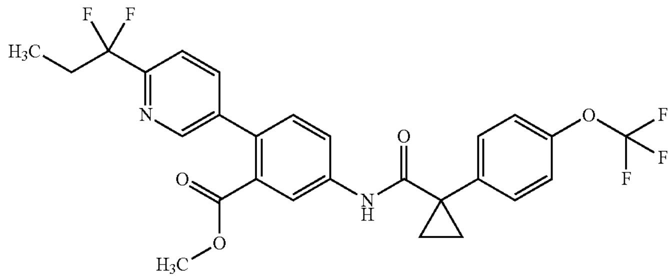 [SMILES: CCC(F)(F)c1ccc(-c2ccc(NC(=O)C3(c4ccc(OC(F)(F)F)cc4)CC3)cc2C(=O)OC)cn1] | Methyl 2-[6-(1,1-difluoropropyl)pyridin-3-yl]-5-[({1-[4-(trifluoromethoxy)phenyl]cyclopropyl}carbonyl)amino]benzoate | ¹H NMR (250 MHz, Methanol-d4) δ [ppm] 8.49 (s, 1H), 8.11 (d, J = 2.3 Hz, 1H), 7.86 (dd, J = 8.1, 2.2 Hz, 1H), 7.79 (dd, J = 8.4, 2.3 Hz, 1H), 7.71 (d, J = 8.1 Hz, 1H), 7.65-7.58 (m, 2H), 7.40-7.31 (m, 3H), 3.69 (s, 3H), 2.46-2.24 (m, 2H), 1.70-1.61 (m, 2H), 1.29-1.22 (m, 2H), 1.02 (t, J = 7.5 Hz, 3H). LCMS (Analytical Method A) Rt = 1.49 min; MS (ESIpos) m/z = 535.05 (M + H)⁺. |
| 210A | 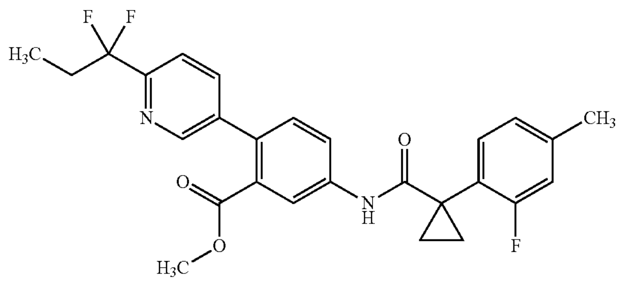 [SMILES: CCC(F)(F)c1ccc(-c2ccc(NC(=O)C3(c4ccc(C)cc4F)CC3)cc2C(=O)OC)cn1] | Methyl 2-[6-(1,1-difluoropropyl)pyridin-3-yl]-5-({[1-(2-fluoro-4-methylphenyl)cyclopropyl]carbonyl}amino)benzoate | ¹H NMR (500 MHz, DMSO-d6) δ [ppm] 9.17 (s, 1H), 8.54 (d, J = 1.7 Hz, 1H), 8.13 (d, J = 2.2 Hz, 1H), 7.92 (dd, J = 8.5, 2.3 Hz, 1H), 7.85 (dd, J = 8.1, 2.2 Hz, 1H), 7.72-7.66 (m, 1H), 7.40 (d, J = 8.4 Hz, 1H), 7.35 (dd, J = 7.9 Hz, 1H), 7.08-7.00 (m, 2H), 3.63 (s, 3H), 2.41-2.30 (m, 5H), 1.61-1.55 (m, 2H), 1.15-1.09 (m, 2H), 0.95 (t, J = 7.5 Hz, 3H). LCMS (Analytical Method A) Rt = 1.47 min, MS (ESIpos): m/z = 483.5 (M + H)⁺. |
| 211A | 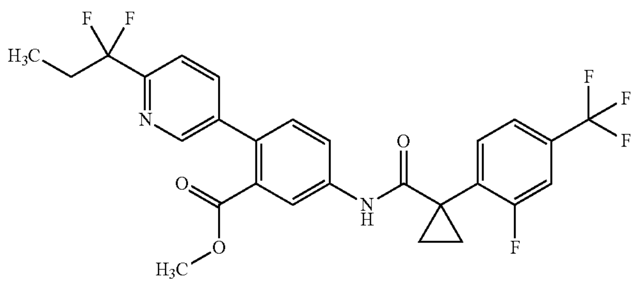 [SMILES: CCC(F)(F)c1ccc(-c2ccc(NC(=O)C3(c4ccc(C(F)(F)F)cc4F)CC3)cc2C(=O)OC)cn1] | Methyl 2-[6-(1,1-difluoropropyl)pyridin-3-yl]-5-[({1-[2-fluoro-4-(trifluoromethyl)phenyl]cyclopropyl}carbonyl)amino]benzoate | ¹H NMR (500 MHz, DMSO-d6) δ [ppm] 9.32 (s, 1H), 8.54 (d, J = 1.7 Hz, 1H), 8.11 (d, J = 2.3 Hz, 1H), 7.91 (dd, J = 8.5, 2.3 Hz, 1H), 7.85 (dd, J = 8.1, 2.3 Hz, 1H), 7.74-7.65 (m, 3H), 7.64-7.58 (m, 1H), 7.41 (d, J = 8.4 Hz, 1H), 3.62 (s, 3H), 2.43-2.28 (m, 2H), 1.75-1.59 (m, 2H), 1.33-1.20 (m, 2H), 0.94 (t, J = 7.5 Hz, 3H). LCMS (Analytical Method F): Rt = 4.42 mins; MS (ESIPos) m/z = 537.1 (M + H)⁺. |
| 212A | 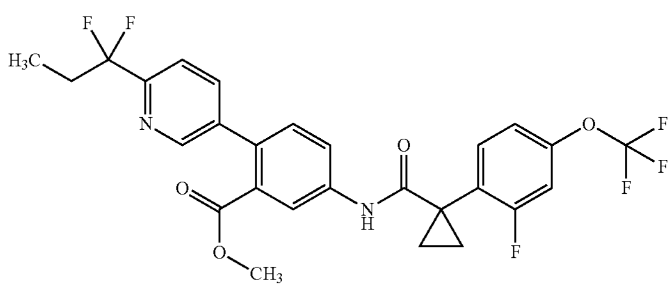 [SMILES: CCC(F)(F)c1ccc(-c2ccc(NC(=O)C3(c4ccc(OC(F)(F)F)cc4F)CC3)cc2C(=O)OC)cn1] | Methyl 2-[6-(1,1-difluoropropyl)pyridin-3-yl]-5-[({1-[2-fluoro-4-(trifluoromethoxy)phenyl]cyclopropyl}carbonyl)amino]benzoate | ¹H NMR (250 MHz, DMSO-d₆) δ [ppm] 9.29 (s, 1H), 8.55 (d, J = 1.6 Hz, 1H), 8.13 (d, J = 2.2 Hz, 1H), 7.97-7.81 (m, 2H), 7.76-7.55 (m, 2H), 7.46-7.35 (m, 2H), 7.32-7.20 (m, 1H), 3.63 (s, 3H), 2.43-2.26 (m, 2H), 1.68-1.57 (m, 2H), 1.28-1.19 (m, 2H), 0.95 (t, J = 7.5 Hz, 3H). LCMS (Analytical Method A) Rt = 1.48 min, MS (ESIpos): m/z = 553.5 (M + H)⁺. |
| 213A | 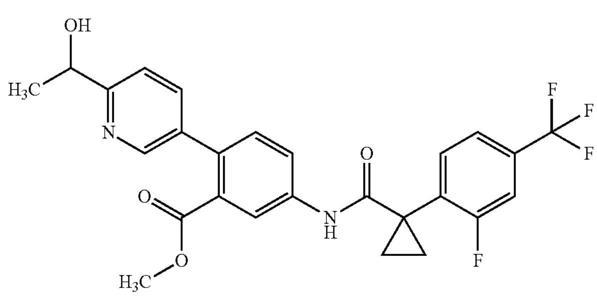 [SMILES: COC(=O)c1cc(NC(=O)C2(c3ccc(C(F)(F)F)cc3F)CC2)ccc1-c1ccc(C(C)O)nc1] | Methyl 5-[({1-[2-fluoro-4-(trifluoromethyl)phenyl]cyclopropyl}carbonyl)amino]-2-[6-(1-hydroxyethyl)pyridin-3-yl]benzoate | ¹H NMR (250 MHz, DMSO-d6) δ [ppm] 9.27 (s, 1H), 8.33 (d, J = 1.7 Hz, 1H), 8.02 (d, J = 2.2 Hz, 1H), 7.90-7.81 (m, 1H), 7.77-7.56 (m, 4H), 7.51 (d, J = 8.1 Hz, 1H), 7.37 (d, J = 8.4 Hz, 1H), 5.38 (d, J = 4.7 Hz, 1H), 4.87-4.65 (m, 1H), 3.63 (s, 3H), 1.72-1.60 (m, 2H), 1.39 (d, J = 6.5 Hz, 3H), 1.33-1.21 (m, 2H). LCMS (Analytical Method A): Rt = 1.13 mins, MS (ESIPos): m/z = 503 (M + H)⁺. |

-continued

| Int. | Structure | Name | Analytical Data |
|---|---|---|---|
| 214A | 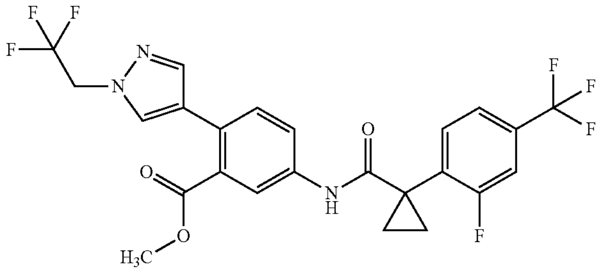 [SMILES: COC(=O)c1cc(NC(=O)C2(c3ccc(C(F)(F)F)cc3F)CC2)ccc1-c1cnn(CC(F)(F)F)c1] | Methyl 5-[({1-[2-fluoro-4-(trifluoromethyl)phenyl]cyclopropyl}carbonyl)amino]-2-[1-(2,2,2-trifluoroethyl)-1H-pyrazol-4-yl]benzoate | ¹H NMR (250 MHz, DMSO-d6) δ [ppm] 9.16 (s, 1H), 7.95-7.87 (m, 1H), 7.84-7.79 (m, 1H), 7.77-7.56 (m, 5H), 7.41 (d, J = 8.5 Hz, 1H), 5.14 (q, J = 9.1 Hz, 2H), 3.72 (s, 3H), 1.68-1.59 (m, 2H), 1.31-1.20 (m, 2H). LCMS (Analytical Method A): Rt = 1.31 mins, MS (ESIPos): m/z = 530 (M + H)⁺. |
| 215A | 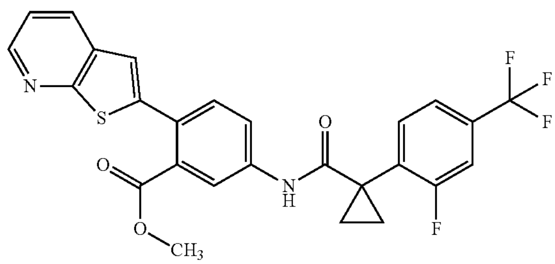 [SMILES: COC(=O)c1cc(NC(=O)C2(c3ccc(C(F)(F)F)cc3F)CC2)ccc1-c1cc2cccnc2s1] | Methyl 5-[({1-[2-fluoro-4-(trifluoromethyl)phenyl]cyclopropyl}carbonyl)amino]-2-(thieno[2,3-b]pyridin-2-yl)benzoate | ¹H NMR (400 MHz, DMSO-d6) δ [ppm] 1.23-1.28 (m, 2H), 1.65-1.68 (m, 2H), 3.69 (s, 3H), 7.35 (s, 1H), 7.46 (dd, 1H), 7.58 (d, 1H), 7.61-7.73 (m, 3H), 7.88 (dd, 1H), 8.25 (dd, 1H), 8.55 (dd, 1H), 9.34 (s, 1H). LCMS (method 1): Rt = 1.41 min; MS (ESIPos) m/z = 515 (M + H)⁺. |
| 216A | 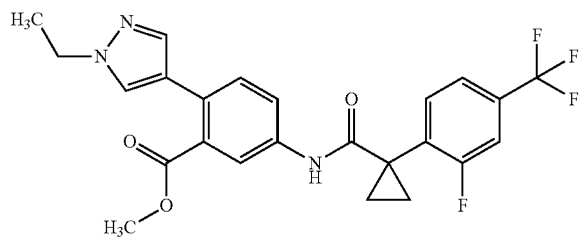 [SMILES: CCn1cc(-c2ccc(NC(=O)C3(c4ccc(C(F)(F)F)cc4F)CC3)cc2C(=O)OC)cn1] | Methyl 2-(1-ethyl-1H-pyrazol-4-yl)-5-[({1-[2-fluoro-4-(trifluoromethyl)phenyl]cyclopropyl}carbonyl)amino]benzoate | ¹H NMR (500 MHz, Chloroform-d) δ [ppm] 7.64-7.56 (m, 3H), 7.53-7.47 (m, 3H), 7.47-7.41 (m, 1H), 7.32-7.28 (m, 1H), 7.01 (s, 1H), 4.16 (q, J = 7.3 Hz, 2H), 3.75 (s, 3H), 1.87-1.76 (m, 2H), 1.49 (t, J = 7.3 Hz, 3H), 1.20-1.13 (m, 2H). LCMS (Analytical Method A): Rt = 1.27 mins; MS (ESIPos) m/z = 476.45 (M + H)⁺. |
| 217A | 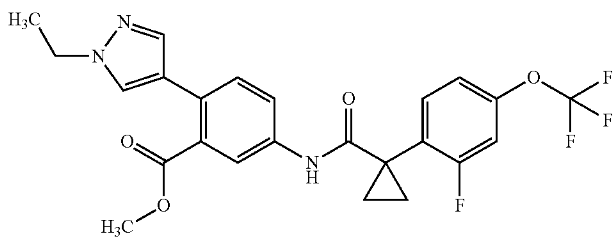 [SMILES: CCn1cc(-c2ccc(NC(=O)C3(c4ccc(OC(F)(F)F)cc4F)CC3)cc2C(=O)OC)cn1] | Methyl 2-(1-ethyl-1H-pyrazol-4-yl)-5-[({1-[2-fluoro-4-(trifluoromethoxy)phenyl]cyclopropyl}carbonyl)amino]benzoate | ¹H NMR (500 MHz, Chloroform-d) δ [ppm] 7.62-7.55 (m, 2H), 7.53-7.45 (m, 3H), 7.29 (d, J = 8.3 Hz, 1H), 7.13-7.03 (m, 3H), 4.16 (q, J = 7.3 Hz, 2H), 3.75 (s, 3H), 1.85-1.72 (m, 2H), 1.49 (t, J = 7.3 Hz, 3H), 1.21-1.09 (m, 2H). LCMS (Analytical Method A): Rt = 1.30 mins; MS (ESIpos) m/z = 492.4 (M + H)⁺. |
| 218A | 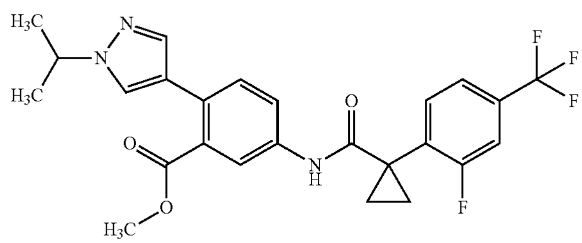 [SMILES: COC(=O)c1cc(NC(=O)C2(c3ccc(C(F)(F)F)cc3F)CC2)ccc1-c1cnn(C(C)C)c1] | Methyl 5-[({1-[2-fluoro-4-(trifluoromethyl)phenyl]cyclopropyl}carbonyl)amino]-2-(1-isopropyl-1H-pyrazol-4-yl)benzoate | ¹H NMR (500 MHz, Chloroform-d) δ [ppm] 7.65-7.58 (m, 2H), 7.56 (d, J = 2.4 Hz, 1H), 7.54-7.49 (m, 3H), 7.48-7.42 (m, 1H), 7.31 (d, J = 8.5 Hz, 1H), 6.98 (s, 1H), 4.49 (hept, J = 6.7 Hz, 1H), 3.75 (s, 3H), 1.90-1.75 (m, 2H), 1.52 (d, J = 6.7 Hz, 6H), 1.21-1.14 (m, 2H). LCMS (Analytical Method A): Rt = 1.31 mins; MS (ESIpos) m/z = 490.4 (M + H)⁺. |
| 219A | 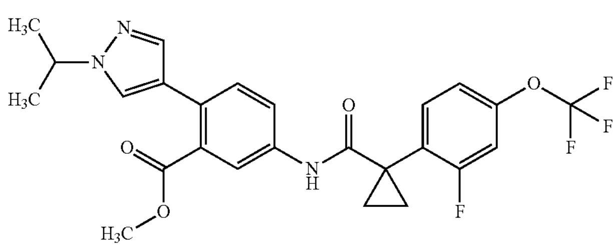 [SMILES: COC(=O)c1cc(NC(=O)C2(c3ccc(OC(F)(F)F)cc3F)CC2)ccc1-c1cnn(C(C)C)c1] | Methyl 5-[({1-[2-fluoro-4-(trifluoromethoxy)phenyl]cyclopropyl}carbonyl)amino]-2-(1-isopropyl-1H-pyrazol-4-yl)benzoate | ¹H NMR (500 MHz, Chloroform-d) δ [ppm] 7.61 (dd, J = 8.5, 2.4 Hz, 1H), 7.57 (d, J = 2.4 Hz, 1H), 7.54-7.53 (m, 1H), 7.53-7.48 (m, 2H), 7.32 (d, J = 8.4 Hz, 1H), 7.14-7.10 (m, 1H), 7.10-7.06 (m, 1H), 7.02 (s, 1H), 4.50 (hept, J = 6.7 Hz, 1H), 3.76 (s, 3H), 1.81 (m, 2H), 1.53 (d, J = 6.7 Hz, 6H), 1.16 (m, 2H). LCMS (Analytical Method A): Rt = 1.32 mins; m/z (ESIPos) = 506.4 (M + H)⁺. |

| Int. | Structure | Name | Analytical Data |
|---|---|---|---|
| 220A | 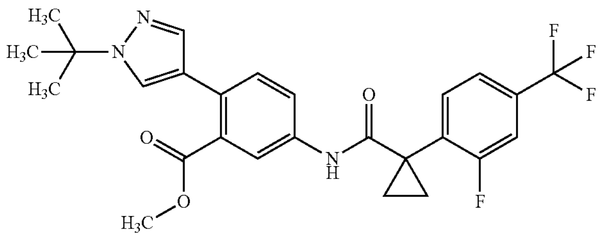 [SMILES: COC(=O)c1cc(NC(=O)C2(c3ccc(C(F)(F)F)cc3F)CC2)ccc1-c1cnn(C(C)(C)C)c1] | Methyl 2-(1-tert-butyl-1H-pyrazol-4-yl)-5-[({1-[2-fluoro-4-(trifluoromethyl)phenyl]cyclopropyl}carbonyl)amino]benzoate | $^1$H NMR (500 MHz, Chloroform-d) δ [ppm] 7.66-7.58 (m, 3H), 7.55 (d, J = 2.4 Hz, 1H), 7.54-7.51 (m, 2H), 7.48-7.44 (m, 1H), 7.32 (d, J = 8.5 Hz, 1H), 6.95 (s, 1H), 3.75 (s, 3H), 1.85-1.81 (m, 2H), 1.61 (s, 9H), 1.21-1.16 (m, 2H). LCMS (Analytical Method A): Rt = 1.33 mins; MS (ESIPos) m/z = 504.5 (M + H)$^+$. |
| 221A | 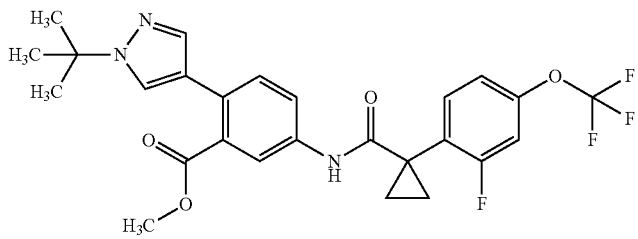 [SMILES: COC(=O)c1cc(NC(=O)C2(c3ccc(OC(F)(F)F)cc3F)CC2)ccc1-c1cnn(C(C)(C)C)c1] | Methyl 2-(1-tert-butyl-1H-pyrazol-4-yl)-5-[({1-[2-fluoro-4-(trifluoromethoxy)phenyl]cyclopropyl}carbonyl)amino]benzoate | $^1$H NMR (500 MHz, Chloroform-d) δ [ppm] 7.64-7.61 (m, 2H), 7.56 (d, J = 2.4 Hz, 1H), 7.54 (s, 1H), 7.53-7.48 (m, 1H), 7.32 (d, J = 8.5 Hz, 1H), 7.14-7.11 (m, 1H), 7.10-7.06 (m, 1H), 7.02 (s, 1H), 3.76 (s, 3H), 1.83-1.78 (m, 2H), 1.61 (s, 9H), 1.20-1.12 (m, 2H). LCMS (Analytical Method A): Rt = 1.39 mins; MS (ESIPos) m/z = 520.4 (M + H)$^+$. |
| 222A | 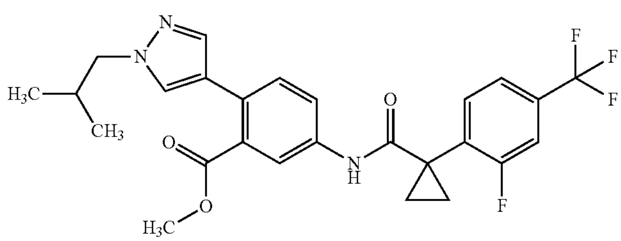 [SMILES: COC(=O)c1cc(NC(=O)C2(c3ccc(C(F)(F)F)cc3F)CC2)ccc1-c1cnn(CC(C)C)c1] | Methyl 5-[({1-[2-fluoro-4-(trifluoromethyl)phenyl]cyclopropyl}carbonyl)amino]-2-(1-isobutyl-1H-pyrazol-4-yl)benzoate | $^1$H NMR (500 MHz, Chloroform-d) δ [ppm] 7.64-7.58 (m, 2H), 7.57 (d, J = 2.3 Hz, 1H), 7.53-7.49 (m, 2H), 7.47-7.42 (m, 2H), 7.30 (d, J = 8.4 Hz, 1H), 7.00 (s, 1H), 3.90 (d, J = 7.3 Hz, 2H), 3.73 (s, 3H), 2.29-2.12 (m, 1H), 1.87-1.77 (m, 2H), 1.23-1.12 (m, 2H), 0.91 (d, J = 6.7 Hz, 6H). LCMS (Analytical Method A): Rt = 1.37 mins; MS (ESIPos) m/z = 504.5 (M + H)$^+$. |
| 223A | 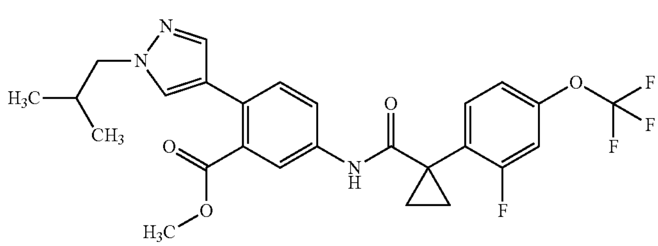 [SMILES: COC(=O)c1cc(NC(=O)C2(c3ccc(OC(F)(F)F)cc3F)CC2)ccc1-c1cnn(CC(C)C)c1] | Methyl 5-[({1-[2-fluoro-4-(trifluoromethoxy)phenyl]cyclopropyl}carbonyl)amino]-2-(1-isobutyl-1H-pyrazol-4-yl)benzoate | $^1$H NMR (500 MHz, Chloroform-d) δ [ppm] 7.61-7.57 (m, 2H), 7.52-7.47 (m, 2H), 7.46-7.44 (m, 1H), 7.32-7.27 (m, 1H), 7.13-7.08 (m, 1H), 7.08-7.03 (m, 2H), 3.89 (d, J = 7.3 Hz, 2H), 3.73 (s, 3H), 2.33-2.12 (m, 1H), 1.85-1.73 (m, 2H), 1.21-1.09 (m, 2H), 0.91 (d, J = 6.7 Hz, 6H). LCMS (Analytical Method A): Rt = 1.37 mins; MS (ESIPos) m/z = 520.45 (M + H)$^+$. |
| 224A | 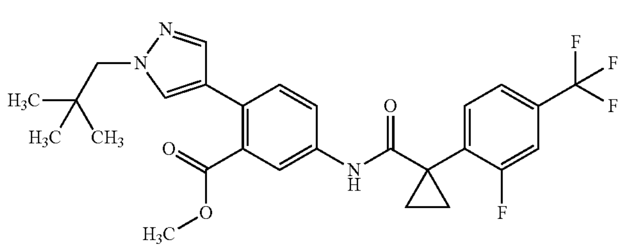 [SMILES: COC(=O)c1cc(NC(=O)C2(c3ccc(C(F)(F)F)cc3F)CC2)ccc1-c1cnn(CC(C)(C)C)c1] | Methyl 2-[1-(2,2-dimethylpropyl)-1H-pyrazol-4-yl]-5-[({1-[2-fluoro-4-(trifluoromethyl)phenyl]cyclopropyl}carbonyl)amino]benzoate | $^1$H NMR (500 MHz, Chloroform-d) δ [ppm] 7.66-7.58 (m, 2H), 7.57 (d, J = 2.4 Hz, 1H), 7.55-7.51 (m, 1H), 7.50 (s, 1H), 7.48-7.44 (m, 2H), 7.32 (d, J = 8.4 Hz, 1H), 6.95 (s, 1H), 3.90 (s, 2H), 3.75 (s, 3H), 1.90-1.78 (m, 2H), 1.27-1.09 (m, 2H), 0.99 (s, 9H). LCMS (Analytical Method A): Rt = 1.49 mins; MS (ESIPos) m/z = 518.1 (M + H)$^+$. |

| Int. | Structure | Name | Analytical Data |
|---|---|---|---|
| 225A | 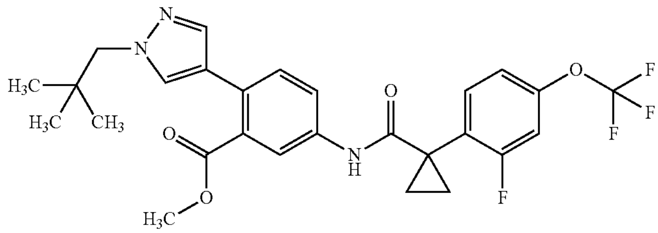 [SMILES: COC(=O)c1cc(NC(=O)C2(c3ccc(OC(F)(F)F)cc3F)CC2)ccc1-c1cnn(CC(C)(C)C)c1] | Methyl 2-[1-(2,2-dimethylpropyl)-1H-pyrazol-4-yl]-5-[({1-[2-fluoro-4-(trifluoromethoxy)phenyl]cyclopropyl}carbonyl)amino]benzoate | $^1$H NMR (500 MHz, Chloroform-d) δ [ppm] 7.61 (dd, J = 8.4, 2.4 Hz, 1H), 7.58 (d, J = 2.3 Hz, 1H), 7.53-7.48 (m, 2H), 7.44 (s, 1H), 7.31 (d, J = 8.4 Hz, 1H), 7.14-7.05 (m, 2H), 7.03 (s, 1H), 3.90 (s, 2H), 3.74 (s, 3H), 1.85-1.75 (m, 2H), 1.22-1.11 (m, 2H), 0.98 (s, 9H). LCMS (Analytical Method A): Rt = 1.56 mins; MS (ESIPos) m/z = 534.15 (M + H)$^+$. |
| 226A | 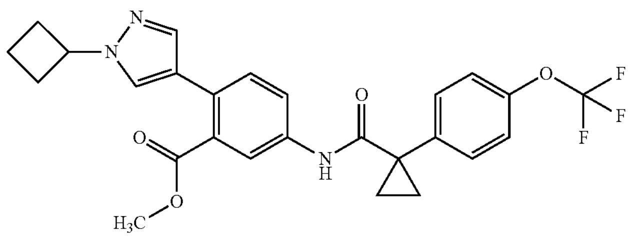 [SMILES: COC(=O)c1cc(NC(=O)C2(c3ccc(OC(F)(F)F)cc3)CC2)ccc1-c1cnn(C2CCC2)c1] | Methyl 2-(1-cyclobutyl-1H-pyrazol-4-yl)-5-[({1-[4-(trifluoromethoxy)phenyl]cyclopropyl}carbonyl)amino]benzoate | $^1$H NMR (500 MHz, Chloroform-d) δ [ppm] 7.61-7.48 (m, 6H), 7.33-7.28 (m, 3H), 7.00 (s, 1H), 4.81-4.68 (m, 1H), 3.77 (s, 3H), 2.64-2.46 (m, 4H), 1.94-1.78 (m, 2H), 1.78-1.73 (m, 2H), 1.20-1.12 (m, 2H). LCMS (Analytical Method A): Rt = 1.40 mins, MS (ESIPos): m/z = 500 (M + H)$^+$. |
| 227A | 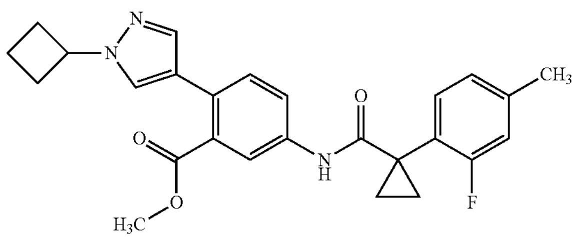 [SMILES: COC(=O)c1cc(NC(=O)C2(c3ccc(C)cc3F)CC2)ccc1-c1cnn(C2CCC2)c1] | Methyl 2-(1-cyclobutyl-1H-pyrazol-4-yl)-5-({[1-(2-fluoro-4-methylphenyl)cyclopropyl]carbonyl}amino)benzoate | $^1$H NMR (250 MHz, Chloroform-d) δ [ppm] 7.69-7.59 (m, 1H), 7.59-7.48 (m, 3H), 7.37-7.27 (m, 2H), 7.20-7.09 (m, 1H), 7.08-6.95 (m, 2H), 4.85-4.68 (m, 1H), 3.76 (s, 3H), 2.64-2.44 (m, 4H), 2.41 (s, 3H), 2.02-1.81 (m, 2H), 1.80-1.72 (m, 2H), 1.18-1.11 (m, 2H). LCMS (Analytical Method A): Rt = 1.34 mins, MS (ESIPos): m/z = 448 (M + H)$^+$. |
| 228A | 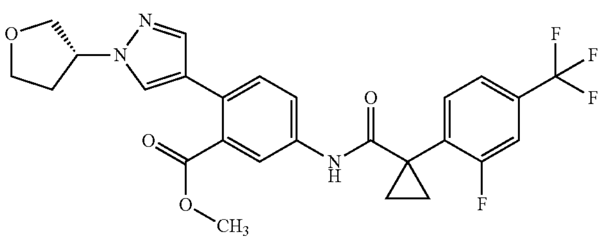 [SMILES: COC(=O)c1cc(NC(=O)C2(c3ccc(C(F)(F)F)cc3F)CC2)ccc1-c1cnn([C@@H]2CCOC2)c1] | Methyl 5-[({1-[2-fluoro-4-(trifluoromethyl)phenyl]cyclopropyl}carbonyl)amino]-2-{1-[(3R)-tetrahydrofuran-3-yl]-1H-pyrazol-4-yl}benzoate | $^1$H NMR (250 MHz, DMSO-d6) δ [ppm] 9.13 (s, 1H), 7.88 (s, 1H), 7.78 (d, J = 2.2 Hz, 1H), 7.74-7.56 (m, 4H), 7.52 (s, 1H), 7.41 (d, J = 8.5 Hz, 1H), 5.10-4.95 (m, 1H), 4.12-3.77 (m, 4H), 3.73 (s, 3H), 2.40-2.19 (m, 2H), 1.68-1.58 (m, 2H), 1.26-1.20 (m, 2H). LCMS (Analytical Method A) Rt = 1.31 min, MS (ESIpos) = 518.1 (M + H)$^+$. |
| 229A | 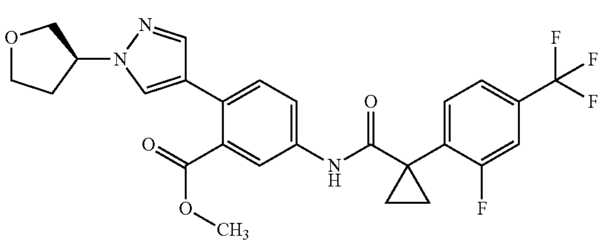 [SMILES: COC(=O)c1cc(NC(=O)C2(c3ccc(C(F)(F)F)cc3F)CC2)ccc1-c1cnn([C@H]2CCOC2)c1] | Methyl 5-[({1-[2-fluoro-4-(trifluoromethyl)phenyl]cyclopropyl}carbonyl)amino]-2-{1-[(3S)-tetrahydrofuran-3-yl]-1H-pyrazol-4-yl}benzoate | 1H NMR (500 MHz, DMSO-d6) δ [ppm] 9.13 (s, 1H), 7.88 (s, 1H), 7.78 (d, J = 2.3 Hz, 1H), 7.74-7.64 (m, 3H), 7.62-7.56 (m, 1H), 7.52 (s, 1H), 7.41 (d, J = 8.5 Hz, 1H), 5.08-4.95 (m, 1H), 4.00-3.94 (m, 2H), 3.89 (dd, J = 9.4, 3.7 Hz, 1H), 3.86-3.79 (m, 1H), 3.73 (s, 3H), 2.42-2.34 (m, 1H), 2.31-2.24 (m, 1H), 1.65-1.61 (m, 2H), 1.25-1.20 (m, 2H). LCMS (Analytical Method A) Rt = 1.28 min, MS (ESIpos): m/z = 518.2 (M + H)$^+$. |
| 230A | 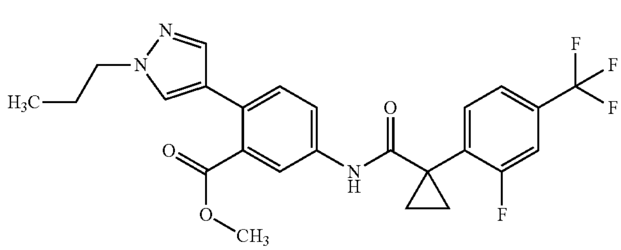 [SMILES: CCCn1cc(-c2ccc(NC(=O)C3(c4ccc(C(F)(F)F)cc4F)CC3)cc2C(=O)OC)cn1] | Methyl 5-[({1-[2-fluoro-4-(trifluoromethyl)phenyl]cyclopropyl}carbonyl)amino]-2-(1-propyl-1H-pyrazol-4-yl)benzoate | $^1$H NMR (250 MHz, Methanol-d4) δ [ppm] 7.68 (d, J = 2.3 Hz, 1H), 7.62 (s, 2H), 7.52-7.37 (m, 4H), 7.26 (d, J = 8.5 Hz, 1H), 4.01 (t, J = 6.9 Hz, 2H), 3.66 (s, 3H), 1.78 (m, 2H), 1.66-1.59 (m, 2H), 1.19-1.13 (m, 2H), 0.81 (t, J = 7.4 Hz, 3H). LCMS (Analytical Method A) Rt = 1.41 min, MS (ESIpos): m/z = 490.1 (M + H)$^+$. |

-continued

| Int. | Structure | Name | Analytical Data |
|---|---|---|---|
| 231A | 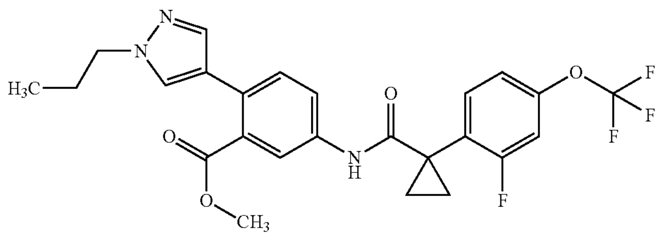 [SMILES: CCCn1cc(-c2ccc(NC(=O)C3(c4ccc(OC(F)(F)F)cc4F)CC3)cc2C(=O)OC)cn1] | Methyl 5-[({1-[2-fluoro-4-(trifluoromethoxy)phenyl]cyclopropyl}carbonyl)amino]-2-(1-propyl-1H-pyrazol-4-yl)benzoate | $^1$H NMR (250 MHz, Methanol-d4) δ [ppm] 7.79 (d, J = 2.2 Hz, 1H), 7.73 (s, 1H), 7.65-7.57 (m, 2H), 7.55-7.52 (m, 1H), 7.38 (d, J = 8.5 Hz, 1H), 7.24-7.15 (m, 2H), 4.13 (t, J = 6.9 Hz, 2H), 3.78 (s, 3H), 1.90 (m, 2H), 1.75-1.68 (m, 2H), 1.27-1.21 (m, 2H), 0.93 (t, J = 7.4 Hz, 3H). LCMS (Analytical Method A) Rt = 1.41 min, MS (ESIpos): m/z = 506.1 (M + H)$^+$. |
| 232A | 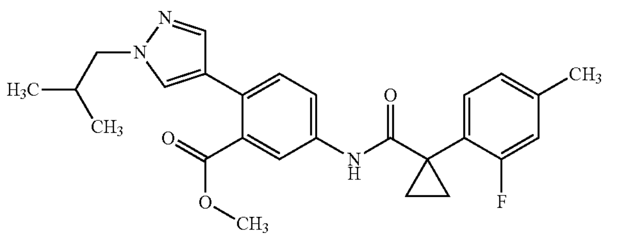 [SMILES: COC(=O)c1cc(NC(=O)C2(c3ccc(C)cc3F)CC2)ccc1-c1cnn(CC(C)C)c1] | Methyl 5-({[1-(2-fluoro-4-methylphenyl)cyclopropyl]carbonyl}amino)-2-(1-isobutyl-1H-pyrazol-4-yl)benzoate | $^1$H NMR (500 MHz, Chloroform-d) δ [ppm] 7.64 (dd, J = 8.5, 2.4 Hz, 1H), 7.54 (d, J = 2.4 Hz, 1H), 7.51-7.49 (m, 1H), 7.45 (s, 1H), 7.34-7.27 (m, 2H), 7.15 (s, 1H), 7.05-7.01 (m, 1H), 7.00-6.96 (m, 1H), 3.91 (d, J = 7.3 Hz, 2H), 3.74 (s, 3H), 2.41 (s, 3H), 2.27-2.16 (m, 1H), 1.79-1.72 (m, 2H), 1.19-1.09 (m, 2H), 0.92 (d, J = 6.7 Hz, 6H). LCMS (Analytical Method A): Rt = 1.39 mins; MS (ESIPos) m/z = 450.1 (M + H)$^+$. |
| 233A | 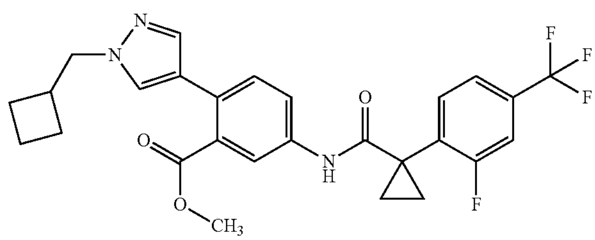 [SMILES: COC(=O)c1cc(NC(=O)C2(c3ccc(C(F)(F)F)cc3F)CC2)ccc1-c1cnn(CC2CCC2)c1] | Methyl 2-[1-(cyclobutylmethyl)-1H-pyrazol-4-yl]-5-[({1-[2-fluoro-4-(trifluoromethyl)phenyl]cyclopropyl}carbonyl)amino]benzoate | $^1$H NMR (250 MHz, Methanol-d4) δ [ppm] 7.79 (d, J = 2.3 Hz, 1H), 7.75-7.67 (m, 2H), 7.64-7.49 (m, 4H), 7.37 (d, J = 8.4 Hz, 1H), 4.17 (d, J = 7.3 Hz, 2H), 3.78 (s, 3H), 2.93-2.78 (m, 1H), 2.14-2.02 (m, 2H), 1.97-1.80 (m, 4H), 1.78-1.71 (m, 2H), 1.30-1.25 (m, 2H). LCMS (Analytical Method A) Rt = 1.46 min, MS (ESIpos): m/z = 516.1 (M + H)$^+$. |
| 234A | 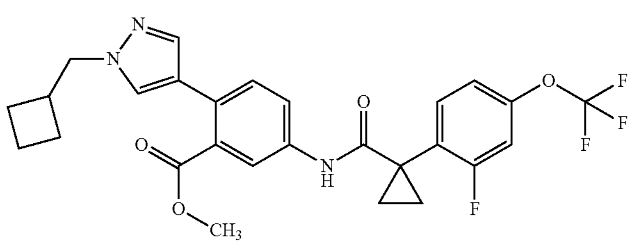 [SMILES: COC(=O)c1cc(NC(=O)C2(c3ccc(OC(F)(F)F)cc3F)CC2)ccc1-c1cnn(CC2CCC2)c1] | Methyl 2-[1-(cyclobutylmethyl)-1H-pyrazol-4-yl]-5-[({1-[2-fluoro-4-(trifluoromethoxy)phenyl]cyclopropyl}carbonyl)amino]benzoate | $^1$H NMR (250 MHz, Methanol-d4) δ [ppm] 7.79 (d, J = 2.3 Hz, 1H), 7.71 (s, 1H), 7.65-7.57 (m, 2H), 7.52 (s, 1H), 7.37 (d, J = 8.4 Hz, 1H), 7.23-7.16 (m, 2H), 4.17 (d, J = 7.3 Hz, 2H), 3.78 (s, 3H), 2.92-2.79 (m, 1H), 2.15-2.02 (m, 2H), 1.97-1.80 (m, 4H), 1.75-1.68 (m, 2H), 1.27-1.21 (m, 2H). LCMS (Analytical Method A) Rt = 1.47 min, MS (ESIpos): m/z = 532.15 (M + H)$^+$. |
| 235A | 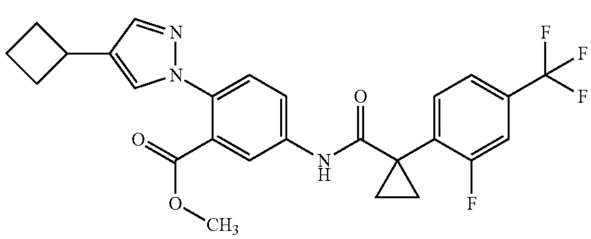 [SMILES: COC(=O)c1cc(NC(=O)C2(c3ccc(C(F)(F)F)cc3F)CC2)ccc1-n1cc(C2CCC2)cn1] | Methyl 2-(4-cyclobutyl-1H-pyrazol-1-yl)-5-[({1-[2-fluoro-4-(trifluoromethyl)phenyl]cyclopropyl}carbonyl)amino]benzoate | $^1$H NMR (500 MHz, Chloroform-d) δ [ppm] 7.81 (dd, J = 8.7, 2.5 Hz, 1H), 7.65-7.59 (m, 1H), 7.55-7.52 (m, 3H), 7.49-7.45 (m, 1H), 7.43 (s, 1H), 7.38 (d, J = 8.7 Hz, 1H), 7.02 (s, 1H), 3.70 (s, 3H), 3.51-3.35 (m, 1H), 2.42-2.26 (m, 2H), 2.11-1.88 (m, 4H), 1.87-1.82 (m, 2H), 1.24-1.18 (m, 2H). LCMS (Analytical Method A): Rt = 1.42 mins; MS (ESIPos) m/z = 502.1 (M + H)$^+$. |

-continued

| Int. | Structure | Name | Analytical Data |
|---|---|---|---|
| 236A | 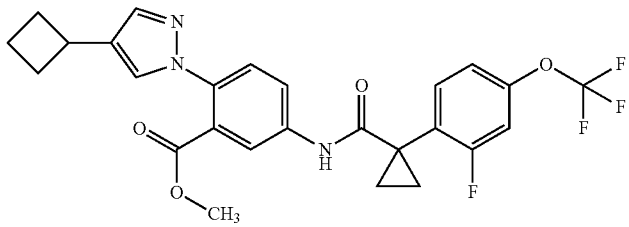 [SMILES: COC(=O)c1cc(NC(=O)C2(c3ccc(OC(F)(F)F)cc3F)CC2)ccc1-n1cc(C2CCC2)cn1] | Methyl 2-(4-cyclobutyl-1H-pyrazol-1-yl)-5-[({1-[2-fluoro-4-(trifluoromethoxy)phenyl]cyclopropyl}carbonyl)amino]benzoate | $^1$H NMR (500 MHz, Chloroform-d) δ [ppm] 7.81 (dd, J = 8.7, 2.5 Hz, 1H), 7.54 (d, J = 2.5 Hz, 1H), 7.52 (s, 1H), 7.50 (d, J = 8.3 Hz, 1H), 7.43 (s, 1H), 7.38 (d, J = 8.7 Hz, 1H), 7.16-7.06 (m, 3H), 3.70 (s, 3H), 3.49-3.39 (m, 1H), 2.42-2.29 (m, 2H), 2.12-1.86 (m, 4H), 1.84-1.78 (m, 2H), 1.23-1.14 (m, 2H). LCMS (Analytical Method A): Rt = 1.44 mins; MS (ESIpos) m/z = 518.1 (M + H)$^+$. |
| 237A | 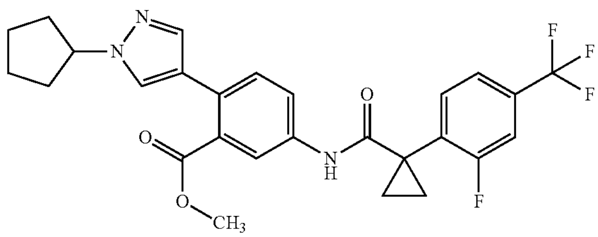 [SMILES: COC(=O)c1cc(NC(=O)C2(c3ccc(C(F)(F)F)cc3F)CC2)ccc1-c1cnn(C2CCCC2)c1] | Methyl 2-(1-cyclopentyl-1H-pyrazol-4-yl)-5-[({1-[2-fluoro-4-(trifluoromethyl)phenyl]cyclopropyl}carbonyl)amino]benzoate | $^1$H NMR (500 MHz, DMSO-d6) δ [ppm] 9.11 (s, 1H), 7.85 (s, 1H), 7.76 (d, J = 2.2 Hz, 1H), 7.72-7.65 (m, 3H), 7.61-7.56 (m, 1H), 7.47 (s, 1H), 7.40 (d, J = 8.5 Hz, 1H), 4.69 (m, 1H), 3.73 (s, 3H), 2.14-2.01 (m, 2H), 1.96-1.86 (m, 2H), 1.82-1.72 (m, 2H), 1.66-1.56 (m, 4H), 1.26-1.20 (m, 2H). LCMS (Analytical Method A) Rt = 1.39 min, MS (ESIpos): m/z = 516.1 (M + H)$^+$. |
| 238A | 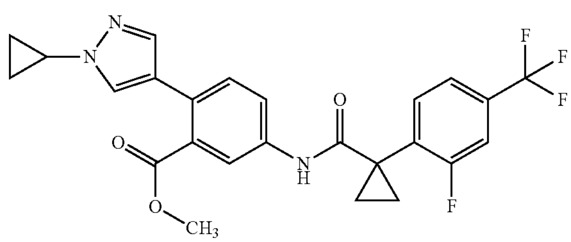 [SMILES: COC(=O)c1cc(NC(=O)C2(c3ccc(C(F)(F)F)cc3F)CC2)ccc1-c1cnn(C2CC2)c1] | Methyl 2-(1-cyclopropyl-1H-pyrazol-4-yl)-5-[({1-[2-fluoro-4-(trifluoromethyl)phenyl]cyclopropyl}carbonyl)amino]benzoate | $^1$H NMR (250 MHz, Chloroform-d) δ [ppm] 7.71-7.55 (m, 5H), 7.54-7.45 (m, 2H), 7.32 (d, J = 8.4 Hz, 1H), 6.97 (s, 1H), 3.79 (s, 3H), 3.68-3.58 (m, 1H), 1.90-1.83 (m, 2H), 1.25-1.13 (m, 4H), 1.09-1.01 (m, 2H). LCMS (Analytical Method A) Rt = 1.28 min, MS (ESIpos): m/z = 488.10 (M + H)$^+$. |
| 239A | 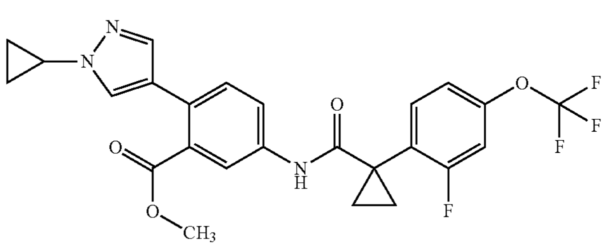 [SMILES: COC(=O)c1cc(NC(=O)C2(c3ccc(OC(F)(F)F)cc3F)CC2)ccc1-c1cnn(C2CC2)c1] | Methyl 2-(1-cyclopropyl-1H-pyrazol-4-yl)-5-[({1-[2-fluoro-4-(trifluoromethoxy)phenyl]cyclopropyl}carbonyl)amino]benzoate | $^1$H NMR (250 MHz, Chloroform-d) δ [ppm] 7.71-7.55 (m, 5H), 7.54-7.45 (m, 2H), 7.32 (d, J = 8.4 Hz, 1H), 6.97 (s, 1H), 3.79 (s, 3H), 3.68-3.58 (m, 1H), 1.90-1.83 (m, 2H), 1.25-1.13 (m, 4H), 1.09-1.01 (m, 2H). LCMS (Analytical Method A) Rt = 1.29 min, MS (ESIpos): m/z = 504.1 (M + H)$^+$. |
| 240A | 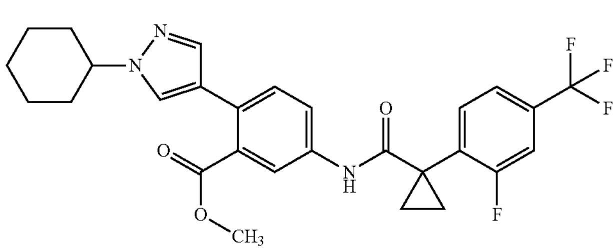 [SMILES: COC(=O)c1cc(NC(=O)C2(c3ccc(C(F)(F)F)cc3F)CC2)ccc1-c1cnn(C2CCCCC2)c1] | Methyl 2-(1-cyclohexyl-1H-pyrazol-4-yl)-5-[({1-[2-fluoro-4-(trifluoromethyl)phenyl]cyclopropyl}carbonyl)amino]benzoate | $^1$H NMR (250 MHz, Methanol-d4) δ [ppm] 7.82-7.75 (m, 2H), 7.75-7.66 (m, 1H), 7.64-7.48 (m, 4H), 7.38 (d, J = 8.4 Hz, 1H), 4.24-4.08 (m, 1H), 3.78 (s, 3H), 2.20-2.05 (m, 2H), 1.97-1.84 (m, 2H), 1.84-1.67 (m, 4H), 1.61-1.45 (m, 2H), 1.44-1.21 (m, 4H). LCMS (Analytical Method A) Rt = 1.38 min, MS (ESIpos): m/z = 530.15 (M + H)$^+$. |

| Int. | Structure | Name | Analytical Data |
|---|---|---|---|
| 241A | 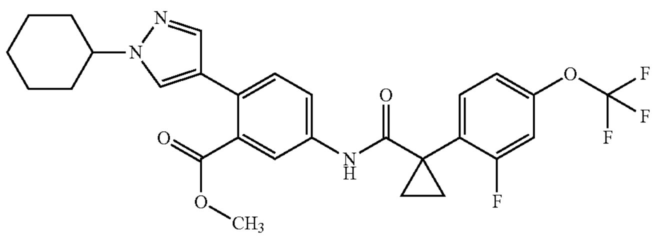 [SMILES: COC(=O)c1cc(NC(=O)C2(c3ccc(OC(F)(F)F)cc3F)CC2)ccc1-c1cnn(C2CCCCC2)c1] | Methyl 2-(1-cyclohexyl-1H-pyrazol-4-yl)-5-[({1-[2-fluoro-4-(trifluoromethoxy)phenyl]cyclopropyl}carbonyl)amino]benzoate | $^1$H NMR (500 MHz, Methanol-d4) δ [ppm] 7.78 (d, J = 2.3 Hz, 1H), 7.77 (s, 1H), 7.63-7.58 (m, 2H), 7.52 (s, 1H), 7.38 (d, J = 8.5 Hz, 1H), 7.21-7.17 (m, 2H), 4.20-4.12 (m, 1H), 3.78 (s, 3H), 2.18-2.09 (m, 2H), 1.97-1.89 (m, 2H), 1.85-1.73 (m, 3H), 1.73-1.69 (m, 2H), 1.56-1.45 (m, 2H), 1.39-1.29 (m, 1H), 1.25-1.23 (m, 2H). LCMS (Analytical Method A) Rt = 1.40 min, MS (ESIpos): m/z = 546.15 (M + H)$^+$. |
| 242A | 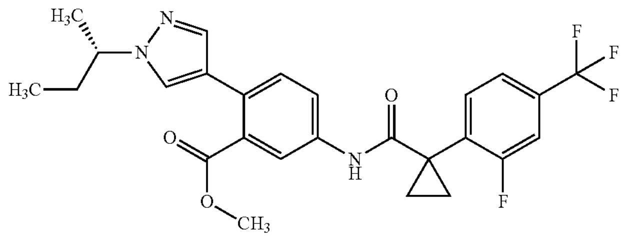 [SMILES: CC[C@H](C)n1cc(-c2ccc(NC(=O)C3(c4ccc(C(F)(F)F)cc4F)CC3)cc2C(=O)OC)cn1] | Methyl 2-{1-[(2S)-butan-2-yl]-1H-pyrazol-4-yl}-5-[({1-[2-fluoro-4-(trifluoromethyl)phenyl]cyclopropyl}carbonyl)amino]benzoate | 1H NMR (500 MHz, Methanol-d4) δ [ppm] 7.79 (d, J = 2.3 Hz, 1H), 7.74 (s, 1H), 7.70 (m, 1H), 7.60 (dd, J = 8.5, 2.4 Hz, 1H), 7.56 (d, J = 8.1 Hz, 1H), 7.55-7.50 (m, 2H), 7.38 (d, J = 8.5 Hz, 1H), 4.32-4.24 (m, 1H), 3.77 (s, 3H), 1.97-1.78 (m, 2H), 1.76-1.71 (m, 2H), 1.51 (d, J = 6.8 Hz, 3H), 1.29-1.26 (m, 2H), 0.83 (t, J = 7.4 Hz, 3H). LCMS (Analytical Method A) Rt = 1.34 min, MS (ESIpos): m/z = 504.15 (M + H)$^+$. |
| 243A | 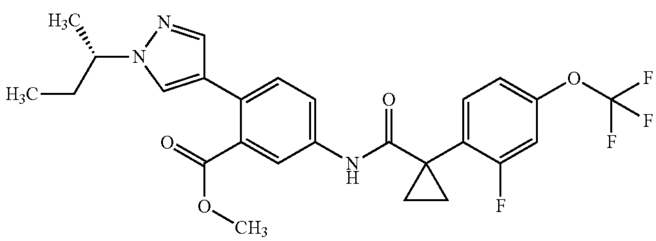 [SMILES: CC[C@H](C)n1cc(-c2ccc(NC(=O)C3(c4ccc(OC(F)(F)F)cc4F)CC3)cc2C(=O)OC)cn1] | Methyl 2-{1-[(2S)-butan-2-yl]-1H-pyrazol-4-yl}-5-[({1-[2-fluoro-4-(trifluoromethoxy)phenyl]cyclopropyl}carbonyl)amino]benzoate | 1H NMR (500 MHz, Methanol-d4) δ [ppm] 7.79 (d, J = 2.3 Hz, 1H), 7.75 (s, 1H), 7.63-7.58 (m, 2H), 7.54 (s, 1H), 7.39 (d, J = 8.4 Hz, 1H), 7.22-7.17 (m, 2H), 4.33-4.24 (m, 1H), 3.78 (s, 3H), 1.97-1.78 (m, 2H), 1.73-1.70 (m, 2H), 1.52 (d, J = 6.8 Hz, 3H), 1.26-1.22 (m, 2H), 0.83 (t, 3H). LCMS (Analytical Method A) Rt = 1.34 min, MS (ESIpos): m/z = 520.15 (M + H)$^+$. |
| 244A | 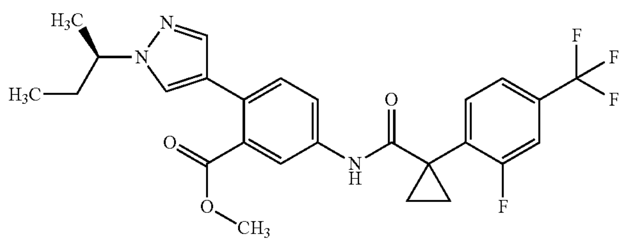 | Methyl 2-{1-[(2R)-butan-2-yl]-1H-pyrazol-4-yl}-5-[({1-[2-fluoro-4-(trifluoromethyl)phenyl]cyclopropyl}carbonyl)amino]benzoate | $^1$H NMR (250 MHz, Methanol-d4) δ [ppm] 7.79 (d, J = 2.3 Hz, 1H), 7.77-7.66 (m, 2H), 7.63-7.49 (m, 4H), 7.38 (d, J = 8.5 Hz, 1H), 4.37-4.20 (m, 1H), 3.77 (s, 3H), 2.00-1.79 (m, 2H), 1.77-1.69 (m, 2H), 1.51 (d, J = 6.8 Hz, 3H), 1.32-1.25 (m, 2H), 0.83 (t, J = 7.4 Hz, 3H). LCMS (Analytical Method A) Rt = 1.33 min, MS (ESIpos): m/z = 504.10 (M + H)$^+$. |
| 245A | 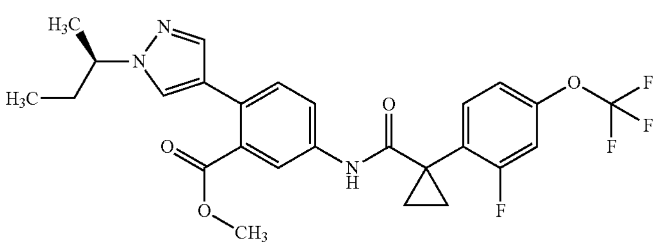 [SMILES: CC[C@@H](C)n1cc(-c2ccc(NC(=O)C3(c4ccc(OC(F)(F)F)cc4F)CC3)cc2C(=O)OC)cn1] | Methyl 2-{1-[(2R)-butan-2-yl]-1H-pyrazol-4-yl}-5-[({1-[2-fluoro-4-(trifluoromethoxy)phenyl]cyclopropyl}carbonyl)amino]benzoate | $^1$H NMR (250 MHz, Methanol-d4) δ [ppm] 7.79 (d, J = 2.3 Hz, 1H), 7.75 (s, 1H), 7.65-7.57 (m, 2H), 7.54 (s, 1H), 7.39 (d, J = 8.4 Hz, 1H), 7.24-7.14 (m, 2H), 4.36-4.21 (m, 1H), 3.78 (s, 3H), 2.00-1.77 (m, 2H), 1.75-1.68 (m, 2H), 1.52 (d, J = 6.8 Hz, 3H), 1.27-1.21 (m, 2H), 0.83 (t, J = 7.4 Hz, 3H). LCMS (Analytical Method A) Rt = 1.35 min, MS (ESIpos): m/z = 520.10 (M + H)$^+$. |

-continued

| Int. | Structure | Name | Analytical Data |
|---|---|---|---|
| 342A | 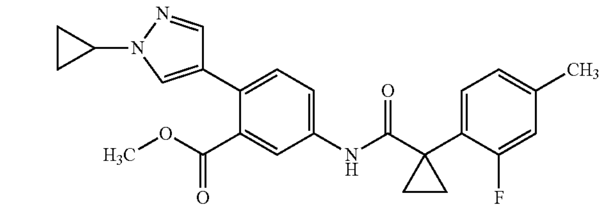 [SMILES: COC(=O)c1cc(NC(=O)C2(c3ccc(C)cc3F)CC2)ccc1-c1cnn(C2CC2)c1] | Methyl 2-(1-cyclopropyl-1H-pyrazol-4-yl)-5-({[1-(2-fluoro-4-methylphenyl)cyclopropyl]carbonyl}amino)benzoate | $^1$H NMR (500 MHz, Chloroform-d) δ [ppm] 7.65 (dd, J = 8.5, 2.4 Hz, 1H), 7.60-7.57 (m, 2H), 7.49 (s, 1H), 7.34 (dd, J = 7.8 Hz, 1H), 7.30 (m, 1H), 7.17 (s, 1H), 7.05 (d, J = 7.8 Hz, 1H), 7.01 (d, J = 10.8 Hz, 1H), 3.78 (s, 3H), 3.66-3.59 (m, 1H), 2.43 (s, 3H), 1.81-1.76 (m, 2H), 1.20-1.14 (m, 4H), 1.07-1.01 (m, 2H). LCMS (Analytical Method A) Rt = 1.25 min, MS (ESIpos): m/z = 434.15 (M + H)$^+$. |
| 343A | 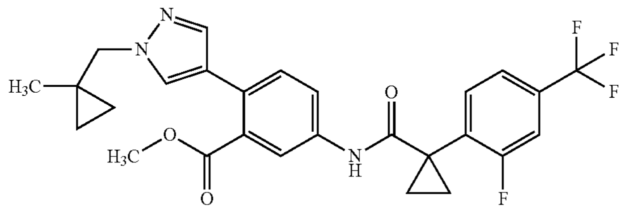 [SMILES: COC(=O)c1cc(NC(=O)C2(c3ccc(C(F)(F)F)cc3F)CC2)ccc1-c1cnn(CC2(C)CC2)c1] | Methyl 5-[({1-[2-fluoro-4-(trifluoromethyl)phenyl]cyclopropyl}carbonyl)amino]-2-{1-[(1-methylcyclopropyl)methyl]-1H-pyrazol-4-yl}benzoate | $^1$H NMR (500 MHz, Chloroform-d) δ [ppm] 7.65-7.60 (m, 2H), 7.58-7.55 (m, 2H), 7.54-7.51 (m, 2H), 7.49-7.43 (m, 1H), 7.33 (d, J = 8.4 Hz, 1H), 6.96 (s, 1H), 3.97 (s, 2H), 3.75 (s, 3H), 1.89-1.78 (m, 2H), 1.25-1.16 (m, 2H), 1.05 (s, 3H), 0.65-0.58 (m, 2H), 0.50-0.41 (m, 2H). LCMS (Analytical Method A): Rt = 1.38 min; MS (ESIPos): m/z = 516 (M + H)$^+$. |
| 344A | 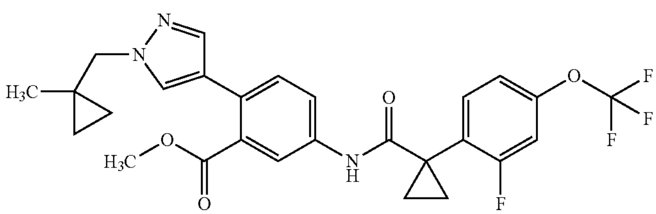 [SMILES: COC(=O)c1cc(NC(=O)C2(c3ccc(OC(F)(F)F)cc3F)CC2)ccc1-c1cnn(CC2(C)CC2)c1] | Methyl 5-[({1-[2-fluoro-4-(trifluoromethoxy)phenyl]cyclopropyl}carbonyl)amino]-2-{1-[(1-methylcyclopropyl)methyl]-1H-pyrazol-4-yl}benzoate | 1H NMR (500 MHz, Chloroform-d) δ [ppm] 7.63 (dd, J = 8.5, 2.4 Hz, 1H), 7.58 (d, J = 2.3 Hz, 1H), 7.57-7.55 (m, 1H), 7.54-7.49 (m, 2H), 7.33 (d, J = 8.4 Hz, 1H), 7.15-7.11 (m, 1H), 7.10-7.07 (m, 1H), 7.02 (s, 1H), 3.97 (s, 2H), 3.76 (s, 3H), 1.87-1.76 (m, 2H), 1.22-1.12 (m, 2H), 1.05 (s, 3H), 0.68-0.57 (m, 2H), 0.52-0.40 (m, 2H). LCMS (Analytical Method A): Rt = 1.39 min; MS(ESIPos): m/z = 532 (M + H)$^+$. |
| 345A | 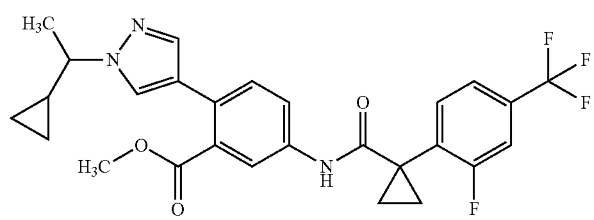 [SMILES: COC(=O)c1cc(NC(=O)C2(c3ccc(C(F)(F)F)cc3F)CC2)ccc1-c1cnn(C(C)C2CC2)c1] | Methyl 2-[1-(1-cyclopropylethyl)-1H-pyrazol-4-yl]-5-[({1-[2-fluoro-4-(trifluoromethyl)phenyl]cyclopropyl}carbonyl)amino]benzoate as a 1:1 mixture of enantiomers | $^1$H NMR (250 MHz, Methanol-d4) δ [ppm] 7.72-7.69 (m, 1H), 7.67 (d, J = 2.2 Hz, 1H), 7.63-7.54 (m, 1H), 7.52-7.37 (m, 4H), 7.27 (d, J = 8.5 Hz, 1H), 3.66 (s, 3H), 3.60-3.45 (m, 1H), 1.66-1.59 (m, 2H), 1.49 (d, J = 6.8 Hz, 3H), 1.20-1.13 (m, 3H), 0.64-0.52 (m, 1H), 0.48-0.38 (m, 1H), 0.30-0.22 (m, 2H). LCMS (Analytical Method A) Rt = 1.33 min, MS (ESIpos): m/z = 516.15 (M + H)$^+$. |
| 346A | 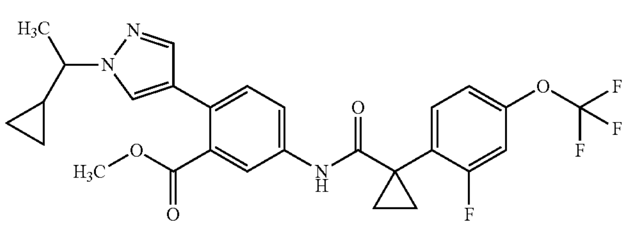 [SMILES: COC(=O)c1cc(NC(=O)C2(c3ccc(OC(F)(F)F)cc3F)CC2)ccc1-c1cnn(C(C)C2CC2)c1] | Methyl 2-[1-(1-cyclopropylethyl)-1H-pyrazol-4-yl]-5-[({1-[2-fluoro-4-(trifluoromethoxy)phenyl]cyclopropyl}carbonyl)amino]benzoate as a 1:1 mixture of enantiomers | $^1$H NMR (250 MHz, Methanol-d4) δ 7.82 (s, 1H), 7.79 (d, J = 2.3 Hz, 1H), 7.65-7.56 (m, 2H), 7.54 (s, 1H), 7.40 (d, J = 8.5 Hz, 1H), 7.21 (s, 1H), 7.18 (s, 1H), 3.79 (s, 3H), 3.71-3.59 (m, 1H), 1.75-1.69 (m, 2H), 1.61 (d, J = 6.8 Hz, 3H), 1.36-1.31 (m, 1H), 1.26-1.21 (m, 2H), 0.76-0.62 (m, 1H), 0.60-0.47 (m, 1H), 0.39 (m, 2H) LCMS (Analytical Method A) Rt = 1.35 min, MS (ESIpos): m/z = 532.15 (M + H)$^+$. |

-continued

| Int. | Structure | Name | Analytical Data |
|---|---|---|---|
| 347A | 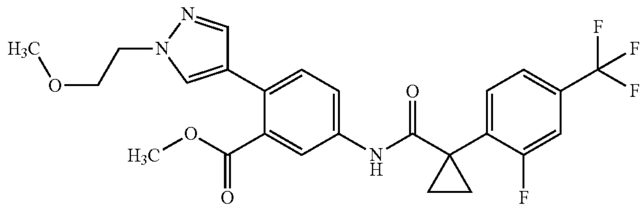 [SMILES: COCCn1cc(-c2ccc(NC(=O)C3(c4ccc(C(F)(F)F)cc4F)CC3)cc2C(=O)OC)cn1] | Methyl 5-[({1-[2-fluoro-4-(trifluoromethyl)phenyl]cyclopropyl}carbonyl)amino]-2-[1-(2-methoxyethyl)-1H-pyrazol-4-yl]benzoate | $^1$H NMR (500 MHz, Chloroform-d) δ [ppm] 7.64-7.58 (m, 2H), 7.58-7.54 (m, 2H), 7.54-7.48 (m, 2H), 7.45 (d, J = 9.5 Hz, 1H), 7.31 (d, J = 8.4 Hz, 1H), 6.99 (s, 1H), 4.28 (t, J = 5.3 Hz, 2H), 3.78-3.72 (m, 5H), 3.33 (s, 3H), 1.86-1.77 (m, 2H), 1.21-1.15 (m, 2H). LCMS (Analytical Method A): Rt = 1.24 mins, MS (ESIPos): m/z = 506 (M + H)$^+$. |
| 352A | 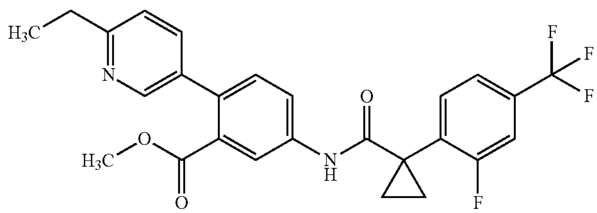 [SMILES: CCc1ccc(-c2ccc(NC(=O)C3(c4ccc(C(F)(F)F)cc4F)CC3)cc2C(=O)OC)cn1] | Methyl 2-(6-ethylpyridin-3-yl)-5-[({1-[2-fluoro-4-(trifluoromethyl)phenyl]cyclopropyl}carbonyl)amino]benzoate | $^1$H NMR (500 MHz, Chloroform-d) δ [ppm] 8.41-8.39 (m, 1H), 7.77-7.73 (m, 2H), 7.65-7.61 (m, 1H), 7.56-7.52 (m, 1H), 7.51 (dd, J = 8.0, 2.4 Hz, 1H), 7.47 (d, J = 9.5 Hz, 1H), 7.26 (d, J = 8.9 Hz, 1H), 7.17 (d, J = 8.0 Hz, 1H), 7.03 (s, 1H), 3.66 (s, 3H), 2.86 (q, J = 7.6 Hz, 2H), 1.92-1.80 (m, 2H), 1.33 (t, J = 7.6 Hz, 3H), 1.25-1.17 (m, 2H). LCMS (Analytical Method A): Rt = 1.26 min; MS (ESIPos): m/z = 487 (M + H)$^+$. |
| 353A | 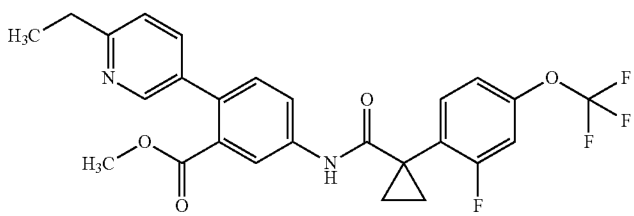 [SMILES: CCc1ccc(-c2ccc(NC(=O)C3(c4ccc(OC(F)(F)F)cc4F)CC3)cc2C(=O)OC)cn1] | Methyl 2-(6-ethylpyridin-3-yl)-5-[({1-[2-fluoro-4-(trifluoromethoxy)phenyl]cyclopropyl}carbonyl)amino]benzoate | $^1$H NMR (500 MHz, Chloroform-d) δ [ppm] 8.42-8.38 (m, 1H), 7.77-7.73 (m, 2H), 7.54-7.49 (m, 2H), 7.29-7.24 (m, 1H), 7.17 (d, J = 8.0 Hz, 1H), 7.15-7.12 (m, 1H), 7.11-7.07 (m, 2H), 3.66 (s, 3H), 2.86 (q, J = 7.6 Hz, 2H), 1.90-1.77 (m, 2H), 1.33 (t, J = 7.6 Hz, 3H), 1.26-1.10 (m, 2H). LCMS (Analytical Method A): Rt = 1.27 min; MS (ESIPos): m/z = 503.1 (M + H)$^+$. |
| 355A | 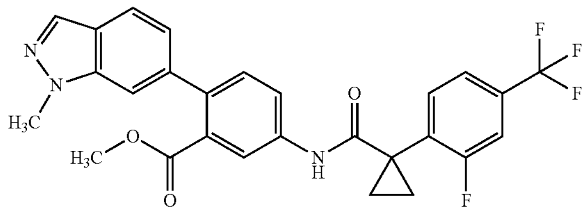 [SMILES: COC(=O)c1cc(NC(=O)C2(c3ccc(C(F)(F)F)cc3F)CC2)ccc1-c1ccc2cnn(C)c2c1] | Methyl 5-[({1-[2-fluoro-4-(trifluoromethyl)phenyl]cyclopropyl}carbonyl)amino]-2-(1-methyl-1H-indazol-6-yl)benzoate | $^1$H NMR (500 MHz, DMSO-d6) δ [ppm] 9.24 (s, 1H), 8.08-8.02 (m, 1H), 7.94 (d, J = 2.2 Hz, 1H), 7.83 (dd, J = 8.5, 2.2 Hz, 1H), 7.75-7.66 (m, 3H), 7.64-7.58 (m, 1H), 7.55-7.51 (m, 1H), 7.45 (d, J = 8.4 Hz, 1H), 6.95 (dd, J = 8.3, 1.2 Hz, 1H), 4.05 (s, 3H), 3.55 (s, 3H), 1.69-1.61 (m, 2H), 1.28-1.21 (m, 2H). LCMS (Analytical Method A) Rt = 1.34 min, MS (ESIpos): m/z = 512.1 (M + H)$^+$. |
| 356A | 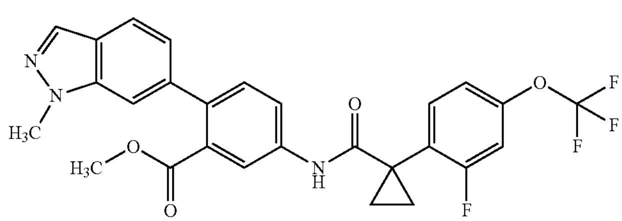 [SMILES: COC(=O)c1cc(NC(=O)C2(c3ccc(OC(F)(F)F)cc3F)CC2)ccc1-c1ccc2cnn(C)c2c1] | Methyl 5-[({1-[2-fluoro-4-(trifluoromethoxy)phenyl]cyclopropyl}carbonyl)amino]-2-(1-methyl-1H-indazol-6-yl)benzoate | $^1$H NMR (500 MHz, DMSO-d6) δ [ppm] 9.22 (s, 1H), 8.05 (d, J = 0.8 Hz, 1H), 7.96 (d, J = 2.3 Hz, 1H), 7.84 (dd, J = 8.5, 2.3 Hz, 1H), 7.72 (d, J = 8.5 Hz, 1H), 7.65-7.58 (m, 1H), 7.56-7.53 (m, 1H), 7.45 (d, J = 8.4 Hz, 1H), 7.40 (dd, J = 10.3, 1.9 Hz, 1H), 7.28-7.23 (m, 1H), 6.95 (dd, J = 8.3, 1.3 Hz, 1H), 4.05 (s, 3H), 3.55 (s, 3H), 1.69-1.59 (m, 2H), 1.23-1.18 (m, 2H). LCMS (Analytical Method A) Rt = 1.38 min, MS (ESIpos): m/z = 528.1 (M + H)$^+$. |

| Int. | Structure | Name | Analytical Data |
|---|---|---|---|
| 359A | 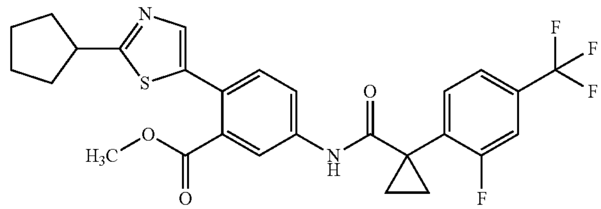 [SMILES: COC(=O)c1cc(NC(=O)C2(c3ccc(C(F)(F)F)cc3F)CC2)ccc1-c1cnc(C2CCCC2)s1] | Methyl 2-(2-cyclopentyl-1,3-thiazol-5-yl)-5-[({1-[2-fluoro-4-(trifluoromethyl)phenyl]cyclopropyl}carbonyl)amino]benzoate | $^1$H NMR (250 MHz, Chloroform-d) δ [ppm] 7.75-7.58 (m, 3H), 7.58-7.42 (m, 3H), 7.42-7.27 (m, 1H), 7.09 (s, 1H), 3.75 (s, 3H), 3.55-3.33 (m, 1H), 2.33-2.10 (m, 2H), 1.96-1.62 (m, 8H), 1.26-1.17 (m, 2H). LCMS (Analytical Method A): Rt = 1.48 mins, MS (ESIPos): m/z = 533 (M + H)$^+$. |
| 361A | 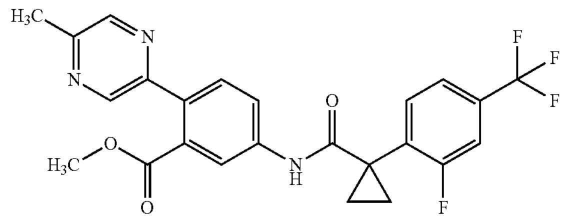 [SMILES: COC(=O)c1cc(NC(=O)C2(c3ccc(C(F)(F)F)cc3F)CC2)ccc1-c1cnc(C)cn1] | Methyl 5-[({1-[2-fluoro-4-(trifluoromethyl)phenyl]cyclopropyl}carbonyl)amino]-2-(5-methylpyrazin-2-yl)benzoate | $^1$H NMR (250 MHz, DMSO-d6) δ [ppm] 9.29 (s, 1H), 8.71 (d, J = 1.4 Hz, 1H), 8.55-8.47 (m, 1H), 7.93 (d, J = 2.1 Hz, 1H), 7.86 (dd, J = 8.5, 2.2 Hz, 1H), 7.76-7.54 (m, 4H), 3.60 (s, 3H), 2.50 (s, 3H), 1.72-1.58 (m, 2H), 1.29-1.21 (m, 2H). LCMS (Analytical Method A) Rt = 1.29 min, MS (ESIpos): m/z = 474.1 (M + H)$^+$. |
| 362A | 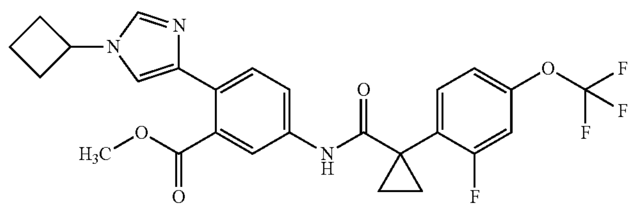 [SMILES: COC(=O)c1cc(NC(=O)C2(c3ccc(OC(F)(F)F)cc3F)CC2)ccc1-c1cn(C2CCC2)cn1] | Methyl 2-(1-cyclobutyl-1H-imidazol-4-yl)-5-[({1-[2-fluoro-4-(trifluoromethoxy)phenyl]cyclopropyl}carbonyl)amino]benzoate | $^1$H NMR (500 MHz, Chloroform-d) δ [ppm] 7.65-7.59 (m, 2H), 7.53-7.47 (m, 3H), 7.20 (d, J = 1.3 Hz, 1H), 7.14-7.10 (m, 1H), 7.09-7.06 (m, 1H), 7.02 (s, 1H), 4.58 (m, 1H), 3.80 (s, 3H), 2.58-2.46 (m, 2H), 2.44-2.32 (m, 2H), 1.96-1.83 (m, 2H), 1.83-1.77 (m, 2H), 1.21-1.12 (m, 2H). LCMS (Analytical Method A): Rt = 1.14 min; MS (ESIPos): m/z = 518.1 (M + H)$^+$. |
| 301A | 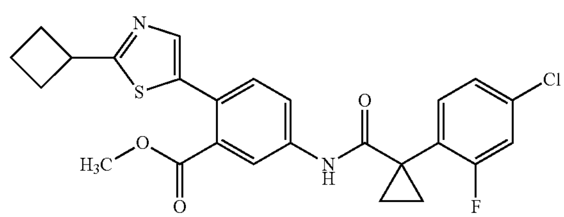 [SMILES: COC(=O)c1cc(NC(=O)C2(c3ccc(Cl)cc3F)CC2)ccc1-c1cnc(C2CCC2)s1] | Methyl 5-({[1-(4-chloro-2-fluorophenyl)cyclopropyl]carbonyl}amino)-2-(2-cyclobutyl-1,3-thiazol-5-yl)benzoate | $^1$H NMR (500 MHz, Chloroform-d) δ [ppm] 7.70 (dd, J = 8.4, 2.4 Hz, 1H), 7.64 (d, J = 2.3 Hz, 1H), 7.49 (s, 1H), 7.44-7.38 (m, 1H), 7.34 (d, J = 8.4 Hz, 1H), 7.26-7.20 (m, 2H), 7.09 (s, 1H), 3.89-3.80 (m, 1H), 3.74 (s, 3H), 2.52-2.43 (m, 2H), 2.43-2.33 (m, 2H), 2.13-2.02 (m, 1H), 2.01-1.92 (m, 1H), 1.85-1.75 (m, 2H), 1.23-1.11 (m, 2H). LCMS (Analytical Method A): Rt = 1.45 min; MS (ESIPos): m/z = 485 (M + H)$^+$. |
| 302A | 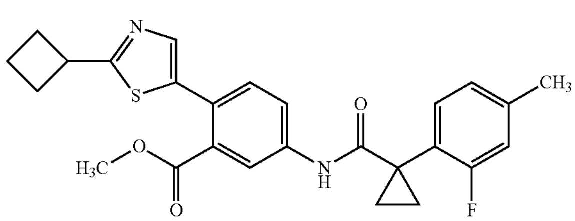 [SMILES: COC(=O)c1cc(NC(=O)C2(c3ccc(C)cc3F)CC2)ccc1-c1cnc(C2CCC2)s1] | Methyl 2-(2-cyclobutyl-1,3-thiazol-5-yl)-5-({[1-(2-fluoro-4-methylphenyl)cyclopropyl]carbonyl}amino)benzoate | $^1$H NMR (500 MHz, Chloroform-d) δ [ppm] 7.71 (dd, J = 8.5, 2.4 Hz, 1H), 7.62 (d, J = 2.3 Hz, 1H), 7.48 (s, 1H), 7.36-7.29 (m, 2H), 7.04 (d, J = 7.8 Hz, 1H), 6.99 (d, J = 10.7 Hz, 1H), 3.89-3.81 (m, 1H), 3.73 (s, 3H), 2.53-2.43 (m, 2H), 2.42 (s, 3H), 2.41-2.33 (m, 2H), 2.13-2.01 (m, 1H), 2.01-1.91 (m, 1H), 1.80-1.71 (m, 2H), 1.20-1.12 (m, 2H). LCMS (Analytical Method A): Rt = 1.43 min; MS (ESIPos): m/z = 465 (M + H)$^+$. |

| Int. | Structure | Name | Analytical Data |
|---|---|---|---|
| 304A | 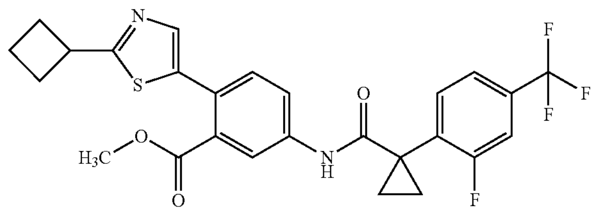 [SMILES: COC(=O)c1cc(NC(=O)C2(c3ccc(C(F)(F)F)cc3F)CC2)ccc1-c1cnc(C2CCC2)s1] | Methyl 2-(2-cyclobutyl-1,3-thiazol-5-yl)-5-[({1-[2-fluoro-4-(trifluoromethyl)phenyl]cyclopropyl}carbonyl)amino]benzoate | $^1$H NMR (250 MHz, Chloroform-d) δ [ppm] 7.69 (dd, J = 8.4, 2.4 Hz, 1H), 7.65 (d, J = 2.3 Hz, 1H), 7.63-7.58 (m, 1H), 7.56-7.50 (m, 1H), 7.50-7.42 (m, 2H), 7.35 (d, J = 8.3 Hz, 1H), 7.01 (s, 1H), 3.93-3.78 (m, 1H), 3.74 (s, 3H), 2.57-2.26 (m, 4H), 2.19-1.91 (m, 2H), 1.90-1.80 (m, 2H), 1.25-1.16 (m, 2H). LCMS (Analytical Method A): Rt = 1.47 min; MS (ESIPos): m/z = 519.1 (M + H)$^+$. |
| 305A | 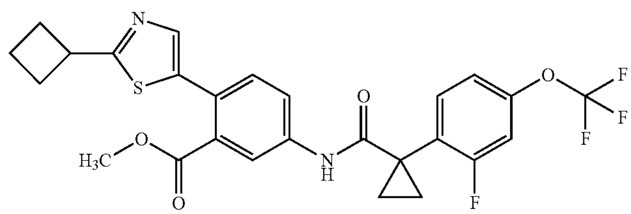 [SMILES: COC(=O)c1cc(NC(=O)C2(c3ccc(OC(F)(F)F)cc3F)CC2)ccc1-c1cnc(C2CCC2)s1] | Methyl 2-(2-cyclobutyl-1,3-thiazol-5-yl)-5-[({1-[2-fluoro-4-(trifluoromethoxy)phenyl]cyclopropyl}carbonyl)amino]benzoate | $^1$H NMR (250 MHz, Chloroform-d) δ [ppm] 7.72-7.63 (m, 2H), 7.56-7.46 (m, 2H), 7.35 (d, J = 8.2 Hz, 1H), 7.18-7.03 (m, 3H), 3.94-3.79 (m, 1H), 3.74 (s, 3H), 2.60-2.26 (m, 4H), 2.19-1.88 (m, 2H), 1.86-1.76 (m, 2H), 1.24-1.12 (m, 2H). LCMS (Analytical Method A): Rt = 1.49 min; MS (ESIPos): m/z = 535.1 (M + H)$^+$. |

Intermediate 246A: Ethyl 5-({[1-(4-chlorophenyl)cyclopropyl]carbonyl}amino)-2-(1-cyclobutyl-1H-pyrazol-4-yl)-3-fluorobenzoate

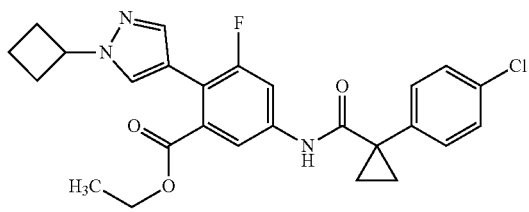 [SMILES: CCOC(=O)c1cc(NC(=O)C2(c3ccc(Cl)cc3)CC2)cc(F)c1-c1cnn(C2CCC2)c1]

To a solution of ethyl 5-amino-2-(1-cyclobutyl-1H-pyrazol-4-yl)-3-fluorobenzoate (Int 113A, 54 mg, 0.18 mmol) and 1-(4-chlorophenyl)cyclopropanecarboxylic acid (42 mg, 0.21 mmol) in DMF (1 mL) was added N,N-diisopropylethylamine (0.09 mL, 0.53 mmol) and HATU (81 mg, 0.21 mmol) and the resulting mixture was stirred at room temperature overnight and then heated at 50° C. for 30 hours. The reaction mixture was then cooled to room temperature, diluted with EtOAc (20 mL) and washed with 2M aq. HCl (10 mL), dried (Na$_2$SO$_4$), filtered and concentrated under reduced pressure. The residue was purified by Biotage Isolera™ chromatography (using a gradient of eluents; 0-40% EtOAc in heptane) giving the title compound (69 mg, 79% yield) as a pale yellow viscous oil.

$^1$H NMR (500 MHz, DMSO-d6) δ [ppm] 9.46 (s, 1H), 7.86 (s, 1H), 7.79 (dd, J=12.6, 2.1 Hz, 1H), 7.66 (d, J=1.8 Hz, 1H), 7.43 (m, 1H), 7.42-7.39 (m, 4H), 4.86 (m, 1H), 4.15 (q, J=7.1 Hz, 2H), 2.48-2.42 (m, 2H), 2.41-2.33 (m, 2H), 1.85-1.68 (m, 2H), 1.52-1.47 (m, 2H), 1.17-1.13 (m, 2H), 1.09 (t, J=7.1 Hz, 3H).

LCMS (Analytical Method A) Rt=1.44 min, MS (ESIpos): m/z=482.1/483.8 (M+H)$^+$.

In analogy to Intermediate 246A, the following intermediates were prepared using the corresponding aniline and carboxylic acid as starting materials.

| Int. | Structure | Name | Analytical Data |
|---|---|---|---|
| 247A | 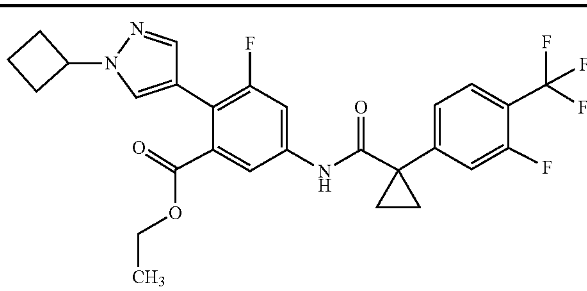 | Ethyl 2-(1-cyclobutyl-1H-pyrazol-4-yl)-3-fluoro-5-[({1-[3-fluoro-4-(trifluoromethyl)phenyl]cyclopropyl}carbonyl)amino]benzoate | $^1$H NMR (500 MHz, DMSO-d6) δ [ppm] 9.59 (s, 1H), 7.86 (s, 1H), 7.81-7.73 (m, 2H), 7.65 (d, J = 1.7 Hz, 1H), 7.52 (d, J = 12.1 Hz, 1H), 7.45-7.40 (m, 2H), 4.87 (m, 1H), 4.15 (q, J = 7.1 Hz, 2H), 2.48-2.43 (m, 2H), 2.41-2.32 (m, 2H), 1.84-1.70 (m, 2H), 1.58-1.54 (m, 2H), 1.32-1.27 (m, 2H), 1.09 (t, J = 7.1 Hz, 3H). LCMS (Analytical Method A) Rt = 1.49 min, MS (ESIpos): m/z = 534.5 (M + H)$^+$. |

-continued

| Int. | Structure | Name | Analytical Data |
|---|---|---|---|
| 248A | 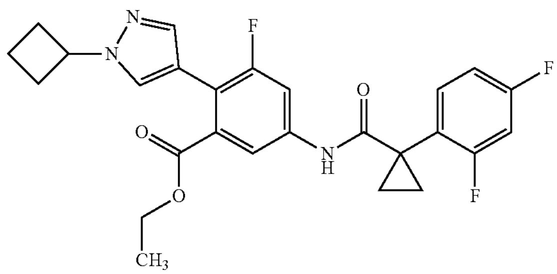 [SMILES: CCOC(=O)c1cc(NC(=O)C2(c3ccc(F)cc3F)CC2)cc(F)c1-c1cnn(C2CCC2)c1] | Ethyl 2-(1-cyclobutyl-1H-pyrazol-4-yl)-5-({[1-(2,4-difluorophenyl)cyclopropyl]carbonyl}amino)-3-fluorobenzoate | $^1$H NMR (500 MHz, DMSO-d6) δ [ppm] 9.17 (s, 1H), 7.86 (s, 1H), 7.77 (dd, J = 12.7, 2.1 Hz, 1H), 7.64 (d, J = 1.6 Hz, 1H), 7.55-7.47 (m, 1H), 7.43 (s, 1H), 7.28-7.21 (m, 1H), 7.13-7.05 (m, 1H), 4.86 (m, 1H), 4.14 (q, J = 7.1 Hz, 2H), 2.48-2.41 (m, 2H), 2.41-2.32 (m, 2H), 1.84-1.69 (m, 2H), 1.62-1.56 (m, 2H), 1.18-1.14 (m, 2H), 1.09 (t, J = 7.1 Hz, 3H). LCMS (Analytical Method A): Rt = 1.38 min, MS (ESIpos) m/z = 484.1 (M + H)$^+$. |
| 249A | 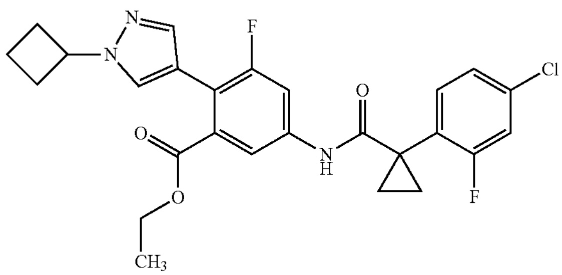 [SMILES: CCOC(=O)c1cc(NC(=O)C2(c3ccc(Cl)cc3F)CC2)cc(F)c1-c1cnn(C2CCC2)c1] | Ethyl 5-({[1-(4-chloro-2-fluorophenyl)cyclopropyl]carbonyl}amino)-2-(1-cyclobutyl-1H-pyrazol-4-yl)-3-fluorobenzoate | $^1$H NMR (500 MHz, DMSO-d6) δ [ppm] 9.22 (s, 1H), 7.86 (s, 1H), 7.76 (dd, J = 12.6, 2.1 Hz, 1H), 7.64 (d, J = 1.8 Hz, 1H), 7.49 (dd, J = 8.3 Hz, 1H), 7.45-7.40 (m, 2H), 7.31 (dd, J = 8.3, 2.0 Hz, 1H), 4.86 (m, 1H), 4.14 (q, J = 7.1 Hz, 2H), 2.48-2.42 (m, 2H), 2.41-2.33 (m, 2H), 1.83-1.72 (m, 2H), 1.62-1.57 (m, 2H), 1.19-1.16 (m, 2H), 1.09 (t, J = 7.1 Hz, 3H). LCMS (Analytical Method A): Rt = 1.44 min, MS (ESIpos) m/z = 500.0/501.7 (M + H)$^+$. |
| 250A | 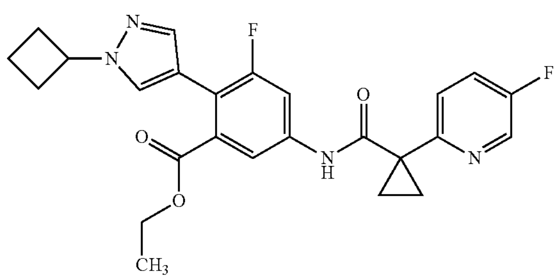 [SMILES: CCOC(=O)c1cc(NC(=O)C2(c3ccc(F)cn3)CC2)cc(F)c1-c1cnn(C2CCC2)c1] | Ethyl 2-(1-cyclobutyl-1H-pyrazol-4-yl)-3-fluoro-5-({[1-(5-fluoropyridin-2-yl)cyclopropyl]carbonyl}amino)benzoate | $^1$H NMR (250 MHz, DMSO-d6) δ [ppm] 10.21 (s, 1H), 8.53 (d, J = 2.9 Hz, 1H), 7.92-7.77 (m, 2H), 7.74-7.62 (m, 2H), 7.49-7.39 (m, 2H), 4.87 (m, 1H), 4.16 (q, J = 7.1 Hz, 2H), 2.47-2.29 (m, 4H), 1.89-1.67 (m, 2H), 1.52 (m, 2H), 1.36 (m, 2H), 1.10 (t, J = 7.1 Hz, 3H). LCMS (Analytical Method A): Rt = 1.31 min, MS (ESIpos) m/z = 467.1 (M + H)$^+$. |
| 251A | 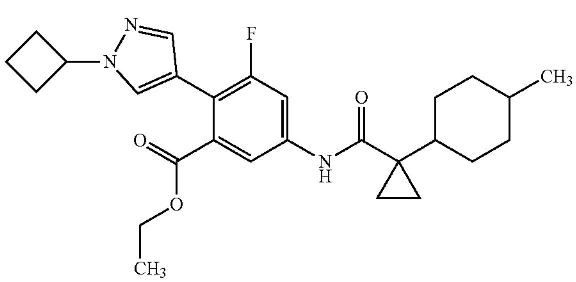 [SMILES: CCOC(=O)c1cc(NC(=O)C2(C3CCC(C)CC3)CC2)cc(F)c1-c1cnn(C2CCC2)c1] | Ethyl 2-(1-cyclobutyl-1H-pyrazol-4-yl)-3-fluoro-5-({[1-(4-methylcyclohexyl)cyclopropyl]carbonyl}amino)benzoate as a 2:1 mixture of diastereoisomers | $^1$H NMR (250 MHz, Chloroform-d) δ 7.84 (m, 1H), 7.60 (m, 1H), 7.55 (m, 1H), 7.45 (m, 1H), 7.41-7.36 (m, 1H), 4.80 (m, 1H), 4.25 (m, 2H), 2.70-2.45 (m, 4H), 2.05-1.73 (m, 4H), 1.58-1.34 (m, 7H), 1.26-1.18 (m, 4H), 1.04 (m, 2H), 0.97 (m, 2H), 0.91 (m, 1H), 0.84-0.76 (m, 2H). LCMS (Analytical Method A): Rt = 1.49 mins; MS (ESIPos) m/z = 468.15 (M + H)$^+$. |
| 252A | 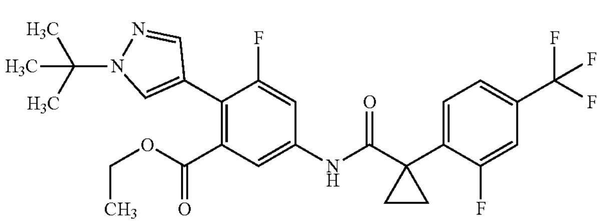 [SMILES: CCOC(=O)c1cc(NC(=O)C2(c3ccc(C(F)(F)F)cc3F)CC2)cc(F)c1-c1cnn(C(C)(C)C)c1] | Ethyl 2-(1-tert-butyl-1H-pyrazol-4-yl)-3-fluoro-5-[({1-[2-fluoro-4-(trifluoromethyl)phenyl]cyclopropyl}carbonyl)amino]benzoate | $^1$H NMR (400 MHz, DMSO-d6) δ [ppm] 1.08 (t, 3H), 1.23-1.27 (m, 2H), 1.53 (s, 9H), 1.64-1.66 (m, 2H), 4.13 (q, 2H), 7.42 (s, 1H), 7.60-7.62 (m, 2H), 7.68-7.72 (m, 2H), 7.76 (dd, 1H), 7.83 (s, 1H), 9.29 (s, 1H). LCMS (method 1): Rt = 1.51 min; MS (ESIPos) m/z = 536 (M + H)$^+$. |

| Int. | Structure | Name | Analytical Data |
|---|---|---|---|
| 253A | 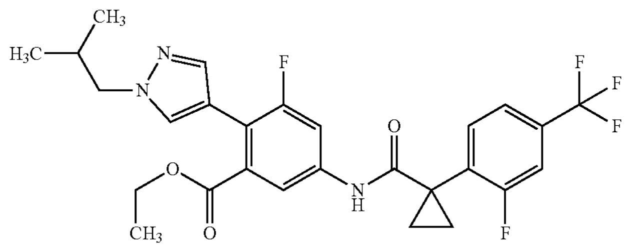 [SMILES: CCOC(=O)c1cc(NC(=O)C2(c3ccc(C(F)(F)F)cc3F)CC2)cc(F)c1-c1cnn(CC(C)C)c1] | Ethyl 3-fluoro-5-[({1-[2-fluoro-4-(trifluoromethyl)phenyl]cyclopropyl}carbonyl)amino]-2-(1-isobutyl-1H-pyrazol-4-yl)benzoate | $^1$H NMR (400 MHz, DMSO-d6) δ [ppm] 0.84 (d, 6H), 1.11 (t, 3H), 1.24-1.27 (m, 2H), 1.64-1.66 (m, 2H), 2.05-2.15 (m, 1H), 3.93 (d, 2H), 4.14 (q, 2H), 7.40 (s, 1H), 7.60-7.62 (m, 2H), 7.68-7.72 (m, 2H), 7.76 (dd, 1H), 7.78 (s, 1H), 9.30 (s, 1H). LCMS (method 1): Rt = 1.51 min; MS (ESIPos) m/z = 536 (M + H)$^+$. |

Intermediate 254A—Ethyl 3-fluoro-5-[({1-[2-fluoro-4-(trifluoromethyl)phenyl]cyclopropyl}carbonyl)amino]-2-[6-(trifluoromethyl)pyridin-3-yl]benzoate

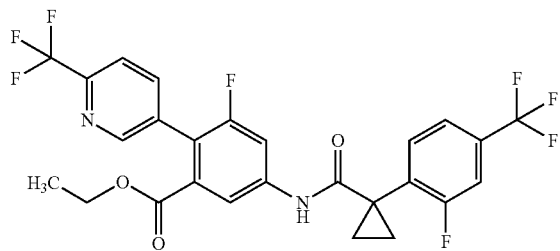 [SMILES: CCOC(=O)c1cc(NC(=O)C2(c3ccc(C(F)(F)F)cc3F)CC2)cc(F)c1-c1ccc(C(F)(F)F)nc1]

To a solution of ethyl 5-amino-3-fluoro-2-[6-(trifluoromethyl)pyridin-3-yl]benzoate (Int 95A, 100 mg, 0.31 mmol) in pyridine (1.8 mL) was added to a solution of 1-[2-fluoro-4-(trifluoromethyl)phenyl]cyclopropanecarbonyl chloride (Int 151A, 106 mg, 0.40 mmol) in dichloromethane (1.2 mL) and the resulting mixture stirred at room temperature for 1 h. The reaction mixture was partitioned between EtOAc and 1M aqueous hydrogen chloride solution and the organic layer collected, washed with further 1M aqueous hydrogen chloride solution. The combined aqueous layers were back extracted with EtOAc. The combined organic fractions were washed with saturated sodium chloride solution, dried (MgSO$_4$), filtered and concentrated at reduced pressure. The residual material was purified by Biotage Isolera™ chromatography (eluting with a gradient of eluents; 100% heptane to 100% EtOAc) giving the title compound (178 mg, 99% yield) as an off-white solid.

$^1$H NMR (250 MHz, Chloroform-d) δ [ppm] 8.57 (s, 1H), 7.97 (dd, J=11.2, 2.2 Hz, 1H), 7.83-7.72 (m, 2H), 7.70-7.42 (m, 4H), 7.14 (s, 1H), 4.08 (q, J=7.1 Hz, 2H), 1.91-1.87 (m, 2H), 1.31-1.25 (m, 2H), 0.98 (t, J=7.1 Hz, 3H).

LCMS (Analytical Method A) Rt=1.44 min, MS (ESIpos) m/z=559.05 (M+H)$^+$.

In analogy to Intermediate 254A, the following intermediates were prepared using the corresponding amine and carboxylic acid chlorides as starting materials:

| Int. | Structure | Name | Analytical Data |
|---|---|---|---|
| 255A | 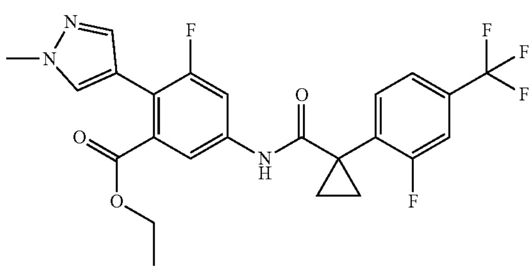 [SMILES: CCOC(=O)c1cc(NC(=O)C2(c3ccc(C(F)(F)F)cc3F)CC2)cc(F)c1-c1cnn(C)c1] | Ethyl 3-fluoro-5-[({1-[2-fluoro-4-(trifluoromethyl)phenyl]cyclopropyl}carbonyl)amino]-2-(1-methyl-1H-pyrazol-4-yl)benzoate | $^1$H NMR (250 MHz, DMSO-d6) δ [ppm] 9.30 (s, 1H), 7.86-7.51 (m, 6H), 7.39 (s, 1H), 4.17 (q, J = 7.1 Hz, 2H), 3.87 (s, 3H), 1.66 (m, 2H), 1.26 (m, 2H), 1.13 (t, J = 7.1 Hz, 3H). LCMS (Analytical Method A): Rt = 1.43 min; MS (ESIpos): m/z = 494.1 (M + H)$^+$. |
| 256A | 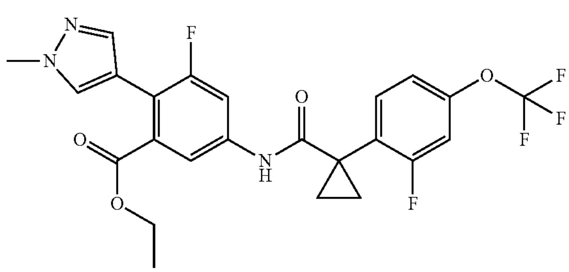 [SMILES: CCOC(=O)c1cc(NC(=O)C2(c3ccc(OC(F)(F)F)cc3F)CC2)cc(F)c1-c1cnn(C)c1] | Ethyl 3-fluoro-5-[({1-[2-fluoro-4-(trifluoromethoxy)phenyl]cyclopropyl}carbonyl)amino]-2-(1-methyl-1H-pyrazol-4-yl)benzoate | $^1$H NMR (250 MHz, DMSO-d6) δ [ppm] 9.27 (s, 1H), 7.81-7.71 (m, 2H), 7.64-7.55 (m, 2H), 7.45-7.33 (m, 2H), 7.33-7.16 (m, 1H), 4.17 (m, 2H), 3.87 (s, 3H), 1.63 (m, 2H), 1.26-1.20 (m, 2H), 1.16-1.09 (m, 3H). LCMS (Analytical Method A): Rt = 1.44 min; MS (ESIpos): m/z = 510.1 (M + H)$^+$. |

| Int. | Structure | Name | Analytical Data |
|---|---|---|---|
| 257A | 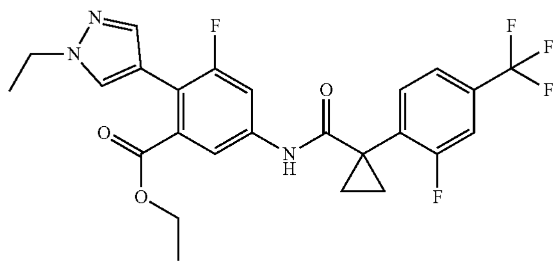 [SMILES: CCOC(=O)c1cc(NC(=O)C2(c3ccc(C(F)(F)F)cc3F)CC2)cc(F)c1-c1cnn(CC)c1] | Ethyl 2-(1-ethyl-1H-pyrazol-4-yl)-3-fluoro-5-[({1-[2-fluoro-4-(trifluoromethyl)phenyl]cyclopropyl}carbonyl)amino]benzoate | $^1$H NMR (250 MHz, DMSO-d6) δ [ppm] 9.35 (s, 1H), 7.87 (s, 1H), 7.85-7.62 (m, 5H), 7.46 (s, 1H), 4.22 (m, 4H), 1.78-1.63 (m, 2H), 1.44 (t, J = 7.3 Hz, 3H), 1.37-1.28 (m, 2H), 1.17 (t, J = 7.1 Hz, 3H). LCMS (Analytical Method A): Rt = 1.47 min; MS (ESIpos): m/z = 508.1 (M + H)$^+$. |
| 258A | 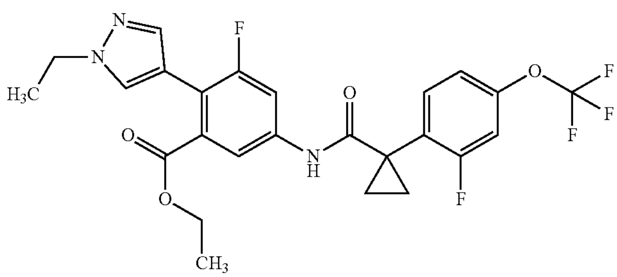 [SMILES: CCOC(=O)c1cc(NC(=O)C2(c3ccc(OC(F)(F)F)cc3F)CC2)cc(F)c1-c1cnn(CC)c1] | Ethyl 2-(1-ethyl-1H-pyrazol-4-yl)-3-fluoro-5-[({1-[2-fluoro-4-(trifluoromethoxy)phenyl]cyclopropyl}carbonyl)amino]benzoate | $^1$H NMR (250 MHz, DMSO-d6) δ [ppm] 9.27 (s, 1H), 7.81 (s, 1H), 7.76 (dd, J = 12.7, 2.1 Hz, 1H), 7.67-7.52 (m, 2H), 7.46-7.34 (m, 2H), 7.31-7.18 (m, 1H), 4.16 (q, J = 7.2 Hz, 4H), 1.68-1.58 (m, 2H), 1.38 (t, J = 7.3 Hz, 3H), 1.28-1.19 (m, 2H), 1.11 (t, J = 7.1 Hz, 3H). LCMS (Analytical Method A): Rt = 1.48 min; MS (ESIpos): m/z = 524.1 (M + H)$^+$. |
| 259A | 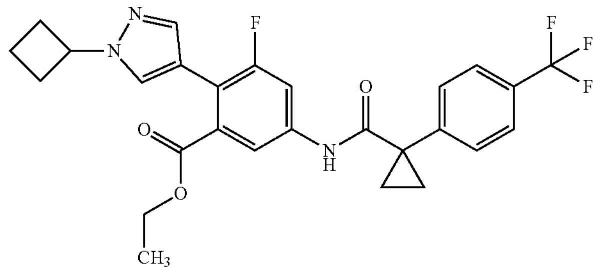 [SMILES: CCOC(=O)c1cc(NC(=O)C2(c3ccc(C(F)(F)F)cc3)CC2)cc(F)c1-c1cnn(C2CCC2)c1] | Ethyl 2-(1-cyclobutyl-1H-pyrazol-4-yl)-3-fluoro-5-[({1-[4-(trifluoromethyl)phenyl]cyclopropyl}carbonyl)amino]benzoate | $^1$H NMR (500 MHz, DMSO-d6) δ [ppm] 9.66 (s, 1H), 7.87 (s, 1H), 7.80 (dd, J = 12.6, 2.1 Hz, 1H), 7.72 (d, J = 8.2 Hz, 2H), 7.67 (d, J = 1.7 Hz, 1H), 7.60 (d, J = 8.1 Hz, 2H), 7.44 (s, 1H), 4.87 (m, 1H), 4.16 (q, J = 7.1 Hz, 2H), 2.45 (m, 2H), 2.42-2.35 (m, 2H), 1.85-1.74 (m, 2H), 1.58-1.54 (m, 2H), 1.27-1.23 (m, 2H), 1.10 (t, J = 7.1 Hz, 3H). LCMS (Analytical Method A) Rt = 1.41 min, MS (ESIpos): m/z = 516.5 (M + H)$^+$. |
| 260A | 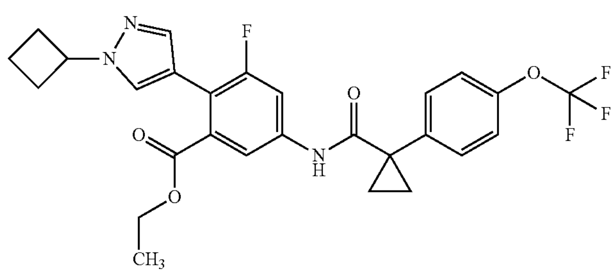 [SMILES: CCOC(=O)c1cc(NC(=O)C2(c3ccc(OC(F)(F)F)cc3)CC2)cc(F)c1-c1cnn(C2CCC2)c1] | Ethyl 2-(1-cyclobutyl-1H-pyrazol-4-yl)-3-fluoro-5-[({1-[4-(trifluoromethoxy)phenyl]cyclopropyl}carbonyl)amino]benzoate | $^1$H NMR (500 MHz, DMSO-d6) δ [ppm] 9.56 (s, 1H), 7.86 (s, 1H), 7.79 (dd, J = 12.6, 2.1 Hz, 1H), 7.66 (d, J = 1.7 Hz, 1H), 7.53-7.48 (m, 2H), 7.43 (s, 1H), 7.34 (d, J = 8.1 Hz, 2H), 4.86 (m, 1H), 4.15 (q, J = 7.1 Hz, 2H), 2.48-2.42 (m, 2H), 2.41-2.33 (m, 2H), 1.85-1.70 (m, 2H), 1.53-1.48 (m, 2H), 1.20-1.16 (m, 2H), 1.09 (t, J = 7.1 Hz, 3H). LCMS (Analytical Method A) Rt = 1.49 min, MS (ESIpos): m/z = 532.5 (M + H)$^+$. |
| 261A | 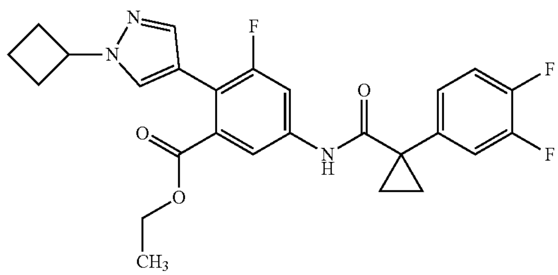 [SMILES: CCOC(=O)c1cc(NC(=O)C2(c3ccc(F)c(F)c3)CC2)cc(F)c1-c1cnn(C2CCC2)c1] | Ethyl 2-(1-cyclobutyl-1H-pyrazol-4-yl)-5-({[1-(3,4-difluorophenyl)cyclopropyl]carbonyl}amino)-3-fluorobenzoate | $^1$H NMR (250 MHz, DMSO-d6) δ [ppm] 9.32 (s, 1H), 7.86 (s, 1H), 7.78 (dd, J = 12.7, 2.2 Hz, 1H), 7.66-7.63 (m, 1H), 7.54-7.34 (m, 3H), 7.30-7.20 (m, 1H), 4.86 (m, 1H), 4.15 (q, J = 7.1 Hz, 2H), 2.47-2.27 (m, 4H), 1.89-1.68 (m, 2H), 1.55-1.46 (m, 2H), 1.21-1.14 (m, 2H), 1.09 (t, J = 7.1 Hz, 3H). LCMS (Analytical Method A) Rt = 1.43 min, MS (ESIpos): m/z = 484.5 (M + H)$^+$. |

| Int. | Structure | Name | Analytical Data |
|---|---|---|---|
| 262A | 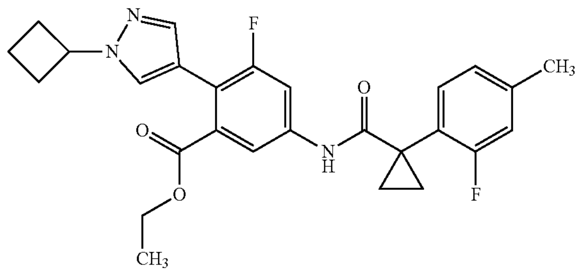 [SMILES: CCOC(=O)c1cc(NC(=O)C2(c3ccc(C)cc3F)CC2)cc(F)c1-c1cnn(C2CCC2)c1] | Ethyl 2-(1-cyclobutyl-1H-pyrazol-4-yl)-3-fluoro-5-({[1-(2-fluoro-4-methylphenyl)cyclopropyl]carbonyl}amino)benzoate | ¹H NMR (500 MHz, DMSO-d6) δ [ppm] 9.16 (s, 1H), 7.85 (s, 1H), 7.77 (dd, J = 12.7, 2.1 Hz, 1H), 7.65 (d, J = 1.7 Hz, 1H), 7.43 (m, 1H), 7.37-7.28 (m, 1H), 7.08-6.99 (m, 2H), 4.86 (m, 1H), 4.14 (q, J = 7.1 Hz, 2H), 2.48-2.42 (m, 2H), 2.41-2.35 (m, 2H), 2.33 (s, 3H), 1.84-1.72 (m, 2H), 1.59-1.53 (m, 2H), 1.14-1.11 (m, 2H), 1.09 (t, J = 7.1 Hz, 3H). LCMS (Analytical Method A) Rt = 1.37 min, MS (ESIpos): m/z = 480.5 (M + H)⁺. |
| 263A | 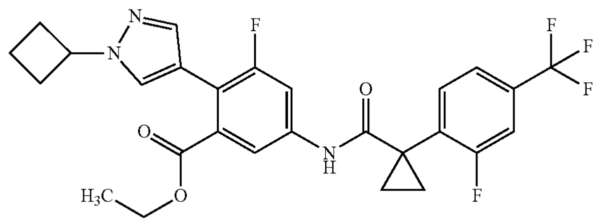 [SMILES: CCOC(=O)c1cc(NC(=O)C2(c3ccc(C(F)(F)F)cc3F)CC2)cc(F)c1-c1cnn(C2CCC2)c1] | Ethyl 2-(1-cyclobutyl-1H-pyrazol-4-yl)-3-fluoro-5-[({1-[2-fluoro-4-(trifluoromethyl)phenyl]cyclopropyl}carbonyl)amino]benzoate | ¹H NMR (250 MHz, Chloroform-d) δ [ppm] 7.65 (m, 1H), 7.59-7.30 (m, 4H), 7.06 (m, 1H), 6.91 (m, 1H), 4.70 (m, 1H), 4.12 (q, J = 7.1 Hz, 2H), 2.60-2.33 (m, 4H), 1.89-1.66 (m, 4H), 1.21-1.16 (m, 2H), 1.09 (t, J = 7.1 Hz, 3H). LCMS (Analytical Method A) Rt = 1.44 min, MS (ESIpos): m/z = 534.45 (M + H)⁺. |
| 264A | 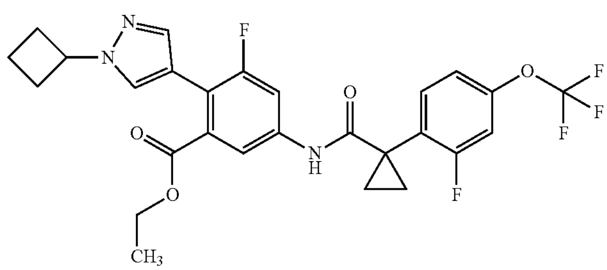 [SMILES: CCOC(=O)c1cc(NC(=O)C2(c3ccc(OC(F)(F)F)cc3F)CC2)cc(F)c1-c1cnn(C2CCC2)c1] | Ethyl 2-(1-cyclobutyl-1H-pyrazol-4-yl)-3-fluoro-5-[({1-[2-fluoro-4-(trifluoromethoxy)phenyl]cyclopropyl}carbonyl)amino]benzoate | ¹H NMR (250 MHz, Chloroform-d) δ [ppm] 7.74 (dd, J = 11.8, 2.2 Hz, 1H), 7.58 (d, J = 1.7 Hz, 1H), 7.57-7.48 (m, 2H), 7.19-7.04 (m, 4H), 4.79 (m, 1H), 4.21 (q, J = 7.1 Hz, 2H), 2.68-2.44 (m, 4H), 1.97-1.86 (m, 2H), 1.86-1.80 (m, 2H), 1.24-1.15 (m, 5H). LCMS (Analytical Method A) Rt = 1.50 min, MS (ESIpos): m/z = 550.45 (M + H)⁺. |
| 265A | 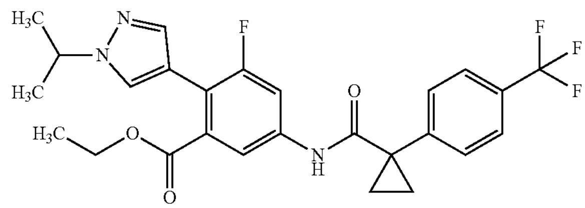 [SMILES: CCOC(=O)c1cc(NC(=O)C2(c3ccc(C(F)(F)F)cc3)CC2)cc(F)c1-c1cnn(C(C)C)c1] | Ethyl 3-fluoro-2-(1-isopropyl-1H-pyrazol-4-yl)-5-[({1-[4-(trifluoromethyl)phenyl]cyclopropyl}carbonyl)amino]benzoate | ¹H NMR (500 MHz, Methanol-d4) δ [ppm] 7.74 (s, 1H), 7.73-7.64 (m, 5H), 7.58 (dd, J = 2.1, 0.9 Hz, 1H), 7.48 (s, 1H), 4.57 (m, 1H), 4.20 (q, J = 7.1 Hz, 2H), 1.68-1.65 (m, 2H), 1.53 (d, J = 6.7 Hz, 6H), 1.30-1.27 (m, 2H), 1.18 (t, J = 7.1 Hz, 3H). LCMS (Analytical Method A) Rt = 1.47 min, MS (ESIpos): m/z = 504.1 (M + H)⁺. |
| 266A | 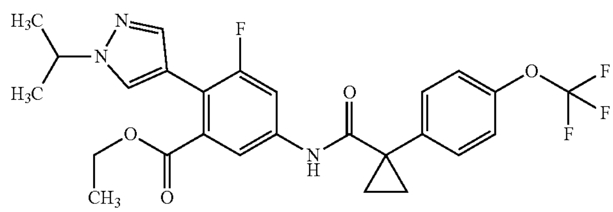 [SMILES: CCOC(=O)c1cc(NC(=O)C2(c3ccc(OC(F)(F)F)cc3)CC2)cc(F)c1-c1cnn(C(C)C)c1] | Ethyl 3-fluoro-2-(1-isopropyl-1H-pyrazol-4-yl)-5-[({1-[4-(trifluoromethoxy)phenyl]cyclopropyl}carbonyl)amino]benzoate | ¹H NMR (500 MHz, Methanol-d4) δ [ppm] 7.75 (s, 1H), 7.70-7.66 (m, 1H), 7.60-7.57 (m, 2H), 7.56 (dd, J = 2.2, 0.9 Hz, 1H), 7.48 (s, 1H), 7.35-7.31 (m, 2H), 4.57 (hept, J = 6.7 Hz, 1H), 4.20 (q, J = 7.1 Hz, 2H), 1.65-1.62 (m, 2H), 1.53 (d, J = 6.7 Hz, 6H), 1.26-1.23 (m, 2H), 1.19 (t, J = 7.1 Hz, 3H). LCMS (Analytical Method A) Rt = 1.48 min, MS (ESIpos): m/z = 520.1 (M + H)⁺. |

| Int. | Name | Analytical Data |
|---|---|---|
| 267A | Ethyl 3-fluoro-5-({[1-(2-fluoro-4-methylphenyl)cyclopropyl]carbonyl}amino)-2-(1-isopropyl-1H-pyrazol-4-yl)benzoate | $^1$H NMR (250 MHz, Methanol-d4) δ [ppm] 7.74 (s, 1H), 7.64 (dd, J = 12.1, 2.2 Hz, 1H), 7.52 (dd, J = 2.2, 1.1 Hz, 1H), 7.47 (s, 1H), 7.36 (m, 1H), 7.07 (d, J = 7.8 Hz, 1H), 7.02 (d, J = 11.4 Hz, 1H), 4.57 (hept, J = 6.8 Hz, 1H), 4.20 (q, J = 7.1 Hz, 2H), 2.40 (s, 3H), 1.69-1.63 (m, 2H), 1.53 (d, J = 6.7 Hz, 6H), 1.22-1.14 (m, 5H). LCMS (Analytical Method A) Rt = 1.49 min, MS (ESIpos): m/z = 468.15 (M + H)$^+$. |
| 268A | Ethyl 3-fluoro-5-[({1-[2-fluoro-4-(trifluoromethyl)phenyl]cyclopropyl}carbonyl)amino]-2-(1-isopropyl-1H-pyrazol-4-yl)benzoate | $^1$H NMR (500 MHz, Methanol-d4) δ [ppm] 7.75 (s, 1H), 7.70 (m, 1H), 7.66 (dd, J = 12.1, 2.2 Hz, 1H), 7.59-7.56 (m, 2H), 7.53 (d, J = 10.0 Hz, 1H), 7.48 (s, 1H), 4.57 (hept, J = 6.7 Hz, 1H), 4.20 (q, J = 7.1 Hz, 2H), 1.77-1.74 (m, 2H), 1.53 (d, J = 6.7 Hz, 6H), 1.30-1.28 (m, 2H), 1.19 (t, J = 7.1 Hz, 3H). LCMS (Analytical Method A) Rt = 1.46 min, MS (ESIpos): m/z = 522.1 (M + H)$^+$. |
| 269A | Ethyl 3-fluoro-5-[({1-[2-fluoro-4-(trifluoromethoxy)phenyl]cyclopropyl}carbonyl)amino]-2-(1-isopropyl-1H-pyrazol-4-yl)benzoate | $^1$H NMR (500 MHz, Methanol-d4) δ [ppm] 7.75 (s, 1H), 7.65 (dd, J = 12.1, 2.2 Hz, 1H), 7.62-7.58 (m, 1H), 7.58-7.56 (m, 1H), 7.48 (s, 1H), 7.21-7.16 (m, 2H), 4.57 (hept, J = 6.7 Hz, 1H), 4.20 (q, J = 7.1 Hz, 2H), 1.74-1.70 (m, 2H), 1.53 (d, J = 6.7 Hz, 6H), 1.27-1.24 (m, 2H), 1.19 (t, J = 7.1 Hz, 3H). LCMS (Analytical Method A) Rt = 1.48 min, MS (ESIpos): m/z = 538.1 (M + H)$^+$. |
| 270A | Ethyl 2-[6-(difluoromethyl)pyridin-3-yl]-3-fluoro-5-[({1-[2-fluoro-4-(trifluoromethyl)phenyl]cyclopropyl}carbonyl)amino]benzoate | $^1$H NMR (250 MHz, Methanol-d4) δ [ppm] 8.50 (s, 1H), 7.94-7.82 (m, 3H), 7.77 (d, J = 8.2 Hz, 1H), 7.70 (d, J = 7.6 Hz, 1H), 7.62-7.49 (m, 2H), 6.79 (t, J = 55.2 Hz, 1H), 4.09 (q, J = 7.1 Hz, 2H), 1.82-1.73 (m, 2H), 1.35-1.27 (m, 2H), 1.03 (t, J = 7.1 Hz, 3H). LCMS (Analytical Method A) Rt = 1.47 min, MS (ESIpos): m/z = 541.05 (M+H)+. |
| 271A | Ethyl 2-[6-(difluoromethyl)pyridin-3-yl]-3-fluoro-5-[({1-[2-fluoro-4-(trifluoromethoxy)phenyl]cyclopropyl}carbonyl)amino]benzoate | $^1$H NMR (250 MHz, Methanol-d4) δ [ppm] 8.50 (s, 1H), 7.93-7.81 (m, 3H), 7.77 (d, J = 8.1 Hz, 1H), 7.62 (m, 1H), 7.25-7.15 (m, 2H), 6.79 (t, J = 55.2 Hz, 1H), 4.09 (q, J = 7.1 Hz, 2H), 1.79-1.71 (m, 2H), 1.32-1.25 (m, 2H), 1.03 (t, J = 7.1 Hz, 3H). LCMS (Analytical Method A) Rt = 1.47 min, MS (ESIpos): m/z = 557.05 (M + H)$^+$. |

-continued

| Int. | Structure | Name | Analytical Data |
|---|---|---|---|
| 272A | 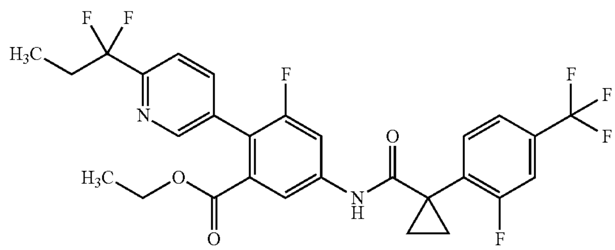 [SMILES: CCOC(=O)c1cc(NC(=O)C2(c3ccc(C(F)(F)F)cc3F)CC2)cc(F)c1-c1ccc(C(F)(F)CC)nc1] | Ethyl 2-[6-(1,1-difluoropropyl)pyridin-3-yl]-3-fluoro-5-[({1-[2-fluoro-4-(trifluoromethyl)phenyl]cyclopropyl}carbonyl)amino]benzoate | $^1$H NMR (250 MHz, Chloroform-d) δ [ppm] 8.50 (s, 1H), 7.97 (dd, J = 11.3, 2.2 Hz, 1H), 7.75-7.47 (m, 5H), 7.39 (s, 1H), 7.12 (s, 1H), 4.05 (q, J = 7.2 Hz, 2H), 2.40 (td, J = 16.7, 7.6 Hz, 2H), 1.92-1.85 (m, 2H), 1.29-1.23 (m, 2H), 1.06 (t, J = 7.5 Hz, 3H), 0.94 (t, J = 7.1 Hz, 3H). LCMS (Analytical Method A) Rt = 1.49 min, MS (ESIpos): m/z = 569.2 (M + H)$^+$. |
| 273A | 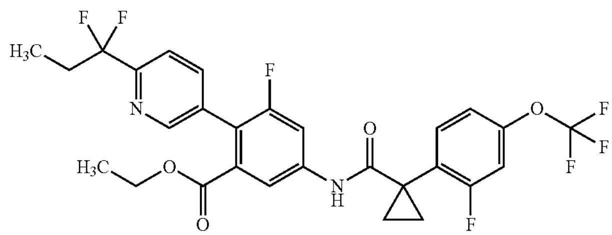 [SMILES: CCOC(=O)c1cc(NC(=O)C2(c3ccc(OC(F)(F)F)cc3F)CC2)cc(F)c1-c1ccc(C(F)(F)CC)nc1] | Ethyl 2-[6-(1,1-difluoropropyl)pyridin-3-yl]-3-fluoro-5-[({1-[2-fluoro-4-(trifluoromethoxy)phenyl]cyclopropyl}carbonyl)amino]benzoate | $^1$H NMR (250 MHz, Chloroform-d) δ [ppm] 8.50 (s, 1H), 7.96 (dd, J = 11.3, 2.2 Hz, 1H), 7.75-7.65 (m, 2H), 7.58-7.49 (m, 1H), 7.41-7.37 (m, 1H), 7.21-7.08 (m, 3H), 4.06 (q, J = 7.1 Hz, 2H), 2.40 (td, J = 16.7, 7.6 Hz, 2H), 1.89-1.82 (m, 2H), 1.26-1.20 (m, 2H), 1.06 (t, J = 7.5 Hz, 3H), 0.95 (t, J = 7.1 Hz, 3H). LCMS (Analytical Method A) Rt = 1.49 min, MS (ESIpos): m/z = 585.25 (M + H)$^+$. |
| 274A | 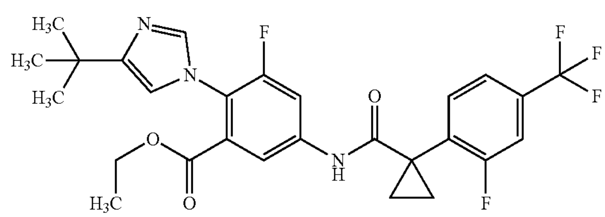 [SMILES: CCOC(=O)c1cc(NC(=O)C2(c3ccc(C(F)(F)F)cc3F)CC2)cc(F)c1-n1cnc(C(C)(C)C)c1] | Ethyl 2-(4-tert-butyl-1H-imidazol-1-yl)-3-fluoro-5-[({1-[2-fluoro-4-(trifluoromethyl)phenyl]cyclopropyl}carbonyl)amino]benzoate | $^1$H NMR (500 MHz, Chloroform-d) δ [ppm] 8.03 (m, 1H), 7.64-7.58 (m, 1H), 7.57-7.52 (m, 1H), 7.50-7.45 (m, 1H), 7.39 (s, 1H), 7.25-7.22 (m, 1H), 7.11 (s, 1H), 6.64 (s, 1H), 4.07 (q, J = 7.1 Hz, 2H), 1.90-1.81 (m, 2H), 1.31 (s, 9H), 1.27-1.19 (m, 2H), 1.04 (t, J = 7.2 Hz, 3H). LCMS (Analytical Method A): Rt = 1.33 mins; MS (ESIpos) m/z = 536.1 (M + H)$^+$. |
| 275A | 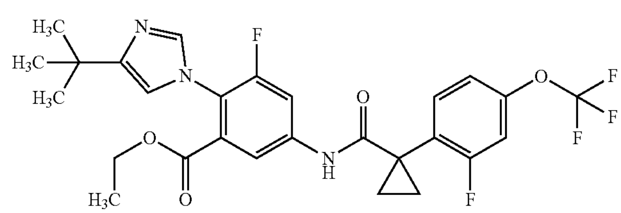 [SMILES: CCOC(=O)c1cc(NC(=O)C2(c3ccc(OC(F)(F)F)cc3F)CC2)cc(F)c1-n1cnc(C(C)(C)C)c1] | Ethyl 2-(4-tert-butyl-1H-imidazol-1-yl)-3-fluoro-5-[({1-[2-fluoro-4-(trifluoromethoxy)phenyl]cyclopropyl}carbonyl)amino]benzoate | $^1$H NMR (500 MHz, Chloroform-d) δ [ppm] 8.03 (m, 1H), 7.54-7.46 (m, 1H), 7.38 (s, 1H), 7.25-7.23 (m, 1H), 7.17 (s, 1H), 7.16-7.12 (m, 1H), 7.11-7.07 (m, 1H), 6.64 (s, 1H), 4.07 (q, J = 7.1 Hz, 2H), 1.85-1.78 (m, 2H), 1.31 (s, 9H), 1.24-1.19 (m, 2H), 1.04 (t, J = 7.2 Hz, 3H). LCMS (Analytical Method A): Rt = 1.27 mins; MS (ESIpos) m/z = 552.05 (M + H)$^+$. |
| 276A | 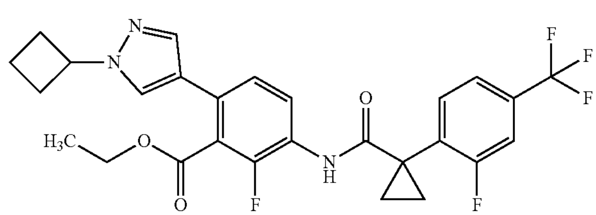 [SMILES: CCOC(=O)c1c(-c2cnn(C3CCC3)c2)ccc(NC(=O)C2(c3ccc(C(F)(F)F)cc3F)CC2)c1F] | Ethyl 6-(1-cyclobutyl-1H-pyrazol-4-yl)-2-fluoro-3-[({1-[2-fluoro-4-(trifluoromethyl)phenyl]cyclopropyl}carbonyl)amino]benzoate | $^1$H NMR (250 MHz, Methanol-d4) δ [ppm] 7.74-7.71 (m, 1H), 7.69-7.59 (m, 1H), 7.58-7.42 (m, 4H), 7.16 (dd, J = 8.4, 1.2 Hz, 1H), 4.74-4.68 (m, 1H), 4.21 (q, J = 7.1 Hz, 2H), 2.55-2.31 (m, 4H), 1.88-1.75 (m, 2H), 1.68-1.62 (m, 2H), 1.21-1.19 (m, 2H), 1.14 (t, J = 7.1 Hz, 3H). LCMS (Analytical Method A) Rt = 1.40 min, MS (ESIpos): m/z = 534.1 (M + H)$^+$. |

-continued

| Int. | Structure | Name | Analytical Data |
|---|---|---|---|
| 277A | 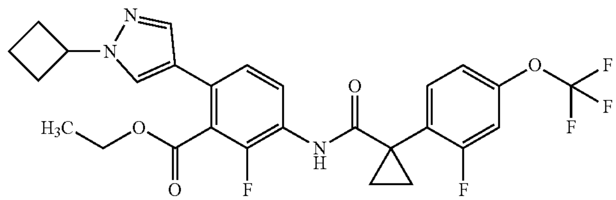 [SMILES: CCOC(=O)c1c(-c2cnn(C3CCC3)c2)ccc(NC(=O)C2(c3ccc(OC(F)(F)F)cc3F)CC2)c1F] | Ethyl 6-(1-cyclobutyl-1H-pyrazol-4-yl)-2-fluoro-3-[({1-[2-fluoro-4-(trifluoromethoxy)phenyl]cyclopropyl}carbonyl)amino]benzoate | $^1$H NMR (250 MHz, Methanol-d4) δ [ppm] 7.83 (s, 1H), 7.73-7.60 (m, 2H), 7.59 (s, 1H), 7.30-7.19 (m, 3H), 4.84-4.78 (m, 1H), 4.31 (q, J = 7.1 Hz, 2H), 2.61-2.46 (m, 4H), 1.92 (m, 2H), 1.75-1.69 (m, 2H), 1.32-1.30 (m, 2H), 1.24 (t, J = 7.2 Hz, 3H). LCMS (Analytical Method A) Rt = 1.42 min, MS (ESIpos): m/z = 550.1 (M + H)$^+$. |
| 278A | 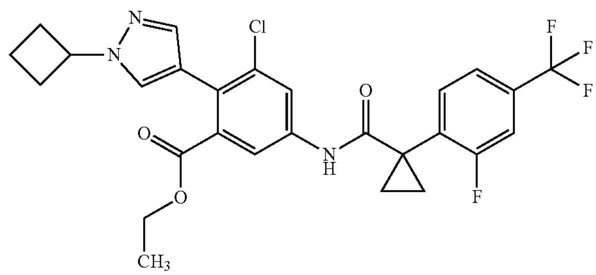 [SMILES: CCOC(=O)c1cc(NC(=O)C2(c3ccc(C(F)(F)F)cc3F)CC2)cc(Cl)c1-c1cnn(C2CCC2)c1] | Ethyl 3-chloro-2-(1-cyclobutyl-1H-pyrazol-4-yl)-5-[({1-[2-fluoro-4-(trifluoromethyl)phenyl]cyclopropyl}carbonyl)amino]benzoate | $^1$H NMR (500 MHz, DMSO-d6) δ [ppm] 9.26 (s, 1H), 7.96 (d, J = 2.2 Hz, 1H), 7.81 (s, 1H), 7.77 (d, J = 2.2 Hz, 1H), 7.72-7.66 (m, 2H), 7.63-7.57 (m, 1H), 7.39 (s, 1H), 4.85 (m, 1H), 4.04 (q, J = 7.1 Hz, 2H), 2.48-2.42 (m, 2H), 2.41-2.30 (m, 2H), 1.84-1.72 (m, 2H), 1.68-1.61 (m, 2H), 1.28-1.23 (m, 2H), 0.98 (t, J = 7.1 Hz, 3H). LCMS (Analytical Method A) Rt = 1.44 min, MS (ESIpos): m/z = 550.4/551.7 (M + H)$^+$. |
| 279A | 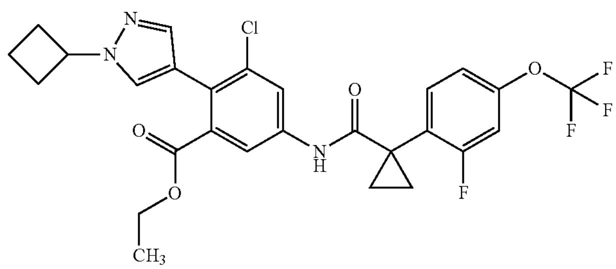 [SMILES: CCOC(=O)c1cc(NC(=O)C2(c3ccc(OC(F)(F)F)cc3F)CC2)cc(Cl)c1-c1cnn(C2CCC2)c1] | Ethyl 3-chloro-2-(1-cyclobutyl-1H-pyrazol-4-yl)-5-[({1-[2-fluoro-4-(trifluoromethoxy)phenyl]cyclopropyl}carbonyl)amino]benzoate | $^1$H NMR (500 MHz, DMSO-d6) δ [ppm] 9.23 (s, 1H), 7.97 (d, J = 2.2 Hz, 1H), 7.81 (m, 1H), 7.78 (d, J = 2.2 Hz, 1H), 7.62-7.56 (m, 1H), 7.42-7.36 (m, 2H), 7.27-7.22 (m, 1H), 4.85 (m, 1H), 4.04 (q, J = 7.1 Hz, 2H), 2.48-2.42 (m, 2H), 2.40-2.32 (m, 2H), 1.84-1.72 (m, 2H), 1.65-1.59 (m, 2H), 1.24-1.19 (m, 2H), 0.98 (t, J = 7.1 Hz, 3H). LCMS (Analytical Method A) Rt = 1.43 min, MS (ESIpos): m/z = 566.1/ 567.8 (M + H)$^+$. |
| 280A | 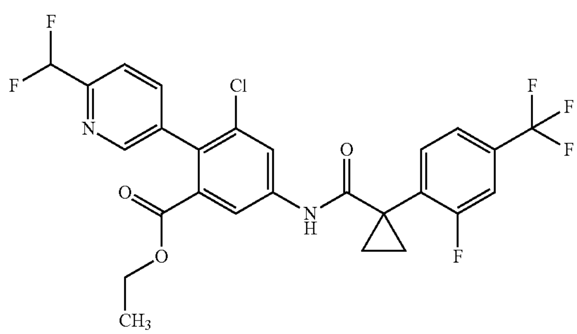 [SMILES: CCOC(=O)c1cc(NC(=O)C2(c3ccc(C(F)(F)F)cc3F)CC2)cc(Cl)c1-c1ccc(C(F)F)nc1] | Ethyl 3-chloro-2-[6-(difluoromethyl)pyridin-3-yl]-5-[({1-[2-fluoro-4-(trifluoromethyl)phenyl]cyclopropyl}carbonyl)amino]benzoate | $^1$H NMR (500 MHz, DMSO-d6) δ [ppm] 9.45 (s, 1H), 8.48 (d, J = 1.7 Hz, 1H), 8.16-8.11 (m, 2H), 7.85 (dd, J = 8.0, 2.1 Hz, 1H), 7.78-7.67 (m, 3H), 7.64-7.60 (m, 1H), 7.02 (t, J = 55.0 Hz, 1H), 4.02-3.88 (m, 2H), 1.73-1.64 (m, 2H), 1.31-1.27 (m, 2H), 0.86 (t, J = 7.1 Hz, 3H). LCMS (Analytical Method A) Rt = 1.49 min, MS (ESIpos): m/z = 557.0/578.7 (M + H)$^+$. |
| 281A | 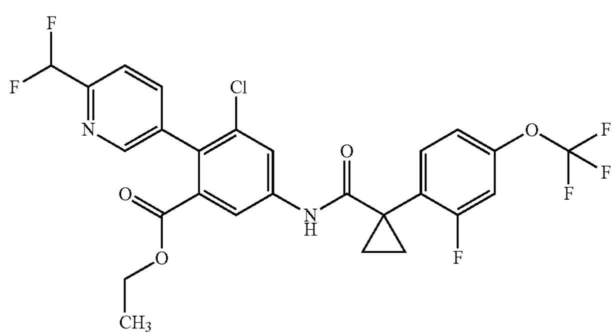 [SMILES: CCOC(=O)c1cc(NC(=O)C2(c3ccc(OC(F)(F)F)cc3F)CC2)cc(Cl)c1-c1ccc(C(F)F)nc1] | Ethyl 3-chloro-2-[6-(difluoromethyl)pyridin-3-yl]-5-[({1-[2-fluoro-4-(trifluoromethoxy)phenyl]cyclopropyl}carbonyl)amino]benzoate | $^1$H NMR (500 MHz, DMSO-d6) δ [ppm] 9.42 (s, 1H), 8.48 (d, J = 1.7 Hz, 1H), 8.16-8.11 (m, 2H), 7.85 (dd, J = 8.0, 2.1 Hz, 1H), 7.76 (d, J = 8.0 Hz, 1H), 7.61 (dd, J = 8.6, 8.6 Hz, 1H), 7.43-7.37 (m, 1H), 7.26 (d, J = 8.6 Hz, 1H), 7.02 (t, J = 55.0 Hz, 1H), 4.02-3.91 (m, 2H), 1.68-1.61 (m, 2H), 1.28-1.21 (m, 2H), 0.86 (t, J = 7.1 Hz, 3H). LCMS (Analytical Method A) Rt = 1.49 min, MS (ESIpos): m/z = 573.0/574.6 (M + H)$^+$. |

-continued

| Int. | Structure | Name | Analytical Data |
|---|---|---|---|
| 282A | 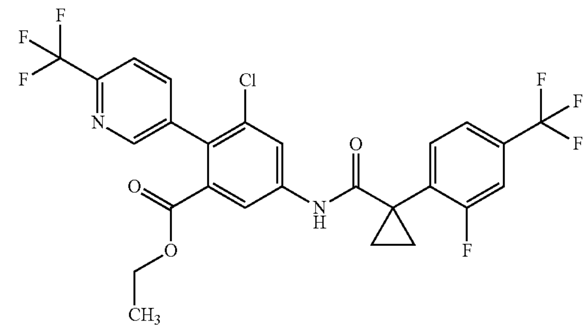 [SMILES: CCOC(=O)c1cc(NC(=O)C2(c3ccc(C(F)(F)F)cc3F)CC2)cc(Cl)c1-c1ccc(C(F)(F)F)nc1] | Ethyl 3-chloro-5-[({1-[2-fluoro-4-(trifluoromethyl)phenyl]cyclopropyl}carbonyl)amino]-2-[6-(trifluoromethyl)pyridin-3-yl]benzoate | $^1$H NMR (500 MHz, DMSO-d6) δ [ppm] 9.55 (s, 1H), 8.68-8.62 (m, 1H), 8.24 (d, J = 2.1 Hz, 1H), 8.22 (d, J = 2.1 Hz, 1H), 8.07-8.00 (m, 2H), 7.81-7.75 (m, 2H), 7.72-7.66 (m, 1H), 4.07-3.99 (m, 2H), 1.79-1.72 (m, 2H), 1.41-1.31 (m, 2H), 0.92 (t, J = 7.1 Hz, 3H). LCMS (Analytical Method A) Rt = 1.49 min, MS (ESIpos): m/z = 575.0/577.9 (M + H)$^+$. |
| 283A | 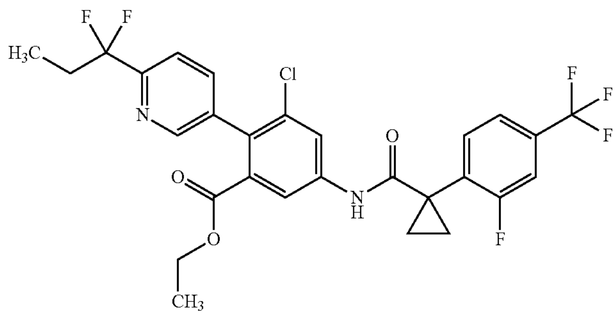 [SMILES: CCOC(=O)c1cc(NC(=O)C2(c3ccc(C(F)(F)F)cc3F)CC2)cc(Cl)c1-c1ccc(C(F)(F)CC)nc1] | Ethyl 3-chloro-2-[6-(1,1-difluoropropyl)pyridin-3-yl]-5-[({1-[2-fluoro-4-(trifluoromethyl)phenyl]cyclopropyl}carbonyl)amino]benzoate | $^1$H NMR (500 MHz, DMSO-d6) δ [ppm] 9.45 (s, 1H), 8.47 (d, J = 1.7 Hz, 1H), 8.13 (d, J = 2.2 Hz, 1H), 8.12 (d, J = 2.2 Hz, 1H), 7.82 (dd, J = 8.1, 2.1 Hz, 1H), 7.76-7.67 (m, 3H), 7.65-7.60 (m, 1H), 4.01-3.88 (m, 2H), 2.44-2.28 (m, 2H), 1.71-1.64 (m, 2H), 1.36-1.24 (m, 2H), 0.95 (t, J = 7.5 Hz, 3H), 0.84 (t, J = 7.1 Hz, 3H). LCMS (Analytical Method A) Rt = 1.56 min, MS (ESIpos): m/z = 585.0/586.9 (M + H)$^+$. |
| 284A | 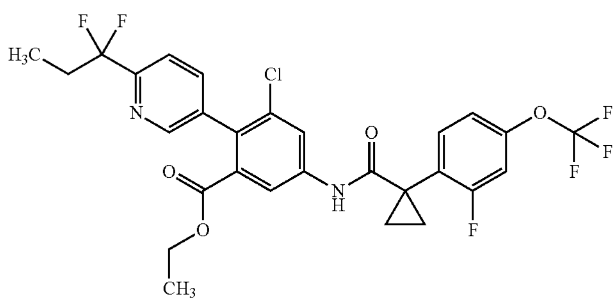 [SMILES: CCOC(=O)c1cc(NC(=O)C2(c3ccc(OC(F)(F)F)cc3F)CC2)cc(Cl)c1-c1ccc(C(F)(F)CC)nc1] | Ethyl 3-chloro-2-[6-(1,1-difluoropropyl)pyridin-3-yl]-5-[({1-[2-fluoro-4-(trifluoromethoxy)phenyl]cyclopropyl}carbonyl)amino]benzoate | $^1$H NMR (500 MHz, DMSO-d6) δ [ppm] 9.41 (s, 1H), 8.47 (d, J = 1.6 Hz, 1H), 8.13 (d, J = 2.1 Hz, 1H), 8.12 (d, J = 2.2 Hz, 1H), 7.82 (dd, J = 8.1, 2.1 Hz, 1H), 7.74 (d, J = 8.0 Hz, 1H), 7.61 (dd, J = 8.5, 8.5 Hz, 1H), 7.43-7.35 (m, 1H), 7.29-7.23 (m, 1H), 3.99-3.91 (m, 2H), 2.43-2.27 (m, 2H), 1.68-1.60 (m, 2H), 1.29-1.21 (m, 2H), 0.95 (t, J = 7.5 Hz, 3H), 0.84 (t, J = 7.1 Hz, 3H). LCMS (Analytical Method A) Rt = 1.58 min, MS (ESIpos): m/z = 601.0/602.7 (M + H)$^+$. |
| 285A | 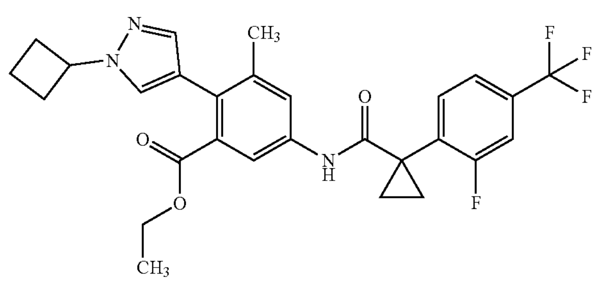 [SMILES: CCOC(=O)c1cc(NC(=O)C2(c3ccc(C(F)(F)F)cc3F)CC2)cc(C)c1-c1cnn(C2CCC2)c1] | Ethyl 2-(1-cyclobutyl-1H-pyrazol-4-yl)-5-[({1-[2-fluoro-4-(trifluoromethyl)phenyl]cyclopropyl}carbonyl)amino]-3-methylbenzoate | $^1$H NMR (250 MHz, Methanol-d4) δ [ppm] 7.71 (m, 1H), 7.63-7.47 (m, 5H), 7.37 (m, 1H), 4.91-4.87 (m, 1H), 4.08 (q, J = 7.1 Hz, 2H), 2.63-2.45 (m, 4H), 2.19 (s, 3H), 1.98-1.84 (m, 2H), 1.77-1.70 (m, 2H), 1.31-1.25 (m, 2H), 1.07 (t, J = 7.1 Hz, 3H). LCMS (Analytical Method A) Rt = 1.44 min, MS (ESIpos): m/z = 530.55 (M + H)$^+$. |
| 286A | 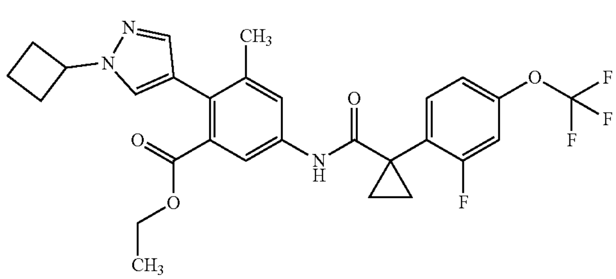 [SMILES: CCOC(=O)c1cc(NC(=O)C2(c3ccc(OC(F)(F)F)cc3F)CC2)cc(C)c1-c1cnn(C2CCC2)c1] | Ethyl 2-(1-cyclobutyl-1H-pyrazol-4-yl)-5-[({1-[2-fluoro-4-(trifluoromethoxy)phenyl]cyclopropyl}carbonyl)amino]-3-methylbenzoate | $^1$H NMR (250 MHz, Methanol-d4) δ [ppm] 7.66-7.56 (m, 3H), 7.49 (d, J = 1.8 Hz, 1H), 7.37 (m, 1H), 7.24-7.15 (m, 2H), 4.94-4.88 (m, 1H), 4.08 (q, J = 7.1 Hz, 2H), 2.67-2.43 (m, 4H), 2.19 (s, 3H), 1.98-1.86 (m, 2H), 1.75-1.68 (m, 2H), 1.27-1.21 (m, 2H), 1.07 (t, J = 7.1 Hz, 3H). LCMS (Analytical Method A) Rt = 1.43 min, MS (ESIpos): m/z = 546.45 (M + H)$^+$. |

-continued

| Int. | Structure | Name | Analytical Data |
|---|---|---|---|
| 287A | 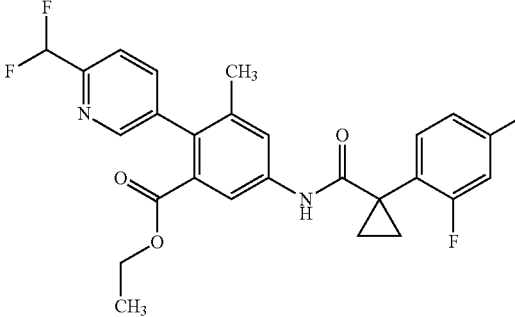 | Ethyl 2-[6-(difluoromethyl)pyridin-3-yl]-5-[({1-[2-fluoro-4-(trifluoromethyl)phenyl]cyclopropyl}carbonyl)amino]-3-methylbenzoate | $^1$H NMR (250 MHz, Methanol-d4) δ [ppm] 8.39 (s, 1H), 7.94 (d, J = 2.0 Hz, 1H), 7.82-7.73 (m, 2H), 7.71 (d, J = 7.4 Hz, 1H), 7.67 (d, J = 1.8 Hz, 1H), 7.62-7.50 (m, 2H), 6.79 (t, J = 55.3 Hz, 1H), 4.01 (q, J = 7.0 Hz, 2H), 2.06 (s, 3H), 1.80-1.72 (m, 2H), 1.34-1.25 (m, 2H), 0.98 (t, J = 7.1 Hz, 3H). LCMS (Analytical Method A) Rt = 1.45 min, MS (ESIpos): m/z = 537.05 (M + H)$^+$. |
| 288A | 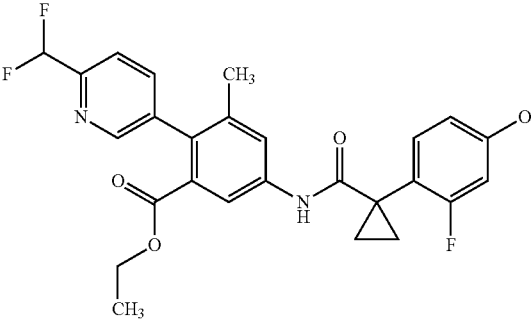 | Ethyl 2-[6-(difluoromethyl)pyridin-3-yl]-5-[({1-[2-fluoro-4-(trifluoromethoxy)phenyl]cyclopropyl}carbonyl)amino]-3-methylbenzoate | 1H NMR (250 MHz, Methanol-d4) δ [ppm] 8.39 (s, 1H), 7.93 (d, J = 2.2 Hz, 1H), 7.83-7.72 (m, 2H), 7.68-7.58 (m, 2H), 7.24-7.16 (m, 2H), 6.80 (t, J = 55.3 Hz, 1H), 4.01 (q, J = 7.1 Hz, 2H), 2.06 (s, 3H), 1.77-1.69 (m, 2H), 1.29-1.23 (m, 2H), 0.99 (t, J = 7.1 Hz, 3H). LCMS (Analytical Method A) Rt = 1.46 min, MS (ESIpos): m/z = 553.05 (M + H)$^+$. |
| 289A | 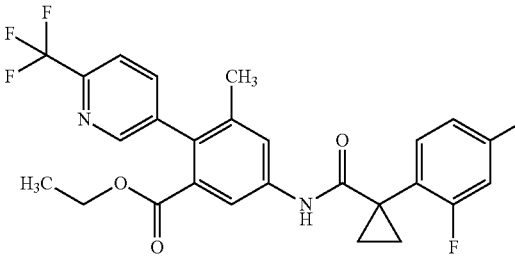 | Ethyl 5-[({1-[2-fluoro-4-(trifluoromethyl)phenyl]cyclopropyl}carbonyl)amino]-3-methyl-2-[6-(trifluoromethyl)pyridin-3-yl]benzoate | $^1$H NMR (250 MHz, Chloroform-d) δ [ppm] 8.50 (s, 1H), 7.80 (d, J = 1.9 Hz, 1H), 7.74 (d, J = 8.1 Hz, 1H), 7.71-7.60 (m, 3H), 7.57 (d, J = 8.1 Hz, 1H), 7.50 (d, J = 9.7 Hz, 1H), 7.06-7.00 (m, 1H), 4.01 (q, J = 7.2, 6.7 Hz, 2H), 2.06 (s, 3H), 1.93-1.83 (m, 2H), 1.28-1.22 (m, 2H), 0.95 (t, J = 7.1 Hz, 3H). LCMS (Analytical Method A) Rt = 1.44 min, MS (ESIpos): m/z = 555.05 (M + H)$^+$. |
| 290A | 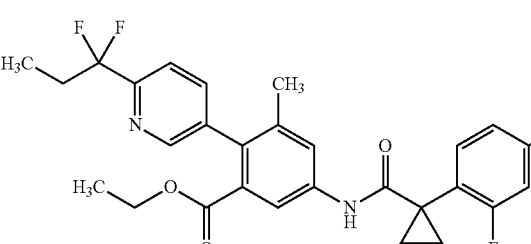 | Ethyl 2-[6-(1,1-difluoropropyl)pyridin-3-yl]-5-[({1-[2-fluoro-4-(trifluoromethyl)phenyl]cyclopropyl}carbonyl)amino]-3-methylbenzoate | $^1$H NMR (250 MHz, Chloroform-d) δ [ppm] 8.42 (s, 1H), 7.79 (s, 1H), 7.71-7.64 (m, 2H), 7.64-7.54 (m, 3H), 7.50 (d, J = 9.6 Hz, 1H), 7.01 (s, 1H), 3.99 (q, J = 7.0 Hz, 2H), 2.41 (td, J = 16.7, 7.5 Hz, 2H), 2.07 (s, 3H), 1.93-1.83 (m, 2H), 1.28-1.20 (m, 2H), 1.07 (t, J = 7.5 Hz, 3H), 0.92 (t, J = 7.1 Hz, 3H). LCMS (Analytical Method A) Rt = 1.49 min, MS (ESIpos): m/z = 565.55 (M + H)$^+$. |
| 291A | 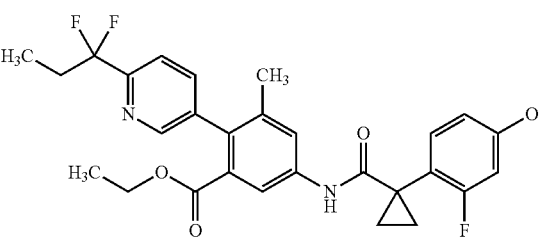 | Ethyl 2-[6-(1,1-difluoropropyl)pyridin-3-yl]-5-[({1-[2-fluoro-4-(trifluoromethoxy)phenyl]cyclopropyl}carbonyl)amino]-3-methylbenzoate | $^1$H NMR (250 MHz, Chloroform-d) δ [ppm] 8.41 (s, 1H), 7.80 (d, J = 2.1 Hz, 1H), 7.68 (d, J = 8.1 Hz, 1H), 7.62-7.49 (m, 3H), 7.20-7.05 (m, 3H), 3.99 (q, J = 7.0 Hz, 2H), 2.41 (td, J = 16.7, 7.6 Hz, 2H), 2.07 (s, 3H), 1.88-1.80 (m, 2H), 1.25-1.18 (m, 2H), 1.07 (t, J = 7.5 Hz, 3H), 0.93 (t, J = 7.1 Hz, 4H). LCMS (Analytical Method A) Rt = 1.50 min, MS (ESIpos): m/z = 581.05 (M +H)$^+$. |

| Int. | Structure | Name | Analytical Data |
|---|---|---|---|
| 292A | 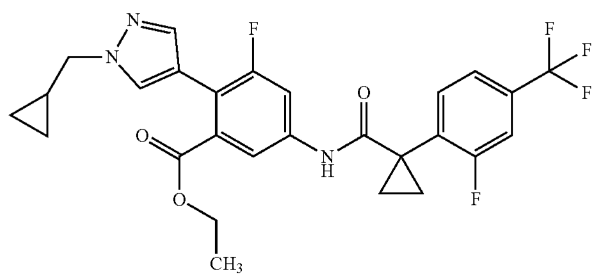 [SMILES: CCOC(=O)c1cc(NC(=O)C2(c3ccc(C(F)(F)F)cc3F)CC2)cc(F)c1-c1cnn(CC2CC2)c1] | Ethyl 2-[1-(cyclopropylmethyl)-1H-pyrazol-4-yl]-3-fluoro-5-[({1-[2-fluoro-4-(trifluoromethyl)phenyl]cyclopropyl}carbonyl)amino]benzoate | $^1$H NMR (250 MHz, Methanol-d4) δ [ppm] 7.78 (s, 1H), 7.74-7.61 (m, 2H), 7.60-7.47 (m, 4H), 4.21 (q, J = 7.1 Hz, 2H), 4.05 (d, J = 7.1 Hz, 2H), 1.79-1.72 (m, 2H), 1.31-1.28 (m, 2H), 1.19 (t, J = 7.1 Hz, 3H), 0.93-0.87 (m, 1H), 0.69-0.59 (m, 2H), 0.47-0.38 (m, 2H). LCMS (Analytical Method A) Rt = 1.52 min, MS (ESIpos): m/z = 534.10 (M + H)$^+$. |
| 293A | 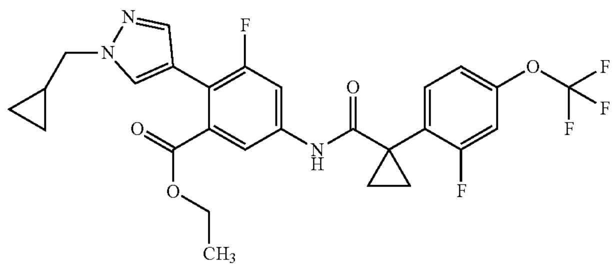 [SMILES: CCOC(=O)c1cc(NC(=O)C2(c3ccc(OC(F)(F)F)cc3F)CC2)cc(F)c1-c1cnn(CC2CC2)c1] | Ethyl 2-[1-(cyclopropylmethyl)-1H-pyrazol-4-yl]-3-fluoro-5-[({1-[2-fluoro-4-(trifluoromethoxy)phenyl]cyclopropyl}carbonyl)amino]benzoate | $^1$H NMR (250 MHz, Methanol-d4) δ [ppm] 7.78 (s, 1H), 7.70-7.55 (m, 3H), 7.48 (s, 1H), 7.22-7.19 (m, 1H), 7.17 (s, 1H), 4.21 (q, J = 7.1 Hz, 2H), 4.05 (d, J = 7.1 Hz, 2H), 1.76-1.68 (m, 2H), 1.31-1.27 (m, 2H), 1.19 (t, J = 7.1 Hz, 3H), 0.92-0.89 (m, 1H), 0.69-0.59 (m, 2H), 0.47-0.39 (m, 2H). LCMS (Analytical Method A) Rt = 1.50 min, MS (ESIpos): m/z = 550.15 (M + H)$^+$. |
| 294A | 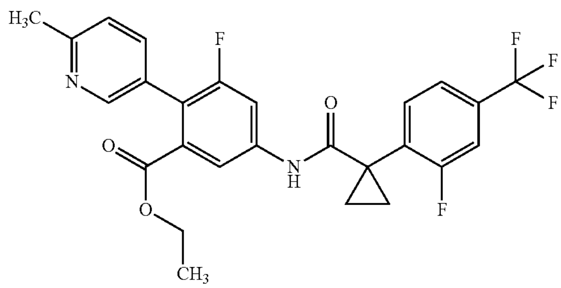 [SMILES: CCOC(=O)c1cc(NC(=O)C2(c3ccc(C(F)(F)F)cc3F)CC2)cc(F)c1-c1ccc(C)nc1] | Ethyl 3-fluoro-5-[({1-[2-fluoro-4-(trifluoromethyl)phenyl]cyclopropyl}carbonyl)amino]-2-(6-methylpyridin-3-yl)benzoate | $^1$H NMR (500 MHz, Chloroform-d) δ [ppm] 8.35-8.29 (m, 1H), 7.86 (dd, J = 11.1, 2.2 Hz, 1H), 7.65-7.59 (m, 1H), 7.57-7.52 (m, 1H), 7.52-7.44 (m, 2H), 7.34-7.31 (m, 1H), 7.19 (d, J = 8.0 Hz, 1H), 7.09-7.04 (m, 1H), 4.05 (q, J = 7.1 Hz, 2H), 2.59 (s, 3H), 1.91-1.81 (m, 2H), 1.26-1.17 (m, 2H), 0.97 (t, J = 7.1 Hz, 3H). LCMS (Analytical Method A): Rt = 1.31 mins, MS (ESIpos): m/z = 505 (M + H)$^+$. |
| 295A | 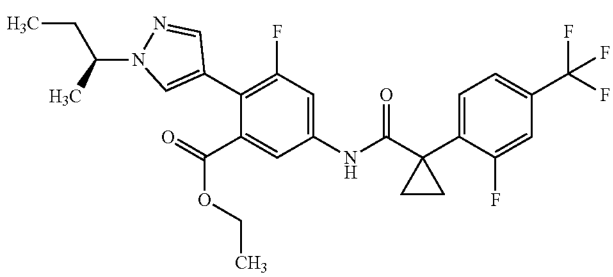 [SMILES: CCOC(=O)c1cc(NC(=O)C2(c3ccc(C(F)(F)F)cc3F)CC2)cc(F)c1-c1cnn([C@@H](C)CC)c1] | Ethyl 2-{1-[(2S)-butan-2-yl]-1H-pyrazol-4-yl}-3-fluoro-5-[({1-[2-fluoro-4-(trifluoromethyl)phenyl]cyclopropyl}carbonyl)amino]benzoate | $^1$H NMR (250 MHz, Methanol-d4) δ [ppm] 7.76-7.62 (m, 3H), 7.61-7.47 (m, 4H), 4.40-4.25 (m, 1H), 4.20 (q, J = 7.1 Hz, 2H), 2.00-1.79 (m, 2H), 1.79-1.72 (m, 2H), 1.52 (d, J = 6.8 Hz, 3H), 1.33-1.25 (m, 2H), 1.20 (t, J = 7.1 Hz, 3H), 0.83 (t, J = 7.4 Hz, 3H). LCMS (Analytical Method A) Rt = 1.58 min, MS (ESIpos): m/z = 536.15 (M + H)$^+$. |
| 296A | 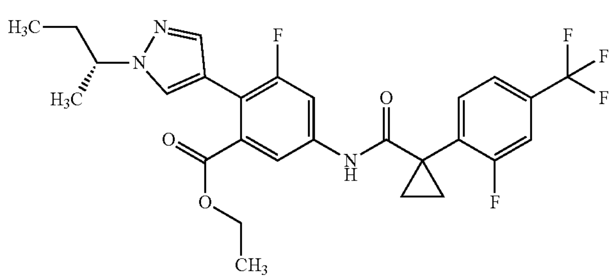 [SMILES: CCOC(=O)c1cc(NC(=O)C2(c3ccc(C(F)(F)F)cc3F)CC2)cc(F)c1-c1cnn([C@H](C)CC)c1] | Ethyl 2-{1-[(2R)-butan-2-yl]-1H-pyrazol-4-yl}-3-fluoro-5-[({1-[2-fluoro-4-(trifluoromethyl)phenyl]cyclopropyl}carbonyl)amino]benzoate | $^1$H NMR (250 MHz, Methanol-d4) δ [ppm] 7.76-7.62 (m, 3H), 7.61-7.47 (m, 4H), 4.40-4.25 (m, 1H), 4.20 (q, J = 7.1 Hz, 2H), 2.00-1.79 (m, 2H), 1.79-1.72 (m, 2H), 1.52 (d, J = 6.8 Hz, 3H), 1.33-1.25 (m, 2H), 1.20 (t, J = 7.1 Hz, 3H), 0.83 (t, J = 7.4 Hz, 3H). LCMS (Analytical Method A) Rt = 1.58 min, MS (ESIpos): m/z = 536.2 (M + H)$^+$. |

-continued

| Int. | Structure | Name | Analytical Data |
|---|---|---|---|
| 348A | 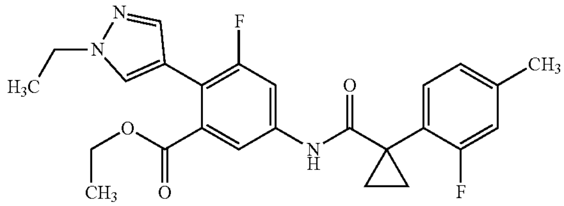 [SMILES: CCOC(=O)c1cc(NC(=O)C2(c3ccc(C)cc3F)CC2)cc(F)c1-c1cnn(CC)c1] | Ethyl 2-(1-ethyl-1H-pyrazol-4-yl)-3-fluoro-5-({[1-(2-fluoro-4-methylphenyl)cyclopropyl]carbonyl}amino)benzoate | $^1$H NMR (500 MHz, DMSO-d6) δ [ppm] 9.15 (s, 1H), 7.80 (s, 1H), 7.76 (dd, J = 12.8, 2.1 Hz, 1H), 7.63 (d, J = 1.8 Hz, 1H), 7.39 (s, 1H), 7.34-7.27 (m, 1H), 7.05-7.00 (m, 2H), 4.18-4.09 (m, 4H), 2.33 (s, 3H), 1.59-1.51 (m, 2H), 1.37 (t, J = 7.3 Hz, 3H), 1.14-1.08 (m, 5H). LCMS (Analytical Method A) Rt = 1.31 min, MS (ESIpos): m/z = 454.2 (M + H)$^+$. |
| 349A | 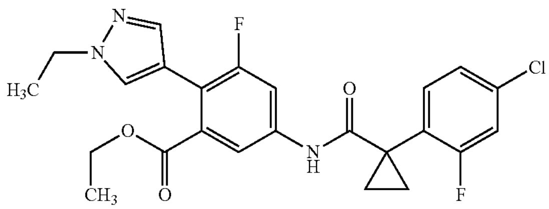 [SMILES: CCOC(=O)c1cc(NC(=O)C2(c3ccc(Cl)cc3F)CC2)cc(F)c1-c1cnn(CC)c1] | Ethyl 5-({[1-(4-chloro-2-fluorophenyl)cyclopropyl]carbonyl}amino)-2-(1-ethyl-1H-pyrazol-4-yl)-3-fluorobenzoate | $^1$H NMR (500 MHz, DMSO-d6) δ [ppm] 9.21 (s, 1H), 7.80 (s, 1H), 7.75 (dd, J = 12.7, 2.1 Hz, 1H), 7.62 (d, J = 1.9 Hz, 1H), 7.50-7.46 (m, 1H), 7.43 (dd, J = 10.0, 2.0 Hz, 1H), 7.39 (s, 1H), 7.30 (dd, J = 8.3, 2.0 Hz, 1H), 4.21-4.08 (m, 4H), 1.62-1.56 (m, 2H), 1.37 (t, J = 7.3 Hz, 3H), 1.20-1.14 (m, 2H), 1.10 (t, J = 7.1 Hz, 3H). LCMS (Analytical Method A) Rt = 1.32 min, MS (ESIpos): m/z = 474.1/476.2 (M + H)$^+$. |
| 350A | 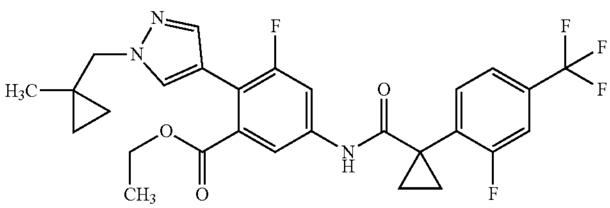 [SMILES: CCOC(=O)c1cc(NC(=O)C2(c3ccc(C(F)(F)F)cc3F)CC2)cc(F)c1-c1cnn(CC2(C)CC2)c1] | Ethyl 3-fluoro-5-[({1-[2-fluoro-4-(trifluoromethyl)phenyl]cyclopropyl}carbonyl)amino]-2-{1-[(1-methylcyclopropyl)methyl]-1H-pyrazol-4-yl}benzoate | $^1$H NMR (500 MHz, Chloroform-d) δ [ppm] 7.72 (dd, J = 11.7, 2.2 Hz, 1H), 7.64-7.57 (m, 2H), 7.56-7.51 (m, 1H), 7.50-7.43 (m, 2H), 7.14-7.11 (m, 1H), 7.00 (s, 1H), 4.18 (q, J = 7.1 Hz, 2H), 3.98 (s, 2H), 1.90-1.76 (m, 2H), 1.23-1.19 (m, 2H), 1.17 (t, J = 7.1 Hz, 3H), 1.04 (s, 3H), 0.67-0.57 (m, 2H), 0.49-0.39 (m, 2H). LCMS (Analytical Method A): Rt = 1.42 min; MS (ESIpos): m/z = 548.15 (M + H)$^+$. |
| 351A | 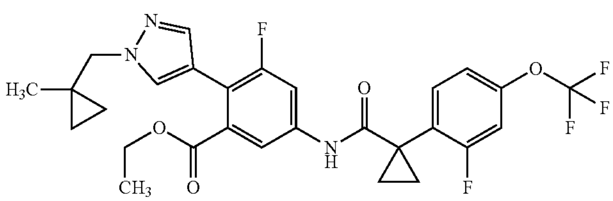 [SMILES: CCOC(=O)c1cc(NC(=O)C2(c3ccc(OC(F)(F)F)cc3F)CC2)cc(F)c1-c1cnn(CC2(C)CC2)c1] | Ethyl 3-fluoro-5-[({1-[2-fluoro-4-(trifluoromethoxy)phenyl]cyclopropyl}carbonyl)amino]-2-{1-[(1-methylcyclopropyl)methyl]-1H-pyrazol-4-yl}benzoate | $^1$H NMR (500 MHz, Chloroform-d) δ 7.72 (dd, J = 11.8, 2.3 Hz, 1H), 7.59 (d, J = 1.3 Hz, 1H), 7.53-7.46 (m, 2H), 7.16-7.02 (m, 4H), 4.19 (q, J = 7.1 Hz, 2H), 3.98 (s, 2H), 1.84-1.77 (m, 2H), 1.22-1.14 (m, 5H), 1.05 (s, 3H), 0.66-0.58 (m, 2H), 0.51-0.42 (m, 2H). LCMS (Analytical Method A): Rt = 1.44 min; MS (ESIpos): m/z = 564.1 (M + H)$^+$. |
| 354A | 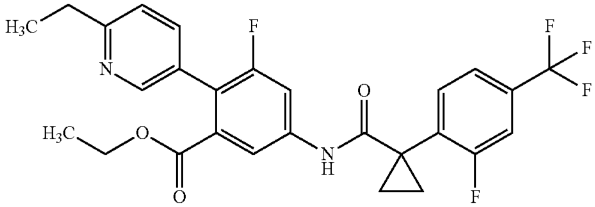 [SMILES: CCOC(=O)c1cc(NC(=O)C2(c3ccc(C(F)(F)F)cc3F)CC2)cc(F)c1-c1ccc(CC)nc1] | Ethyl 2-(6-ethylpyridin-3-yl)-3-fluoro-5-[({1-[2-fluoro-4-(trifluoromethyl)phenyl]cyclopropyl}carbonyl)amino]benzoate | $^1$H NMR (500 MHz, Chloroform-d) δ [ppm] 8.35 (d, J = 2.2 Hz, 1H), 7.88 (dd, J = 11.2, 2.2 Hz, 1H), 7.65-7.59 (m, 1H), 7.57-7.52 (m, 1H), 7.51 (dd, J = 8.0, 1.7 Hz, 1H), 7.49-7.45 (m, 1H), 7.34-7.30 (m, 1H), 7.20 (d, J = 8.0 Hz, 1H), 7.07 (s, 1H), 4.04 (q, J = 7.1 Hz, 2H), 2.86 (q, J = 7.6 Hz, 2H), 1.91-1.80 (m, 2H), 1.33 (t, J = 7.6 Hz, 3H), 1.26-1.17 (m, 2H), 0.93 (t, J = 7.1 Hz, 3H). LCMS (Analytical Method A): Rt = 1.28 mins; MS (ESIpos): m/z = 519 (M + H)$^+$. |

| Int. | Structure | Name | Analytical Data |
|---|---|---|---|
| 357A | 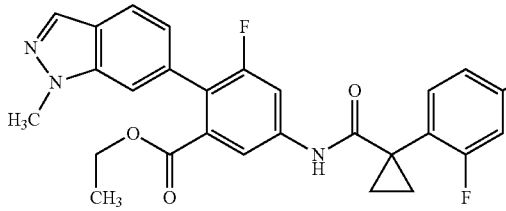 | Ethyl 3-fluoro-5-[({1-[2-fluoro-4-(trifluoromethyl)phenyl]cyclopropyl}carbonyl)amino]-2-(1-methyl-1H-indazol-6-yl)benzoate | $^1$H NMR (250 MHz, DMSO-d6) δ [ppm] 9.41 (s, 1H), 8.07 (d, J = 0.9 Hz, 1H), 7.91-7.80 (m, 2H), 7.79-7.58 (m, 4H), 7.53-7.47 (m, 1H), 7.01-6.89 (m, 1H), 4.03 (s, 3H), 3.93 (q, J = 7.1 Hz, 2H), 1.75-1.62 (m, 2H), 1.33-1.24 (m, 2H), 0.76 (t, J = 7.1 Hz, 3H). LCMS (Analytical Method A) Rt = 1.47 min, MS (ESIpos): m/z = 544.2 (M + H)$^+$. |
| 358A | 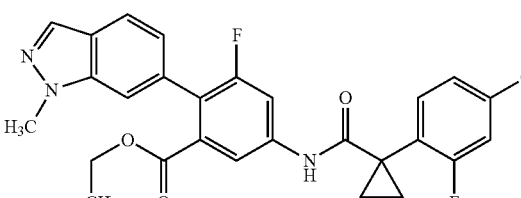 | Ethyl 3-fluoro-5-[({1-[2-fluoro-4-(trifluoromethoxy)phenyl]cyclopropyl}carbonyl)amino]-2-(1-methyl-1H-indazol-6-yl)benzoate | $^1$H NMR (250 MHz, DMSO-d6) δ [ppm] 9.38 (s, 1H), 8.07 (d, J = 0.9 Hz, 1H), 7.90-7.81 (m, 2H), 7.76 (dd, J = 8.3, 0.7 Hz, 1H), 7.62 (dd, J = 8.5 Hz, 1H), 7.53-7.49 (m, 1H), 7.40 (dd, J = 10.6, 1.6 Hz, 1H), 7.32-7.20 (m, 1H), 6.99-6.92 (m, 1H), 4.03 (s, 3H), 3.93 (q, J = 7.1 Hz, 2H), 1.73-1.57 (m, 2H), 1.27-1.21 (m, 2H), 0.76 (t, J = 7.1 Hz, 3H). LCMS (Analytical Method A) Rt = 1.48 min, MS (ESIpos): m/z = 560.2 (M + H)$^+$. |
| 360A | 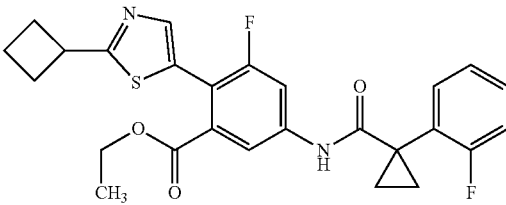 | Ethyl 2-(2-cyclobutyl-1,3-thiazol-5-yl)-3-fluoro-5-[({1-[2-fluoro-4-(trifluoromethyl)phenyl]cyclopropyl}carbonyl)amino]benzoate | $^1$H NMR (500 MHz, Chloroform-d) δ [ppm] 7.63 (dd, J = 11.2, 2.2 Hz, 1H), 7.44-7.38 (m, 1H), 7.33 (d, J = 8.1 Hz, 1H), 7.27 (m, 2H), 7.06-7.02 (m, 1H), 6.93 (s, 1H), 3.92 (q, J = 7.1 Hz, 2H), 3.72-3.59 (m, 1H), 2.34-2.23 (m, 2H), 2.23-2.10 (m, 2H), 1.96-1.81 (m, 1H), 1.81-1.71 (m, 1H), 1.68-1.61 (m, 2H), 1.05-0.99 (m, 2H), 0.87 (t, J = 7.1 Hz, 3H). LCMS (Analytical Method A): Rt = 1.53 mins, MS (ESIPos): m/z = 551 (M + H)$^+$. |
| 365A | 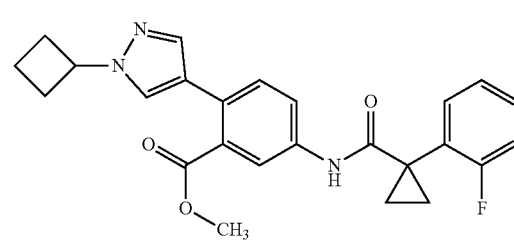 | Methyl 2-(1-cyclobutyl-1H-pyrazol-4-yl)-5-({[1-(2-fluoro-4-methoxyphenyl)cyclopropyl]carbonyl}amino)benzoate | LCMS (method 4): Rt = 1.32 min; MS (ESIPos) m/z = 464 (M + H)$^+$. |
| 366A | 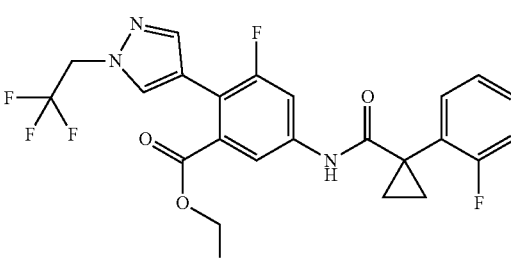 | Ethyl 3-fluoro-5-[({1-[2-fluoro-4-(trifluoromethyl)phenyl]cyclopropyl}carbonyl)amino]-2-[1-(2,2,2-trifluoroethyl)-1H-pyrazol-4-yl]benzoate | $^1$H NMR (400 MHz, DMSO-d6) δ [ppm] 1.08 (t, 3H), 1.25-1.28 (m, 2H), 1.64-1.67 (m, 2H), 4.13 (q, 2H), 5.18 (q, 2H), 7.57 (s, 1H), 7.60-7.62 (m, 1H), 7.67-7.72 (m, 3H), 7.79 (dd, 1H), 7.93 (s, 1H), 9.34 (s, 1H). LCMS (method 1): Rt = 1.43 min; MS (ESIPos) m/z = 562 (M + H)$^+$. |

Example 1: 2-(1-Benzothiophen-2-yl)-5-[({1-[2-fluoro-4-(trifluoromethyl)phenyl]cyclopropyl}carbonyl)amino]benzoic acid

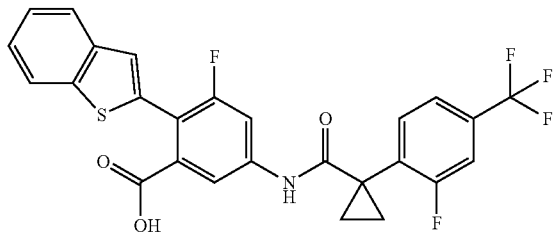 [SMILES: O=C(O)c1cc(NC(=O)C2(c3ccc(C(F)(F)F)cc3F)CC2)cc(F)c1-c1cc2ccccc2s1]

To a stirred solution of methyl 2-(1-benzothiophen-2-yl)-5-[({1-[2-fluoro-4-(trifluoromethyl)phenyl]cyclopropyl}carbonyl)amino]benzoate (151.8 mg, 0.536 mmol) in THF (1 mL) was added LiOH (1 mL of a 2M aqueous solution, 2 mmol). The reaction was stirred at RT for 2 days then heated to 60° C. for 24 hours. The reaction mixture was concentrated in vacuo and purified by prep-HPLC (Method A). Fractions containing product were combined and concentrated in vacuo to remove excess MeCN and concentrated HCl was added and the product precipitated as a white solid. The solid was collected by filtration, washed with water and dried giving the title compound as a white solid (48 mg, 49% yield).

$^1$H NMR (500 MHz, DMSO-d6) δ [ppm] 9.25 (s, 1H), 7.95 (d, J=7.7 Hz, 1H), 7.89 (d, J=2.1 Hz, 1H), 7.86-7.77 (m, 2H), 7.75-7.65 (m, 2H), 7.61 (d, J=8.0 Hz, 1H), 7.49 (d, J=8.5 Hz, 1H), 7.42-7.31 (m, 3H), 1.73-1.60 (m, 2H), 1.32-1.19 (m, 2H).

LCMS (Analytical Method D) Rt=4.83 min, MS (ESI-Pos): m/z=500.0 (M+H)$^+$.

Example 2: 2-[6-(1,1-Difluoropropyl)pyridin-3-yl]-5-[({1-[2-fluoro-4-(trifluoro-methyl)phenyl]cyclopropyl}carbonyl)amino]benzoic acid

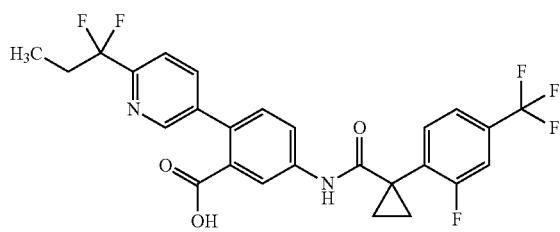 [SMILES: CCC(F)(F)c1ccc(-c2ccc(NC(=O)C3(c4ccc(C(F)(F)F)cc4F)CC3)cc2C(=O)O)cn1]

To a stirred solution of methyl 2-[6-(1,1-difluoropropyl)pyridin-3-yl]-5-[({1-[2-fluoro-4-(trifluoromethyl)phenyl]cyclopropyl}carbonyl)amino]benzoate (Int. 211A, 60 mg, 0.112 mmol) in THF (2 mL) was added 1M aqueous lithium hydroxide solution (0.224 mL). The mixture was stirred intensively at room temperature for 16 hours. The reaction mixture was diluted with ethyl acetate (30 mL), washed with 2M HCl (20 mL) and brine (20 mL), dried (Na$_2$SO$_4$), filtered and concentrated under reduced pressure. The residue was purified by prep-HPLC (Method A) and product containing fractions concentrated to remove excess MeCN and acidified with concentrated HCL. The resulting precipitate was collected by filtration, washed with water (~5 mL) and dried in the vacuum oven at 40° C. for 4 hours to give the title compound (51 mg, 86% yield) as a white solid.

$^1$H NMR (500 MHz, DMSO-d6) δ [ppm] 12.95 (s, 1H), 9.26 (s, 1H), 8.55 (d, J=1.8 Hz, 1H), 8.07 (d, J=2.3 Hz, 1H), 7.90-7.84 (m, 2H), 7.75-7.66 (m, 3H), 7.64-7.58 (m, 1H), 7.36 (d, J=8.4 Hz, 1H), 2.43-2.28 (m, 2H), 1.71-1.60 (m, 2H), 1.32-1.19 (m, 2H), 0.94 (t, J=7.5 Hz, 3H);

LCMS (Analytical Method F) Rt=3.97 mins; MS (ESI-Pos) m/z=523.1 (M+H)$^+$.

Example 3: 2-(1-Cyclobutyl-1H-pyrazol-4-yl)-5-[({1-[2-fluoro-4-(trifluoromethyl)-phenyl]cyclopropyl}carbonyl)amino]benzoic acid

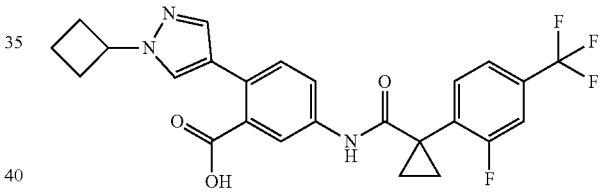

To a stirred solution of methyl 2-(1-cyclobutyl-1H-pyrazol-4-yl)-5-[({1-[2-fluoro-4-(trifluoromethyl)phenyl]cyclopropyl}carbonyl)amino]benzoate (Int. 156A, 112 mg, 0.22 mmol) in THF (2 mL) was added lithium hydroxide (16 mg, 0.67 mmol) dissolved in water (0.26 mL). The mixture was stirred rapidly at 80° C. for approximately 16 hours. The reaction mixture was cooled to RT and 1M HCl (10 mL) was added (resulting pH ca. 2) and stirred for further 10 min. The mixture was extracted with EtOAc (3×15 mL), the combined organic layers were washed with water (10 mL), brine (10 mL), dried (Na$_2$SO$_4$), filtered and concentrated under reduced pressure. Purification by prep-HPLC gave the title compound (57 mg, 52% yield) as a white solid.

$^1$H NMR (400 MHz, DMSO-d6) δ [ppm] 1.19-1.23 (m, 2H), 1.60-1.63 (m, 2H), 1.72-1.80 (m, 2H), 2.32-2.41 (m, 2H), 2.42-2.50 (m, 2H), 4.80 (m, 1H), 7.32-7.34 (m, 1H), 7.58-7.61 (m, 4H), 7.66-7.71 (m, 2H), 7.96 (d, 1H), 9.03 (s, 1H).

LCMS (Method 1): Rt=1.25 min; MS (ESIPos) m/z=488 (M+H)$^+$.

In analogy to Example 2, the following examples were prepared using the corresponding esters as starting material with heating the reaction mixtures at between 40° C. and 80° C. and using either THF in water or MeOH in water as solvent mixtures.

| Ex. | Structure | Name | Analytical Data |
|---|---|---|---|
| 4 | 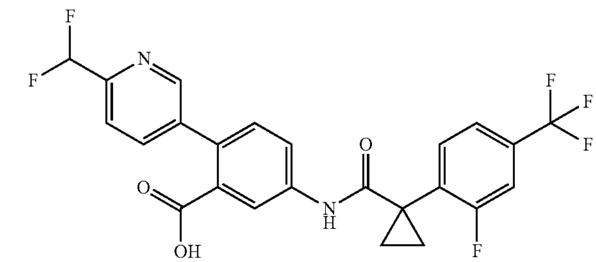 [SMILES: O=C(O)c1cc(NC(=O)C2(c3ccc(C(F)(F)F)cc3F)CC2)ccc1-c1ccc(C(F)F)nc1] | 2-[6-(Difluoromethyl)pyridin-3-yl]-5-[({1-[2-fluoro-4-(trifluoromethyl)phenyl]cyclopropyl}carbonyl)amino]benzoic acid | $^1$H NMR (400 MHz, DMSO-d6) δ [ppm] 1.22-1.25 (m, 2H), 1.63-1.66 (m, 2H), 6.98 (t, J = 55 Hz, 1H), 7.30 (d, 1H), 7.61 (dd, 1H), 7.67-7.73 (m, 3H), 7.80 (dd, 1H), 7.89-7.93 (m, 2H), 8.58 (d, 1H), 9.21 (s, 1H).<br>LCMS (Method 1): Rt = 1.26 min; MS (ESIPos) m/z = 495 (M + H)$^+$. |
| 5 | 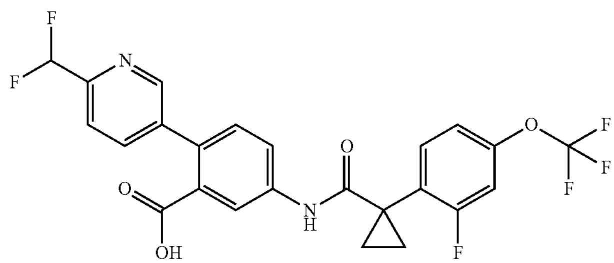 [SMILES: O=C(O)c1cc(NC(=O)C2(c3ccc(OC(F)(F)F)cc3F)CC2)ccc1-c1ccc(C(F)F)nc1] | 2-[6-(Difluoromethyl)pyridin-3-yl]-5-[({1-[2-fluoro-4-(trifluoromethoxy)phenyl]cyclopropyl}carbonyl)amino]benzoic acid | $^1$H NMR (400 MHz, DMSO-d6) δ [ppm] 1.19-1.22 (m, 2H), 1.61-1.64 (m, 2H), 6.99 (t, J = 55 Hz, 1H), 7.24-7.27 (m, 1H), 7.33 (d, 1H), 7.40 (dd, 1H), 7.61 (t, 1H), 7.69 (d, 1H), 7.85 (dd, 1H), 7.90 (dd, 1H), 8.01 (s, br, 1H), 8.57 (d, 1H), 9.22 (s, 1H).<br>LCMS (Method 1): Rt = 1.29 min; MS (ESIPos) m/z = 511 (M + H)$^+$. |
| 6 | 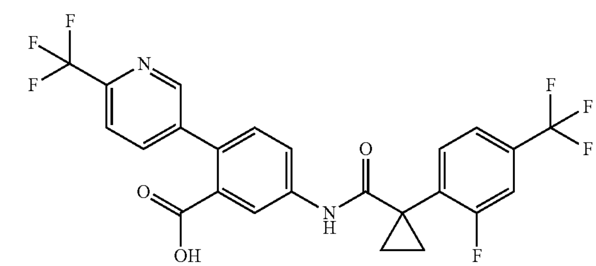 [SMILES: O=C(O)c1cc(NC(=O)C2(c3ccc(C(F)(F)F)cc3F)CC2)ccc1-c1ccc(C(F)(F)F)nc1] | 5-[({1-[2-Fluoro-4-(trifluoromethyl)phenyl]cyclopropyl}carbonyl)amino]-2-[6-(trifluoromethyl)pyridin-3-yl]benzoic acid | $^1$H NMR (400 MHz, DMSO-d6) δ [ppm] 1.24-1.27 (m, 2H), 1.65-1.67 (m, 2H), 7.38 (d, 1H), 7.62 (dd, 1H), 7.68-7.73 (m, 2H), 7.89-7.93 (m, 2H), 7.99 (dd, 1H), 8.13 (d, 1H), 8.66 (d, 1H), 9.31 (s, 1H), 13.0 (s, br, 1H).<br>LCMS (Method 1): Rt = 1.33 min; MS (ESIPos) m/z = 513 (M + H)$^+$. |
| 7 | 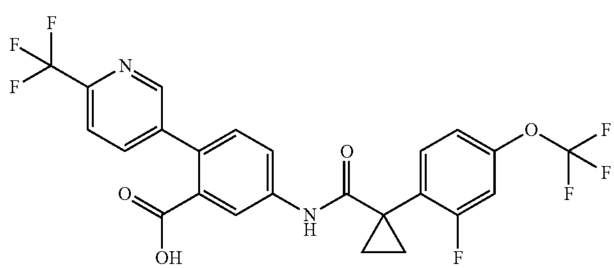 [SMILES: O=C(O)c1cc(NC(=O)C2(c3ccc(OC(F)(F)F)cc3F)CC2)ccc1-c1ccc(C(F)(F)F)nc1] | 5-[({1-[2-Fluoro-4-(trifluoromethoxy)phenyl]cyclopropyl}carbonyl)amino]-2-[6-(trifluoromethyl)pyridin-3-yl]benzoic acid | $^1$H NMR (400 MHz, DMSO-d6) δ [ppm] 1.20-1.23 (m, 2H), 1.61-1.64 (m, 2H), 7.25-7.27 (m, 1H), 7.38 (d, 1H), 7.40 (dd, br, 1H), 7.61 (t, 1H), 7.88-7.92 (m, 2H), 7.99 (dd, 1H), 8.12 (d, 1H), 8.66 (d, 1H), 9.27 (s, 1H) 13.0 (s, br, 1H).<br>LCMS (Method 1): Rt = 1.34 min; MS (ESIPos) m/z = 529 (M + H)$^+$. |
| 8 | 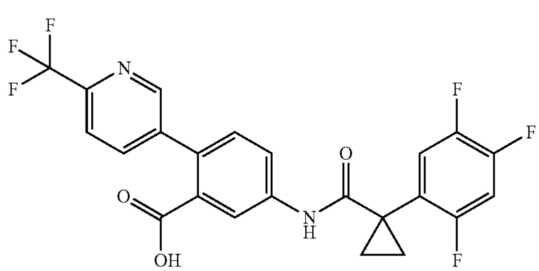 [SMILES: O=C(O)c1cc(NC(=O)C2(c3cc(F)c(F)cc3F)CC2)ccc1-c1ccc(C(F)(F)F)nc1] | 2-[6-(Trifluoromethyl)pyridin-3-yl]-5-({[1-(2,4,5-trifluorophenyl)cyclopropyl]carbonyl}amino)benzoic acid | 1H NMR (400 MHz, DMSO-d6) δ [ppm] 1.18-1.21 (m, 2H), 1.56-1.59 (m, 2H), 7.30 (d, 1H), 7.53-7.67 (m, 2H), 7.80 (dd, 1H), 7.86 (d, 1H), 7.91 (d, 1H), 7.98 (dd, 1H), 8.66 (d, 1H), 9.13 (s, 1H).<br>LCMS (Method 1): Rt = 1.24 min; MS (ESIPos) m/z = 481 (M + H)$^+$. |
| 9 | 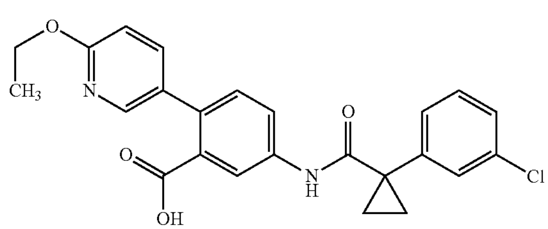 [SMILES: CCOc1ccc(-c2ccc(NC(=O)C3(c4cccc(Cl)c4)CC3)cc2C(=O)O)cn1] | 5-({[1-(3-Chlorophenyl)cyclopropyl]carbonyl}amino)-2-(6-ethoxypyridin-3-yl)benzoic acid | $^1$H NMR (400 MHz, DMSO-d6) δ [ppm] 1.16-1.19 (m, 2H), 1.33 (t, 3H), 1.47-1.49 (m, 2H), 4.31 (q, 2H), 6.77 (dd, 1H), 7.25 (d, 1H), 7.34-7.39 (m, 3H), 7.42-7.44 (m, 1H), 7.62 (dd, 1H), 7.76 (dd, 1H), 7.89 (s, br, 1H), 8.05 (dd, 1H), 9.43 (s, 1H).<br>LCMS (Method 1): Rt = 1.26 min; MS (ESIPos) m/z = 437 (M + H)$^+$. |

-continued

| Ex. | Structure | Name | Analytical Data |
|---|---|---|---|
| 10 | 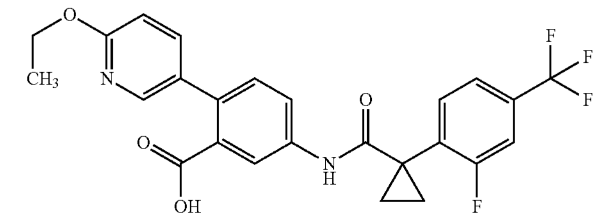 [SMILES: CCOc1ccc(-c2ccc(NC(=O)C3(c4ccc(C(F)(F)F)cc4F)CC3)cc2C(=O)O)cn1] | 2-(6-Ethoxypyridin-3-yl)-5-[({1-[2-fluoro-4-(trifluoromethyl)phenyl]cyclopropyl}carbonyl)amino]benzoic acid | $^1$H NMR (400 MHz, DMSO-d6) δ [ppm] 1.21-1.24 (m, 2H), 1.32 (t, 3H), 1.62-1.65 (m, 2H), 4.31 (q, 2H), 6.77 (d, 1H), 7.24 (d, 1H), 7.59-7.63 (m, 2H), 7.67-7.74 (m, 3H), 7.83 (s, br, 1H), 8.05 (d, 1H), 9.15 (s, 1H). LCMS (Method 4): Rt = 0.79 min; MS (ESIPos) m/z = 489 (M + H)$^+$. |
| 11 | 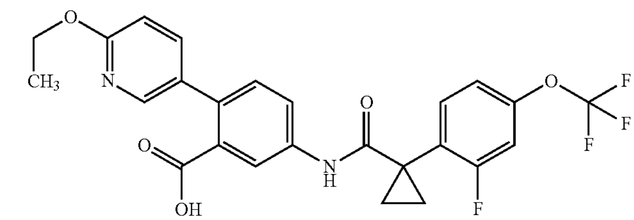 [SMILES: CCOc1ccc(-c2ccc(NC(=O)C3(c4ccc(OC(F)(F)F)cc4F)CC3)cc2C(=O)O)cn1] | 2-(6-Ethoxypyridin-3-yl)-5-[({1-[2-fluoro-4-(trifluoromethoxy)phenyl]cyclopropyl}carbonyl)amino]benzoic acid | $^1$H NMR (400 MHz, DMSO-d6) δ [ppm] 1.15-1.18 (m, 2H), 1.32 (t, 3H), 1.58-1.60 (m, 2H), 4.30 (q, 2H), 6.73 (dd, 1H), 7.17 (d, 1H), 7.22-7.25 (m, 1H), 7.38 (dd, 1H), 7.58-7.66 (m, 4H), 8.08 (dd, 1H), 9.04 (s, 1H). LCMS (Method 1): Rt = 1.33 min; MS (ESIPos) m/z = 505 (M + H)$^+$. |
| 12 | 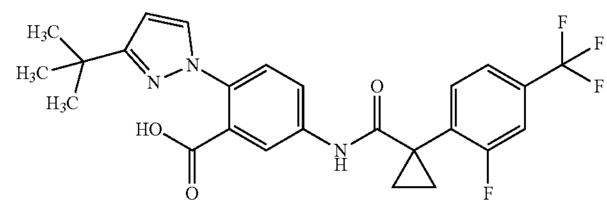 [SMILES: CC(C)(C)c1ccn(-c2ccc(NC(=O)C3(c4ccc(C(F)(F)F)cc4F)CC3)cc2C(=O)O)n1] | 2-(3-tert-Butyl-1H-pyrazol-1-yl)-5-[({1-[2-fluoro-4-(trifluoromethyl)phenyl]cyclopropyl}carbonyl)amino]benzoic acid | $^1$H NMR (500 MHz, DMSO-d6) δ [ppm] 9.18 (s, 1H), 7.87 (d, J = 2.3 Hz, 1H), 7.81 (s, 1H), 7.77 (d, J = 8.7 Hz, 1H), 7.70 (m, 2H), 7.60 (d, J = 8.1 Hz, 1H), 7.45 (d, J = 8.7 Hz, 1H), 6.31 (d, J = 2.4 Hz, 1H), 1.65 (m, 2H), 1.25 (m, 11H). LCMS (Analytical Method D): Rt = 4.62 mins; MS (ESIPos): m/z = 490.4 (M + H)$^+$. |
| 13 | 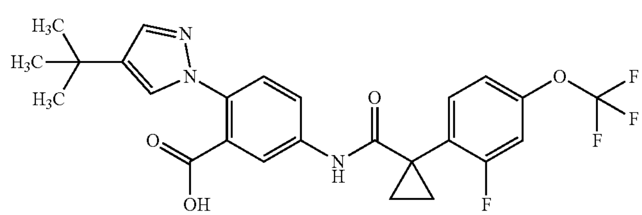 [SMILES: CC(C)(C)c1cnn(-c2ccc(NC(=O)C3(c4ccc(OC(F)(F)F)cc4F)CC3)cc2C(=O)O)c1] | 2-(4-tert-Butyl-1H-pyrazol-1-yl)-5-[({1-[2-fluoro-4-(trifluoromethoxy)phenyl]cyclopropyl}carbonyl)amino]benzoic acid | $^1$H NMR (500 MHz, DMSO-d6) δ [ppm] 12.83 (s, 1H), 9.17 (s, 1H), 7.85 (s, 1H), 7.83-7.81 (m, 1H), 7.79 (dd, J = 8.8, 2.2 Hz, 1H), 7.65-7.59 (m, 1H), 7.56 (s, 1H), 7.46 (d, J = 8.7 Hz, 1H), 7.42-7.37 (m, 1H), 7.27-7.22 (m, 1H), 1.65-1.60 (m, 2H), 1.26 (s, 9H), 1.23-1.19 (m, 2H). LCMS (Analytical Method F): Rt = 3.98 min, MS (ESIpos): m/z = 506.1 (M + H)$^+$. |
| 14 | 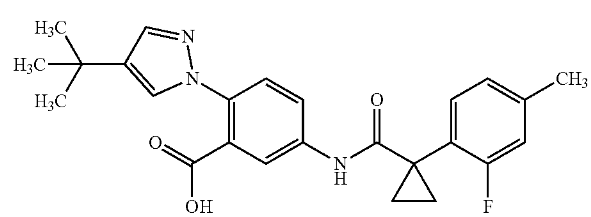 [SMILES: Cc1ccc(C2(C(=O)Nc3ccc(-n4cc(C(C)(C)C)cn4)c(C(=O)O)c3)CC2)c(F)c1] | 2-(4-tert-Butyl-1H-pyrazol-1-yl)-5-({[1-(2-fluoro-4-methylphenyl)cyclopropyl]carbonyl}amino)benzoic acid | $^1$H NMR (500 MHz, DMSO-d6) δ [ppm] 12.84 (s, 1H), 9.02 (s, 1H), 7.85 (s, 1H), 7.83-7.80 (m, 1H), 7.79-7.74 (m, 1H), 7.56 (s, 1H), 7.43 (d, J = 8.7 Hz, 1H), 7.38-7.29 (m, 1H), 7.07-7.00 (m, 2H), 2.34 (s, 3H), 1.59-1.52 (m, 2H), 1.26 (s, 9H), 1.14-1.09 (m, 2H). LCMS (Analytical Method D): Rt = 3.75 min, MS (ESIpos): m/z = 436.1 (M + H)$^+$. |
| 15 | 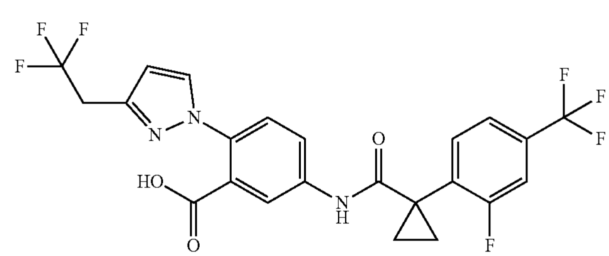 [SMILES: O=C(O)c1cc(NC(=O)C2(c3ccc(C(F)(F)F)cc3F)CC2)ccc1-n1ccc(CC(F)(F)F)n1] | 5-[({1-[2-Fluoro-4-(trifluoromethyl)phenyl]cyclopropyl}carbonyl)amino]-2-[3-(2,2,2-trifluoroethyl)-1H-pyrazol-1-yl]benzoic acid | $^1$H NMR (500 MHz, DMSO-d6) δ [ppm] 12.96 (s, 1H), 9.26 (s, 1H), 7.98 (d, J = 2.4 Hz, 1H), 7.93 (d, J = 2.5 Hz, 1H), 7.84 (dd, J = 8.7, 2.5 Hz, 1H), 7.74-7.65 (m, 2H), 7.61 (d, J = 8.0 Hz, 1H), 7.45 (d, J = 8.7 Hz, 1H), 6.41 (d, J = 2.3 Hz, 1H), 3.66 (q, J = 11.4 Hz, 2H), 1.73-1.59 (m, 2H), 1.30-1.20 (m, 2H). LCMS (Analytical Method F): Rt = 3.68 mins; MS (ESIPos) m/z = 516.0 (M + H)$^+$. |

| Ex. | Structure | Name | Analytical Data |
|---|---|---|---|
| 16 | 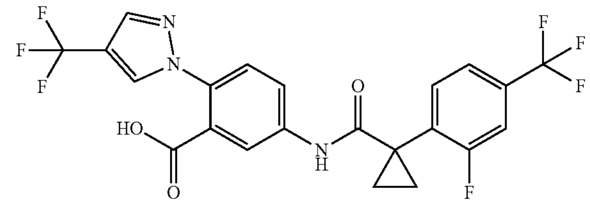 [SMILES: O=C(O)c1cc(NC(=O)C2(c3ccc(C(F)(F)F)cc3F)CC2)ccc1-n1cc(C(F)(F)F)cn1] | 5-[({1-[2-Fluoro-4-(trifluoromethyl)phenyl]cyclopropyl}carbonyl)amino]-2-[4-(trifluoromethyl)-1H-pyrazol-1-yl]benzoic acid | $^1$H NMR (250 MHz, DMSO-d6) δ [ppm] 12.98 (br s, 1H), 9.33 (s, 1H), 8.75 (s, 1H), 8.05 (d, J = 14.9 Hz, 2H), 7.91 (d, J = 8.5 Hz, 1H), 7.79-7.58 (m, 3H), 7.52 (d, J = 8.7 Hz, 1H), 1.67 (m, 2H), 1.27 (m, 2H). LCMS (Analytical Method D) Rt = 4.48 min, MS (ESIpos): m/z = 502.0 (M + H)$^+$. |
| 17 | 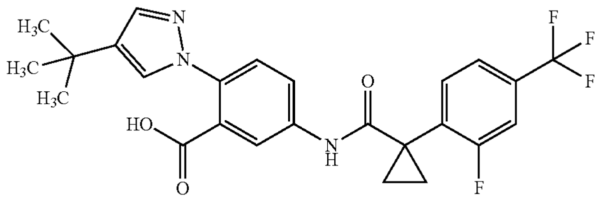 [SMILES: CC(C)(C)c1cnn(-c2ccc(NC(=O)C3(c4ccc(C(F)(F)F)cc4F)CC3)cc2C(=O)O)c1] | 2-(4-tert-Butyl-1H-pyrazol-1-yl)-5-[({1-[2-fluoro-4-(trifluoromethyl)phenyl]cyclopropyl}carbonyl)amino]benzoic acid | $^1$H NMR (500 MHz, DMSO-d6) δ [ppm] 9.19 (s, 1H), 7.84 (s, 1H), 7.81 (s, 1H), 7.79-7.75 (m, 1H), 7.70 (m, 2H), 7.60 (d, J = 8.1 Hz, 1H), 7.56 (s, 1H), 7.45 (d, J = 8.7 Hz, 1H), 1.70-1.61 (m, 2H), 1.25 (m, 11H). LCMS (Analytical Method D): Rt = 4.58 mins; MS (ESIpos): m/z = 490.05 (M + H)$^+$. |
| 18 | 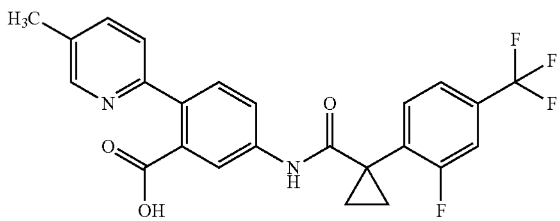 | 5-[({1-[2-Fluoro-4-(trifluoromethyl)phenyl]cyclopropyl}carbonyl)amino]-2-(5-methylpyridin-2-yl)benzoic acid | $^1$H NMR (500 MHz, DMSO-d6) δ [ppm] 9.12 (br s, 1H), 8.38 (s, 1H), 7.78 (s, 1H), 7.75-7.65 (m, 3H), 7.63-7.56 (m, 2H), 7.48-7.46 (m, 2H), 2.32 (s, 3H), 1.65 (m, 2H), 1.24 (m, 2H). LCMS (Analytical Method D) Rt = 3.74 min, MS (ESIpos): m/z = 459.0 (M + H)$^+$. |
| 19 | 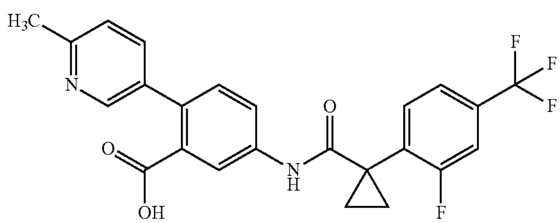 [SMILES: Cc1ccc(-c2ccc(NC(=O)C3(c4ccc(C(F)(F)F)cc4F)CC3)cc2C(=O)O)cn1] | 5-[({1-[2-Fluoro-4-(trifluoromethyl)phenyl]cyclopropyl}carbonyl)amino]-2-(6-methylpyridin-3-yl)benzoic acid | $^1$H NMR (500 MHz, DMSO-d6) δ [ppm] 12.86 (s, 1H), 9.21 (s, 1H), 8.32 (d, J = 2.3 Hz, 1H), 7.99 (d, J = 2.3 Hz, 1H), 7.82 (dd, J = 8.4, 2.3 Hz, 1H), 7.74-7.65 (m, 2H), 7.60 (d, J = 8.1 Hz, 1H), 7.58 (dd, J = 8.0, 2.4 Hz, 1H), 7.30 (d, J = 8.4 Hz, 1H), 7.25 (d, J = 8.0 Hz, 1H), 2.49 (s, 3H), 1.71-1.57 (m, 2H), 1.32-1.17 (m, 2H). LCMS (Analytical Method F): Rt = 2.50 mins; MS (ESIPos) m/z = 459.1 (M + H)$^+$. |
| 20 | 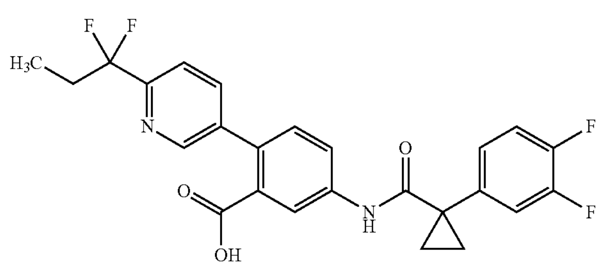 [SMILES: CCC(F)(F)c1ccc(-c2ccc(NC(=O)C3(c4ccc(F)c(F)c4)CC3)cc2C(=O)O)cn1] | 5-({[1-(3,4-Difluorophenyl)cyclopropyl]carbonyl}amino)-2-[6-(1,1-difluoropropyl)pyridin-3-yl]benzoic acid | $^1$H NMR (500 MHz, DMSO-d6) δ [ppm] 13.00 (s, 1H), 9.34 (s, 1H), 8.56 (d, J = 1.7 Hz, 1H), 8.11 (d, J = 2.1 Hz, 1H), 7.94-7.85 (m, 2H), 7.70 (d, J = 8.1 Hz, 1H), 7.51 (m, 1H), 7.46-7.39 (m, 1H), 7.37 (d, J = 8.4 Hz, 1H), 7.31-7.26 (m, 1H), 2.44-2.26 (m, 2H), 1.54-1.48 (m, 2H), 1.22-1.14 (m, 2H), 0.95 (t, J = 7.5 Hz, 3H). LCMS (Analytical Method F) Rt = 3.74 min, MS (ESIpos): m/z = 473.1 (M + H)$^+$. |
| 21 | 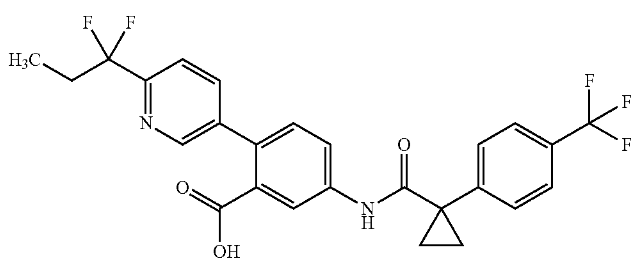 [SMILES: CCC(F)(F)c1ccc(-c2ccc(NC(=O)C3(c4ccc(C(F)(F)F)cc4)CC3)cc2C(=O)O)cn1] | 2-[6-(1,1-Difluoropropyl)pyridin-3-yl]-5-[({1-[4-(trifluoromethyl)phenyl]cyclopropyl}carbonyl)amino]benzoic acid | $^1$H NMR (250 MHz, DMSO-d6) δ [ppm] 9.64 (s, 1H), 8.56 (s, 1H), 8.14 (d, J = 2.1 Hz, 1H), 7.96-7.83 (m, 2H), 7.77-7.67 (m, 3H), 7.65-7.57 (m, 2H), 7.38 (d, J = 8.5 Hz, 1H), 2.43-2.27 (m, 2H), 1.62-1.52 (m, 2H), 1.31-1.20 (m, 2H), 0.95 (t, J = 7.4 Hz, 3H). LCMS (Analytical Method D) Rt = 4.67 min, MS (ESIpos): m/z = 505.65 (M + H)$^+$. |

| Ex. | Structure | Name | Analytical Data |
|---|---|---|---|
| 22 | 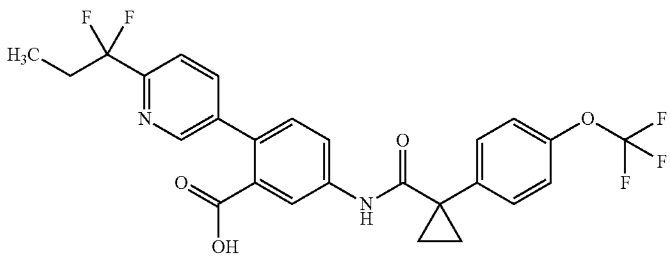 [SMILES: CCC(F)(F)c1ccc(-c2ccc(NC(=O)C3(c4ccc(OC(F)(F)F)cc4)CC3)cc2C(=O)O)cn1] | 2-[6-(1,1-Difluoropropyl)pyridin-3-yl]-5-[({1-[4-(trifluoromethoxy)phenyl]cyclopropyl}carbonyl)amino]benzoic acid | $^1$H NMR (250 MHz, DMSO-d6) δ [ppm] 12.93 (s, 1H), 9.55 (s, 1H), 8.56 (s, 1H), 8.14 (s, 1H), 7.96-7.82 (m, 2H), 7.70 (d, J = 7.9 Hz, 1H), 7.58-7.50 (m, 2H), 7.43-7.29 (m, 3H), 2.43-2.27 (m, 2H), 1.58-1.45 (m, 2H), 1.25-1.14 (m, 2H), 0.95 (t, J = 7.4 Hz, 3H). LCMS (Analytical Method D) Rt = 5.02 min, MS (ESIpos): m/z = 521.4 (M + H)$^+$. |
| 23 | 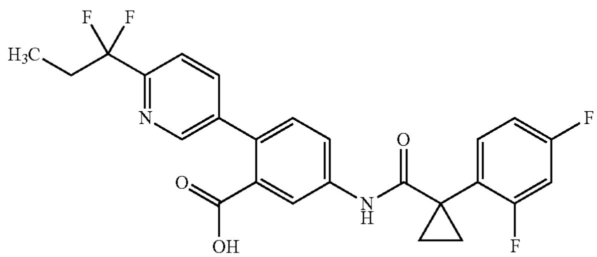 [SMILES: CCC(F)(F)c1ccc(-c2ccc(NC(=O)C3(c4ccc(F)cc4F)CC3)cc2C(=O)O)cn1] | 5-({[1-(2,4-Difluorophenyl)cyclopropyl]carbonyl}amino)-2-[6-(1,1-difluoropropyl)pyridin-3-yl]benzoic acid | $^1$H NMR (250 MHz, DMSO-d6) δ [ppm] 12.95 (s, 1H), 9.16 (s, 1H), 8.56 (s, 1H), 8.09 (d, J = 2.1 Hz, 1H), 7.90 (dd, J = 3.6, 2.3 Hz, 1H), 7.88-7.84 (m, 1H), 7.69 (d, J = 8.2 Hz, 1H), 7.61-7.46 (m, 1H), 7.36 (d, J = 8.4 Hz, 1H), 7.32-7.19 (m, 1H), 7.17-7.05 (m, 1H), 2.46-2.26 (m, 2H), 1.66-1.57 (m, 2H), 1.21-1.13 (m, 2H), 0.95 (t, J = 7.4 Hz, 3H). LCMS (Analytical Method D) Rt = 4.61 min, MS (ESIpos): m/z = 473.05 (M + H)$^+$. |
| 24 | 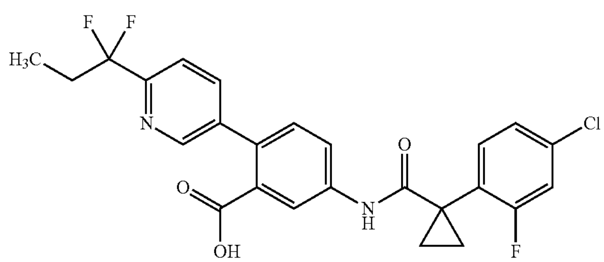 [SMILES: CCC(F)(F)c1ccc(-c2ccc(NC(=O)C3(c4ccc(Cl)cc4F)CC3)cc2C(=O)O)cn1] | 5-({[1-(4-Chloro-2-fluorophenyl)cyclopropyl]carbonyl}amino)-2-[6-(1,1-difluoropropyl)pyridin-3-yl]benzoic acid | $^1$H NMR (250 MHz, DMSO-d6) δ [ppm] 12.95 (s, 1H), 9.20 (s, 1H), 8.56 (s, 1H), 8.08 (s, 1H), 7.95-7.80 (m, 2H), 7.70 (d, J = 8.1 Hz, 1H), 7.58-7.41 (m, 2H), 7.40-7.27 (m, 2H), 2.46-2.26 (m, 2H), 1.68-1.56 (m, 2H), 1.22-1.14 (m, 2H), 0.95 (t, J = 7.4 Hz, 3H). LCMS (Analytical Method D) Rt = 4.79 min, MS (ESIpos): m/z = 489.05 (M + H)$^+$. |
| 25 | 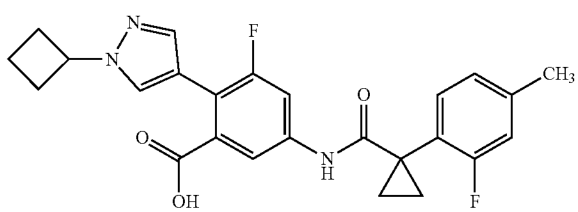 [SMILES: Cc1ccc(C2(C(=O)Nc3cc(F)c(-c4cnn(C5CCC5)c4)c(C(=O)O)c3)CC2)c(F)c1] | 2-(1-Cyclobutyl-1H-pyrazol-4-yl)-3-fluoro-5-({[1-(2-fluoro-4-methylphenyl)cyclopropyl]carbonyl}amino)benzoic acid | $^1$H NMR (500 MHz, DMSO-d6) δ [ppm] 13.09 (s, 1H), 9.10 (s, 1H), 7.88 (s, 1H), 7.74 (dd, J = 12.8, 2.0 Hz, 1H), 7.64-7.60 (m, 1H), 7.47 (m, 1H), 7.35-7.28 (m, 1H), 7.04 (d, J = 3.4 Hz, 1H), 7.02 (s, 1H), 4.85 (m, 1H), 2.48-2.42 (m, 2H), 2.41-2.34 (m, 2H), 2.33 (s, 3H), 1.85-1.70 (m, 2H), 1.59-1.49 (m, 2H), 1.13-1.08 (m, 2H). LCMS (Analytical Method F) Rt = 3.59 min, MS (ESIpos): m/z = 452.1 (M + H)$^+$. |
| 26 | 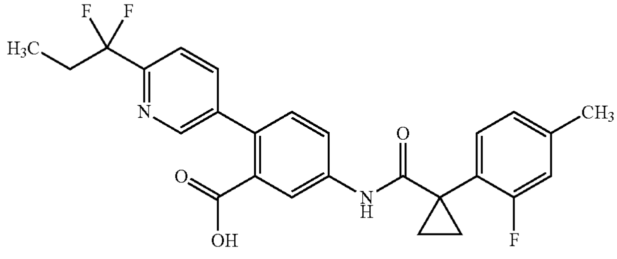 [SMILES: CCC(F)(F)c1ccc(-c2ccc(NC(=O)C3(c4ccc(C)cc4F)CC3)cc2C(=O)O)cn1] | 2-[6-(1,1-Difluoropropyl)pyridin-3-yl]-5-({[1-(2-fluoro-4-methylphenyl)cyclopropyl]carbonyl}amino)benzoic acid | $^1$H NMR (500 MHz, DMSO-d6) δ [ppm] 12.97 (s, 1H), 9.12 (s, 1H), 8.56 (d, J = 1.6 Hz, 1H), 8.08 (d, J = 1.8 Hz, 1H), 7.92-7.82 (m, 2H), 7.69 (d, J = 8.1 Hz, 1H), 7.39-7.28 (m, 2H), 7.09-6.98 (m, 2H), 2.42-2.28 (m, 5H), 1.63-1.51 (m, 2H), 1.17-1.09 (m, 2H), 0.95 (t, J = 7.5 Hz, 3H). LCMS (Analytical Method F): Rt = 3.81 min, MS (ESIpos): m/z = 469.1 (M + H)$^+$. |

| Ex. | Structure | Name | Analytical Data |
|---|---|---|---|
| 27 | 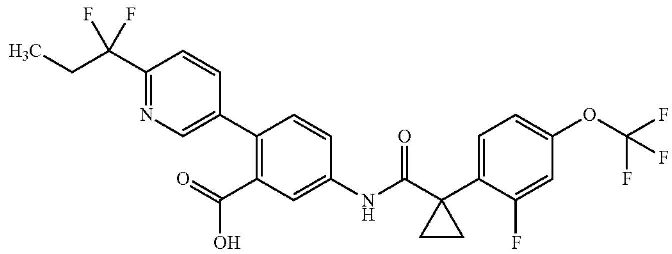 [SMILES: CCC(F)(F)c1ccc(-c2ccc(NC(=O)C3(c4ccc(OC(F)(F)F)cc4F)CC3)cc2C(=O)O)cn1] | 2-[6-(1,1-Difluoropropyl)pyridin-3-yl]-5-[({1-[2-fluoro-4-(trifluoromethoxy)phenyl]cyclopropyl}carbonyl)amino]benzoic acid | $^1$H NMR (500 MHz, DMSO-d6) δ [ppm] 13.01 (s, 1H), 9.25 (s, 1H), 8.61-8.49 (m, 1H), 8.13-8.02 (m, 1H), 7.92-7.82 (m, 2H), 7.69 (d, J = 8.1 Hz, 1H), 7.62 (dd, J = 8.5 Hz, 1H), 7.44-7.38 (m, 1H), 7.36 (d, J = 8.4 Hz, 1H), 7.29-7.22 (m, 1H), 2.42-2.28 (m, 2H), 1.73-1.53 (m, 2H), 1.26-1.17 (m, 2H), 0.95 (t, J = 7.4 Hz, 3H). LCMS (Analytical Method F) Rt = 4.04 min, MS (ESIpos): m/z = 539.1 (M + H)$^+$. |
| 28 | 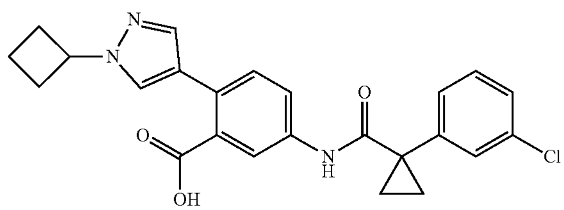 [SMILES: O=C(O)c1cc(NC(=O)C2(c3cccc(Cl)c3)CC2)ccc1-c1cnn(C2CCC2)c1] | 5-({[1-(3-Chlorophenyl)cyclopropyl]carbonyl}amino)-2-(1-cyclobutyl-1H-pyrazol-4-yl)benzoic acid | $^1$H NMR (400 MHz, DMSO-d6) δ [ppm] 1.14-1.17 (m, 2H), 1.45-1.48 (m, 2H), 1.72-1.82 (m, 2H), 2.32-2.41 (m, 2H), 2.42-2.50 (m, 2H), 4.80 (quint, 1H), 7.33-7.39 (m, 4H), 7.42-7.43 (m, 1H), 7.57 (s, 1H), 7.64 (dd, 1H), 7.69 (s, br, 1H), 7.96 (d, 1H), 9.31 (s, 1H). LCMS (Method 1): Rt = 1.20 min; MS (ESIPos) m/z = 436 (M + H)$^+$. |
| 29 | 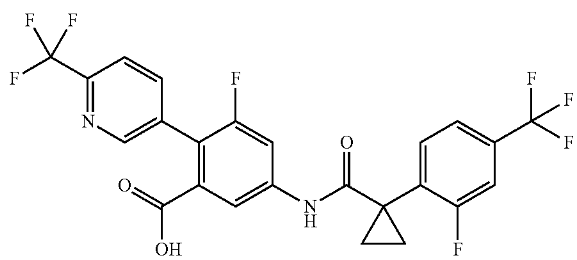 [SMILES: O=C(O)c1cc(NC(=O)C2(c3ccc(C(F)(F)F)cc3F)CC2)cc(F)c1-c1ccc(C(F)(F)F)nc1] | 3-Fluoro-5-[({1-[2-fluoro-4-(trifluoromethyl)phenyl]cyclopropyl}carbonyl)amino]-2-[6-(trifluoromethyl)pyridin-3-yl]benzoic acid | $^1$H NMR (500 MHz, DMSO-d6) δ [ppm] 13.22 (br s, 1H), 9.47 (s, 1H), 8.66 (s, 1H), 8.03-8.01 (m, 2H), 7.99-7.92 (m, 2H), 7.76-7.67 (m, 2H), 7.63 (d, J = 7.9 Hz, 1H), 1.70-1.68 (m, 2H), 1.31-1.28 (m, 2H). LCMS (Analytical Method D) Rt = 4.76 min, MS (ESIpos) m/z = 530.95 (M + H)$^+$. |
| 30 | 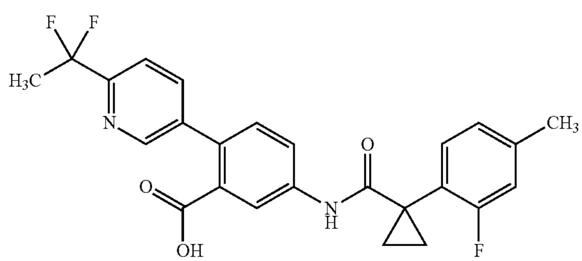 [SMILES: Cc1ccc(C2(C(=O)Nc3ccc(-c4ccc(C(C)(F)F)nc4)c(C(=O)O)c3)CC2)c(F)c1] | 2-[6-(1,1-Difluoroethyl)pyridin-3-yl]-5-({[1-(2-fluoro-4-methylphenyl)cyclopropyl]carbonyl}amino)benzoic acid | $^1$H NMR (500 MHz, DMSO-d6) δ [ppm] 12.93 (s, 1H), 9.11 (s, 1H), 8.54 (s, 1H), 8.16-8.02 (m, 1H), 7.97-7.81 (m, 2H), 7.76-7.65 (m, 1H), 7.42-7.23 (m, 2H), 7.09-6.95 (m, 2H), 2.34 (s, 3H), 2.03 (t, J = 19.1 Hz, 3H), 1.65-1.49 (m, 2H), 1.19-1.04 (m, 2H). LCMS (Analytical Method F): Rt = 3.63 mins, MS (ESIPos): m/z = 455 (M + H)$^+$. |
| 31 | 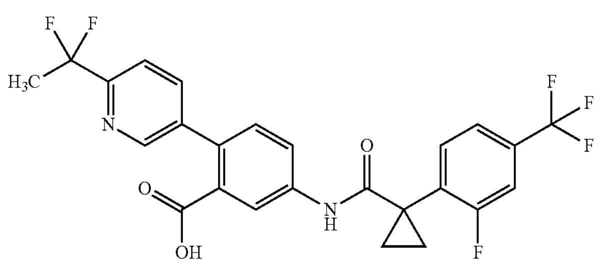 [SMILES: CC(F)(F)c1ccc(-c2ccc(NC(=O)C3(c4ccc(C(F)(F)F)cc4F)CC3)cc2C(=O)O)cn1] | 2-[6-(1,1-Difluoroethyl)pyridin-3-yl]-5-[({1-[2-fluoro-4-(trifluoromethyl)phenyl]cyclopropyl}carbonyl)amino]benzoic acid | $^1$H NMR (500 MHz, DMSO-d6) δ [ppm] 9.27 (s, 1H), 8.58-8.49 (m, 1H), 8.08 (d, J = 2.0 Hz, 1H), 7.90-7.83 (m, 2H), 7.75-7.56 (m, 4H), 7.35 (d, J = 8.4 Hz, 1H), 2.03 (t, J = 19.1 Hz, 3H), 1.71-1.59 (m, 2H), 1.30-1.18 (m, 2H). LCMS (Analytical Method F): Rt = 3.80 mins, MS (ESIPos): m/z = 509 (M + H)$^+$. |
| 32 | 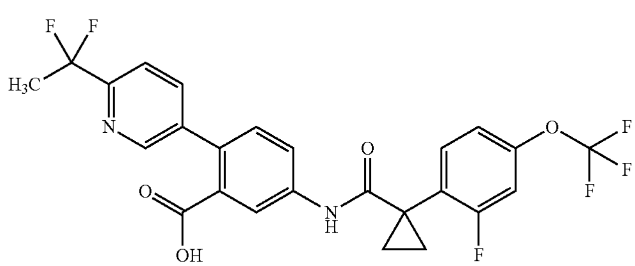 [SMILES: CC(F)(F)c1ccc(-c2ccc(NC(=O)C3(c4ccc(OC(F)(F)F)cc4F)CC3)cc2C(=O)O)cn1] | 2-[6-(1,1-Difluoroethyl)pyridin-3-yl]-5-[({1-[2-fluoro-4-(trifluoromethoxy)phenyl]cyclopropyl}carbonyl)amino]benzoic acid | $^1$H NMR (500 MHz, DMSO-d6) δ [ppm] 9.24 (s, 1H), 8.59-8.50 (m, 1H), 8.12-8.03 (m, 1H), 7.93-7.80 (m, 2H), 7.71 (d, J = 8.1 Hz, 1H), 7.65-7.56 (m, 1H), 7.44-7.30 (m, 2H), 7.25 (d, J = 8.6 Hz, 1H), 2.03 (t, J = 19.1 Hz, 3H), 1.68-1.55 (m, 2H), 1.33-1.13 (m, 2H). LCMS (Analytical Method F): Rt = 3.87 mins, MS (ESIPos): m/z = 525 (M + H)$^+$. |

| Ex. | Structure | Name | Analytical Data |
|---|---|---|---|
| 33 | 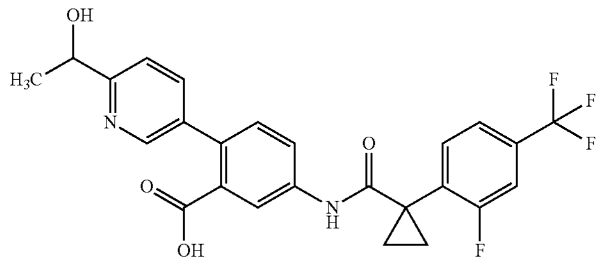 [SMILES: CC(O)c1ccc(-c2ccc(NC(=O)C3(c4ccc(C(F)(F)F)cc4F)CC3)cc2C(=O)O)cn1] | 5-[({1-[2-Fluoro-4-(trifluoromethyl)phenyl]cyclopropyl}carbonyl)amino]-2-[6-(1-hydroxyethyl)pyridin-3-yl]benzoic acid | ¹H NMR (500 MHz, DMSO-d6) δ [ppm] 9.21 (s, 1H), 8.36 (d, J = 2.1 Hz, 1H), 7.97 (s, 1H), 7.81 (dd, J = 8.4, 2.1 Hz, 1H), 7.73-7.64 (m, 3H), 7.61 (d, J = 8.1 Hz, 1H), 7.50 (d, J = 8.1 Hz, 1H), 7.31 (d, J = 8.4 Hz, 1H), 5.37 (d, J = 4.6 Hz, 1H), 4.80-4.69 (m, 1H), 1.69-1.59 (m, 2H), 1.39 (d, J = 6.6 Hz, 3H), 1.29-1.20 (m, 2H). LCMS (Analytical Method F): Rt = 1.89 mins, MS (ESIPos): m/z = 489 (M + H)⁺. |
| 34 | 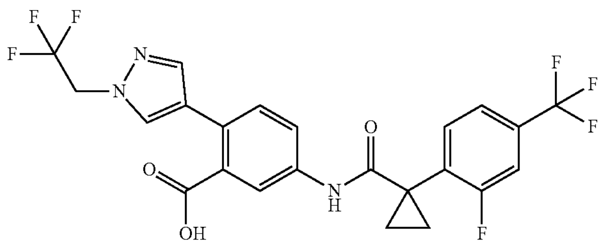 [SMILES: O=C(O)c1cc(NC(=O)C2(c3ccc(C(F)(F)F)cc3F)CC2)ccc1-c1cnn(CC(F)(F)F)c1] | 5-[({1-[2-Fluoro-4-(trifluoromethyl)phenyl]cyclopropyl}carbonyl)amino]-2-[1-(2,2,2-trifluoroethyl)-1H-pyrazol-4-yl]benzoic acid | ¹H NMR (500 MHz, DMSO-d6) δ [ppm] 9.12 (s, 1H), 7.97 (s, 1H), 7.80 (d, J = 2.2 Hz, 1H), 7.77-7.62 (m, 4H), 7.60 (d, J = 8.0 Hz, 1H), 7.37 (d, J = 8.5 Hz, 1H), 5.14 (q, J = 9.1 Hz, 2H), 1.70-1.55 (m, 2H), 1.29-1.16 (m, 2H). LCMS (Analytical Method F): Rt = 3.54 mins, MS (ESIPos): m/z = 516 (M + H)⁺. |
| 35 | 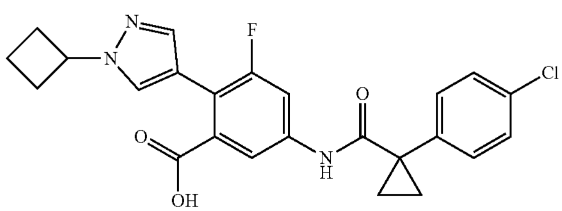 [SMILES: O=C(O)c1cc(NC(=O)C2(c3ccc(Cl)cc3)CC2)cc(F)c1-c1cnn(C2CCC2)c1] | 5-({[1-(4-Chlorophenyl)cyclopropyl]carbonyl}amino)-2-(1-cyclobutyl-1H-pyrazol-4-yl)-3-fluorobenzoic acid | ¹H NMR (500 MHz, DMSO-d6) δ [ppm] 13.13 (s, 1H), 9.40 (s, 1H), 7.88 (s, 1H), 7.75 (dd, J = 12.8, 2.0 Hz, 1H), 7.63 (d, J = 1.6 Hz, 1H), 7.48 (m, 1H), 7.44-7.36 (m, 4H), 4.86 (m, 1H), 2.48-2.42 (m, 2H), 2.41-2.33 (m, 2H), 1.84-1.69 (m, 2H), 1.52-1.45 (m, 2H), 1.17-1.12 (m, 2H). LCMS (Analytical Method F) Rt = 3.68 min, MS (ESIpos): m/z = 454.2/456.1 (M + H)⁺. |
| 36 | 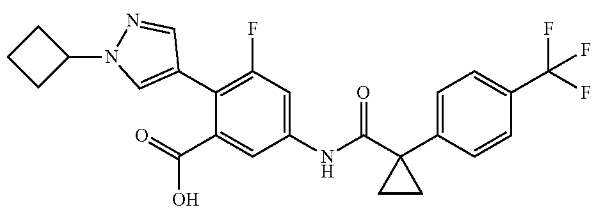 [SMILES: O=C(O)c1cc(NC(=O)C2(c3ccc(C(F)(F)F)cc3)CC2)cc(F)c1-c1cnn(C2CCC2)c1] | 2-(1-Cyclobutyl-1H-pyrazol-4-yl)-3-fluoro-5-[({1-[4-(trifluoromethyl)phenyl]cyclopropyl}carbonyl)amino]benzoic acid | ¹H NMR (500 MHz, DMSO-d6) δ [ppm] 13.13 (s, 1H), 9.59 (s, 1H), 7.88 (s, 1H), 7.75 (dd, J = 12.7, 2.0 Hz, 1H), 7.71 (d, J = 8.3 Hz, 2H), 7.63 (d, J = 1.6 Hz, 1H), 7.59 (d, J = 8.1 Hz, 2H), 7.48 (s, 1H), 4.86 (m, 1H), 2.48-2.42 (m, 2H), 2.41-2.34 (m, 2H), 1.84-1.71 (m, 2H), 1.58-1.52 (m, 2H), 1.25-1.19 (m, 2H). LCMS (Analytical Method F) Rt = 3.76 min, MS (ESIpos): m/z = 488.1 (M + H)⁺. |
| 37 | 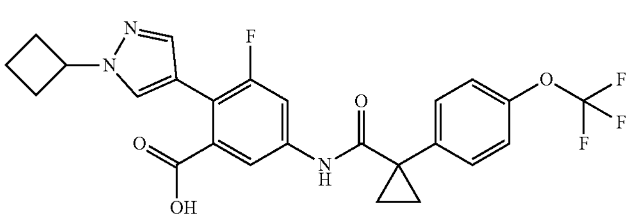 [SMILES: O=C(O)c1cc(NC(=O)C2(c3ccc(OC(F)(F)F)cc3)CC2)cc(F)c1-c1cnn(C2CCC2)c1] | 2-(1-Cyclobutyl-1H-pyrazol-4-yl)-3-fluoro-5-[({1-[4-(trifluoromethoxy)phenyl]cyclopropyl}carbonyl)amino]benzoic acid | ¹H NMR (500 MHz, DMSO-d6) δ [ppm] 13.17 (s, 1H), 9.50 (s, 1H), 7.88 (s, 1H), 7.74 (dd, J = 12.7, 1.8 Hz, 1H), 7.63-7.59 (m, 1H), 7.54-7.45 (m, 3H), 7.36-7.29 (m, 2H), 4.85 (m, 1H), 2.48-2.42 (m, 2H), 2.41-2.32 (m, 2H), 1.86-1.66 (m, 2H), 1.55-1.44 (m, 2H), 1.21-1.13 (m, 2H). LCMS (Analytical Method F) Rt = 3.84 min, MS (ESIpos): m/z = 504.1 (M + H)⁺. |

| Ex. | Structure | Name | Analytical Data |
|---|---|---|---|
| 38 | 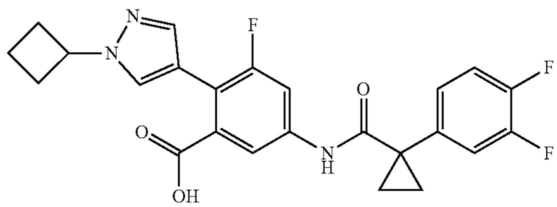 [SMILES: O=C(O)c1cc(NC(=O)C2(c3ccc(F)c(F)c3)CC2)cc(F)c1-c1cnn(C2CCC2)c1] | 2-(1-Cyclobutyl-1H-pyrazol-4-yl)-5-({[1-(3,4-difluorophenyl)cyclopropyl]carbonyl}amino)-3-fluorobenzoic acid | $^1$H NMR (500 MHz, DMSO-d6) δ [ppm] 13.17 (s, 1H), 9.28 (s, 1H), 7.89 (s, 1H), 7.76 (dd, J = 12.7, 2.1 Hz, 1H), 7.62 (d, J = 1.8 Hz, 1H), 7.53-7.46 (m, 2H), 7.45-7.37 (m, 1H), 7.29-7.22 (m, 1H), 4.86 (m, 1H), 2.48-2.42 (m, 2H), 2.41-2.33 (m, 2H), 1.83-1.72 (m, 2H), 1.51-1.47 (m, 2H), 1.20-1.14 (m, 2H). LCMS (Analytical Method F) Rt = 3.53 min, MS (ESIpos): m/z = 456.2 (M + H)$^+$. |
| 39 | 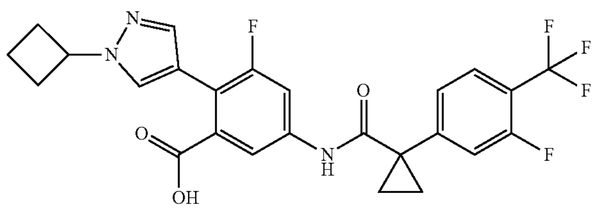 [SMILES: O=C(O)c1cc(NC(=O)C2(c3ccc(C(F)(F)F)c(F)c3)CC2)cc(F)c1-c1cnn(C2CCC2)c1] | 2-(1-Cyclobutyl-1H-pyrazol-4-yl)-3-fluoro-5-[({1-[3-fluoro-4-(trifluoromethyl)phenyl]cyclopropyl}carbonyl)amino]benzoic acid | $^1$H NMR (500 MHz, DMSO-d6) δ [ppm] 13.20 (s, 1H), 9.53 (s, 1H), 7.89 (s, 1H), 7.79-7.69 (m, 2H), 7.60 (d, J = 1.4 Hz, 1H), 7.54-7.48 (m, 2H), 7.42 (d, J = 8.2 Hz, 1H), 4.86 (m, 1H), 2.48-2.43 (m, 2H), 2.41-2.32 (m, 2H), 1.85-1.69 (m, 2H), 1.58-1.53 (m, 2H), 1.30-1.25 (m, 2H). LCMS (Analytical Method F) Rt = 3.81 min, MS (ESIpos): m/z = 506.1 (M + H)$^+$. |
| 40 | 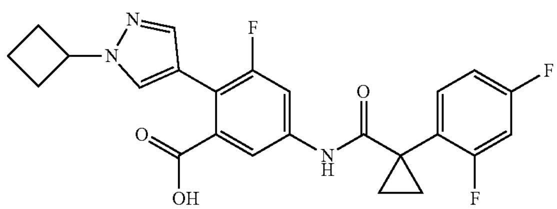 [SMILES: O=C(O)c1cc(NC(=O)C2(c3ccc(F)cc3F)CC2)cc(F)c1-c1cnn(C2CCC2)c1] | 2-(1-Cyclobutyl-1H-pyrazol-4-yl)-5-({[1-(2,4-difluorophenyl)cyclopropyl]carbonyl}amino)-3-fluorobenzoic acid | $^1$H NMR (500 MHz, DMSO-d6) δ [ppm] 13.12 (s, 1H), 9.12 (s, 1H), 7.88 (s, 1H), 7.74 (dd, J = 12.8, 2.0 Hz, 1H), 7.63-7.59 (m, 1H), 7.54-7.45 (m, 2H), 7.29-7.21 (m, 1H), 7.12-7.06 (m, 1H), 4.85 (m, 1H), 2.48-2.43 (m, 2H), 2.42-2.32 (m, 2H), 1.84-1.71 (m, 2H), 1.60-1.56 (m, 2H), 1.18-1.13 (m, 2H). LCMS (Analytical Method F) Rt = 3.45 min, MS (ESIpos): m/z = 456.2 (M + H)$^+$. |
| 41 | 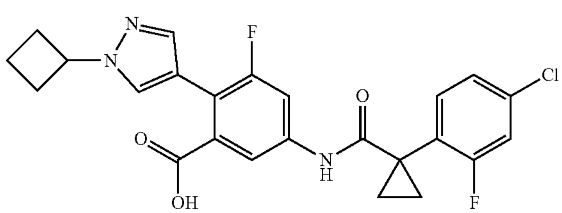 [SMILES: O=C(O)c1cc(NC(=O)C2(c3ccc(Cl)cc3F)CC2)cc(F)c1-c1cnn(C2CCC2)c1] | 5-({[1-(4-Chloro-2-fluorophenyl)cyclopropyl]carbonyl}amino)-2-(1-cyclobutyl-1H-pyrazol-4-yl)-3-fluorobenzoic acid | $^1$H NMR (500 MHz, DMSO-d6) δ [ppm] 13.13 (s, 1H), 9.16 (s, 1H), 7.88 (s, 1H), 7.73 (dd, J = 12.8, 2.0 Hz, 1H), 7.61 (d, J = 1.6 Hz, 1H), 7.52-7.40 (m, 3H), 7.30 (dd, J = 8.3, 1.9 Hz, 1H), 4.85 (m, 1H), 2.48-2.41 (m, 2H), 2.41-2.29 (m, 2H), 1.84-1.71 (m, 2H), 1.62-1.56 (m, 2H), 1.19-1.14 (m, 2H). LCMS (Analytical Method F) Rt = 3.67 min, MS (ESIpos): m/z = 472.1/474.1 (M + H)$^+$. |
| 42 | 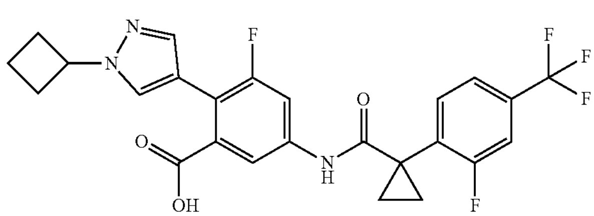 [SMILES: O=C(O)c1cc(NC(=O)C2(c3ccc(C(F)(F)F)cc3F)CC2)cc(F)c1-c1cnn(C2CCC2)c1] | 2-(1-Cyclobutyl-1H-pyrazol-4-yl)-3-fluoro-5-[({1-[2-fluoro-4-(trifluoromethyl)phenyl]cyclopropyl}carbonyl)amino]benzoic acid | $^1$H NMR (250 MHz, DMSO-d6) δ [ppm] 12.93 (s, 1H), 9.25 (s, 1H), 7.89 (s, 1H), 7.82-7.58 (m, 5H), 7.49 (s, 1H), 4.86 (m, 1H), 2.48-2.27 (m, 4H), 1.88-1.71 (m, 2H), 1.71-1.61 (m, 2H), 1.33-1.20 (m, 2H). LCMS (Analytical Method F) Rt = 3.77 min, MS (ESIpos): m/z = 506.1 (M + H)$^+$. |

| Ex. | Structure | Name | Analytical Data |
|---|---|---|---|
| 43 | 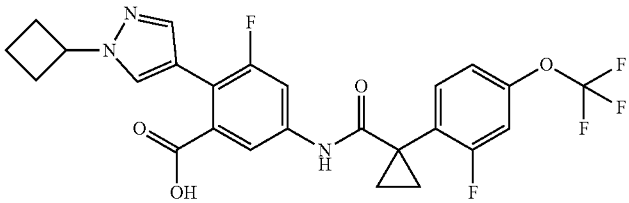 | 2-(1-Cyclobutyl-1H-pyrazol-4-yl)-3-fluoro-5-[({1-[2-fluoro-4-(trifluoromethoxy)phenyl]cyclopropyl}carbonyl)amino]benzoic acid | $^1$H NMR (500 MHz, DMSO-d6) δ [ppm] 13.14 (s, 1H), 9.22 (s, 1H), 7.89 (s, 1H), 7.74 (dd, J = 12.8, 2.0 Hz, 1H), 7.65-7.57 (m, 2H), 7.49 (s, 1H), 7.39 (d, J = 10.3 Hz, 1H), 7.25 (d, J = 8.6 Hz, 1H), 4.86 (m, 1H), 2.48-2.44 (m, 2H), 2.41-2.34 (m, 2H), 1.83-1.73 (m, 2H), 1.67-1.60 (m, 2H), 1.26-1.20 (m, 2H). LCMS (Analytical Method D) Rt = 5.04 min, MS (ESIpos): m/z = 522.05 (M + H)$^+$. |
| 44 | 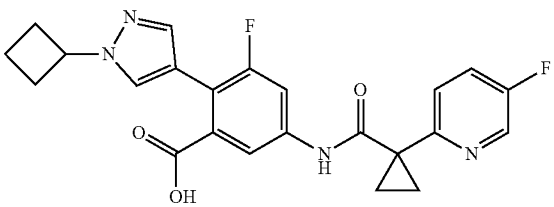 [SMILES: O=C(O)c1cc(NC(=O)C2(c3ccc(F)cn3)CC2)cc(F)c1-c1cnn(C2CCC2)c1] | 2-(1-Cyclobutyl-1H-pyrazol-4-yl)-3-fluoro-5-({[1-(5-fluoropyridin-2-yl)cyclopropyl]carbonyl}amino)benzoic acid | $^1$H NMR (500 MHz, DMSO-d6) δ [ppm] 13.18 (s, 1H), 10.18 (s, 1H), 8.53 (d, J = 3.0 Hz, 1H), 7.90 (s, 1H), 7.79 (dd, J = 12.7, 2.1 Hz, 1H), 7.70 (m, 1H), 7.66 (d, J = 1.7 Hz, 1H), 7.49 (s, 1H), 7.44 (dd, J = 8.8, 4.3 Hz, 1H), 4.86 (m, 1H), 2.48-2.43 (m, 2H), 2.41-2.33 (m, 2H), 1.85-1.71 (m, 2H), 1.54-1.48 (m, 2H), 1.38-1.29 (m, 2H). LCMS (Analytical Method F) Rt = 3.04 min, MS (ESIpos): m/z = 439.2 (M + H)$^+$. |
| 45 | 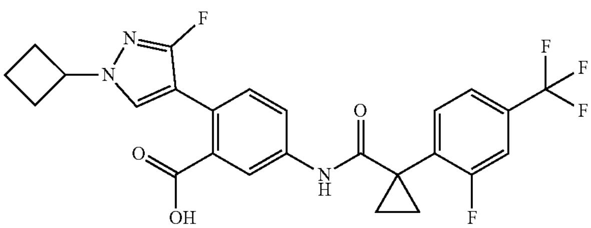 [SMILES: O=C(O)c1cc(NC(=O)C2(c3ccc(C(F)(F)F)cc3F)CC2)ccc1-c1cn(C2CCC2)nc1F] | 2-(1-Cyclobutyl-3-fluoro-1H-pyrazol-4-yl)-5-[({1-[2-fluoro-4-(trifluoromethyl)phenyl]cyclopropyl}carbonyl)amino]benzoic acid | $^1$H NMR (400 MHz, DMSO-d6) δ [ppm] 1.19-1.26 (m, 2H), 1.60-1.64 (m, 2H), 1.70-1.80 (m, 2H), 2.30-2.46 (m, 4H), 4.70 (m, 1H), 7.29 (d, 1H), 7.59-7.77 (m, 4H), 7.89-7.91 (m, 2H), 9.16 (s, 1H), 12.8 (s, br, 1H). LCMS (Method 1): Rt = 1.32 min; MS (ESIPos) m/z = 506 (M + H)$^+$. |
| 46 | 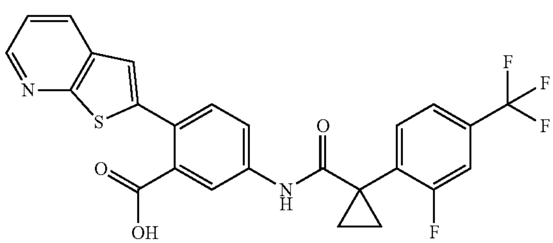 | 5-[({1-[2-Fluoro-4-(trifluoromethyl)phenyl]cyclopropyl}carbonyl)amino]-2-(thieno[2,3-b]pyridin-2-yl)benzoic acid | $^1$H NMR (400 MHz, DMSO-d6) δ [ppm] 1.24-1.27 (m, 2H), 1.65-1.67 (m, 2H), 7.36 (s, 1H), 7.43 (dd, 1H), 7.51 (d, 1H), 7.61 (dd, 1H), 7.69-7.73 (m, 2H), 7.84 (dd, 1H), 7.93 (s, 1H), 8.23 (dd, 1H), 8.53 (dd, 1H), 9.29 (s, 1H). LCMS (Method 2): Rt = 1.26 min; MS (ESIPos) m/z = 501 (M + H)$^+$. |
| 47 | 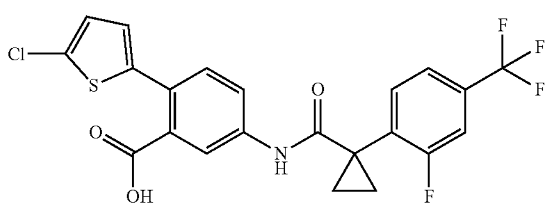 [SMILES: O=C(O)c1cc(NC(=O)C2(c3ccc(C(F)(F)F)cc3F)CC2)ccc1-c1ccc(Cl)s1] | 2-(5-Chloro-2-thienyl)-5-[({1-[2-fluoro-4-(trifluoromethyl)phenyl]cyclopropyl}carbonyl)amino]benzoic acid | $^1$H NMR (400 MHz, DMSO-d6) δ [ppm] 1.22-1.25 (m, 2H), 1.62-1.65 (m, 2H), 6.94 (d, 1H), 7.09 (d, 1H), 7.37 (d, 1H), 7.59-7.61 (m, 1H), 7.67-7.76 (m, 3H), 7.82 (s, 1H), 9.22 (s, 1H). LCMS (Method 1): Rt = 1.39 min; MS (ESIPos) m/z = 484 (M + H)$^+$. |
| 48 | 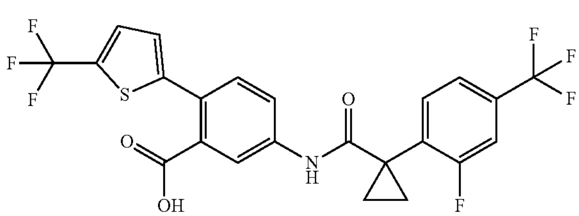 [SMILES: O=C(O)c1cc(NC(=O)C2(c3ccc(C(F)(F)F)cc3F)CC2)ccc1-c1ccc(C(F)(F)F)s1] | 5-[({1-[2-Fluoro-4-(trifluoromethyl)phenyl]cyclopropyl}carbonyl)amino]-2-[5-(trifluoromethyl)-2-thienyl]benzoic acid | $^1$H NMR (400 MHz, DMSO-d6) δ [ppm] 1.23-1.26 (m, 2H), 1.63-1.66 (m, 2H), 7.17 (d, 1H), 7.43 (d, 1H), 7.59-7.72 (m, 4H), 7.77 (dd, 1H), 7.85 (s, 1H), 9.25 (s, 1H). LCMS (Method 1): Rt = 1.43 min; MS (ESIPos) m/z = 518 (M + H)$^+$. |

| Ex. | Structure | Name | Analytical Data |
|---|---|---|---|
| 49 | 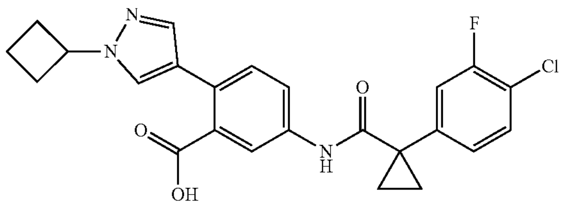 [SMILES: O=C(O)c1cc(NC(=O)C2(c3ccc(Cl)c(F)c3)CC2)ccc1-c1cnn(C2CCC2)c1] | 5-({[1-(4-Chloro-3-fluorophenyl)cyclopropyl]carbonyl}amino)-2-(1-cyclobutyl-1H-pyrazol-4-yl)benzoic acid | $^1$H NMR (400 MHz, DMSO-d6) δ [ppm] 1.15-1.18 (m, 2H), 1.47-1.50 (m, 2H), 1.70-1.80 (m, 2H), 2.31-2.38 (m, 2H), 2.40-2.48 (m, 2H), 4.80 (m, 1H), 7.26 (dd, 1H), 7.35 (d, 1H), 7.44 (dd, 1H), 7.55 (m, 1H), 7.58 (s, 1H), 7.64 (dd, 1H), 7.69 (d, 1H), 7.97 (s, 1H), 9.19 (s, 1H).<br><br>LCMS (Method 1): Rt = 1.21 min; MS (ESIPos) m/z = 454 (M + H)$^+$. |
| 50 | 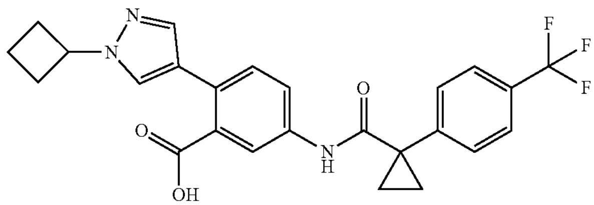 [SMILES: O=C(O)c1cc(NC(=O)C2(c3ccc(C(F)(F)F)cc3)CC2)ccc1-c1cnn(C2CCC2)c1] | 2-(1-Cyclobutyl-1H-pyrazol-4-yl)-5-[({1-[4-(trifluoromethyl)phenyl]cyclopropyl}carbonyl)amino]benzoic acid | $^1$H NMR (400 MHz, DMSO-d6) δ [ppm] 1.18-1.21 (m, 2H), 1.51-1.54 (m, 2H), 1.71-1.80 (m, 2H), 2.32-2.37 (m, 2H), 2.37-2.48 (m, 2H), 4.79 (m, 1H), 7.35 (d, 1H), 7.58-7.60 (m, 3H), 7.63 (dd, 1H), 7.68-7.72 (m, 3H), 7.97 (s, 1H), 9.39 (s, 1H).<br>LCMS (Method 1): Rt = 1.23 min; MS (ESIPos) m/z = 470 (M + H)$^+$. |
| 51 | 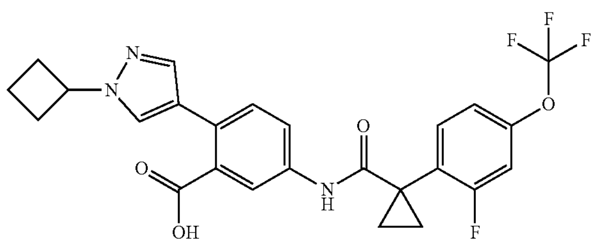 [SMILES: O=C(O)c1cc(NC(=O)C2(c3ccc(OC(F)(F)F)cc3F)CC2)ccc1-c1cnn(C2CCC2)c1] | 2-(1-Cyclobutyl-1H-pyrazol-4-yl)-5-[({1-[2-fluoro-4-(trifluoromethoxy)phenyl]cyclopropyl}carbonyl)amino]benzoic acid | $^1$H NMR (400 MHz, DMSO-d6) δ [ppm] 1.16-1.19 (m, 2H), 1.58-1.61 (m, 2H), 1.72-1.80 (m, 2H), 2.32-2.39 (m, 2H), 2.40-2.49 (m, 2H), 4.80 (m, 1H), 7.23-7.25 (m, 1H), 7.35 (d, 1H), 7.37-7.40 (m, 1H), 7.57 (s, 1H), 7.57-7.66 (m, 3H), 7.96 (s, 1H), 9.02 (s, 1H).<br>LCMS (Method 1): Rt = 1.26 min; MS (ESIPos) m/z = 504 (M + H)$^+$. |
| 52 | 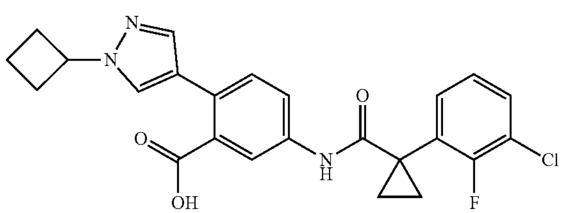 [SMILES: O=C(O)c1cc(NC(=O)C2(c3cccc(Cl)c3F)CC2)ccc1-c1cnn(C2CCC2)c1] | 5-({[1-(3-Chloro-2-fluorophenyl)cyclopropyl]carbonyl}amino)-2-(1-cyclobutyl-1H-pyrazol-4-yl)benzoic acid | $^1$H NMR (400 MHz, DMSO-d6) δ [ppm] 1.16-1.19 (m, 2H), 1.59-1.62 (m, 2H), 1.72-1.81 (m, 2H), 2.34-2.39 (m, 2H), 2.39-2.50 (m, 2H), 4.81 (m, 1H), 7.21-7.25 (m, 1H), 7.35 (d, 1H), 7.42-7.46 (m, 1H), 7.54-7.58 (m, 2H), 7.61-7.66 (m, 2H), 7.96 (s, 1H), 9.01 (s, 1H).<br>LCMS (Method 1): Rt = 1.17 min; MS (ESIPos) m/z = 454 (M + H)$^+$. |
| 53 | 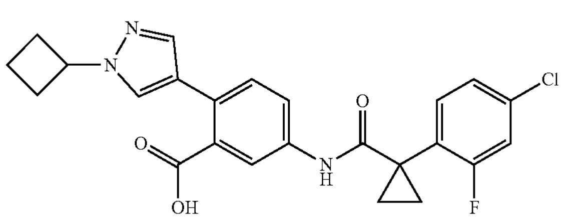 [SMILES: O=C(O)c1cc(NC(=O)C2(c3ccc(Cl)cc3F)CC2)ccc1-c1cnn(C2CCC2)c1] | 5-({[1-(4-Chloro-2-fluorophenyl)cyclopropyl]carbonyl}amino)-2-(1-cyclobutyl-1H-pyrazol-4-yl)benzoic acid | $^1$H NMR (400 MHz, DMSO-d6) δ [ppm] 1.12-1.14 (m, 2H), 1.55-1.58 (m, 2H), 1.71-1.80 (m, 2H), 2.31-2.39 (m, 2H), 2.39-2.49 (m, 2H), 4.79 (m, 1H), 7.29 (dd, 1H), 7.33 (d, 1H), 7.43 (dd, 1H), 7.48 (t, 1H), 7.58-7.61 (m, 3H), 7.97 (s, 1H), 8.96 (s, 1H).<br>LCMS (Method 1): Rt = 1.20 min; MS (ESIPos) m/z = 454 (M + H)$^+$. |
| 54 | 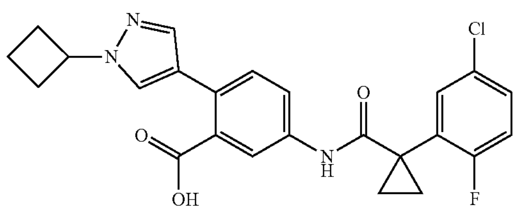 [SMILES: O=C(O)c1cc(NC(=O)C2(c3cc(Cl)ccc3F)CC2)ccc1-c1cnn(C2CCC2)c1] | 5-({[1-(5-Chloro-2-fluorophenyl)cyclopropyl]carbonyl}amino)-2-(1-cyclobutyl-1H-pyrazol-4-yl)benzoic acid | 1H NMR (400 MHz, DMSO-d6) δ [ppm] 1.17-1.20 (m, 2H), 1.54-1.57 (m, 2H), 1.70-1.79 (m, 2H), 2.30-2.38 (m, 2H), 2.40-2.49 (m, 2H), 4.79 (quint, 1H), 7.25 (m, 1H), 7.34 (d, 1H), 7.42-7.46 (m, 1H), 7.52 (dd, 1H), 7.59-7.61 (m, 3H), 7.98 (s, 1H), 9.04 (s, 1H).<br>LCMS (Method 1): Rt = 1.18 min; MS (ESIPos) m/z = 454 (M + H)$^+$. |

| Ex. | Structure | Name | Analytical Data |
|---|---|---|---|
| 55 | 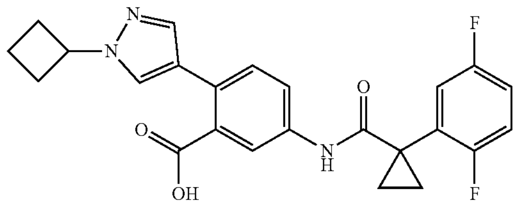 | 2-(1-Cyclobutyl-1H-pyrazol-4-yl)-5-({[1-(2,5-difluorophenyl)cyclopropyl]carbonyl}amino)benzoic acid | ¹H NMR (400 MHz, DMSO-d6) δ [ppm] 1.15-1.18 (m, 2H), 1.54-1.56 (m, 2H), 1.71-1.80 (m, 2H), 2.31-2.37 (m, 2H), 2.37-2.49 (m, 2H), 4.79 (m, 1H), 7.18-7.28 (m, 2H), 7.31-7.35 (m, 2H), 7.56-7.60 (m, 3H), 7.98 (s, 1H), 8.97 (s, 1H).<br>LCMS (Method 1): Rt = 1.11 min; MS (ESIPos) m/z = 438 (M + H)⁺. |
| 56 | 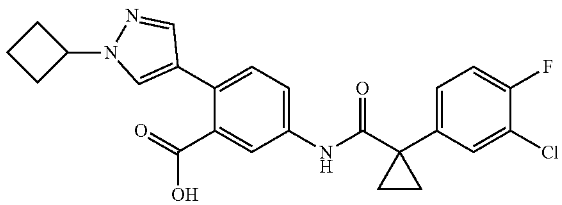 [SMILES: O=C(O)c1cc(NC(=O)C2(c3ccc(F)c(Cl)c3)CC2)ccc1-c1cnn(C2CCC2)c1] | 5-({[1-(3-Chloro-4-fluorophenyl)cyclopropyl]carbonyl}amino)-2-(1-cyclobutyl-1H-pyrazol-4-yl)benzoic acid | ¹H NMR (400 MHz, DMSO-d6) δ [ppm] 1.14-1.17 (m, 2H), 1.46-1.49 (m, 2H), 1.73-1.81 (m, 2H), 2.34-2.41 (m, 2H), 2.41-2.50 (m, 2H), 4.82 (m, 1H), 7.35-7.45 (m, 3H), 7.53 (s, 1H), 7.62 (dd, 1H), 6.69 (dd, 1H), 7.78 (d, 1H), 7.93 (s, 1H), 9.16 (s, 1H).<br>LCMS (Method 1): Rt = 1.21 min; MS (ESIPos) m/z = 454 (M + H)⁺. |
| 57 | 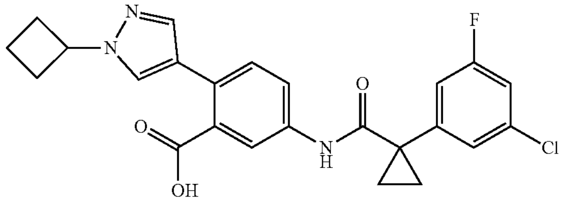 [SMILES: O=C(O)c1cc(NC(=O)C2(c3cc(F)cc(Cl)c3)CC2)ccc1-c1cnn(C2CCC2)c1] | 5-({[1-(3-Chloro-5-fluorophenyl)cyclopropyl]carbonyl}amino)-2-(1-cyclobutyl-1H-pyrazol-4-yl)benzoic acid | ¹H NMR (400 MHz, DMSO-d6) δ [ppm] 1.19-1.22 (m, 2H), 1.47-1.50 (m, 2H), 1.73-1.81 (m, 2H), 2.35-2.49 (m, 4H), 4.82 (m, 1H), 7.23-7.27 (m, 1H), 7.31 (m, 1H), 7.35-7.38 (m, 2H), 7.54 (s, 1H), 7.70 (dd, 1H), 7.80 (d, 1H), 7.93 (s, 1H), 9.32 (s, 1H).<br>LCMS (Method 1): Rt = 1.22 min; MS (ESIPos) m/z = 454 (M + H)⁺. |
| 58 | 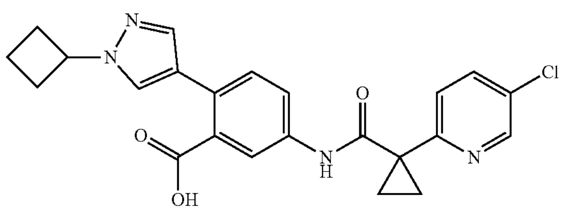 [SMILES: O=C(O)c1cc(NC(=O)C2(c3ccc(Cl)cn3)CC2)ccc1-c1cnn(C2CCC2)c1] | 5-({[1-(5-Chloropyridin-2-yl)cyclopropyl]carbonyl}amino)-2-(1-cyclobutyl-1H-pyrazol-4-yl)benzoic acid | ¹H NMR (400 MHz, DMSO-d6) δ [ppm] 1.35-1.38 (m, 2H), 1.51-1.53 (m, 2H), 1.73-1.82 (m, 2H), 2.33-2.49 (m, 4H), 4.83 (m, 1H), 7.40 (dd, 2H), 7.55 (s, 1H), 7.74 (dd, 1H), 7.86-7.89 (m, 2H), 7.94 (s, 1H), 8.58 (d, 1H), 10.1 (s, 1H).<br>LCMS (Method 1): Rt = 1.07 min; MS (ESIPos) m/z = 437 (M + H)⁺. |
| 59 | 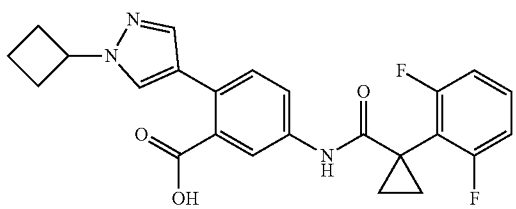 [SMILES: O=C(O)c1cc(NC(=O)C2(c3c(F)cccc3F)CC2)ccc1-c1cnn(C2CCC2)c1] | 2-(1-Cyclobutyl-1H-pyrazol-4-yl)-5-({[1-(2,6-difluorophenyl)cyclopropyl]carbonyl}amino)benzoic acid | ¹H NMR (400 MHz, DMSO-d6) δ [ppm] 1.15-1.18 (m, 2H), 1.69-1.72 (m, 2H), 1.73-1.81 (m, 2H), 2.33-2.49 (m, 4H), 4.82 (m, 1H), 7.08-7.14 (m, 2H), 7.36 (d, 1H), 7.41-7.49 (m, 1H), 7.54 (s, 1H), 7.68 (dd, 1H), 7.75 (d, 1H), 7.94 (s, 1H), 9.06 (s, 1H).<br>LCMS (Method 1): Rt = 1.11 min; MS (ESIPos) m/z = 438 (M + H)⁺. |
| 60 | 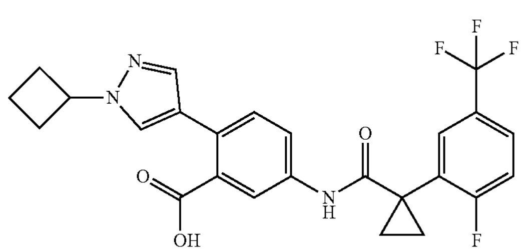 [SMILES: O=C(O)c1cc(NC(=O)C2(c3cc(C(F)(F)F)ccc3F)CC2)ccc1-c1cnn(C2CCC2)c1] | 2-(1-Cyclobutyl-1H-pyrazol-4-yl)-5-[({1-[2-fluoro-5-(trifluoromethyl)phenyl]cyclopropyl}carbonyl)amino]benzoic acid | ¹H NMR (400 MHz, DMSO-d6) δ [ppm] 1.23-1.26 (m, 2H), 1.60-1.63 (m, 2H), 1.72-1.80 (m, 2H), 2.33-2.49 (m, 4H), 4.82 (m, 1H), 7.36 (d, 1H), 7.45 (m, 1H), 7.54 (s, 1H), 7.66 (dd, 1H), 7.73 (d, 1H), 7.78-7.82 (m, 2H), 7.93 (s, 1H), 9.12 (s, 1H).<br>LCMS (Method 1): Rt = 1.23 min; MS (ESIPos) m/z = 488 (M + H)⁺. |
| 61 | 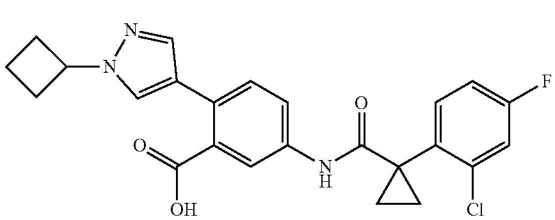 [SMILES: O=C(O)c1cc(NC(=O)C2(c3ccc(F)cc3Cl)CC2)ccc1-c1cnn(C2CCC2)c1] | 5-({[1-(2-Chloro-4-fluorophenyl)cyclopropyl]carbonyl}amino)-2-(1-cyclobutyl-1H-pyrazol-4-yl)benzoic acid | LCMS (Method 1): Rt = 1.16 min; MS (ESIPos) m/z = 454 (M + H)⁺. |

| Ex. | Structure | Name | Analytical Data |
|---|---|---|---|
| 62 | 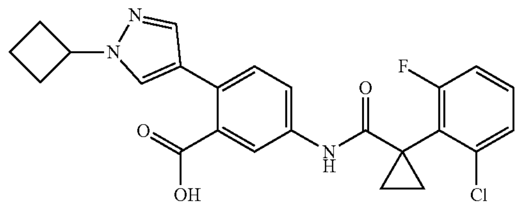 | 5-({[1-(2-Chloro-6-fluorophenyl)cyclopropyl]carbonyl}amino)-2-(1-cyclobutyl-1H-pyrazol-4-yl)benzoic acid | $^1$H NMR (400 MHz, DMSO-d6) δ [ppm] 1.11-1.14 (m, 2H), 1.61-1.64 (m, 2H), 1.73-1.81 (m, 2H), 2.34-2.42 (m, 2H), 2.42-2.49 (m, 2H), 4.82 (m, 1H), 7.25 (m, 1H), 7.35 (d, 1H), 7.49 (dd, 1H), 7.53 (s, 1H), 7.58 (dd, 1H), 7.66 (dd, 1H), 7.72 (d, 1H), 7.93 (s, 1H), 8.81 (s, 1H)<br>LCMS (Method 1): Rt = 1.18 min; MS (ESIPos) m/z = 454 (M + H)$^+$. |
| 63 | 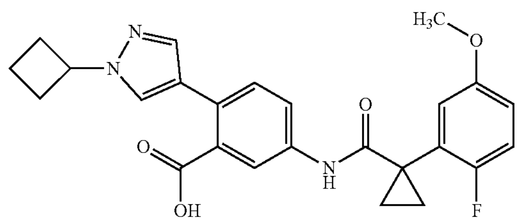 [SMILES: COc1ccc(F)c(C2(C(=O)Nc3ccc(-c4cnn(C5CCC5)c4)c(C(=O)O)c3)CC2)c1] | 2-(1-Cyclobutyl-1H-pyrazol-4-yl)-5-({[1-(2-fluoro-5-methoxyphenyl)cyclopropyl]carbonyl}amino)benzoic acid | $^1$H NMR (400 MHz, DMSO-d6) δ [ppm] 1.13-1.16 (m, 2H), 1.52-1.55 (m, 2H), 1.73-1.81 (m, 2H), 2.33-2.42 (m, 2H), 2.42-2.49 (m, 2H), 4.82 (m, 1H), 6.89-6.93 (m, 1H), 6.98 (dd, 1H), 7.12 (m, 1H), 7.35 (d, 1H), 7.53 (s, 1H), 7.67 (dd, 1H), 7.76 (d, 1H), 7.93 (s, 1H), 8.96 (s, 1H).<br>LCMS (Method 1): Rt = 1.12 min; MS (ESIPos) m/z = 450 (M + H)$^+$. |
| 64 | 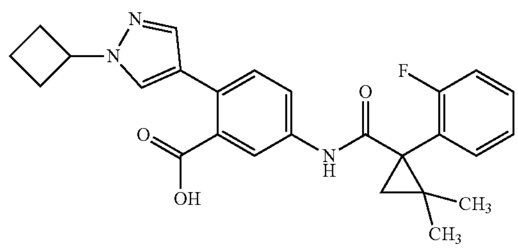 [SMILES: CC1(C)CC1(C(=O)Nc1ccc(-c2cnn(C3CCC3)c2)c(C(=O)O)c1)c1ccccc1F] | 2-(1-Cyclobutyl-1H-pyrazol-4-yl)-5-({[1-(2-fluorophenyl)-2,2-dimethylcyclopropyl]carbonyl}amino)benzoic acid | $^1$H NMR (400 MHz, DMSO-d6) δ [ppm] 0.96 (s, 3H), 0.99 (d, 1H), 1.25 (s, 3H), 1.66 (d, 1H), 1.72-1.81 (m, 2H), 2.32-2.49 (m, 4H), 4.81 (quint, 1H), 7.15-7.22 (m, 2H), 7.31-7.36 (m, 1H), 7.35 (d, 1H), 7.53 (s, 1H), 7.64-7.71 (m, 2H), 7.82 (d, 1H), 7.93 (s, 1H), 9.45 (s, 1H).<br>LCMS (Method 1): Rt = 1.22 min; MS (ESIPos) m/z = 448 (M + H)$^+$. |
| 65 | 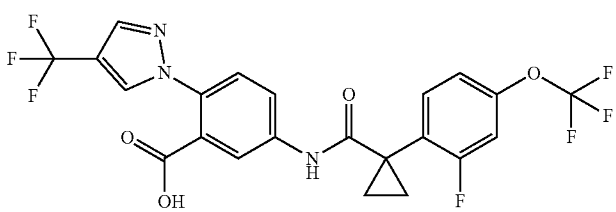 [SMILES: O=C(O)c1cc(NC(=O)C2(c3ccc(OC(F)(F)F)cc3F)CC2)ccc1-n1cc(C(F)(F)F)cn1] | 5-[({1-[2-Fluoro-4-(trifluoromethoxy)phenyl]cyclopropyl}carbonyl)amino]-2-[4-(trifluoromethyl)-1H-pyrazol-1-yl]benzoic acid | 1H NMR (400 MHz, DMSO-d6) δ [ppm] 1.18-1.23 (m, 2H), 1.62-1.64 (m, 2H), 7.26 (dd, 1H), 7.40 (dd, 1H), 7.51 (d, 1H), 7.61 (m, 1H), 7.90 (dd, 1H), 8.01 (d, 1H), 8.08 (s, 1H), 8.75 (s, 1H), 9.30 (s, 1H).<br>LCMS (Method 2): Rt = 1.31 min; MS (ESIPos) m/z = 518 (M + H)$^+$. |
| 66 | 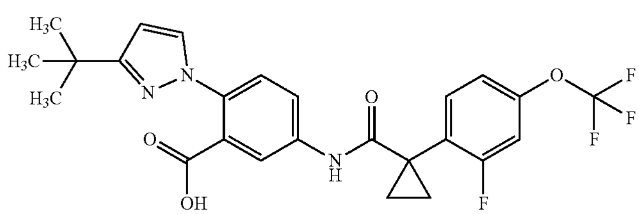 [SMILES: CC(C)(C)c1ccn(-c2ccc(NC(=O)C3(c4ccc(OC(F)(F)F)cc4F)CC3)cc2C(=O)O)n1] | 2-(3-tert-Butyl-1H-pyrazol-1-yl)-5-[({1-[2-fluoro-4-(trifluoromethoxy)phenyl]cyclopropyl}carbonyl)amino]benzoic acid | 1H NMR (400 MHz, DMSO-d6) δ [ppm] 1.17-1.21 (m, 2H), 1.25 (s, 9H), 1.60-1.63 (m, 2H), 6.31 (d, 1H), 7.25 (d, 1H), 7.40 (dd, 1H), 7.45 (d, 1H), 7.60 (t, 1H), 7.78 (dd, 1H), 7.82 (d, 1H), 7.88 (d, 1H), 9.17 (s, 1H).<br>LCMS (Method 2): Rt = 1.37 min; MS (ESIPos) m/z = 506 (M + H)$^+$. |
| 67 | 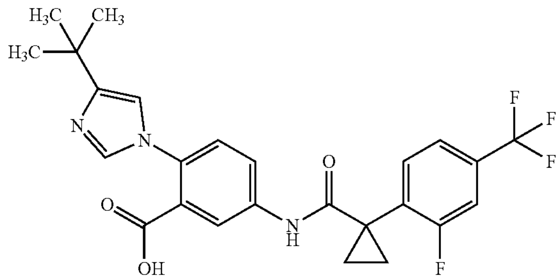 [SMILES: CC(C)(C)c1cn(-c2ccc(NC(=O)C3(c4ccc(C(F)(F)F)cc4F)CC3)cc2C(=O)O)cn1] | 2-(4-tert-Butyl-1H-imidazol-1-yl)-5-[({1-[2-fluoro-4-(trifluoromethyl)phenyl]cyclopropyl}carbonyl)amino]benzoic acid | LCMS (method 2): Rt = 1.04 min; MS (ESIPos) m/z = 490 (M + H)$^+$. |

-continued

| Ex. | Structure | Name | Analytical Data |
|---|---|---|---|
| 68 | 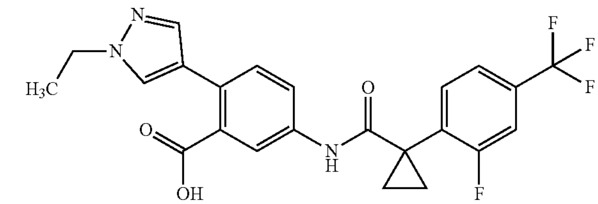 [SMILES: CCn1cc(-c2ccc(NC(=O)C3(c4ccc(C(F)(F)F)cc4F)CC3)cc2C(=O)O)cn1] | 2-(1-Ethyl-1H-pyrazol-4-yl)-5-[({1-[2-fluoro-4-(trifluoromethyl)phenyl]cyclopropyl}carbonyl)amino]benzoic acid | $^1$H NMR (500 MHz, DMSO-d6) δ [ppm] 12.91 (s, 1H), 9.08 (s, 1H), 7.86 (s, 1H), 7.73 (d, J = 2.3 Hz, 1H), 7.72-7.64 (m, 3H), 7.62-7.56 (m, 1H), 7.53-7.50 (m, 1H), 7.35 (d, J = 8.5 Hz, 1H), 4.12 (q, J = 7.3 Hz, 2H), 1.69-1.57 (m, 2H), 1.38 (t, J = 7.3 Hz, 3H), 1.28-1.15 (m, 2H). LCMS (Analytical Method F) Rt = 3.34 min, MS (ESIpos): m/z = 462.1 (M + H)$^+$. |
| 69 | 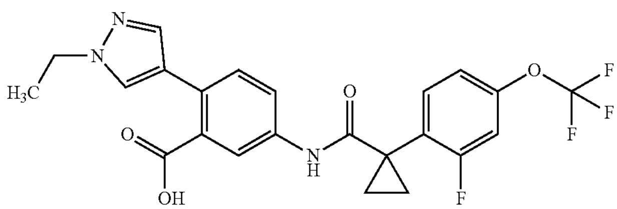 [SMILES: CCn1cc(-c2ccc(NC(=O)C3(c4ccc(OC(F)(F)F)cc4F)CC3)cc2C(=O)O)cn1] | 2-(1-Ethyl-1H-pyrazol-4-yl)-5-[({1-[2-fluoro-4-(trifluoromethoxy)phenyl]cyclopropyl}carbonyl)amino]benzoic acid | $^1$H NMR (500 MHz, DMSO-d6) δ [ppm] 12.91 (s, 1H), 9.04 (s, 1H), 7.88-7.83 (m, 1H), 7.74 (d, J = 2.3 Hz, 1H), 7.67 (dd, J = 8.5, 2.3 Hz, 1H), 7.63-7.56 (m, 1H), 7.51 (d, J = 0.7 Hz, 1H), 7.41-7.32 (m, 2H), 7.27-7.21 (m, 1H), 4.12 (q, J = 7.3 Hz, 2H), 1.66-1.54 (m, 2H), 1.38 (t, J = 7.3 Hz, 3H), 1.23-1.12 (m, 2H). LCMS (Analytical Method F) Rt = 3.42 min, MS (ESIpos): m/z = 478.1 (M + H)$^+$. |
| 70 | 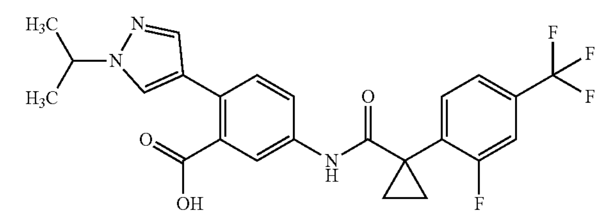 [SMILES: CC(C)n1cc(-c2ccc(NC(=O)C3(c4ccc(C(F)(F)F)cc4F)CC3)cc2C(=O)O)cn1] | 5-[({1-[2-Fluoro-4-(trifluoromethyl)phenyl]cyclopropyl}carbonyl)amino]-2-[1-(propan-2-yl)-1H-pyrazol-4-yl]benzoic acid | $^1$H NMR (500 MHz, DMSO-d6) δ [ppm] 12.93 (s, 1H), 9.07 (s, 1H), 7.92-7.84 (m, 1H), 7.73 (d, J = 2.3 Hz, 1H), 7.72-7.63 (m, 3H), 7.62-7.57 (m, 1H), 7.51 (d, J = 0.6 Hz, 1H), 7.37 (d, J = 8.5 Hz, 1H), 4.48 (hept, J = 6.6 Hz, 1H), 1.68-1.58 (m, 2H), 1.42 (d, J = 6.7 Hz, 6H), 1.27-1.16 (m, 2H). LCMS (Analytical Method F) Rt = 3.48 min, MS (ESIpos): m/z = 476.1 (M + H)$^+$. |
| 71 | 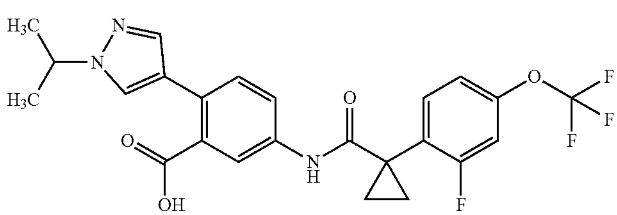 [SMILES: CC(C)n1cc(-c2ccc(NC(=O)C3(c4ccc(OC(F)(F)F)cc4F)CC3)cc2C(=O)O)cn1] | 5-[({1-[2-Fluoro-4-(trifluoromethoxy)phenyl]cyclopropyl}carbonyl)amino]-2-[1-(propan-2-yl)-1H-pyrazol-4-yl]benzoic acid | 1H NMR (500 MHz, DMSO-d6) δ [ppm] 12.92 (s, 1H), 9.04 (s, 1H), 7.89 (s, 1H), 7.73 (d, J = 2.3 Hz, 1H), 7.66 (dd, J = 8.5, 2.3 Hz, 1H), 7.63-7.56 (m, 1H), 7.51 (s, 1H), 7.41-7.34 (m, 2H), 7.27-7.20 (m, 1H), 4.48 (hept, J = 6.7 Hz, 1H), 1.65-1.55 (m, 2H), 1.42 (d, J = 6.7 Hz, 6H), 1.23-1.13 (m, 2H). LCMS (Analytical Method F) Rt = 3.56 min, MS (ESIpos): m/z = 492.1 (M + H)$^+$. |
| 72 | 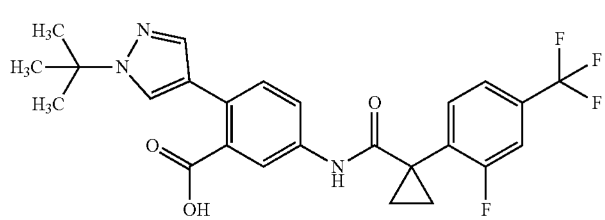 [SMILES: CC(C)(C)n1cc(-c2ccc(NC(=O)C3(c4ccc(C(F)(F)F)cc4F)CC3)cc2C(=O)O)cn1] | 2-(1-tert-Butyl-1H-pyrazol-4-yl)-5-[({1-[2-fluoro-4-(trifluoromethyl)phenyl]cyclopropyl}carbonyl)amino]benzoic acid | 1H NMR (500 MHz, DMSO-d6) δ [ppm] 12.98 (s, 1H), 9.08 (s, 1H), 7.96 (d, J = 0.6 Hz, 1H), 7.73 (d, J = 2.3 Hz, 1H), 7.72-7.63 (m, 3H), 7.62-7.57 (m, 1H), 7.54 (s, 1H), 7.40 (d, J = 8.5 Hz, 1H), 1.68-1.58 (m, 2H), 1.53 (s, 9H), 1.28-1.16 (m, 2H). LCMS (Analytical Method F) Rt = 3.65 min, MS (ESIpos): m/z = 490.1 (M + H)$^+$. |

-continued

| Ex. | Structure | Name | Analytical Data |
|---|---|---|---|
| 73 | 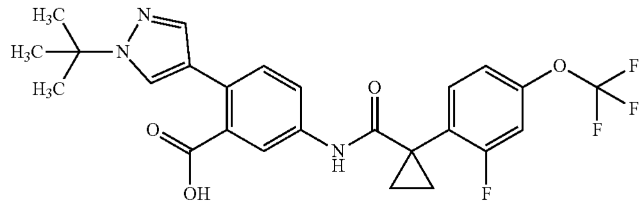 [SMILES: CC(C)(C)n1cc(-c2ccc(NC(=O)C3(c4ccc(OC(F)(F)F)cc4F)CC3)cc2C(=O)O)cn1] | 2-(1-tert-Butyl-1H-pyrazol-4-yl)-5-[({1-[2-fluoro-4-(trifluoromethoxy)phenyl]cyclopropyl}carbonyl)amino]benzoic acid | 1H NMR (500 MHz, DMSO-d6) δ [ppm] 12.99 (s, 1H), 9.04 (s, 1H), 7.96 (d, J = 0.6 Hz, 1H), 7.72 (d, J = 2.3 Hz, 1H), 7.66 (dd, J = 8.5, 2.3 Hz, 1H), 7.63-7.57 (m, 1H), 7.54 (s, 1H), 7.43-7.36 (m, 2H), 7.28-7.21 (m, 1H), 1.62-1.57 (m, 2H), 1.52 (s, 9H), 1.25-1.09 (m, 2H). LCMS (Analytical Method F) Rt = 3.72 min, MS (ESIpos): m/z = 506.2 (M + H)⁺. |
| 74 | 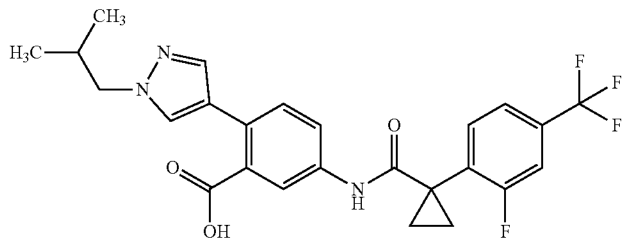 [SMILES: CC(C)Cn1cc(-c2ccc(NC(=O)C3(c4ccc(C(F)(F)F)cc4F)CC3)cc2C(=O)O)cn1] | 5-[({1-[2-Fluoro-4-(trifluoromethyl)phenyl]cyclopropyl}carbonyl)amino]-2-[1-(2-methylpropyl)-1H-pyrazol-4-yl]benzoic acid | ¹H NMR (500 MHz, DMSO-d6) δ [ppm] 12.90 (s, 1H), 9.08 (s, 1H), 7.80 (s, 1H), 7.74 (d, J = 2.3 Hz, 1H), 7.72-7.64 (m, 3H), 7.62-7.57 (m, 1H), 7.52 (d, J = 0.6 Hz, 1H), 7.35 (d, J = 8.5 Hz, 1H), 3.90 (d, J = 7.2 Hz, 2H), 2.16-2.01 (m, 1H), 1.69-1.57 (m, 2H), 1.29-1.13 (m, 2H), 0.85 (d, J = 6.7 Hz, 6H). LCMS (Analytical Method F) Rt = 3.76 min, MS (ESIpos): m/z = 490.1 (M + H)⁺. |
| 75 | 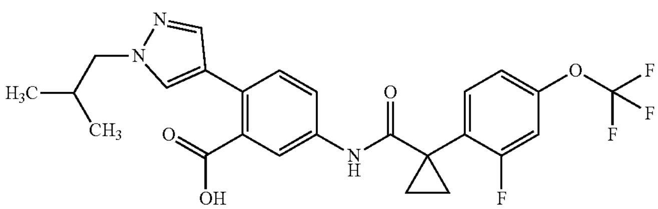 [SMILES: CC(C)Cn1cc(-c2ccc(NC(=O)C3(c4ccc(OC(F)(F)F)cc4F)CC3)cc2C(=O)O)cn1] | 5-[({1-[2-Fluoro-4-(trifluoromethoxy)phenyl]cyclopropyl}carbonyl)amino]-2-[1-(2-methylpropyl)-1H-pyrazol-4-yl]benzoic acid | ¹H NMR (500 MHz, DMSO-d6) δ [ppm] 12.88 (s, 1H), 9.04 (s, 1H), 7.82-7.78 (m, 1H), 7.74 (d, J = 2.3 Hz, 1H), 7.67 (dd, J = 8.5, 2.3 Hz, 1H), 7.63-7.56 (m, 1H), 7.52 (d, J = 0.6 Hz, 1H), 7.37 (dd, J = 10.5, 1.9 Hz, 1H), 7.35 (d, J = 8.5 Hz, 1H), 7.26-7.21 (m, 1H), 3.90 (d, J = 7.2 Hz, 2H), 2.18-2.00 (m, 1H), 1.68-1.53 (m, 2H), 1.25-1.10 (m, 2H), 0.85 (d, J = 6.7 Hz, 6H). LCMS (Analytical Method F) Rt = 3.73 min, MS (ESIpos): m/z = 506.1 (M + H)⁺. |
| 76 | 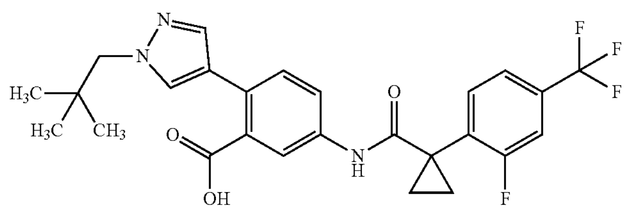 [SMILES: CC(C)(C)Cn1cc(-c2ccc(NC(=O)C3(c4ccc(C(F)(F)F)cc4F)CC3)cc2C(=O)O)cn1] | 2-[1-(2,2-Dimethylpropyl)-1H-pyrazol-4-yl]-5-[({1-[2-fluoro-4-(trifluoromethyl)phenyl]cyclopropyl}carbonyl)amino]benzoic acid | ¹H NMR (500 MHz, DMSO-d6) δ [ppm] 12.92 (s, 1H), 9.08 (s, 1H), 7.76 (s, 1H), 7.74 (d, J = 2.3 Hz, 1H), 7.72-7.64 (m, 3H), 7.62-7.57 (m, 1H), 7.53 (s, 1H), 7.36 (d, J = 8.5 Hz, 1H), 3.89 (s, 2H), 1.69-1.57 (m, 2H), 1.27-1.16 (m, 2H), 0.91 (s, 9H). LCMS (Analytical Method D) Rt = 5.24 min, MS (ESIpos): m/z = 504.1 (M + H)⁺. |
| 77 | 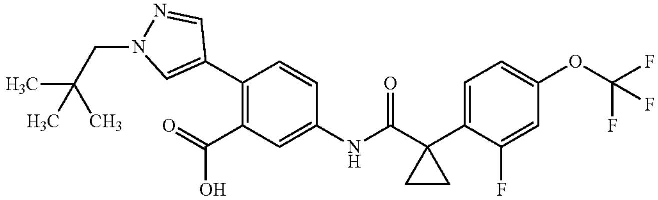 [SMILES: CC(C)(C)Cn1cc(-c2ccc(NC(=O)C3(c4ccc(OC(F)(F)F)cc4F)CC3)cc2C(=O)O)cn1] | 2-[1-(2,2-Dimethylpropyl)-1H-pyrazol-4-yl]-5-[({1-[2-fluoro-4-(trifluoromethoxy)phenyl]cyclopropyl}carbonyl)amino]benzoic acid | ¹H NMR (500 MHz, DMSO-d6) δ [ppm] 12.91 (s, 1H), 9.04 (s, 1H), 7.78-7.72 (m, 2H), 7.67 (dd, J = 8.5, 2.3 Hz, 1H), 7.63-7.56 (m, 1H), 7.53 (s, 1H), 7.40-7.33 (m, 2H), 7.24 (d, J = 8.6 Hz, 1H), 3.89 (s, 2H), 1.67-1.53 (m, 2H), 1.24-1.13 (m, 2H), 0.91 (s, 9H). LCMS (Analytical Method D) Rt = 4.67 min, MS (ESIpos): m/z = 520.1 (M + H)⁺. |

| Ex. | Structure | Name | Analytical Data |
|---|---|---|---|
| 78 | 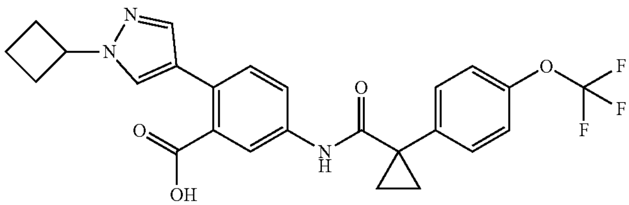 [SMILES: O=C(O)c1cc(NC(=O)C2(c3ccc(OC(F)(F)F)cc3)CC2)ccc1-c1cnn(C2CCC2)c1] | 2-(1-Cyclobutyl-1H-pyrazol-4-yl)-5-[({1-[4-(trifluoromethoxy)phenyl]cyclopropyl}carbonyl)amino]benzoic acid | ¹H NMR (500 MHz, DMSO-d6) δ [ppm] 12.92 (s, 1H), 9.33 (s, 1H), 7.92 (d, J = 0.6 Hz, 1H), 7.81 (d, J = 2.3 Hz, 1H), 7.69 (dd, J = 8.5, 2.3 Hz, 1H), 7.55-7.53 (m, 1H), 7.53-7.49 (m, 2H), 7.37 (d, J = 8.5 Hz, 1H), 7.35-7.31 (m, 2H), 4.87-4.77 (m, 1H), 2.48-2.33 (m, 4H), 1.84-1.71 (m, 2H), 1.54-1.43 (m, 2H), 1.21-1.09 (m, 2H). LCMS (Analytical Method F) Rt = 3.68 min, MS (ESIpos): m/z = 486.1 (M + H)⁺. |
| 79 | 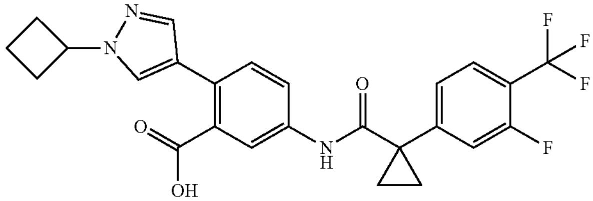 [SMILES: O=C(O)c1cc(NC(=O)C2(c3ccc(C(F)(F)F)c(F)c3)CC2)ccc1-c1cnn(C2CCC2)c1] | 2-(1-Cyclobutyl-1H-pyrazol-4-yl)-5-[({1-[3-fluoro-4-(trifluoromethyl)phenyl]cyclopropyl}carbonyl)amino]benzoic acid | ¹H NMR (500 MHz, DMSO-d6) δ [ppm] 12.93 (s, 1H), 9.38 (s, 1H), 7.93 (s, 1H), 7.80 (d, J = 2.3 Hz, 1H), 7.78-7.72 (m, 1H), 7.69 (dd, J = 8.5, 2.3 Hz, 1H), 7.54 (s, 1H), 7.53-7.48 (m, 1H), 7.45-7.40 (m, 1H), 7.38 (d, J = 8.5 Hz, 1H), 4.88-4.76 (m, 1H), 2.49-2.31 (m, 4H), 1.86-1.70 (m, 2H), 1.59-1.49 (m, 2H), 1.32-1.19 (m, 2H). LCMS (Analytical Method D) Rt = 5.12 min, MS (ESIpos): m/z = 488.1 (M + H)⁺. |
| 80 | 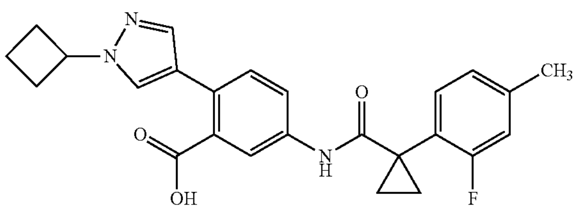 [SMILES: Cc1ccc(C2(C(=O)Nc3ccc(-c4cnn(C5CCC5)c4)c(C(=O)O)c3)CC2)c(F)c1] | 2-(1-Cyclobutyl-1H-pyrazol-4-yl)-5-({[1-(2-fluoro-4-methylphenyl)cyclopropyl]carbonyl}amino)benzoic acid | ¹H NMR (500 MHz, DMSO-d6) δ [ppm] 12.90 (s, 1H), 8.90 (s, 1H), 7.97-7.89 (m, 1H), 7.76 (d, J = 2.3 Hz, 1H), 7.67 (dd, J = 8.5, 2.3 Hz, 1H), 7.53 (s, 1H), 7.37-7.30 (m, 2H), 7.05-7.02 (m, 1H), 7.02 (s, 1H), 4.87-4.77 (m, 1H), 2.48-2.34 (m, 4H), 2.33 (s, 3H), 1.86-1.70 (m, 2H), 1.59-1.48 (m, 2H), 1.15-1.03 (m, 2H). LCMS (Analytical Method F) Rt = 3.42 min, MS (ESIpos): m/z = 434.2 (M + H)⁺. |
| 81 | 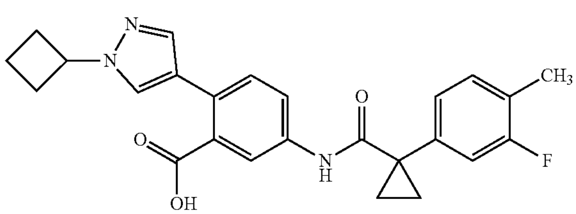 [SMILES: Cc1ccc(C2(C(=O)Nc3ccc(-c4cnn(C5CCC5)c4)c(C(=O)O)c3)CC2)cc1F] | 2-(1-Cyclobutyl-1H-pyrazol-4-yl)-5-({[1-(3-fluoro-4-methylphenyl)cyclopropyl]carbonyl}amino)benzoic acid | ¹H NMR (400 MHz, DMSO-d6) δ [ppm] 1.10-1.12 (m, 2H), 1.43-1.45 (m, 2H), 1.71-1.80 (m, 2H), 2.22 (s, 3H), 2.31-2.50 (m, 4H), 4.80 (m, 1H), 7.12-7.17 (m, 2H), 7.25 (m, 1H), 7.34 (d, 1H), 7.58 (s, 1H), 7.64 (dd, 1H), 7.69 (d, 1H), 7.96 (s, 1H), 9.16 (s, 1H). LCMS (method 1): Rt = 1.20 min; MS (ESIPos) m/z = 434 (M + H)⁺. |
| 82 | 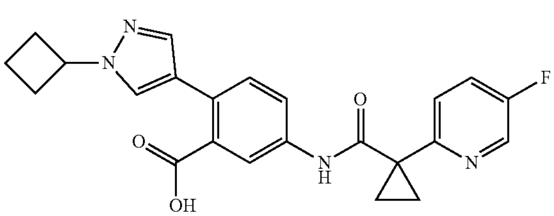 [SMILES: O=C(O)c1cc(NC(=O)C2(c3ccc(F)cn3)CC2)ccc1-c1cnn(C2CCC2)c1] | 2-(1-Cyclobutyl-1H-pyrazol-4-yl)-5-({[1-(5-fluoropyridin-2-yl)cyclopropyl]carbonyl}amino)benzoic acid | ¹H NMR (500 MHz, DMSO-d6) δ [ppm] 9.98 (s, 1H), 8.53 (d, J = 3.0 Hz, 1H), 7.95 (s, 1H), 7.82 (d, J = 2.0 Hz, 1H), 7.69 (td, J = 8.8, 3.0 Hz, 2H), 7.58 (s, 1H), 7.44 (dd, J = 8.8, 4.3 Hz, 1H), 7.38 (d, J = 8.5 Hz, 1H), 4.87-4.75 (m, 1H), 2.48-2.33 (m, 4H), 1.86-1.70 (m, 2H), 1.56-1.45 (m, 2H), 1.40-1.28 (m, 2H). LCMS (Analytical Method E): Rt = 2.83 mins; MS (ESIpos) m/z = 421.2 (M + H)⁺. |

| Ex. | Structure | Name | Analytical Data |
|---|---|---|---|
| 83 | 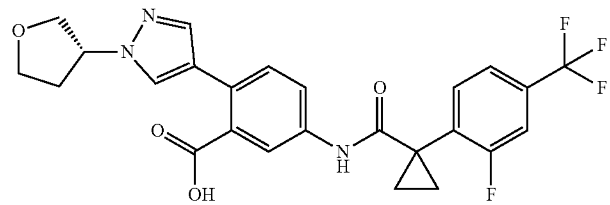 [SMILES: O=C(O)c1cc(NC(=O)C2(c3ccc(C(F)(F)F)cc3F)CC2)ccc1-c1cnn([C@@H]2CCOC2)c1] | 5-[({1-[2-Fluoro-4-(trifluoromethyl)phenyl]cyclopropyl}carbonyl)amino]-2-{1-[(3R)-tetrahydrofuran-3-yl]-1H-pyrazol-4-yl}benzoic acid | ¹H NMR (500 MHz, DMSO-d6) δ [ppm] 12.94 (s, 1H), 9.08 (s, 1H), 7.91 (s, 1H), 7.75 (d, J = 2.3 Hz, 1H), 7.72-7.64 (m, 3H), 7.61-7.58 (m, 1H), 7.56 (s, 1H), 7.37 (d, J = 8.5 Hz, 1H), 5.06-4.94 (m, 1H), 4.01-3.93 (m, 2H), 3.89 (dd, J = 9.3, 3.7 Hz, 1H), 3.86-3.78 (m, 1H), 2.42-2.32 (m, 1H), 2.30-2.22 (m, 1H), 1.67-1.56 (m, 2H), 1.29-1.13 (m, 2H). LCMS (Analytical Method F) Rt = 3.27 min, MS (ESIpos): m/z = 504.2 (M + H)⁺. |
| 84 | 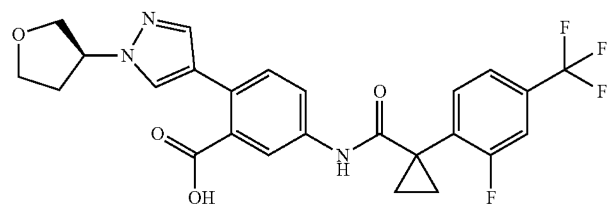 [SMILES: O=C(O)c1cc(NC(=O)C2(c3ccc(C(F)(F)F)cc3F)CC2)ccc1-c1cnn([C@H]2CCOC2)c1] | 5-[({1-[2-Fluoro-4-(trifluoromethyl)phenyl]cyclopropyl}carbonyl)amino]-2-{1-[(3S)-tetrahydrofuran-3-yl]-1H-pyrazol-4-yl}benzoic acid | ¹H NMR (500 MHz, DMSO-d6) δ 9.02 (s, 1H), 7.95 (s, 1H), 7.75-7.52 (m, 6H), 7.43-7.28 (m, 1H), 5.03-4.91 (m, 1H), 4.01-3.92 (m, 2H), 3.92-3.85 (m, 1H), 3.85-3.78 (m, 1H), 2.41-2.31 (m, 1H), 2.31-2.20 (m, 1H), 1.65-1.57 (m, 2H), 1.23-1.18 (m, 2H). LCMS (Analytical Method D): Rt = 1.91 mins, MS (ESIpos): m/z = 504 (M + H)⁺. |
| 85 | 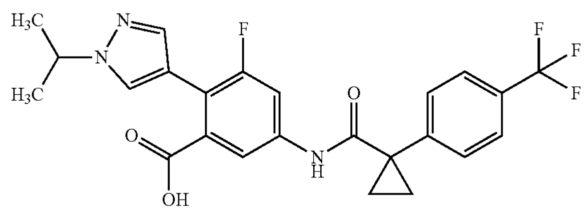 [SMILES: CC(C)n1cc(-c2c(F)cc(NC(=O)C3(c4ccc(C(F)(F)F)cc4)CC3)cc2C(=O)O)cn1] | 3-Fluoro-2-[1-(propan-2-yl)-1H-pyrazol-4-yl]-5-[({1-[4-(trifluoromethyl)phenyl]cyclopropyl}carbonyl)amino]benzoic acid | ¹H NMR (250 MHz, DMSO-d6) δ [ppm] 13.16 (s, 1H), 9.59 (s, 1H), 7.87-7.82 (m, 1H), 7.81-7.67 (m, 3H), 7.66-7.56 (m, 3H), 7.47 (s, 1H), 4.53 (hept, J = 6.6 Hz, 1H), 1.59-1.53 (m, 2H), 1.43 (d, J = 6.7 Hz, 6H), 1.26-1.20 (m, 2H). LCMS (Analytical Method D) Rt = 5.08 min, MS (ESIpos): m/z = 476.05 (M + H)⁺. |
| 86 | 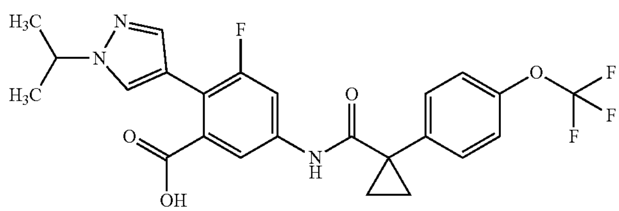 [SMILES: CC(C)n1cc(-c2c(F)cc(NC(=O)C3(c4ccc(OC(F)(F)F)cc4)CC3)cc2C(=O)O)cn1] | 3-Fluoro-2-[1-(propan-2-yl)-1H-pyrazol-4-yl]-5-[({1-[4-(trifluoromethoxy)phenyl]cyclopropyl}carbonyl)amino]benzoic acid | ¹H NMR (250 MHz, DMSO-d6) δ [ppm] 13.13 (s, 1H), 9.50 (s, 1H), 7.85 (s, 1H), 7.76 (d, J = 13.2 Hz, 1H), 7.63 (s, 1H), 7.60-7.43 (m, 3H), 7.35 (d, J = 8.1 Hz, 2H), 4.62-4.42 (m, 1H), 1.58-1.49 (m, 2H), 1.43 (d, J = 6.6 Hz, 6H), 1.24-1.13 (m,2H). LCMS (Analytical Method D) Rt = 5.08 min, MS (ESIpos): m/z = 492 (M + H)⁺. |
| 87 | 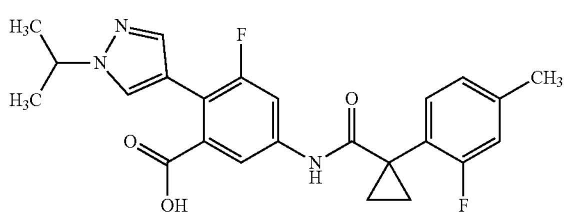 [SMILES: Cc1ccc(C2(C(=O)Nc3cc(F)c(-c4cnn(C(C)C)c4)c(C(=O)O)c3)CC2)c(F)c1] | 3-Fluoro-5-({[1-(2-fluoro-4-methylphenyl)cyclopropyl]carbonyl}amino)-2-[1-(propan-2-yl)-1H-pyrazol-4-yl]benzoic acid | ¹H NMR (500 MHz, DMSO-d6) δ [ppm] 13.11 (s, 1H), 9.09 (s, 1H), 7.88-7.79 (m, 1H), 7.74 (dd, J = 12.9, 2.1 Hz, 1H), 7.61 (d, J = 1.6 Hz, 1H), 7.45 (s, 1H), 7.37-7.26 (m, 1H), 7.06-7.00 (m, 2H), 4.52 (hept, J = 6.6 Hz, 1H), 2.33 (s, 3H), 1.61-1.50 (m, 2H), 1.42 (d, J = 6.7 Hz, 6H), 1.17-1.06 (m, 2H). LCMS (Analytical Method F): Rt = 3.47 mins; MS (ESIpos) m/z = 440.2 (M + H)⁺. |

| Ex. | Structure | Name | Analytical Data |
|---|---|---|---|
| 88 | 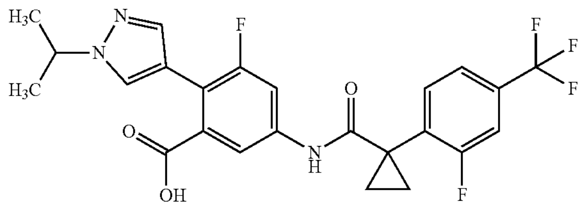 [SMILES: CC(C)n1cc(-c2c(F)cc(NC(=O)C3(c4ccc(C(F)(F)F)cc4F)CC3)cc2C(=O)O)cn1] | 3-Fluoro-5-[({1-[2-fluoro-4-(trifluoromethyl)phenyl]cyclopropyl}carbonyl)amino]-2-[1-(propan-2-yl)-1H-pyrazol-4-yl]benzoic acid | $^1$H NMR (250 MHz, DMSO-d6) δ [ppm] 13.14 (s, 1H), 9.24 (s, 1H), 7.85 (s, 1H), 7.80-7.65 (m, 3H), 7.65-7.57 (m, 2H), 7.47 (s, 1H), 4.53 (hept, J = 6.6 Hz, 1H), 1.70-1.60 (m, 2H), 1.43 (d, J = 6.6 Hz, 6H), 1.29-1.22 (m, 2H). LCMS (Analytical Method D) Rt = 5.08 min, MS (ESIpos): m/z = 494.05 (M + H)$^+$. |
| 89 | 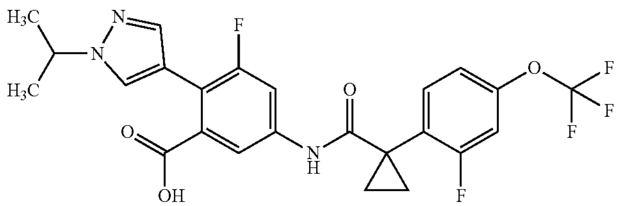 [SMILES: CC(C)n1cc(-c2c(F)cc(NC(=O)C3(c4ccc(OC(F)(F)F)cc4F)CC3)cc2C(=O)O)cn1] | 3-Fluoro-5-[({1-[2-fluoro-4-(trifluoromethoxy)phenyl]cyclopropyl}carbonyl)amino]-2-[1-(propan-2-yl)-1H-pyrazol-4-yl]benzoic acid | $^1$H NMR (250 MHz, DMSO-d6) δ [ppm] 13.14 (s, 1H), 9.21 (s, 1H), 7.85 (s, 1H), 7.73 (dd, J = 12.9, 2.1 Hz, 1H), 7.65-7.56 (m, 2H), 7.46 (s, 1H), 7.39 (d, J = 10.7 Hz, 1H), 7.25 (d, J = 8.5 Hz, 1H), 4.61-4.43 (m, 1H), 1.67-1.59 (m, 2H), 1.43 (d, J = 6.7 Hz, 6H), 1.25-1.18 (m, 2H). LCMS (Analytical Method D) Rt = 5.05 min, MS (ESIpos): m/z = 510 (M + H)$^+$. |
| 90 | 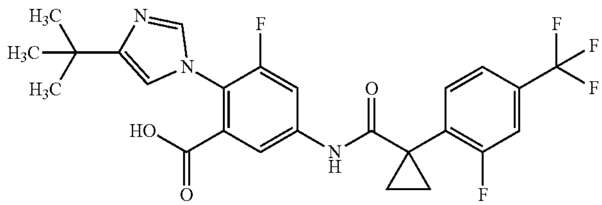 [SMILES: CC(C)(C)c1cn(-c2c(F)cc(NC(=O)C3(c4ccc(C(F)(F)F)cc4F)CC3)cc2C(=O)O)cn1] | 2-(4-tert-Butyl-1H-imidazol-1-yl)-3-fluoro-5-[({1-[2-fluoro-4-(trifluoromethyl)phenyl]cyclopropyl}carbonyl)amino]benzoic acid | $^1$H NMR (500 MHz, DMSO-d6) δ [ppm] 9.57 (s, 1H), 8.55 (s, 1H), 8.05 (dd, J = 12.2, 2.3 Hz, 1H), 8.02 (s, 1H), 7.76-7.66 (m, 2H), 7.65-7.58 (m, 1H), 7.33 (s, 1H), 1.75-1.64 (m, 2H), 1.33-1.29 (m, 2H), 1.28 (s, 9H) LCMS (Analytical Method D): Rt = 4.14 mins, MS (ESIPos) m/z = 508.05 (M + H)$^+$. |
| 91 | 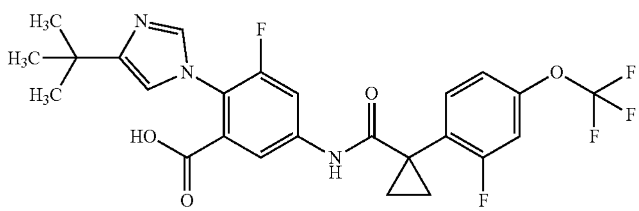 [SMILES: CC(C)(C)c1cn(-c2c(F)cc(NC(=O)C3(c4ccc(OC(F)(F)F)cc4F)CC3)cc2C(=O)O)cn1] | 2-(4-tert-Butyl-1H-imidazol-1-yl)-3-fluoro-5-[({1-[2-fluoro-4-(trifluoromethoxy)phenyl]cyclopropyl}carbonyl)amino]benzoic acid | $^1$H NMR (500 MHz, DMSO-d6) δ [ppm] 9.63 (s, 1H), 9.23 (s, 1H), 8.17-8.08 (m, 2H), 7.70-7.56 (m, 2H), 7.40 (dd, J = 10.4, 1.8 Hz, 1H), 7.27 (d, J = 8.6 Hz, 1H), 1.73-1.62 (m, 2H), 1.33 (s, 9H), 1.30-1.22 (m, 2H) LCMS (Analytical Method D): Rt = 4.27 mins; MS (ESIPos) m/z = 524.15 (M + H)$^+$. |
| 92 | 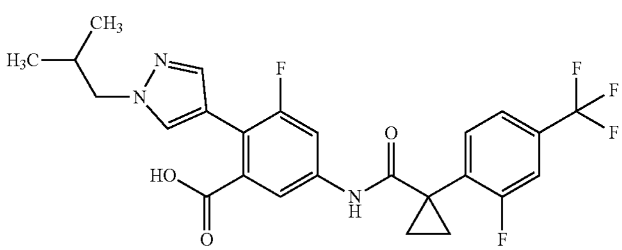 [SMILES: CC(C)Cn1cc(-c2c(F)cc(NC(=O)C3(c4ccc(C(F)(F)F)cc4F)CC3)cc2C(=O)O)cn1] | 3-Fluoro-5-[({1-[2-fluoro-4-(trifluoromethyl)phenyl]cyclopropyl}carbonyl)amino]-2-(1-isobutyl-1H-pyrazol-4-yl)benzoic acid | $^1$H NMR (400 MHz, DMSO-d6) δ [ppm] 0.84 (d, 6H), 1.23-1.26 (m, 2H), 1.63-1.66 (m, 2H), 2.05-2.14 (m, 1H), 3.92 (d, 2H), 7.44 (s, 1H), 7.60-7.62 (m, 2H), 7.68-7.78 (m, 4H), 9.26 (s, 1H). LCMS (Method 1): Rt = 1.32 min; MS (ESIPos) m/z = 508 (M + H)$^+$. |
| 93 | 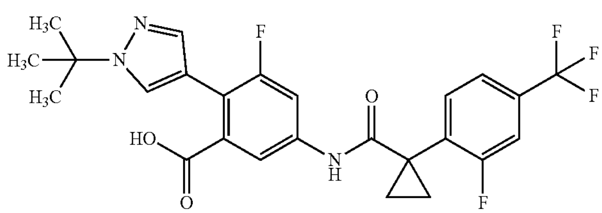 [SMILES: CC(C)(C)n1cc(-c2c(F)cc(NC(=O)C3(c4ccc(C(F)(F)F)cc4F)CC3)cc2C(=O)O)cn1] | 2-(1-tert-Butyl-1H-pyrazol-4-yl)-3-fluoro-5-[({1-[2-fluoro-4-(trifluoromethyl)phenyl]cyclopropyl}carbonyl)amino]benzoic acid | $^1$H NMR (400 MHz, DMSO-d6) δ [ppm] 1.23-1.26 (m, 2H), 1.53 (s, 9H), 1.63-1.66 (m, 2H), 7.48 (s, 1H), 7.60-7.75 (m, 5H), 7.87 (s, 1H), 9.24 (s, 1H). LCMS (Method 1): Rt = 1.32 min; MS (ESIPos) m/z = 508 (M + H)$^+$. |

| Ex. | Structure | Name | Analytical Data |
|---|---|---|---|
| 94 | 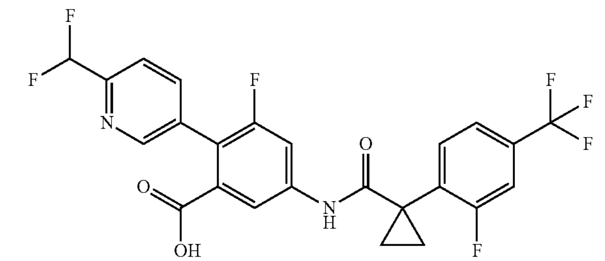 [SMILES: O=C(O)c1cc(NC(=O)C2(c3ccc(C(F)(F)F)cc3F)CC2)cc(F)c1-c1ccc(C(F)F)nc1] | 2-[6-(Difluoromethyl)pyridin-3-yl]-3-fluoro-5-[({1-[2-fluoro-4-(trifluoromethyl)phenyl]cyclopropyl}carbonyl)amino]benzoic acid | 1H NMR (250 MHz, DMSO-d6) δ [ppm] 13.11 (s, 1H), 9.45 (s, 1H), 8.55 (s, 1H), 8.02-7.86 (m, 3H), 7.80-7.57 (m, 4H), 7.01 (t, J = 55.0 Hz, 1H), 1.75-1.64 (m, 2H), 1.36-1.19 (m, 2H). LCMS (Analytical Method D) Rt = 4.79 min, MS (ESIpos): m/z = 513.0 (M + H)+. |
| 95 | 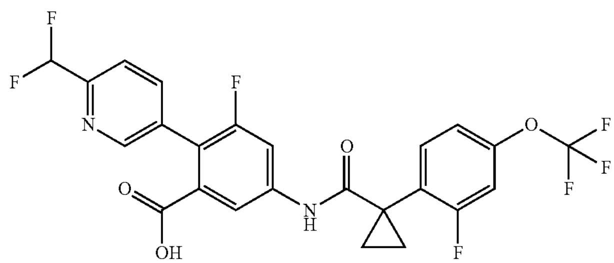 [SMILES: O=C(O)c1cc(NC(=O)C2(c3ccc(OC(F)(F)F)cc3F)CC2)cc(F)c1-c1ccc(C(F)F)nc1] | 2-[6-(Difluoromethyl)pyridin-3-yl]-3-fluoro-5-[({1-[2-fluoro-4-(trifluoromethoxy)phenyl]cyclopropyl}carbonyl)amino]benzoic acid | 1H NMR (250 MHz, DMSO-d6) δ [ppm] 13.05 (s, 1H), 9.42 (s, 1H), 8.55 (s, 1H), 8.02-7.87 (m, 3H), 7.75 (d, J = 8.1 Hz, 1H), 7.62 (t, J = 8.6 Hz, 1H), 7.40 (d, J = 10.3 Hz, 1H), 7.27 (d, J = 8.6 Hz, 1H), 7.01 (t, J = 55.0 Hz, 1H), 1.70-1.61 (m, 2H), 1.30-1.20 (m, 2H). LCMS (Analytical Method D) Rt = 4.88 min, MS (ESIpos): m/z = 529.0 (M + H)+. |
| 96 | 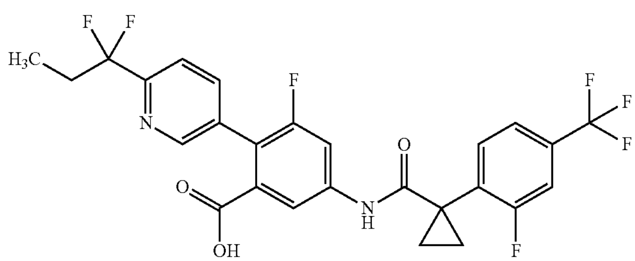 [SMILES: CCC(F)(F)c1ccc(-c2c(F)cc(NC(=O)C3(c4ccc(C(F)(F)F)cc4F)CC3)cc2C(=O)O)cn1] | 2-[6-(1,1-Difluoropropyl)pyridin-3-yl]-3-fluoro-5-[({1-[2-fluoro-4-(trifluoromethyl)phenyl]cyclopropyl}carbonyl)amino]benzoic acid | 1H NMR (250 MHz, DMSO-d6) δ [ppm] 9.44 (s, 1H), 8.53 (s, 1H), 7.95-7.87 (m, 3H), 7.73-7.60 (m, 4H), 2.40-2.34 (m, 2H), 1.70-1.67 (m, 2H), 1.31-1.26 (m, 2H), 0.94 (t, J = 7.4 Hz, 3H). LCMS (Analytical Method D) Rt = 4.80 min, MS (ESIpos): m/z = 541.20 (M + H)+. |
| 97 | 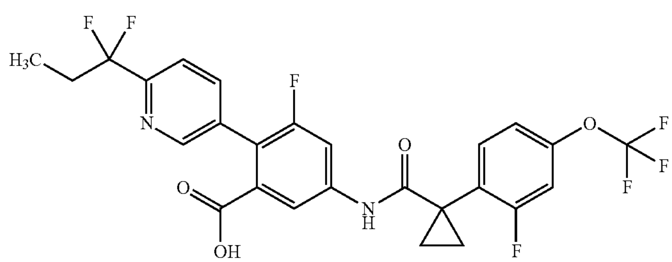 [SMILES: CCC(F)(F)c1ccc(-c2c(F)cc(NC(=O)C3(c4ccc(OC(F)(F)F)cc4F)CC3)cc2C(=O)O)cn1] | 2-[6-(1,1-Difluoropropyl)pyridin-3-yl]-3-fluoro-5-[({1-[2-fluoro-4-(trifluoromethoxy)phenyl]cyclopropyl}carbonyl)amino]benzoic acid | 1H NMR (250 MHz, DMSO-d6) δ [ppm] 9.37 (s, 1H), 8.49 (s, 1H), 7.92-7.83 (m, 3H), 7.68 (d, J = 8.0 Hz, 1H), 7.57 (t, J = 8.5 Hz, 1H), 7.36 (d, J = 9.9 Hz, 1H), 7.23 (d, J = 8.4 Hz, 1H), 2.40-2.20 (m, 2H), 1.63-1.55 (m, 2H), 1.24-1.17 (m, 2H), 0.90 (t, J = 7.4 Hz, 3H). LCMS (Analytical Method D) Rt = 4.85 min, MS (ESIpos): m/z = 557.15 (M + H)+. |
| 98 | 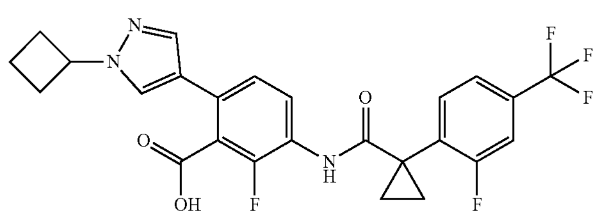 [SMILES: O=C(O)c1c(-c2cnn(C3CCC3)c2)ccc(NC(=O)C2(c3ccc(C(F)(F)F)cc3F)CC2)c1F] | 6-(1-Cyclobutyl-1H-pyrazol-4-yl)-2-fluoro-3-[({1-[2-fluoro-4-(trifluoromethyl)phenyl]cyclopropyl}carbonyl)amino]benzoic acid | 1H NMR (250 MHz, DMSO-d6) δ [ppm] 13.75 (s, 1H), 8.83 (s, 1H), 8.02 (s, 1H), 7.79-7.53 (m, 4H), 7.44-7.24 (m, 2H), 4.86 (m, 1H), 2.44-2.35 (m, 4H), 1.88-1.73 (m, 2H), 1.65-1.55 (m, 2H), 1.29-1.18 (m, 2H). LCMS (Analytical Method D) Rt = 4.63 min, MS (ESIpos): m/z = 506.0 (M + H)+. |
| 99 | 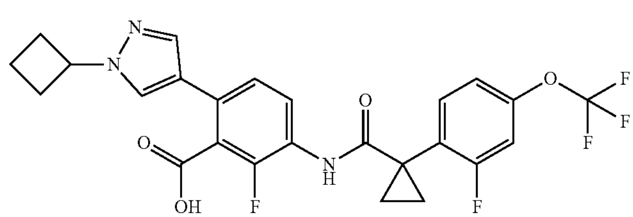 [SMILES: O=C(O)c1c(-c2cnn(C3CCC3)c2)ccc(NC(=O)C2(c3ccc(OC(F)(F)F)cc3F)CC2)c1F] | 6-(1-Cyclobutyl-1H-pyrazol-4-yl)-2-fluoro-3-[({1-[2-fluoro-4-(trifluoromethoxy)phenyl]cyclopropyl}carbonyl)amino]benzoic acid | 1H NMR (250 MHz, DMSO-d6) δ [ppm] 13.74 (s, 1H), 8.76 (s, 1H), 8.02 (s, 1H), 7.69-7.56 (m, 2H), 7.47-7.34 (m, 2H), 7.33-7.21 (m, 2H), 4.93-4.77 (m, 1H), 2.45-2.33 (m, 4H), 1.89-1.73 (m, 2H), 1.62-1.52 (m, 2H), 1.26-1.13 (m, 2H). LCMS (Analytical Method D) Rt = 4.68 min, MS (ESIpos): m/z = 522.4 (M + H)+. |

| Ex. | Structure | Name | Analytical Data |
|---|---|---|---|
| 100 | 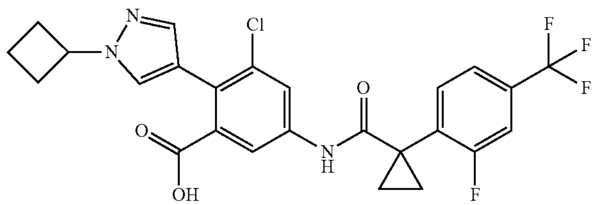 | 3-Chloro-2-(1-cyclobutyl-1H-pyrazol-4-yl)-5-[({1-[2-fluoro-4-(trifluoromethyl)phenyl]cyclopropyl}carbonyl)amino]benzoic acid | ¹H NMR (250 MHz, DMSO-d6) δ [ppm] 9.21 (s, 1H), 7.91 (d, J = 2.1 Hz, 1H), 7.83 (s, 1H), 7.74-7.56 (m, 4H), 7.42 (s, 1H), 4.84 (m, 1H), 2.47-2.29 (m, 4H), 1.92-1.70 (m, 2H), 1.69-1.60 (m, 2H), 1.33-1.17 (m, 2H). LCMS (Analytical Method F) Rt = 3.88 min, MS (ESIpos): m/z = 522.0/ 524.0 (M + H)⁺. |
| 101 | 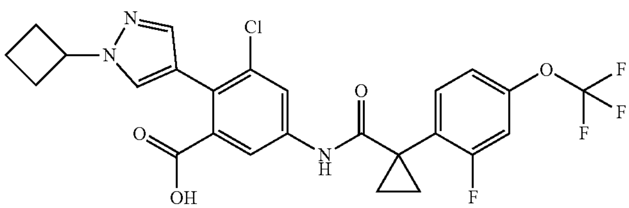 [SMILES: O=C(O)c1cc(NC(=O)C2(c3ccc(OC(F)(F)F)cc3F)CC2)cc(Cl)c1-c1cnn(C2CCC2)c1] | 3-Chloro-2-(1-cyclobutyl-1H-pyrazol-4-yl)-5-[({1-[2-fluoro-4-(trifluoromethoxy)phenyl]cyclopropyl}carbonyl)amino]benzoic acid | ¹H NMR (250 MHz, DMSO-d6) δ [ppm] 9.18 (s, 1H), 7.92 (d, J = 2.2 Hz, 1H), 7.83 (m, 1H), 7.73 (d, J = 2.2 Hz, 1H), 7.64-7.54 (m, 1H), 7.46-7.33 (m, 2H), 7.29-7.19 (m, 1H), 4.84 (m, 1H), 2.48-2.30 (m, 4H), 1.86-1.69 (m, 2H), 1.66-1.57 (m, 2H), 1.26-1.15 (m, 2H). LCMS (Analytical Method F) Rt = 3.94 min, MS (ESIpos): m/z = 538.0/540.0 (M + H)⁺. |
| 102 | 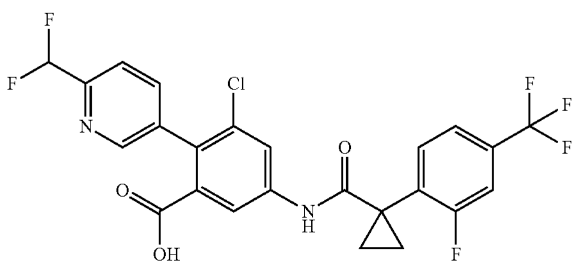 | 3-Chloro-2-[6-(difluoromethyl)pyridin-3-yl]-5-[({1-[2-fluoro-4-(trifluoromethyl)phenyl]cyclopropyl}carbonyl)amino]benzoic acid | ¹H NMR (500 MHz, DMSO-d6) δ [ppm] 13.11 (s, 1H), 9.40 (s, 1H), 8.47 (d, J = 1.8 Hz, 1H), 8.12 (d, J = 2.2 Hz, 1H), 8.11 (d, J = 2.2 Hz, 1H), 7.84 (dd, J = 8.0, 2.1 Hz, 1H), 7.76-7.66 (m, 3H), 7.64-7.60 (m, 1H), 7.01 (t, J = 55.0 Hz, 1H), 1.69-1.64 (m, 2H), 1.31-1.23 (m, 2H). LCMS (Analytical Method F) Rt = 3.94 min, MS (ESIpos): m/z = 529.1/531.1 (M + H)⁺. |
| 103 | 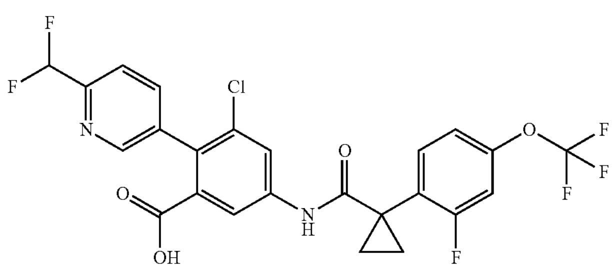 [SMILES: O=C(O)c1cc(NC(=O)C2(c3ccc(OC(F)(F)F)cc3F)CC2)cc(Cl)c1-c1ccc(C(F)F)nc1] | 3-Chloro-2-[6-(difluoromethyl)pyridin-3-yl]-5-[({1-[2-fluoro-4-(trifluoromethoxy)phenyl]cyclopropyl}carbonyl)amino]benzoic acid | ¹H NMR (500 MHz, DMSO-d6) δ [ppm] 13.09 (s, 1H), 9.37 (s, 1H), 8.47 (d, J = 1.8 Hz, 1H), 8.13 (d, J = 2.1 Hz, 1H), 8.11 (d, J = 2.2 Hz, 1H), 7.84 (dd, J = 8.0, 2.1 Hz, 1H), 7.74 (d, J = 8.0 Hz, 1H), 7.61 (dd, J = 8.6, 8.6 Hz, 1H), 7.40 (dd, J = 10.3, 1.8 Hz, 1H), 7.29-7.22 (m, 1H), 7.01 (t, J = 55.0 Hz, 1H), 1.67-1.60 (m, 2H), 1.26-1.19 (m, 2H). LCMS (Analytical Method F) Rt = 4.01 min, MS (ESIpos): m/z = 545.1/547.1 (M + H)⁺. |
| 104 | 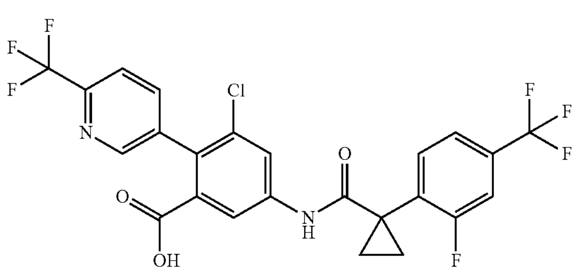 [SMILES: O=C(O)c1cc(NC(=O)C2(c3ccc(C(F)(F)F)cc3F)CC2)cc(Cl)c1-c1ccc(C(F)(F)F)nc1] | 3-Chloro-5-[({1-[2-fluoro-4-(trifluoromethyl)phenyl]cyclopropyl}carbonyl)amino]-2-[6-(trifluoromethyl)pyridin-3-yl]benzoic acid | ¹H NMR (500 MHz, DMSO-d6) δ [ppm] 9.43 (s, 1H), 8.60-8.57 (m, 1H), 8.17 (d, J = 2.1 Hz, 1H), 8.14 (d, J = 2.1 Hz, 1H), 7.99-7.92 (m, 2H), 7.75-7.66 (m, 2H), 7.65-7.60 (m, 1H), 1.81-1.62 (m, 2H), 1.40-1.17 (m, 2H). LCMS (Analytical Method F) Rt = 4.16 min, MS (ESIpos): m/z = 547.0/548.9 (M + H)⁺. |

| Ex. | Structure | Name | Analytical Data |
|---|---|---|---|
| 105 | 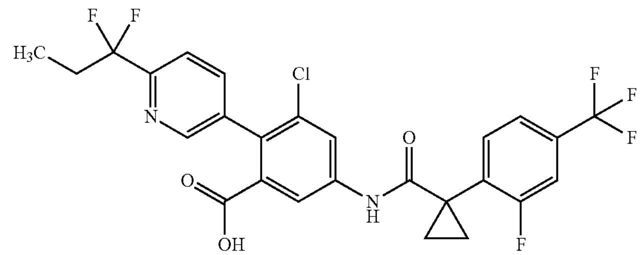 [SMILES: CCC(F)(F)c1ccc(-c2c(Cl)cc(NC(=O)C3(c4ccc(C(F)(F)F)cc4F)CC3)cc2C(=O)O)cn1] | 3-Chloro-2-[6-(1,1-difluoropropyl)pyridin-3-yl]-5-[({1-[2-fluoro-4-(trifluoromethyl)phenyl]cyclopropyl}carbonyl)amino]benzoic acid | $^1$H NMR (500 MHz, DMSO-d6) δ [ppm] 13.09 (s, 1H), 9.39 (s, 1H), 8.46 (d, J = 1.8 Hz, 1H), 8.14-8.07 (m, 2H), 7.81 (dd, J = 8.1, 2.1 Hz, 1H), 7.74-7.66 (m, 3H), 7.65-7.57 (m, 1H), 2.35 (tq, J = 15.2, 7.4 Hz, 2H), 1.71-1.64 (m, 2H), 1.32-1.23 (m, 2H), 0.93 (t, J = 7.5 Hz, 3H). LCMS (Analytical Method F) Rt = 4.25 min, MS (ESIpos): m/z = 557.1/559.1 (M + H)$^+$. |
| 106 | 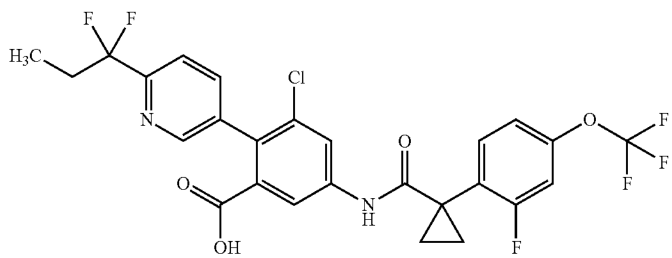 [SMILES: CCC(F)(F)c1ccc(-c2c(Cl)cc(NC(=O)C3(c4ccc(OC(F)(F)F)cc4F)CC3)cc2C(=O)O)cn1] | 3-Chloro-2-[6-(1,1-difluoropropyl)pyridin-3-yl]-5-[({1-[2-fluoro-4-(trifluoromethoxy)phenyl]cyclopropyl}carbonyl)amino]benzoic acid | $^1$H NMR (500 MHz, DMSO-d6) δ [ppm] 13.09 (s, 1H), 9.36 (s, 1H), 8.45 (d, J = 1.7 Hz, 1H), 8.13-8.09 (m, 2H), 7.81 (dd, J = 8.1, 2.2 Hz, 1H), 7.71 (d, J = 8.0 Hz, 1H), 7.61 (dd, J = 8.6, 8.6 Hz, 1H), 7.40 (dd, J = 10.4, 1.7 Hz, 1H), 7.26 (d, J = 8.5 Hz, 1H), 2.35 (tq, J = 15.2, 7.4 Hz, 2H), 1.67-1.61 (m, 2H), 1.29-1.19 (m, 2H), 0.93 (t, J = 7.5 Hz, 3H). LCMS (Analytical Method F) Rt = 4.31 min, MS (ESIpos): m/z = 573.1/575.1 (M + H)$^+$. |
| 107 | 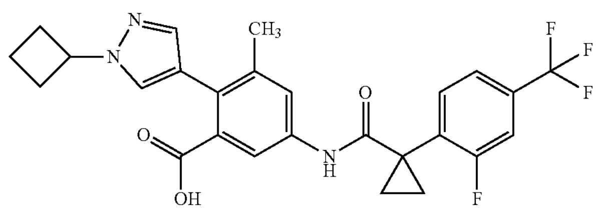 [SMILES: Cc1cc(NC(=O)C2(c3ccc(C(F)(F)F)cc3F)CC2)cc(C(=O)O)c1-c1cnn(C2CCC2)c1] | 2-(1-Cyclobutyl-1H-pyrazol-4-yl)-5-[({1-[2-fluoro-4-(trifluoromethyl)phenyl]cyclopropyl}carbonyl)amino]-3-methylbenzoic acid | $^1$H NMR (250 MHz, DMSO-d6) δ [ppm] 12.59 (s, 1H), 9.02 (s, 1H), 7.77-7.64 (m, 3H), 7.64-7.52 (m, 3H), 7.34 (m, 1H), 4.83 (m, 1H), 2.47-2.34 (m, 4H), 2.13 (s, 3H), 1.87-1.72 (m, 2H), 1.67-1.59 (m, 2H), 1.26-1.17 (m, 2H). LCMS (Analytical Method D) Rt = 4.71 min, MS (ESIpos): m/z = 502.45 (M + H)$^+$. |
| 108 | 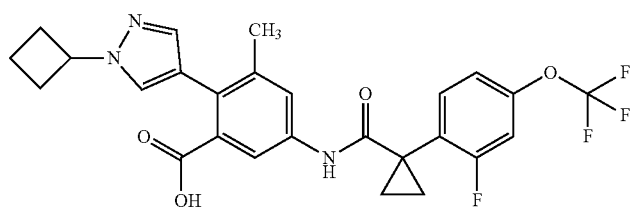 [SMILES: Cc1cc(NC(=O)C2(c3ccc(OC(F)(F)F)cc3F)CC2)cc(C(=O)O)c1-c1cnn(C2CCC2)c1] | 2-(1-Cyclobutyl-1H-pyrazol-4-yl)-5-[({1-[2-fluoro-4-(trifluoromethoxy)phenyl]cyclopropyl}carbonyl)amino]-3-methylbenzoic acid | $^1$H NMR (250 MHz, DMSO-d6) δ [ppm] 12.53 (s, 1H), 8.98 (s, 1H), 7.74 (s, 1H), 7.67-7.52 (m, 3H), 7.45-7.31 (m, 2H), 7.25 (d, J = 8.7 Hz, 1H), 4.91-4.75 (m, 1H), 2.46-2.34 (m, 4H), 2.13 (s, 3H), 1.87-1.71 (m, 2H), 1.64-1.54 (m, 2H), 1.23-1.12 (m, 2H). LCMS (Analytical Method D) Rt = 4.69 min, MS (ESIpos): m/z = 518.05 (M + H)$^+$. |
| 109 | 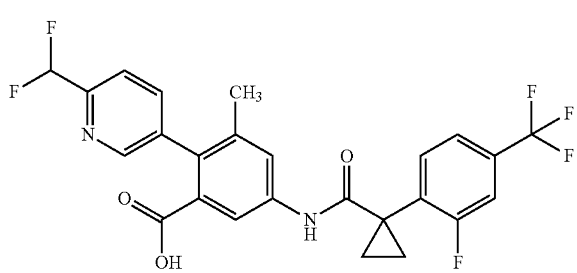 [SMILES: Cc1cc(NC(=O)C2(c3ccc(C(F)(F)F)cc3F)CC2)cc(C(=O)O)c1-c1ccc(C(F)F)nc1] | 2-[6-(Difluoromethyl)pyridin-3-yl]-5-[({1-[2-fluoro-4-(trifluoromethyl)phenyl]cyclopropyl}carbonyl)amino]-3-methylbenzoic acid | $^1$H NMR (250 MHz, DMSO-d6) δ [ppm] 12.79 (s, 1H), 9.18 (s, 1H), 8.42 (s, 1H), 7.94 (s, 1H), 7.82-7.57 (m, 6H), 7.00 (t, J = 55.1 Hz, 1H), 1.98 (s, 3H), 1.72-1.58 (m, 2H), 1.31-1.20 (m, 2H). LCMS (Analytical Method D) Rt = 4.75 min, MS (ESIpos): m/z = 509.0 (M + H)$^+$. |

| Ex. | Structure | Name | Analytical Data |
|---|---|---|---|
| 110 | 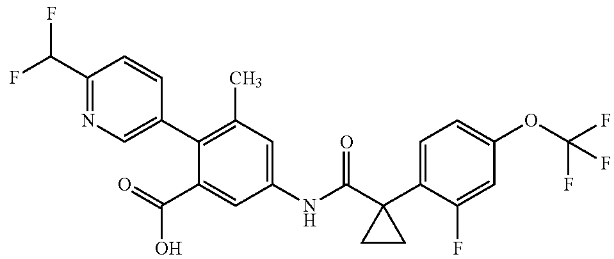 [SMILES: Cc1cc(NC(=O)C2(c3ccc(OC(F)(F)F)cc3F)CC2)cc(C(=O)O)c1-c1ccc(C(F)F)nc1] | 2-[6-(Difluoromethyl)pyridin-3-yl]-5-[({1-[2-fluoro-4-(trifluoromethoxy)phenyl]cyclopropyl}carbonyl)amino]-3-methylbenzoic acid | $^1$H NMR (250 MHz, DMSO-d6) δ [ppm] 12.69 (s, 1H), 9.15 (s, 1H), 8.42 (s, 1H), 7.96 (s, 1H), 7.87-7.55 (m, 4H), 7.45-6.75 (m, 3H), 1.98 (s, 3H), 1.72-1.50 (m, 2H), 1.31-1.12 (m, 2H). LCMS (Analytical Method D) Rt = 4.77 min, MS (ESIpos): m/z = 525.0 (M + H)$^+$. |
| 111 | 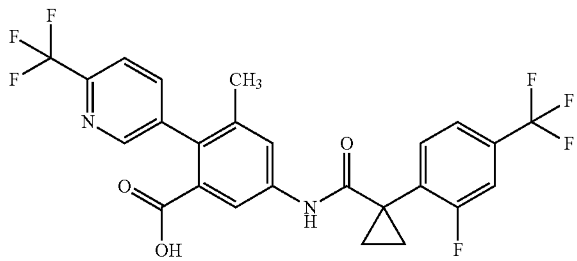 | 5-[({1-[2-Fluoro-4-(trifluoromethyl)phenyl]cyclopropyl}carbonyl)amino]-3-methyl-2-[6-(trifluoromethyl)pyridin-3-yl]benzoic acid | $^1$H NMR (250 MHz, DMSO-d6) δ [ppm] 9.20 (s, 1H), 8.52 (s, 1H), 7.99 (s, 1H), 7.96-7.83 (m, 2H), 7.79-7.65 (m, 3H), 7.62 (d, J =8.1 Hz, 1H), 1.98 (s, 3H), 1.70-1.62 (m, 2H), 1.30-1.21 (m, 2H). LCMS (Analytical Method D) Rt = 4.68 min, MS (ESIpos): m/z = 527.2 (M + H)$^+$. |
| 112 | 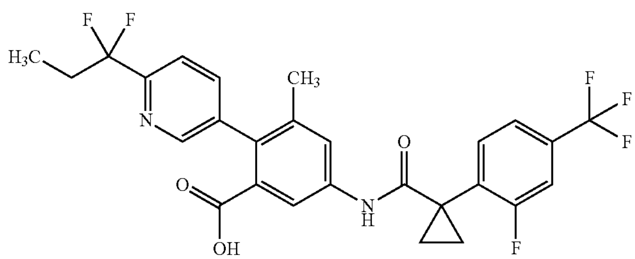 | 2-[6-(1,1-Difluoropropyl)pyridin-3-yl]-5-[({1-[2-fluoro-4-(trifluoromethyl)phenyl]cyclopropyl}carbonyl)amino]-3-methylbenzoic acid | $^1$H NMR (250 MHz, DMSO-d6) δ [ppm] 9.16 (s, 1H), 8.40 (s, 1H), 7.92 (s, 1H), 7.77-7.57 (m, 6H), 2.42-2.28 (m, 2H), 1.98 (s, 3H), 1.70-1.61 (m, 2H), 1.29-1.19 (m, 2H), 0.94 (t, J = 7.4 Hz, 3H). LCMS (Analytical Method D) Rt = 4.75 min, MS (ESIpos): m/z = 537.25 (M + H)$^+$. |
| 113 | 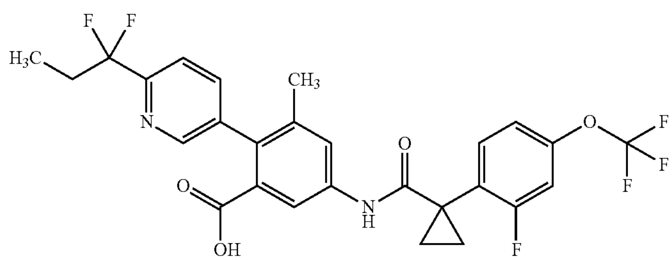 [SMILES: CCC(F)(F)c1ccc(-c2c(C)cc(NC(=O)C3(c4ccc(OC(F)(F)F)cc4F)CC3)cc2C(=O)O)cn1] | 2-[6-(1,1-Difluoropropyl)pyridin-3-yl]-5-[({1-[2-fluoro-4-(trifluoromethoxy)phenyl]cyclopropyl}carbonyl)amino]-3-methylbenzoic acid | $^1$H NMR (250 MHz, DMSO-d6) δ [ppm] 9.14 (s, 1H), 8.40 (s, 1H), 7.92 (s, 1H), 7.79-7.55 (m, 4H), 7.39 (d, J = 10.1 Hz, 1H), 7.26 (d, J = 8.6 Hz, 1H), 2.41-2.26 (m, 2H), 1.98 (s, 3H), 1.66-1.56 (m, 2H), 1.28-1.16 (m, 2H), 0.94 (t, J = 7.4 Hz, 3H). LCMS (Analytical Method D) Rt = 4.80 min, MS (ESIpos): m/z = 553.25 (M + H)$^+$. |
| 114 | 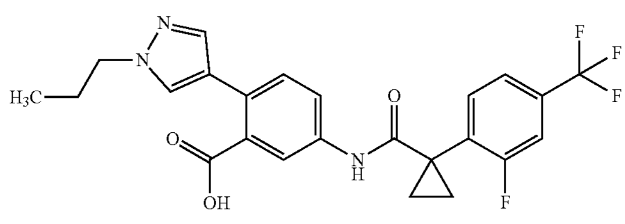 [SMILES: CCCn1cc(-c2ccc(NC(=O)C3(c4ccc(C(F)(F)F)cc4F)CC3)cc2C(=O)O)cn1] | 5-[({1-[2-Fluoro-4-(trifluoromethyl)phenyl]cyclopropyl}carbonyl)amino]-2-(1-propyl-1H-pyrazol-4-yl)benzoic acid | 1H NMR (250 MHz, DMSO-d6) δ [ppm] 12.89 (s, 1H), 9.08 (s, 1H), 7.84 (s, 1H), 7.77-7.55 (m, 5H), 7.53 (s, 1H), 7.36 (d, J = 8.5 Hz, 1H), 4.05 (t, J = 6.8 Hz, 2H), 1.88-1.69 (m, 2H), 1.69-1.58 (m, 2H), 1.31-1.11 (m, 2H), 0.84 (t, J = 7.3 Hz, 3H). LCMS (Analytical Method D) Rt = 4.51 min, MS (ESIpos): m/z = 476.05 (M + H)$^+$. |
| 115 | 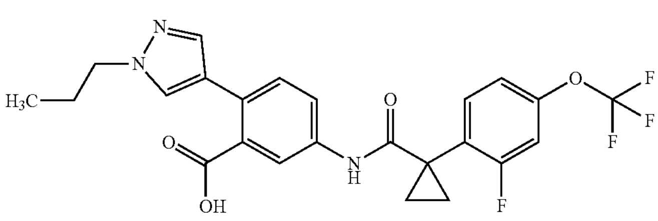 [SMILES: CCCn1cc(-c2ccc(NC(=O)C3(c4ccc(OC(F)(F)F)cc4F)CC3)cc2C(=O)O)cn1] | 5-[({1-[2-Fluoro-4-(trifluoromethoxy)phenyl]cyclopropyl}carbonyl)amino]-2-(1-propyl-1H-pyrazol-4-yl)benzoic acid | 1H NMR (250 MHz, DMSO-d6) δ [ppm] 12.91 (s, 1H), 9.05 (s, 1H), 7.84 (s, 1H), 7.74 (d, J = 2.2 Hz, 1H), 7.67 (dd, J = 8.5, 2.3 Hz, 1H), 7.65-7.56 (m, 1H), 7.53 (s, 1H), 7.43-7.32 (m, 2H), 7.25 (d, J = 8.6 Hz, 1H), 4.06 (t, J = 6.9 Hz, 2H), 1.79 (h, J = 7.1 Hz, 2H), 1.64-1.57 (m, 2H), 1.22-1.13 (m, 2H), 0.85 (t, J = 7.4 Hz, 3H). LCMS (Analytical Method D) Rt = 4.49 min, MS (ESIpos): m/z = 492.1 (M + H)$^+$. |

| Ex. | Structure | Name | Analytical Data |
|---|---|---|---|
| 116 | 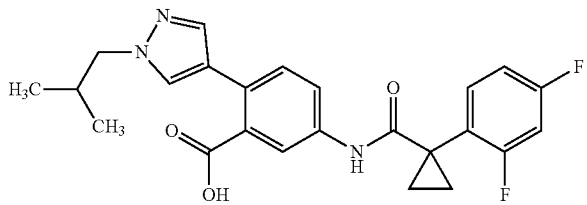 [SMILES: CC(C)Cn1cc(-c2ccc(NC(=O)C3(c4ccc(F)cc4F)CC3)cc2C(=O)O)cn1] | 5-({[1-(2,4-Difluorophenyl)cyclopropyl]carbonyl}amino)-2-(1-isobutyl-1H-pyrazol-4-yl)benzoic acid | 1H NMR (500 MHz, DMSO-d6) δ [ppm] 12.90 (s, 1H), 8.95 (s, 1H), 7.80 (s, 1H), 7.75 (d, J = 2.3 Hz, 1H), 7.67 (dd, J = 8.5, 2.3 Hz, 1H), 7.55-7.47 (m, 2H), 7.34 (d, J = 8.5 Hz, 1H), 7.28-7.20 (m, 1H), 7.13-7.05 (m, 1H), 3.90 (d, J = 7.2 Hz, 2H), 2.15-2.04 (m, 1H), 1.62-1.51 (m, 2H), 1.19-1.07 (m, 2H), 0.85 (d, J = 6.7 Hz, 6H) LCMS (Analytical Method F): Rt = 3.31 mins; MS (ESI) m/z = 440.3 (M + H)+. |
| 117 | 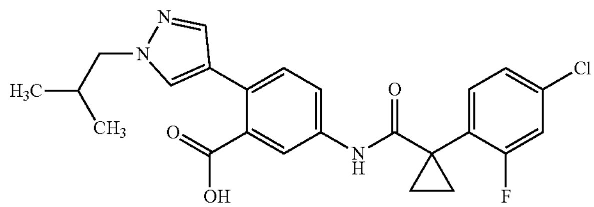 [SMILES: CC(C)Cn1cc(-c2ccc(NC(=O)C3(c4ccc(Cl)cc4F)CC3)cc2C(=O)O)cn1] | 5-({[1-(4-Chloro-2-fluorophenyl)cyclopropyl]carbonyl}amino)-2-(1-isobutyl-1H-pyrazol-4-yl)benzoic acid | 1H NMR (500 MHz, DMSO-d6) δ [ppm] 12.89 (s, 1H), 9.00 (s, 1H), 7.80 (s, 1H), 7.74 (d, J = 2.2 Hz, 1H), 7.67 (dd, J = 8.5, 2.3 Hz, 1H), 7.52 (s, 1H), 7.51-7.46 (m, 1H), 7.43 (dd, J = 10.0, 2.0 Hz, 1H), 7.34 (d, J = 8.5 Hz, 1H), 7.30 (dd, J = 8.3, 2.0 Hz, 1H), 3.90 (d, J = 7.1 Hz, 2H), 2.18-2.01 (m, 1H), 1.66-1.48 (m, 2H), 1.21-1.06 (m, 2H), 0.85 (d, J = 6.7 Hz, 6H). LCMS (Analytical Method F): Rt = 3.54 mins; MS (ESIpos) m/z = 456.3 (M + H)+. |
| 118 | 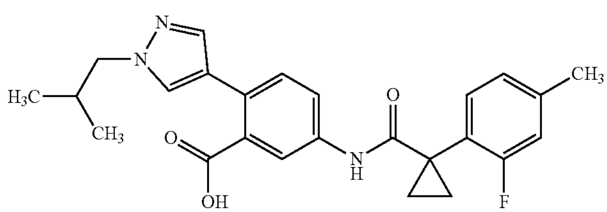 [SMILES: Cc1ccc(C2(C(=O)Nc3ccc(-c4cnn(CC(C)C)c4)c(C(=O)O)c3)CC2)c(F)c1] | 5-({[1-(2-Fluoro-4-methylphenyl)cyclopropyl]carbonyl}amino)-2-(1-isobutyl-1H-pyrazol-4-yl)benzoic acid | 1H NMR (500 MHz, DMSO-d6) δ [ppm] 12.89 (s, 1H), 8.89 (s, 1H), 7.79 (s, 1H), 7.75 (d, J = 2.3 Hz, 1H), 7.67 (dd, J = 8.5, 2.3 Hz, 1H), 7.51 (s, 1H), 7.37-7.29 (m, 2H), 7.06-6.99 (m, 2H), 3.90 (d, J = 7.1 Hz, 2H), 2.33 (s, 3H), 2.15-2.03 (m, 1H), 1.60-1.48 (m, 2H), 1.17-1.02 (m, 2H), 0.84 (d, J = 6.7 Hz, 6H). LCMS (Analytical Method F): Rt = 3.47 mins; MS (ESIpos) m/z = 436.3 (M + H)+. |
| 119 | 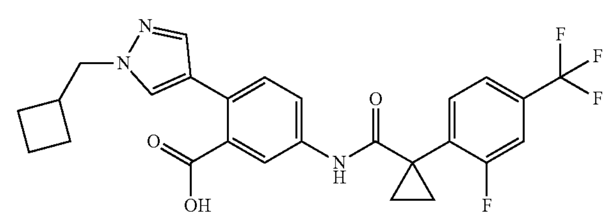 [SMILES: O=C(O)c1cc(NC(=O)C2(c3ccc(C(F)(F)F)cc3F)CC2)ccc1-c1cnn(CC2CCC2)c1] | 2-[1-(Cyclobutylmethyl)-1H-pyrazol-4-yl]-5-[({1-[2-fluoro-4-(trifluoromethyl)phenyl]cyclopropyl}carbonyl)amino]benzoic acid | 1H NMR (250 MHz, DMSO-d6) δ [ppm] 12.94 (s, 1H), 9.09 (s, 1H), 7.82 (s, 1H), 7.78-7.56 (m, 5H), 7.52 (s, 1H), 7.36 (d, J = 8.5 Hz, 1H), 4.12 (d, J = 7.2 Hz, 2H), 2.86-2.65 (m, 1H), 2.09-1.91 (m, 2H), 1.91-1.69 (m, 4H), 1.69-1.56 (m, 2H), 1.31-1.14 (m, 2H). LCMS (Analytical Method F) Rt = 4.64 min, MS (ESIpos): m/z = 502.1 (M + H)+. |
| 120 | 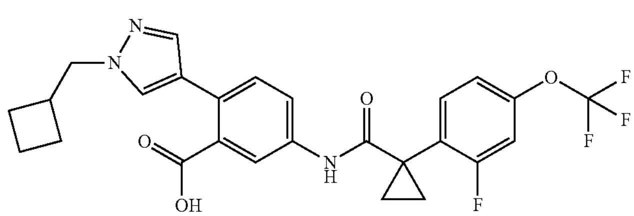 [SMILES: O=C(O)c1cc(NC(=O)C2(c3ccc(OC(F)(F)F)cc3F)CC2)ccc1-c1cnn(CC2CCC2)c1] | 2-[1-(Cyclobutylmethyl)-1H-pyrazol-4-yl]-5-[({1-[2-fluoro-4-(trifluoromethoxy)phenyl]cyclopropyl}carbonyl)amino]benzoic acid | 1H NMR (250 MHz, DMSO-d6) δ [ppm] 12.86 (s, 1H), 9.05 (s, 1H), 7.82 (s, 1H), 7.78-7.56 (m, 3H), 7.52 (s, 1H), 7.37 (m, 2H), 7.24 (d, J = 8.5 Hz, 1H), 4.12 (d, J = 7.2 Hz, 2H), 2.82-2.68 (m, 1H), 2.05-1.93 (m, 2H), 1.90-1.74 (m, 4H), 1.64-1.57 (m, 2H), 1.24-1.13 (m, 2H). LCMS (Analytical Method D) Rt = 4.67 min, MS (ESIpos): m/z = 518.05 (M + H)+. |

| Ex. | Structure | Name | Analytical Data |
|---|---|---|---|
| 121 | 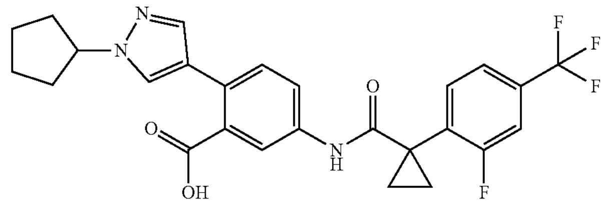 [SMILES: O=C(O)c1cc(NC(=O)C2(c3ccc(C(F)(F)F)cc3F)CC2)ccc1-c1cnn(C2CCCC2)c1] | 2-(1-Cyclopentyl-1H-pyrazol-4-yl)-5-[({1-[2-fluoro-4-(trifluoromethyl)phenyl]cyclopropyl}carbonyl)amino]benzoic acid | $^1$H NMR (500 MHz, DMSO-d6) δ 9.04 (s, 1H), 7.92-7.87 (m, 1H), 7.72-7.64 (m, 3H), 7.64-7.56 (m, 2H), 7.56-7.52 (m, 1H), 7.35 (d, J = 8.5 Hz, 1H), 4.72-4.58 (m, 1H), 2.14-1.99 (m, 2H), 1.99-1.85 (m, 2H), 1.85-1.73 (m, 2H), 1.73-1.53 (m, 4H), 1.26-1.16 (m, 2H). LCMS (Analytical Method D): Rt = 2.13 mins, MS (ESIpos): m/z = 502 (M + H)$^+$. |
| 122 | 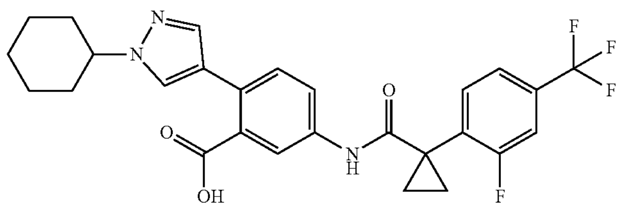 [SMILES: O=C(O)c1cc(NC(=O)C2(c3ccc(C(F)(F)F)cc3F)CC2)ccc1-c1cnn(C2CCCCC2)c1] | 2-(1-Cyclohexyl-1H-pyrazol-4-yl)-5-[({1-[2-fluoro-4-(trifluoromethyl)phenyl]cyclopropyl}carbonyl)amino]benzoic acid | $^1$H NMR (500 MHz, DMSO-d6) [ppm] 12.93 (s, 1H), 9.08 (s, 1H), 7.89 (s, 1H), 7.73 (d, J = 2.2 Hz, 1H), 7.72-7.64 (m, 3H), 7.63-7.58 (m, 1H), 7.52 (s, 1H), 7.38 (d, J = 8.5 Hz, 1H), 4.12 (m, 1H), 2.06-1.99 (m, 2H), 1.86-1.77 (m, 2H), 1.76-1.61 (m, 5H), 1.46-1.34 (m, 2H), 1.29-1.16 (m, 3H). LCMS (Analytical Method D) Rt = 4.59 min, MS (ESIpos): m/z = 516.15 (M + H)$^+$. |
| 123 | 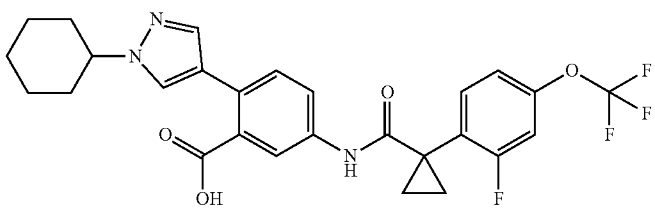 [SMILES: O=C(O)c1cc(NC(=O)C2(c3ccc(OC(F)(F)F)cc3F)CC2)ccc1-c1cnn(C2CCCCC2)c1] | 2-(1-Cyclohexyl-1H-pyrazol-4-yl)-5-[({1-[2-fluoro-4-(trifluoromethoxy)phenyl]cyclopropyl}carbonyl)amino]benzoic acid | $^1$H NMR (500 MHz, DMSO-d6) [ppm] 12.93 (s, 1H), 9.04 (s, 1H), 7.89 (s, 1H), 7.74 (d, J = 2.2 Hz, 1H), 7.67 (dd, J = 8.5, 2.2 Hz, 1H), 7.63-7.57 (m, 1H), 7.52 (s, 1H), 7.41-7.35 (m, 2H), 7.28-7.22 (m, 1H), 4.12 (m, 1H), 2.07-1.99 (m, 2H), 1.87-1.77 (m, 2H), 1.76-1.63 (m, 3H), 1.63-1.58 (m, 2H), 1.47-1.34 (m, 2H), 1.27-1.14 (m, 3H). LCMS (Analytical Method D) Rt = 4.65 min, MS (ESIpos): m/z = 532.10 (M + H)$^+$. |
| 124 | 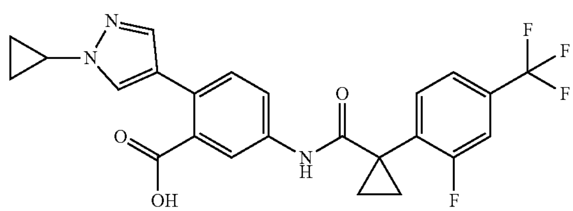 [SMILES: O=C(O)c1cc(NC(=O)C2(c3ccc(C(F)(F)F)cc3F)CC2)ccc1-c1cnn(C2CC2)c1] | 2-(1-Cyclopropyl-1H-pyrazol-4-yl)-5-[({1-[2-fluoro-4-(trifluoromethyl)phenyl]cyclopropyl}carbonyl)amino]benzoic acid | $^1$H NMR (500 MHz, DMSO-d6) [ppm] 12.94 (s, 1H), 9.08 (s, 1H), 7.90 (s, 1H), 7.78-7.57 (m, 5H), 7.50 (s, 1H), 7.36 (d, J = 8.5 Hz, 1H), 3.73 (m, 1H), 1.66-1.61 (m, 2H), 1.26-1.19 (m, 2H), 1.08-1.02 (m, 2H), 0.99-0.94 (m, 2H). LCMS (Analytical Method A) Rt = 4.24 min, MS (ESIpos): m/z = 474.05 (M + H)$^+$. |
| 125 | 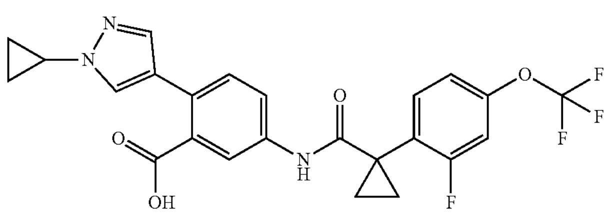 [SMILES: O=C(O)c1cc(NC(=O)C2(c3ccc(OC(F)(F)F)cc3F)CC2)ccc1-c1cnn(C2CC2)c1] | 2-(1-Cyclopropyl-1H-pyrazol-4-yl)-5-[({1-[2-fluoro-4-(trifluoromethoxy)phenyl]cyclopropyl}carbonyl)amino]benzoic acid | $^1$H NMR (500 MHz, DMSO-d6) [ppm] 12.94 (s, 1H), 9.05 (s, 1H), 7.90 (s, 1H), 7.75 (d, J = 2.1 Hz, 1H), 7.67 (dd, J = 8.5, 2.3 Hz, 1H), 7.60 (m, 1H), 7.50 (s, 1H), 7.41-7.34 (m, 2H), 7.24 (d, J = 8.5 Hz, 1H), 3.73 (m, 1H), 1.64-1.57 (m, 2H), 1.22-1.16 (m, 2H), 1.08-1.02 (m, 2H), 0.99-0.94 (m, 2H). LCMS (Analytical Method D) Rt = 4.30 min, MS (ESIpos): m/z = 490.05 (M + H)$^+$. |

-continued

| Ex. | Structure | Name | Analytical Data |
|---|---|---|---|
| 126 | 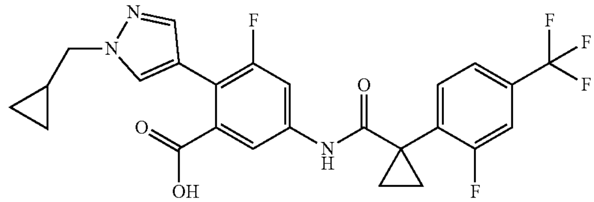 [SMILES: O=C(O)c1cc(NC(=O)C2(c3ccc(C(F)(F)F)cc3F)CC2)cc(F)c1-c1cnn(CC2CC2)c1] | 2-[1-(Cyclopropylmethyl)-1H-pyrazol-4-yl]-3-fluoro-5-[({1-[2-fluoro-4-(trifluoromethyl)phenyl]cyclopropyl}carbonyl)amino]benzoic acid | $^1$H NMR (250 MHz, DMSO-d6) δ [ppm] 13.16 (s, 1H), 9.24 (s, 1H), 7.87 (s, 1H), 7.82-7.55 (m, 5H), 7.47 (s, 1H), 4.00 (d, J = 6.6 Hz, 2H), 1.72-1.58 (m, 2H), 1.38-1.14 (m, 3H), 0.62-0.45 (m, 2H), 0.42-0.28 (m, 2H). LCMS (Analytical Method D) Rt = 5.04 min, MS (ESIpos): m/z = 506.1 (M + H)$^+$. |
| 127 | 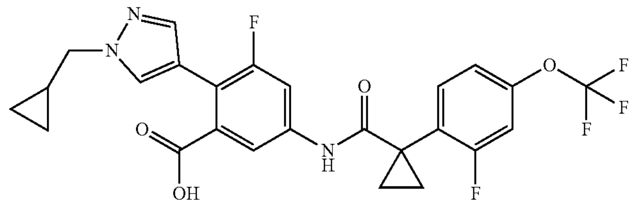 [SMILES: O=C(O)c1cc(NC(=O)C2(c3ccc(OC(F)(F)F)cc3F)CC2)cc(F)c1-c1cnn(CC2CC2)c1] | 2-[1-(Cyclopropylmethyl)-1H-pyrazol-4-yl]-3-fluoro-5-[({1-[2-fluoro-4-(trifluoromethoxy)phenyl]cyclopropyl}carbonyl)amino]benzoic acid | $^1$H NMR (250 MHz, DMSO-d6) δ [ppm] 13.11 (s, 1H), 9.21 (s, 1H), 7.87 (s, 1H), 7.74 (d, J = 13.2 Hz, 1H), 7.67-7.54 (m, 2H), 7.47 (s, 1H), 7.39 (d, J = 10.3 Hz, 1H), 7.25 (d, J = 7.4 Hz, 1H), 4.00 (d, J = 6.7 Hz, 2H), 1.71-1.56 (m, 2H), 1.30-1.14 (m, 3H), 0.60-0.47 (m, 2H), 0.42-0.28 (m, 2H). LCMS (Analytical Method D) Rt = 5.05 min, MS (ESIpos): m/z = 522.1 (M + H)$^+$. |
| 128 | 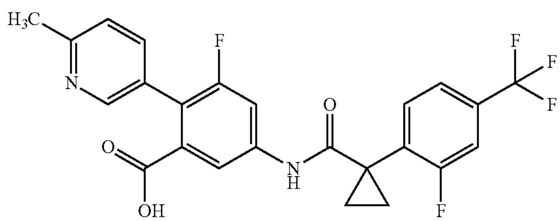 [SMILES: Cc1ccc(-c2c(F)cc(NC(=O)C3(c4ccc(C(F)(F)F)cc4F)CC3)cc2C(=O)O)cn1] | 3-Fluoro-5-[({1-[2-fluoro-4-(trifluoromethyl)phenyl]cyclopropyl}carbonyl)amino]-2-(6-methylpyridin-3-yl)benzoic acid | $^1$H NMR (500 MHz, DMSO-d6) δ [ppm] 9.34 (s, 1H), 8.27 (s, 1H), 7.79 (d, J = 13.8 Hz, 2H), 7.74-7.64 (m, 2H), 7.61 (d, J = 8.0 Hz, 1H), 7.56 (dd, J = 7.9, 1.9 Hz, 1H), 7.26 (d, J = 8.0 Hz, 1H), 2.50 (s, 3H), 1.69-1.61 (m, 2H), 1.30-1.21 (m, 2H). LCMS (Analytical Method D): Rt = 2.07 mins, MS (ESIpos): m/z = 477 (M + H)$^+$. |
| 129 | 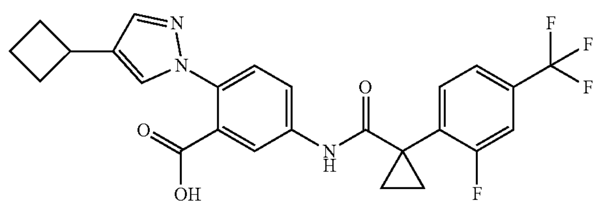 [SMILES: O=C(O)c1cc(NC(=O)C2(c3ccc(C(F)(F)F)cc3F)CC2)ccc1-n1cc(C2CCC2)cn1] | 2-(4-Cyclobutyl-1H-pyrazol-1-yl)-5-[({1-[2-fluoro-4-(trifluoromethyl)phenyl]cyclopropyl}carbonyl)amino]benzoic acid | $^1$H NMR (500 MHz, DMSO-d6) δ [ppm] 12.83 (s, 1H), 9.20 (s, 1H), 7.87 (s, 1H), 7.83 (d, J = 2.4 Hz, 1H), 7.79 (dd, J = 8.7, 2.4 Hz, 1H), 7.74-7.65 (m, 2H), 7.63-7.57 (m, 1H), 7.53 (s, 1H), 7.44 (d, J = 8.7 Hz, 1H), 3.40 (m, 1H), 2.32-2.23 (m, 2H), 2.09-1.99 (m, 2H), 1.98-1.78 (m, 2H), 1.71-1.59 (m, 2H), 1.30-1.18 (m, 2H). LCMS (Analytical Method F): Rt = 3.87 mins; m/z (ESIPos) = 488.3 (M + H)$^+$. |
| 130 | 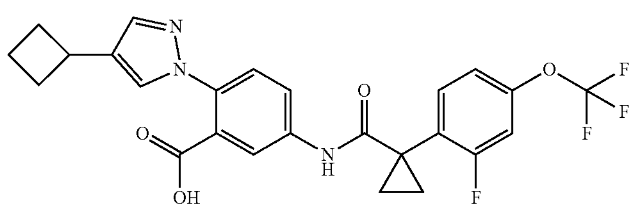 [SMILES: O=C(O)c1cc(NC(=O)C2(c3ccc(OC(F)(F)F)cc3F)CC2)ccc1-n1cc(C2CCC2)cn1] | 2-(4-Cyclobutyl-1H-pyrazol-1-yl)-5-[({1-[2-fluoro-4-(trifluoromethoxy)phenyl]cyclopropyl}carbonyl)amino]benzoic acid | $^1$H NMR (500 MHz, DMSO-d6) δ 12.83 (s, 1H), 9.17 (s, 1H), 7.87 (s, 1H), 7.83 (d, J = 2.4 Hz, 1H), 7.79 (dd, J = 8.7, 2.5 Hz, 1H), 7.63-7.57 (m, 1H), 7.53 (s, 1H), 7.44 (d, J = 8.7 Hz, 1H), 7.41-7.35 (m, 1H), 7.27-7.22 (m, 1H), 3.47-3.37 (m, 1H), 2.33-2.22 (m, 2H), 2.08-1.99 (m, 2H), 1.97-1.87 (m, 1H), 1.87-1.78 (m, 1H), 1.69-1.56 (m, 2H), 1.30-1.11 (m, 2H). LCMS (Analytical Method F): Rt = 3.94 mins; m/z (ESIPos) = 504.3 (M + H)$^+$. |

| Ex. | Structure | Name | Analytical Data |
|---|---|---|---|
| 131 | 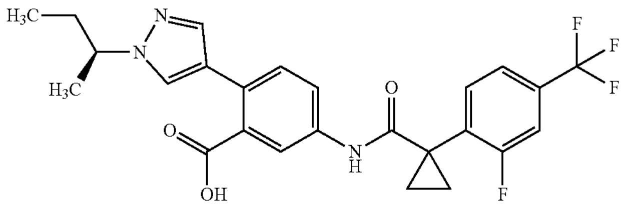 [SMILES: CC[C@H](C)n1cc(-c2ccc(NC(=O)C3(c4ccc(C(F)(F)F)cc4F)CC3)cc2C(=O)O)cn1] | 2-{1-[(2S)-Butan-2-yl]-1H-pyrazol-4-yl}-5-[({1-[2-fluoro-4-(trifluoromethyl)phenyl]cyclopropyl}carbonyl)amino]benzoic acid | ¹H NMR (500 MHz, DMSO-d6) δ [ppm] 12.93 (s, 1H), 9.08 (s, 1H), 7.87 (s, 1H), 7.74 (d, J = 2.2 Hz, 1H), 7.73-7.65 (m, 3H), 7.63-7.57 (m, 1H), 7.53 (s, 1H), 7.37 (d, J = 8.5 Hz, 1H), 4.29-4.19 (m, 1H), 1.87-1.69 (m, 2H), 1.68-1.60 (m, 2H), 1.42 (d, J = 6.7 Hz, 3H), 1.27-1.18 (m, 2H), 0.74 (t, J = 7.4 Hz, 3H). LCMS (Analytical Method D) Rt = 4.43 min, MS (ESIpos): m/z = 490.1 (M + H)⁺. |
| 132 | 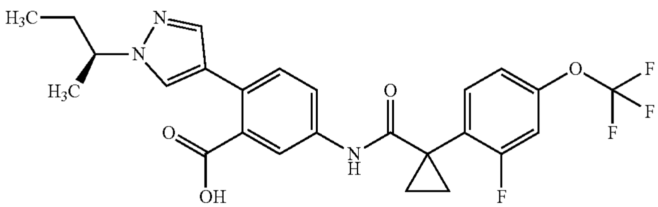 [SMILES: CC[C@H](C)n1cc(-c2ccc(NC(=O)C3(c4ccc(OC(F)(F)F)cc4F)CC3)cc2C(=O)O)cn1] | 2-{1-[(2S)-Butan-2-yl]-1H-pyrazol-4-yl}-5-[({1-[2-fluoro-4-(trifluoromethoxy)phenyl]cyclopropyl}carbonyl)amino]benzoic acid | ¹H NMR (500 MHz, DMSO-d6) δ [ppm] 12.92 (s, 1H), 9.04 (s, 1H), 7.87 (s, 1H), 7.74 (d, J = 2.3 Hz, 1H), 7.67 (dd, J = 8.5, 2.3 Hz, 1H), 7.64-7.57 (m, 1H), 7.53 (s, 1H), 7.42-7.34 (m, 2H), 7.28-7.21 (m, 1H), 4.32-4.18 (m, 1H), 1.86-1.67 (m, 2H), 1.66-1.56 (m, 2H), 1.42 (d, J = 6.7 Hz, 3H), 1.24-1.14 (m, 2H), 0.74 (t, J = 7.4 Hz, 3H). LCMS (Analytical Method D) Rt = 4.49 min, MS (ESIpos): m/z = 506.10 (M + H)⁺. |
| 133 | 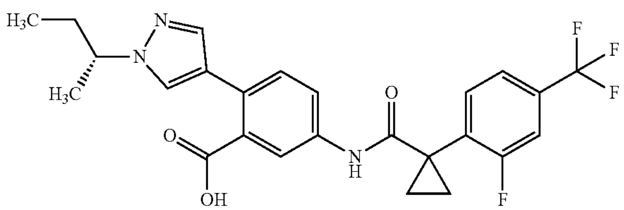 [SMILES: CC[C@@H](C)n1cc(-c2ccc(NC(=O)C3(c4ccc(C(F)(F)F)cc4F)CC3)cc2C(=O)O)cn1] | 2-{1-[(2R)-Butan-2-yl]-1H-pyrazol-4-yl}-5-[({1-[2-fluoro-4-(trifluoromethyl)phenyl]cyclopropyl}carbonyl)amino]benzoic acid | ¹H NMR (500 MHz, DMSO-d6) δ [ppm] 9.03 (s, 1H), 7.86 (s, 1H), 7.72 (d, J = 2.2 Hz, 1H), 7.66 (dd, J = 8.5, 2.3 Hz, 1H), 7.62-7.56 (m, 1H), 7.53 (s, 1H), 7.40-7.34 (m, 2H), 7.26-7.21 (m, 1H), 4.30-4.16 (m, 1H), 1.85-1.64 (m, 2H), 1.64-1.54 (m, 2H), 1.41 (d, J = 6.7 Hz, 3H), 1.22-1.14 (m, 2H), 0.73 (t, J = 7.4 Hz, 3H). LCMS (Analytical Method F) Rt = 3.62 mins, MS (ESIpos): m/z = 490.2 (M + H)⁺. |
| 134 | 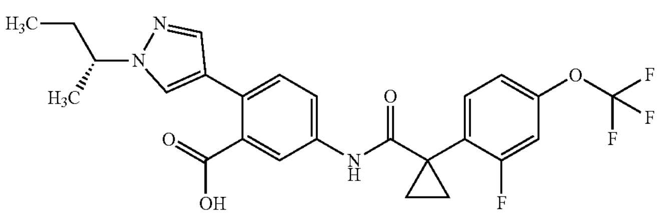 [SMILES: CC[C@@H](C)n1cc(-c2ccc(NC(=O)C3(c4ccc(OC(F)(F)F)cc4F)CC3)cc2C(=O)O)cn1] | 2-{1-[(2R)-Butan-2-yl]-1H-pyrazol-4-yl}-5-[({1-[2-fluoro-4-(trifluoromethoxy)phenyl]cyclopropyl}carbonyl)amino]benzoic acid | ¹H NMR (500 MHz, DMSO-d6) δ [ppm] 9.07 (s, 1H), 7.86 (s, 1H), 7.74-7.62 (m, 4H), 7.62-7.57 (m, 1H), 7.53 (s, 1H), 7.36 (d, J = 8.5 Hz, 1H), 4.27-4.18 (m, 1H), 1.85-1.66 (m, 2H), 1.66-1.59 (m, 2H), 1.41 (d, J = 6.7 Hz, 3H), 1.24-1.18 (m, 2H), 0.73 (t, J = 7.4 Hz, 3H). LCMS (Analytical Method F) Rt = 3.69 mins, MS (ESIpos): m/z = 506.2 (M + H)⁺. |
| 135 | 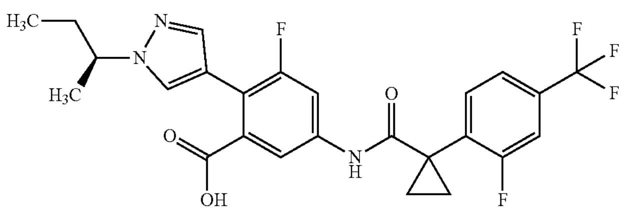 | 2-{1-[(2S)-Butan-2-yl]-1H-pyrazol-4-yl}-3-fluoro-5-[({1-[2-fluoro-4-(trifluoromethyl)phenyl]cyclopropyl}carbonyl)amino]benzoic acid | ¹H NMR (250 MHz, DMSO-d6) δ 9.25 (s, 1H), 7.82 (s, 1H), 7.78-7.65 (m, 3H), 7.64-7.59 (m, 2H), 7.47 (s, 1H), 4.36-4.20 (m, 1H), 1.85-1.71 (m, 2H), 1.69-1.63 (m, 2H), 1.42 (d, J = 6.7 Hz, 3H), 1.29-1.22 (m, 2H), 0.72 (t, J = 7.4 Hz, 3H). LCMS (Analytical Method D) Rt = 4.76 min, MS (ESIpos): m/z = 508.1 (M + H)⁺. |

| Ex. | Structure | Name | Analytical Data |
|---|---|---|---|
| 136 | 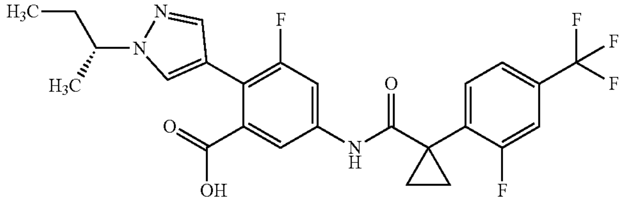 [SMILES: CC[C@@H](C)n1cc(-c2c(F)cc(NC(=O)C3(c4ccc(C(F)(F)F)cc4F)CC3)cc2C(=O)O)cn1] | 2-{1-[(2R)-Butan-2-yl]-1H-pyrazol-4-yl}-3-fluoro-5-[({1-[2-fluoro-4-(trifluoromethyl)phenyl]cyclopropyl}carbonyl)amino]benzoic acid | $^1$H NMR (250 MHz, DMSO-d6) δ 9.25 (s, 1H), 7.82 (s, 1H), 7.78-7.65 (m, 3H), 7.64-7.59 (m, 2H), 7.47 (s, 1H), 4.36-4.20 (m, 1H), 1.85-1.71 (m, 2H), 1.69-1.63 (m, 2H), 1.42 (d, J = 6.7 Hz, 3H), 1.29-1.22 (m, 2H), 0.72 (t, J = 7.4 Hz, 3H). LCMS (Analytical Method D) Rt = 4.76 min, MS (ESIpos): m/z = 508.1 (M + H)$^+$. |
| 137 | 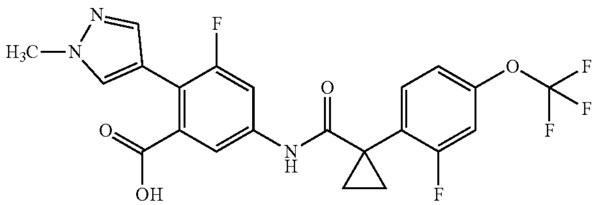 [SMILES: Cn1cc(-c2c(F)cc(NC(=O)C3(c4ccc(OC(F)(F)F)cc4F)CC3)cc2C(=O)O)cn1] | 3-Fluoro-5-[{1-[2-fluoro-4-(trifluoromethoxy)phenyl]cyclopropyl}carbonyl)amino]-2-(1-methyl-1H-pyrazol-4-yl)benzoic acid | $^1$H NMR (500 MHz, DMSO-d6) δ [ppm] 13.14 (s, 1H), 9.22 (s, 1H), 7.80 (s, 1H), 7.73 (d, J = 12.7 Hz, 1H), 7.63-7.58 (m, 2H), 7.44 (s, 1H), 7.39 (d, J = 10.4 Hz, 1H), 7.25 (d, J = 8.3 Hz, 1H), 3.86 (s, 3H), 1.65-1.60 (m, 2H), 1.25-1.18 (m, 2H). LCMS (Analytical Method D): Rt = 5.25 min; MS (ESIpos) m/z = 482.1 (M + H)$^+$. |
| 138 | 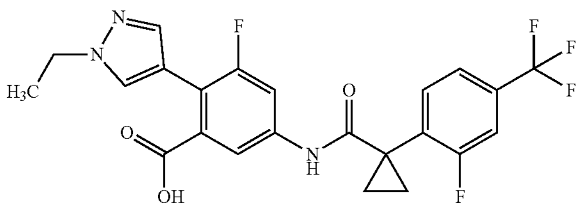 [SMILES: CCn1cc(-c2c(F)cc(NC(=O)C3(c4ccc(C(F)(F)F)cc4F)CC3)cc2C(=O)O)cn1] | 2-(1-Ethyl-1H-pyrazol-4-yl)-3-fluoro-5-[({1-[2-fluoro-4-(trifluoromethyl)phenyl]cyclopropyl}carbonyl)amino]benzoic acid | 1H NMR (500 MHz, DMSO-d6) δ [ppm] 13.15 (s, 1H), 9.24 (s, 1H), 7.84 (s, 1H), 7.76-7.66 (m, 3H), 7.63-7.59 (m, 2H), 7.46 (s, 1H), 4.16 (q, J = 7.3 Hz, 2H), 1.68-1.63 (m, 2H), 1.39 (t, J = 7.3 Hz, 3H), 1.28-1.23 (m, 2H). LCMS (Analytical Method D): Rt = 5.24 min; MS (ESIpos): m/z = 480.1 (M + H)$^+$. |
| 139 | 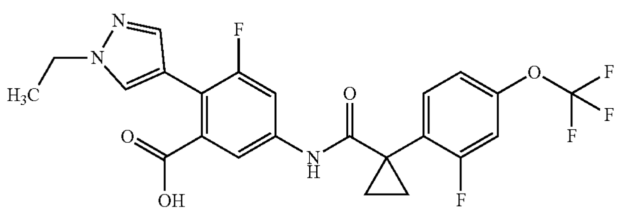 [SMILES: CCn1cc(-c2c(F)cc(NC(=O)C3(c4ccc(OC(F)(F)F)cc4F)CC3)cc2C(=O)O)cn1] | 2-(1-Ethyl-1H-pyrazol-4-yl)-3-fluoro-5-[({1-[2-fluoro-4-(trifluoromethoxy)phenyl]cyclopropyl}carbonyl)amino]benzoic acid | $^1$H NMR (500 MHz, DMSO-d6) δ [ppm] 13.13 (s, 1H), 9.21 (s, 1H), 7.84 (s, 1H), 7.73 (d, J = 12.8 Hz, 1H), 7.63-7.58 (m, 2H), 7.46 (s, 1H), 7.39 (d, J = 10.3 Hz, 1H), 7.25 (d, J = 8.5 Hz, 1H), 4.15 (q, J = 7.3 Hz, 2H), 1.65-1.60 (m, 2H), 1.38 (t, J = 7.3 Hz, 3H), 1.23-1.19 (m, 2H). LCMS (Analytical Method D): Rt = 5.30 min; MS (ESIpos): m/z = 496.1 (M + H)$^+$. |
| 140 | 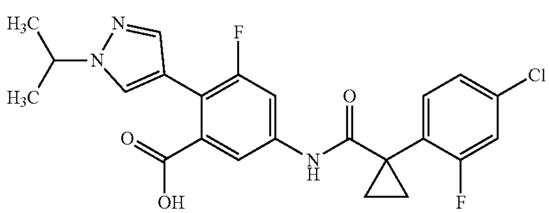 [SMILES: CC(C)n1cc(-c2c(F)cc(NC(=O)C3(c4ccc(Cl)cc4F)CC3)cc2C(=O)O)cn1] | 5-({[1-(4-Chloro-2-fluorophenyl)cyclopropyl]carbonyl}amino)-3-fluoro-2-(1-isopropyl-1H-pyrazol-4-yl)benzoic acid | $^1$H NMR (250 MHz, DMSO-d6) δ [ppm] 9.16 (s, 1H), 7.85 (d, J = 1.4 Hz, 1H), 7.73 (dd, J = 12.9, 2.1 Hz, 1H), 7.60 (d, J = 1H), 7.54-7.38 (m, 3H), 7.31 (dd, J = 8.2, 1.8 Hz, 1H), 4.53 (hept, J = 13.3, 6.8 Hz, 1H), 1.62-1.58 (m, 2H), 1.43 (d, J = 6.7 Hz, 6H), 1.20-1.16 (m, 2H). LCMS (Analytical Method D): Rt = 5.37 min, MS (ESIpos): m/z = 460.05 (M + H)$^+$. |
| 141 | 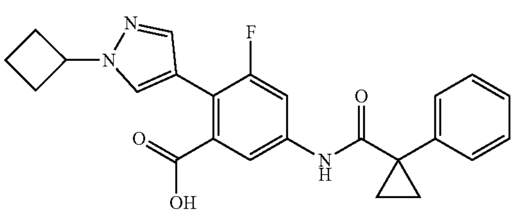 [SMILES: O=C(O)c1cc(NC(=O)C2(c3ccccc3)CC2)cc(F)c1-c1cnn(C2CCC2)c1] | 2-(1-Cyclobutyl-1H-pyrazol-4-yl)-3-fluoro-5-{[(1-phenylcyclopropyl)carbonyl]amino}benzoic acid | $^1$H NMR (500 MHz, DMSO-d6) δ 9.46 (s, 1H), 7.88 (s, 1H), 7.76 (dd, J = 12.7, 1.9 Hz, 1H), 7.67-7.60 (m, 1H), 7.49 (s, 1H), 7.42-7.34 (m, 4H), 7.32-7.26 (m, 1H), 4.95-4.70 (m, 1H), 2.49-2.43 (m, 2H), 2.42-2.33 (m, 2H), 1.86-1.70 (m, 2H), 1.53-1.44 (m, 2H), 1.17-1.01 (m, 2H). LCMS (Analytical Method D): Rt = 3.38 min, MS (ESIPos): m/z = 420.3 (M + H)$^+$. |

| Ex. | Structure | Name | Analytical Data |
|---|---|---|---|
| 142 | 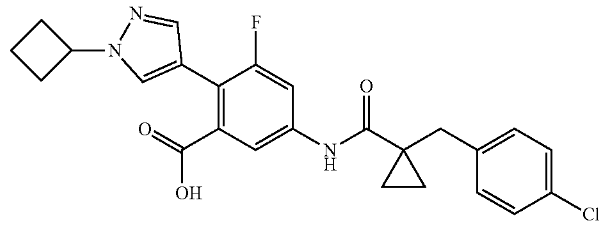 [SMILES: O=C(O)c1cc(NC(=O)C2(Cc3ccc(Cl)cc3)CC2)cc(F)c1-c1cnn(C2CCC2)c1] | 5-({[1-(4-Chlorobenzyl)cyclopropyl]carbonyl}amino)-2-(1-cyclobutyl-1H-pyrazol-4-yl)-3-fluorobenzoic acid | 1H NMR (500 MHz, DMSO-d6) δ 9.61 (s, 1H), 7.88 (s, 1H), 7.72 (dd, J = 12.7, 2.0 Hz, 1H), 7.64 (d, J = 1.7 Hz, 1H), 7.49 (s, 1H), 7.36-7.26 (m, 4H), 4.99-4.71 (m, 1H), 3.09 (s, 2H), 2.49-2.42 (m, 2H), 2.42-2.33 (m, 2H), 1.85-1.70 (m, 2H), 1.28-1.15 (m, 2H), 0.92-0.78 (m, 2H).<br>LCMS (Analytical Method D): Rt = 3.61 min, MS (ESIPos): m/z = 468.2 (M + H)+. |
| 143 | 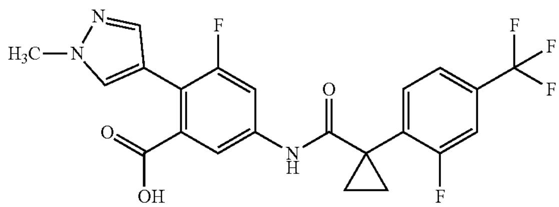 [SMILES: Cn1cc(-c2c(F)cc(NC(=O)C3(c4ccc(C(F)(F)F)cc4F)CC3)cc2C(=O)O)cn1] | 3-Fluoro-5-[({1-[2-fluoro-4-(trifluoromethyl)phenyl]cyclopropyl}carbonyl)amino]-2-(1-methyl-1H-pyrazol-4-yl)benzoic acid | 1H NMR (500 MHz, DMSO-d6) δ [ppm] 13.16 (s, 1H), 9.25 (s, 1H), 7.80 (s, 1H), 7.76-7.66 (m, 3H), 7.63-7.59 (m, 2H), 7.44 (s, 1H), 3.86 (s, 3H), 1.69-1.62 (m, 2H), 1.28-1.22 (m, 2H).<br>LCMS (Analytical Method D): Rt = 5.20 min; MS (ESIpos) m/z = 466.1 (M + H)+. |

Example 144: 2-(1-Cyclobutyl-1H-pyrazol-4-yl)-3-fluoro-5-({[1-(4-methylcyclohexyl) cyclopropyl]carbonyl}amino)benzoic acid, as an 8:2 mixture of diastereoisomers

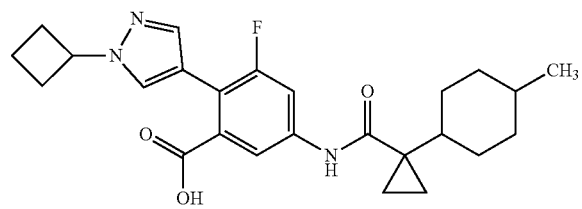 [SMILES: CC1CCC(C2(C(=O)Nc3cc(F)c(-c4cnn(C5CCC5)c4)c(C(=O)O)c3)CC2)CC1]

LiOH (80 mg, 1.90 mmol) in 2:1 THF/water (3.9 mL) was added to ethyl 2-(1-cyclobutyl-1H-pyrazol-4-yl)-3-fluoro-5-({[1-(4-methylcyclohexyl)cyclopropyl]-carbonyl}amino)benzoate (as a 2:1 mixture of major:minor diastereoisomers; Int 251A, 178 mg, 0.38 mmol) and the resulting solution was heated to 60° C. for 16 h. The reaction was then cooled to room temperature, concentrated under reduced pressure and partitioned between EtOAc and 2M aqueous lithium hydroxide solution. The organic layer was washed with 2M aqueous lithium hydroxide solution, saturated aqueous sodium chloride solution, dried (MgSO4), filtered and concentrated under reduced pressure. The residue obtained was purified via preparative HPLC (Method A) giving the title compound (as a 4:1 mixture of major/minor diastereoisomers; 66 mg, 33% yield) as a white solid. The stereochemistry of the major and minor diastereoisomers is unknown.

1H NMR (500 MHz, DMSO-d6) δ [ppm] 13.15 (m, 1H), 9.72-9.60 (m, 1H), 7.89 (m, 1H), 7.79 (m, 1H), 7.70 (m, 1H), 7.49 (m, 1H), 4.91-4.84 (m, 1H), 2.47-2.45 (m, 2H), 2.41-2.35 (m, 2H), 1.93-1.85 (m, 1H), 1.84-1.75 (m, 2H), 1.71-1.60 (m, 2H), 1.55-1.37 (m, 5H), 1.34-1.22 (m, 2H), 0.90 (d, J=7.1 Hz, 5H), 0.75-0.69 (m, 2H).

LCMS (Analytical Method D): Rt=5.03 mins; MS (ESIpos) m/z=440.15 (M+H)+.

Example 145: 2-(1-Cyclobutyl-1H-pyrazol-4-yl)-3-fluoro-5-({[1-(4-methylcyclohexyl) cyclopropyl]carbonyl}amino)benzoic acid, as a single unknown diastereoisomer

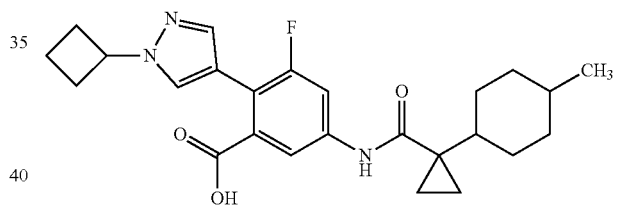

LiOH (80 mg, 1.90 mmol) in 2:1 THF/water (3.9 mL) was added to ethyl 2-(1-cyclobutyl-1H-pyrazol-4-yl)-3-fluoro-5-({[1-(4-methylcyclohexyl)cyclopropyl]-carbonyl}amino)benzoate (as a 2:1 mixture of major:minor diastereoisomers; Int 251A, 178 mg, 0.38 mmol) and the resulting solution was heated to 60° C. for 16 h. The reaction was then cooled to room temperature, concentrated under reduced pressure and partitioned between EtOAc and 2M aqueous lithium hydroxide solution. The organic layer was washed with 2M aqueous lithium hydroxide solution, saturated aqueous sodium chloride solution, dried (MgSO4), filtered, and concentrated under reduced pressure. The residue obtained was purified via preparative HPLC (Method A) giving the title compound (as the minor diastereoisomer from the reaction mixture; 4.7 mg, 3% yield) as a white solid. The stereochemistry of the title compound is unknown.

1H NMR (500 MHz, DMSO-d6) δ [ppm] 13.15 (s, 1H), 9.68 (s, 1H), 7.89 (s, 1H), 7.78 (dd, J=12.8, 1.9 Hz, 1H), 7.70 (s, 1H), 7.50 (s, 1H), 4.93-4.81 (m, 1H), 2.49-2.46 (m, 2H), 2.43-2.37 (m, 2H), 1.84-1.75 (m, 2H), 1.71-1.60 (m, 5H), 1.31-1.20 (m, 1H), 1.11-1.01 (m, 2H), 0.96-0.88 (m, 4H), 0.85 (d, J=6.5 Hz, 3H), 0.72-0.68 (m, 2H).

LCMS (Analytical Method D): Rt=5.05 mins, MS (ESI-pos) m/z=440.15 (M+H)⁺.

In analogy to Example 2, the following examples were prepared using the corresponding esters as starting material with heating the reaction mixtures at between 40° C. and 80° C. and using either THF in water or MeOH in water as solvent mixtures.

| Ex. | Structure | Name | Analytical Data |
| --- | --- | --- | --- |
| 146 | 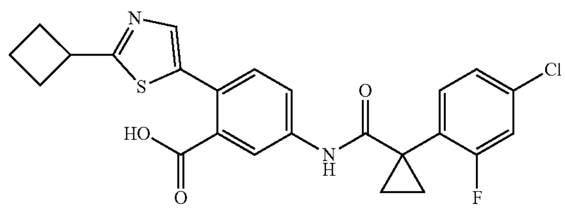 [SMILES: O=C(O)c1cc(NC(=O)C2(c3ccc(Cl)cc3F)CC2)ccc1-c1cnc(C2CCC2)s1] | 5-({[1-(4-Chloro-2-fluorophenyl)cyclopropyl]carbonyl}amino)-2-(2-cyclobutyl-1,3-thiazol-5-yl)benzoic acid | ¹H NMR (500 MHz, DMSO-d6) δ [ppm] 13.09 (s, 1H), 9.16 (s, 1H), 7.90 (d, J = 2.3 Hz, 1H), 7.79 (dd, J = 8.5, 2.3 Hz, 1H), 7.58 (s, 1H), 7.52-7.46 (m, 1H), 7.43 (dd, J = 10.0, 2.0 Hz, 1H), 7.39 (d, J = 8.5 Hz, 1H), 7.30 (dd, J = 8.3, 2.0 Hz, 1H), 3.85 (m, 1H), 2.39 (m, 2H), 2.27 (m, 2H), 2.08-1.95 (m, 1H), 1.94-1.83 (m, 1H), 1.67-1.50 (m, 2H), 1.25-1.10 (m, 2H). LCMS (Analytical Method F): Rt = 3.79 mins; MS (ESIPos): m/z = 471.2 (M + H)⁺. |
| 147 | 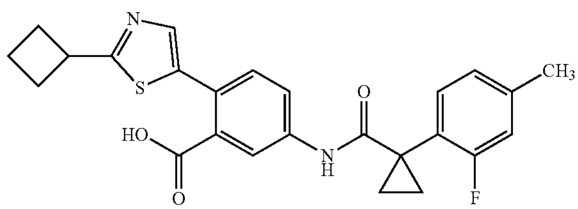 [SMILES: Cc1ccc(C2(C(=O)Nc3ccc(-c4cnc(C5CCC5)s4)c(C(=O)O)c3)CC2)c(F)c1] | 2-(2-Cyclobutyl-1,3-thiazol-5-yl)-5-({[1-(2-fluoro-4-methylphenyl)cyclopropyl]carbonyl}amino)benzoic acid | ¹H NMR (500 MHz, DMSO-d6) δ [ppm] 13.09 (s, 1H), 9.07 (s, 1H), 7.91 (d, J = 2.3 Hz, 1H), 7.78 (dd, J = 8.5, 2.3 Hz, 1H), 7.58 (s, 1H), 7.38 (d, J = 8.5 Hz, 1H), 7.36-7.30 (m, 1H), 7.05-7.03 (m, 1H), 7.02 (s, 1H), 3.89-3.80 (m, 1H), 2.45-2.35 (m, 2H), 2.33 (s, 3H), 2.31-2.22 (m, 2H), 2.08-1.96 (m, 1H), 1.94-1.84 (m, 1H), 1.61-1.49 (m, 2H), 1.17-1.05 (m, 2H) LCMS (Analytical Method F): Rt = 3.73 min; MS (ESIPos): m/z = 451.2 (M + H)⁺. |
| 148 | 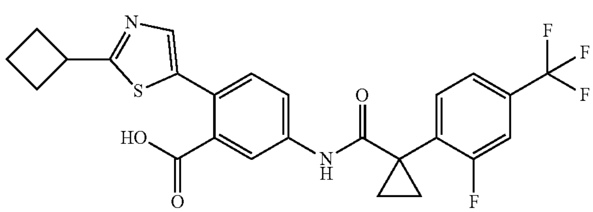 [SMILES: O=C(O)c1cc(NC(=O)C2(c3ccc(C(F)(F)F)cc3F)CC2)ccc1-c1cnc(C2CCC2)s1] | 2-(2-Cyclobutyl-1,3-thiazol-5-yl)-5-[({1-[2-fluoro-4-(trifluoromethyl)phenyl]cyclopropyl}carbonyl)amino]benzoic acid | ¹H NMR (500 MHz, DMSO-d6) δ [ppm] 13.10 (s, 1H), 9.23 (s, 1H), 7.90 (d, J = 2.3 Hz, 1H), 7.78 (dd, J = 8.5, 2.3 Hz, 1H), 7.73-7.65 (m, 2H), 7.64-7.59 (m, 1H), 7.58 (s, 1H), 7.40 (d, J = 8.5 Hz, 1H), 3.89-3.80 (m, 1H), 2.45-2.34 (m, 2H), 2.32-2.21 (m, 2H), 2.08-1.95 (m, 1H), 1.94-1.83 (m, 1H), 1.71-1.57 (m, 2H), 1.30-1.18 (m, 2H). LCMS (Analytical Method F): Rt = 3.89 min; MS (ESIPos): m/z = 505.3 (M + H)⁺. |
| 149 | 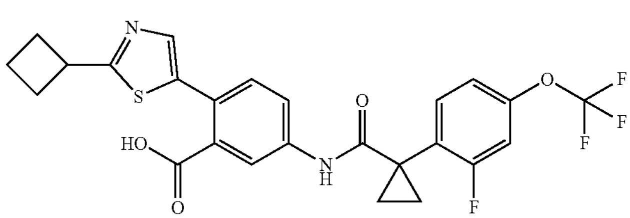 [SMILES: O=C(O)c1cc(NC(=O)C2(c3ccc(OC(F)(F)F)cc3F)CC2)ccc1-c1cnc(C2CCC2)s1] | 2-(2-Cyclobutyl-1,3-thiazol-5-yl)-5-[({1-[2-fluoro-4-(trifluoromethoxy)phenyl]cyclopropyl}carbonyl)amino]benzoic acid | ¹H NMR (500 MHz, DMSO-d6) δ [ppm] 13.10 (s, 1H), 9.20 (s, 1H), 7.90 (d, J = 2.3 Hz, 1H), 7.78 (dd, J = 8.5, 2.3 Hz, 1H), 7.63-7.57 (m, 2H), 7.43-7.36 (m, 2H), 7.27-7.22 (m, 1H), 3.90-3.80 (m, 1H), 2.44-2.34 (m, 2H), 2.33-2.21 (m, 2H), 2.02 (m, 1H), 1.95-1.83 (m, 1H), 1.69-1.55 (m, 2H), 1.27-1.14 (m, 2H). LCMS (Analytical Method F): Rt = 3.96 mins; MS (ESIPos): m/z = 521.2 (M + H)⁺. |

| Ex. | Structure | Name | Analytical Data |
|---|---|---|---|
| 150 | 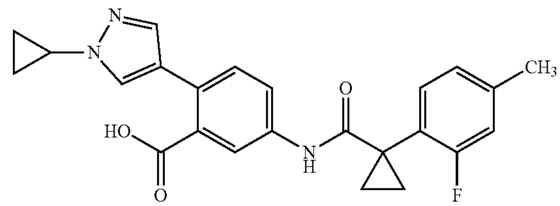 [SMILES: Cc1ccc(C2(C(=O)Nc3ccc(-c4cnn(C5CC5)c4)c(C(=O)O)c3)CC2)c(F)c1] | 2-(1-Cyclopropyl-1H-pyrazol-4-yl)-5-({[1-(2-fluoro-4-methylphenyl)cyclopropyl]carbonyl}amino)benzoic acid | $^1$H NMR (500 MHz, DMSO-d6) δ [ppm] 8.89 (s, 1H), 7.89 (s, 1H), 7.75 (s, 1H), 7.71-7.63 (m, 1H), 7.49 (s, 1H), 7.39-7.29 (m, 2H), 7.08-6.98 (m, 2H), 3.75-3.69 (m, 1H), 2.34 (s, 3H), 1.57-1.51 (m, 2H), 1.13-1.07 (m, 2H), 1.07-1.02 (m, 2H), 0.99-0.94 (m, 2H). LCMS (Analytical Method D) Rt = 4.14 min, MS (ESIpos): m/z = 420.15 (M + H)$^+$. |
| 151 | 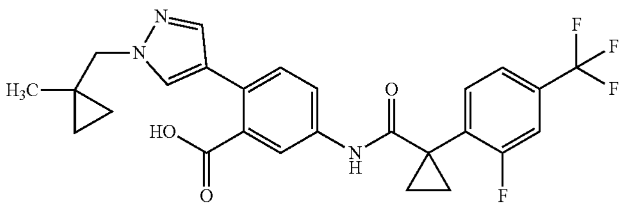 [SMILES: CC1(Cn2cc(-c3ccc(NC(=O)C4(c5ccc(C(F)(F)F)cc5F)CC4)cc3C(=O)O)cn2)CC1] | 5-[({1-[2-Fluoro-4-(trifluoromethyl)phenyl]cyclopropyl}carbonyl)amino]-2-{1-[(1-methylcyclopropyl)methyl]-1H-pyrazol-4-yl}benzoic acid | $^1$H NMR (500 MHz, DMSO-d6) δ [ppm] 12.95 (s, 1H), 9.10 (s, 1H), 7.87-7.84 (m, 1H), 7.75 (d, J = 2.3 Hz, 1H), 7.73-7.66 (m, 3H), 7.63-7.58 (m, 1H), 7.55-7.51 (m, 1H), 7.38 (d, J = 8.5 Hz, 1H), 3.96 (s, 2H), 1.73-1.53 (m, 2H), 1.31-1.16 (m, 2H), 0.99 (s, 3H), 0.70-0.56 (m, 2H), 0.44-0.28 (m, 2H). LCMS (Analytical Method D): Rt = 4.46 min; MS(ESIPos): m/z = 502.1 (M + H)$^+$. |
| 152 | 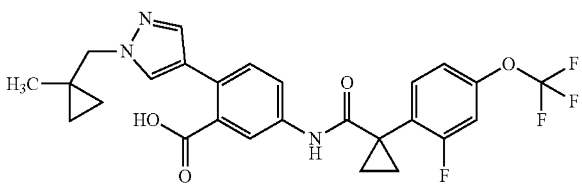 [SMILES: CC1(Cn2cc(-c3ccc(NC(=O)C4(c5ccc(OC(F)(F)F)cc5F)CC4)cc3C(=O)O)cn2)CC1] | 5-[({1-[2-Fluoro-4-(trifluoromethoxy)phenyl]cyclopropyl}carbonyl)amino]-2-{1-[(1-methylcyclopropyl)methyl]-1H-pyrazol-4-yl}benzoic acid | $^1$H NMR (500 MHz, DMSO-d6) δ [ppm] 12.99 (s, 1H), 9.04 (s, 1H), 7.86 (s, 1H), 7.73 (d, J = 2.1 Hz, 1H), 7.66 (dd, J = 8.5, 2.3 Hz, 1H), 7.63-7.56 (m, 1H), 7.53 (s, 1H), 7.41-7.34 (m, 2H), 7.26-7.21 (m, 1H), 3.94 (s, 2H), 1.67-1.54 (m, 2H), 1.28-1.12 (m, 2H), 0.98 (s, 3H), 0.67-0.53 (m, 2H), 0.44-0.28 (m, 2H). LCMS (Analytical Method D): Rt = 4.51 min; MS(ESIPos): m/z = 518.1 (M + H)$^+$. |
| 153 | 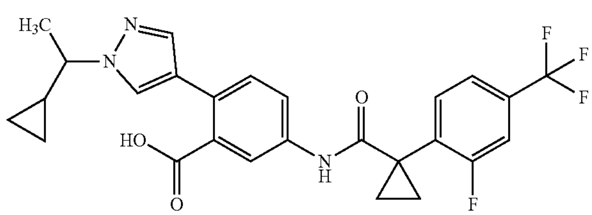 [SMILES: CC(C1CC1)n1cc(-c2ccc(NC(=O)C3(c4ccc(C(F)(F)F)cc4F)CC3)cc2C(=O)O)cn1] | 2-[1-(1-Cyclopropylethyl)-1H-pyrazol-4-yl]-5-[({1-[2-fluoro-4-(trifluoromethyl)phenyl]cyclopropyl}carbonyl)amino]benzoic acid as a 1:1 mixture of enantiomers | $^1$H NMR (500 MHz, DMSO-d6) δ [ppm] 12.96 (s, 1H), 9.08 (s, 1H), 7.93 (s, 1H), 7.75-7.64 (m, 4H), 7.60 (d, J = 7.7 Hz, 1H), 7.54 (s, 1H), 7.38 (d, J = 8.5 Hz, 1H), 3.69-3.61 (m, 1H), 1.66-1.62 (m, 2H), 1.51 (d, J = 6.8 Hz, 3H), 1.25-1.20 (m, 3H), 0.62-0.55 (m, 1H), 0.48-0.42 (m, 1H), 0.37-0.30 (m, 2H). LCMS (Analytical Method F) Rt = 4.56 mins, MS (ESIpos): m/z = 502.15 (M + H)$^+$. |
| 154 | 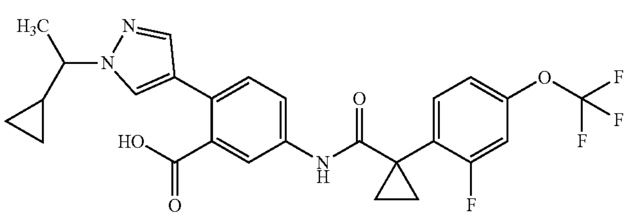 [SMILES: CC(C1CC1)n1cc(-c2ccc(NC(=O)C3(c4ccc(OC(F)(F)F)cc4F)CC3)cc2C(=O)O)cn1] | 2-[1-(1-Cyclopropylethyl)-1H-pyrazol-4-yl]-5-[({1-[2-fluoro-4-(trifluoromethoxy)phenyl]cyclopropyl}carbonyl)amino]benzoic acid as a 1:1 mixture of enantiomers | $^1$H NMR (500 MHz, DMSO-d6) δ [ppm] 12.94 (s, 1H), 9.04 (s, 1H), 7.93 (s, 1H), 7.74 (d, J = 2.1 Hz, 1H), 7.67 (dd, J = 8.5, 2.3 Hz, 1H), 7.60 (d, J = 8.5 Hz, 1H), 7.54 (s, 1H), 7.39 (s, 1H), 7.37 (s, 1H), 7.25 (d, J = 8.4 Hz, 1H), 3.69-3.61 (m, 1H), 1.63-1.58 (m, 2H), 1.51 (d, J = 6.8 Hz, 3H), 1.27-1.20 (m, 1H), 1.20-1.17 (m, 2H), 0.61-0.56 (m, 1H), 0.49-0.41 (m, 1H), 0.36-0.30 (m, 2H). LCMS (Analytical Method D) Rt = 4.53 mins, MS (ESIpos): m/z = 518.15 (M + H)$^+$. |

| Ex. | Structure | Name | Analytical Data |
|---|---|---|---|
| 155 | 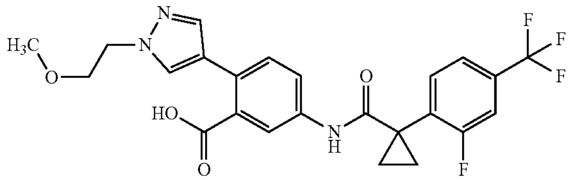 [SMILES: COCCn1cc(-c2ccc(NC(=O)C3(c4ccc(C(F)(F)F)cc4F)CC3)cc2C(=O)O)cn1] | 5-[({1-[2-Fluoro-4-(trifluoromethyl)phenyl]cyclopropyl}carbonyl)amino]-2-[1-(2-methoxyethyl)-1H-pyrazol-4-yl]benzoic acid | ¹H NMR (500 MHz, DMSO-d6) δ [ppm] 9.08 (s, 1H), 7.84 (s, 1H), 7.74-7.62 (m, 4H), 7.59 (d, J = 8.0 Hz, 1H), 7.54 (s, 1H), 7.36 (d, J = 8.5 Hz, 1H), 4.24 (t, J = 5.3 Hz, 2H), 3.69 (t, J = 5.4 Hz, 2H), 3.23 (s, 3H), 1.67-1.57 (m, 2H), 1.27-1.15 (m, 2H). LCMS (Analytical Method F): Rt = 3.24 mins, MS (ESIPos): m/z = 492 (M + H)⁺. |
| 156 | 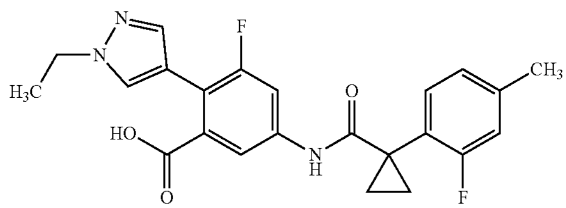 [SMILES: CCn1cc(-c2c(F)cc(NC(=O)C3(c4ccc(C)cc4F)CC3)cc2C(=O)O)cn1] | 2-(1-Ethyl-1H-pyrazol-4-yl)-3-fluoro-5-({[1-(2-fluoro-4-methylphenyl)cyclopropyl]carbonyl}amino)benzoic acid | 1H NMR (500 MHz, DMSO-d6) δ [ppm] 9.09 (s, 1H), 7.84-7.79 (m, 1H), 7.71 (dd, J = 12.8, 2.0 Hz, 1H), 7.60 (d, J = 1.6 Hz, 1H), 7.47-7.41 (m, 1H), 7.35-7.25 (m, 1H), 7.05-7.02 (m, 1H), 7.02-7.00 (m, 1H), 4.14 (q, J = 7.3 Hz, 2H), 2.33 (s, 3H), 1.60-1.48 (m, 2H), 1.37 (t, J = 7.3 Hz, 3H), 1.16-0.97 (m, 2H). LCMS (Analytical Method F) Rt = 3.30 min, MS (ESIPos): m/z = 426.3 (M + H)⁺. |
| 157 | 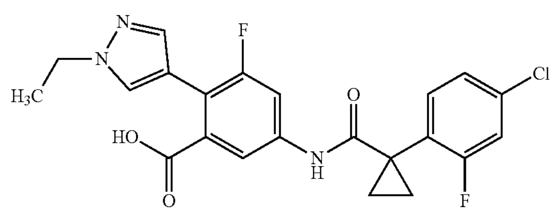 [SMILES: CCn1cc(-c2c(F)cc(NC(=O)C3(c4ccc(Cl)cc4F)CC3)cc2C(=O)O)cn1] | 5-({[1-(4-Chloro-2-fluorophenyl)cyclopropyl]carbonyl}amino)-2-(1-ethyl-1H-pyrazol-4-yl)-3-fluorobenzoic acid | ¹H NMR (500 MHz, DMSO-d6) δ [ppm] 9.16 (s, 1H), 7.85-7.81 (m, 1H), 7.70 (dd, J = 12.8, 2.0 Hz, 1H), 7.59-7.57 (m, 1H), 7.50-7.45 (m, 1H), 7.45-7.44 (m, 1H), 7.42 (dd, J = 10.0, 2.0 Hz, 1H), 7.30 (dd, J = 8.3, 2.0 Hz, 1H), 4.14 (q, J = 7.3 Hz, 2H), 1.63-1.52 (m, 2H), 1.37 (t, J = 7.3 Hz, 3H), 1.18-1.15 (m, 2H). LCMS (Analytical Method F) Rt = 3.37 min, MS (ESIPos): m/z = 446.2/448.2 (M + H)⁺. |
| 158 | 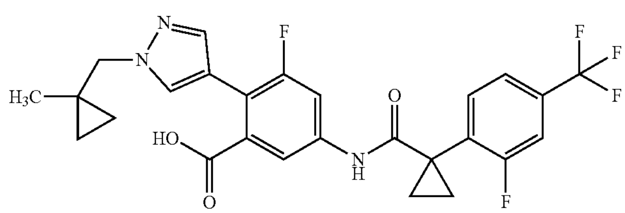 | 3-Fluoro-5-[({1-[2-fluoro-4-(trifluoromethyl)phenyl]cyclopropyl}carbonyl)amino]-2-{1-[(1-methylcyclopropyl)methyl]-1H-pyrazol-4-yl}benzoic acid | ¹H NMR (500 MHz, DMSO-d6) δ [ppm] 13.13 (s, 1H), 9.24 (s, 1H), 7.82 (s, 1H), 7.76-7.66 (m, 3H), 7.61 (d, J = 8.0 Hz, 2H), 7.45 (s, 1H), 3.97 (s, 2H), 1.74-1.57 (m, 2H), 1.32-1.19 (m, 2H), 0.97 (s, 3H), 0.67-0.55 (m, 2H), 0.40-0.28 (m, 2H). LCMS (Analytical Method F): Rt = 3.82 min; MS(ESIPos): m/z = 520.2 (M + H)⁺. |
| 159 | 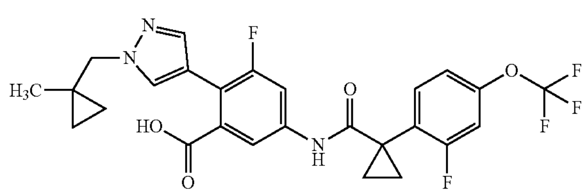 [SMILES: CC1(Cn2cc(-c3c(F)cc(NC(=O)C4(c5ccc(OC(F)(F)F)cc5F)CC4)cc3C(=O)O)cn2)CC1] | 3-Fluoro-5-[({1-[2-fluoro-4-(trifluoromethoxy)phenyl]cyclopropyl}carbonyl)amino]-2-{1-[(1-methylcyclopropyl)methyl]-1H-pyrazol-4-yl}benzoic acid | ¹H NMR (500 MHz, DMSO-d6) δ [ppm] 13.14 (s, 1H), 9.21 (s, 1H), 7.82 (s, 1H), 7.73 (dd, J = 12.7, 2.1 Hz, 1H), 7.64-7.55 (m, 2H), 7.45 (s, 1H), 7.41-7.36 (m, 1H), 7.27-7.22 (m, 1H), 3.97 (s, 2H), 1.73-1.53 (m, 2H), 1.31-1.16 (m, 2H), 0.97 (s, 3H), 0.69-0.53 (m, 2H), 0.42-0.28 (m, 2H). LCMS (Analytical Method F): Rt = 3.90 min; MS (ESIPos): m/z = 536.3 (M + H)⁺. |

| Ex. | Structure | Name | Analytical Data |
|---|---|---|---|
| 160 | 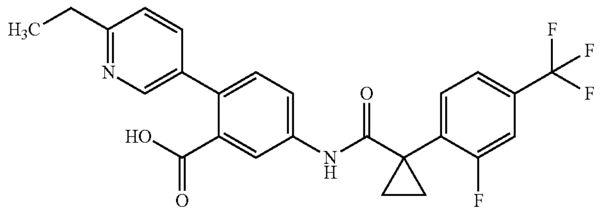 [SMILES: CCc1ccc(-c2ccc(NC(=O)C3(c4ccc(C(F)(F)F)cc4F)CC3)cc2C(=O)O)cn1] | 2-(6-Ethylpyridin-3-yl)-5-[({1-[2-fluoro-4-(trifluoromethyl)phenyl]cyclopropyl}carbonyl)amino]benzoic acid | ¹H NMR (500 MHz, DMSO-d6) δ [ppm] 12.88 (s, 1H), 9.21 (s, 1H), 8.36 (d, J = 2.2 Hz, 1H), 7.97 (d, J = 2.1 Hz, 1H), 7.81 (dd, J = 8.4, 2.2 Hz, 1H), 7.74-7.65 (m, 2H), 7.60 (m, 2H), 7.30 (d, J = 8.4 Hz, 1H), 7.26 (d, J = 8.0 Hz, 1H), 2.77 (q, J = 7.6 Hz, 2H), 1.71-1.59 (m, 2H), 1.32-1.19 (m, 5H). LCMS (Analytical Method F): Rt = 2.57 min; MS(ESIPos): m/z = 473.3 (M + H)⁺. |
| 161 | 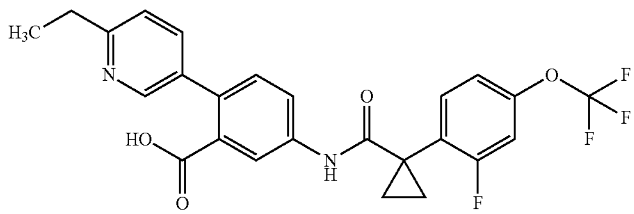 [SMILES: CCc1ccc(-c2ccc(NC(=O)C3(c4ccc(OC(F)(F)F)cc4F)CC3)cc2C(=O)O)cn1] | 2-(6-Ethylpyridin-3-yl)-5-[({1-[2-fluoro-4-(trifluoromethoxy)phenyl]cyclopropyl}carbonyl)amino]benzoic acid | ¹H NMR (500 MHz, DMSO-d6) δ [ppm] 12.90 (s, 1H), 9.18 (s, 1H), 8.41-8.30 (m, 1H), 7.97 (d, J = 2.0 Hz, 1H), 7.81 (dd, J = 8.4, 2.1 Hz, 1H), 7.63-7.57 (m, 2H), 7.39 (dd, J = 10.3, 1.8 Hz, 1H), 7.30 (d, J = 8.4 Hz, 1H), 7.28-7.21 (m, 2H), 2.77 (q, J = 7.6 Hz, 2H), 1.68-1.52 (m, 2H), 1.25 (t, J = 7.6 Hz, 3H), 1.22-1.17 (m, 2H). LCMS (Analytical Method F): Rt = 2.64 min; MS (ESIPos): m/z = 489.2 (M + H)⁺. |
| 162 | 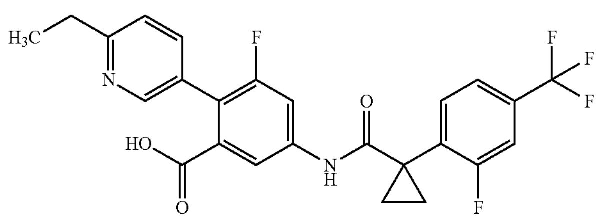 [SMILES: CCc1ccc(-c2c(F)cc(NC(=O)C3(c4ccc(C(F)(F)F)cc4F)CC3)cc2C(=O)O)cn1] | 2-(6-Ethylpyridin-3-yl)-3-fluoro-5-[({1-[2-fluoro-4-(trifluoromethyl)phenyl]cyclopropyl}carbonyl)amino]benzoic acid | ¹H NMR (500 MHz, DMSO-d6) δ [ppm] 13.07 (s, 1H), 9.39 (s, 1H), 8.31 (d, J = 2.1 Hz, 1H), 7.90-7.82 (m, 2H), 7.75-7.67 (m, 2H), 7.65-7.56 (m, 2H), 7.30 (d, J = 8.0 Hz, 1H), 2.79 (q, J = 7.6 Hz, 2H), 1.73-1.62 (m, 2H), 1.32-1.21 (m, 5H). LCMS (Analytical Method F): Rt = 2.82 min; MS (ESIPos): m/z = 491.2 (M + H)⁺. |
| 163 | 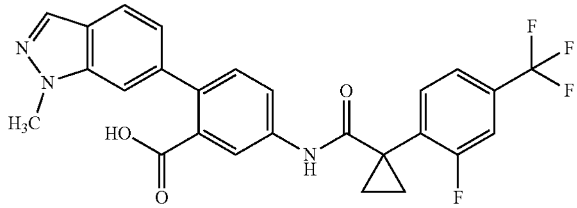 [SMILES: Cn1ncc2ccc(-c3ccc(NC(=O)C4(c5ccc(C(F)(F)F)cc5F)CC4)cc3C(=O)O)cc21] | 5-[({1-[2-Fluoro-4-(trifluoromethyl)phenyl]cyclopropyl}carbonyl)amino]-2-(1-methyl-1H-indazol-6-yl)benzoic acid | ¹H NMR (500 MHz, DMSO-d6) δ [ppm] 9.20 (s, 1H), 8.03 (s, 1H), 7.92 (d, J = 2.2 Hz, 1H), 7.79 (dd, J = 8.4, 2.3 Hz, 1H), 7.69 (m, 3H), 7.63-7.58 (m, 1H), 7.54-7.51 (m, 1H), 7.38 (d, J = 8.4 Hz, 1H), 7.01 (dd, J = 8.3, 1.2 Hz, 1H), 4.04 (s, 3H), 1.68-1.59 (m, 2H), 1.31-1.06 (m, 2H). LCMS (Analytical Method F) Rt = 3.61 min, MS (ESIpos): m/z = 498.3 (M + H)⁺. |
| 164 | 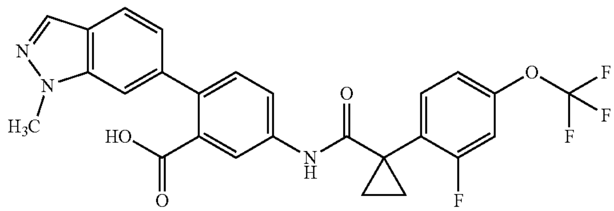 [SMILES: Cn1ncc2ccc(-c3ccc(NC(=O)C4(c5ccc(OC(F)(F)F)cc5F)CC4)cc3C(=O)O)cc21] | 5-[({1-[2-Fluoro-4-(trifluoromethoxy)phenyl]cyclopropyl}carbonyl)amino]-2-(1-methyl-1H-indazol-6-yl)benzoic acid | ¹H NMR (500 MHz, DMSO-d6) δ [ppm] 12.76 (s, 1H), 9.17 (s, 1H), 8.06-8.01 (m, 1H), 7.94 (d, J = 2.2 Hz, 1H), 7.80 (dd, J = 8.4, 2.2 Hz, 1H), 7.70 (d, J = 8.3 Hz, 1H), 7.62 (dd, J = 8.5, 8.5 Hz, 1H), 7.57-7.51 (m, 1H), 7.43-7.35 (m, 2H), 7.29-7.22 (m, 1H), 7.02 (dd, J = 8.3, 1.2 Hz, 1H), 4.04 (s, 3H), 1.68-1.54 (m, 2H), 1.29-1.11 (m, 2H). LCMS (Analytical Method F) Rt = 3.67 min, MS (ESIPos): m/z = 514.2 (M + H)⁺. |

-continued

| Ex. | Structure | Name | Analytical Data |
|---|---|---|---|
| 165 | 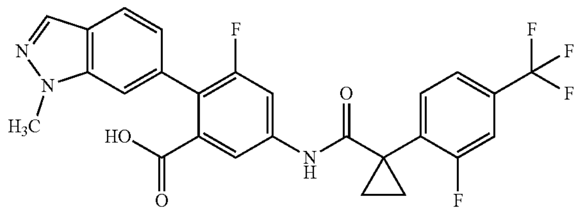 [SMILES: Cn1ncc2ccc(-c3c(F)cc(NC(=O)C4(c5ccc(C(F)(F)F)cc5F)CC4)cc3C(=O)O)cc21] | 3-Fluoro-5-[({1-[2-fluoro-4-(trifluoromethyl)phenyl]cyclopropyl}carbonyl)amino]-2-(1-methyl-1H-indazol-6-yl)benzoic acid | $^1$H NMR (500 MHz, DMSO-d6) δ [ppm] 12.90 (s, 1H), 9.36 (s, 1H), 8.06 (s, 1H), 7.86-7.80 (m, 2H), 7.76-7.67 (m, 3H), 7.64-7.60 (m, 1H), 7.54-7.50 (m, 1H), 6.97 (d, J = 8.4 Hz, 1H), 4.03 (s, 3H), 1.73-1.62 (m, 2H), 1.31-1.24 (m, 2H). LCMS (Analytical Method F) Rt = 3.72 min, MS (ESIpos): m/z = 516.2 (M + H)$^+$. |
| 166 | 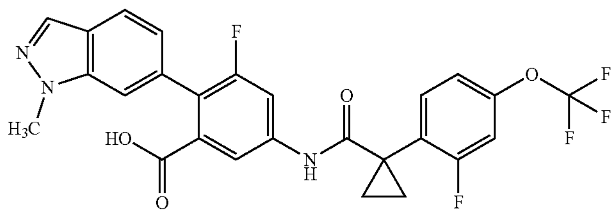 [SMILES: Cn1ncc2ccc(-c3c(F)cc(NC(=O)C4(c5ccc(OC(F)(F)F)cc5F)CC4)cc3C(=O)O)cc21] | 3-Fluoro-5-[({1-[2-fluoro-4-(trifluoromethoxy)phenyl]cyclopropyl}carbonyl)amino]-2-(1-methyl-1H-indazol-6-yl)benzoic acid | $^1$H NMR (500 MHz, DMSO-d6) δ [ppm] 12.90 (s, 1H), 9.33 (s, 1H), 8.06 (d, J = 0.9 Hz, 1H), 7.87-7.81 (m, 2H), 7.75-7.72 (m, 1H), 7.61 (dd, J = 8.6 Hz, 1H), 7.55-7.50 (m, 1H), 7.41 (dd, J = 10.3, 1.9 Hz, 1H), 7.28-7.24 (m, 1H), 7.00-6.92 (m, 1H), 4.03 (s, 3H), 1.68-1.60 (m, 2H), 1.27-1.19 (m, 2H). LCMS (Analytical Method F) Rt = 3.79 min, MS (ESIpos): m/z = 532.2 (M + H)$^+$. |
| 167 | 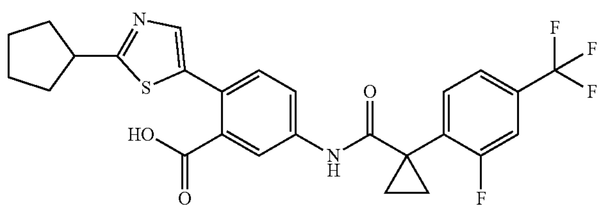 [SMILES: O=C(O)c1cc(NC(=O)C2(c3ccc(C(F)(F)F)cc3F)CC2)ccc1-c1cnc(C2CCCC2)s1] | 2-(2-Cyclopentyl-1,3-thiazol-5-yl)-5-[({1-[2-fluoro-4-(trifluoromethyl)phenyl]cyclopropyl}carbonyl)amino]benzoic acid | $^1$H NMR (500 MHz, DMSO-d6) δ [ppm] 9.22 (s, 1H), 7.88 (d, J = 2.3 Hz, 1H), 7.76 (dd, J = 8.5, 2.3 Hz, 1H), 7.73-7.65 (m, 2H), 7.60 (d, J = 8.0 Hz, 1H), 7.55 (s, 1H), 7.39 (d, J = 8.5 Hz, 1H), 3.42 (m, 1H), 2.17-2.03 (m, 2H), 1.81-1.55 (m, 8H), 1.30-1.19 (m, 2H). LCMS (Analytical Method F): Rt = 4.05 mins, MS (ESIPos): m/z = 519 (M + H)$^+$. |
| 168 | 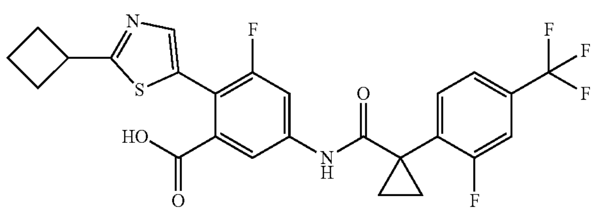 [SMILES: O=C(O)c1cc(NC(=O)C2(c3ccc(C(F)(F)F)cc3F)CC2)cc(F)c1-c1cnc(C2CCC2)s1] | 2-(2-Cyclobutyl-1,3-thiazol-5-yl)-3-fluoro-5-[({1-[2-fluoro-4-(trifluoromethyl)phenyl]cyclopropyl}carbonyl)amino]benzoic acid | $^1$H NMR (500 MHz, DMSO-d6) δ [ppm] 9.40 (s, 1H), 7.83 (dd, J = 12.3, 2.1 Hz, 1H), 7.77 (d, J = 1.7 Hz, 1H), 7.72-7.65 (m, 2H), 7.63-7.58 (m, 1H), 7.55 (s, 1H), 3.93-3.83 (m, 1H), 2.45-2.35 (m, 2H), 2.33-2.20 (m, 2H), 2.09-1.95 (m, 1H), 1.95-1.81 (m, 1H), 1.70-1.59 (m, 2H), 1.31-1.19 (m, 2H). LCMS (Analytical Method D): Rt = 2.35 mins, MS (ESIPos): m/z = 523 (M + H)$^+$. |
| 169 | 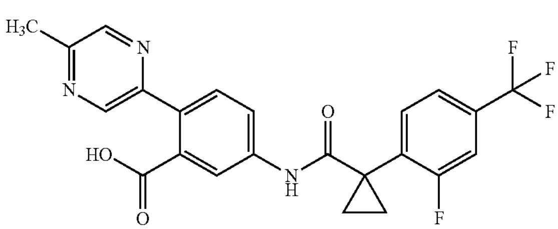 [SMILES: Cc1cnc(-c2ccc(NC(=O)C3(c4ccc(C(F)(F)F)cc4F)CC3)cc2C(=O)O)cn1] | 5-[({1-[2-Fluoro-4-(trifluoromethyl)phenyl]cyclopropyl}carbonyl)amino]-2-(5-methylpyrazin-2-yl)benzoic acid | $^1$H NMR (250 MHz, DMSO-d6) δ [ppm] 12.87 (s, 1H), 9.26 (s, 1H), 8.63 (d, J = 1.4 Hz, 1H), 8.55-8.43 (m, 1H), 7.98 (d, J = 2.1 Hz, 1H), 7.86 (dd, J = 8.5, 2.2 Hz, 1H), 7.78-7.59 (m, 3H), 7.54 (d, J = 8.4 Hz, 1H), 2.53 (s, 3H), 1.75-1.57 (m, 2H), 1.32-1.17 (m, 2H). LCMS (Analytical Method F) Rt = 3.25 min, MS (ESIpos): m/z = 460.3 (M + H)$^+$. |

-continued

| Ex. | Structure | Name | Analytical Data |
|---|---|---|---|
| 170 | 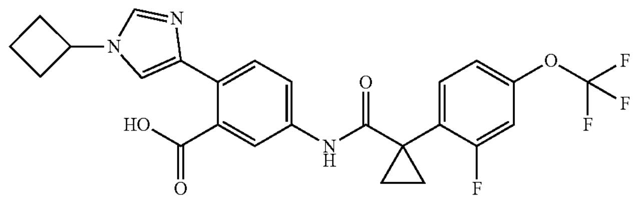 [SMILES: O=C(O)c1cc(NC(=O)C2(c3ccc(OC(F)(F)F)cc3F)CC2)ccc1-c1cn(C2CCC2)cn1] | 2-(1-Cyclobutyl-1H-imidazol-4-yl)-5-[({1-[2-fluoro-4-(trifluoromethoxy)phenyl]cyclopropyl}carbonyl)amino]benzoic acid | $^1$H NMR (500 MHz, DMSO-d6) δ [ppm] 9.08 (s, 1H), 7.94-7.91 (m, 1H), 7.82 (d, J = 2.1 Hz, 1H), 7.73-7.69 (m, 2H), 7.66 (d, J = 8.6 Hz, 1H), 7.62-7.57 (m, 1H), 7.41-7.35 (m, 1H), 7.27-7.21 (m, 1H), 4.80-4.68 (m, 1H), 2.44-2.34 (m, 4H), 1.88-1.70 (m, 2H), 1.66-1.54 (m, 2H), 1.24-1.11 (m, 2H). LCMS (Analytical Method F): Rt = 2.68 min; MS (ESIPos): m/z = 504.2 (M + H)$^+$. |
| 171 | 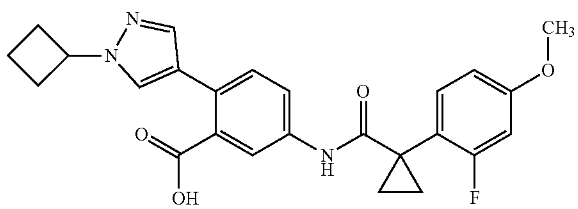 [SMILES: COc1ccc(C2(C(=O)Nc3ccc(-c4cnn(C5CCC5)c4)c(C(=O)O)c3)CC2)c(F)c1] | 2-(1-Cyclobutyl-1H-pyrazol-4-yl)-5-({[1-(2-fluoro-4-methoxyphenyl)cyclopropyl]carbonyl}amino)benzoic acid | $^1$H NMR (400 MHz, DMSO-d6) δ [ppm] 1.05-1.08 (m, 2H), 1.50-1.53 (m, 2H), 1.71-1.81 (m, 2H), 2.32-2.46 (m, 4H), 3.78 (s, 3H), 4.81 (quint, 1H), 6.79 (dd, 1H), 6.84 (dd, 1H), 7.32-7.38 (m, 2H), 7.54 (s, 1H), 7.62-7.75 (m, 2H), 7.93 (s, 1H), 8.87 (s, 1H). LCMS (method 1): Rt = 1.12 min; MS (ESIPos) m/z = 450 (M + H)$^+$. |
| 172 | 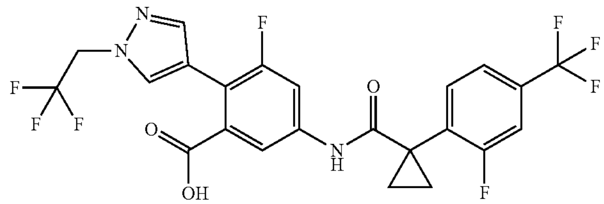 [SMILES: O=C(O)c1cc(NC(=O)C2(c3ccc(C(F)(F)F)cc3F)CC2)cc(F)c1-c1cnn(CC(F)(F)F)c1] | 3-Fluoro-5-[({1-[2-fluoro-4-(trifluoromethyl)phenyl]cyclopropyl}carbonyl)amino]-2-[1-(2,2,2-trifluoroethyl)-1H-pyrazol-4-yl]benzoic acid | $^1$H NMR (400 MHz, DMSO-d6) δ [ppm] 1.23-1.27 (m, 2H), 1.64-1.66 (m, 2H), 5.17 (q, 2H), 7.57-7.72 (m, 5H), 7.77 (dd, 1H), 7.96 (s, 1H), 9.29 (s, 1H), 13.2 (s, br, 1H). LCMS (method 1): Rt = 1.26 min; MS (ESIPos) m/z = 534 (M + H)$^+$. |

BIOLOGICAL ASSAYS

Compound examples were tested in selected biological assays one or more times. When tested more than once, data are reported as either average values or as median values, wherein
The average value, also referred to as the arithmetic mean value, represents the sum of the values obtained divided by the number of times tested, and
The median value represents the middle number of the group of values when ranked in ascending or descending order. If the number of values in the data set is odd, the median is the middle value. If the number of values in the data set is even, the median is the arithmetic mean of the two middle values.

Compound examples were synthesised one or more times. When synthesised more than once, data from biological assays represent average values or median values calculated utilising data sets obtained from testing of one or more synthetic batch.

The potency to inhibit the Bradykinin B1 receptor was determined for the Compound Examples of this invention in a cell-based fluorescent calcium-mobilisation assay. The assay measures the ability of Compound Examples to inhibit Bradykinin B1 receptor agonist-induced increase of intracellular free $Ca^{2+}$ in the cell line expressing Bradykinin B1 receptor. Specifically, calcium indicator-loaded cells are pre-incubated in the absence or presence of different concentrations of Compound Examples followed by the stimulation with a selective Bradykinin B1 receptor agonist peptide. The change of the intracellular $Ca^{2+}$ concentration is monitored with a fluorescent plate reader FLIPR $^{TETRA}$@ (Molecular Devices).

1. Calcium Flux Assays

Calcium Flux Assays (FLIPR) with Cells Expressing Human Bradykinin B1 Receptor (hB1)

Calcium flux Assay (FLIPR) with recombinant cells for Bradykinin B1 receptor antagonist, either in the presence (hB1 IC$_{50}$) or absence (hB1 free IC$_{50}$) of 0.1% Bovine Serum Albumin (BSA) in assay buffer.

CHO-K1 cell line expressing human Bradykinin B1 receptor is purchased from Euroscreen (Gosselies, Belgium, with reference name hB1-D1). The cells are grown in Nutrient Mixture Ham's F12 (Sigma) containing 10% Foetal bovine serum (Sigma) and 400 µg/mL G418 (Sigma), 5 µg/mL puromycin (Sigma).

Notably, Compound Examples are tested in the FLIPR assays either in the presence (hB1 IC50) or absence (hB1 free IC50) of 0.1% BSA in assay buffer, in order to assess the potency shifts due to serum protein binding of Compound Examples. The effect of BSA on the potency of endothelin receptor antagonists have been described in the prior art (Wu-Wong, J. R. et al. (1997), JPET 281: 791-798). The teaching can be applied in analogy to testing the potency of Bradykinin B1 receptor antagonist in the FLIPR assays.

For the calcium flux assay, 80% confluent cells are detached from the culture vessels with Versene (Gibco), and seeded into 384-well plates (Cell binding Surface; Corning, NY; #3683) at a density of 15,000 cells per well. Cells are seeded in a volume of 50 µL in medium without antibiotics and incubated overnight in a humidified atmosphere with 5% $CO_2$ at 37° C. The following day, the medium is replaced with 20 µL of 5 µM Fluo-4AM dye (Molecular Probes) in assay buffer (2.5 mM probenicid, 1 mg/mL pluronic acid, 135 mM NaCl, 5 mM KCl, 1.8 mM CaCl, 1 mM MgCl2, 10 mM HEPES, 5.6 mM glucose, and 0.05% gelatine, pH 7.4), which contains or lacks 0.1% BSA for determination of compound potency units as hB1 IC50 or hB1 free IC50, respectively. The calcium indicator loaded cells are incubated at 37° C. for 2 hrs. Extracellular dye is then removed and each well is filled with 45 μL of assay buffer. Cell plates are kept in dark until used. Compound examples are assayed at 8 concentrations in triplicate. Serial 10-fold dilutions in 100% DMSO are made at a 100-times higher concentration than the final concentration, and then diluted 1:10 in assay buffer. 5 μL of each diluted compound is added to the well of cell plates (yielding final concentration with 1% DMSO), and incubated for 30 min at 28° C. before the addition of Bradykinin B1 receptor agonist on the FLIPR instrument.

Agonist plates contain the agonist Lys-(Des-Arg)-Bradykinin (Bachem, Brackley) at 3.5×EC90 in assay buffer with 1% DMSO. The addition of agonist 20 μl per well to the assay plate is carried out on the FLIPR instrument while continuously monitoring Ca2+-dependent fluorescence at 538 nm. A peptide antagonist Lys-(Des-Arg-Leu)-Bradykinin (Bachem, Brackley) at 20 □M is used to determine the full inhibition as control.

Peak fluorescence is used to determine the response to agonist obtained at each concentration of Compound Examples by the following equation:

% Response=100*(RFU(compound)−RFU(control))/(RFU(DMSO)−RFU(control))

RFU means relative fluorescence units.

Control means full inhibition by the peptide antagonist Lys-(Des-Arg-Leu)-Bradykinin at 20 □M.

The response values are plotted against the logarithm of the compound concentrations. The Compound Examples are tested in triplicates per plate and mean values are plotted in Excel XLfit to determine IC50 values, percentage of maximal inhibition and the Hill slopes.

$IC_{50}$ values of Compound Examples in Calcium flux Assay (FLIPR) as shown in table 1 were determined according to the protocol described above in the absence of 0.1% BSA in assay buffer.

Calcium Flux Assay (FLIPR) with Human Fibroblasts Expressing Bradykinin B1 Receptor (hB1 IMR-90)

The Calcium flux Assay was carried out utilising IMR-90 human foetal lung fibroblasts (American Type Culture Collection, Rockville, Md.; and Coriell Institute, Camden, N.J.), which express native human Bradykinin B1 receptor after induction with human IL-1beta.

The fibroblasts were cultured in complete growth media comprised of Dulbecco's modified Eagle's medium (DMEM; Sigma) containing 10% foetal bovine serum, 4 mM L-glutamine, and 1% nonessential amino acids. The cells were maintained in a humidified atmosphere with 5% $CO_2$ at 37° C. and were sub-cultured at a ratio of 1:3, every other day.

For the assay, IMR-90 fibroblasts were harvested using TrypLE Express (GIBCO/Invitrogen) and seeded into 384-well plates (Corning Cellbinding Surface, Cat. 3683) at a density of 15000 cells/well. The following day, cells were treated with 0.35 ng/mL human IL-1beta in 10% FBS/MEM for 3 h to up-regulate Bradykinin B1 receptor. Induced cells were loaded with fluorescent calcium indicator by incubation with 2.5 μM Fluo-4/AM (Invitrogen) at 37° C., 5% $CO_2$ for 2 h in the presence of 2.5 mM probenecid in 1% FBS/MEM. Extracellular dye was removed by washing with assay buffer (2.5 mM probenecid and 0.1% BSA in 20 mM HEPES/HBSS without bicarbonate or phenol red, pH 7.5).

Compound examples were assayed at 8 concentrations in triplicate. After addition of Compound Examples to the cell plate and incubation for 30 min at 28° C., the addition of Bradykinin B1 agonist Lys-(Des-Arg)-Bradykinin (Bachem, Brackley) at a final concentration of EC90 was carried out on the FLIPR instrument while continuously monitoring Ca2+-dependent fluorescence at 538 nm. A peptide antagonist Lys-(Des-Arg-Leu)-Bradykinin (Bachem, Brackley) at 20 OM was used to determine the full inhibition as control. IC50 values were determined by the same way described for the FLIPR assay with recombinant cells.

TABLE 1

$IC_{50}$ values of Compound Examples in Calcium flux Assay (FLIPR) (Blank spaces indicate that the appropriate $IC_{50}$ value has not been determined)

| Example | hB1 free $IC_{50}$ [nM] | hB1 IMR90 $IC_{50}$ [nM] |
|---|---|---|
| 1 | 6.5 | 72 |
| 2 | 24 | 44 |
| 3 | 18 | 12 |
| 4 | 110 | 3400 |
| 5 | 86 | 2700 |
| 6 | 210 | 550 |
| 7 | 200 | 1100 |
| 8 | 690 | |
| 9 | 140 | 320 |
| 10 | 18 | 33 |
| 11 | 19 | 25 |
| 12 | 1200 | 2900 |
| 13 | 110 | 310 |
| 14 | 1000 | 1100 |
| 15 | 3600 | |
| 16 | 2800 | |
| 17 | 230 | 100 |
| 18 | 270 | 830 |
| 19 | 67 | 130 |
| 20 | 2500 | 1700 |
| 21 | 710 | |
| 22 | 290 | |
| 23 | 2400 | |
| 24 | 290 | |
| 25 | 14 | 5.9 |
| 26 | 140 | 130 |
| 27 | 33 | 73 |
| 28 | 300 | 460 |
| 29 | 13 | 21 |
| 30 | 410 | |
| 31 | 130 | |
| 32 | 190 | |
| 33 | 460 | |
| 34 | 31 | |
| 35 | 26 | |
| 36 | 6.0 | 14 |
| 37 | 20 | 5.6 |
| 38 | 22 | |
| 39 | 18 | 6.1 |
| 40 | 16 | 11 |
| 41 | 8.8 | 3.7 |
| 42 | 6.3 | 4.1 |
| 43 | 7.0 | 2.8 |
| 44 | 45 | 58 |
| 45 | 55 | |
| 46 | 58 | |
| 47 | 230 | |
| 48 | 220 | |
| 49 | 47 | |
| 50 | 62 | |
| 51 | 17 | 19 |
| 52 | 740 | |
| 53 | 32 | 15 |
| 54 | 26 | 22 |
| 55 | 280 | |
| 56 | 85 | |
| 57 | 840 | |
| 58 | 360 | |

TABLE 1-continued

IC$_{50}$ values of Compound Examples in Calcium flux Assay (FLIPR) (Blank spaces indicate that the appropriate IC$_{50}$ value has not been determined)

| Example | hB1 free IC$_{50}$ [nM] | hB1 IMR90 IC$_{50}$ [nM] |
|---|---|---|
| 59 | 1100 | |
| 60 | 62 | |
| 61 | 200 | |
| 62 | 89 | |
| 63 | 3000 | |
| 64 | 1300 | |
| 65 | 2600 | |
| 66 | 2100 | |
| 67 | 61 | 41 |
| 68 | 36 | |
| 69 | 28 | |
| 70 | 34 | 49 |
| 71 | 47 | 28 |
| 72 | 28 | |
| 73 | 21 | 44 |
| 74 | 17 | 15 |
| 75 | 11 | 18 |
| 76 | 11 | |
| 77 | 17 | 13 |
| 78 | 300 | |
| 79 | 60 | |
| 80 | 120 | |
| 81 | 680 | |
| 82 | 2500 | |
| 83 | 560 | |
| 84 | 570 | |
| 85 | 71 | |
| 86 | 69 | |
| 87 | 38 | |
| 88 | 32 | 10 |
| 89 | 32 | 14 |
| 90 | 24 | |
| 91 | 20 | 7.6 |
| 92 | 29 | |
| 93 | 61 | |
| 94 | 20 | |
| 95 | 13 | 21 |
| 96 | 8.1 | 25 |
| 97 | 10 | 25 |
| 98 | 2700 | |
| 99 | 2000 | |
| 100 | 8.9 | 13 |
| 101 | 3.5 | 5.5 |
| 102 | 110 | |
| 103 | 62 | |
| 104 | 130 | |
| 105 | 17 | 74 |
| 106 | 8.4 | 35 |
| 107 | 22 | 36 |
| 108 | 14 | 13 |
| 109 | 770 | |
| 110 | 580 | |
| 111 | 2400 | |
| 112 | 240 | |
| 113 | 120 | |
| 114 | 85 | |
| 115 | 120 | |
| 116 | 210 | |
| 117 | 56 | |
| 118 | 130 | |
| 119 | 25 | |
| 120 | 17 | |
| 121 | 18 | |
| 122 | 13 | |
| 123 | 22 | |
| 124 | 200 | |
| 125 | 170 | |
| 126 | 14 | |
| 127 | 11 | |
| 128 | 37 | |
| 129 | 620 | |
| 130 | 590 | |
| 131 | 50 | |
| 132 | 56 | |
| 133 | 59 | |
| 134 | 44 | |
| 135 | 33 | |
| 136 | 28 | |
| 137 | 70 | |
| 138 | 18 | |
| 139 | 13 | |
| 140 | 21 | |
| 141 | 2800 | |
| 142 | 3100 | |
| 143 | 78 | |
| 144 | 320 | |
| 145 | 160 | |
| 146 | 3.7 | |
| 147 | 13 | |
| 148 | 3.4 | |
| 149 | 3.2 | |
| 150 | 500 | |
| 151 | 22 | |
| 152 | 8.1 | |
| 153 | 8.7 | |
| 155 | 270 | |
| 160 | 21 | |
| 161 | 15 | |
| 162 | 14 | |
| 164 | 120 | |
| 165 | 63 | |
| 166 | 24 | |
| 167 | 3.4 | |
| 168 | 3.3 | |
| 169 | 2100 | |
| 170 | 2100 | |
| 171 | 390 | |
| 172 | 30 | |

2. Inhibitory Activity on Bradykinin B1 Agonist-Induced Secretion of IL-6 and IL-8 in Human IMR-90 Cells The effect of the Compound Examples on secretion of the cytokine IL-6 and IL-8 has been investigated in the human foetal lung fibroblast IMR-90 cell line. Here the induction of the cytokine secretion was induced by the Bradykinin B1 agonists Lys-[Des-Arg9]Bradykinin (CAS 71800-36-7, Tocris Bioscience) and Sar-[D-Phe8]-des-Arg9-Bradykinin (CAS 126959-88-4, Tocris Bioscience) leading to the activation of the Bradykinin B1i-driven signalling pathway. The inhibitory activity of the tested Compound Examples on Bradykinin B1 agonist-induced secretion of IL-6 and IL-8 is indicative for the compounds' prominent anti-inflammatory mode of action in kinin driven inflammation.

IMR-90 cells were cultured in Eagle's Minimum Essential Medium (EMEM) containing 2 mM L-glutamine, 1 g/L glucose, 1.5 g/L NaHCO$_3$, 1 mM sodium pyruvate and non-essential amino acids (ATCC, 30-2003™) supplemented with 10% FBS (Biochrom, S0615) and 50 U/mL Penicillin, 50 µg/mL Streptomycin (PAA, P11-010). The assay was performed in EMEM and a cell density of 5×10-4 IMR-90 cells/96-well. The Compound Examples have been serial diluted in 100% DMSO and evaluated at 8 different concentrations within the range of 3 nM and 10 µM and a final DMSO concentration of 0.4%. The IMR-90 cells have been incubated with the respective concentration of the compound for 30 min. The enhanced secretion of IL-6 and IL-8 was induced by the stimulation of these cells with 0.1 µM Lys-[Des-Arg9]Bradykinin (Tocris, catalogue no. 3225) and 0.1 µM Sar-[D-Phe8]-des-Arg9-Bradykinin (Tocris, catalogue no. 3230) for 5 hours at 37° C. and 5% C02. Further, cells have been treated with Lys-[Des-Arg9]Bradykinin and Sar-[D-Phe8]-des-Arg9-Bradykinin as neutral control and with 0.1% DMSO as inhibitor control. The amount of IL-6 and IL-8 in the supernatant was determined using the Human ProInflammatory Panel II (4-Plex) (MSD, K15025B) according to manufacturer's instruction. Briefly, supernatants were added onto assay plates and incubated at room temperature for 1-2 h with vigorous shaking at 600 rpm. Detection antibodies were then added onto the supernatants and incubated at room temperature for an additional 1-2 h with vigorous shaking at 600 rpm. Plates were washed three times with phosphate-buffered saline (PBS; 137 mM NaCl, 2.7 mM KC1, 6.5 mM Na2HPO4, 1.7 mM KH2P04) containing 0.05% Tween-20 (Bio-Rad, 161-0781) and electrochemiluminescence detected using the MSD Sector Imager 6000 plate reader. The cell viability was measured using the CellTiter-Glo Luminescent Assay (Promega, G7571) following the manufacturers protocol. Briefly, the CellTiter-Glo Reagent was diluted with PBS (1:1) and added directly to cells. After incubation and shaking for 10 minutes luminescent signal was measured which is proportional to the amount of ATP present.

The effect of the compound on the amount of secreted cytokine has been calculated as 100/(measured cytokine concentration of neutral control-measured cytokine concentration of inhibitor control)*(measured cytokine concentration of compound dose-measured cytokine concentration of inhibitor control). $IC_{50}$ values are determined using 4-parameter-fit.

The cell viability was measured using the CellTiter-Glo Luminescent Assay (Promega, G7571) following the manufacturer's protocol. The homogeneous assay procedure involves adding the single reagent (CellTiter-Glo Reagent) directly to cells cultured in serum-supplemented medium. Cell washing, removal of medium and multiple pipetting steps are not required. The system is able to detect as few as 15 cells/well in a 384-well format in 10 minutes after adding reagent and mixing. The homogeneous add-mix-measure format results in cell lysis and generation of a luminescent signal proportional to the amount of ATP present. The amount of ATP is directly proportional to the number of cells present in culture. The CellTiter-Glo Assay generates a glow-type luminescent signal, which has a half-life generally greater than five hours, depending on cell type and medium used. The extended half-life eliminates the need to use reagent injectors and provides flexibility for continuous or batch mode processing of multiple plates. The unique homogeneous format avoids errors that may be introduced by other ATP measurement methods that require multiple steps.

The Compound Examples were tested in triplicates per plate and the inhibitory activity was determined as the relation between neutral and inhibitor control in percent. $IC_{50}$ values were calculated using the 4-parameter logistic model.

The Compound Examples listed in Table 2 showed no effect on the cell viability of the stimulated IMR-90 cells. The effect on the secretion of Il-6 and IL-8 is shown in Table 2:

TABLE 2

Effect on the secretion of Il-6 and IL-8. (Blank spaces indicate that the appropriate $IC_{50}$ value are >10 μM or no secretion)

| Example | IL-6 secretion $IC_{50}$ (nM) | IL-8 secretion $IC_{50}$ (nM) |
|---|---|---|
| 1 | 149 | 245 |
| 2 | 113 | 303 |
| 3 | 47 | 53 |
| 5 | 290 | 483 |
| 6 | 443 | 205 |
| 29 | 600 | 489 |
| 42 | 70 | 85 |

3. Rat CFA In Vivo Model

Male Sprague Dawley rats were used. Mechanical hyperalgesia was induced by injecting 25 μL of Complete Freund's Adjuvant (CFA) into the plantar surface of one hind paw. Mechanical hyperalgesia was measured using the Pressure Application Measurement apparatus (Ugo Basile, Gemonio, Italy). Briefly, a linearly increasing pressure was applied to an area of ~50 mm$^2$ of the plantar side of the hind paw until a behavioural response (paw withdrawal) was observed or until the pressure reached 1000 gf. The pressure at which the behavioural response occurred was recorded as the "Paw Withdrawal Threshold" (PWT). Both CFA-injected and contralateral PWTs were determined for each rat, in each treatment group and at each time point of the studies. The Compound Examples were administered orally in a vehicle of dimethylsulfoxide (DMSO), Polyethylenglycol (PEG) and 2-hydroxypropyl-beta-cyclodextrin (HPCD) (v/v/v=3:20:77). Rats received a first dose of 5 mL/kg bodyweight of Compound Example per kg body weight 1 hour before CFA injection and a second dose 24 hours after the CFA injection. Mechanical hyperalgesia testing was performed approximately 2 hours before CFA injection, then 2 and 4 hours after the second dose of Compound Example (i.e. 26 and 28 hours after CFA treatment). Data were expressed as the mean±S.D. Area Under the Curve (AUC) of PWTs (defined in table 3 as "AUC of Paw withdrawal threshold (AUC 0-4 hours) post-vehicle" with respect to vehicle group or "AUC of Paw withdrawal threshold (AUC 0-4 hours) post-drug" with respect to Compound Example). Data were analysed by performing a one-way ANOVA followed by a Dunnett's post hoc test. For p values less than 0.05 the results were deemed to be statistically significant.

TABLE 3

Paw withdrawal threshold after treatment with Compound Example 3

| Example | Paw withdrawal threshold 2 hours post-vehicle | Dose, p.o. | Paw withdrawal threshold 2 hours post-compound |
|---|---|---|---|
| 3 | 589 ± 37 gf | 0.75 mg/kg | 659 ± 20 gf (ns) |
| 3 | 589 ± 37 gf | 3 mg/kg | 782 ± 50 gf (****) |
| 3 | 589 ± 37 gf | 15 mg/kg | 812 ± 44 gf (****) |
| 3 | 589 ± 37 gf | 60 mg/kg | 885 ± 30 gf (****) |

(****) $p < 0.001$, Dunnett's post-hoc test, different from vehicle group

TABLE 4

Paw withdrawal threshold after treatment with Compound Example 43

| Example | Paw withdrawal threshold 4 hours post-vehicle | Dose, p.o. | Paw withdrawal threshold 4 hours post-compound |
|---|---|---|---|
| 43 | 562 ± 29 gf | 0.75 mg/kg | 599 ± 28 gf (ns) |
| 43 | 562 ± 29 gf | 3 mg/kg | 610 ± 21 gf (ns) |
| 43 | 562 ± 29 gf | 15 mg/kg | 709 ± 18 gf (****) |

(****) $p < 0.001$, Dunnett's post-hoc test, different from vehicle group

TABLE 5

Paw withdrawal threshold after treatment with Compound Example 71

| Example | Paw withdrawal threshold 2 hours post-vehicle | Dose, p.o. | Paw withdrawal threshold 2 hours post-compound |
|---|---|---|---|
| 71 | 562 ± 26 gf | 0.75 mg/kg | 591 ± 20 gf (ns) |
| 71 | 562 ± 26 gf | 3 mg/kg | 628 ± 17 gf (ns) |
| 71 | 562 ± 26 gf | 10 mg/kg | 742 ± 49 gf (****) |

(****) $p < 0.001$, Dunnett's post-hoc test, different from vehicle group

4. Rat Model for Endometriosis, Acute Phase

Female Brown Norway rats (Charles-River) were treated p.o. with Compound Example 3 (doses: 1 mg/kg, 5 mg/kg, 15 mg/kg, 60 mg/kg) or vehicle alone (10% DMSO+90% phosphate buffered saline (PBS)). 2 h later all animals got under deep anesthesia a transplantation of 6 uterus pieces in the peritoneal cavity. The tissue was obtained from donor animals which were pre-treated with 3 µg s.c. Estradiol (E2) for 2 days to guarantee standardized conditions of the uterus tissue. The animals were treated once daily p.o. with Compound Example 3 (doses: 1 mg/kg, 5 mg/kg, 15 mg/kg, 60 mg/kg) or vehicle alone (10% DMSO+90% phosphate buffered saline (PBS). 4 days later the animals were sacrificed and the transplants as surrogate endometriosis lesion tissue were analyzed for markers of lesion activity (inflammatory cytokines and proliferation marker). This approach is mimicking the early inflammatory phase of endometriosis close to menstruation.

Analysis

For RNA expression analysis the lesions, were excised. RNA was isolated after homogenization of tissues in guanidinium thiocyanate using the RNeasy mini Kit (Qiagen) with DNase digestion. One microgram of RNA was reversely transcribed with random hexamers using the SuperScript III First-Strand Synthesis System (Invitrogen). Real-time Taqman PCR analysis was performed using the 7900HT Real Time PCR-System (Applied Biosystems). Prevalidated probes and primers (Rn01514538_g1) for proliferating cell nuclear antigen (PCNA) in the rat were used. TATA-Binding Protein (TBP) was used as a reference housekeeping gene. Relative mRNA levels were calculated using the comparative CT method using the RQ-Manager software (Applied Biosystems).

For ex vivo cytokine analysis, animals were sacrificed and tissues (endometriosis lesions) were frozen at −80° C. For cytokine extraction, tissues were homogenized in 300 µl PBS containing protease inhibitor mix using Precellys 24 Homogenisator at 5200 rpm for 2×20 sec. After centrifugation at 13.000 U/min (Eppendorf) supernatants were analyzed for cytokine levels using Bio-Plex Pro™ Rat Cytokine 24-plex (Bio Rad Assay #171K1001M) or the Bio-Plex Pro™ Mouse Cytokine 23-Plex (Bio Rad Assay #M600009RDPD) according to the manufacturer's protocols.

Result

Daily treatment of rats in the 4 day endometriosis model with Compound Example 3 decreased expression of proliferation marker and expression of inflammatory cytokines (FIG. 1-FIG. 4). The model reflects the effect on acute inflammation and the situation during establishment of new lesions. The lesions were already adhered to the peritoneal tissue. Strong vascularization of the tissue was observed.

5. Rat Model for Endometriosis, Late Phase

Female Brown Norway rats (Charles-River) were treated with Compound Example 3 (doses: 5 mg/kg, 30 mg/kg, 60 mg/kg) or vehicle alone (10% DMSO+90% phosphate buffered saline (PBS). 2 h later all animals got under deep anesthesia a transplantation of 6 uterus pieces in the peritoneal cavity. The tissue was obtained from donor animals which were pre-treated with 3 µg s.c. Estradiol for 2 days to guarantee standardized conditions of the uterus tissue. The animals were treated once daily p.o. with Compound Example 3 (doses: 5 mg/kg, 30 mg/kg, 60 mg/kg) or respective vehicle (10% DMSO+90% phosphate buffered saline (PBS). 15 days later the animals were sacrificed and the transplants as surrogate endometriosis lesion tissue were analyzed for markers of lesion activity (inflammatory cytokines). This approach is mimicking the long term effect on established inflammation in endometriosis.

Analysis

For ex vivo cytokine analysis, animals were sacrificed and tissues (endometriosis lesions) were frozen at −80° C. For cytokine extraction, tissues were homogenized in 300 µl PBS containing protease inhibitor mix using Precellys 24 Homogenisator at 5200 rpm for 2×20 sec. After centrifugation at 13.000 U/min (Eppendorf) supernatants were analyzed for cytokine levels using Bio-Plex Pro™ Rat Cytokine 24-plex (Bio Rad Assay #171K1001M) or the Bio-Plex Pro™ Mouse Cytokine 23-Plex (Bio Rad Assay #M600009RDPD) according to the manufacturer's protocols.

Result

Figure 5:
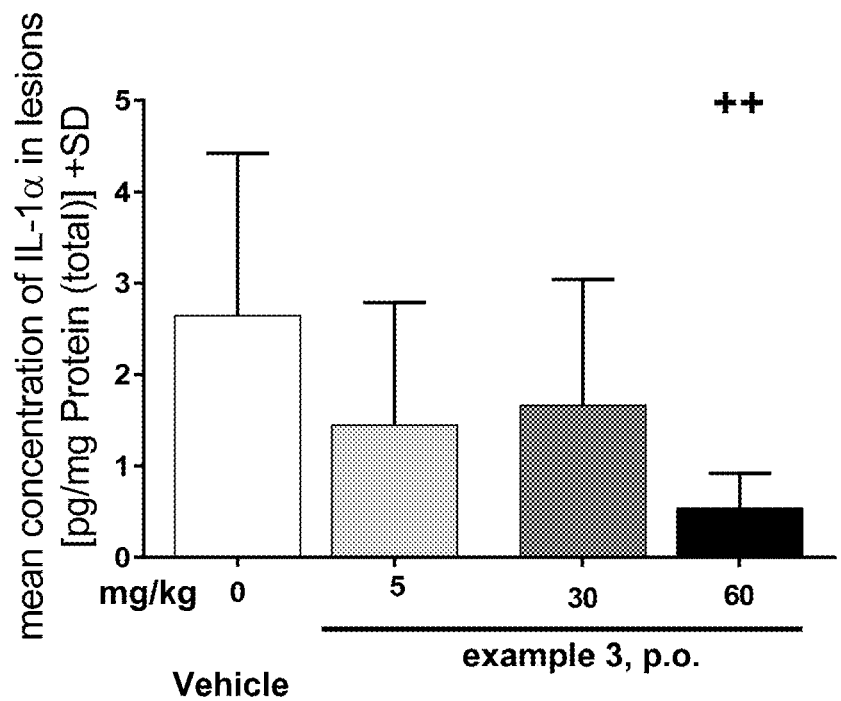
Figure 6:
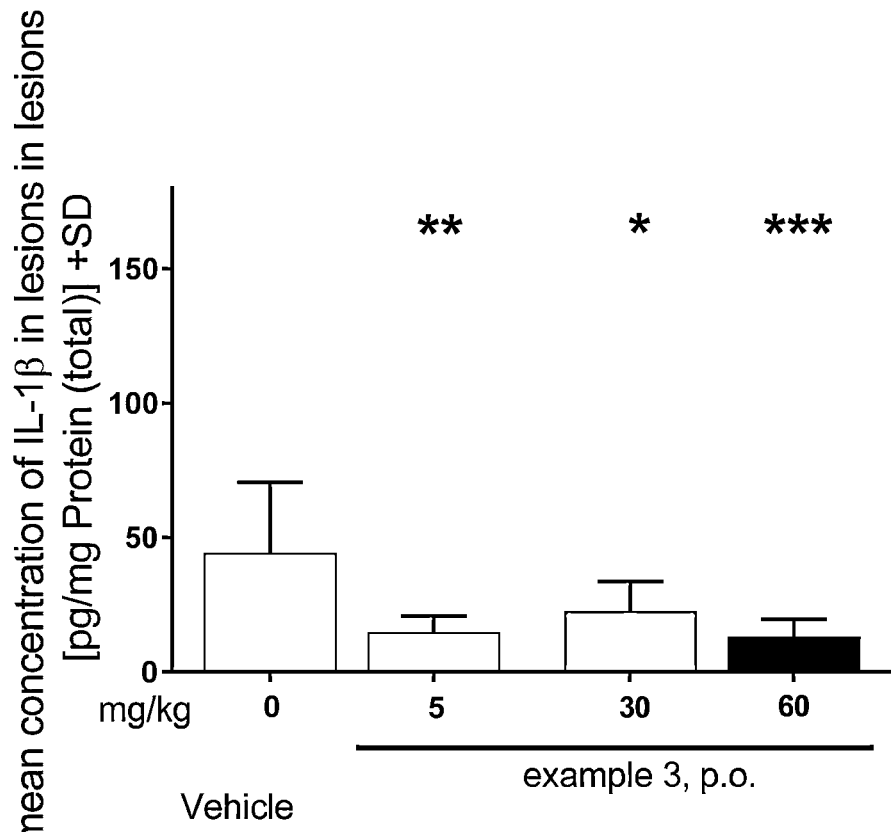

Daily treatment of rats in the 15 day endometriosis model with Compound Example 3 decreased expression of inflammatory cytokines in the lesions (FIG. 5-FIG. 6). This shows that treatment with Compound Example 3 reduces inflammatory lesion activity in the endometriosis model mimicking the stage of established endometriosis lesions. In consequence the irritation of the highly innervated peritoneal tissue surrounding the endometriosis lesion by interleukins which trigger pain sensation should be strongly attenuated.

6. Mouse Model for Peritonitis

Black 6 (B6)-Mice expressing the human B1 receptor, lacking the murine B1 receptors which were specifically generated (B6-hBDKRB1<tm1Arte>/N) and employed for a thioglycollate induced peritonitis model to test for effects of Bradykinin B1 receptor antagonism on peritoneal inflammation and related leukocyte trafficking which reflects the mode of actions underlying endometriosis.

Method

Animals were treated p.o. with Compound Example 3 (doses: 30 mg/kg, 100 mg/kg) or respective vehicle (10%

DMSO+90% phosphate buffered saline (PBS) alone 1 h before i.p. application of 1 ml 4% thioglycollate medium (in sterile PBS, matured for >4 weeks). The treatment with vehicle or Compound Example 3 was repeated 3 and 24 hours after induction of peritonitis. 24 h after peritonitis induction the animals were sacrificed and a lavage of peritoneal fluid performed. The resulting lavage is analysed for peroxidase enzyme activity which is reflecting number of activated neutrophils in the peritoneal cavity by peroxidase activity assay as follows:

Tetramethylbenzidine (TMB) dihydrochloride is used as a sensitive chromogen substrate for peroxidase.

To convert TMB into TMB dihydrochloride, 34 µl of 3.7% hydrochloric acid (equimolar) is added to 5 mg of TMB.

Then 1 ml of DMSO is added. This stock solution is slowly added to sodium acetate-citric acid buffer (0.1 mol/l, pH 6) in a ratio 1:100. 200 µl of this TMB-solution, 40 µl of the homogenized sample (homogenate buffer contains 0.5% HTAB and 10 mM MOPS) and 25 µl of 1 mM $H_2O_2$ are added to a microtiter plate to start the reaction. The reaction is stopped after 30 min with 45 µl of 1 N $H_2SO_4$ and stirred thoroughly. Changes in optical densities (OD) are monitored in an ELISA plate-reader at 450 nm at 25° Celsius against the mixture of all solutions without the added sample homogenate. Absolute extinction numbers are used to express peroxidase activity.

Result

Figure 7:
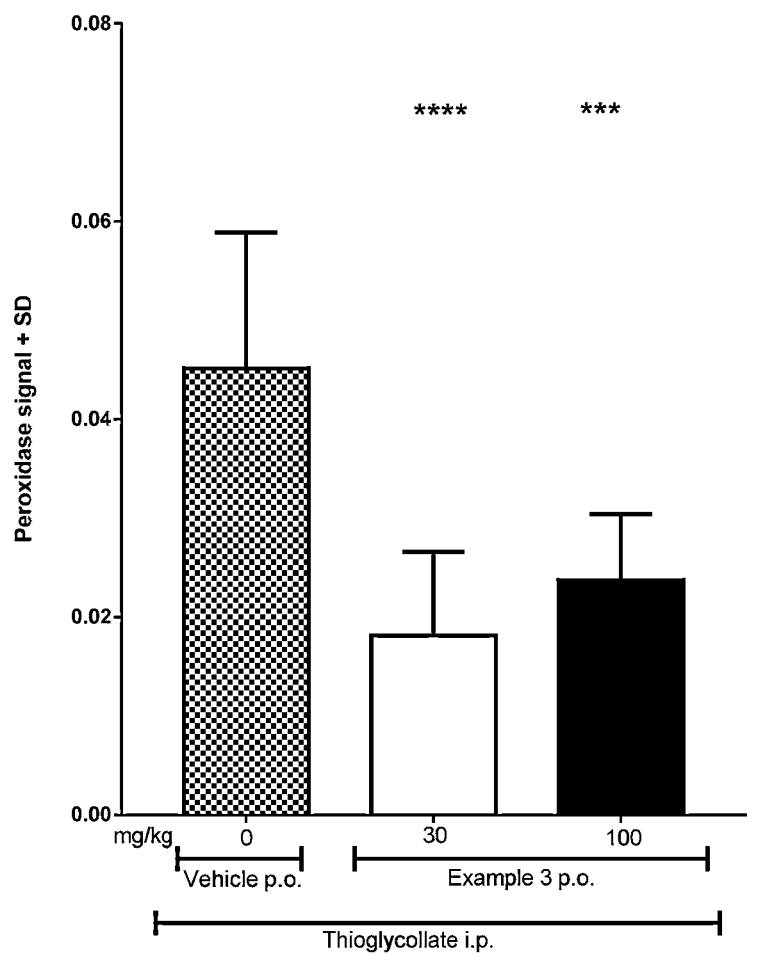
Figure 8:
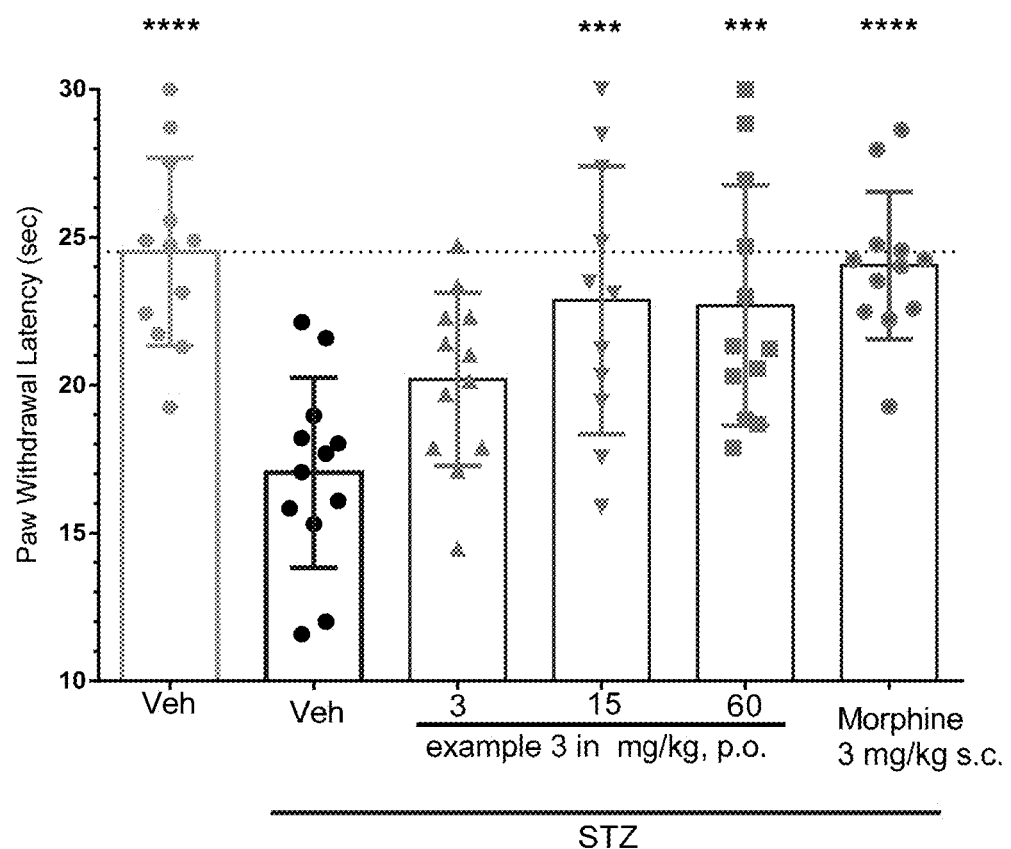

Compound Example 3 reduced the signal specific for neutrophil influx into inflamed tissue in a peritonitis model significantly (FIG. 7). This result was shown in mice expressing the human B1 receptor, lacking the murine B1 receptors which were specifically generated.

7. Rat STZ Model for Diabetic Neuropathy (Diabetic Neuropathic Pain, Diabetes Induced Nerve Degeneration)

The streptozotocin (STZ) diabetic rat is the most extensively studied animal model of diabetic neuropathy. The animals develop rapidly allodynia and hyperalgesia. Reduced nerve conduction velocity together with loss of intra-epidermal nerve fibers (IENF) in skin biopsies has also been demonstrated in STZ-rats.

Male Sprague-Dawley rats (~200 g) were used. They were rendered diabetic by intravenous injection of streptozotocin (55 mg/kg; day 0). Four days (day 4) later, diabetes was confirmed in STZ-injected rats by obtaining a blood sample from the tail vein and by measuring the glucose concentration using a glucose monitor. Only STZ-treated rats with plasma-glucose >260 mg/dl were deemed "diabetic". The body weight of rats was recorded on daily basis from day 4 to 40.

72 animals were randomly assigned to different groups (12 rats per group).

Drug Treatment

Compound example 3 was prepared in 10% DMSO in PBS (v/v). The compound was prepared at a concentration of 3, 15 and 60 mg/ml which were applied orally (p.o.) at a dosage volume of 5 ml/kg. The treatment was performed on daily basis (twice a day: morning and afternoon) from day 4 until day 40. On the day where behavioral measures are performed, compound or vehicle was given 60 min prior the assessment. On the day where electrophysiological measure was performed, treatment was performed after the assessment.

For positive control regarding analgesia, morphine was dissolved in 0.9% NaCl, and administrated subcutaneously (s.c.) at the dose of 3 mg/kg 45 min prior the tests.

Experimental Plan:

Day 0: induction of diabetes by injection of STZ for all groups except the control group injected with the STZ vehicle Day 4: glycemia monitoring for all groups and start of the treatment for all groups, except the morphine group. On day 4 rats received only the evening treatment.

Day 10: cold and warm allodynia test for all groups. Treatment is given 60 min prior to the assessment. On that day, the time between the morning and the evening treatment was reduced.

Day 21: Mechanical hyperalgesia test for all groups. Compound or vehicle was given 60 min prior to the assessment. On that day, the time between the morning and the evening treatment was reduced.

Day 22: Termination of rats in the morphine group.

Day 25-26: measurement of sensory nerve conduction velocity (SNCV). On that day, rats only received the evening treatment.

Day 39-40: measurement of sensory nerve conduction velocity (SNCV). On that day, rats only received the evening treatment.

Day 41: skin biopsy from all rats (histology processing and immunostaining of skin biopsy from 7 rats per group take about 4 weeks).

Cold Plate Test on Day 10

The animals were placed into a glass cylinder on a cold platform (0-1° C.). The latency before the first reaction (brisk move of the paw, little leaps) was recorded with a maximal time of 30 s. Results can be seen in table 6.

Warm Plate Test on Day 10

The animals were placed into a glass cylinder on a hot plate adjusted to 42° C. The latency of the first reaction was recorded (paw lifting or licking, leaps or a jump to escape the heat). Results can be seen in FIG. 8 and table 6.

The Compound Examples, in particular Compound Example 3, show significant effects in all endpoints (warm/cold/mechanical) of neuropathic pain.

Paw Pressure Test

Paw pressure test is used to assess the hyperalgesia of animals in response to noxious mechanical stimulus. The nociceptive flexion reflex was quantified using the Randall-Selitto paw pressure device (Bioseb, France), which applies a linearly increasing mechanical force to the dorsum of the rat's hind paw. The mechanical nociceptive threshold is defined as the force in grams at which the rat withdraws its paw. The cut off pressure was set to 250 g. Results can be seen in table 6.

Electrophysiological Measurements (SNCV)

Electrophysiological recordings of SNCV were performed using a Keypoint Electromyograph (EMG) (Medtronic, France). Rats were anaesthetized by intraperitoneal injection of 60 mg/kg ketamine chlorhydrate and 4 mg/kg xylazine. SNCV was recorded in the tail. Electrodes were placed as follows: The recording needle electrode was inserted near the base of the tail and stimulating needle electrode is placed about 50 mm away from the recording electrode towards the extremity of the tail. A ground needle electrode is inserted between the recording and the stimulation electrodes. The caudal nerve was stimulated with a series of 20 pulses (for 0.2 ins) at an intensity of 12.8 mA. The velocity is expressed as m/s.

TABLE 6

Result overview in STZ model on day 10 and day 21 after treatment with Compound Example 3

| | Day 10 | | | Day 21 | |
|---|---|---|---|---|---|
| Groups | Weight (g) | Latency in Warm plate (s) | Latency in Cold plate (s) | Weight (g) | Paw pressure (g) |
| Vehicle/Vehicle | 295 | 21.29 | 30.00 | 389 | 195 |
| Vehicle/Vehicle | 313 | 27.53 | 27.69 | 426 | 190 |
| Vehicle/Vehicle | 309 | 23.12 | 22.44 | 410 | 180 |
| Vehicle/Vehicle | 302 | 30.00 | 22.38 | 396 | 175 |
| Vehicle/Vehicle | 280 | 21.74 | 21.19 | 356 | 250 |
| Vehicle/Vehicle | 303 | 24.72 | 27.50 | 390 | 170 |
| Vehicle/Vehicle | 266 | 25.57 | 20.42 | 340 | 145 |
| Vehicle/Vehicle | 302 | 24.89 | 24.02 | 398 | 180 |
| Vehicle/Vehicle | 309 | 24.89 | 23.38 | 406 | 215 |
| Vehicle/Vehicle | 286 | 28.71 | 24.28 | 365 | 135 |
| Vehicle/Vehicle | 288 | 22.42 | 22.10 | 380 | 165 |
| Vehicle/Vehicle | 274 | 19.25 | 19.21 | 353 | 245 |
| STZ/Vehicle | 308 | 15.31 | 17.78 | 395 | 75 |
| STZ/Vehicle | 256 | 16.09 | 16.53 | 305 | 85 |
| STZ/Vehicle | 255 | 18.03 | 18.50 | 290 | 80 |
| STZ/Vehicle | 261 | 21.59 | 9.81 | 323 | 135 |
| STZ/Vehicle | 256 | 11.58 | 15.22 | 310 | 85 |
| STZ/Vehicle | 236 | 17.06 | 12.84 | 280 | 100 |
| STZ/Vehicle | 237 | 12.01 | 16.91 | 285 | 70 |
| STZ/Vehicle | 268 | 17.69 | 18.62 | 315 | 85 |
| STZ/Vehicle | 263 | 15.84 | 21.62 | 318 | 105 |
| STZ/Vehicle | 220 | 18.21 | 20.65 | 225 | 110 |
| STZ/Vehicle | 246 | 18.97 | 18.65 | 284 | 115 |
| STZ/Vehicle | 246 | 22.13 | 26.00 | 293 | 105 |
| STZ/Example 3 3 mg/kg | 265 | 19.71 | 14.39 | 321 | 125 |
| STZ/Example 3 3 mg/kg | 250 | 21.41 | 14.46 | 314 | 150 |
| STZ/Example 3 3 mg/kg | 246 | 22.31 | 22.78 | 282 | 105 |
| STZ/Example 3 3 mg/kg | 271 | 20.16 | 15.84 | 354 | 150 |
| STZ/Example 3 3 mg/kg | 257 | 14.49 | 16.87 | 305 | 125 |
| STZ/Example 3 3 mg/kg | 252 | 17.12 | 16.18 | 300 | 105 |
| STZ/Example 3 3 mg/kg | 271 | 22.29 | 21.38 | 285 | 105 |
| STZ/Example 3 3 mg/kg | 223 | 17.89 | 20.52 | 264 | 115 |
| STZ/Example 3 3 mg/kg | 248 | 23.35 | 17.93 | 294 | 140 |
| STZ/Example 3 3 mg/kg | 265 | 17.89 | 15.23 | 293 | 125 |
| STZ/Example 3 3 mg/kg | 249 | 24.72 | 26.66 | 278 | 100 |
| STZ/Example 3 3 mg/kg | 257 | 21.04 | 23.47 | 293 | 105 |
| STZ/Example 3 15 mg/kg | 251 | 21.21 | 22.94 | 307 | 100 |
| STZ/Example 3 15 mg/kg | 253 | 17.56 | 18.19 | 308 | 125 |
| STZ/Example 3 15 mg/kg | 237 | 30.00 | 23.62 | 288 | 135 |
| STZ/Example 3 15 mg/kg | 233 | 23.09 | 18.66 | 282 | 120 |
| STZ/Example 3 15 mg/kg | 247 | 23.47 | 20.23 | 306 | 110 |
| STZ/Example 3 15 mg/kg | 234 | 19.44 | 19.51 | 273 | 125 |
| STZ/Example 3 15 mg/kg | 258 | 28.47 | 23.02 | 300 | 135 |
| STZ/Example 3 15 mg/kg | 235 | 15.88 | 17.08 | 278 | 110 |
| STZ/Example 3 15 mg/kg | 226 | 24.82 | 24.66 | 235 | 85 |
| STZ/Example 3 15 mg/kg | 246 | 20.31 | 24.25 | 274 | 105 |
| STZ/Example 3 15 mg/kg | 275 | 27.35 | 20.00 | 333 | 110 |
| STZ/Example 3 60 mg/kg | 240 | 24.69 | 15.60 | 323 | 165 |
| STZ/Example 3 60 mg/kg | 218 | 21.32 | 17.29 | 241 | 95 |
| STZ/Example 3 60 mg/kg | 227 | 18.69 | 19.84 | 295 | 115 |
| STZ/Example 3 60 mg/kg | 243 | 21.23 | 14.52 | 303 | 140 |
| STZ/Example 3 60 mg/kg | 230 | 28.84 | 13.66 | 300 | 115 |
| STZ/Example 3 60 mg/kg | 233 | 18.84 | 22.28 | 270 | 120 |
| STZ/Example 3 60 mg/kg | 267 | 30.00 | 24.12 | 312 | 110 |
| STZ/Example 3 60 mg/kg | 249 | 23.02 | 21.12 | 289 | 110 |
| STZ/Example 3 60 mg/kg | 221 | 20.56 | 17.48 | 285 | 115 |
| STZ/Example 3 60 mg/kg | 260 | 26.94 | 22.45 | 324 | 190 |
| STZ/Example 3 60 mg/kg | 229 | 20.31 | 16.59 | 266 | 110 |
| STZ/Example 3 60 mg/kg | 239 | 17.88 | 20.21 | 286 | 105 |

8. Chronic Constriction Injury (CCI) of the Sciatic Nerve in Rats (Model for Neuropathic Pain)

The objective of the present study is to evaluate the therapeutic effect of Compound Examples, in the model of neuropathic pain induced by Chronic Constriction Injury (CCI) of the sciatic nerve in rats.

The principle of the study is based on the Chronic Constriction Injury model for studying pain in rats (Dias Q M et al. An improved experimental model for peripheral neuropathy in rats, Braz J Med Bioi Res 2013; 46:253-256; Bennett G J and Xie Y K, A peripheral mononeuropathy in rat that produces disorders of pain sensation like those seen in man, Pain 1988; 33:87-107; Farghaly H S et al., The effects of dexmedetomidine alone and in combination with tramadol or amitriptyline in a neuropathic pain model, Pain Physician, 2014; 17(2):187-195; and Deseure K and Hans G H, Chronic Constriction Injury of the Rat's Infraorbital Nerve (IoN-CCI) to Study Trigeminal Neuropathic Pain, J Vis Exp. 2015; (103). doi: 10.3791/53167).

A peripheral mononeuropathy is produced in adult rats by placing constrictive ligatures loosely around the common sciatic nerve. The postoperative behavior of these rats indicates that hyperalgesia, allodynia and, possibly, spontaneous pain (or dysesthesia) is produced. Hyperalgesic responses to noxious radiant heat is evident on the second postoperative day and lasts for over 2 months. Hyperalgesic responses to chemogenic pain is also present. The presence of allodynia is inferred from the nocifensive responses evoked by standing on an innocuous, chilled metal floor or by innocuous mechanical stimulation, and by the rats' persistence in holding the hind paw in a guarded position. Experiments with this animal model may advance our understanding of the neural mechanisms of neuropathic pain disorders in humans (Bennett G J and Xie Y K, A peripheral mononeuropathy in rat that produces disorders of pain sensation like those seen in man, Pain 1988; 33:87-107).

Drug Treatment

The respective Compound Example is weighed into a vial, a small amount of vehicle (DMSO/Water (5/95) (v/v)) is added to the vial until the substances are covered. Suspension is stirred slowly until no larger powder aggregates are visible, then the rest of the vehicle is added stepwise under continuous stirring until the respective final dose level is reached in a dose volume of 5 ml/kg body weight. A homogeneous suspension forms under continuous stirring. The suspension is prepared freshly every week. The doses of the Compound Example to be tested, the vehicle as a negative control and Pregabalin, Duloxetin, and/or Gabapentin as positive controls are applied to intact male rats—Sprague Dawley according to the following table.

TABLE 7

Dosing scheme

| Group Code | Group Size* | Treatment | Route | Dose Level (mg/kg) | Dosing Regime | Testing Regime |
|---|---|---|---|---|---|---|
| 1 | N = 13 | Vehicle (negative control) | p.o. | NA | QD; starting on Study Day 14 until Day 25 | Von Frey test and cold plate*** test on Study Days −1 (baseline), 13 (inclusion only VF), 14, 18 and 23, 2 hours post AM dosing Hargreaves test on Study Days −1 (baseline), 15, 19 and 24, 2 hours post AM dosing. |
| 2 | N = 13 | Compound Example (blinded) | | 3 | | |
| 3 | N = 13 | Compound Example (blinded) | | 15 | | |
| 4 | N = 13 | Compound Example (blinded) | | 60 | | |
| 5 | N = 13 | Pregabalin (positive control/ standard of care) | | 15 | | |
| 6 | N = 13 | Duloxetin (positive control) | | 30 | | |
| 7 | N = 13 | Morphine (positive technical control) | i.p. + p.o. | 5 | On testing days | Von Frey test and cold plate*** test on Study Days −1 (baseline), 13 (inclusion only VF), 14, 18 and 23, 45 minutes post dosing Hargreaves test on Study Days −1 (baseline), 15, 19 and 24, 45 minutes post dosing. |

TABLE 8

Treatment scheme

| Study Day | Tasks and Tests performed |
|---|---|
| Days −3 and −2 | 1. Habituation to Von Frey apparatus. |
| −1 | 1. Body weight measurements (baseline). |
| | 2. Von Frey response measurements (baseline). |
| | 3. Cold allodynia measurements (baseline). |
| | 4. Hargreaves measurements (baseline). |
| 0 | 1. CCI operation. |
| 7 | 1. Body weight measurements (all groups). |
| 13 | 1. Von Frey response measurements (Inclusion). |
| | 2. Group Selection. |
| 14 | 1. Body weight measurements (all groups). |
| | 2. Morphine administration 45 min before von Frey and Cold allodynia testing. |
| | 3. Vehicle and Test Items administration (morning (AM) dosing). |
| | 4. Von Frey and Cold allodynia testing 45 min post Morphine dosing or 2 hours post Compound Example/Vehicle AM dosing. |

TABLE 8-continued

Treatment scheme

| Study Day | Tasks and Tests performed |
|---|---|
| | 5. Vehicle and Test Items administration (evening (PM) dosing). |
| 15 | 1. Morphine administration 45 min before Hargreaves testing. |
| | 2. Vehicle and Test Items administration (AM dosing). |
| | 3. Hargreaves testing 45 min post Morphine dosing or two hours post TI/Vehicle AM dosing. |
| | 4. Vehicle and Test Items administration (PM dosing). |
| 16-17 | 1. Vehicle and Test Items administration bi-daily (twice a day (BID) or once daily (QD). |
| 18 | 1. Morphine administration 45 min before von Frey and Cold allodynia testing |
| | 2. Vehicle and Test Items administration (AM dosing). |
| | 3. Von Frey and Cold allodynia testing 45 min post Morphine dosing or 2 hours post TI/Vehicle AM dosing. |
| | 4. Vehicle and Test Items administration (PM dosing). |
| 19 | 1. Morphine administration 45 min before Hargreaves testing |
| | 2. Vehicle and Test Items administration (AM dosing). |
| | 3. Hargreaves testing 45 min post Morphine dosing or two hours post TI/Vehicle AM dosing. |
| | 4. Vehicle and Test Items administration (PM dosing). |
| 20 | 1. Vehicle and Test Items administration BID or QD. |
| 21 | 1. Body weight measurements (all groups). |
| | 2. Vehicle and Test Items administration BID or QD. |
| 22 | 1. Vehicle and Test Items administration BID or QD. |
| 23 | 1. Morphine administration 45 min before von Frey, Cold allodynia and Hargreaves testing. |
| | 2. Vehicle and Test Items administration (AM dosing). |
| | 3. Von Frey, Cold allodynia and Hargreaves testing 45 min post Morphine dosing or 2 hours post TI/Vehicle AM dosing. |
| | 4. Vehicle and Test Items administration (PM dosing). |
| 24 | 1. Morphine administration 45 min before Hargreaves testing |
| | 2. Vehicle and Test Items administration (AM dosing). |
| | 3. Hargreaves testing 45 min post Morphine dosing or two hours post TI/Vehicle AM dosing. |
| | 4. Vehicle and Test Items administration (PM dosing). |
| 25 | 1. Vehicle and Test Items administration. |
| | 2. Termination: Bleeding for plasma two hours post TI administration. Organ collection. |

Neuropathic Pain Induction

Animals are anesthetized by a combination of sodium ketamine 35 mg/kg intraperitoneal (i.p. or IP) and xylazine HCl 8 mg/kg IP. While under anesthesia, the rat is placed in a prone position and the left sciatic nerve is exposed at a location above the femoral joint. Three loose knots with cat gut 4-0 suture material are applied to the sciatic nerve. The skin is then closed by a clamp.

Inclusion/Exclusion Criteria

Selection of animals is performed on post-operative Day 13 before animals are placed into their experimental groups. Animals with a pain threshold of s 15 g for an operated leg following Von Frey testing and with a withdrawal time <baseline in response to cold stimulation, are included in the study.

Clinical Observations

The animals are observed for toxic/adverse symptoms: continuously during 60 minutes post administration, with special attention during two hours following treatment. Thereafter, the animals are observed once daily until study termination.

Body Weight

Body weight is measured on Study Day −1 for baseline values and then again on Study Days 7, 14 and 21.

Pain Response Evaluation

Mechanical Allodynia Evaluation (Von Frey Testing):

Allodynic response to tactile stimulation is assessed using the Von Frey apparatus (Touch Test®). The rat is placed in an enclosure and positioned on a metal mesh surface, but allowed to move freely. The rats' cabins are covered with red cellophane to diminish environmental disturbances. The test begins after a cessation of exploratory behavior. The set of Von Frey monofilaments provide an approximate logarithmic scale of actual force and a linear scale of perceived intensity.

The operating principle: When the tip of a fiber of given length and diameter is pressed against the skin at right angles, the force of application increases as long as the researcher continues to advance the probe until the fiber bends. After the fiber bends, the probe continues to advance, causing the fiber to bend more, but without additional force being applied.

TABLE 9

Combination of sizes and applied forces

| Size $Log^{10}$ of ($10*$force (mg)) | Force (g) |
|---|---|
| 1.65 | 0.008 |
| 2.36 | 0.02 |
| 2.44 | 0.04 |
| 2.83 | 0.07 |
| 3.22 | 0.16 |
| 3.61 | 0.40 |

TABLE 9-continued

Combination of sizes and applied forces

| Size Log$^{10}$ of (10*force (mg)) | Force (g) |
|---|---|
| 3.84 | 060 |
| 4.08 | 1.00 |
| 4.17 | 1.40 |
| 4.31 | 2.00 |
| 4.56 | 4.00 |
| 4.74 | 6.00 |
| 4.93 | 8.00 |
| 5.07 | 10.0 |
| 5.18 | 15.0 |
| 5.46 | 26.0 |
| 5.88 | 60.0 |
| 6.10 | 100 |
| 6.45 | 180 |
| 6.65 | 300 |

Rodents exhibit a paw withdrawal reflex when the paw is unexpectedly touched. The Touch Test™ Sensory Evaluator is used on the plantar surfaces of the rat's foot. The animal will indicate sensation by pulling back its paw. The minimal force needed to elevate the withdrawal reflex is considered/designated as the value of reference. In order to achieve paw withdrawal, the pressure applied is sometimes higher than 60 g, often requiring the researcher to apply enough pressure with the Von Frey to actually lift the paw of the naive animal. Decreases in force needed to induce withdrawal are indicative of allodynia, as the force applied is a non-painful stimulus under normal conditions. Von Frey test is performed on Study Days –I, 13, on Study Days 14, 18 and 23 (two hours post TI/Vehicle AM dosing or 45 m in post Morphine dosing).

Cold Plate Evaluation

Animals are placed on cold plate apparatus (2±1° C. and the time until first response is observed is recorded. Cold plate is measured on Study Day –1 for baseline values and then again on Study Days 14, 18 and 23 (two hours post TI/Vehicle AM dosing or 45 min post Morphine dosing).

Measurement of Hyperalgesia Using Heat Stimulation (Hargreaves Method)

Thermal hyperalgesia is tested using plantar test 37370 apparatus (UGO BASILE). Each rat is placed within a plastic box (W100×L200×H145 mm) atop a glass floor. A light beam under the floor is aimed at the plantar surface of the right (operated) hind paw. Once the light beam is triggered, this starts the timer. The rising temperature on the surface causes the animal to move its foot. This stops the timer. Latency to move the foot is recorded in seconds. The intensity of the light is adjusted with latency of normal paw at approximately 12 seconds and a cut-off latency of 30 seconds. The withdrawal latency for each animal is defined as the heat pain threshold. Thermal hyperalgesia is measured on Study Day –1 for baseline values and then again on Study Days 15, 19 and 24 (two hours post TI/Vehicle AM dosing or 45 min post Morphine dosing).

Data Compilation

Evaluation is based primarily on the means±SEM of mechanical allodynia, cold plate measurements and hyperalgesia measurements using heat stimulation. Each treatment group is compared to the relevant vehicle group using appropriate statistical tests.

Statistical Analysis

Numerical results are given as means and standard deviation or standard error of the mean. The results will be subjected to t-test or ANOVA analysis followed by contrast analysis between the groups whenever appropriate, using GraphPad Prism 5 software or newer versions thereof.

9. Analgesic Effects in the SNL Model of Neuropathic Pain Employing Mechanical and Thermal Stimulation.

Neuropathic pain is a severe chronic pain condition that can occur as a complication of diabetes, herpes or nerve injury. Symptoms of neuropathic pain include pain that occurs spontaneously and pain that occurs in response to touch. Indeed, even a light touch can be painful events for some patients. This kind of pain (abnormal pain following light touch or brushing) is called mechanical allodynia.

The goal of this project is to test Compound Examples for the treatment of chronic neuropathic pain, such as low back pain, in the spinal nerve ligation (SNL) model of neuropathic pain. The SNL model is chosen because of its wide acceptance as a reliable and reproducible model for neuropathic pain (Kim S H and Chung J M (1992) An experimental model for peripheral neuropathy produced by segmental spinal nerve ligation in the rat. Pain 50:355-63). After surgery, the animal develops a pain state in one hind paw that is similar to the human condition. The effect of experimental treatments on this pain state is tested.

Neuropathic pain is induced by tight ligation of the L5 and L6 spinal nerves. Mechanical allodynia is assessed using VF monofilaments and thermal nociception is assessed using a cold plate. On Day 0 (17±3 days after SNL surgery), mechanical allodynia and thermal nociception are assessed prior to dosing with test article. On Day 0, 4, and 9, mechanical allodynia and thermal nociception are assessed approximately 2 hours post-dosing.

Drug Treatment

Compound is weighed into a vial, a small amount of vehicle (DMSO/Water (5/95) (v/v)) added (until the substance is covered). Suspension is stirred slowly until no larger powder aggregates are visible, then the rest of the vehicle is added stepwise under continuous stirring until a final dose volume of 5 ml/kg body weight is reached. A homogeneous suspension forms under continuous stirring. The suspension is prepared freshly every week. The doses of the Compound Example to be tested, the vehicle as a negative control and Pregabalin, Duloxetin, and/or Gabapentin as positive controls are applied to intact male rats—Sprague Dawley according to the following table.

TABLE 10

| Group # | Treatment | Number of animals | Dose (mg/kg) | Vehicle | Day of Admin./ Frequency |
|---|---|---|---|---|---|
| 1 | Vehicle | 10 | NA | DMSO/ Water (5:95) (v/v) | QD, 10 days |
| 2 | Compound Example | 10 | 3 | DMSO/ Water (5:95) (v/v) | QD, 10 days |
| 3 | Compound Example | 10: | 15 | DMSO/ Water (5:95) (v/v) | QD, 10 days |
| 4 | Compound Example | 10 | 60 | DMSO/ Water (5:95) (v/v) | QD, 10 days |
| 5 | Pregabalin (positive control/ standard of care) | 10 | 15 | DMSO/ Water (5:95) (v/v) | SID, 10 days |

TABLE 10-continued

| Group # | Treatment | Number of animals | Dose (mg/kg) | Vehicle | Day of Admin./ Frequency |
| --- | --- | --- | --- | --- | --- |
| 6 | Duloxetin (positive control) | 10 | 30 | DMSO/ Water (5:95) (v/v) | SID, 10 days |
| 7 | Gabapentin (positive technical control) | 10 | 100 | Water | SID, 10 days |

Mechanical Allodynia-Rat (Von Frey Test; VF)

Pre-Injury, pre-dosing, post-dosing on Day 0, and Day 4 and Day 9

Mechanical allodynia is measured using 8 Semmes-Weinstein filaments (Stoelting©; Wood Dale, Ill., USA) with varying stiffness (0.4, 0.6, 1.0, 2.0, 4.0, 6.0, 8.0, and 15 g) according to the up-down method (Chaplan, S. R., F. W. Bach, J. W. Pogre, J. M. Chung, and T. L. Yaksh. "Quantitative Assessment of Tactile Allodynia in the Rat Paw." J. Neurosci. Meth. 53.1 (1994): 56-63). Animals are placed in individual acrylic chambers on a metal mesh surface and allowed to acclimate to their surroundings for a minimum of 15 minutes before testing. Each filament is presented perpendicular to the plantar surface with sufficient force to cause slight buckling against the paw and held for approximately 6 seconds or until a positive response is noted (paw sharply withdrawn). Testing is initiated with the 2.0 g filament. In the absence of a paw withdrawal response, the next stronger stimulus is presented. In the event of paw withdrawal, the next weaker stimulus is used. This process is repeated until 4 responses after the initial change in response (no response to positive response or positive response to no response) are obtained. If the animal does not respond after reaching the strongest filament or if the animal responded after reaching the weakest filament, the testing is stopped for that time point. The 50% response threshold is calculated using the formula:

$$50\% \text{ response threshold (g)} = (10(Xf + k\delta))/10{,}000$$

Xf=value (in log units) of the final von Frey filament used k=tabular value for the pattern of positive/negative responses (Chaplan et al. 1994, appendix 1, page 62)

δ=mean difference (in log units) between stimuli

The mean and standard error of the mean (SEM) is determined for each paw for each treatment group at each time point.

Thermal Nociception (Cold Plate; CP)

Pre-Injury, pre-dosing, post-dosing on Day 0, and Day 4 and Day 9

Cold plate latencies are measured using a cold plate apparatus (CP, IITC Life Science; Woodland Hills, Calif.). Animals are allowed to acclimate to the testing room for a minimum of 15 minutes before testing. The surface of the cold plate is cooled to a temperature of 4° C.±1° C. Animals are placed individually on the cold plate in a clear acrylic enclosure and the timer is activated. Cold plate latency values are recorded at the first observed nocifensive behavior (hind paw lick, hind paw flick, vocalization, or jump). One reading per animal is taken at each time point and a maximum cutoff latency of 30 seconds is used to prevent injury to the animal. The mean and standard error of the mean (SEM) are determined for each treatment group at each time point.

10. In Vivo Adjuvant-Induced Arthritis (AIA) Model

The AIA model is characterized by a rapid onset and progression to polyarticular inflammation. Following the injection of CFA, signs of arthritis usually develop between day 10 and day 14. Typically, the disease is severe and leads to permanent joint malformations, including ankylosis. Joint swelling, lymphocyte infiltration, and cartilage degradation are shared features with human autoimmune arthritis.

To determine the anti-inflammatory activity of the Compound Examples, they were examined for their in vivo efficacy in an arthritis model. For this purpose, male Lewis rats (about 100 to 125 g, Charles River Laboratories, Germany) were each administered 100 µl of a complete Freund's adjuvant (CFA) solution (*M. tuberculosis* H37Ra [Difo Lab, Cat. No. 231141] dissolved in Incomplete Freund's adjuvant [Difco Lab, Cat. No. 263910]) into the tailhead subcutaneously on day 0. There were n=8 rats in each group. Both, a healthy control group and a disease control group treated with the vehicle only were included in the study. Each control group was given oral (p.o. or PO) treatment only with the vehicle (5% DMSO/95% PBS) of the Compound Examples. The treatment with different dosages of the Compound Examples dissolved in the vehicle was conducted in a preventative manner, i.e. starting from day 0 and continued to day 20, the end of the study, by daily oral administration. On day 0, the starting condition of the animals was determined in terms of the disease activity scores (rating of the severity of arthritis based on a points system). Here, points were awarded according to the extent of joint inflammation from 0 to 4 for the presence of an erythema including joint swelling (0=none; 1=slight; 2=moderate; 3=distinct; 4=severe) for both hind paws and were summed up to a single value. During the experiment, disease activity score and thereby treatment effects of Compound Examples were determined daily starting from day 8, when the animals first exhibit signs of arthritis, until the end of the study (day 20). In addition, the extent of joint swelling was detected by measuring the ankles of hind paws sagittal x transversal [in $mm^2$] using an automated caliper (Bayer AG, Germany). Next to this, the grip strength, as a measure for hyperalgesia, using an automated grip strength test meter (IITC Life Science Inc., USA) was evaluated.

Statistical analysis of obtained results for all parameters were done with one way Anova (ANOVA; Analysis of variance) and the comparison to the control group via multiple reference analysis (Dunnett-test).

Results

Figure 14:
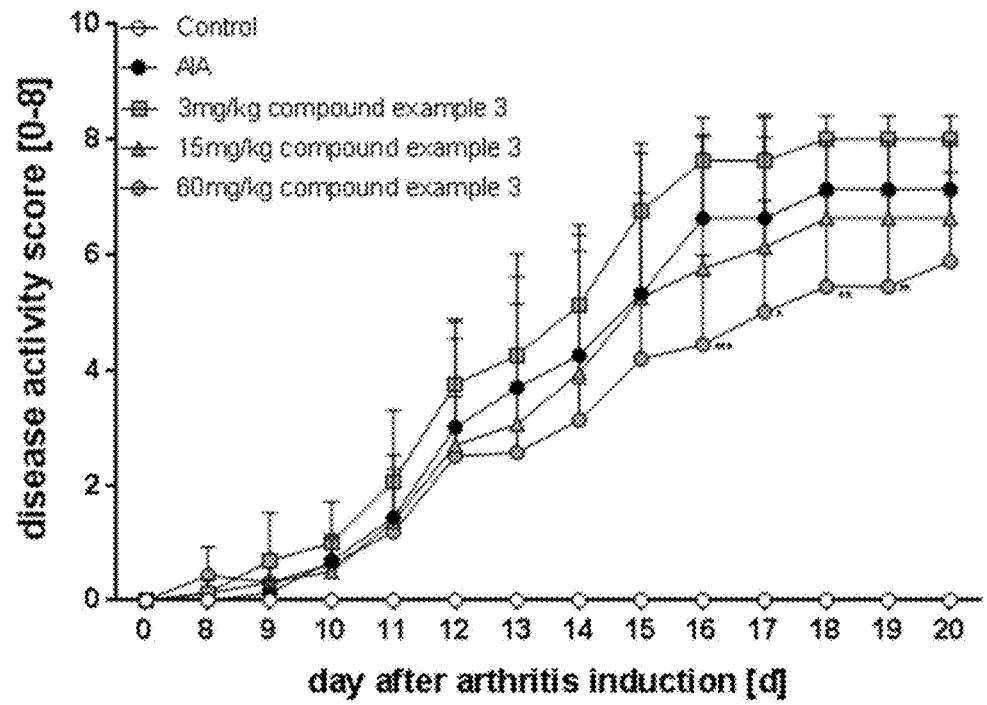
Figure 14:
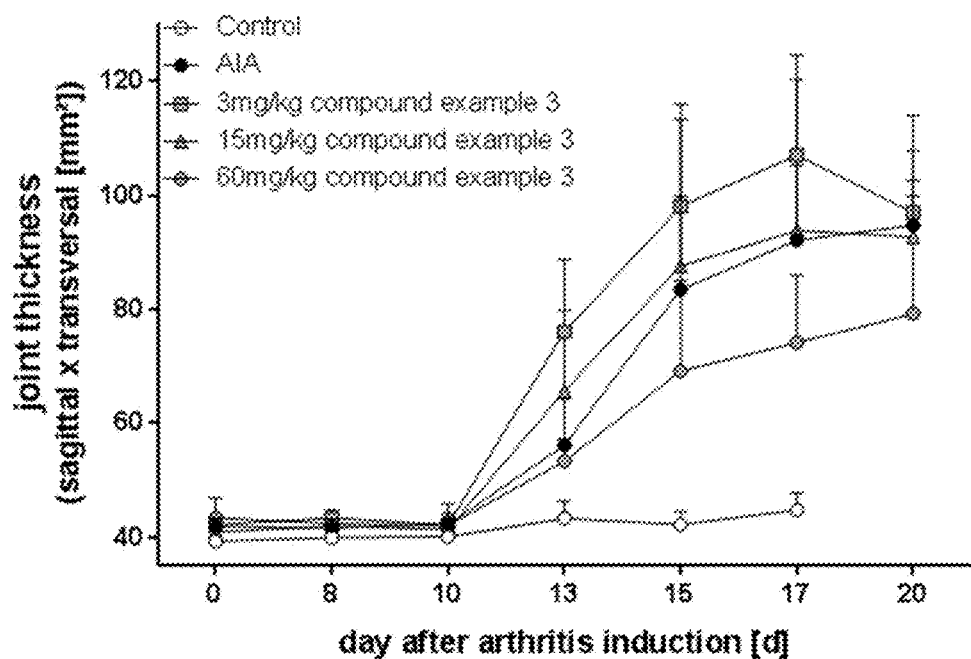

The tested Compound Example 3 showed a clear dose-dependency in the adjuant-induced arthritis (AIA) model. The severity of rat AIA was significantly inhibited by oral treatment with 60 mg/kg once daily of Compound Example 3. This anti-inflammatory effect of Compound Example 3 is shown in FIG. 14 by reduction of the disease activity score (14A) and the extent of joint swelling (14B). Next to this, inhibitory effects on hyperalgesia were observed by Compound Example 3 as shown in FIG. 15 by increase in grip strength.

11. Isovolumetric Bladder Contraction Model (Rat)

The aim of this study was to test the efficacy of Compound Examples on bladder function, in particularly on contraction frequency/intercontraction interval and contraction magnitude/contraction amplitude.

The experimental setup for performing the isovolumetric bladder measurements was adapted to a previous descripted protocol (Yoshiyama M, de Groat W C. Am J Physiol Regul Integr Comp Physiol 280: R1414-R1419, 2001).

Strong presence and target induction of BDKRB1 in comparison to BDKRB2 has been verified by gene expression analysis in bladders removed from rats after performance of the isovolumetric bladder contraction model in contrast to bladders of naive, untreated rats. Immunohistochemistry confirmed the presence of BDKRB1 in bladders of rats after contraction, too.

Briefly, female Sprague Daley rats (~200 g) were housed under normal conditions for laboratory rats in a 12:12-h light:dark cycle. Experiments were performed on urethane-anesthetized (1.2 g/kg i.p.) rats. For i.v. administration of Compound Examples a PE-50 catheter was inserted into Vena jugularis. A transurethral bladder catheter (PE-50) had been connected to a 3-way tap, which was connected to a pressure transducer on one side and an infusion pump (B. Braun) on the other. The pressure transducer was connected via an amplifier (both from ADIstruments) to the data acquisition software program (LabChart, ADInstruments) and a computer to record the bladder pressure isovolumetrically with the urethral outlet ligated. The bladder was filled via the bladder catheter and the infusion pump by incremental volumes of physiological saline (3 ml/h) until spontaneous bladder contractions occurred. For isovolumetric recording, the ureters were tied distally and cut and the urethral outlet was ligated. At least five cycles of isovolumetric bladder contractions were recorded before the Compound Examples or vehicle alone (PEG400/Water (50/50(v/v))) were administered via the catheter in the Vena jugularis at different dosages. About 2 minutes after compound administration the next nine contraction cycles were recorded. The change in contraction amplitude and inter-contraction interval of the recorded bladder pressure and bladder contractions was calculated by comparing the means before and after compound administration using GraphPad Prism 7 program.

Results

Single therapeutic gavage of the tested Compound Example 3 (1 mg/kg & 15 mg/kg) showed significant efficacy on prolonging the intercontraction interval (ICI) (FIG. 5) compared to vehicle in the isovolumetric bladder contraction (IBC) model, whereas maximal pressure of bladder contractions remained unchanged (FIG. 6). Data are shown as mean+/−SEM of 8-11 rats per group. One-sided Mann-Whitney U test, *$p<0.05$ compared to vehicle group.

12. Cyclophosphamide-Induced Overactive Bladder and Cystitis (Rats)

The aim of this study was to test the efficacy of Compound Examples on overactive bladder as well as on interstitial cystitis and bladder pain syndrome in cyclophosphamide-treated rats.

The experimental setup is adapted to a previous described protocol (Lecci A et al, *Br J Pharmacol* 130: 331-38, 2000).

Strong presence and target induction of BDKRB1 in comparison to BDKRB2 has been verified by gene expression analysis in bladders removed from rats after cyclophosphamide (100 mg/kg and 150 mg/kg i.p.) induction in contrast to bladders of naive, untreated rats. Immunohistochemistry confirmed the presence of BDKRB1 in bladders of rats after model induction, too. A BDKRB1 agonist (des-Arg9-Bradykinin) induced strong and dose-dependent contractions in isolated bladder stripes prepared from previously cyclophosphamide (150 mg/kg i.p.)-treated rats and confirmed the functionality of BDKRB1 in this model.

Briefly, female Sprague Daley rats (~200 g) were housed under normal conditions for laboratory rats in a 12:12-h light:dark cycle. Rats have been weighed, the tested Compound Examples were dissolved in relevant vehicle (e.g. DMSO/Water) (5/95) (v/v) and have been administrated by oral gavage in different concentrations one hour before application of cyclophosphamide (150 mg/kg) by i.p. injection. Additional 1.5 hours after cyclophosphamide administration each rat was transferred to a metabolic cage and voiding frequency has been recorded for the next 15 hours. Total amount of urine (ml) was collected via a plastic tube attached to the metabolic cages. The urine collecting tube was connected to a weight-sensitive sensor and a pressure transducer connected via an amplifier (ADIstruments) to the data acquisition software program (LabChart, ADInstruments) and a computer. The micturitions per hour have been recorded and the area under the curve (AUC) during the plateau phase of the micturition (4 to 10 hours after transfer to metabolic cages) has been calculated for each animal with GraphPad Prism 7 program. At the end of the experiment rats have been weighed and killed under isoflurane anaesthesia and bladders have been removed and weighed. The bladders' wet weight was normalized to 100 g of body weight of each rat and analysis has been performed using GraphPad Prism 7 program.

Results

Figure 10:
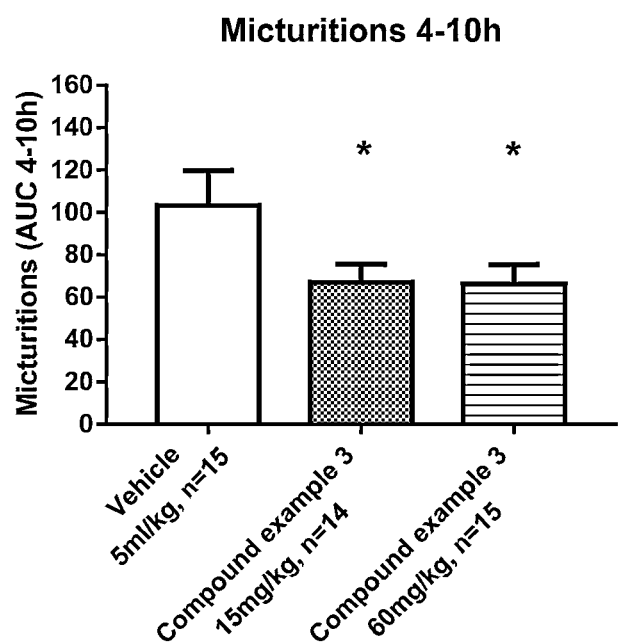
Figure 11:
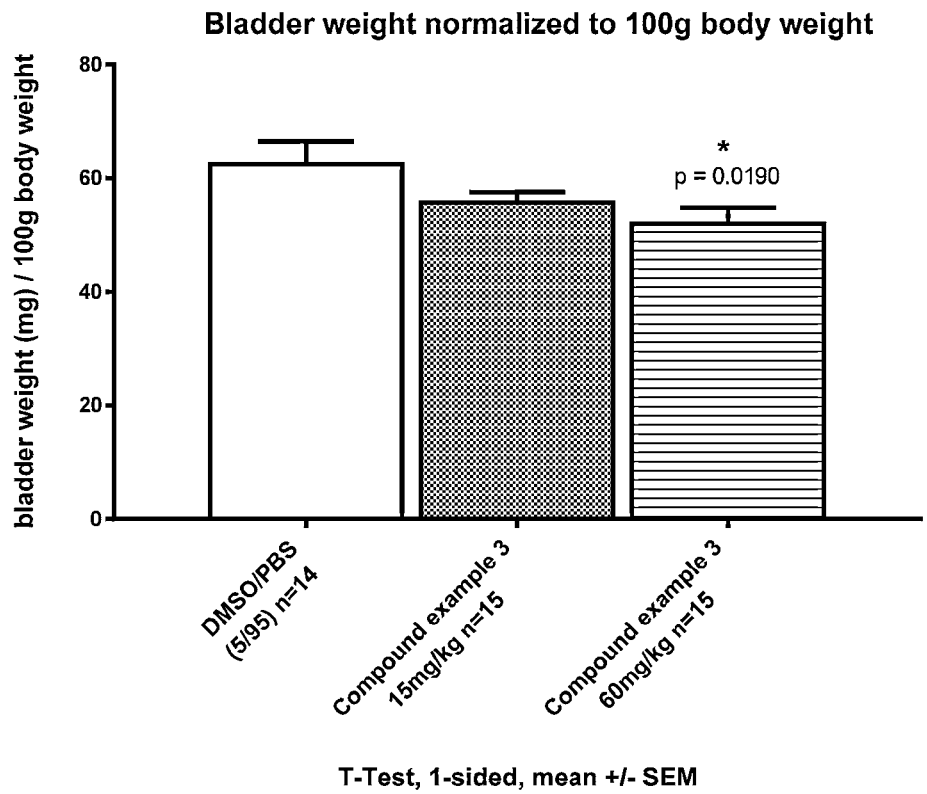

Preventive single gavage of tested Compound Example 3 (15 mg & 60 mg/kg) showed efficacy on reducing the number of micturitions/hour (FIG. 9) compared to vehicle (DMSO/PBS) and both tested dosages significantly reduced the calculated AUC during the plateau phase of the micturition (4-10 hours after transfer to metabolic cages) (FIG. 10). Compound example 3 (60 mg/kg) significantly reduced the bladder weight normalized to 100 g of body weight of the rats compared to vehicle treatment (FIG. 11). Data are shown as mean+/−SEM of 14-15 rats per group. One-sided t-test, *$p<0.05$ compared with vehicle group.

13. Isolated Bladder Stripes in the Organbath System (Rat)

The aim of this study is to test the efficacy of a compound on prevention and therapeutic attenuation of BDKRB1 agonist induced bladder stripe contractions.

5 l of Krebs-Ringer-solution are freshly prepared by adding NaCl (34.5 g), $NaHCO_3$ (10.5 g), glucose (9.9 g), $MgSO_4$ (1.5 g) and $KH_2PO_4$ (0.8 g) to 4984.65 ml of water, stirring, and adding 8.5 ml of 10% KCL in water (m/v) and 6.85 ml of 20% $CaCl_2$ in water (m/v). The solution is pre-heated to 37° C. in the organ bath system (DMT, DMT750TOBS) before the start of the experiment.

After removing the bladder of naive rats (Sprague Dawley, female, Charles River Sulzfeld) for comparison and cyclophosphamide (150 mg/kg, i.p., sigma aldrich) pre-treated rats (Sprague Dawley, female, Charles River Sulzfeld), bladder strips (approx. 2×8 mm) are cut from the bladder and are mounted under 1-5 g of resting tension in glass organ baths, while the bath is continuously bubbled with carbogen gas (95% $O_2$ and 5% $CO_2$) and thermostated at 37° C. Contractile responses of the bladder stripes are measured using isometric tension transducers (DMT) and are recorded using a data acquisition system (PowerLab and LabChart 8 software, ADInstruments).

After two hours of equilibration, tissues are treated with KCl 50 mM to check viability. 1 µM of carbachol is added to the organ bath, either before or at the end of the experiments, to elicit maximum contractile response and after five minutes of incubation it is washed out.

a) Preventive experimental setting: After e.g. 30 min of resting period a single concentration (e.g. 0.5 µM) of des-Arg$^9$-Bradykinin, a BDKRB1 agonist (sigma aldrich), is added to the organ baths, incubated for e.g. 20 minutes and contractility is measured and set to 100%. After wash-out of the BDKRB1 agonist and additional e.g. 60 minutes of restring period different concentrations of the Compound Example to be tested (each concentration of the Compound Example is tested on a fresh bladder stripe, no repeated measurement per bladder stripe) are added to the organ baths and incubated for e.g. 15 minutes. Des-Arg9-Bradykinin (e.g. 0.5 μM) is added, incubated for e.g. 20 minutes and washed out. The effect of compound on inhibition of contractile response of the bladder stripes induced by des-Arg$^9$-Bradykinin is measured and expressed as "% inhibition of des-Arg9-Bradykinin-induced plateau of contraction". $IC_{50}$ value of the compound is calculated. Data analysis and generation of a dose-response-curve are performed by GraphPad Prism 7 program.

b) Therapeutic experimental setting: After e.g. 30 min of resting period a single concentration (e.g. 0.5 μM) of des-Arg$^9$-Bradykinin, a BDKRB1 agonist (sigma aldrich), is added to the organ baths, incubated for e.g. 20 minutes and contractility is measured and set 100%. After wash-out of the BDKRB1 agonist and an additional resting period of e.g. 60 min, the BDKRB1 agonist is added to the organ baths (e.g. 0.5 μM), incubated for e.g. 20 min and a low concentration of the respective Compound Example is therapeutically added to the organ baths and incubated for e.g. 15 minutes. The effect of different increasing dosages of the Compound Examples is tested (adding a higher dose every e.g. 20 min, incubation for e.g. 15 min; starting with a low dose) on inhibition of contractile response of the bladder stripes induced by des-Arg9-Bradykinin, which is measured and expressed as "% inhibition of des-Arg$^9$-Bradykinin-induced plateau of contraction". The procedure is repeated using the same bladder stripes but increasing concentrations of the respective Compound Examples. $IC_{50}$ value is calculated. Data analysis and generation of a dose-response-curve are performed by GraphPad Prism 7 program.

14. Diet-Induced Obese Rat Model (Type 2 Diabetes Model)

The diet-induced obese rat model is a relevant model to evaluate compounds targeting insulin sensitivity. In addition glucose-, fat-, muscle- and liver-dependent metabolic changes can be evaluated. Male Sprague-Dawley rats, at 8 weeks of age, are housed in small groups in ventilated and enriched housing cages. After acclimation phase, rats are randomized into groups (n=10-12, each). One group receives normal control chow (e.g. Research Diets, Inc., Research Diet ref #D12489B) during the whole experiment. Other groups receive normal control chow diet during the acclimation period, and then high fat/high sucrose diet (e.g. Research Diets, Inc., Research Diet ref #D12266B) until the end of the experiment.

After feeding the high fat/high sucrose diet for eight weeks, rats are fasted for 6-hours, and bled. Fasting blood glucose (mg/dL) and plasma insulin (pU/mL) are measured to calculate the Homeostatic Model Assessment (HOMA) of Insulin Resistance (IR) HOMA-IR index ([mM×pU/mL]/22.5).

Body weight is measured and rats are randomized to treatment groups according to their body weight and HOMA-IR index. Once daily p.o.-treatment of 5 ml/kg body weight of Compound Examples dissolved in suitable vehicle (e.g. DMSO/Water) (5/95) (v/v)) starts in the high fat/high sucrose groups. Pioglitazone is chosen as positive control. Treatment in the groups is continued for e.g. 30 days as follows:

Group 1: normal chow, no treatment
Group 2: high fat/high sucrose diet, Compound Examples vehicle
Group 3: high fat/high sucrose diet, Compound Examples e.g. 15 mg/kg
Group 4: high fat/high sucrose diet, Compound Examples of higher dose, e.g. 60 mg/kg
Group 5: high fat/high sucrose diet, 0.5% methyl cellulose vehicle
Group 6: high fat/high sucrose diet, pioglitazone 10 mg/kg At day 14 and day 26 of treatment, rats are weighed and 6-hour fasted and bled to measure fasting blood glucose and plasma insulin, plasma triglycerides, free fatty acids and total cholesterol. HOMA-IR index is calculated from blood glucose and plasma insulin values. In addition, at treatment day 26, glycated hemoglobin (HbA1C) and leptin are measured and rats undergo an insulin tolerance test with insulin (e.g. 0.5 U/kg, 0.5 mL/kg body weight) which is injected intraperitoneally. Blood glucose is measured at different timepoints 0 to 120 minutes after insulin injection.

After recovery, at day 28 of treatment, rats are weighed and 6-hour fasted and bled to measure fasting blood glucose and plasma insulin. Rats undergo an oral glucose tolerance test with glucose (2.5 g/kg) which is administered orally. Blood glucose is measured at different timepoints 0 to 150 minutes after glucose load. Plasma insulin levels are measured as well.

At day 30 of treatment, rats are sacrificed; plasma is withdrawn for pharmacokinetic evaluation of Compound Examples. Fat, muscle, pancreas and liver are dissected and processed to allow gene expression analysis and histological evaluation. Liver specimens are histologically processed, e.g. hematoxylin-eosin staining, sirius red staining to evaluate fat and lipid deposition, inflammatory cell infiltration, degree of fibrotic changes, hepatocyte ballooning, apoptosis and necrosis.

15. High Glucose-Feeding (Rat) (Type 2 Diabetes Model)

The aim of this study is to test the efficacy of Compound Examples on attenuation of insulin resistance and associated complications in a model of Type 2 Diabetes and insulin resistance in rats.

The high glucose-feeding rat model is a relevant model to evaluate compounds targeting insulin resistance and Type 2 Diabetes and associated complications. In addition, glucose-, body weight-, fat and lipid-, muscle- and liver-dependent metabolic changes can be evaluated. Young male Sprague-Dawley or Wistar rats are used. Rats are housed in small groups in ventilated housing cages under controlled conditions of temperature and humidity on a 12-h light-dark cycle. After acclimation phase (feeding normal chow and tap water ad libitum), rats are randomized into groups (e.g. n=10-15, each) and are allowed free access to normal chow diet and tap water (control rats) or normal chow diet and 10% D-glucose in the drinking water (glucose rats) for a period of up to 10-15 weeks ad libitum. At the end of model induction phase (after 8-14 weeks feeding normal chow+tap water or normal chow+10% D-glucose in the drinking water), all rats are fasted for e.g. 6-hours, and bled. Fasting blood glucose and plasma insulin are measured to calculate the Homeostatic Model Assessment (HOMA) of Insulin Resistance (IR) HOMA-IR index ([mM×pU/mL]/22.5). Bodyweight is measured and rats are randomized to treatment groups according to their body weight and HOMA-IR index.

Once daily p.o.-treatment of e.g. 5 ml/kg body weight of Compound Examples dissolved in suitable vehicle (e.g. DMSO/Water) (5/95) (v/v)) or vehicle alone starts at the end of model induction phase and is continued until end of the experiment, (e.g. treatment in the groups is continued for e.g. 6-1 weeks while feeding regime is continued) as follows:

Group 1: tap water+normal chow, vehicle
Group 2: tap water+normal chow, Compound Examples, low dose (e.g. 15 mg/kg)
Group 3: tap water+normal chow, Compound Examples, high dose (e.g. 60 mg/kg)
Group 4: 10% D-glucose in water+normal chow, vehicle
Group 5: 10% D-glucose in water+normal chow, Compound Examples, low dose (e.g. 15 mg/kg)
Group 6: 10% D-glucose in water+normal chow, Compound Examples, high dose (e.g. 60 mg/kg)

Body weight is measured on a daily basis.

At least once during treatment phase and at the end of the experiment, rats are weighed and 6-hour fasted and bled to measure fasting blood glucose and plasma insulin. HOMA-IR index is calculated from blood glucose and plasma insulin values. In addition, leptin, plasma triglycerides, free fatty acids and total cholesterol are measured and a few days before the end of the experiment, rats undergo an insulin tolerance test with insulin (e.g. 0.5 U/kg, 0.5 mL/kg body weight) which is injected intraperitoneally. Blood glucose is measured at different timepoints e.g. 0 to 120 minutes after insulin injection.

After recovery, e.g. at the end of the experiment, rats are weighed and 6-hour fasted and bled to measure fasting blood glucose and plasma insulin. Rats undergo an oral glucose tolerance test with glucose (e.g. 2.5 g/kg) which is administered orally. Blood glucose is measured at different timepoints e.g. 0 to 150 minutes after glucose load.

Plasma insulin levels are measured.

At the last day of the experiment, rats are sacrificed; plasma is withdrawn for pharmacokinetic evaluation of Compound Examples. Tissues, e.g. fat, muscle, pancreas and liver are collected, weighted and stored at −80° C. Tissue samples are processed to allow gene expression analysis and histological evaluation. All data of the respective parameters are evaluated and calculated with e.g. GraphPad Prism 7 program.

The invention claimed is:

1. A compound selected from the group consisting of:

2-(1-benzothiophen-2-yl)-5-[({1-[2-fluoro-4-(trifluoromethyl)phenyl]cyclopropyl}carbonyl)amino]benzoic acid;

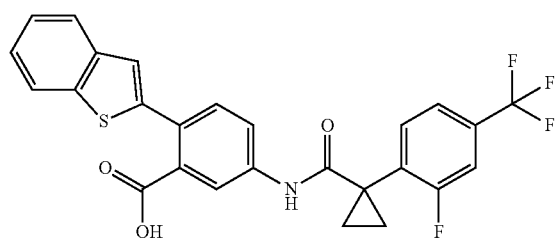 [SMILES: O=C(O)c1cc(NC(=O)C2(c3ccc(C(F)(F)F)cc3F)CC2)ccc1-c1cc2ccccc2s1]

2-[6-(1,1-difluoropropyl)pyridin-3-yl]-5-[({1-[2-fluoro-4-(trifluoromethyl)phenyl]cyclopropyl}carbonyl)amino]benzoic acid;

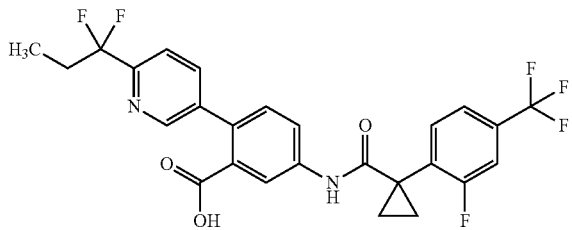 [SMILES: CCC(F)(F)c1ccc(-c2ccc(NC(=O)C3(c4ccc(C(F)(F)F)cc4F)CC3)cc2C(=O)O)cn1]

2-(1-cyclobutyl-1H-pyrazol-4-yl)-5-[({1-[2-fluoro-4-(trifluoromethyl)phenyl]cyclopropyl}carbonyl)amino]benzoic acid;

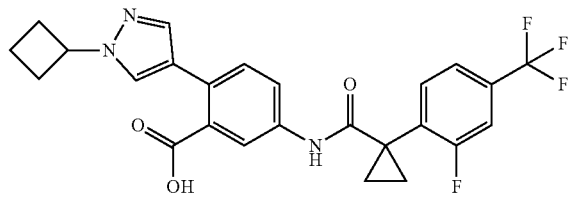 [SMILES: O=C(O)c1cc(NC(=O)C2(c3ccc(C(F)(F)F)cc3F)CC2)ccc1-c1cnn(C2CCC2)c1]

2-(6-ethoxypyridin-3-yl)-5-[({1-[2-fluoro-4-(trifluoromethyl)phenyl]cyclopropyl}carbonyl)amino]benzoic acid;

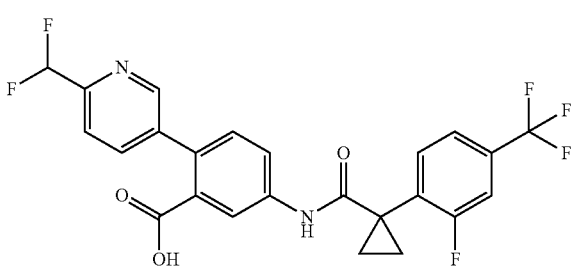 [SMILES: O=C(O)c1cc(NC(=O)C2(c3ccc(C(F)(F)F)cc3F)CC2)ccc1-c1ccc(C(F)F)nc1]

2-(6-ethoxypyridin-3-yl)-5-[({1-[2-fluoro-4-(trifluoromethoxy)phenyl]cyclopropyl}carbonyl)amino]benzoic acid;

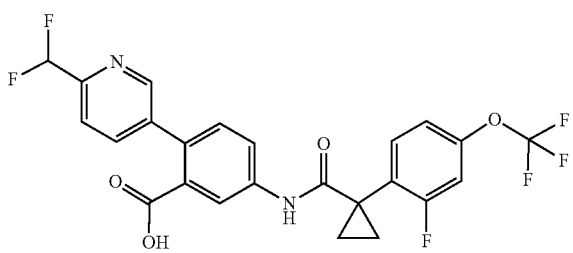 [SMILES: O=C(O)c1cc(NC(=O)C2(c3ccc(OC(F)(F)F)cc3F)CC2)ccc1-c1ccc(C(F)F)nc1]

2-(1-cyclobutyl-1H-pyrazol-4-yl)-3-fluoro-5-({[1-(2-fluoro-4-methylphenyl)cyclopropyl]carbonyl}amino)benzoic acid;

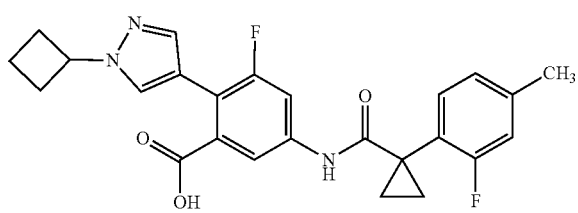 [SMILES: Cc1ccc(C2(C(=O)Nc3cc(F)c(-c4cnn(C5CCC5)c4)c(C(=O)O)c3)CC2)c(F)c1]

2-[6-(1,1-difluoropropyl)pyridin-3-yl]-5-[({1-[2-fluoro-4-(trifluoromethoxy)phenyl]cyclopropyl}carbonyl)amino]benzoic acid;

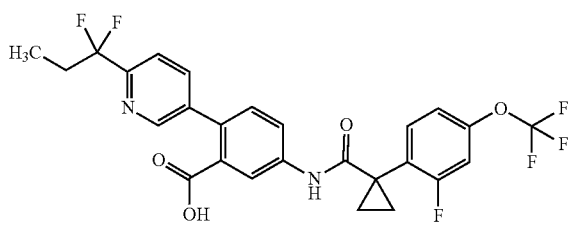 [SMILES: CCC(F)(F)c1ccc(-c2ccc(NC(=O)C3(c4ccc(OC(F)(F)F)cc4F)CC3)cc2C(=O)O)cn1]

3-fluoro-5-[({1-[2-fluoro-4-(trifluoromethyl)phenyl]cyclopropyl}carbonyl)amino]-2-[6-(trifluoromethyl)pyridin-3-yl]benzoic acid;

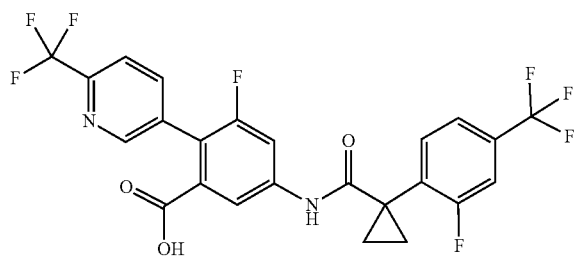 [SMILES: O=C(O)c1cc(NC(=O)C2(c3ccc(C(F)(F)F)cc3F)CC2)cc(F)c1-c1ccc(C(F)(F)F)nc1]

5-[({1-[2-fluoro-4-(trifluoromethyl)phenyl]cyclopropyl}carbonyl)amino]-2-[1-(2,2,2-trifluoroethyl)-1H-pyrazol-4-yl]benzoic acid;

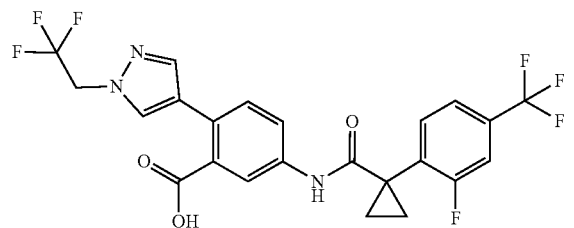 [SMILES: O=C(O)c1cc(NC(=O)C2(c3ccc(C(F)(F)F)cc3F)CC2)ccc1-c1cnn(CC(F)(F)F)c1]

5-({[1-(4-chlorophenyl)cyclopropyl]carbonyl}amino)-2-(1-cyclobutyl-1H-pyrazol-4-yl)-3-fluorobenzoic acid;

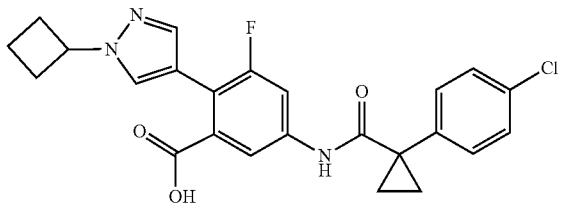 [SMILES: O=C(O)c1cc(NC(=O)C2(c3ccc(Cl)cc3)CC2)cc(F)c1-c1cnn(C2CCC2)c1]

2-(1-cyclobutyl-1H-pyrazol-4-yl)-3-fluoro-5-[({1-[4-(trifluoromethyl)phenyl]cyclopropyl}carbonyl)amino]benzoic acid;

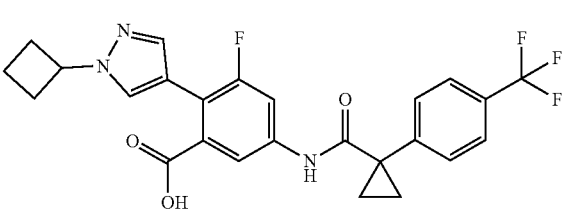 [SMILES: O=C(O)c1cc(NC(=O)C2(c3ccc(C(F)(F)F)cc3)CC2)cc(F)c1-c1cnn(C2CCC2)c1]

2-(1-cyclobutyl-1H-pyrazol-4-yl)-3-fluoro-5-[({1-[4-(trifluoromethoxy)phenyl]cyclopropyl}carbonyl)amino]benzoic acid;

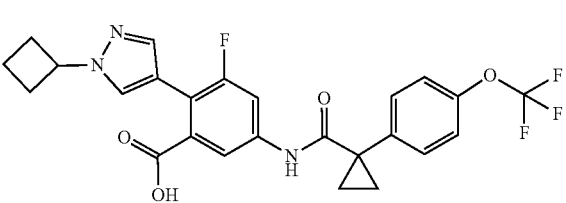 [SMILES: O=C(O)c1cc(NC(=O)C2(c3ccc(OC(F)(F)F)cc3)CC2)cc(F)c1-c1cnn(C2CCC2)c1]

2-(1-cyclobutyl-1H-pyrazol-4-yl)-5-({[1-(3,4-difluorophenyl)cyclopropyl]carbonyl}amino)-3-fluorobenzoic acid;

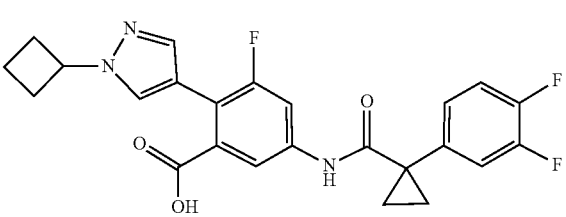 [SMILES: O=C(O)c1cc(NC(=O)C2(c3ccc(F)c(F)c3)CC2)cc(F)c1-c1cnn(C2CCC2)c1]

2-(1-cyclobutyl-1H-pyrazol-4-yl)-3-fluoro-5-[({1-[3-fluoro-4-(trifluoromethyl)phenyl]cyclopropyl}carbonyl)amino]benzoic acid;

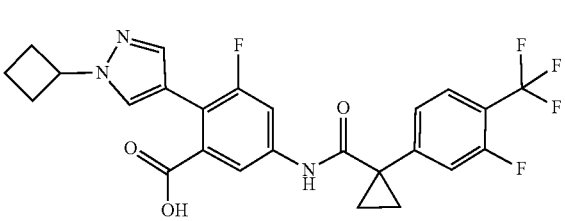 [SMILES: O=C(O)c1cc(NC(=O)C2(c3ccc(C(F)(F)F)c(F)c3)CC2)cc(F)c1-c1cnn(C2CCC2)c1]

2-(1-cyclobutyl-1H-pyrazol-4-yl)-5-({[1-(2,4-difluorophenyl)cyclopropyl]carbonyl}amino)-3-fluorobenzoic acid;

341

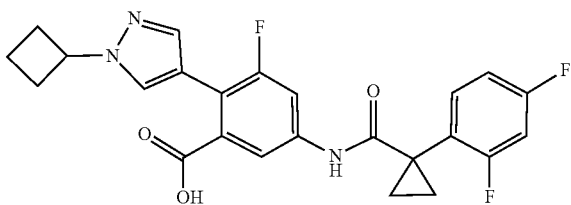 [SMILES: O=C(O)c1cc(NC(=O)C2(c3ccc(F)cc3F)CC2)cc(F)c1-c1cnn(C2CCC2)c1]

5-({[1-(4-chloro-2-fluorophenyl)cyclopropyl]
carbonyl}amino)-2-(1-cyclobutyl-1H-pyrazol-4-yl)-3-
fluorobenzoic acid;

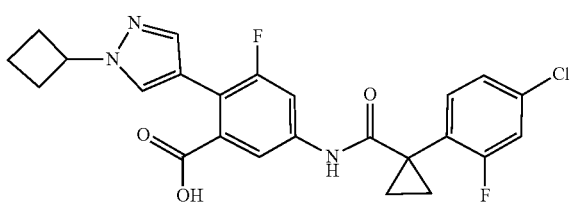 [SMILES: O=C(O)c1cc(NC(=O)C2(c3ccc(Cl)cc3F)CC2)cc(F)c1-c1cnn(C2CCC2)c1]

2-(1-cyclobutyl-1H-pyrazol-4-yl)-3-fluoro-5-[({1-[2-
fluoro-4-(trifluoromethyl)phenyl]
cyclopropyl}cabonyl)amino]benzoic acid;

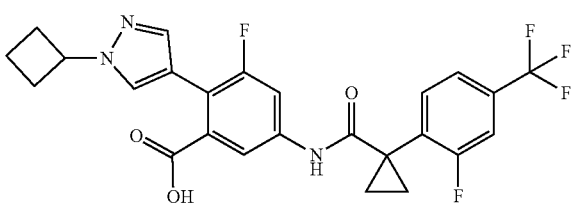 [SMILES: O=C(O)c1cc(NC(=O)C2(c3ccc(C(F)(F)F)cc3F)CC2)cc(F)c1-c1cnn(C2CCC2)c1]

2-(1-cyclobutyl-1H-pyrazol-4-yl)-3-fluoro-5-[({1-[2-
fluoro-4-(trifluoromethoxy)phenyl]
cyclopropyl}carbonyl)amino]benzoic acid;

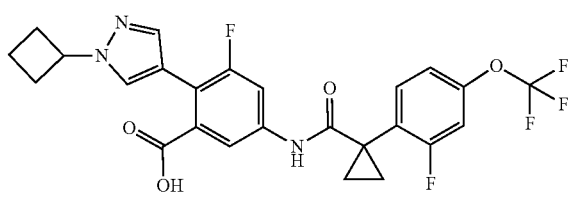 [SMILES: O=C(O)c1cc(NC(=O)C2(c3ccc(OC(F)(F)F)cc3F)CC2)cc(F)c1-c1cnn(C2CCC2)c1]

2-(1-cyclobutyl-1H-pyrazol-4-yl)-3-fluoro-5-({[1-(5-
fluoropyridin-2-yl)cyclopropyl]carbonyl}amino)ben-
zoic acid;

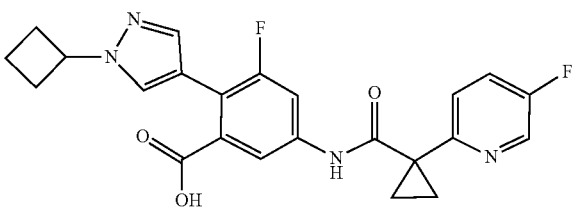 [SMILES: O=C(O)c1cc(NC(=O)C2(c3ccc(F)cn3)CC2)cc(F)c1-c1cnn(C2CCC2)c1]

2-(1-cyclobutyl-3-fluoro-1H-pyrazol-4-yl)-5-[({1-[2-
fluoro-4-(trifluoromethyl)phenyl]
cyclopropyl}carbonyl)amino]benzoic acid;

342

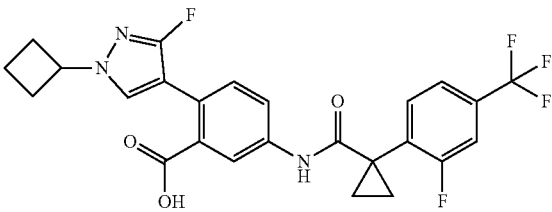 [SMILES: O=C(O)c1cc(NC(=O)C2(c3ccc(C(F)(F)F)cc3F)CC2)ccc1-c1cn(C2CCC2)nc1F]

5-({[1-(4-chloro-3-fluorophenyl)cyclopropyl]
carbonyl}amino)-2-(1-cyclobutyl-1H-pyrazol-4-yl)
benzoic acid;

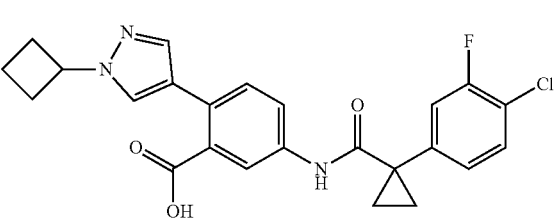 [SMILES: O=C(O)c1cc(NC(=O)C2(c3ccc(Cl)c(F)c3)CC2)ccc1-c1cnn(C2CCC2)c1]

2-(1-cyclobutyl-1H-pyrazol-4-yl)-5-[({1-[2-fluoro-4-(tri-
fluoromethoxy)phenyl]cyclopropyl}carbonyl)amino]
benzoic acid;

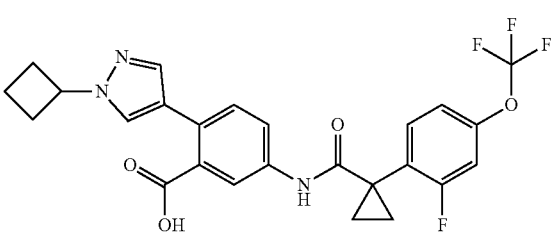 [SMILES: O=C(O)c1cc(NC(=O)C2(c3ccc(OC(F)(F)F)cc3F)CC2)ccc1-c1cnn(C2CCC2)c1]

5-({[1-(4-chloro-2-fluorophenyl)cyclopropyl]
carbonyl}amino)-2-(1-cyclobutyl-1H-pyrazol-4-yl)
benzoic acid;

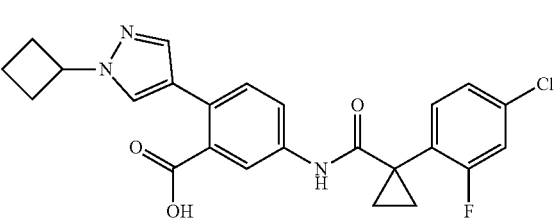 [SMILES: O=C(O)c1cc(NC(=O)C2(c3ccc(Cl)cc3F)CC2)ccc1-c1cnn(C2CCC2)c1]

5-({[1-(5-chloro-2-fluorophenyl)cyclopropyl]
carbonyl}amino)-2-(1-cyclobutyl-1H-pyrazol-4-yl)
benzoic acid;

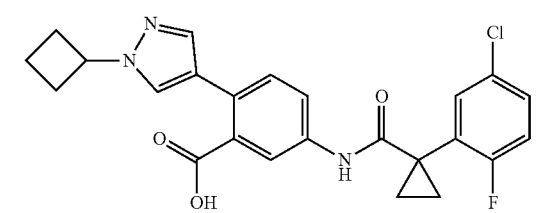

343

2-(1-ethyl-1H-pyrazol-4-yl)-5-[({1-[2-fluoro-4-(trifluoromethyl)phenyl]cyclopropyl}carbonyl)amino]benzoic acid;

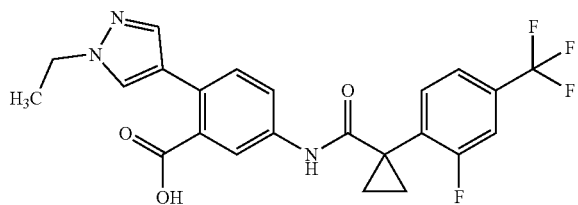 [SMILES: CCn1cc(-c2ccc(NC(=O)C3(c4ccc(C(F)(F)F)cc4F)CC3)cc2C(=O)O)cn1]

2-(1-ethyl-1H-pyrazol-4-yl)-5-[({1-[2-fluoro-4-(trifluoromethoxy)phenyl]cyclopropyl}carbonyl)amino]benzoic acid;

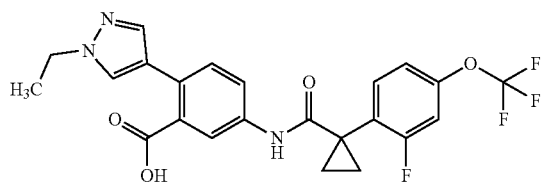 [SMILES: CCn1cc(-c2ccc(NC(=O)C3(c4ccc(OC(F)(F)F)cc4F)CC3)cc2C(=O)O)cn1]

5-[({1-[2-fluoro-4-(trifluoromethyl)phenyl]cyclopropyl}carbonyl)amino]-2-[1-(propan-2-yl)-1H-pyrazol-4-yl]benzoic acid;

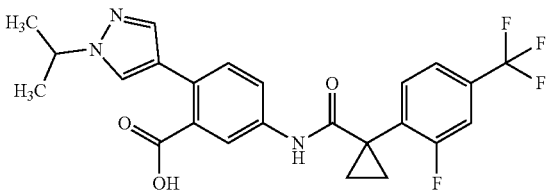 [SMILES: CC(C)n1cc(-c2ccc(NC(=O)C3(c4ccc(C(F)(F)F)cc4F)CC3)cc2C(=O)O)cn1]

5-[({1-[2-fluoro-4-(trifluoromethoxy)phenyl]cyclopropyl}carbonyl)amino]-2-[1-(propan-2-yl)-1H-pyrazol-4-yl]benzoic acid;

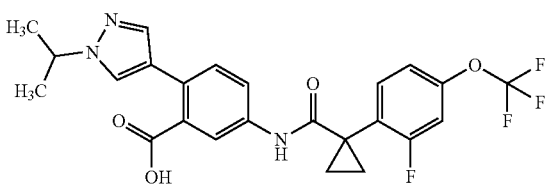 [SMILES: CC(C)n1cc(-c2ccc(NC(=O)C3(c4ccc(OC(F)(F)F)cc4F)CC3)cc2C(=O)O)cn1]

2-(1-tert-butyl-1H-pyrazol-4-yl)-5-[({1-[2-fluoro-4-(trifluoromethyl)phenyl]cyclopropyl}carbonyl)amino]benzoic acid;

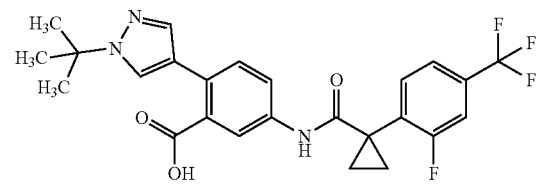 [SMILES: CC(C)(C)n1cc(-c2ccc(NC(=O)C3(c4ccc(C(F)(F)F)cc4F)CC3)cc2C(=O)O)cn1]

344

2-(1-tert-butyl-1H-pyrazol-4-yl)-5-[({1-[2-fluoro-4-(trifluoromethoxy)phenyl]cyclopropyl}carbonyl)amino]benzoic acid;

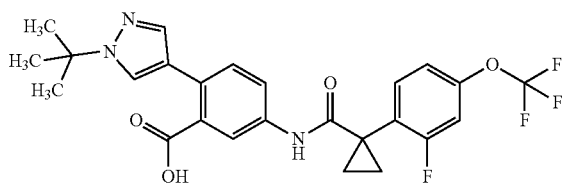 [SMILES: CC(C)(C)n1cc(-c2ccc(NC(=O)C3(c4ccc(OC(F)(F)F)cc4F)CC3)cc2C(=O)O)cn1]

5-[({1-[2-fluoro-4-(trifluoromethyl)phenyl]cyclopropyl}carbonyl)amino]-2-[1-(2-methylpropyl)-1H-pyrazol-4-yl]benzoic acid;

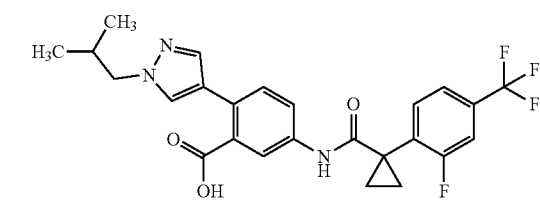 [SMILES: CC(C)Cn1cc(-c2ccc(NC(=O)C3(c4ccc(C(F)(F)F)cc4F)CC3)cc2C(=O)O)cn1]

5-[({1-[2-fluoro-4-(trifluoromethoxy)phenyl]cyclopropyl}carbonyl)amino]-2-[1-(2-methylpropyl)-1H-pyrazol-4-yl]benzoic acid;

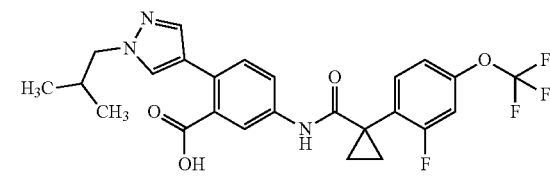 [SMILES: CC(C)Cn1cc(-c2ccc(NC(=O)C3(c4ccc(OC(F)(F)F)cc4F)CC3)cc2C(=O)O)cn1]

2-[1-(2,2-dimethylpropyl)-1H-pyrazol-4-yl]-5-[({1-[2-fluoro-4-(trifluoromethyl)phenyl]cyclopropyl}carbonyl)amino]benzoic acid;

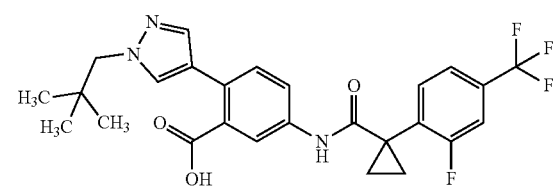 [SMILES: CC(C)(C)Cn1cc(-c2ccc(NC(=O)C3(c4ccc(C(F)(F)F)cc4F)CC3)cc2C(=O)O)cn1]

2-[1-(2,2-dimethylpropyl)-1H-pyrazol-4-yl]-5-[({1-[2-fluoro-4-(trifluoromethoxy)phenyl]cyclopropyl}carbonyl)amino]benzoic acid;

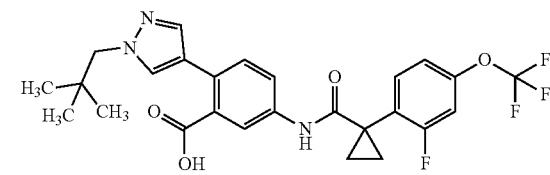 [SMILES: CC(C)(C)Cn1cc(-c2ccc(NC(=O)C3(c4ccc(OC(F)(F)F)cc4F)CC3)cc2C(=O)O)cn1]

3-fluoro-5-({[1-(2-fluoro-4-methylphenyl)cyclopropyl]
carbonyl}amino)-2-[1-(propan-2-yl)-1H-pyrazol-4-yl]
benzoic acid;

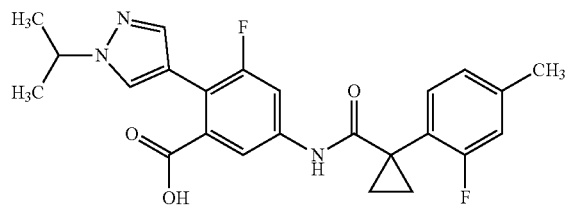

3-fluoro-5-[({1-[2-fluoro-4-(trifluoromethyl)phenyl]
cyclopropyl}carbonyl)amino]-2-[1-(propan-2-yl)-1H-
pyrazol-4-yl]benzoic acid;

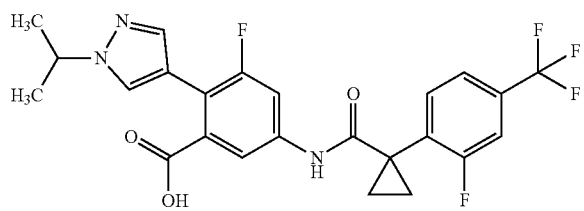 [SMILES: CC(C)n1cc(-c2c(F)cc(NC(=O)C3(c4ccc(C(F)(F)F)cc4F)CC3)cc2C(=O)O)cn1]

3-fluoro-5-[({1-[2-fluoro-4-(trifluoromethoxy)phenyl]
cyclopropyl}carbonyl)amino]-2-[1-(propan-2-yl)-1H-
pyrazol-4-yl]benzoic acid;

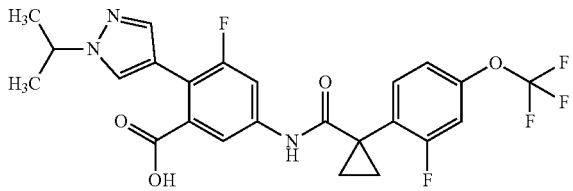

2-(4-tert-butyl-1H-imidazol-1-yl)-3-fluoro-5-[({1-[2-
fluoro-4-(trifluoromethyl)phenyl]
cyclopropyl}carbonyl)amino]benzoic acid;

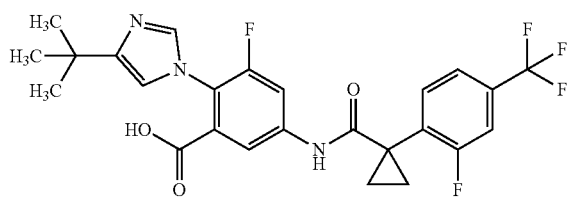 [SMILES: CC(C)(C)c1cn(-c2c(F)cc(NC(=O)C3(c4ccc(C(F)(F)F)cc4F)CC3)cc2C(=O)O)cn1]

2-(4-tert-butyl-1H-imidazol-1-yl)-3-fluoro-5-[({1-[2-
fluoro-4-(trifluoromethoxy)phenyl]
cyclopropyl}carbonyl)amino]benzoic acid;

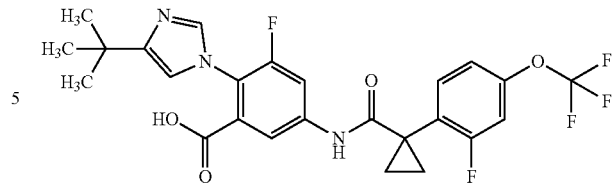

3-fluoro-5-[({1-[2-fluoro-4-(trifluoromethyl)phenyl]
cyclopropyl}carbonyl)amino]-2-[1-(2-methylpropyl)-
1H-pyrazol-4-yl]benzoic acid;

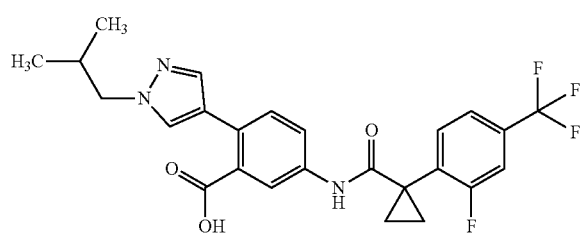 [SMILES: CC(C)Cn1cc(-c2ccc(NC(=O)C3(c4ccc(C(F)(F)F)cc4F)CC3)cc2C(=O)O)cn1]

2-[6-(difluoromethyl)pyridin-3-yl]-3-fluoro-5-[({1-[2-
fluoro-4-(trifluoromethyl)phenyl]
cyclopropyl}carbonyl)amino]benzoic acid;

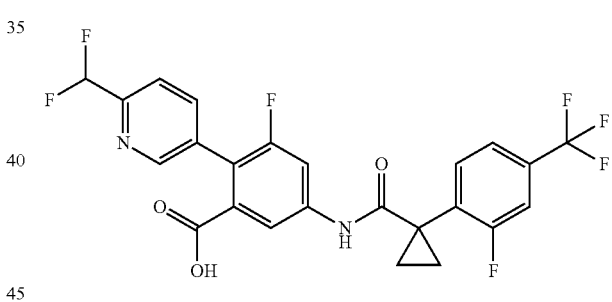

2-[6-(difluoromethyl)pyridin-3-yl]-3-fluoro-5-[({1-[2-
fluoro-4-(trifluoromethoxy)phenyl]
cyclopropyl}carbonyl)amino]benzoic acid;

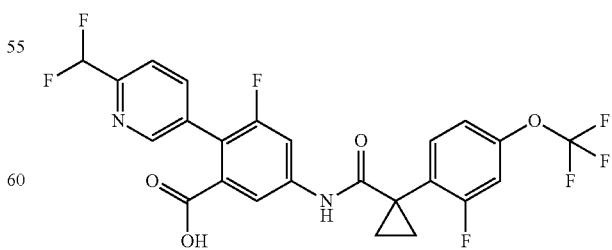

2-[6-(1,1-difluoropropyl)pyridin-3-yl]-3-fluoro-5-[({1-
[2-fluoro-4-(trifluoromethyl)phenyl]
cyclopropyl}carbonyl)amino]benzoic acid;

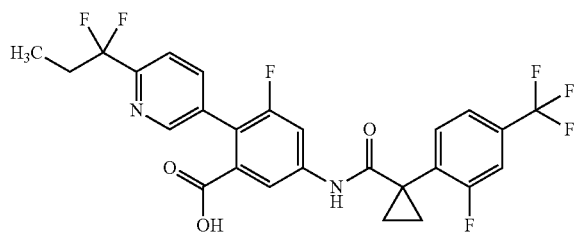 [SMILES: CCC(F)(F)c1ccc(-c2c(F)cc(NC(=O)C3(c4ccc(C(F)(F)F)cc4F)CC3)cc2C(=O)O)cn1]

2-[6-(1,1-difluoropropyl)pyridin-3-yl]-3-fluoro-5-[({1-[2-fluoro-4-(trifluoromethoxy)phenyl]cyclopropyl}carbonyl)amino]benzoic acid;

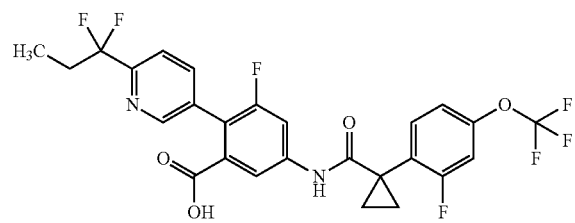 [SMILES: CCC(F)(F)c1ccc(-c2c(F)cc(NC(=O)C3(c4ccc(OC(F)(F)F)cc4F)CC3)cc2C(=O)O)cn1]

3-chloro-2-(1-cyclobutyl-1H-pyrazol-4-yl)-5-[({1-[2-fluoro-4-(trifluoromethyl)phenyl]cyclopropyl}carbonyl)amino]benzoic acid;

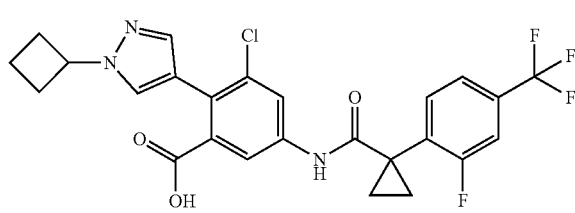

3-chloro-2-(1-cyclobutyl-1H-pyrazol-4-yl)-5-[({1-[2-fluoro-4-(trifluoromethoxy)phenyl]cyclopropyl}carbonyl)amino]benzoic acid;

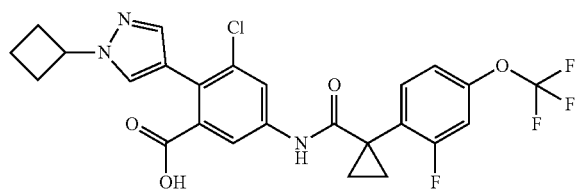 [SMILES: O=C(O)c1cc(NC(=O)C2(c3ccc(OC(F)(F)F)cc3F)CC2)cc(Cl)c1-c1cnn(C2CCC2)c1]

3-chloro-2-[6-(1,1-difluoropropyl)pyridin-3-yl]-5-[({1-[2-fluoro-4-(trifluoromethyl)phenyl]cyclopropyl}carbonyl)amino]benzoic acid;

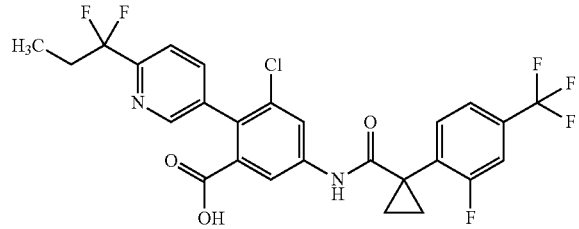

3-chloro-2-[6-(1,1-difluoropropyl)pyridin-3-yl]-5-[({1-[2-fluoro-4-(trifluoromethoxy)phenyl]cyclopropyl}carbonyl)amino]benzoic acid;

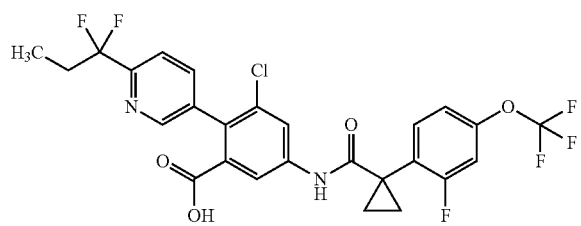 [SMILES: CCC(F)(F)c1ccc(-c2c(Cl)cc(NC(=O)C3(c4ccc(OC(F)(F)F)cc4F)CC3)cc2C(=O)O)cn1]

2-(1-cyclobutyl-1H-pyrazol-4-yl)-5-[({1-[2-fluoro-4-(trifluoromethyl)phenyl]cyclopropyl}carbonyl)amino]-3-methylbenzoic acid;

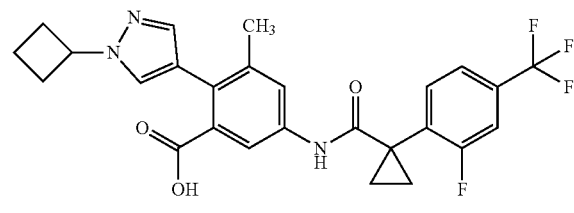 [SMILES: Cc1cc(NC(=O)C2(c3ccc(C(F)(F)F)cc3F)CC2)cc(C(=O)O)c1-c1cnn(C2CCC2)c1]

2-(1-cyclobutyl-1H-pyrazol-4-yl)-5-[({1-[2-fluoro-4-(trifluoromethoxy)phenyl]cyclopropyl}carbonyl)amino]-3-methylbenzoic acid;

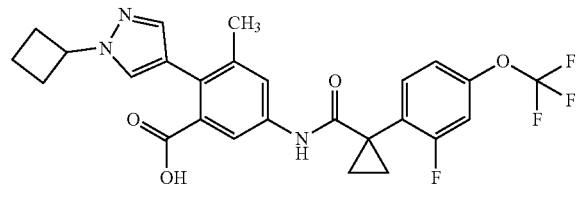 [SMILES: Cc1cc(NC(=O)C2(c3ccc(OC(F)(F)F)cc3F)CC2)cc(C(=O)O)c1-c1cnn(C2CCC2)c1]

2-[1-(cyclobutylmethyl)-1H-pyrazol-4-yl]-5-[({1-[2-fluoro-4-(trifluoromethyl)phenyl]cyclopropyl}carbonyl)amino]benzoic acid;

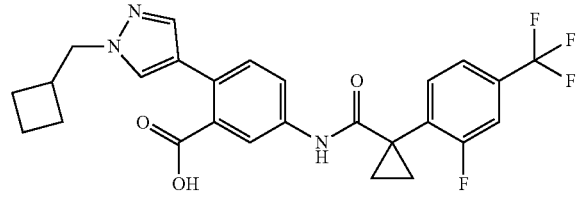 [SMILES: O=C(O)c1cc(NC(=O)C2(c3ccc(C(F)(F)F)cc3F)CC2)ccc1-c1cnn(CC2CCC2)c1]

2-[1-(cyclobutylmethyl)-1H-pyrazol-4-yl]-5-[({1-[2-fluoro-4-(trifluoromethoxy)phenyl]cyclopropyl}carbonyl)amino]benzoic acid;

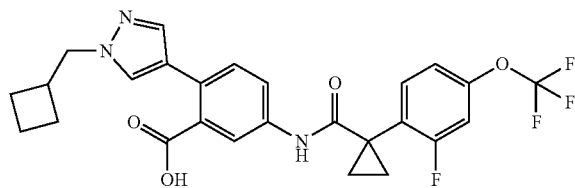 [SMILES: O=C(O)c1cc(NC(=O)C2(c3ccc(OC(F)(F)F)cc3F)CC2)ccc1-c1cnn(CC2CCC2)c1]

2-(1-cyclopentyl-1H-pyrazol-4-yl)-5-[({1-[2-fluoro-4-(trifluoromethyl)phenyl]cyclopropyl}carbonyl)amino]benzoic acid;

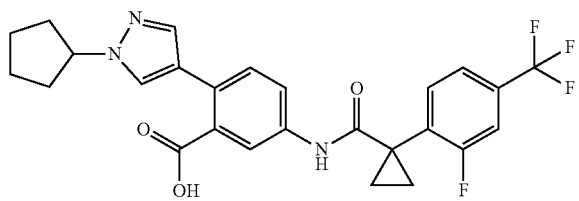 [SMILES: O=C(O)c1cc(NC(=O)C2(c3ccc(C(F)(F)F)cc3F)CC2)ccc1-c1cnn(C2CCCC2)c1]

2-(1-cyclohexyl-1H-pyrazol-4-yl)-5-[({1-[2-fluoro-4-(trifluoromethyl)phenyl]cyclopropyl}carbonyl)amino]benzoic acid;

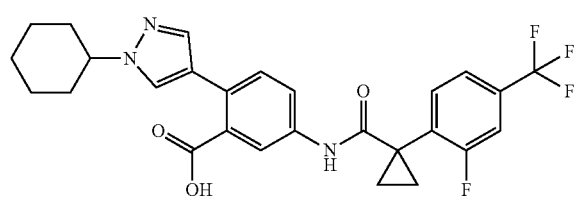 [SMILES: O=C(O)c1cc(NC(=O)C2(c3ccc(C(F)(F)F)cc3F)CC2)ccc1-c1cnn(C2CCCCC2)c1]

2-(1-cyclohexyl-1H-pyrazol-4-yl)-5-[({1-[2-fluoro-4-(trifluoromethoxy)phenyl]cyclopropyl}carbonyl)amino]benzoic acid;

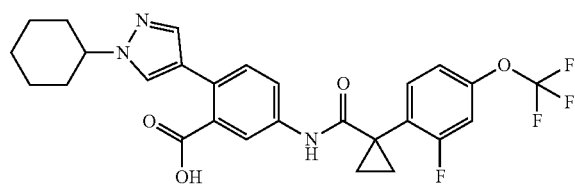 [SMILES: O=C(O)c1cc(NC(=O)C2(c3ccc(OC(F)(F)F)cc3F)CC2)ccc1-c1cnn(C2CCCCC2)c1]

2-[1-(cyclopropylmethyl)-1H-pyrazol-4-yl]-3-fluoro-5-[({1-[2-fluoro-4-(trifluoromethyl)phenyl]cyclopropyl}carbonyl)amino]benzoic acid;

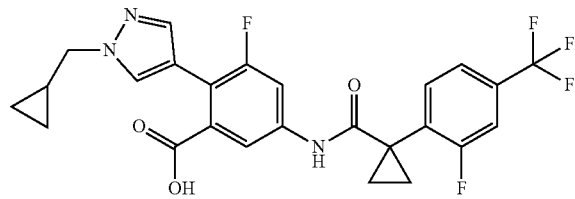 [SMILES: O=C(O)c1cc(NC(=O)C2(c3ccc(C(F)(F)F)cc3F)CC2)cc(F)c1-c1cnn(CC2CC2)c1]

2-[1-(cyclopropylmethyl)-1H-pyrazol-4-yl]-3-fluoro-5-[({1-[2-fluoro-4-(trifluoromethoxy)phenyl]cyclopropyl}carbonyl)amino]benzoic acid;

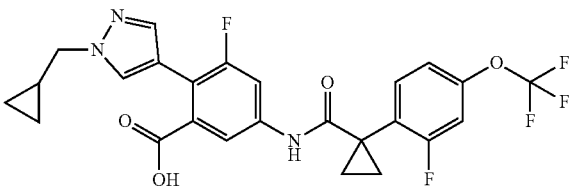 [SMILES: O=C(O)c1cc(NC(=O)C2(c3ccc(OC(F)(F)F)cc3F)CC2)cc(F)c1-c1cnn(CC2CC2)c1]

3-fluoro-5-[({1-[2-fluoro-4-(trifluoromethyl)phenyl]cyclopropyl}carbonyl)amino]-2-(6-methylpyridin-3-yl)benzoic acid;

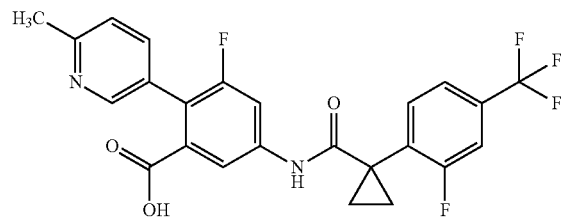 [SMILES: Cc1ccc(-c2c(F)cc(NC(=O)C3(c4ccc(C(F)(F)F)cc4F)CC3)cc2C(=O)O)cn1]

2-{1-[(2S)-butan-2-yl]-1H-pyrazol-4-yl}-5-[({1-[2-fluoro-4-(trifluoromethyl)phenyl]cyclopropyl}carbonyl)amino]benzoic acid;

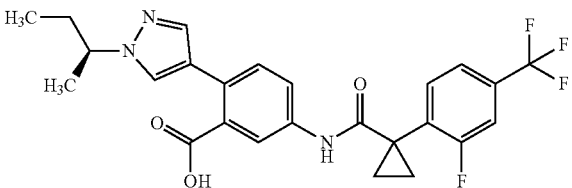 [SMILES: CC[C@H](C)n1cc(-c2ccc(NC(=O)C3(c4ccc(C(F)(F)F)cc4F)CC3)cc2C(=O)O)cn1]

2-{1-[(2R)-butan-2-yl]-1H-pyrazol-4-yl}-5-[({1-[2-fluoro-4-(trifluoromethoxy)phenyl]cyclopropyl}carbonyl)amino]benzoic acid;

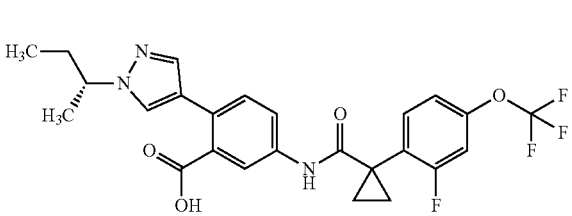 [SMILES: CC[C@@H](C)n1cc(-c2ccc(NC(=O)C3(c4ccc(OC(F)(F)F)cc4F)CC3)cc2C(=O)O)cn1]

2-{1-[(2S)-butan-2-yl]-1H-pyrazol-4-yl}-3-fluoro-5-[({1-[2-fluoro-4-(trifluoromethyl)phenyl]cyclopropyl}carbonyl)amino]benzoic acid;

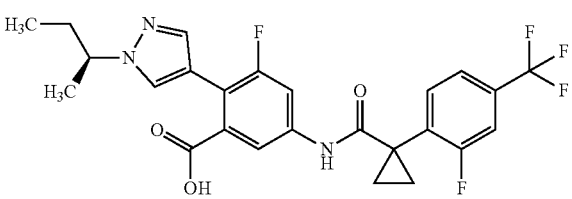 [SMILES: CC[C@H](C)n1cc(-c2c(F)cc(NC(=O)C3(c4ccc(C(F)(F)F)cc4F)CC3)cc2C(=O)O)cn1]

2-{1-[(2R)-butan-2-yl]-1H-pyrazol-4-yl}-3-fluoro-5-
[({1-[2-fluoro-4-(trifluoromethyl)phenyl]
cyclopropyl}carbonyl)amino]benzoic acid;

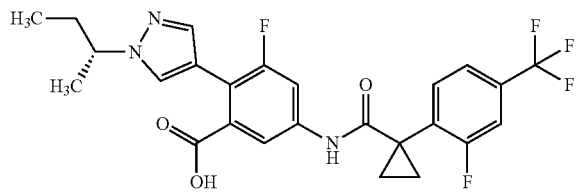

2-(1-ethyl-1H-pyrazol-4-yl)-3-fluoro-5-[({1-[2-fluoro-4-
(trifluoromethyl)phenyl]cyclopropyl}carbonyl)amino]
benzoic acid;

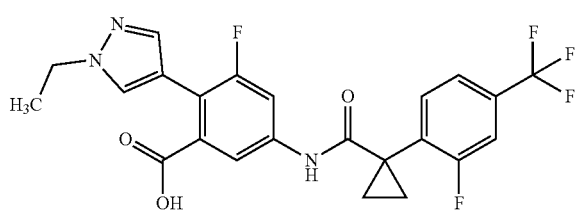 [SMILES: CCn1cc(-c2c(F)cc(NC(=O)C3(c4ccc(C(F)(F)F)cc4F)CC3)cc2C(=O)O)cn1]

2-(1-ethyl-1H-pyrazol-4-yl)-3-fluoro-5-[({1-[2-fluoro-4-
(trifluoromethoxy)phenyl]cyclopropyl}carbonyl)
amino]benzoic acid;

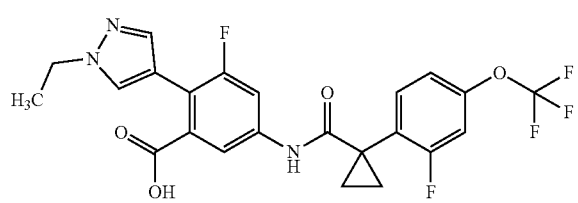 [SMILES: CCn1cc(-c2c(F)cc(NC(=O)C3(c4ccc(OC(F)(F)F)cc4F)CC3)cc2C(=O)O)cn1]

5-({[1-(4-chloro-2-fluorophenyl)cyclopropyl]
carbonyl}amino)-3-fluoro-2-[1-(propan-2-yl)-1H-
pyrazol-4-yl]benzoic acid;

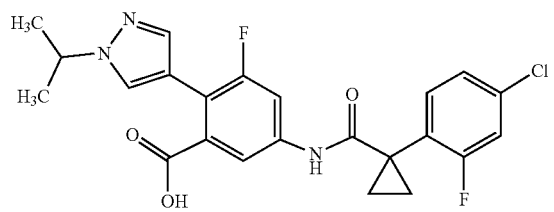 [SMILES: CC(C)n1cc(-c2c(F)cc(NC(=O)C3(c4ccc(Cl)cc4F)CC3)cc2C(=O)O)cn1]

5-({[1-(4-chloro-2-fluorophenyl)cyclopropyl]
carbonyl}amino)-2-(2-cyclobutyl-1,3-thiazol-5-yl)
benzoic acid;

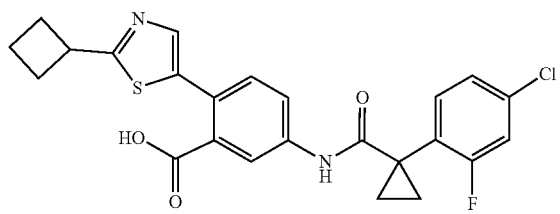 [SMILES: O=C(O)c1cc(NC(=O)C2(c3ccc(Cl)cc3F)CC2)ccc1-c1cnc(C2CCC2)s1]

2-(2-cyclobutyl-1,3-thiazol-5-yl)-5-({[1-(2-fluoro-4-
methylphenyl)cyclopropyl]carbonyl}amino)benzoic
acid;

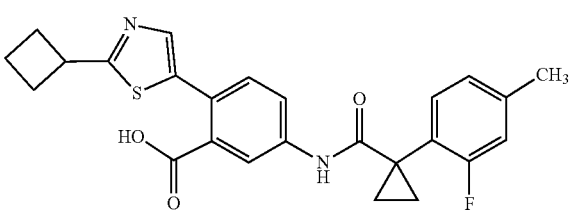 [SMILES: Cc1ccc(C2(C(=O)Nc3ccc(-c4cnc(C5CCC5)s4)c(C(=O)O)c3)CC2)c(F)c1]

2-(2-cyclobutyl-1,3-thiazol-5-yl)-5-[({1-[2-fluoro-4-(trif-
luoromethyl)phenyl]cyclopropyl}carbonyl)amino]ben-
zoic acid;

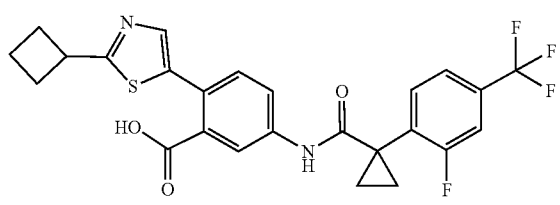 [SMILES: O=C(O)c1cc(NC(=O)C2(c3ccc(C(F)(F)F)cc3F)CC2)ccc1-c1cnc(C2CCC2)s1]

2-(2-cyclobutyl-1,3-thiazol-5-yl)-5-[({1-[2-fluoro-4-(trif-
luoromethoxy)phenyl]cyclopropyl}carbonyl)amino]
benzoic acid;

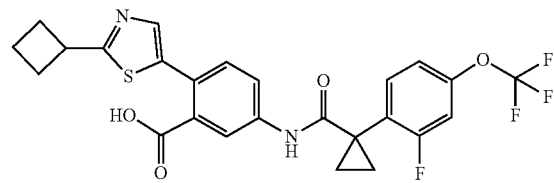 [SMILES: O=C(O)c1cc(NC(=O)C2(c3ccc(OC(F)(F)F)cc3F)CC2)ccc1-c1cnc(C2CCC2)s1]

5-[({1-[2-fluoro-4-(trifluoromethyl)phenyl]
cyclopropyl}carbonyl)amino]-2-{1-[(1-methylcyclo-
propyl)methyl]-1H-pyrazol-4-yl}benzoic acid;

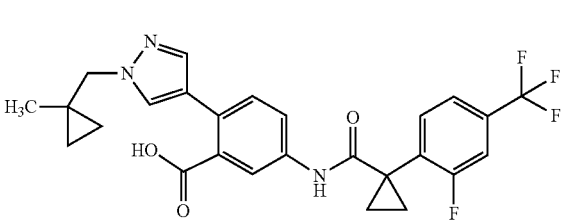 [SMILES: CC1(Cn2cc(-c3ccc(NC(=O)C4(c5ccc(C(F)(F)F)cc5F)CC4)cc3C(=O)O)cn2)CC1]

5-[({1-[2-fluoro-4-(trifluoromethoxy)phenyl]
cyclopropyl}carbonyl)amino]-2-{1-[(1-methylcyclo-
propyl)methyl]-1H-pyrazol-4-yl}benzoic acid;

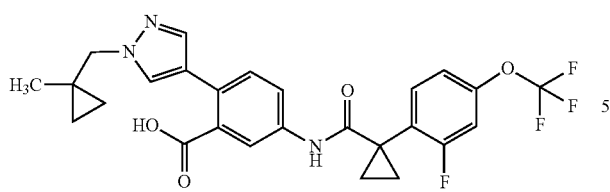

2-{1-[(1S)-1-cyclopropylethyl]-1H-pyrazol-4-yl}-5-[({1-[2-fluoro-4-(trifluoromethyl)phenyl]cyclopropyl}carbonyl)amino]benzoic acid;

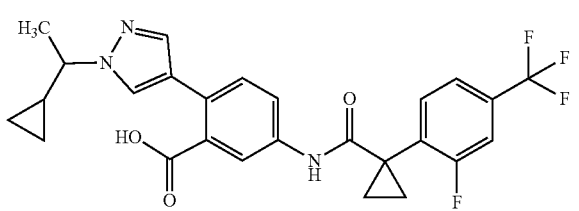 [SMILES: CC(C1CC1)n1cc(-c2ccc(NC(=O)C3(c4ccc(C(F)(F)F)cc4F)CC3)cc2C(=O)O)cn1]

2-(6-ethylpyridin-3-yl)-5-[({1-[2-fluoro-4-(trifluoromethyl)phenyl]cyclopropyl}carbonyl)amino]benzoic acid;

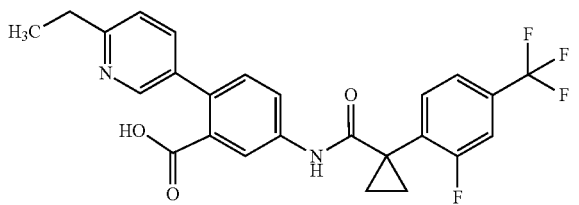 [SMILES: CCc1ccc(-c2ccc(NC(=O)C3(c4ccc(C(F)(F)F)cc4F)CC3)cc2C(=O)O)cn1]

2-(6-ethylpyridin-3-yl)-5-[({1-[2-fluoro-4-(trifluoromethoxy)phenyl]cyclopropyl}carbonyl)amino]benzoic acid;

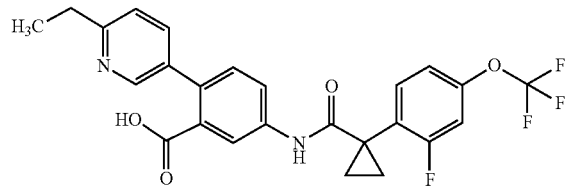 [SMILES: CCc1ccc(-c2ccc(NC(=O)C3(c4ccc(OC(F)(F)F)cc4F)CC3)cc2C(=O)O)cn1]

2-(6-ethylpyridin-3-yl)-3-fluoro-5-[({1-[2-fluoro-4-(trifluoromethyl)phenyl]cyclopropyl}carbonyl)amino]benzoic acid;

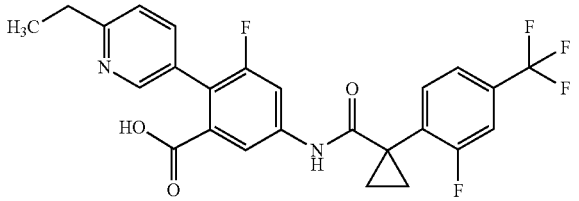 [SMILES: CCc1ccc(-c2c(F)cc(NC(=O)C3(c4ccc(C(F)(F)F)cc4F)CC3)cc2C(=O)O)cn1]

3-fluoro-5-[({1-[2-fluoro-4-(trifluoromethoxy)phenyl]cyclopropyl}carbonyl)amino]-2-(1-methyl-1H-indazol-6-yl)benzoic acid;

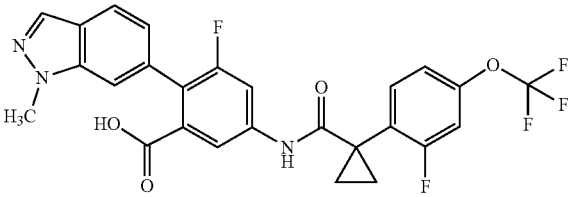 [SMILES: Cn1ncc2ccc(-c3c(F)cc(NC(=O)C4(c5ccc(OC(F)(F)F)cc5F)CC4)cc3C(=O)O)cc21]

2-(2-cyclopentyl-1,3-thiazol-5-yl)-5-[({1-[2-fluoro-4-(trifluoromethyl)phenyl]cyclopropyl}carbonyl)amino]benzoic acid;

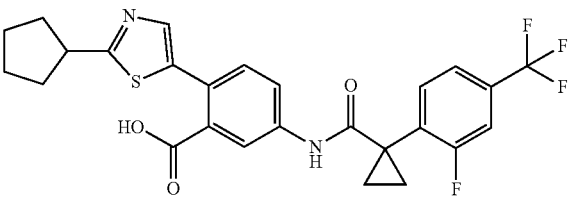 [SMILES: O=C(O)c1cc(NC(=O)C2(c3ccc(C(F)(F)F)cc3F)CC2)ccc1-c1cnc(C2CCCC2)s1]

2-(2-cyclobutyl-1,3-thiazol-5-yl)-3-fluoro-5-[({1-[2-fluoro-4-(trifluoromethyl)phenyl]cyclopropyl}carbonyl)amino]benzoic acid;

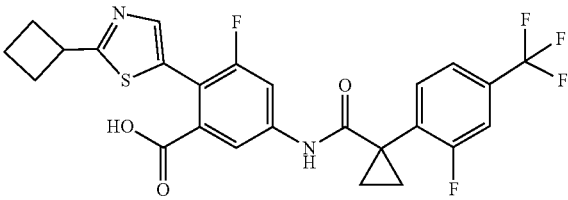 [SMILES: O=C(O)c1cc(NC(=O)C2(c3ccc(C(F)(F)F)cc3F)CC2)cc(F)c1-c1cnc(C2CCC2)s1]

and
3-fluoro-5-[({1-[2-fluoro-4-(trifluoromethyl)phenyl]cyclopropyl}carbonyl)amino]-2-[1-(2,2,2-trifluoroethyl)-1H-pyrazol-4-yl]benzoic acid;

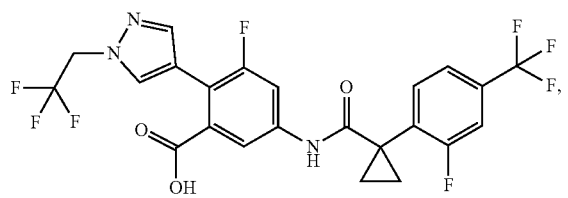 [SMILES: O=C(O)c1cc(NC(=O)C2(c3ccc(C(F)(F)F)cc3F)CC2)cc(F)c1-c1cnn(CC(F)(F)F)c1]

or a pharmaceutically acceptable salt thereof or an isomer, enantiomer, diastereomer, racemate, hydrate, solvate, or a salt thereof, optionally a pharmaceutically acceptable salt thereof, or a mixture of the same.

2. A pharmaceutical composition comprising a compound according to claim 1, and a pharmaceutically acceptable diluent or carrier.

3. The compound according to claim 1 in the form of a pharmaceutically acceptable salt.

* * * * *